(12) United States Patent
Hatakeyama et al.

(10) Patent No.: US 8,497,476 B2
(45) Date of Patent: Jul. 30, 2013

(54) INSPECTION DEVICE

(75) Inventors: Masahiro Hatakeyama, Tokyo (JP);
Shoji Yoshikawa, Tokyo (JP); Takeshi Murakami, Tokyo (JP); Kenji Watanabe, Tokyo (JP); Yoshihiko Naito, Tokyo (JP); Yasushi Toma, Tokyo (JP); Tsutomu Karimata, Tokyo (JP); Takehide Hayashi, Tokyo (JP); Kiwamu Tsukamoto, Tokyo (JP); Tatsuya Kohama, Tokyo (JP); Noboru Kobayashi, Tokyo (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 13/420,731

(22) Filed: Mar. 15, 2012

(65) Prior Publication Data

US 2012/0235036 A1 Sep. 20, 2012

(30) Foreign Application Priority Data

Mar. 15, 2011 (JP) .................. 2011-057312
May 10, 2011 (JP) .................. 2011-105751
Jan. 27, 2012 (JP) .................. 2012-015875

(51) Int. Cl.
*G01N 23/225* (2006.01)
(52) U.S. Cl.
USPC .......... 250/310; 250/306; 250/309; 250/311; 250/491.1; 250/492.3
(58) Field of Classification Search
USPC .............. 250/306, 307, 309, 310, 311, 491.1, 250/492.1, 492.3
See application file for complete search history.

(56) References Cited

U.S. PATENT DOCUMENTS

| | | | |
|---|---|---|---|
| 6,265,719 B1 | 7/2001 | Yamazaki et al. | |
| 6,317,514 B1 | 11/2001 | Reinhorn et al. | |
| 6,956,644 B2 | 10/2005 | Biellak et al. | |
| 6,979,819 B2 | 12/2005 | Adler et al. | |
| 7,135,676 B2 * | 11/2006 | Nakasuji et al. | 250/310 |
| 7,501,625 B2 | 3/2009 | Koyama et al. | |
| 7,928,382 B2 | 4/2011 | Hatakeyama et al. | |
| 2002/0028399 A1 * | 3/2002 | Nakasuji et al. | 430/30 |
| 2005/0158653 A1 | 7/2005 | Hatakeyama et al. | |
| 2010/0237243 A1 * | 9/2010 | Noji et al. | 250/310 |
| 2011/0155905 A1 * | 6/2011 | Hatakeyama et al. | 250/307 |

FOREIGN PATENT DOCUMENTS

| | | |
|---|---|---|
| JP | 3-155033 A | 7/1991 |
| JP | 11-224630 A | 8/1999 |
| JP | 11-224631 A | 8/1999 |
| JP | 2010-165725 A | 7/2010 |
| JP | 2011-222352 A | 11/2011 |

\* cited by examiner

*Primary Examiner* — Michael Logie
(74) *Attorney, Agent, or Firm* — Westerman, Hattori, Daniels & Adrian, LLP

(57) ABSTRACT

An inspection device for inspecting a surface of an inspection object using a beam includes a beam generator capable of generating one of either charge particles or an electromagnetic wave as a beam, a primary optical system capable of guiding and irradiating the beam to the inspection object supported within a working chamber, a secondary optical system capable of including a first movable numerical aperture and a first detector which detects secondary charge particles generated from the inspection object, the secondary charge particles passing through the first movable numerical aperture, an image processing system capable of forming an image based on the secondary charge particles detected by the first detector; and a second detector arranged between the first movable numerical aperture and the first detector and which detects a location and shape at a cross over location of the secondary charge particles generated from the inspection object.

10 Claims, 201 Drawing Sheets

(A)

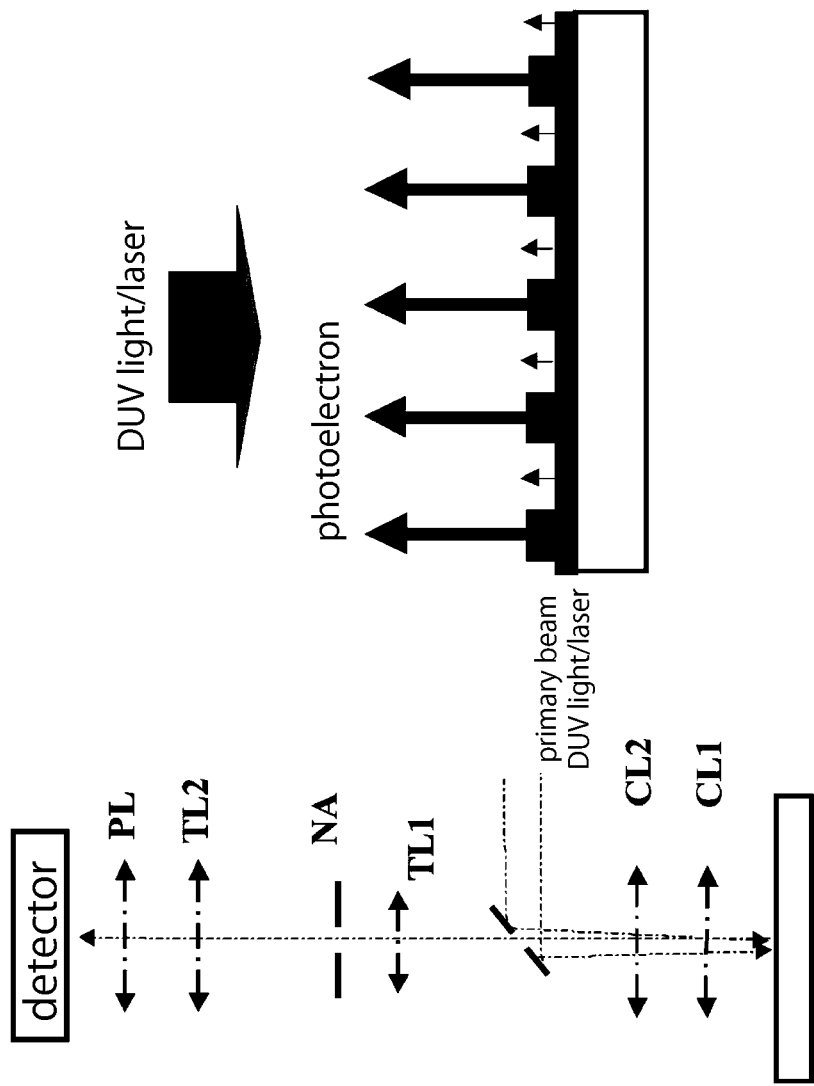

Fig.34
(a)
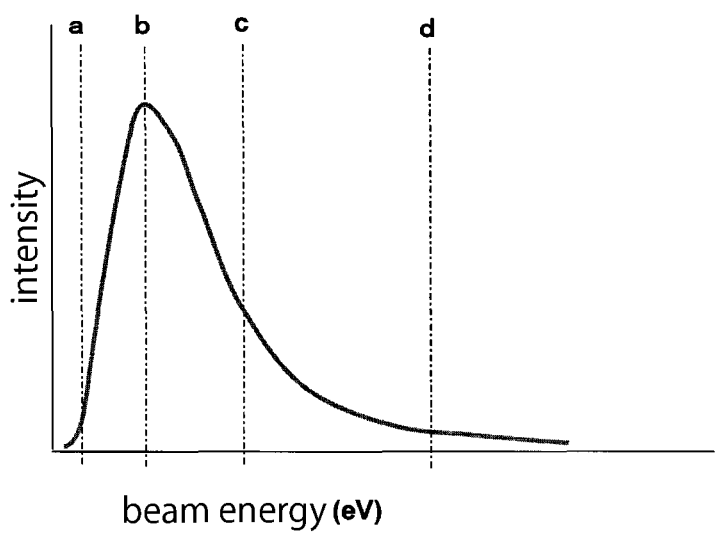
(b)
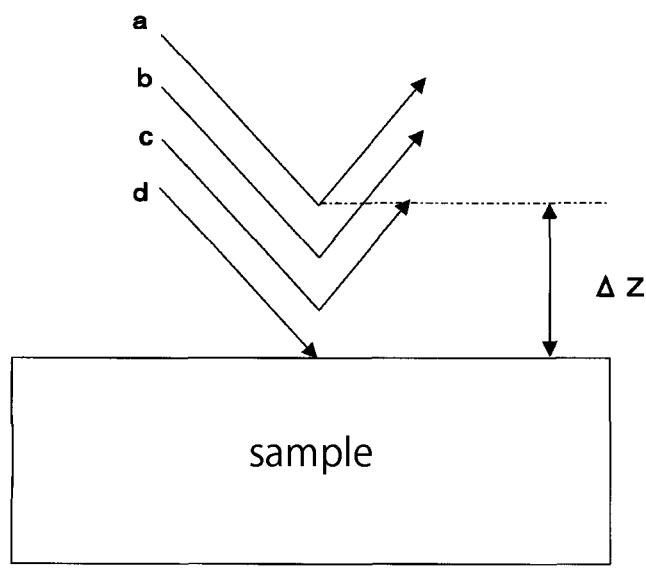

Fig. 47
(a)
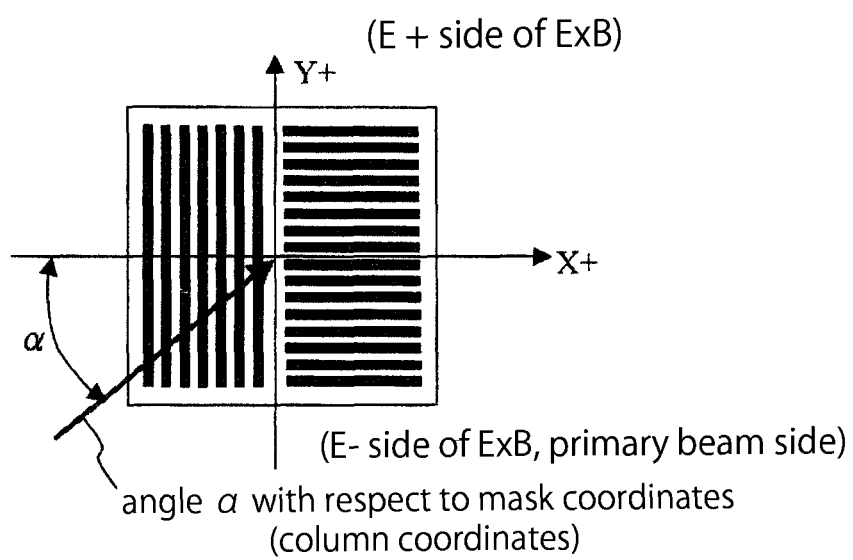
(b)
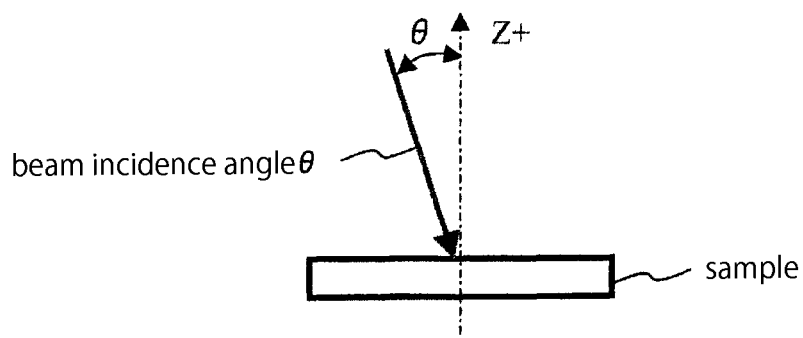

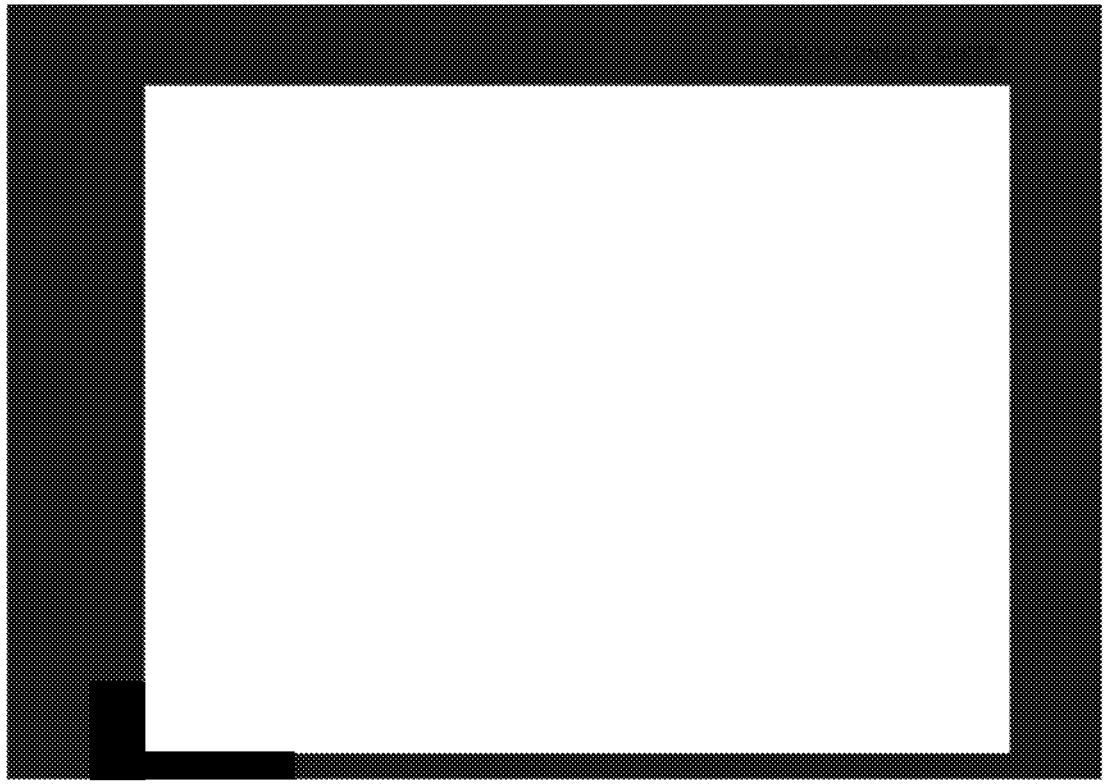
Fig.60
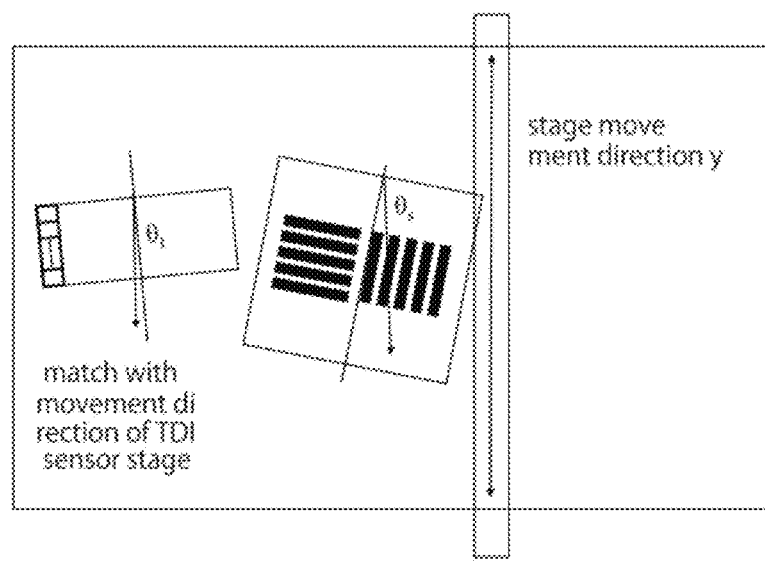

Fig. 65
(a)
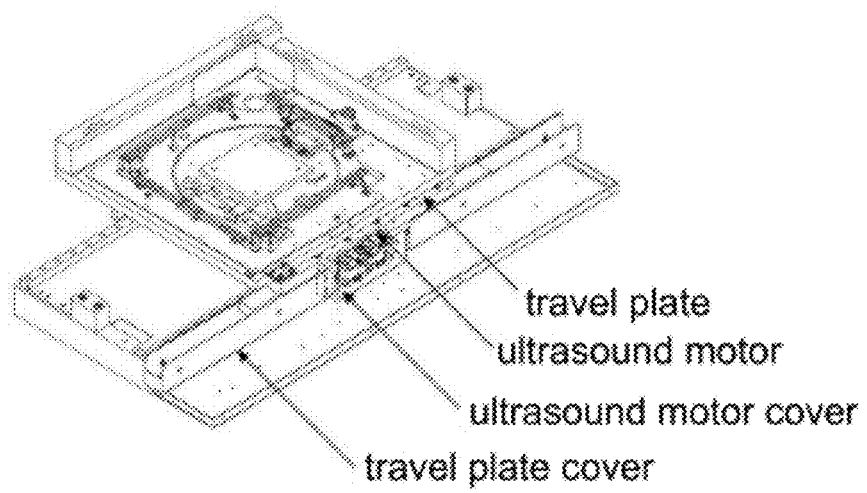
(b)
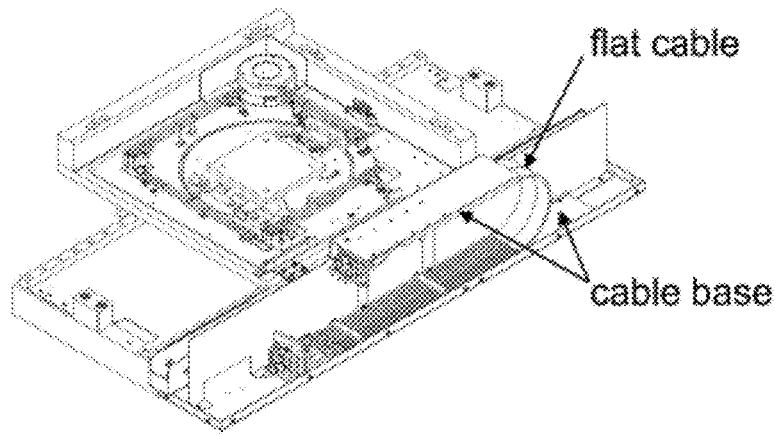

C.O (same as ec in Fig. 68)
distribution of mirror electrons and secondary electrons
in Fig. 1 (perpendicular incidence)

Fig. 74
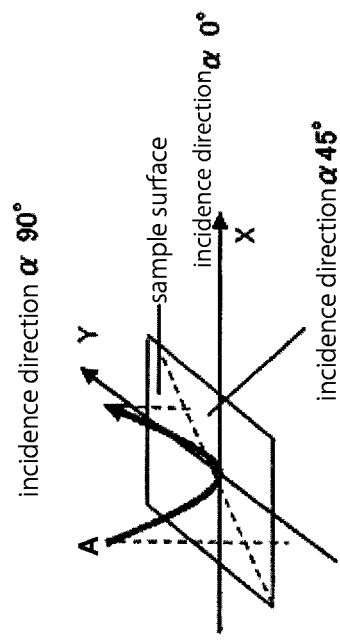
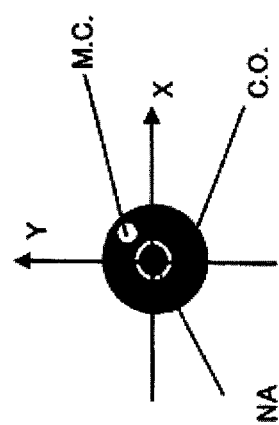

SiO2

|     | X    | Y    |
|-----|------|------|
| BA1 | −64V | −88V |
| BA2 | 70V  | +93V |

| MC relative position (a.u) | contrast | SN  |
|---|---|---|
| 0.3 | 0.2  | 8   |
| 1   | 0.35 | 7   |
| 1.5 | 0.4  | 5.8 |
| 2   | 0.45 | 5   |
| 2.5 | 0.5  | 5.5 |
| 3.5 | 0.55 | 5   |
| 4   | 0.57 | 4.5 |
| 4.5 | 0.58 | 4.3 |
| 5   | 0.58 | 3   |

Fig. 78
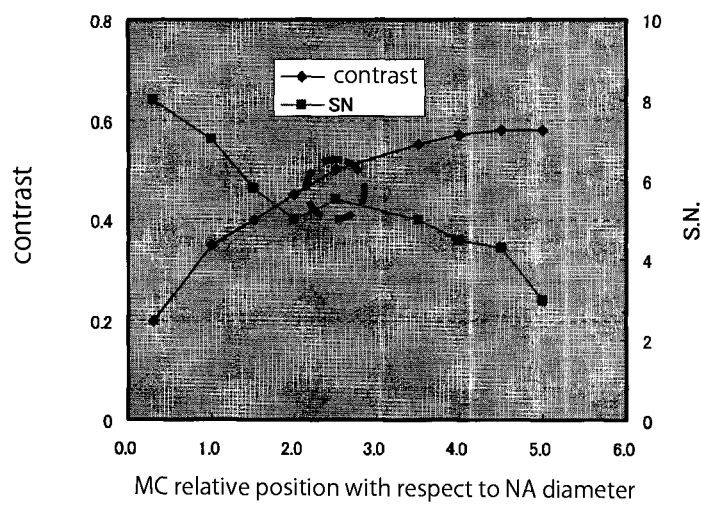
MC relative position with respect to NA diameter
Fig. 79
|  | X | Y |
|---|---|---|
| BA1 | 0 | −88V |
| BA2 | 0 | +93V |
Fig. 80
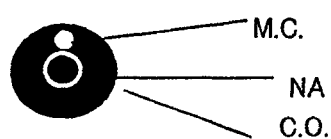
M.C.
NA
C.O.

Fig. 81
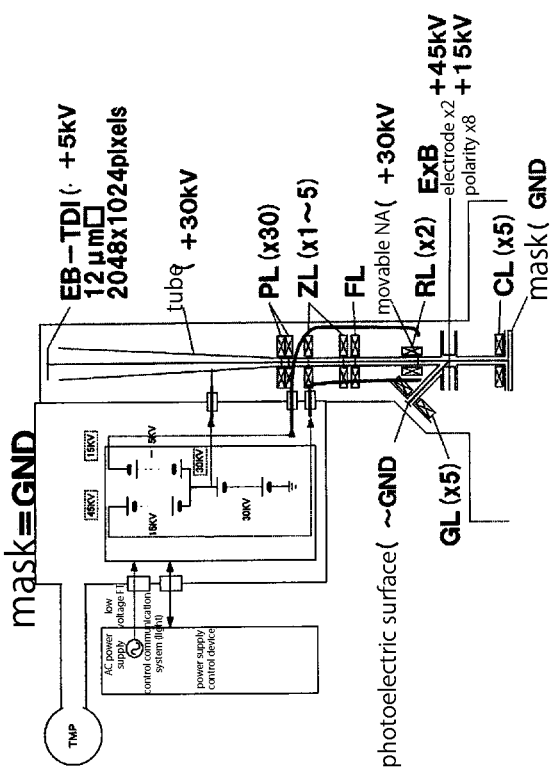
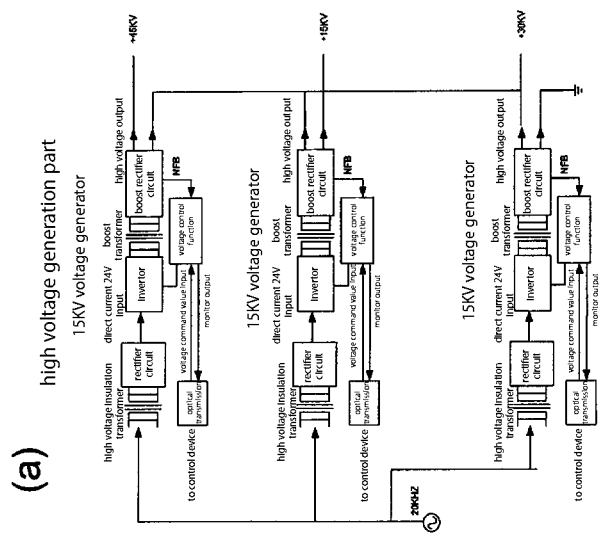

Fig. 95
(a)
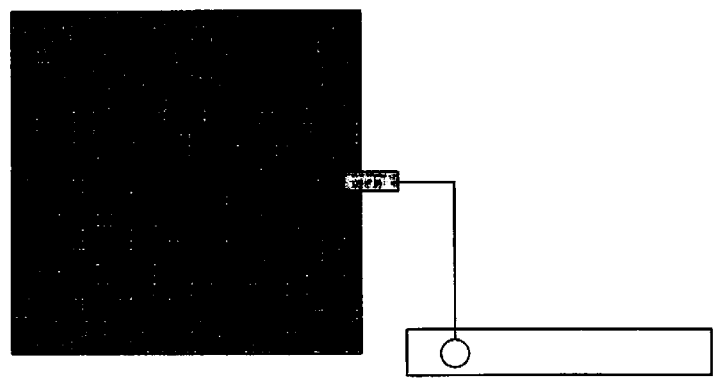
(b)
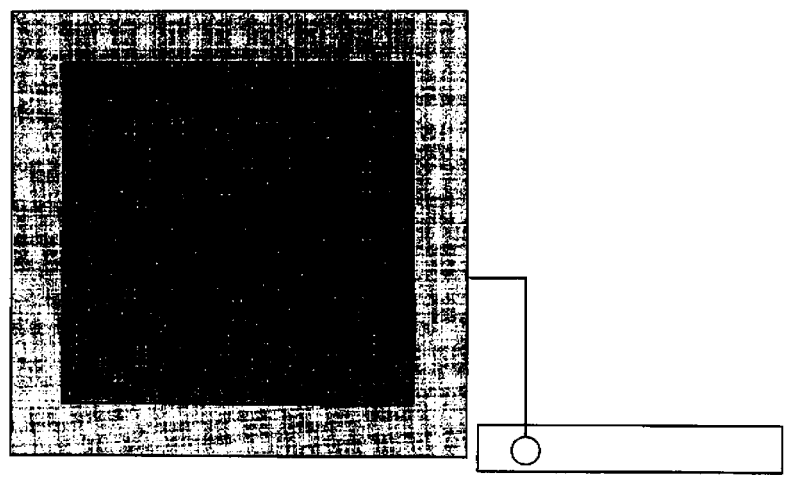

the part to which the sample application electrode is attached is called a frame and the sample can be inserted inside by moving the frame up and down,
when the frame is in a lowered state, the sample application electrode contacts the sample surface, and it is possible to supply a uniform voltage to the sample

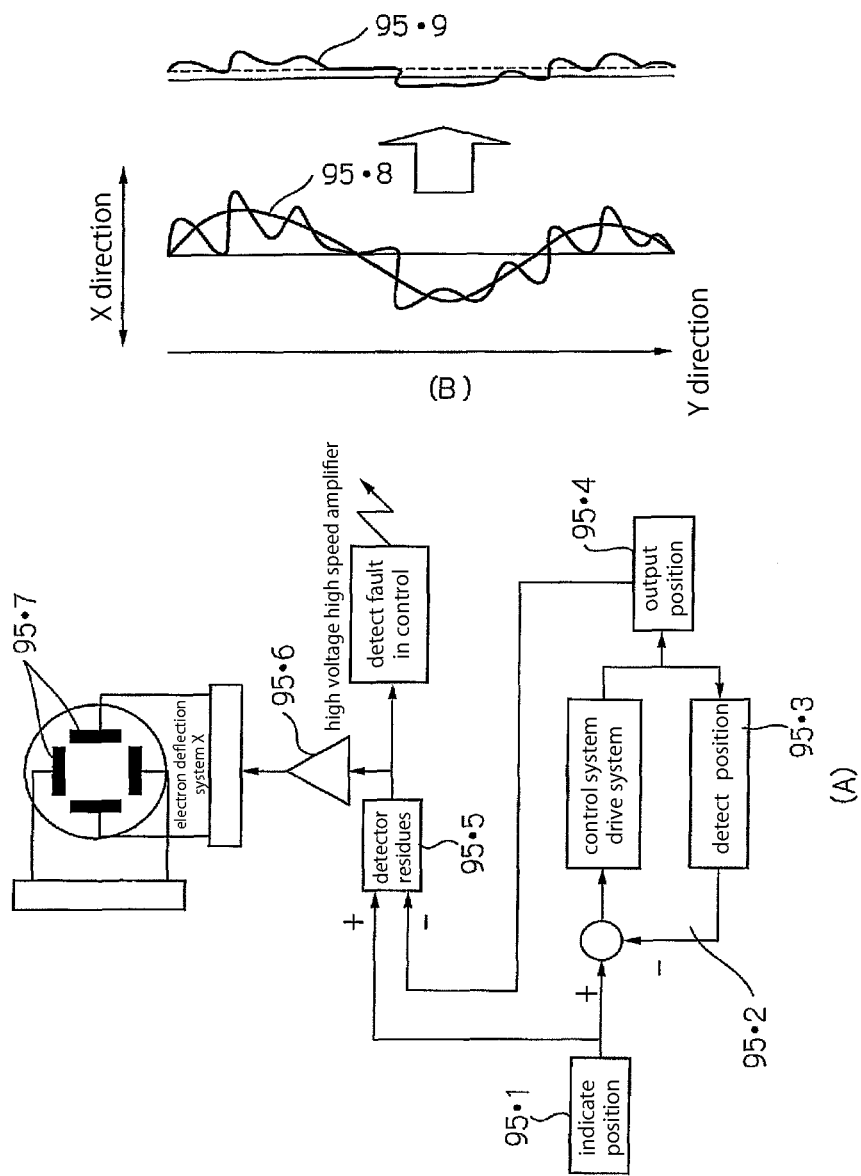

Fig. 1111

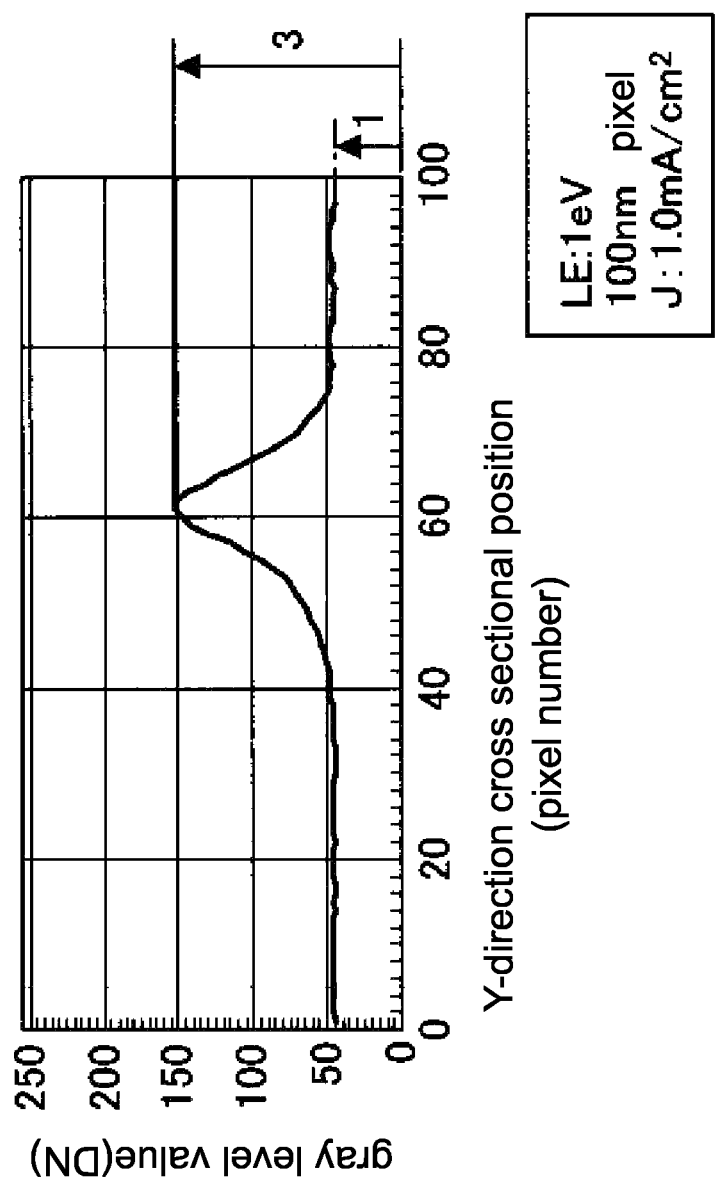

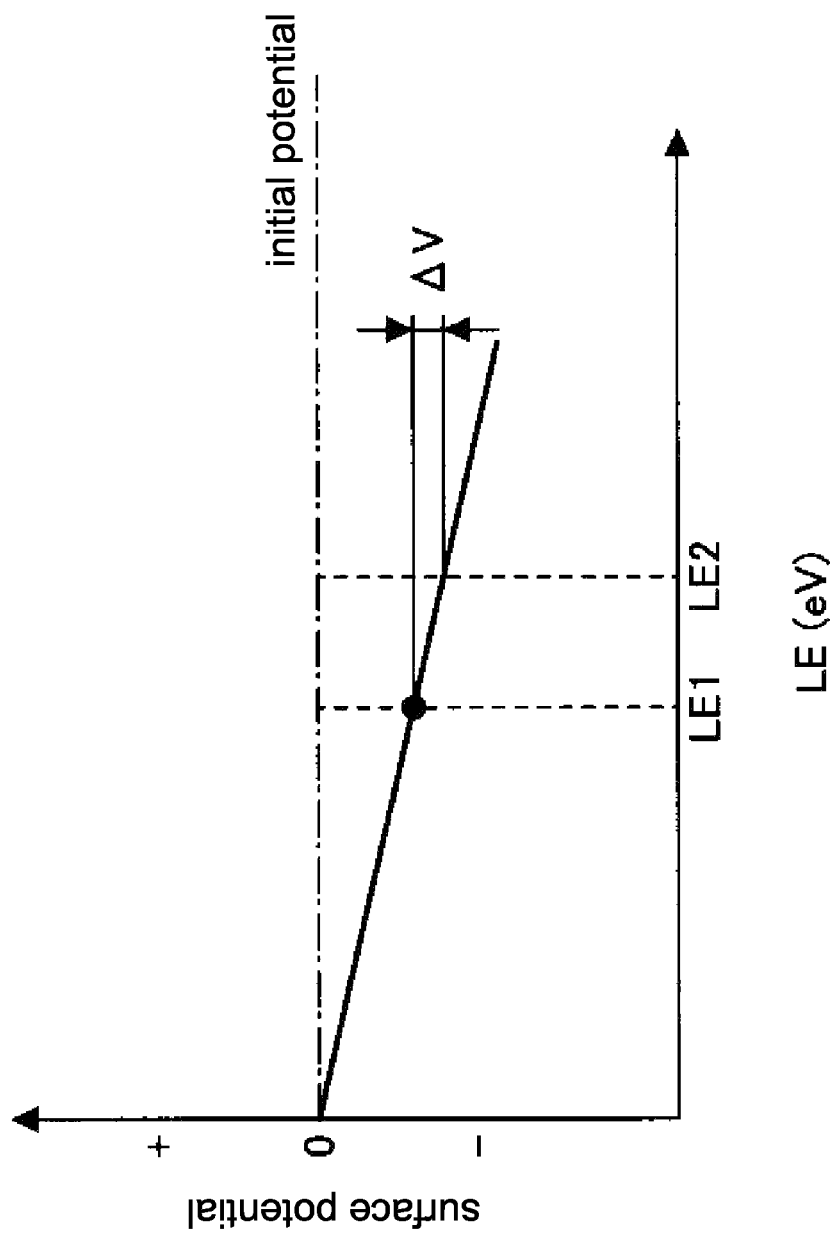

when the foreign material is represented by
secondary emission electrons(black signal)

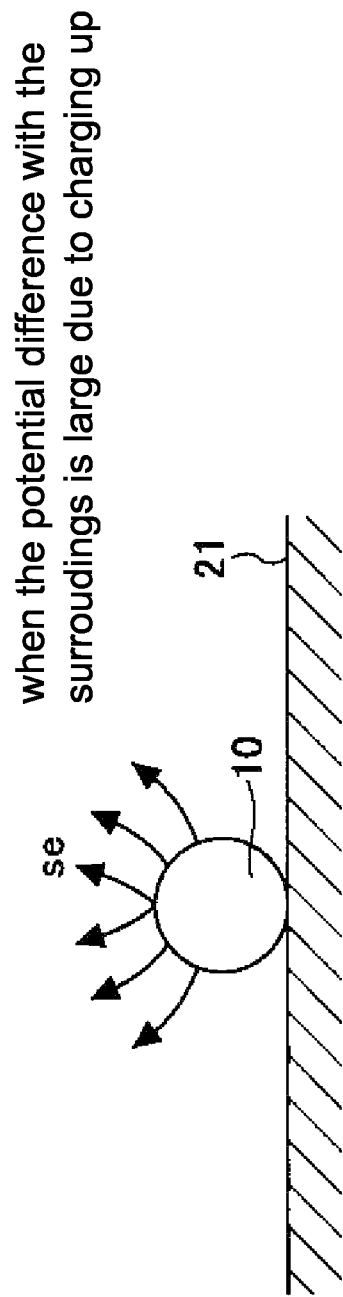

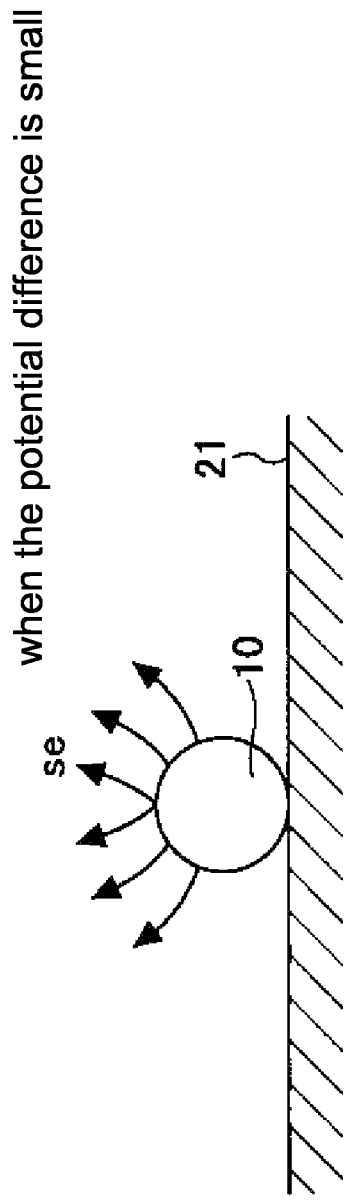

Fig. 181
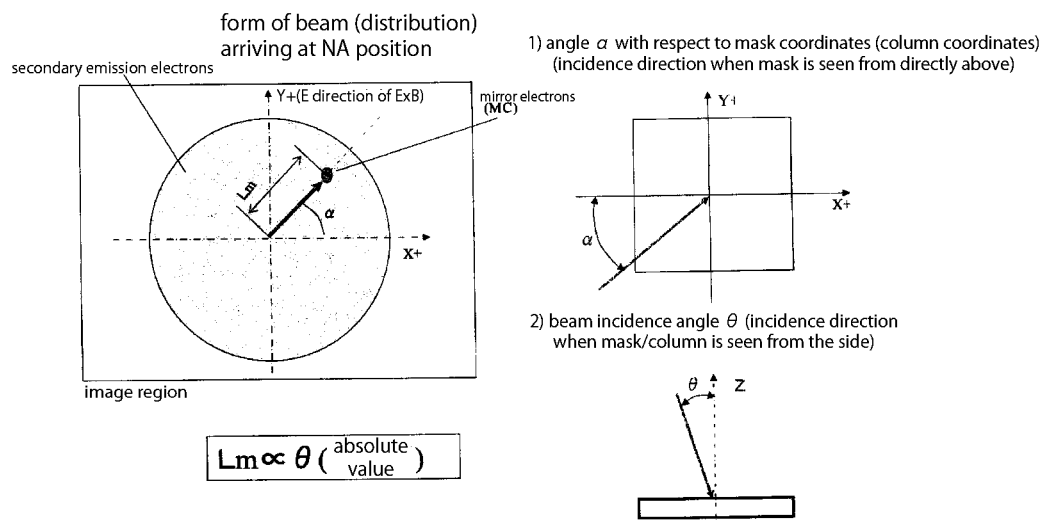
Fig. 182
where θ is small          where θ is large
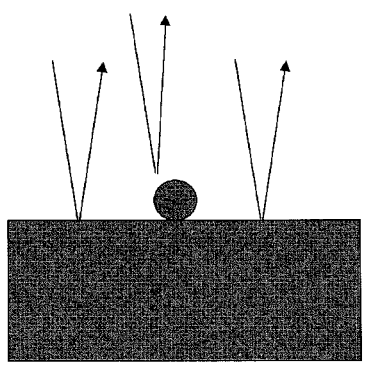 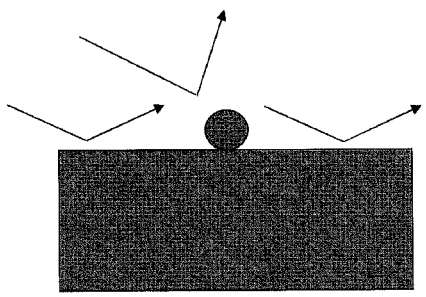

(A)

(B)

Fig. 202
(a)
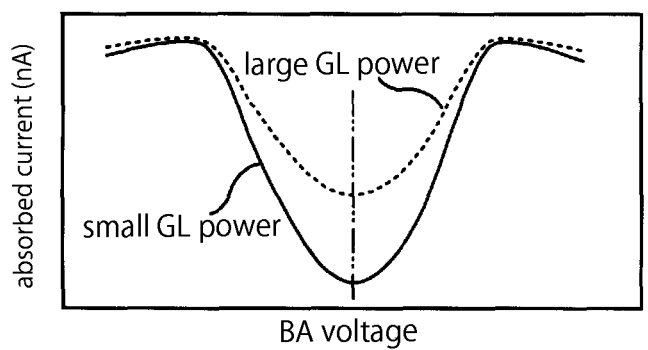
(b)
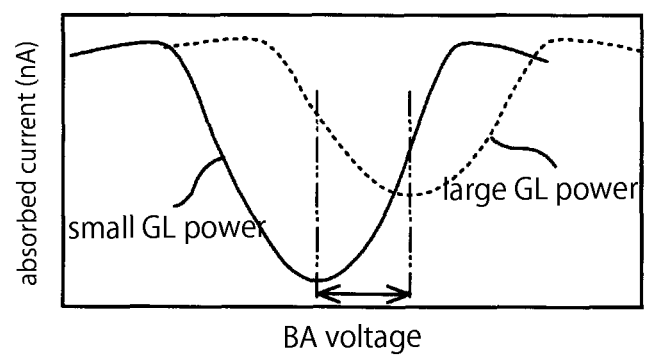

Fig. 218
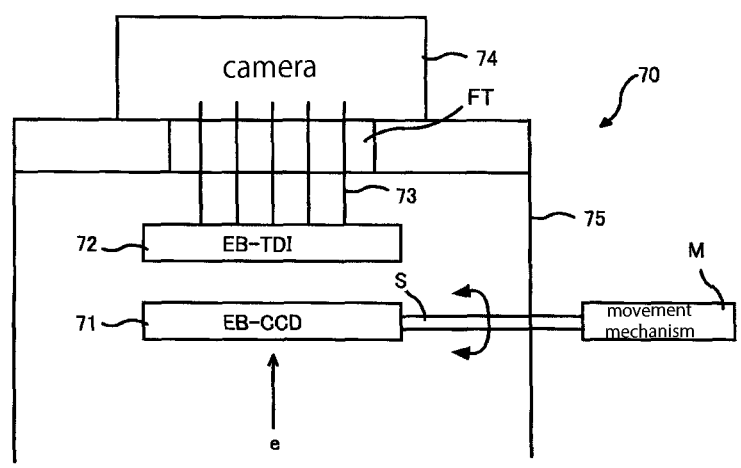
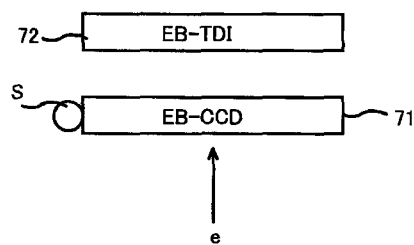
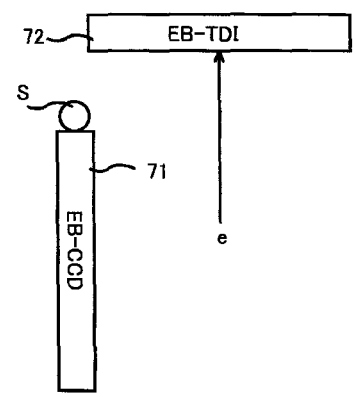

Fig. 219
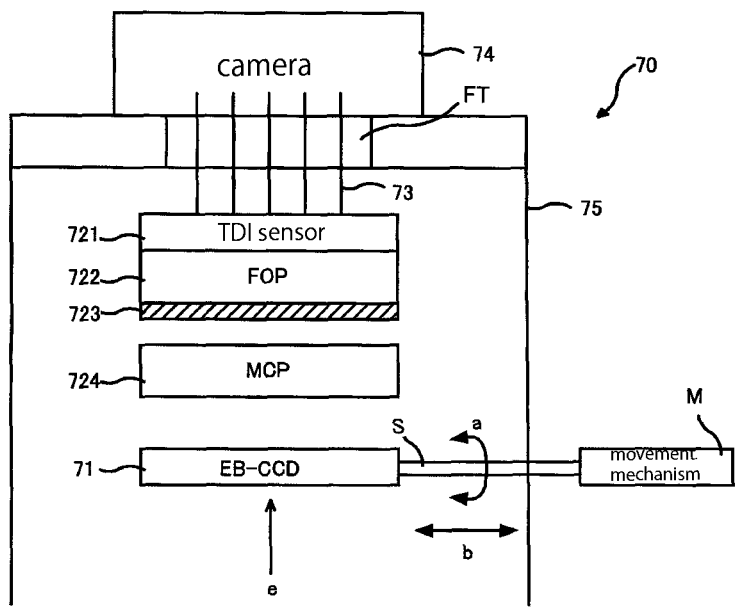
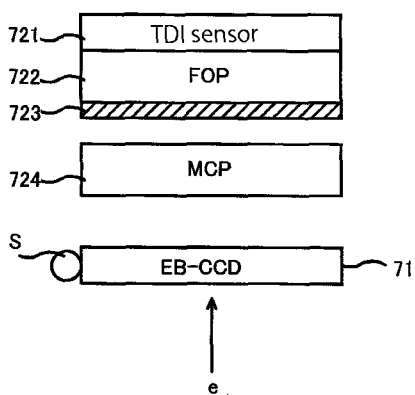
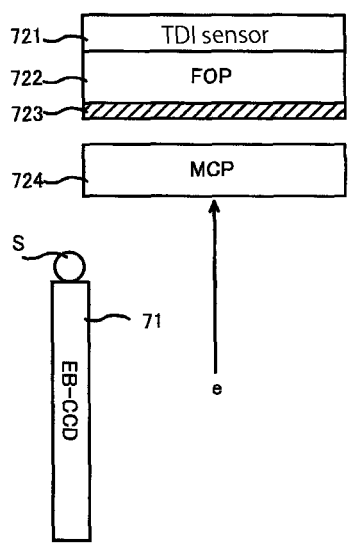

Fig. 220
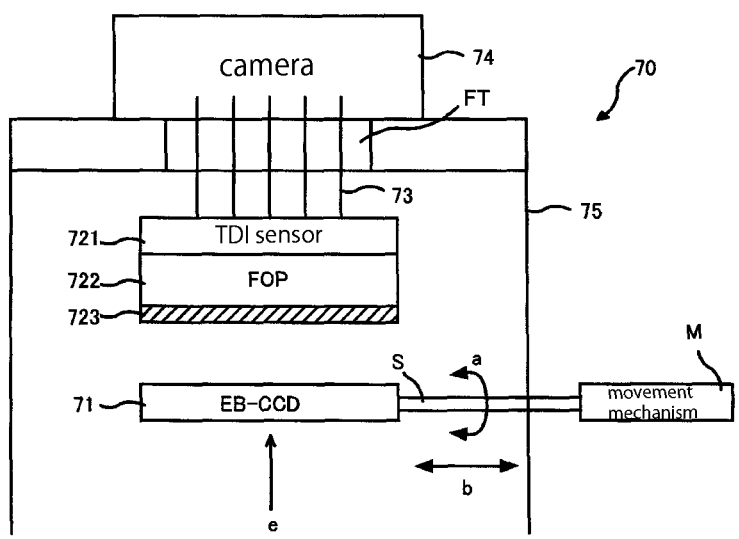
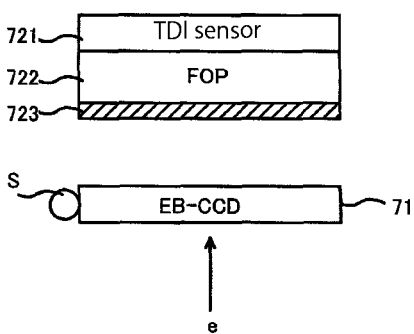
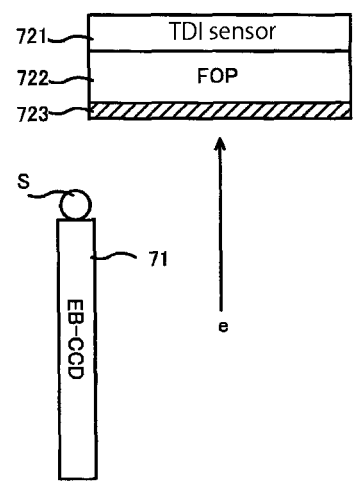

Fig. 221
(a)
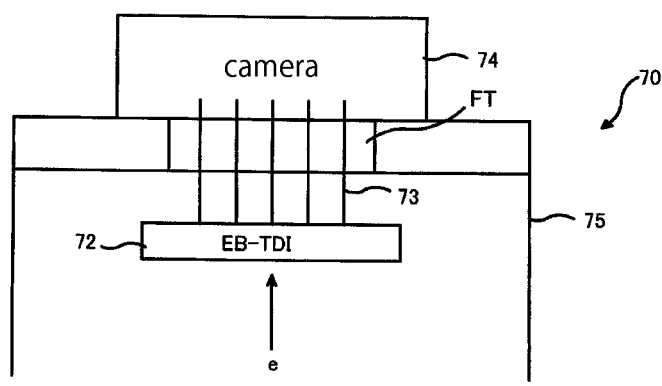
(b)
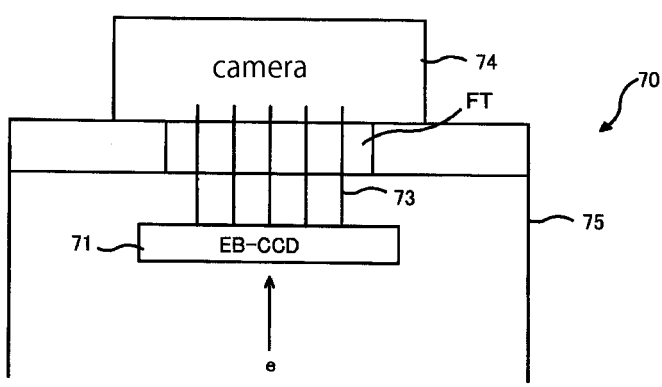

Fig. 222
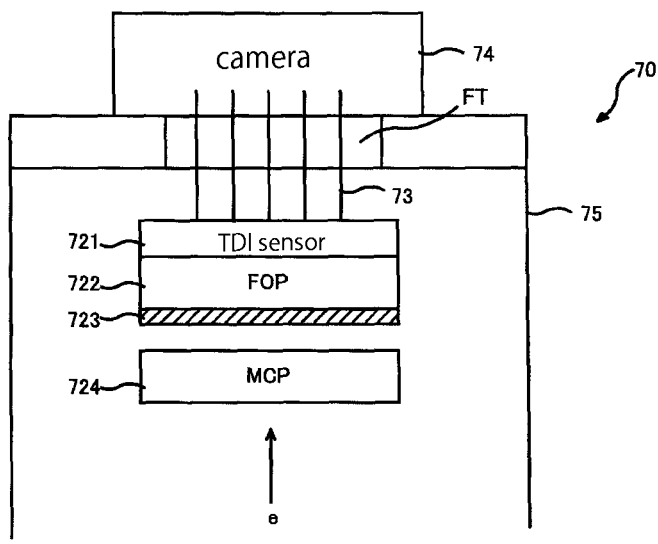
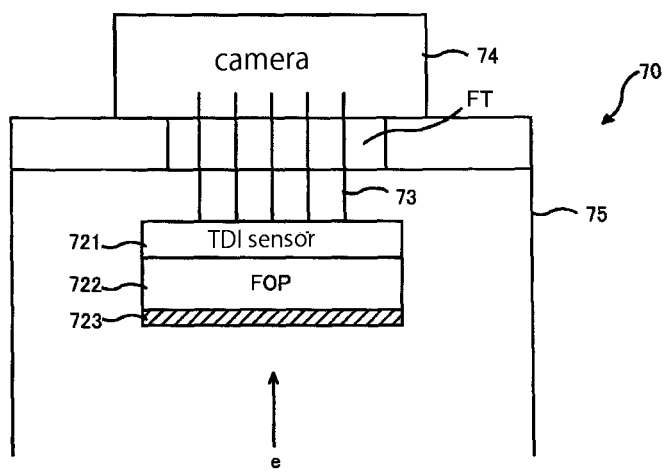

INSPECTION DEVICE

CROSS-REFERENCE TO RELATED APPLICATIONS

This application is based upon and claims the benefit of priority from the prior Japanese Patent Application No. 2012-15875, filed on 27 Jan. 2012, the prior Japanese Patent Application No. 2011-57312, filed on 15 Mar. 2011, and the prior Japanese Patent Application No. 2011-105751, filed on 10 May 2011, the entire contents of which are incorporated herein by reference.

FIELD

The present invention relates to an inspection device and methods for inspecting foreign materials, particles, and/or defects in patterns formed on the surface of an object to be inspected, and more particularly, to an inspection device and inspection method in which secondary electrons which vary in accordance with the properties of the surface are captured thereof to form image data, and inspecting patterns formed on the surface of the object to be inspected based on the image data at a high throughput.

BACKGROUND

Conventional semiconductor inspection devices were compatible with 100 mm design rules. However, samples of the object to be inspected are becoming diversified such as a wafer, exposure mask, EUV mask, NIL (nano imprint lithography) mask and substrate and presently devices and technology which are compatible with sample design rules of 5~30 nm are being demanded. That is, devices and technology in which L/S (line space) or hp (half pitch) node are in the 5~30 nm generation are being demanded. It is necessary to obtain a high resolution capability when inspecting such samples using an inspection device.

Here, a sample can be an exposure mask, an EUV mask, a nano print mask (and template) a semiconductor wafer, an optical element substrate, or optical circuit substrate etc. These are separated into those with patterns and those without patterns. Those that include patterns are further separated into those that have uneven structure and those that do not. A pattern that does not include uneven structure is formed using a different material. Those that do not include patterns are separated into those that are coated with an oxide film and those that are not coated with an oxide film.

Here, the problems associated with inspection devices having conventional technologies are summarized as follows.

The first problem is related to a deficiency in resolution and throughput. In the conventional technology of mapping optical systems pixel size was about 50 nm and aberration was about 200 nm. Further, it was necessary to reduce aberration, reduce the energy width of an irradiation current, reduce pixel size and increase the amount of current in order to improve high resolution capabilities and throughput.

Secondly, in an SEM type inspection, when objects having a fine structure are increasingly inspected the greater the problem of throughput becomes. This is because the image resolution is insufficient if a smaller pixel size is not used. These are the cause of a SEM mainly forming an image due to edge contrast and performing defect inspection. For example, an inspection requires 6 hr/cm$_2$ at 5 nmP×size and 200 MPPS. This would require 20~50 times the amount of time required for a mapping projection type which is unrealistic for an inspection. International Publication WO20002/001596, Japanese Laid Open Patent No. 2007-48686, and Japanese Laid Open Patent H11-132975 are referred to as conventional technology.

SUMMARY

Thus, the present invention aims to provide an inspection method and an inspection device which solves the defects of a conventional inspection device described above, can improve inspection accuracy and can be applied to 5~30 nm design rules.

In addition, according to one embodiment of the present invention, an inspection device for inspecting a surface of an inspection object using a beam is provide including a beam generator which is capable of generating one of either charge particles or an electromagnetic wave as a beam, a primary optical system which is capable of guiding and irradiating the beam to the inspection object supported within a working chamber, a secondary optical system which is capable of including a first movable numerical aperture and a first detector which detects secondary charge particles generated from the inspection object, the secondary charge particles passing through the first movable numerical aperture, an image processing system which is capable of forming an image based on the secondary charge particles detected by the first detector, and a second detector arranged between the first movable numerical aperture and the first detector and which detects a location and shape at a cross over location of the secondary charge particles generated from the inspection object.

The first detector may detect the secondary charge particles in a state where the location of the first movable numerical aperture is adjusted based on a detection result of the second detector.

The beam may be a beam of charged particles, and the beam generator may include a photoelectron element formed by coating a photoelectron material on a planar part of a base material comprised from a transmittance part including the planar part, the photoelectron element receiving light irradiated from the photoelectron material to generate photoelectrons, one or more lenses each arranged at a predetermined intervals after the photoelectron element respectively, the one or more lenses accelerating photoelectrons generated from the photoelectron element, a second numerical aperture arranged on the lower side of the one or more lenses, and a cathode lens arranged after the numerical aperture.

The beam may be an electromagnetic wave beam, the beam generator may generate a plurality of beams with different wavelengths.

The first detector may detect the secondary charge particles generated from a surface of the inspection object irradiated with the beam.

The first detector may detect the secondary charge particles generated from a surface opposite a surface of the inspection object irradiated with the beam.

The first detector may include a TDI.

The second detector may include an EB-CDD.

The first movable numerical aperture may include an open part formed by a plus shape or slit.

The inspection device 1 may further include an optical microscope and a SEM (scanning type electron microscope) which observes the inspection object, wherein the beam generator, the primary optical system, the secondary optical system, the image processing system, the optical microscope and the SEM are arranged in the working chamber.

The secondary charge particles described above may be a part of or a mixture of secondary emission electrons, mirror electrons and photoelectrons. Photoelectrons are generated from a sample surface when an electromagnetic wave is irradiated. Secondary emission electrons are generated when charge particles such an electron beam is irradiated to a sample surface. Alternatively, mirror electrons are formed. Secondary emission electrons are generated when an electron beam collides with a sample surface. That is, secondary emission electrons are a part of or mixture of secondary electrons, reflected electrons and back scattered electrons. In addition, electrons reflected near a surface where an irradiated electron beam does not collide with a sample surface are called mirror electrons.

BRIEF DESCRIPTION OF DRAWINGS

FIG. 28B is a diagram related to one embodiment of the present invention;

FIG. 32B is a diagram related to one embodiment of the present invention;

FIG. 34 is a diagram related to one embodiment of the present invention;

FIG. 47 is a diagram related to one embodiment of the present invention;

FIG. 60 is a diagram related to one embodiment of the present invention;
FIG. 65 is a diagram related to one embodiment of the present invention;
FIG. 74 is a diagram related to one embodiment of the present invention;
FIG. 78 is a diagram related to one embodiment of the present invention;
FIG. 79 is a diagram related to one embodiment of the present invention;
FIG. 80 is a diagram related to one embodiment of the present invention;
FIG. 81 is a diagram related to one embodiment of the present invention;
FIG. 95 is a diagram related to one embodiment of the present invention;
FIG. 97 is a diagram related to one embodiment of the present invention.

FIG. 151B is a diagram related to one embodiment of the present invention;
FIG. 154 is a diagram related to one embodiment of the present invention;
FIG. 157A is a diagram related to one embodiment of the present invention;
FIG. 157B is a diagram related to one embodiment of the present invention.

FIG. 181 is a diagram related to one embodiment of the present invention;

FIG. 182 is a diagram related to one embodiment of the present invention;

FIG. 202 is a diagram related to one embodiment of the present invention;

FIG. 218 is a diagram related to one embodiment of the present invention;

FIG. 219 is a diagram related to one embodiment of the present invention;

FIG. 220 is a diagram related to one embodiment of the present invention;

FIG. 221 is a diagram related to one embodiment of the present invention;

FIG. 222 is a diagram related to one embodiment of the present invention;

DESCRIPTION OF EMBODIMENTS

The embodiments of the present invention will be explained using a substrate formed with a pattern on the surface as an object of inspection, that is, as a semiconductor inspection device for inspecting a wafer while referring to the diagrams. According to the present invention, it is possible to provide an inspection method and an inspection device in which inspection accuracy is improved. Furthermore, the embodiments herein are examples of the inspection device and inspection method of the present invention and are not limited to these examples.

Figure 1:
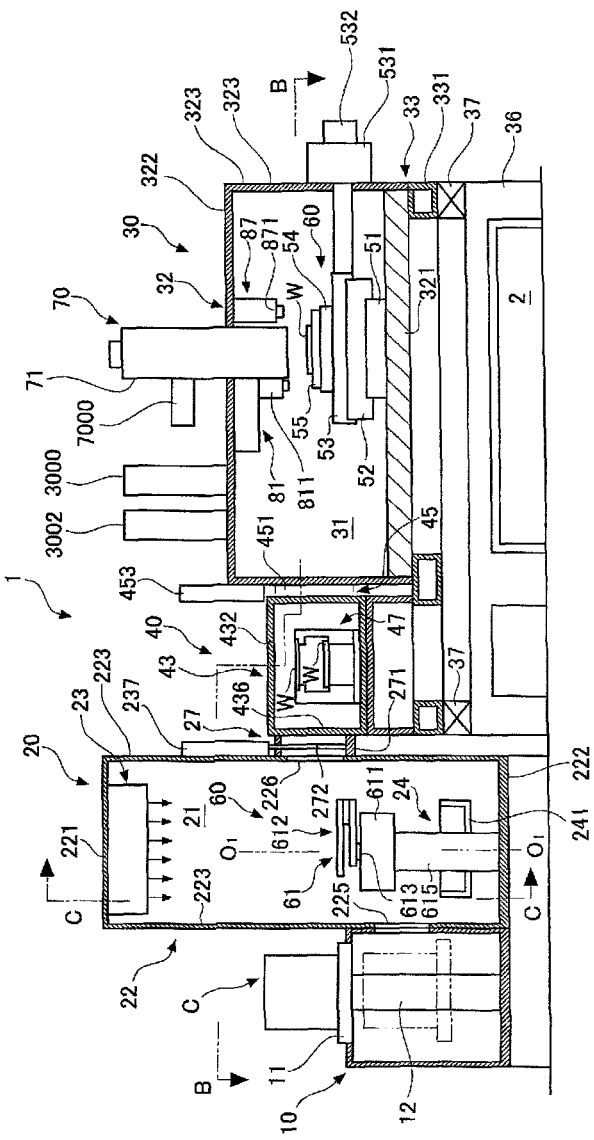
FIG. 1 is an elevated view diagram which shows the main structural elements of an inspection device of the present invention related to one embodiment, seen along the line A-A in FIG. 2.
Figure 2A:
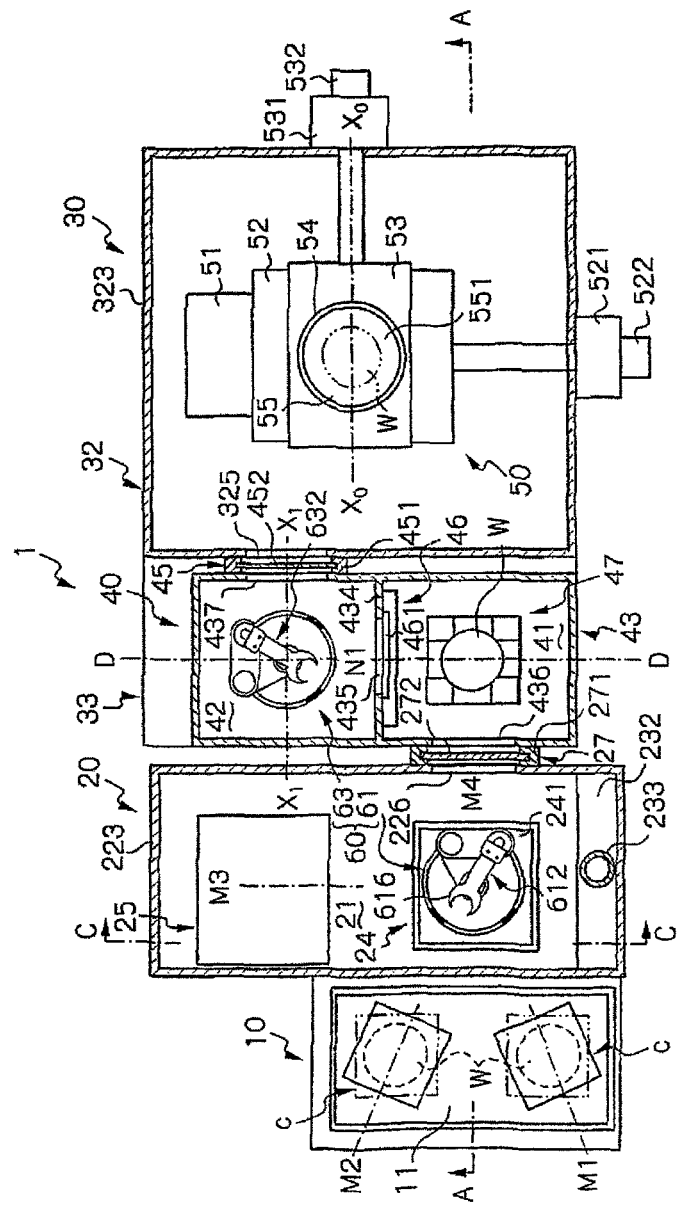
FIG. 2A is a planar view diagram of the main structural elements of the inspection device shown in FIG. 1, seen along the line B-B in FIG. 1.

An elevated view and a planar view of the main structural elements of a semiconductor inspection device 1 of the present embodiment, are shown in FIG. 1 and FIG. 2A.

The semiconductor inspection apparatus 1 of the present embodiment comprises a cassette holder 10 for holding cassettes which store a plurality of wafers; a mini-environment chamber 20; a main housing 30 which defines a working chamber; a loader housing 40 disposed between the mini-environment chamber 20 and the main housing 30 to define two loading chambers; a loader 60 for loading a wafer from the cassette holder 10 onto a stage device 50 disposed in the main housing 30; an electron-optical device 70 installed in a vacuum housing 30; and a scanning type electron microscope (SEM) 3002. These components are arranged in a positional relationship as illustrated in FIGS. 1 and 2A. The semiconductor inspection apparatus 1 further comprises a precharge unit 81 disposed in the vacuum main housing 30; a potential applying mechanism 83 (see in FIG. 14) for applying potential to a wafer; an electron beam calibration mechanism 85 (see in FIG. 15); and an optical microscope 871 which forms part of an alignment controller 87 for aligning the wafer on the stage device 50. The electron-optical device 70 includes a lens column 71 and a light source column 7000. The internal structure of the electron-optical device 70 is described below.

Cassette Holder

The cassette holder 10 is configured to hold a plurality (two in this embodiment) of cassettes c (for example, closed cassettes such as SMIF, FOUP manufactured by Assist Co.) in which a plurality (for example, 25) of wafers are stacked in parallel in the vertical direction. The cassette holder 10 can be arbitrarily selected for installation adapted to a particular loading mechanism. Specifically, when a cassette, carried to the cassette holder 10, is automatically loaded into the cassette holder 10 by a robot or the like, the cassette holder 10 having a structure adapted to the automatic loading can be installed. When a cassette is manually loaded into the cassette holder 10, the cassette holder 10 having an open cassette structure can be installed. In this embodiment, the cassette holder 10 is of a type adapted to the automatic cassette loading, and comprises, for example, an up/down table 11, and an elevating mechanism 12 for moving the up/down table 11 up and down. The cassette c can be automatically set onto the up/down table 11 in a state indicated by chain lines in FIG. 2A. After the setting, the cassette c is automatically rotated to a state indicated by solid lines in FIG. 2A so that it is directed to the axis of pivotal movement of a first carrier unit within the mini-environment chamber 20. In addition, the up/down table 11 is moved down to a state indicated by chain lines in FIG. 1. In this way, the cassette holder 10 for use in automatic loading, or the cassette holder 10 for use in manual loading may be configured in known structures, so that detailed description on their structures and functions are omitted.

Figure 2B:
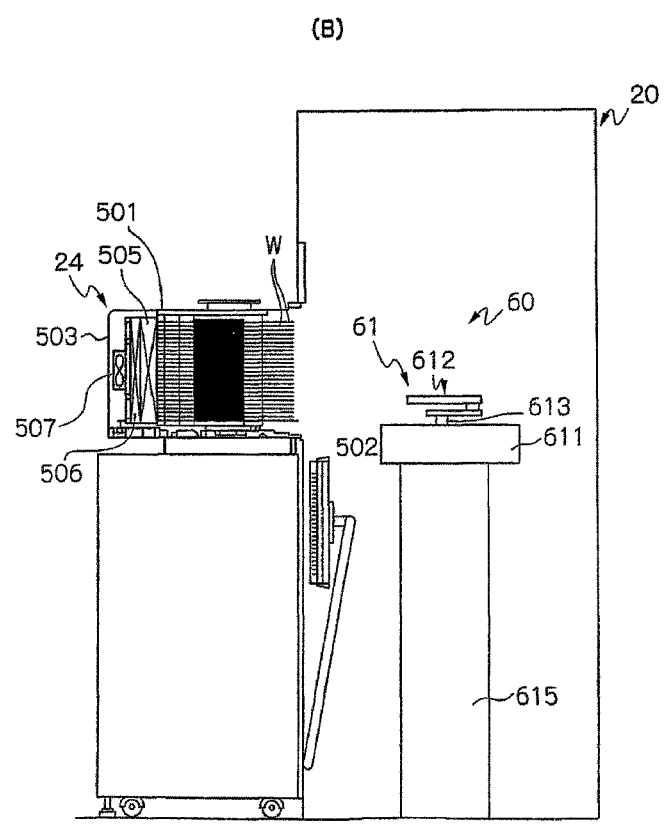
FIG. 2B is an approximate cross-sectional diagram which shows another example of a substrate transfer device in the inspection device of the present invention related to one embodiment.

In another embodiment, as shown in FIG. 2B, a plurality of 300 mm substrates is accommodated so that each is contained in a slot-like pocket fixedly mounted in an inner side of a box main body 501 so as to be transferred and stored. This substrate carrier box 24 is composed of a box main body 501 of cylinder with angular section, a door 502 for carrying the substrate in and out, which is coupled with an automatic opening/closing unit of the door for carrying the substrate in and out so as to be capable of mechanically opening and closing an opening in a side face of the box main body 501, a lid body 503 disposed in an opposite side of said opening, for covering another opening through which filters and a fan motor are to be attached or detached, a slot-like pocket (not shown in the diagram) for holding a substrate W, a ULPA filter 505, a chemical filter 506, and a fan motor 507. In this embodiment, the substrate is carried in or out by a first carrier unit 612 of robot type in a loader 60.

It should be noted that substrates, that is, wafers accommodated in the cassette c are wafers subjected to inspecting which is generally performed after a process for processing the wafers or in the middle of the process within a semiconductor manufacturing processes. Specifically, accommodated in the cassette are substrates or wafers which have undergone a deposition process, CMP, ion implantation and so on; wafers with circuit patterns on the surface thereof; or wafers which have not been formed with circuit patterns. Since a large number of wafers accommodated in the cassette c are spaced from each other in the vertical direction and arranged in parallel, the first carrier unit has an arm which is vertically movable such that a wafer at an arbitrary position can be held by the first carrier unit, as described later in detail.

Mini-Environment Chamber

Figure 3:
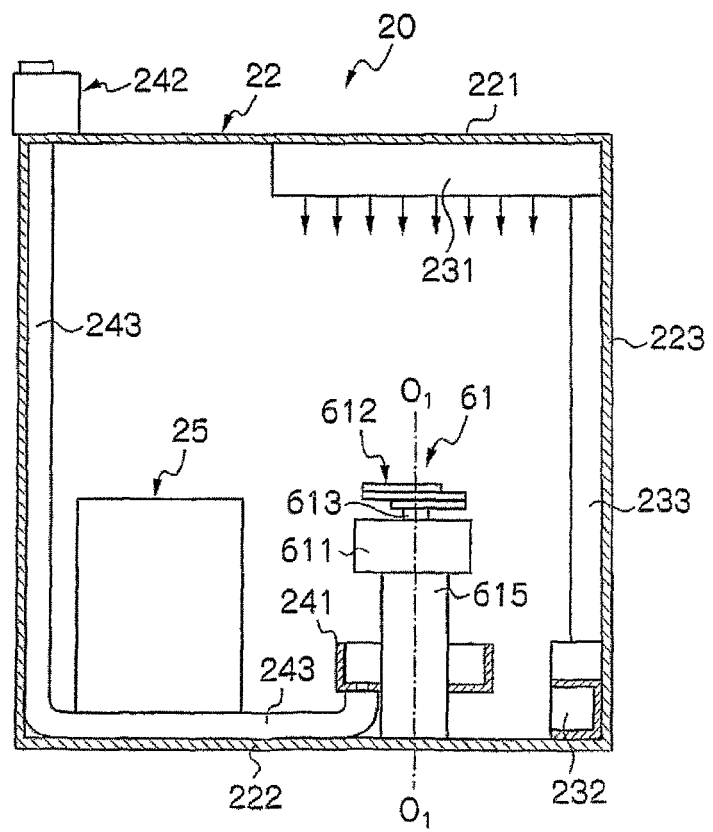
FIG. 3 is a cross-sectional diagram which shows the mini environment in FIG. 1 seen along the line C-C.

In FIG. 1 through 3, the mini-environment chamber 20 comprises a housing 22 which defines a mini-environment space 21 with a controlled atmosphere; a gas circulator 23 for circulating a gas such as clean air within the mini-environment space 21 for the atmosphere control; a discharger 24 for recovering a portion of air supplied into the mini-environment space 21 for discharging; and a prealigner 25 for roughly aligning a substrate, i.e., a wafer to be inspected, which is placed in the mini-environment space 21.

The housing 22 has a top wall 221, a bottom wall 222, and peripheral wall(s) 223 which surrounds four sides of the housing 22 to provide a structure for isolating the mini-environment space 21 from the outside. For controlling the atmosphere in the mini-environment space 21, the gas circulator 23 comprises a gas supply unit 231 attached to the top wall 221 within the mini-environment space 21 as illustrated in FIG. 3 for cleaning a gas (air in this embodiment) and delivering the cleaned gas downward through one or more gas nozzles (not shown in the diagram) in laminar flow; a recovery duct 232 disposed on the bottom wall 222 within the mini-environment space for recovering air which has flowed to the bottom; and a conduit 233 for connecting the recovery duct 232 to the gas supply unit 231 for returning recovered air to the gas supply unit 231. In this embodiment, the gas supply unit 231 constantly replaces about 20% of air to be supplied, with the air taken from the outside of the housing 22 for cleaning. However, the percentage of gas taken from the outside may be arbitrarily selected. The gas supply unit 231 comprises a HEPA or ULPA filter of a known structure for creating cleaned air. The laminar downflow of cleaned air is mainly supplied such that the air passes a carrying surface of the first carrier unit 61, later described, disposed within the mini-environment space 21 to prevent dust particles, which could be produced by the carrier unit, from attaching to the wafer. Therefore, the downflow nozzles need not be positioned near the top wall as illustrated, but are only required to be above the carrying surface of the carrier unit 61. In addition, the air need not be supplied over the entire mini-environment space 21. It should be noted that an ion wind may be used as cleaned air to ensure the cleanliness as the case may be. Also, a sensor may be provided within the mini-environment space 21 for observing the cleanliness such that the apparatus is shut down when the cleanliness is below a predetermined level. An access port 225 is formed in a portion of the peripheral wall 223 of the housing 22 that is adjacent to the cassette holder 10. A shutter device of a known structure may be provided near the access port 225 to shut the access port 225 from the mini-environment chamber 20. The laminar downflow near the wafer may be, for example, at a rate of 0.3 to 0.4 m/sec. The gas supply unit 231 may be disposed outside the mini-environment space 21 instead of within the mini-environment space 21.

The discharger 24 comprises a suction duct 241 disposed at a position below the wafer carrying surface of the carrier unit 61 and below the carrier unit 61; a blower 242 disposed outside the housing 22; and a conduit 243 for connecting the suction duct 241 to the blower 242. The discharger 24 sucks a gas flowing down around the carrier unit and including dust, which could be produced by the carrier unit, through the suction duct 241, and discharges the gas outside the housing 22 through the conduits 243, 244 and the blower 242. In this event, the gas may be discharged into an exhaust pipe (not shown in the diagram) which is laid to the vicinity of the housing 22.

The aligner 25 disposed within the mini-environment space 21 optically or mechanically detects an orientation flat (which refers to a flat portion formed along the outer periphery of a circular wafer) formed on the wafer, or one or more V-shaped notches formed on the outer peripheral edge of the wafer to previously align the orientation of the wafer in a rotating direction about the axis of the wafer at an accuracy of approximately ±one degree. The prealigner forms part of a mechanism for determining the coordinates of an object to be inspected, which is a feature of the claimed invention, and is responsible for rough alignment of an object to be inspected. Since the pre-aligner itself may be of a known structure, description on its structure and operation is omitted.

Though not shown in the diagram, a recovery duct for the discharger 24 may also be provided below the pre-aligner such that air including dust, discharged from the pre-aligner, is discharged to the outside.

Main Housing

In FIGS. 1 and 2, the main housing 30, which defines the working chamber 31, comprises a housing body 32 that is supported by a housing supporting device 33 carried on a vibration isolator 37 disposed on a base frame 36. The housing supporting device 33 comprises a frame structure 331 assembled into a rectangular form. The housing body 32 comprises a bottom wall 321 securely carried on the frame structure 331; a top wall 322; and a peripheral wall 323 which is connected to the bottom wall 321 and the top wall 322 and surrounds four sides of the housing body 32, and isolates the working chamber 31 from the outside. In this embodiment, the bottom wall 321 is made of a relatively thick steel plate to prevent distortion due to the weight of equipment carried thereon such as the stage device 50. Alternatively, another structure may be employed. In this embodiment, the housing body 32 and the housing supporting device 33 are assembled into a rigid construction, and the vibration isolator 37 blocks vibrations from the floor, on which the base frame 36 is installed, from being transmitted to the rigid structure. A portion of the peripheral wall 323 of the housing body 32 that adjoins the loader housing 40, later described, is formed with an access port 325 for introducing and removing a wafer.

The vibration isolator 37 may be either of an active type which has an air spring, a magnetic bearing and so on, or a passive type likewise having these components. Since any known structure may be employed for the vibration isolator 37, description on the structure and functions of the vibration isolator itself is omitted. The working chamber 31 is held in a vacuum atmosphere by a vacuum system (not shown in the diagram) of a known structure. A controller 2 for controlling the operation of the overall apparatus is disposed below the base frame 36.

Loader Housing

Figure 4:
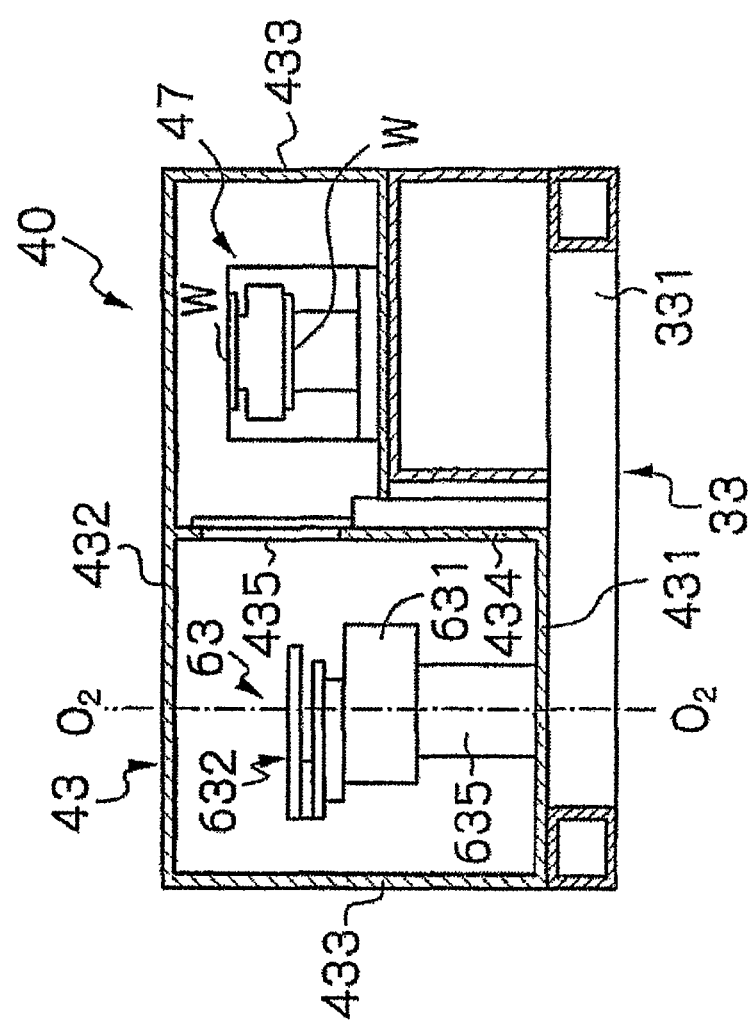
FIG. 4 is a diagram which shows the loader housing in FIG. 1 seen along the line D-D in FIG. 2.

In FIGS. 1, 2 and 4, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 such that both the loading chambers can be isolated from the outside. The partition wall 434 is formed with an opening, i.e., an access port 435 for passing a wafer between both the loading chambers. Also, a portion of the peripheral wall 433 that adjoins the mini-environment device 20 and the main housing 30 is formed with access ports 436, 437. The housing body 43 of the loader housing 40 is carried on and supported by the frame structure 331 of the housing supporting device 33. This prevents vibrations from the floor from being transmitted to the loader housing 40 as well. The access port 436 of the loader housing 40 is in alignment with the access port 226 of the housing 22 of the mini-environment device 20, and a shutter device 27 is provided for selectively blocking communication between the mini-environment space 21 and the first loading chamber 41. The shutter device 27 has a sealing material 271 which surrounds the peripheries of the access ports 226, 436 and is fixed to the side wall 433 in close contact therewith; a door 272 for blocking air from flowing through the access ports in cooperation with the sealing material 271; and a driver 273 for moving the door 272. Likewise, the access port 437 of the loader housing 40 is in alignment with the access port 325 of the housing body 32, and a shutter 45 is provided for selectively blocking communication between the second loading chamber 42 and the working chamber 31 in a hermetic manner. The shutter 45 comprises a sealing material 451 which surrounds the peripheries of the access ports 437, 325 and is fixed to side walls 433, 323 in close contact therewith; a door 452 for blocking air from flowing through the access ports in cooperation with the sealing material 451; and a driver 453 for moving the door 452. Further, the opening 435 formed through the partition wall 434 is provided with a shutter 46 for closing the opening with the door 461 to selectively blocking communication between the first and second loading chambers in a hermetic manner. These shutter devices 27, 45, 46 are configured to provide air-tight sealing for the respective chambers when they are in a closed state. Since these shutter devices may be implemented by known ones, detailed description of their structures and operations is omitted. It should be noted that the method of supporting the housing 22 of the mini-environment device 20 is different from the method of supporting the loader housing 40. Therefore, for preventing vibrations from being transmitted from the floor through the minienvironment device 20 to the loader housing 40 and the main housing 30, a vibration-proof cushion material may be disposed between the housing 22 and the loader housing 40 to provide air-tight sealing for the peripheries of the access ports.

Figure 5:
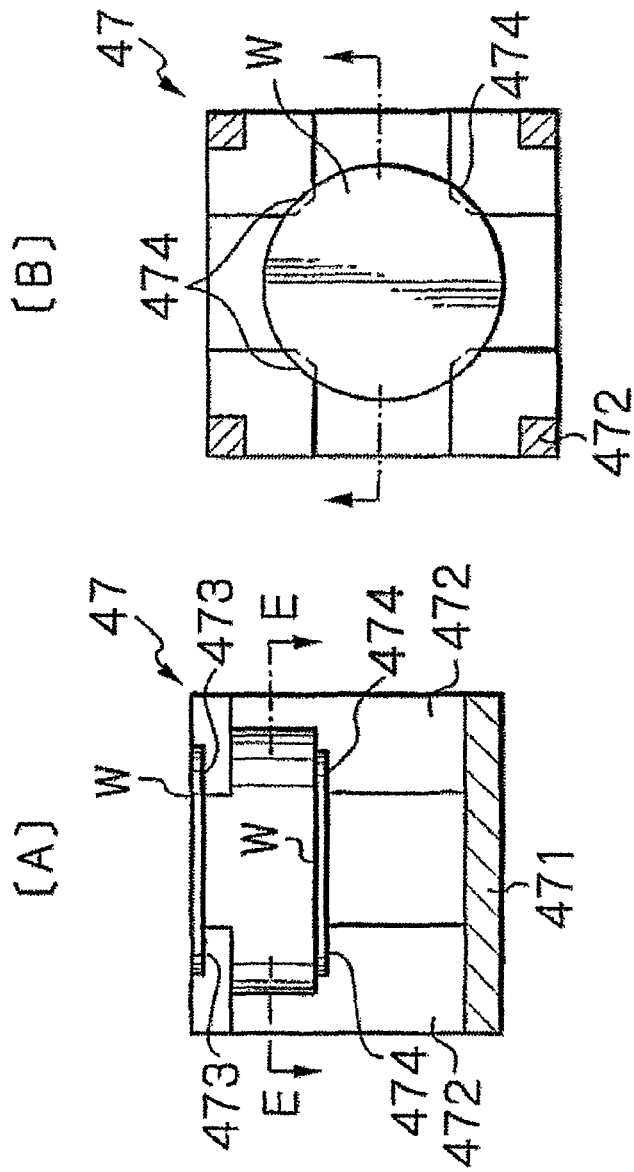
FIG. 5 is an expanded view diagram of a wafer rack, [A] is a side view diagram and [B] is a cross-sectional view diagram seen along the line E-E of [A]

Within the first loading chamber 41, a wafer rack 47 is disposed for supporting a plurality (two in this embodiment) of wafers spaced in the vertical direction and maintained in a horizontal state. As illustrated in FIG. 5, the wafer rack 47 comprises posts 472 fixed at four corners of a rectangular base plate 471, spaced from one another, in an upright state. Each of the posts 472 is formed with supporting portions 473, 474 in two stages, such that peripheral edges of wafers W are carried on and held by these supporting portions. Then, leading ends of arms of the first and second carrier units 61, 63, later described, are brought closer to wafers from adjacent posts and grasp the wafers.

The atmosphere of the loading chambers 41, 42 can be controlled so as to be maintained in a high vacuum state (at a vacuum degree of $10^{-5}$ to $10^{-6}$ Pa) by a vacuum evacuator (not shown in the diagram) in a known structure including a vacuum pump, not shown. In this event, the first loading chamber 41 may be held in a low vacuum atmosphere as a low vacuum chamber, while the second loading chamber 42 may be held in a high vacuum atmosphere as a high vacuum chamber, to effectively prevent contamination of wafers. The employment of such a structure allows a wafer, which is accommodated in the loading chamber and is next subjected to the defect inspection, to be carried into the working chamber without delay. The employment of such a loading chambers provides for an improved throughput for the defect inspection, and the highest possible vacuum state around the electron beam source which is required to be kept in a high vacuum state.

The first and second loading chambers 41, 42 are connected to a vacuum exhaust pipe and a vent pipe for an inert gas (for example, dried pure nitrogen) (neither of which are shown in the diagram), respectively. In this way, the atmospheric state within each loading chamber is attained by an inert gas vent (which injects an inert gas to prevent oxygen and non-inert gases from contacting the surface). Since an apparatus itself for implementing the inert gas vent is known in structure, detailed description thereon is omitted.

Stage Device

The stage device 50 comprises a fixed table 51 disposed on the bottom wall 321 of the main housing 30; a Y-table 52 movable in the Y-direction on the fixed table 51 (the direction vertical to the drawing sheet in FIG. 1); an X-table 53 movable in the X-direction on the Y-table 52 (in the left-to-right direction in FIG. 1); a turntable 54 rotatable on the X-table; and a holder 55 disposed on the turntable 54. A wafer W is releasably held on a wafer carrying surface 551 of the holder 55. The holder 55 may be of a known structure which is capable of releasably holding a wafer by means of a mechanical or electrostatic chuck feature. The stage device 50 uses servo motors, encoders and a variety of sensors (not shown) to operate a plurality of tables as mentioned above to permit highly accurate alignment of a wafer W held on the carrying surface 551 by the holder 55 in the X-direction, Y-direction and Z-direction (in the up-down direction in FIG. 1) with respect to an electron beam irradiated from the electron-optical system 70, and in a direction about the axis normal to the wafer supporting surface (θ direction). The alignment in the Z-direction may be made such that the position on the carrying surface 551 of the holder 55, for example, can be finely adjusted in the Z-direction. In this event, a reference position on the carrying surface 551 is sensed by a position measuring device using a laser of small diameter (a laser interference range finder using the principles of an interferometer) to control the position by a feedback circuit, which is not shown in the diagram. Additionally or alternatively, the position of a notch or the orientation flat of a wafer is measured to sense the plane position and the rotational position of the wafer relative to the electron beam to control the position of the wafer by rotating the turntable 54 by a stepping motor which can be controlled in extremely small angular increments. In order to maximally prevent dust produced within the working chamber, servo motors 521, 531 and encoders 522, 532 for the stage device 50 are disposed outside the main housing 30. Since the stage device 50 may be of a known structure used, for example, in steppers and so on, detailed description of its structure and operation is omitted. Likewise, since the laser interference range finder may also be of a known structure, detailed description of its structure and operation is also omitted.

It is also possible to establish a basis for signals which are generated by previously inputting a rotational position, and X-, Y-positions of a wafer relative to the electron beam in a signal detecting system or an image processing system, later described. The wafer chucking mechanism provided in the holder 55 is configured to apply a voltage for chucking a wafer to an electrode of an electrostatic chuck, and the alignment is made by holding three points on the outer periphery of the wafer (preferably spaced equally in the circumferential direction). The wafer chucking mechanism comprises two fixed aligning pins and a push-type clamp pin. The clamp pin can realize automatic chucking and automatic releasing, and constitutes an electric conducting portion for applying the voltage.

While in this embodiment, the X-table is defined as a table which is movable in the left-to-right or right-to-left direction in FIG. 2; and the Y-table as a table which is movable in the up-down direction, a table movable in the left-to-right or right-to-left direction in FIG. 2 may also be defined as the Y-table; and a table movable in the up-down direction as the X-table.

Loader

The loader 60 comprises a robot-type first carrier unit 61 disposed within the housing 22 of the mini-environment device 20; and a robot-type second carrier unit 63 disposed within the second loading chamber 42.

The first carrier unit 61 comprises an articulated arm 612 rotatable about an axis $O_1$-$O_1$ with respect to a driver 611. While an arbitrary structure may be used for the articulated arm, the articulated arm in this embodiment has three parts which are pivotably attached to each other. One part of the arm 612 of the first carrier unit 61, i.e., the first part closest to the driver 611 is attached to a rotatable shaft 613 by a driving mechanism (not shown in the diagram) of a known structure, disposed within the driver 611. The arm 612 is pivotable about the axis $O_1$-$O_1$ by means of the shaft 613, and radially telescopic as a whole with respect to the axis $O_1$-$O_1$ through relative rotations among the parts. At a leading end of the third part of the arm 612 furthest away from the shaft 613, a clamp 616 in a known structure for clamping a wafer, such as a mechanical chuck or an electrostatic chuck, is disposed. The driver 611 is movable in the vertical direction by an elevating mechanism 615 is of a known structure.

The first carrier unit 61 extends the arm 612 in either a direction MI or a direction M2 within two cassettes c held in the cassette holder 10, and removes a wafer accommodated in a cassette c by carrying the wafer on the arm or by clamping the wafer with the chuck (not shown in the diagram) attached at the leading end of the arm. Subsequently, the arm is retracted (in a state as illustrated in FIG. 2), and then rotated to a position at which the arm can extend in a direction M3 toward the pre-aligner 25, and stopped at this position. Then, the arm is extended to transfer the wafer held on the arm to the pre-aligner 25. After receiving a wafer from the pre-aligner 25, contrary to the foregoing, the arm is further rotated and stopped at a position at which it can extend to the second loading chamber 41 (in the direction M4), and transfers the wafer to a wafer receiver 47 within the second loading chamber 41. For mechanically clamping a wafer, the wafer should be clamped at a peripheral region (in a range of approximately 5 mm from the peripheral edge). This is because the wafer is formed with devices (circuit pattern) over the entire surface except for the peripheral region, and clamping the inner region would result in failed or defective devices.

The second carrier unit 63 is basically identical to the first carrier unit 61 in structure except that the second carrier unit 63 carries a wafer between the wafer rack 47 and the carrying surface of the stage device 50, so that detailed description thereon is omitted.

In the loader 60, the first and second carrier units 61, 63 carry a wafer from a cassette held in the cassette holder 10 to the stage device 50 disposed in the working chamber 31 and vice versa, while keeping the wafer substantially in a horizontal state. The arms of the carrier units are moved in the vertical direction only when a wafer is removed from and inserted into a cassette, when a wafer is carried on and removed from the wafer rack, and when a wafer is carried on and removed from the stage device 50. It is therefore possible to smoothly carry a wafer even if it is a large one, for example, a wafer having a diameter of 30 cm.

Transfer of Wafer

Next, the transfer of a wafer in the apparatus will be described in sequence from the cassette c held by the cassette holder 10 to the stage device 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette c is set on the up/down table 11 of the cassette holder 10, the up/down table 11 is moved down by the elevating mechanism 12 to align the cassette c with the access port 225.

As the cassette is aligned with the access port 225, a cover (not shown in the diagram) provided for the cassette is opened, and a cylindrical cover is applied between the cassette c and the access port 225 of the mini-environment to block the cassette and the mini-environment space 21 from the outside. Since these structures are known, detailed description of their structures and operations is omitted. When the minienvironment device 20 is provided with a shutter for opening and closing the access port 225, the shutter is operated to open the access port 225.

On the other hand, the arm 612 of the first carrier unit 61 remains oriented in either the direction M1 or M2 (in the direction M2 in this description). As the access port 225 is opened, the arm 612 extends to receive one of the wafers accommodated in the cassette at the leading end. While the arm and a wafer to be removed from the cassette are adjusted in the vertical position by moving up or down the driver 611 and the arm 612 of the first carrier unit 61 in this embodiment, the adjustment may be made by moving the up/down table 11 of the cassette holder 10, or made by both.

As the arm 612 receives the wafer, the arm 612 is retracted, and the shutter is operated to close the access port (when the shutter is provided). Next, the arm 612 is pivoted about the axis $O_1$-$O_1$ such that it can extend in the direction M3. Then, the arm 612 is extended and transfers the wafer carried at the leading end or clamped by the chuck onto the pre-aligner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the prealigner 25 to the leading end of the arm 612, and rotates the arm 612 to a position in which the arm 612 can be extended in a direction M4. Then, the door 272 of the shutter device 27 is moved to open the access ports 226, 436, and the arm 612 is extended to place the wafer on the upper stage or the lower stage of the wafer rack 47 within the first loading chamber 41. It should be noted that before the shutter device 27 opens the access ports 226, 436 to transfer the wafer to the wafer rack 47, the opening 435 formed through the partition wall 434 is closed by the door 461 of the shutter 46 in an air-tight state.

In the process of carrying a wafer by the first carrier unit, clean air flows (as downflow) in laminar flow from the gas supply unit 231 disposed on the housing of the minienvironment device to prevent dust from attaching to the upper surface of the wafer while being carried. A portion of the air near the carrier unit (in this embodiment, about 20% of the air supplied from the supply unit 231, which is substantially contaminated air) is sucked from the suction duct 241 of the discharger 24 and discharged outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the shutter device 27 is closed to seal the loading chamber 41. Then, the first loading chamber 41 is filled with an inert gas to expel air. Subsequently, the inert gas is also discharged so that a vacuum atmosphere dominates within the loading chamber 41. The vacuum atmosphere within the loading chamber 41 may be at a low vacuum degree. When a certain degree of vacuum is formed within the loading chamber 41, the shutter 46 is operated to open the access port 434 which has been sealed by the door 461, and the arm 632 of the second carrier unit 63 is extended to receive one wafer from the wafer receiver 47 with the clamp at the leading end (the wafer is carried on the leading end or clamped by the chuck attached to the leading end). Upon completion of the receipt of the wafer, the arm 632 is retracted, followed by the shutter 46 again operated to close the access port 435 by the door 461. It should be noted that the arm 632 previously takes a posture in which it can extend in the direction NI of the wafer rack 47 before the shutter 46 is operated to open the access port 435. Also, as described above, the access ports 437, 325 are closed by the door 452 of the shutter 45 before the shutter 46 is opened to block communication between the second loading chamber 42 and the working chamber 31 in an air-tight state, so that the second loading chamber 42 can be evacuated.

As the shutter 46 is operated to close the access port 435, the second loading chamber 42 is again evacuated at a higher degree of vacuum than the first loading chamber 41. Meanwhile, the arm 632 of the second carrier unit 63 is rotated to a position from which it can extend toward the stage device 50 within the working chamber 31. On the other hand, in the stage device 50 within the working chamber 31, the Y-table 52 is moved upward, as viewed in FIG. 2, to a position at which the center line $X_0$-$X_0$ of the X-table 53 substantially aligns with an X-axis $X_1$-$X_1$ which passes a pivotal axis $O_2$-$O_2$ of the second carrier unit 63. The X-table 53 in turn is moved to the position closest to the leftmost position in FIG. 2, and remains at this position. When the second loading chamber 42 is evacuated to substantially the same degree of vacuum as the working chamber 31, the door 452 of the shutter 45 is moved to open the access ports 437, 325, allowing the arm 632 to extend so that the leading end of the arm 632, which holds a wafer, approaches the stage device 50 within the working chamber 31. Then, the wafer is placed on the carrying surface 551 of the stage device 50. As the wafer has been placed on the carrying surface 551, the arm 632 is retracted, followed by the shutter 45 operated to close the access ports 437, 325.

The description above explained the operations in which a wafer in the cassette c is carried and placed on the stage device 50. For returning a wafer, which has been carried on the stage device 50 and processed, from the stage device 50 to the cassette c, the operation reverse to the above description is performed. Since a plurality of wafers are stored in the wafer rack 47, the first carrier unit 61 can carry a wafer between the cassette and the wafer rack 47 while the second carrier unit 63 can carry a wafer between the wafer rack 47 and the stage device 50, so that the inspecting operation can be efficiently carried out.

Specifically, when there is a wafer A, which has been already been processed, and a wafer B, which has not yet been processed, in a wafer rack 47 of a second carrier unit, (1) first, the wafer B which has not yet been processed is transferred to the stage 50 and the processing is started;
(2) during this processing, the wafer A which has already been processed is transferred from the stage 50 to the wafer rack 47 by an arm, a wafer C which has not yet been processed is picked up from the wafer rack again by the arm, which after having been positioned by a pre-aligner, is further transferred to the wafer rack 47 of a loading chamber 41.

This procedure may allow the wafer A, which has already been processed, to be substituted by the wafer C, which has not yet been processed, in the wafer rack 47, during processing of wafer B.

Alternatively, depending on how such an apparatus executes an inspection and/or an evaluation, a plurality of stage units 50 may be arranged in parallel, and in this case, wafers are transferred from one wafer rack 47 for each of the stage units 50, thereby providing simultaneous processing of a plurality of wafers.

Figure 6:
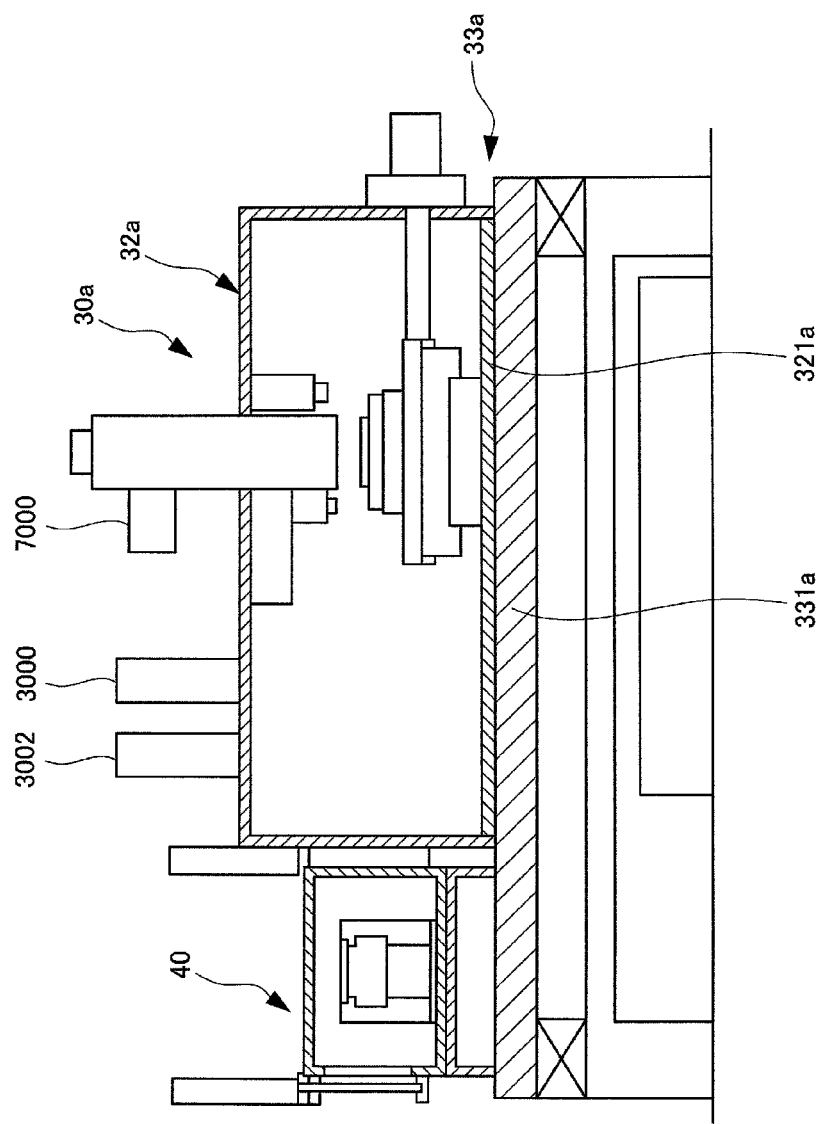
FIG. 6 is a diagram which shows modifications of a method for supporting a main housing.

FIG. 6 illustrates typical modifications to the method of supporting the main housing 30. In a typical modification illustrated in FIG. 6, a housing supporting device 33*a* is made of a thick rectangular steel plate 331*a*, and a housing body 32*a* is carried on the steel plate. Therefore, the bottom wall 321*a* of the housing body 32*a* is thinner than the bottom wall 222 of the housing body 32 in the foregoing embodiment. In a typical modification illustrated in FIG. 7, a housing body 32*b* and a loader housing 40*b* are suspended from a frame structure 336*b* of a housing supporting device 33*b*. Lower ends of a plurality of vertical frames 337*b* fixed to the frame structure 336*b* are fixed to four corners of a bottom wall 321*b* of the housing body 32*b*, such that the peripheral wall and the top wall are supported by the bottom wall. Then, a vibration isolator 37*b* is disposed between the frame structure 336*b* and a base frame 36*b*. Likewise, the loader housing 40*b* is suspended by a suspending member 49*b* fixed to the frame structure 336. In the typical modification of the housing body 32*b* illustrated in FIG. 7, the housing body 32*b* is supported in suspension, the center of gravity of the main housing and a variety of devices disposed therein, as a whole, can be brought downward. The methods of supporting the main housing and the loader housing, including the typical modifications described above, are configured to prevent vibrations from being transmitted from the floor to the main housing and the loader housing.

In another typical modification, not shown in the diagram, only the housing body of the main housing is supported by the housing supporting device from below, while the loader housing may be placed on the floor in the same way as the adjacent mini-environment device. Alternatively, in a further typical modification, not shown in the diagram, only the housing body of the main housing is supported by suspension from the frame structure while the loader housing may be placed on the floor in the same way as the adjacent mini-environment device.

According to the embodiment described above, the following advantages are provided:

(A) the general configuration can be established for an inspection apparatus in accordance with an electron beam based projection scheme, which can process objects under inspection at a high throughput;
(B) a clean gas is forced to flow onto an object to be inspected within the mini-environment space to prevent dust from attaching to the object to be inspected, and a sensor is provided for observing the cleanliness, thereby making it possible to inspect the object to be inspected while monitoring dust within the space;
(C) when the loading chamber and the working chamber are integrally supported through a vibration isolator, an object to be inspected can be carried to the stage device and inspected thereon without being affected by the external environment.

Electron-Optical-System

The electron-optical system 70 comprises a column 71 fixed on the housing body 32. Disposed within the column 71 are an optical system comprised of a primary light source optical system (hereinafter simply called the "primary optical system") 72 and a secondary electron optical system (hereinafter simply called the "secondary optical system") 74, and a detecting system 76, as illustrated generally in FIG. 8. The primary optical system 72, which is an optical system for irradiating the surface of a wafer W to be inspected with an electron beam, comprises a light source 10000 (beam generator) for emitting an electron beam; and a mirror 10001 for changing the angle of the light beam. In this embodiment, the optical axis of a light beam 10000A emitted from the light source 10000 is oblique to the optical axis of irradiation along which the wafer W to be inspected is irradiated with the photoelectron beam (perpendicular to the surface of the wafer).

The detecting system 76 comprises a detector 761 and an image processing unit 763 which are disposed on a focal plane of the lens system 741.

Light Source (Light Beam Source)

In the present embodiment a DUV laser beam source is used in the light source 10000. The DUV laser beam is emitted from the DUV laser beam source 10000. Further, other beam sources (beam generator) may be used if a photoelectron is emitted from a substrate which is irradiated with a light from a light source 10000 such as UV, DUV, EUV light and laser, and X ray and X ray laser etc.

Primary Optical System

A section for forming a light beam irradiated from the light source 10000 and irradiating the light beam against a wafer W surface, which forms a rectangle or circle (ellipse) on said wafer W surface, said section is called the primary optical system. The light beam irradiated from the light source 10000 is irradiated as a primary light beam on a wafer WF on the stage device 50 after passing through the lens optical system 724.

Secondary Optical System

A two-dimensional secondary electron (photoelectron) image generated by a light beam or laser beam irradiated onto a wafer W is formed into an image by passing through a hole formed on the mirror 10001, passing through a numerical aperture 10008 by electrostatic lenses (Transfer Lenses) 10006 and 10009 formed on a location of field stop and magnified and projected by a subsequent stage of lens 741. Said image-forming and projecting optical system is called the secondary optical system 74.

At that time, a negative bias voltage is applied to the wafer. The photoelectrons generated from the sample surface by the potential difference between the electrostatic lenses 724 (lens 724-1 and 724-2) are accelerated which effectively reduces chromatic aberration. The extraction field in this lens optical system 724 is 3 kV/mm~10 kV/mm which is a high electric field. The relationship where aberration is effectively decreased and resolution is improved is caused by increasing the extraction field. However, when the extraction field is increased, voltage gradient increases and discharge occurs easily. Therefore, it is important that the extraction field is used by selecting an appropriate value. Electrons which are magnified by a certain magnification by the lenses 724 (CL) are converged by the lens (TL1) 10006, and a cross over (CO) is formed on the numerical aperture 10008 (NA). In addition, it is possible to zoom the magnification by a combination of lens (TL1) 10006 and lens (TL2) 10009. Following this, an image is magnified and projected by lens (PL) 741 in an MCP (Micro Channel Plate) in the detector 761. The present optical system is formed by disposing an NA between TL1-TL2 and further optimization of this optical system can reduce off-axis aberrations.

Detector

An electron image from the wafer, which is formed into an image by the secondary optical system, is primarily amplified in the micro-channel plate (MCP) and then impinges against a fluorescent screen to be converted into an optical image. As for the principle of the MCP, millions of very thin glass capillaries made of conductive material, each having a diameter of 6 to 25 μm and a length of 0.24 to 1.0 mm, are bundled and formed into a thin plate, and application of a specified voltage makes each of the capillaries work as an individual electron amplifier so as to form the electron amplifier as a whole.

The image that has been converted into the light by said detector is projected on the TDI (Time Delay Integration)-CCD (Charge Coupled Device) by the FOP (Fiber Optical Plate) system disposed in the atmosphere through a vacuum permeable window on a one-to-one basis. In addition, as an alternative method, the FOP coated with a fluorescent material connects with the surface of the TDI sensor and an electron/light converted signal in the vacuum is introduced to the TDI sensor. This method has greater transmittance and MTF (Modulation Transfer function) efficiency than when places in an atmosphere. For example, a high value of ×5~×10 can be obtained in transmittance and MTF. At this time, as described above, MCP+TDI is sometimes used as a detector. However, EB (Electron Bombardment)-TDI or EB-CCD may also be used instead. When EB-TDI is used, because photoelectrons generated form the sample surface and which form a two dimensional image are directly irradiated into the EB-TDI sensor surface, an image signal can be formed without deterioration in resolution. For example, when MCP+TDI is used, after electrons are amplified by the MCP they are converted to light by a fluorescent material or scintillator are this light image data is delivered to the TDI sensor. In contrast to this, in an EB-TDI, EB-CDD sensor, a signal is delivered to the sensor without image deterioration because there is no transmitted part or loss in electron light conversion and light amplification data. For example, MTF or contrast becomes ½~⅓ when MCP+TDI is used compared to when EB-TDI or EB-CDD is used.

Furthermore, in the present embodiment, the lens system 724 is applied with a high voltage of 10 to 50 kV and a wafer W is disposed.

Figure 9:
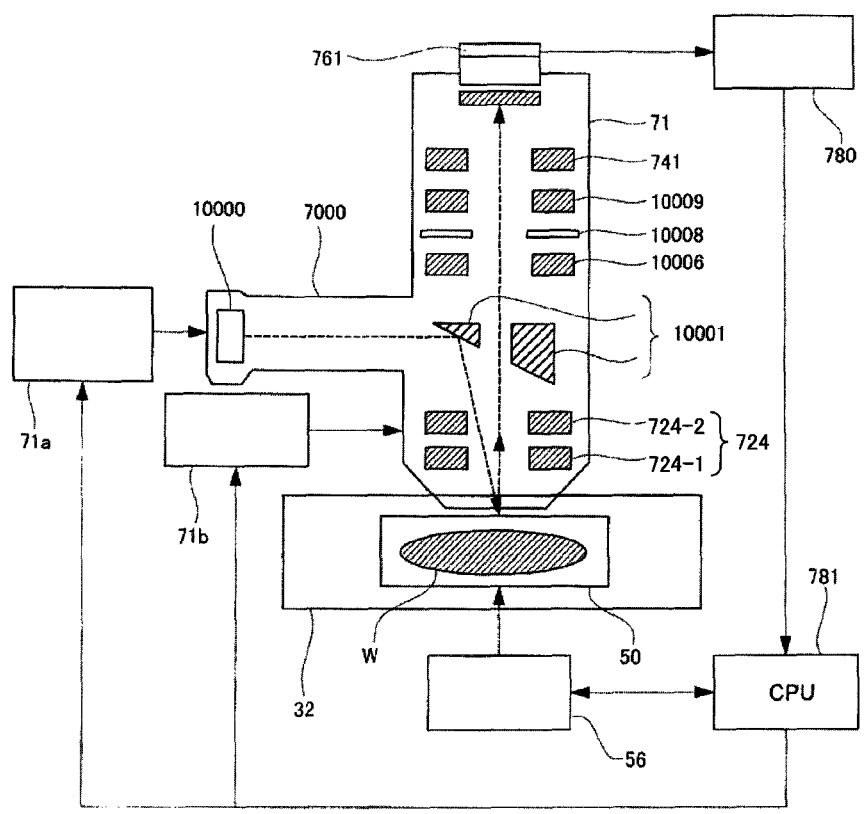
FIG. 9 is a diagram related to one embodiment of the present invention.

Description of the Relationship Among Main Functions in the Projecting Method and its General View A schematic general view of an inspection device according to the present invention is shown in FIG. 9. However, some components are omitted for illustration.

In FIG. 9, the inspection device has a lens column 71, a light source column 7000 and a chamber 32. A light source 10000 is arranged on the inside of the light source column 7000, and a primary optical system 72 is disposed along the optical axis of a light beam (a primary light beam) irradiated from the light source 10000. Further, a stage 50 is installed in the interior of the chamber 32 and a wafer W is loaded on the stage 50.

On the other hand, in the interior of the lens column 71, a cathode lens 724 (724-1 and 724-2), transfer lenses 10006 and 10009, a numerical aperture (NA) 10008, a lens 741, and a detector 761 are located on the optical axis of the secondary electron beam emanating from the wafer W. It is to be noted that the numerical aperture (NA) 10008 corresponds to an aperture diaphragm, which is a thin plate made of metal (Mo or the like) having a circular aperture formed therein.

On the other hand, the output from the detector 761 is input into a control unit 780, and the output from the control unit 780 is input into a CPU 781. A control signal from the CPU 781 is input into a light source control unit 71a, a lens column control unit 71b and a stage driving mechanism 56. The light source control unit 71a controls the power supply of the light source 10000, and the lens column control unit 71b controls lens voltages in the cathode lens 724, the lenses 10006 and 10009 and the lens 741 and also a voltage (amount of deviation) of an aligner (not shown in the diagram).

Further, the stage driving mechanism 56 transmits position data of the stage to the CPU 781. Still further, the light source column 7000, lens column 71, and the chamber 32 are connected to the vacuum exhausting system (not shown in the diagram) and exhausted by a turbo pump in the vacuum exhausting system so as to maintain the interior thereof in a vacuum. In addition, a roughing vacuum exhaust device system formed from a usual dry pump or rotary pump is disposed on the downstream of the turbo pump.

When the primary light beam is irradiated onto the sample, photoelectrons are generated as a secondary beam from the light beam irradiated surface of the wafer W.

The secondary beam is led to the detector via the TL lens group 10006 and 10009 and the lens (PL) 741 thereby to form an image.

The cathode lens 724 is formed by three electrodes. Among those electrodes, the one at the lowest position is designed to form a positive electric field between the potentials in the sample W side and itself, and to take in electrons (particularly, secondary electrons with smaller directivities) so that the electrons may be efficiently introduced into the lens. As a result, the cathode lenses are effective when they become telecentric. The secondary beam which forms an image via the cathode lens passed through a hole of the mirror 10001.

If the secondary beam is formed into an image only by one stage of the cathode lens 724, the lens effect may be great and an aberration is more likely to occur. Accordingly, the cathode lens 724 may be combined with a second lens to perform first image forming. In this case, an intermediate image forming position is between the lens (TL1) 10006 and the cathode lens 724. In addition, at this time, by making the lenses telecentric it is extremely effective for reducing aberration as described above. The secondary beam is converged on the numerical aperture (NA) 10008 via the cathode lens 724 and lens (TL1), lens 10008 and a cross over is formed. An image is first formed between the lens 724 and lens (TL1) 10006, then an intermediate magnification is determined by the lens (TL1) 10006 and lens (TL2) 10009 and an image is formed on the detector 761 after magnification by the lens (PL). In other words, an image is formed a total of 3 times in this example.

In addition, each of the lenses 10006, 10009, and lens 714 should be a lens symmetrical with respect to a rotating axis of the kind referred to as a uni-potential lens or Einzell lens. Each lens is composed of three electrodes, in which typically the outer two electrodes have zero potentials and a voltage applied to the center electrode is used to cause a controlling lens effect. Further, not limited to this lens structure, a structure having a focus adjustment electrode on the first stage, second stage or both stages of the lens 724, or a fourth or fifth dynamic focus adjustment electrode may be disposed. Also, a field lens function may be added to the PL lens 741 and it is effective to add a fourth or fifth electrode for reducing off-axis aberrations and increased magnification.

The secondary beam is magnified and projected by the secondary optical system and formed into an image on the detection plane of the detector 761. The detector 761 comprises a MCP for amplifying an electron, a fluorescent screen for converting the electrons into light, lenses and other optical elements for use as a relay and transmitting an optical image between the vacuum system and external components, and an image sensor (CCD or the like). The secondary beam is formed into an image on the MCP detection plane and amplified, and then the electrons are converted into light signals by the fluorescent screen, which are in turn converted into photoelectric signals by the image sensor.

The control unit 780 reads out the image signal of the wafer W from the detector 761 and transmits it to the CPU 781. The CPU 781 performs a defect inspection of the pattern by template matching and so forth from the image signal. In addition, the stage 50 is adapted to be movable in the X and Y directions by a stage driving mechanism 56. The CPU 781 reads the position of the stage 50 and outputs a drive control signal to the stage driving mechanism 56 to drive the stage 50, allowing for sequential detection and inspection of the images.

In addition, even if the setting magnification of the lens conditions of lens 10006 and 10009 are changed, a uniform image over the field of view can be obtained in the detection side. Further, although an even and uniform image can be obtained in the present embodiment, typically, increasing the magnification may problematically cause deterioration in the brightness of the image. Accordingly, in order to improve this problematic condition, when the lens condition for the secondary optical system is changed to vary the magnification factor, the lens condition for the primary optical system should be set such that the amount of electrons discharged per unit pixel be constant.

Precharge Unit

The precharge unit 81, as illustrated in FIG. 1, is disposed adjacent to the lens column 71 of the electron-optical system 70 within the working chamber 31. Since this inspection apparatus is configured to inspect device patterns or the like formed on the surface of a substrate or wafer to be inspected by irradiating the wafer with an electron beam, so that the photoelectrons generated by the irradiation of the light beam are used as information on the surface of the wafer. However, the surface of the wafer may be charged up depending on conditions such as the wafer material, the wavelength or energy of the irradiated light or laser beam, and so on. Further, on the surface of a wafer, some regions may be highly charged, while other regions may be lightly charged. Variations in the amount of charge on the surface of the wafer cause corresponding variations in information provided by the resulting photoelectrons, thereby failing to provide correct information. For preventing such variations, in this embodiment, the precharge unit 81 is provided with a charged particle irradiating unit 811. Before electrons for inspection are irradiated to a predetermined region on a wafer to be inspected, charged particles are irradiated from the charged particle irradiating unit 811 of the precharge unit 81 to eliminate variations in charge. The charges on the surface of the wafer may be detected by previously forming an image of the surface of the wafer to be inspected, and by evaluating the image, and the precharge unit 81 can be operated based on such detection.

Figure 10:
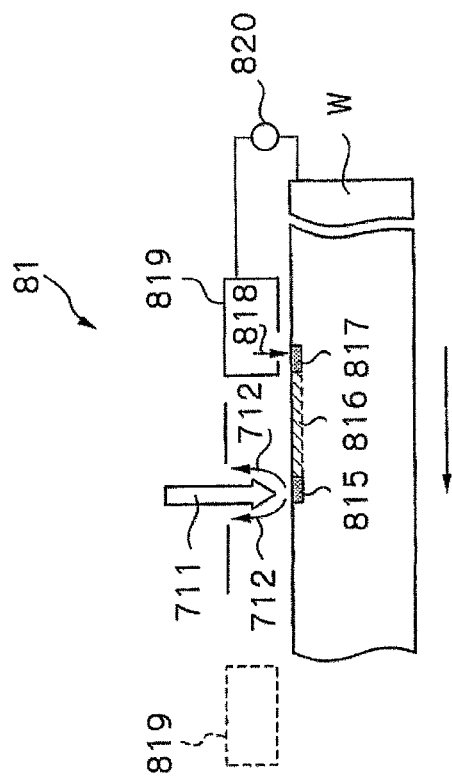
FIG. 10 is a diagram related to one embodiment of the present invention.

FIG. 10 shows the main components of a precharge unit of an embodiment according to the present invention.

Charged particles 818 from a charged particle irradiation source 819 are accelerated with a voltage determined by a bias supply 820 so as to be irradiated onto a wafer W. An inspecting region 815, and a region 816 as well, are indicated as locations that have been already exposed to the charged particle irradiation for a pre-treatment, and the region 817 is indicated as a location which is currently exposed to the charged particle irradiation. In the diagram, although the sample substrate W is shown to be scanned in the direction indicated with an arrow, another charged particle beam source 819 may be arranged on the opposite side to the first electron beam source as shown with the dotted line in the drawing, so that the charged particle beam sources 819 and 819 may be alternately turned on and off in synchrony with the direction of the scanning of the sample W. In this case, if the energy of the charged particles is too high, the secondary electron yield from an insulating portion of the sample substrate W would exceed 1, thus causing the surface to be positively charged, and even a yield of not more than 1 would still make the phenomenon complicated with the generated secondary electrons thus decreasing the irradiation effect, and accordingly, it is preferred that the voltage for the energy of the charged particles should be set to a landing voltage of 100 eV or lower (preferably higher than 0 eV and lower than 30 eV), which can significantly reduce the generation of the secondary electrons.

Figure 11:
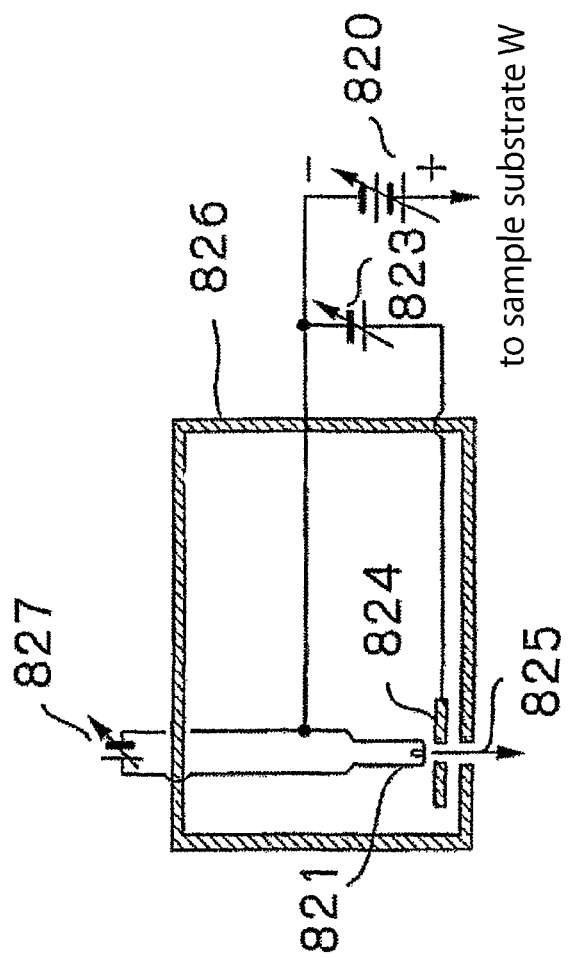
FIG. 11 is a diagram related to one embodiment of the present invention.

FIG. 11 shows a second embodiment of a precharge unit of the present invention. FIG. 11 shows an irradiation source of such type that irradiates an electron beam as a charged particle beam. The irradiation source comprises a hot filament 821, a deriving electrode 824, a shield case 826, a filament power supply 827, and an electron deriving power supply 823. The deriving electrode 824 is 0.1 mm in thickness, has a slit 0.2 mm wide and 1.0 mm long, and is arranged relative to the filament 821 of a diameter of 0.1 mm so as to take the form of a three electrode type electron gun. The shield case 826 is also provided with a slit of 1 mm wide and 2 mm long, and is assembled so that the shield case 826 is spaced from the deriving electrode 824 by 1 mm with its slit center being aligned with the slit center of the deriving electrode 824. The filament is made of tungsten (W), and it is found that an electron current of in the order of μA can be obtained with a current of 2 A being supplied to the filament when a deriving voltage of 20 V and a bias voltage of −30 V are applied.

The example has been shown for illustrative purposes only and the filament may be made of other materials, for example, a high melting point metal such as Ta, Ir, Re or the like, thoria-coated W, or an oxide electrode, and in this case, needless to say, the filament current should be varied depending on the material, the line diameter and the line length to be used. Further, other kinds of electron guns may be used as long as the electron beam irradiated area, the electron current and the energy can be respectively set to appropriate value.

Figure 12:
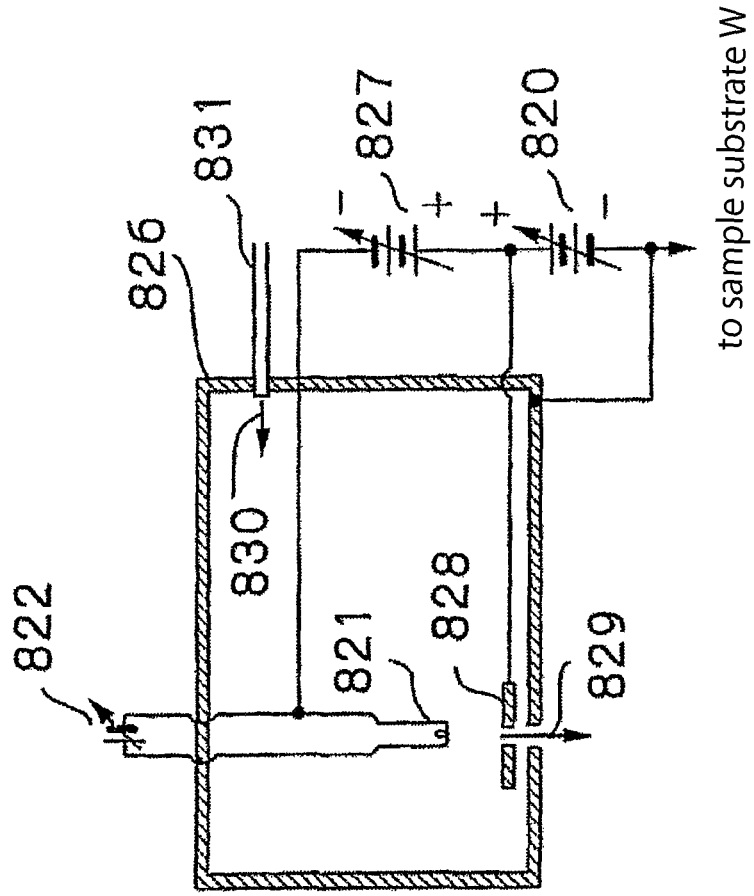
FIG. 12 is a diagram related to one embodiment of the present invention.

FIG. 12 shows a third embodiment of a precharge unit of the present invention. FIG. 12 shows an irradiation source of a type that irradiates ions 829 as a charged particle beam. This irradiation source comprises a filament 821, a filament power supply 822, an electric discharge power supply 827, and an anode shield case 826, in which both of anode 828 and the shield case 826 have the same sized slit of 1 mm×2 mm respectively formed there through, and they are assembled so that the centers of both slits are aligned with each other. Ar gas 830 is introduced into the shield case 826 through a pipe 831 with about 1 Pa and this irradiation source is operated by way of an arc discharge caused by the hot filament 821. The bias voltage is set to a positive value.

Figure 13:
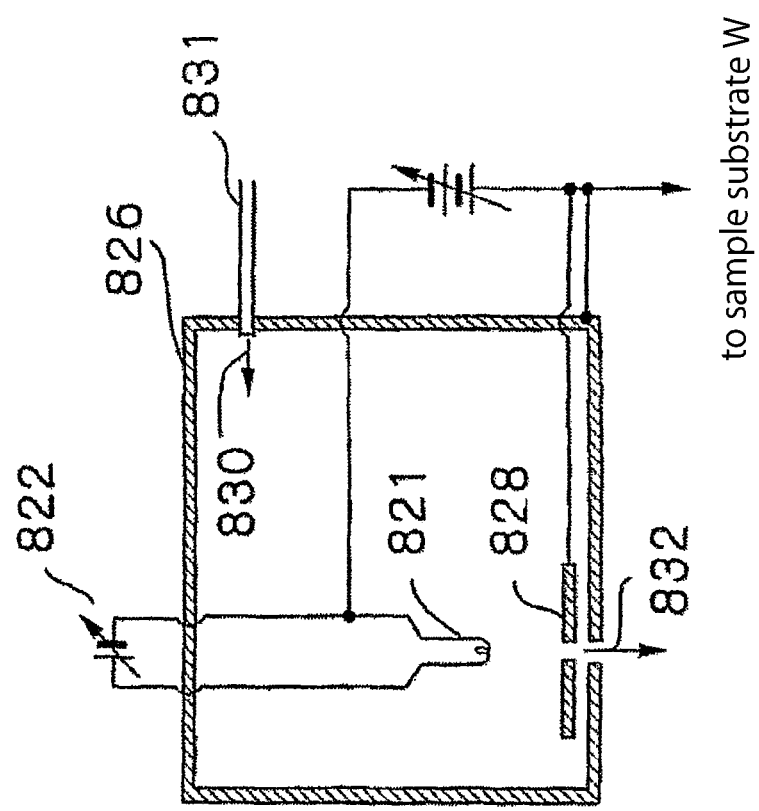
FIG. 13 is a diagram related to one embodiment of the present invention.

FIG. 13 shows a plasma irradiation type of a fourth embodiment of a precharge unit according to the present invention. It has the same structure as that of FIG. 20. The operation thereof, similarly to the above description, is made effective by way of the arc discharge by the hot filament 821, in which by setting the bias potential to 0V, the plasmas 832 are forced by gas pressure to effuse through the slit to be irradiated onto a sample substrate. Since in the plasma irradiation method, the beam is composed of a group of particles that has both positive and negative charges, which is different from the other irradiation methods, it allows both positive and negative surface potentials in the surface of the sample substrate to approach zero.

A charged particle irradiating section 819 arranged in the proximity of the wafer W has a configuration as illustrated in any of FIGS. 10 to 13, which is designed to irradiate charged particles 818 onto the sample substrate with a suitable condition depending on the difference in the surface structure, e.g., silicon dioxide film or silicon nitride film, of the wafer W, or depending on a different requirement for each sample substrate after respective different processes, and in which after performing the irradiation to the sample substrate under the optimal irradiation condition, that is, after smoothing the potential in the surface of the wafer W or saturating the potential therein with the charged particles, an image is formed by the irradiated light, or laser or electron beam 711 and secondary charged particles 712 to be used to detect any defects.

As described above, since according to the subject embodiment, pre-treatment by means of charged particle irradiation is employed just before measurement and thereby an evaluated image distortion by the charging would not occur or would be negligible, any defects can be accurately detected.

Further, according to the embodiment according to the present invention, since a large amount of an irradiated light, laser or primary electron beam is irradiated for scanning a stage has caused problems in the prior art, a large number of secondary electrons of an electron beam, secondary emitted electrons or mirror electrons can be detected and a detection signal having a good S/N ratio can be obtained, thus improving the reliability of defect detection.

Still further, with a larger S/N ratio, faster scanning of the stage still can produce good image data, thus allowing inspection throughput to be greater.

Potential Applying Mechanism

Figure 14:
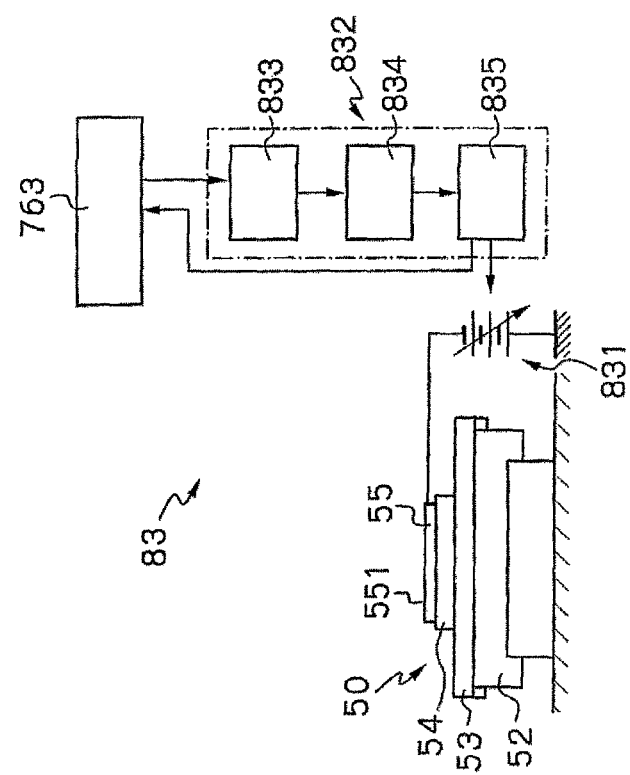
FIG. 14 is a diagram related to one embodiment of the present invention.

Referring next to FIG. 14, the potential applying mechanism 83 applies a potential of ±several volts to a carrier of a stage, on which the wafer is placed, to control the generation of secondary electrons based on the fact that the generation rate of secondary electron charged particles emitted from the wafer or secondary system transmittance rate depend on the potential on the wafer. In addition, in the case of irradiating an electron beam in the primary system, the potential applying mechanism 83 also serves to decelerate the energy originally possessed by irradiated electrons to provide the wafer with irradiated electron energy of approximately 0 to 500 eV. In addition, the energy of the electrons which move through the secondary system is determined by forming a reference voltage of the wafer which is the sample.

As illustrated in FIG. 14, the potential applying mechanism 83 comprises a voltage applying device 831 electrically connected to the carrying surface 541 of the stage device 50; and a charging examining/voltage determining system (hereinafter referred to as examining/determining system) 832. The examining/determining system 832 comprises a monitor 833 electrically connected to an image forming unit 763 of the detecting system 76 in the electron-optical system 70; an operator 834 connected to the monitor 833; and a CPU 835 connected to the operator 834. The CPU 835 supplies a signal to the voltage applying device 831.

The potential applying mechanism 83 is designed to find a potential at which the wafer to be inspected is hardly charged, and to apply such potential to the carrying surface 541.

In a method for inspecting an electrical defect on a sample to be inspected, the defect on the portion which is designed to be electrically insulated can be detected based on the fact that there is a voltage difference therein between the normal case where the portion is insulated and the defective case where the portion is in a conductive condition.

In this method, at first the electric charges are applied to the sample in advance, so that a voltage difference is generated between the voltage in the portion essentially insulated electrically and the voltage in another portion which is designed to be electrically insulated but is in a conductive condition due to the existence of any defects, then the beam of the present invention is applied thereto to obtain data about the voltage difference, which is then analyzed to detect the conductive condition.

Irradiation Beam Calibration Mechanism

Figure 15:
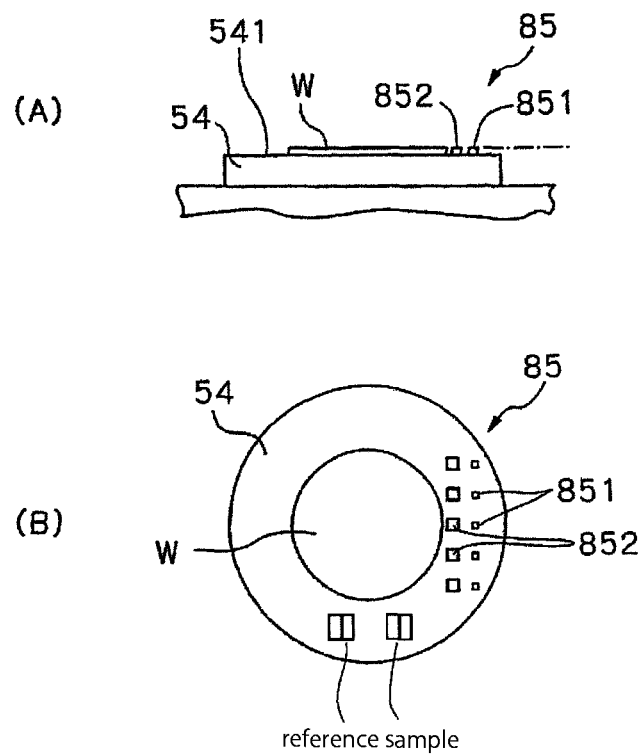
FIG. 15 is a diagram related to one embodiment of the present invention.

Referring next to FIG. 15, the irradiation beam calibration mechanism 85 comprises a plurality of Faraday cups 851, 852 for measuring a beam current, disposed at a plurality of positions in a lateral region of the wafer carrying surface 541 on the turntable 54, and a reference sample 853. A material including a matrix pattern formed with a part of a plane surface without a pattern and a matrix pattern reference pitch can be used as the reference sample 853. A conductive material is used for the plane surface. When light or a laser is irradiated on these parts, in order to be able to measure the irradiated region of the beam an electron image generated from the part irradiated at a low magnification is imaged and calculated by its gray profile. A stable measurement can be made because the surface potential is stable when conductive. In addition, it is possible to measure the size of an irradiated part from the profile of an electron image of the irradiated part and the size of an irradiated part and intensity profile from the pitch relationship at for example, a pitch of 2 μm because the pitch can be obtained when there is a matrix pattern. In addition, it is also possible use Faraday cups. When Faraday cups are used, light or a laser is irradiated into parts having holes, and an electron image of the obtained irradiated region is obtained. Then, it is possible to measure the size and coordinates of the irradiated region by comparing the size of the holes of the Faraday cups and the irradiated region. Also, it is possible to use original Faraday cups when an electron beam is used as the irradiation beam. When an electron beam is irradiated into the Faraday cup, it is possible to measure the current of the electron beam. The Faraday cups 851 are provided for a narrow beam (approximately φ2 μm), while the Faraday cuts 852 for a wide beam (approximately φ30 μm). The Faraday cups 851 are provided for a narrow beam measure a beam profile by driving the turntable 54 step by step, while the Faraday cups 852 for a wide beam measure a total amount of current. The Faraday cups 851, 852 are mounted on the wafer carrying surface 541 such that their top surfaces are coplanar with the upper surface of the wafer W carried on the carrying surface 541. In this way, the primary electron beam emitted from the electron gun is monitored at all times. This is because the electron gun cannot emit a constant electron beam at all times but varies in its emission intensity as it is used over a period of time.

Alignment Controller

The alignment controller 87 aligns the wafer W with the electron-optical device 70 using the stage device 50, and it performs the control for rough alignment through wide view field observation using the optical microscope 871 (a measurement with a lower magnification than the measurement made by the electron-optical system); high magnification alignment using the electron-optical system of the electron-optical device 70; focus adjustment; inspecting region setting; pattern alignment; and so on. The reason why the wafer is inspected at a low magnification using the optical microscope in this way is that an alignment mark must be readily detected by a photoelectron image when the wafer is aligned by observing patterns on the wafer in a small field using the light or laser beam irradiation for automatically inspecting patterns on the wafer. At this time, an electron beam can be used instead of a photoelectron for the irradiation beam.

Figure 16:
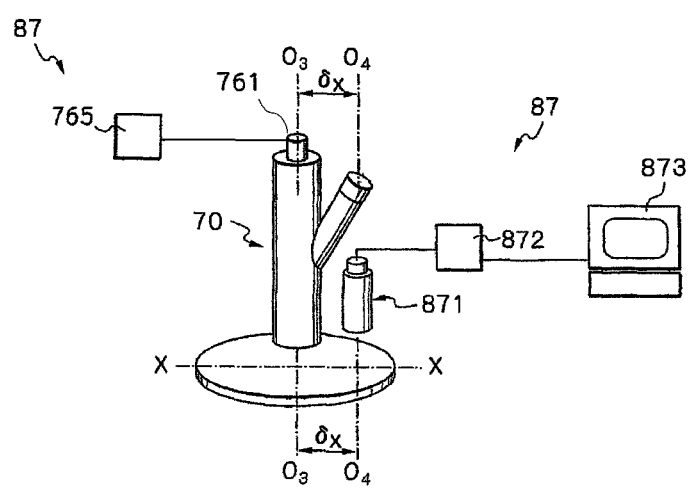
FIG. 16 is a diagram related to one embodiment of the present invention.

The optical microscope 871 is disposed on the housing 30 (alternatively, it may be movably disposed within the housing 30), with a light source, not shown in the diagram, being additionally disposed within the housing 30 for operating the optical microscope. The electron-optical system for observing the wafer at a high magnification shares the electron optical systems (primary optical system 72 and secondary optical system 74) of the electron-optical device 70. The configuration may be generally illustrated in FIG. 16. For observing a point of interest on a wafer at a low magnification, the X-stage 53 of the stage device 50 is moved in the X-direction to move the point of interest on the wafer into a field of the optical microscope 871. The wafer is viewed in a wide field by the optical microscope 871, and the point of interest on the wafer to be observed is displayed on a monitor 873 through a CCD 872 to roughly determine a position to be observed. In this occurrence, the magnification of the optical microscope may be changed from a low to a high magnification.

Next, the stage system 50 is moved by a distance corresponding to a spacing δx between the optical axis $O_3$-$O_3$ of the electron-optical system 70 and the optical axis $O_4$-$O_4$ of the optical microscope 871 to move the point on the wafer under observation, previously determined by the optical microscope 871, to a point in the field of the electron-optical system 70. In this occurrence, since the distance δx between the axis $O_3$-$O_3$ of the electron-optical system and the axis $O_4$-$O_4$ of the optical microscope 871 is previously known (while it is assumed that the electron optical system 70 is deviated from the optical microscope 871 in the direction along the X-axis in this embodiment, it may be deviated in the Y-axis direction as well as in the X-axis direction), the point under observation can be moved to the viewing position by moving the stage system 50 by the distance δx. After the point under observation has been moved to the viewing position of the electron-optical system 70, the point under observation is imaged by the electron optical system at a high magnification for storing a resulting image or displaying the image on the monitor 765 through the detector 761. At this time, light or a laser beam is irradiated as the primary system and it is possible to use as a photoelectron image. In addition, when an electron beam is used as the primary system, secondary emitting electrons or an electron image is obtained and can be used in alignment.

After the point under observation on the wafer imaged by the electron-optical system at a high magnification is displayed on the monitor 765, misalignment of the wafer in its rotating direction with respect to the center of rotation of the turntable 54 of the stage system 50, and misalignment δθ of the wafer in its rotating direction with respect to the optical axis $O_3$-$O_3$ of the electron-optical system are detected by a known method; misalignment of a predetermined pattern with respect to the electron-optical system in the X-axis and Y-axis is also detected. Then, the operation of the stage system 50 is controlled to align the wafer based on the detected values and data on an inspection mark attached on the wafer or data on the shape of the patterns on the wafer which have been obtained in separation.

Vacuum Exhausting System

A vacuum exhausting system is comprised of a vacuum pump, a vacuum valve, a vacuum gauge, a vacuum pipe and the like, and exhausts to vacuum an electron-optical system, a detector section, a sample chamber, a load-lock chamber and the like according to a predetermined sequence. In each of those sections, the vacuum valve is controlled so as to accomplish a required vacuum level. The vacuum level is regularly monitored, and in the case of irregularity, an interlock mechanism executes an emergency control of an isolation valve or the like to secure the vacuum level. As for the vacuum pump, a turbo molecular pump may be used for the main exhaust.

A dry pump of Roots type may be used as a roughing vacuum pump. A pressure at an inspection spot (an electron beam irradiating section) is practically in a range of $10^{-3}$ to $10^{-5}$ Pa, but more preferably, in a range of $10^{-4}$ to $10^{-6}$ Pa.

Control System

A control system is mainly comprised of a main controller, a controlling controller, and a stage controller.

The main controller is equipped with a man-machine interface, through which an operator manipulates the controller (a variety of instructions/commands, an entry of recipe, an instruction to start an inspection, a switching between an automatic inspection mode and a manual inspection mode, an input of all of the commands required in the manual inspection mode and so forth). In addition, the main controller may further execute communication with a host computer of a factory, a control of a vacuum exhausting system, a control of a carrying and positioning operations of a sample such as a wafer, an operation for sending commands and receiving information to/from the other controllers and/or stage controller and so forth. Further, the main controller has the following functions: to obtain an image signal from an optical microscope; a stage vibration compensating function for compensating a deterioration in the image by feeding back a fluctuation signal of the stage to an electronic-optical system; and an automatic focal point compensating function for detecting a displacement of the sample observation point in the Z direction (in the axial direction of the secondary optical system) and feeding back the detected displacement to the electron-optical system so as to automatically compensate the focal point. Sending and receiving operations of the feedback signal to and from the electron-optical system and sending and receiving operations of the signal to and from the stage are performed via the controlling controller and the stage controller respectively.

The controlling controller is mainly responsible for the control of the primary optical system and the secondary electron optical system (a light source, a laser beam source, a mirror, an optical system lens, an electron optical system lens, an aligner, a control of a high-precision power supply for a Wien filter or the like). Specifically, the controlling controller performs a control operation, for example, an automatic voltage setting for each of the lens systems and the aligners in response to each operation mode (gang control), so that a constant electron current may be regularly irradiated against the irradiation region even if the magnification is changed, and a voltage to be applied to each of the lens systems and the aligners may be automatically set in response to each magnification. In addition, when the magnification changes, it is effective to preform control in order to change the density of the irradiation beam so that the electron number per Px (electron number/Px Px: Pixel) obtained by the detector is maintained constant. It is possible to obtain an electron image with a different magnification at a constant level of luminosity.

The stage controller is mainly responsible for a control regarding to the movement of the stage so that a precise movement in the X and the Y directions may be performed in the order of μm (with tolerance of about ±0.05 μm). Further, in the present stage, a control in the rotational direction (θ control) is also performed with a tolerance equal to or less than about ±0.1 seconds.

Cleaning of an Electrode

When an electron beam apparatus according to the present invention is operated, a target substance floats due to a proximity interaction (charging of particles in the proximity of a surface) and is attracted to a high-voltage region, an organic substance will be deposited on a variety of electrodes used for forming or deflecting an electron beam. Since the insulating material gradually being deposited on the surface of the electrodes by the electric charge adversely affects the forming or deflecting mechanism for the electron beam, accordingly, this deposited insulating material must be periodically removed. To remove the insulating material periodically, an electrode adjacent to the region where the insulating material has been deposited is used to produce plasma of hydrogen, oxygen, fluorine, composition including these elements, $HF$, $O_2$, $H_2O$, $O_M F_N$ or the like, to maintain the plasma potential in the space to the degree (several kV, e.g. 20 V~5 kV) so that sputtering is caused on the electrode surface, thereby allowing only the organic substance to be removed by oxidization, hydrogenation or fluorination.

Modified Embodiment of the Stage Device

Figure 17:
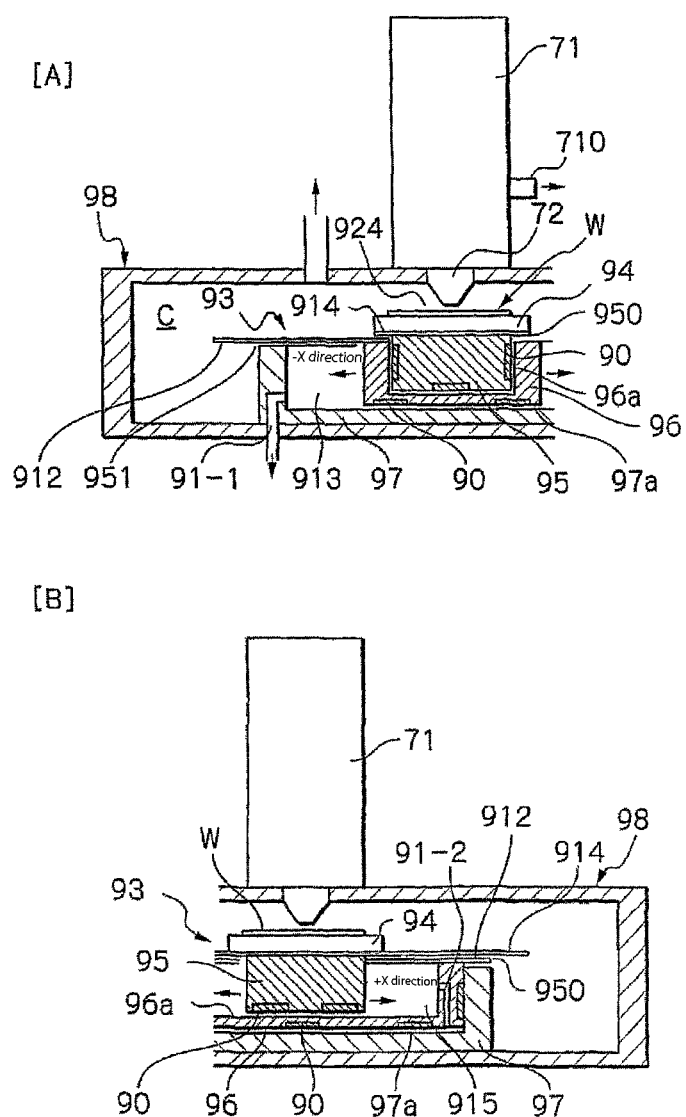
FIG. 17 is a diagram related to one embodiment of the present invention.

FIG. 17 shows a modified embodiment of a stage device in the detector according to the present invention. A division plate 914 is attached onto an upper face of a Y directionally movable unit 95 of a stage 93, wherein said division plate 914 overhangs to a considerable degree, approximately horizontally in the +Y direction and the −Y direction (the lateral direction in FIG. 17 (B)), so that between an upper face of an X directionally movable unit 96 and said division plate 914 there is always provided a narrow gap 950. Also, a similar division plate 912 is attached onto the upper face of the X directionally movable unit 96 so as to overhang in the ±X direction (the lateral direction in FIG. 17(A)), so that a narrow gap 951 may be constantly formed between an upper face of a stage table 97 and said division plate 912. The stage table 97 is fixedly secured onto a bottom wall within a housing 98 using a known method.

In this way, since the narrow gaps 950 and 951 are constantly formed wherever the sample table 94 may move, and the gaps 950 and 951 can prevent the movement of a desorbed gas even if a gas is desorbed or leaked along the guiding plane 96a or 97a upon movement of the movable unit 95 or 96, any increase in pressure can be considerably reduced in a space 924 adjacent to the sample against which the charged particles beam is irradiated.

Figure 18:
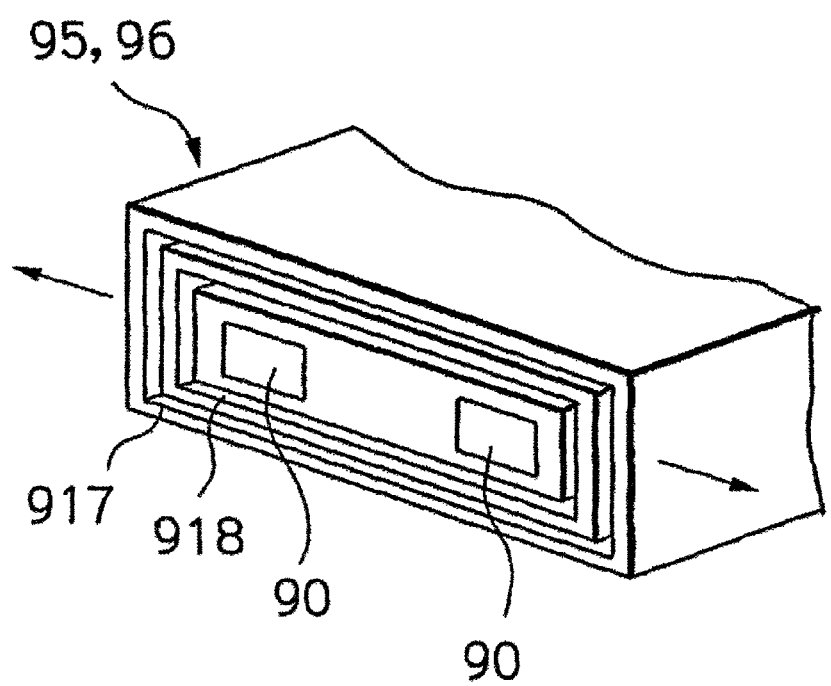
FIG. 18 is a diagram related to one embodiment of the present invention.

In a side-face and an under face of the movable unit 95 and also in an under face of the movable unit 96 of the stage 93, there are provided grooves, for differential exhausting formed surrounding hydrostatic bearings 90, as shown in FIG. 18, and which work for vacuum-exhausting; therefore, in a case where narrow gaps 950 and 951 have been formed, the desorbed gas from the guiding planes is mainly evacuated by these differential exhausting sections. Because of this, the pressures in spaces 913 and 915 within the stage are kept at higher levels than the pressure within chamber C. Accordingly, if there are more portions provided for vacuum-exhausting the spaces 913 and 915, in addition to the differential exhausting grooves 917 and 918, the pressure within the spaces 913 and 915 can be decreased, and the pressure rise of the space 924 in the vicinity of the sample can be controlled so as to be kept lower. For this purpose, vacuum exhausting channels 91-1 and 91-2 are provided. The vacuum exhausting channel 91-1 extends through the stage table 97 and the housing 98 to communicate with an outside of the housing 98. On the other hand, the exhausting channel 91-2 is formed in the X directionally movable unit 96 and opens in an under face thereof.

It is to be noted that though arranging the division plates 912 and 914 might cause a problem requiring the chamber C to be extended so that it does not interfere with the division plates, this can be improved by employing division plates of stretchable material or structure. One embodiment in this regard may be suggested, which employs the division plates made of rubber or in a form of bellows, the ends portions of which are fixedly secured respectively in the direction of movement so that each end of the division plate 914 is secured to the X directionally movable unit 96 and that of the division plate 912 to the inner wall of the housing 98.

Figure 19:
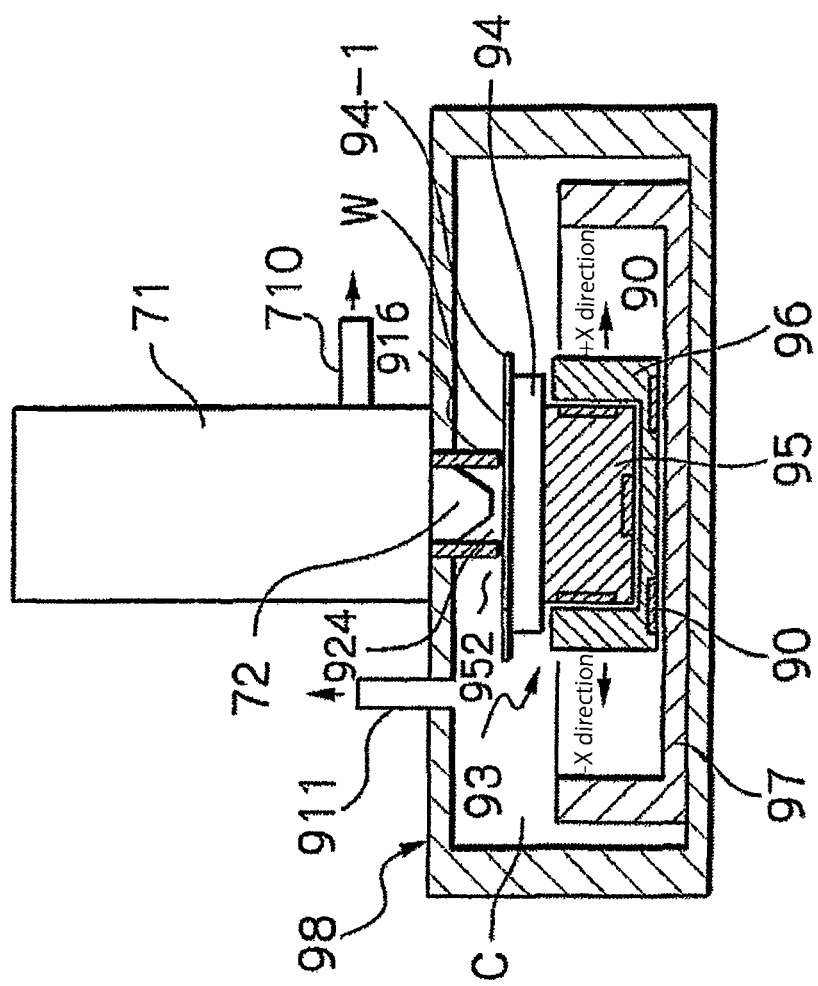
FIG. 19 is a diagram related to one embodiment of the present invention.

FIG. 19 shows a second modified embodiment of a stage device.

In this embodiment, a cylindrical divider 916 is disposed surrounding the tip portion of the lens column or the charged particles beam irradiating section 72 so that a narrow gap may be produced between an upper face of a sample W and the tip portion of the lens column. In such configuration, even if the gas is desorbed from the XY stage, and increases the pressure within the chamber C, since a space 924 within the divider has been isolated by the divider 916 and exhausted with a vacuum pipe 710, there could be generated a pressure difference between the pressure in the chamber C and that in the space 924 within the divider, thus controlling the pressure rise in the space 924 within the divider 916 so that it is kept low. Preferably, the gap between the divider 916 and the sample surface should be approximately some ten μm to several mm, depending on the pressure level to be maintained within the chamber C and in the surrounding of the irradiating section 72. It is to be understood that the interior of the divider 916 is made to communicate with the vacuum pipe by the known method.

On the other hand, the charged particles beam irradiation apparatus may sometimes apply a high voltage of a few kV to the sample W, and so it is feared that any conductive materials adjacent to the sample could cause an electric discharge. In this case, the divider 916 made of insulating material such as ceramic or the surface of an insulating material such as a polyimide coat (10~50 μm) may be used in order to prevent any discharge between the sample W and the divider 916.

It is to be noted that a ring member 94-1 arranged so as to surround the sample W (a wafer) is a plate-like adjusting part fixedly mounted on the sample table 94 and set to have the same height as the wafer so that a micro gap 952 may be formed throughout a full circle of the tip portion of the divider 916 even when the charged particles beam is being irradiated against an edge portion of the sample such as the wafer. Thereby, whichever location on the sample W may be irradiated by the charged particles beam, the constant micro gap 952 can always be formed at the tip portion of the divider 916 so as to maintain a stable pressure in the space 924 surrounding the lens column tip portion.

Figure 20:
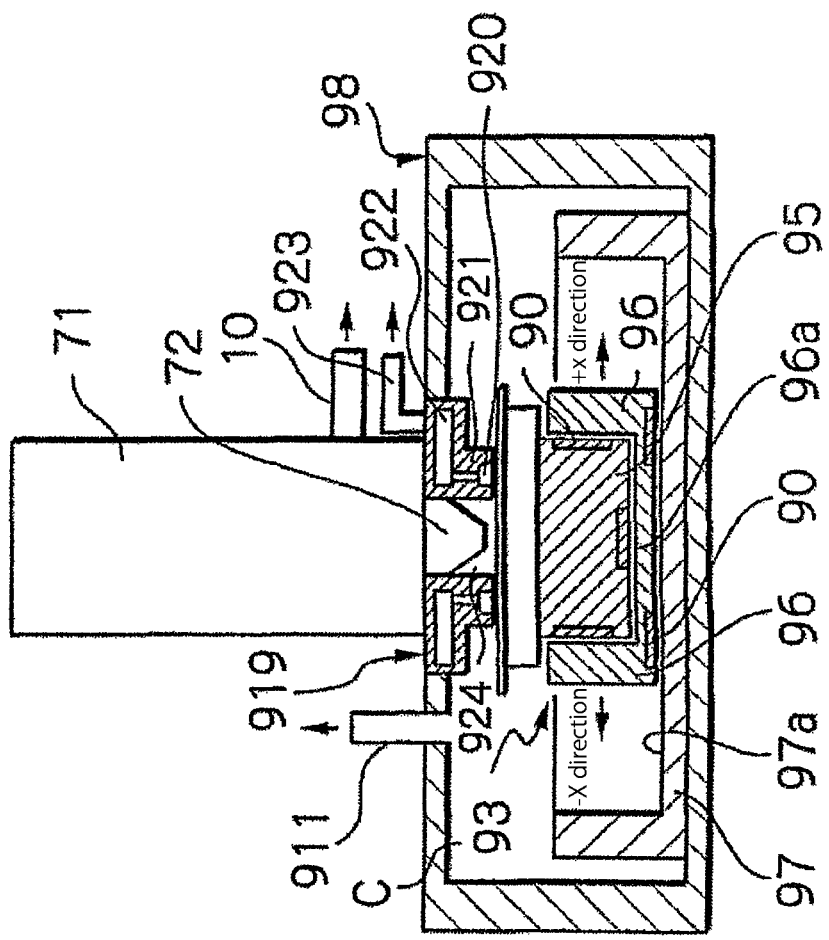
FIG. 20 is a diagram related to one embodiment of the present invention.

FIG. 20 shows another modified embodiment.

A divider 919 having a differential exhausting structure integrated therein is arranged so as to surround the charged particles beam irradiating section 72 of a lens column 71. The divider 919 is cylindrical in shape and has a circular channel 920 formed inside thereof and an exhausting path 921 extending upwardly from said circular channel 920. Said exhausting path 921 is connected to a vacuum pipe 923 via an inner space 922. A micro space as narrow as some ten μm to several mm is formed between the lower end of the divider 919 and the upper face of the sample W.

With such configuration, even if the gas is discharged from the stage in association with the movement of the stage resulting in an increase of the pressure within the chamber C, and eventually flows into the space of tip portion or the charged particles beam irradiating section 72, any flow of gas is blocked by the divider 919, which has reduced the gap between the sample W and itself so as to make the conductance very low, thus reducing the flow rate. Further, since any gas that has entered can be exhausted through the circular channel 920 to the vacuum pipe 923, there will be almost no gas remained to flow into the space 924 surrounding the charged particles beam irradiating section 72; accordingly, the pressure of the space surrounding the charged particles beam irradiating section 72 can be maintained at the desired high vacuum level.

Figure 21:
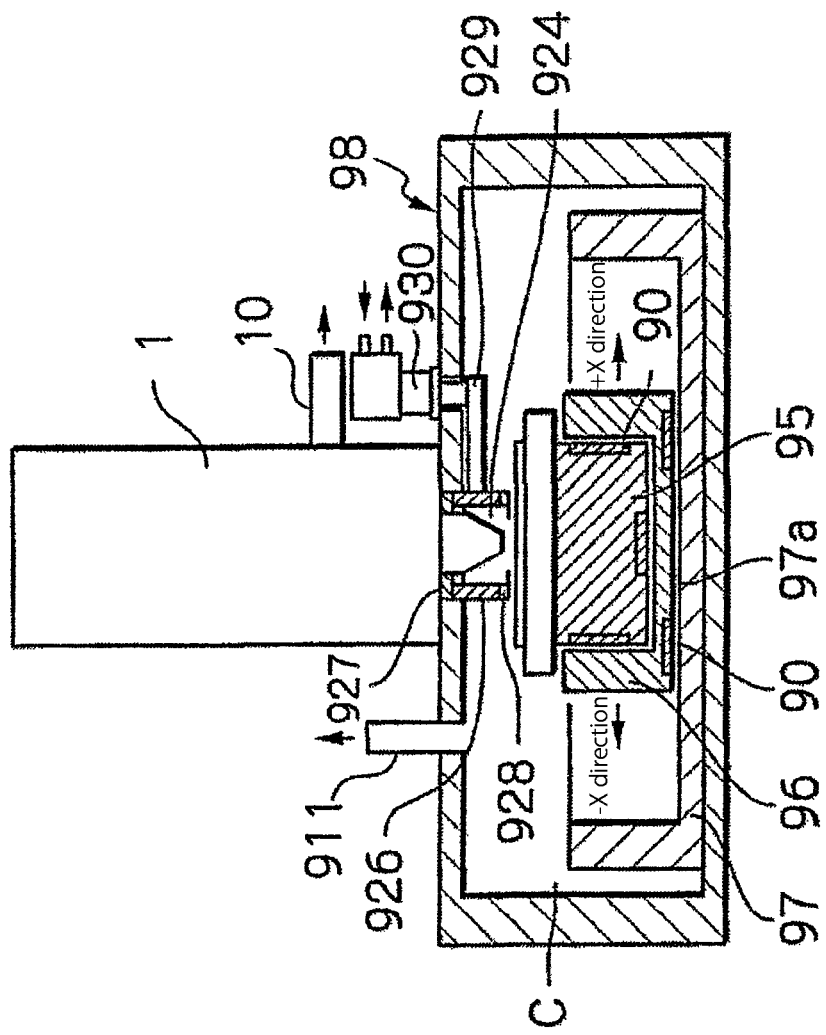
FIG. 21 is a diagram related to one embodiment of the present invention.

FIG. 21 shows yet another modified embodiment.

A divider 926 is arranged so as to surround the charged particles beam irradiating section 72 in the chamber C, thus isolating the charged particles beam irradiating section 72 from the chamber C. This divider 926 is coupled to a refrigerating machine 930 via a support member 929 made of material of high thermal conductivity such as copper or aluminum, and is kept as cool as −100° C. to −200° C. A member 927 is provided for blocking a thermal conduction between the cooled divider 926 and the lens column and is made of material of low thermal conductivity such as ceramic, resin or the like. Further, a member 928 is made of a non-insulating material such as ceramic or the like and is attached to the lower end of the divider 926 so as to prevent any electric discharge between the sample W and the divider 926.

With such configuration, any gas molecules attempting to flow into the space surrounding the charged particles beam irradiating section from the chamber C are blocked by the divider 926, and even if some molecules manage to flow into the section, they are frozen to be captured on the surface of the divider 926, thus allowing the pressure in the space 924 surrounding the charged particles beam irradiating section to be kept low. In this way, vacuum exhausting using a freezing gas repair device or a cryopanel is extremely effective for local exhausting.

Furthermore, various types of refrigerating machines may be used for the refrigerating machine in this embodiment, for example, a cooling machine using liquid nitrogen, a He refrigerating machine, a pulse-tube type refrigerating machine or the like.

Figure 22:
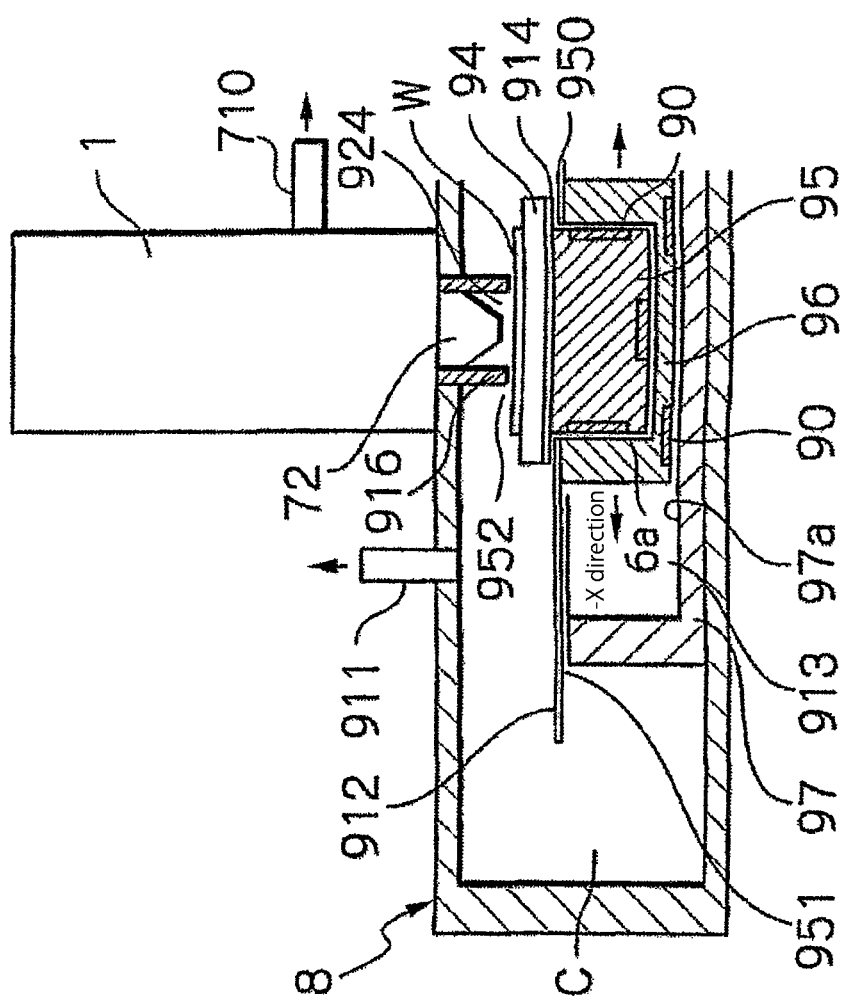
FIG. 22 is a diagram related to one embodiment of the present invention.

FIG. 22 shows yet another modified embodiment.

The division plates 912 and 914 are arranged on both movable units of the stage 93 similarly to those illustrated in FIG. 17, and thereby, if the sample table 94 is moved to any location, the space 913 within the stage is separated from the inner space of the chamber C by those division plates through the narrow gaps 950 and 951. Further, another divider 916 similar to that as illustrated in FIG. 19 is formed surrounding the charged particles beam irradiating section 72 so as to separate a space 924 accommodating the charged particles beam irradiating section 72 therein from the interior of the chamber C with a narrow gap 952 disposed therebetween. Owing to this, upon movement of the stage, even if the gas adsorbed on the stage is desorbed into the space 913 to increase the pressure in this space, the pressure increase in the chamber C is controlled so that it is kept low, and the pressure increase in the space 924 is also kept even lower. This allows the pressure in the space 924 for irradiating the charged particles beam to be maintained at a low level. Alternatively, employing the divider 919 having the differential exhausting mechanism integrated therein as explained with reference to the divider 916, (see FIG. 20), or the divider 926 cooled with the refrigerating machine as shown in FIG. 21 allows the space 924 to be maintained stably with further lowered pressure.

According to the subject embodiment, the following effects may be obtained.

(A) The stage device can enhance accurate positioning within a vacuum atmosphere and the pressure in the space surrounding the charged particles beam irradiating location is hardly increased. That is, it allows the charged particles beam processing to be applied to the sample with high accuracy.

(B) It is almost impossible for the gas desorbed or leaked from the hydrostatic bearing to go through the divider and reach the space for the charged particles beam irradiating system. Thereby, the vacuum level in the space surrounding the charged particles beam irradiating location can be further stabilized.

(C) It is harder for the desorbed gas to go through to the space for the charged particles beam irradiating system, and it is easier to maintain the stability of the vacuum level in the space surrounding the charged particles beam irradiating location.

(D) The interior of the vacuum chamber is partitioned into three chambers, i.e., a charged particles beam irradiation chamber, a hydrostatic bearing chamber and an intermediate chamber; each can communicate with the other via a small conductance. Further, the vacuum exhausting system is constructed so that the pressures in the respective chambers are controlled sequentially, so that the pressure in the charged particles beam irradiation chamber is the lowest, that in the intermediate chamber is in the middle range, and that in the hydrostatic bearing chamber is the highest. The pressure fluctuation in the intermediate chamber can be reduced by the divider, and the pressure fluctuation in the charged particles beam irradiation chamber can be further reduced by another step of divider, so that the pressure fluctuation therein can be reduced substantially to a non-problematic level.

(E) The pressure increase upon movement of the stage can be controlled so that it is kept low.

(F) The pressure increase upon movement of the stage can be further controlled so that it is kept even lower (G) Since a defect inspection apparatus with highly accurate stage positioning performance and with a stable vacuum level in the charged particles beam irradiating region can be accomplished, an inspection apparatus with high inspection performance and without any fear of contamination of the sample can be provided.

(H) Since a defect inspection apparatus with highly accurate stage positioning performance and with a stable vacuum level in the charged particles beam irradiating region can be accomplished, an exposing apparatus with high exposing accuracy and without any fear of contamination of the sample can be provided.

(I) Manufacturing the semiconductor by using the apparatus with highly accurate stage positioning performance and with a stable vacuum level in the charged particles beam irradiating region allows a miniaturized micro semiconductor circuit to be formed.

Furthermore, it is apparent that the stage device shown in FIGS. 17~22 can be applied to the stage device 50 shown in FIG. 1.

Further embodiments of the XY stage according to the present invention will now be described with reference to FIGS. 23 to 25. It is also to be appreciated that a term "vacuum" used in this specification means a vacuum as referred to in the field pertaining to this art and does not necessarily refer to an absolute vacuum.

Figure 23:
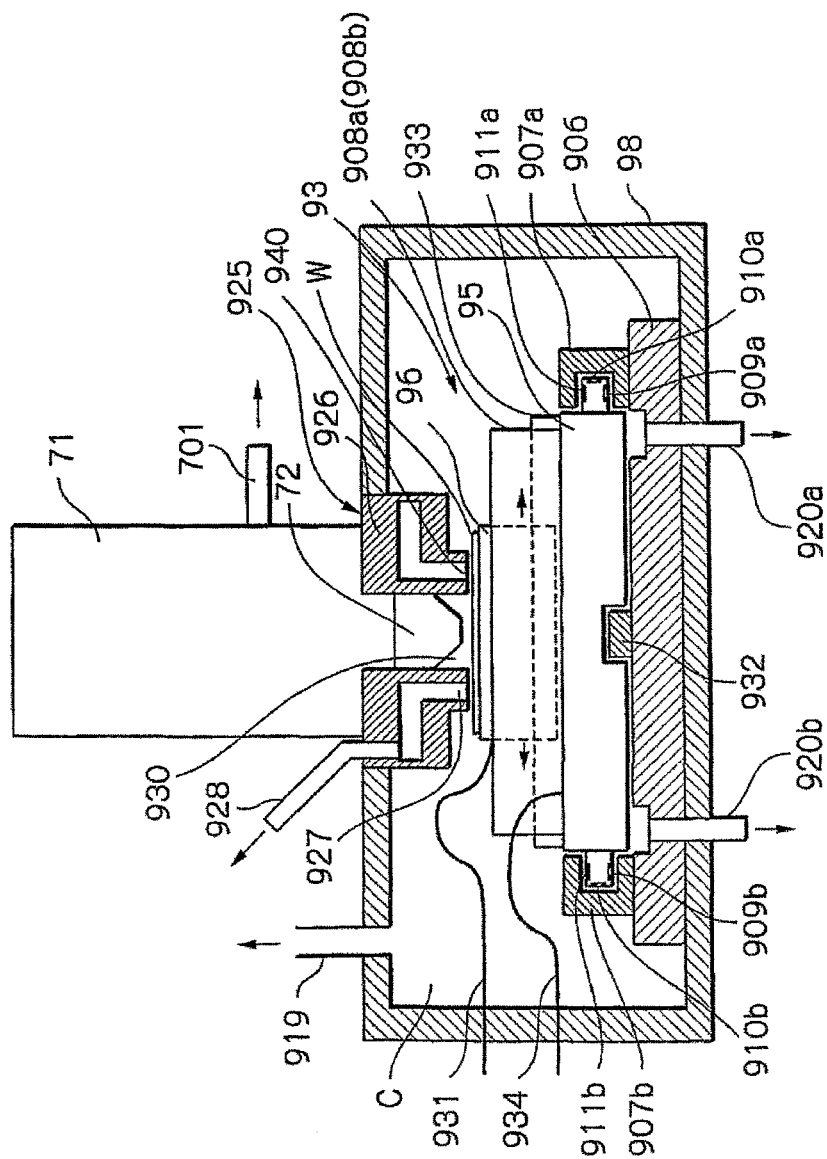
FIG. 23 is a diagram related to one embodiment of the present invention.

FIG. 23 shows another embodiment of the XY stage.

A tip portion of a lens column 71 or a charged particles beam irradiating section 72, which functions to irradiate a charged particles beam against a sample, is mounted on a housing 98 defining a vacuum chamber C. The sample W loaded on a table of an XY stage 93 movable in the X direction (the lateral direction in FIG. 23) is adapted to be positioned immediately under the lens column 71. The XY stage 93 of high precision allows the charged particles beam to be irradiated onto this sample W accurately in any arbitrary location of the sample surface.

A pedestal 906 of the XY stage 93 is fixedly mounted on a bottom wall of the housing 98, and a Y table 95 movable in the Y direction (the vertical direction on paper in FIG. 23) is loaded on the pedestal 906. Bump portions are formed on both opposite sidewall faces (the left and the right side faces in FIG. 23) of the Y table 95 respectively, each of which projects into a hollow groove formed on a side surface facing the Y table in either of a pair of Y-directional guides 907a and 907b mounted on the pedestal 906. The hollow groove extends along approximately the full length of the Y directional guide in the Y direction. A top, a bottom and a side face of respective bump portions protruding into the grooves are provided with known hydrostatic bearings 911a, 909a, 911b and 909b respectively, through which a high-pressure gas is expelled and thereby the Y table 95 is supported to the Y directional guides 907a and 907b in non-contact manner so as to be movable smoothly reciprocating in the Y direction. Further, a linear motor 932 of known structure is arranged between the pedestal 906 and the Y table 95 for driving the Y table 95 in the Y direction. The Y table 95 is supplied with the high pressure gas through a flexible pipe 934 for supplying a high-pressure gas, and the high-pressure gas is further supplied to the above-described hydrostatic bearings 909a to 911a and 909b to 911b though a gas passage (not shown in the diagram) formed within the Y table. The high-pressure gas supplied to the hydrostatic bearings is expelled into a gap of from several microns to several tens of microns in thickness formed respectively between the bearings and the opposing guide planes of the Y directional guide so as to position the Y table accurately with respect to the guide planes in the X and Z directions (up and down directions in FIG. 23).

The X table 96 is loaded on the Y table so as to be movable in the X direction (the lateral direction in FIG. 23). A pair of X directional guides 908a and 908b (only 908a is illustrated in the diagram) with the same configuration as of the Y directional guides 907a and 907b is arranged on the Y table 95 with the X table 96 sandwiched therebetween. Hollow grooves are also formed in the X directional guides on the sides facing the X table and bump portions are formed on the side portions of the X table (side portions facing the X directional guides). The hollow groove extends approximately along the full length of the X directional guide. A top, a bottom and a side face of respective bump portions of the X table protruding into the hollow grooves are provided with hydrostatic bearings (not shown in the diagram) similar to those hydrostatic bearings 911a, 909a, 910a, 911b, 909b and 910b in the similar arrangements. A linear motor 933 of known configuration is disposed between the Y table 95 and the X table 96 so as to drive the X table in the X direction. Further, the X table 96 is supplied with a high-pressure gas through a flexible pipe 931, and thus the high-pressure gas is supplied to the hydrostatic bearings. The X table 96 is supported highly precisely with respect to the Y directional guide in a non-contact manner by way of said high-pressure gas blowing out from the hydrostatic bearings to the guide planes of the X-directional guides. The vacuum chamber C is exhausted through vacuum pipes 919, 920a and 920b coupled to a vacuum pump of a known structure. Those pipes 920a and 920b penetrate the pedestal 906 at the top surface thereof to open their inlet sides (inner side of the vacuum chamber) in the proximity of the locations to which the high-pressure gas is ejected from the XY stage 93, so that the pressure in the vacuum chamber may be prevented to the utmost from rising up by the gas expelled from the hydrostatic bearings.

A differential exhausting mechanism 925 is arranged so as to surround the tip portion of the lens column 71 or the charged particles beam irradiating section 72, so that the pressure in a charged particles beam irradiation space 930 can be controlled so that it is sufficiently low even if there exists high pressure in the vacuum chamber C. That is to say, an annular member 926 of the differential exhausting mechanism 925, mounted so as to surround the charged particles beam irradiating section 72, is positioned with respect to the housing 98 so that a micro gap (of a thickness ranging from several microns to several hundred microns) 940 can be formed between the lower face thereof (the surface facing to the sample) and the sample, and an annular groove 927 is formed in the lower face thereof. That annular groove 927 is coupled to a vacuum pump or the like (not shown), through an exhausting pipe 928. Accordingly, the micro gap 940 can be exhausted through the annular groove 927 and the exhausting pipe 928, and if any gaseous molecules from the chamber C attempt to enter the space 930 circumscribed by the annular member 926, they can be exhausted. Thereby, the pressure within the charged particles beam irradiation space 930 can be kept low and thus the charged particles beam can be irradiated without any problems.

The size of said annular groove may be doubled or tripled, depending on the pressure in the chamber C and the pressure within the charged particles beam irradiation space 930.

Typically, dry nitrogen is used as the high-pressure gas to be supplied to the hydrostatic bearings. If available, however, a much higher-purity inert gas should preferably be used instead. This is because any impurities such as water, oil or fat included in the gas could stick on the inner surface of the housing defining the vacuum chamber or on the surfaces of the stage components leading to the deterioration in vacuum level, or could stick on the sample surface leading to the deterioration in vacuum level in the charged particles beam irradiation space. In addition, a clean dry air is often used because costs are the biggest operational reason when used in a factory. At this time, each type of chemical filter is used in order to remove impurities, and an ultra-precision filter is often used to reduce particles. For example, clean dry air is often introduced using a 1 μm filer and 3 nm filter in series.

It should be appreciated that although typically the sample W is not placed directly on the X table but may be placed on a sample table having a function to detachably carry the sample and/or a function to make a fine tuning of the position of the sample relative to the XY stage 93, an explanation therefor is omitted in the above description for simplicity due to the reason that the presence and structure of the sample table has no concern with the principal concept of the present embodiment.

Since a stage mechanism of a hydrostatic bearing used in the atmospheric pressure can be used in the above described charged particles beam apparatus mostly as it is, a stage having an equivalent level of precision with equivalent cost and size to those of the stage of high-precision fitted for a use in the atmospheric pressure, which is typically used in an exposing apparatus or the likes, may be accomplished for an XY stage to be used in a charged particles beam apparatus.

It should be also appreciated that the configuration and arrangement of the hydrostatic guide and the actuator (the linear motor) have been only illustratively explained in the above description, and any hydrostatic guides and actuators usable in the atmospheric pressure may be applicable. For example, a combination of a the linear motor as the Y direction and ultrasound monitor as the x direction, or the linear motor as the y direction and an air drive positioning stage as the x direction, or the linear motor as the y direction and a ball screw pulse motor drive as the x direction may be applied.

Figure 24:
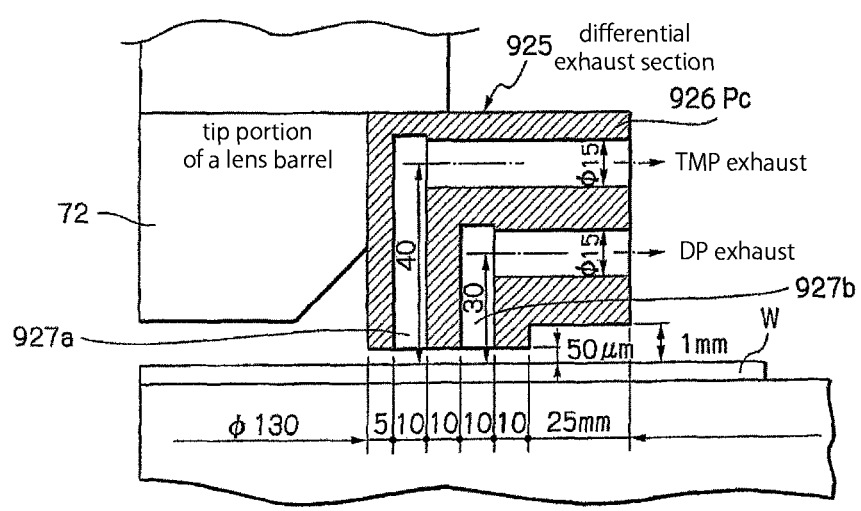
FIG. 24 is a diagram related to one embodiment of the present invention.

FIG. 24 shows an example of numerical values representative of the sizes of the annular member 926 and the annular groove formed in the annular member 926 of the differential exhausting mechanism. It is to be noted that in this example, the size of the annular groove is twice that of the structure of 927a and 927b, which are separated from each other in the radial direction.

The flow rate of the high-pressure gas supplied to the hydrostatic bearing is in the order of about 20 L/min (in the conversion into the atmospheric pressure). Assuming that the vacuum chamber C is exhausted by a dry pump having an exhaust velocity of 20000 L/min via a vacuum pipe having an inner diameter of 50 mm and a length of 2 m, the pressure in the vacuum chamber C will be about 160 Pa (about 1.2 Torr). At that time, with the applied size of the annular member 926, the annular groove and others of the differential exhausting mechanism as described in FIG. 24, the pressure within the charged particles beam irradiation space 930 can be controlled to $10^{-4}$ Pa ($10^{-6}$ Torr).

Figure 25:
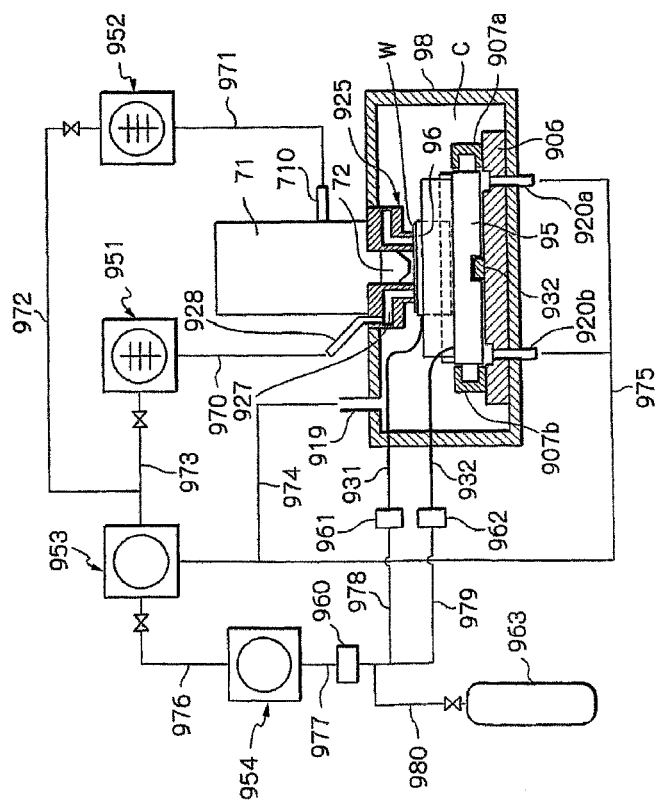
FIG. 25 is a diagram related to one embodiment of the present invention.

FIG. 25 shows a further embodiment of the XY stage. A vacuum chamber C defined by a housing 98 is connected with a dry vacuum pump 953 via vacuum pipes 974 and 975. An annular groove 927 of a differential exhausting mechanism 925 is connected with an ultra-high vacuum pump or a turbo molecular pump 951 via a vacuum pipe 970 connected to an exhaust port 928. Further, the interior of a lens column 71 is connected with a turbo molecular pump 952 via a vacuum pipe 971 connected to an exhaust port 710. Those turbo molecular pumps 951 and 952 are connected to the dry vacuum pump 953 through vacuum pipes 972 and 973. (In the diagram, the single dry vacuum pump is used to serve both as a roughing vacuum pump of the turbo molecular pump and as a pump for vacuum exhausting of the chamber, but multiple dry vacuum pumps of separate systems may be employed for exhausting, depending on the flow rate of the high-pressure gas supplied to the hydrostatic bearings of the XY stage, the volume and inner surface area of the vacuum chamber and the inner diameter and length of the vacuum pipes.)

A high-purity inert gas ($N_2$ gas, Ar gas or the like) is supplied to a hydrostatic bearing of an XY stage 93 through flexible pipes 921 and 922. The gaseous molecules expelled from the hydrostatic bearing are diffused into the vacuum chamber and exhausted by the dry vacuum pump 953 through exhaust ports 919, 920a and 920b. Further, the gaseous molecules that have entered the differential exhausting mechanism and/or the charged particles beam irradiation space are sucked from the annular groove 927 or the tip portion of the lens column 72 through the exhausting ports 928 and 710 to be exhausted by the turbo molecular pumps 951 and 952; then, after having been exhausted by the turbo molecular pumps, the gaseous molecules are further exhausted by the dry vacuum pump 953.

In this way, the high-purity inert gas supplied to the hydrostatic bearing is collected in the dry vacuum pump and then exhausted.

On the other hand, the exhaust port of the dry vacuum pump 953 is connected to a compressor 954 via a pipe 976, and the exhaust port of the compressor 954 is connected to flexible pipes 931 and 932 via pipes 977, 978 and 979 and regulators 961 and 962. As a result of this configuration, the high-purity inert gas exhausted from the dry vacuum pump 953 is compressed again by the compressor 954 and then the gas, after being regulated to an appropriate pressure by the regulators 961 and 962, is supplied again to the hydrostatic bearings of the XY stage.

In this regard, since the gas to be supplied to the hydrostatic bearings is required to be as highly purified as possible in order not to have any water contents or oil and fat contents included therein, as described above, the turbo molecular pump, the dry pump and the compressor must have structures that prevent any water contents or oil and fat contents from entering the gas flow path. It is also considered effective for a cold trap, filter or the like (960) to be provided along the outlet side piping 977 of the compressor so as to trap any impurities such as water, oil or fat contents included in the circulating gas and prevent them from being supplied to the hydrostatic bearings.

This may allow the high purity inert gas to be circulated and reused, and thus allows the high-purity inert gas to be saved, while the inert gas would not remain desorbed into a room where the present apparatus is installed, thereby eliminating a fear that any accidents such as suffocation or the like would be caused by the inert gas.

It is to be noted that a circulation piping system is connected with the high-purity inert gas supply system 963, said system 963 serving not only to fill up, with the high-purity inert gas, all of the circulation systems including the vacuum chamber C, the vacuum pipes 970 to 975, and the pipes in compression side 976 to 980, prior to the commencement of the gas circulation, but also to supply gas if the flow rate of the circulation gas decreases for some reason.

Further, a single dry vacuum pump 953, if provided with a function to compress to a level equal to or greater than the atmospheric pressure, may be used as both the dry vacuum pump 953 and the compressor 954.

Further, as to the ultra-high vacuum pump to be used for exhausting the lens column, other pumps including an ion pump and a getter pump may be used instead of the turbo molecular pump. It is to be noted that in the case where reservoir type pumps are used, it is prohibited to build circulation systems in those areas. It is also evident that instead of the dry vacuum pump, other type of dry pumps, for example, a dry pump of diaphragm type, may be used.

(Second Embodiment)

Figure 26A:
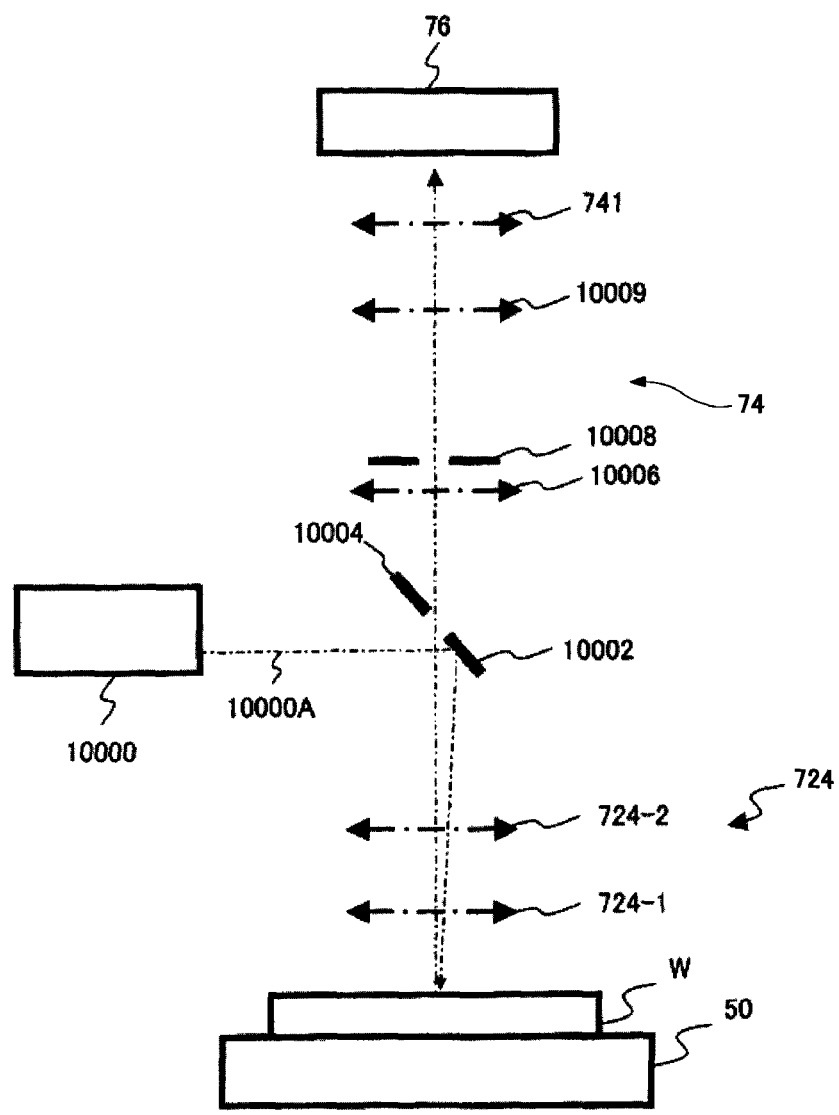
FIG. 26A is a diagram related to one embodiment of the present invention.

Here, FIG. 26A is referred to. FIG. 26A is a schematic diagram of an optical system used in the electron-optical device 70 of the inspection device 1 of the present invention related to the present embodiment. The electron-optical device 70 includes a light source 10000, a mirror 10002 and 10004, a lens optical system 724 (lenses 724-1 and 724-2), electrostatic lenses 10006 and 10009, numerical aperture 10008, electrostatic lens optical system 741 and a detection system 76. In the present embodiment, a UV laser beam source may be used as the light source 10000, however, as in the first embodiment, other light sources may be used if a photoelectron beam is emitted from a substrate which is irradiated with light from a light source such as UV, DUV, EUV light and laser, and X ray and X ray laser etc. Furthermore, the same reference symbols are used for the same structural components as the first embodiments.

Two laser beams are generated from the light source 10000 and each are irradiated to the mirrors 10002 and 10004, reflected by the mirrors reflection surfaces, and bent in a forward direction to a wafer WF on a stage device 50. The laser beam reflected by the reflection surface of the mirrors 10002 and 10004 pass through the lens optical system 724 and is irradiated as a primary beam onto the wafer WF on the stage 50. A two dimensional image produced by secondary emitting photoelectrons generated by the primary beam irradiated on the wafer is formed at a location of a field stop, after passing between the mirrors 10002 and 10004 and passing through numerical aperture 10008 via the electro-static lenses 10006, 10009 and magnified and projected by a subsequent stage of lens 741 and detected by the detection system 76.

Figure 26B:
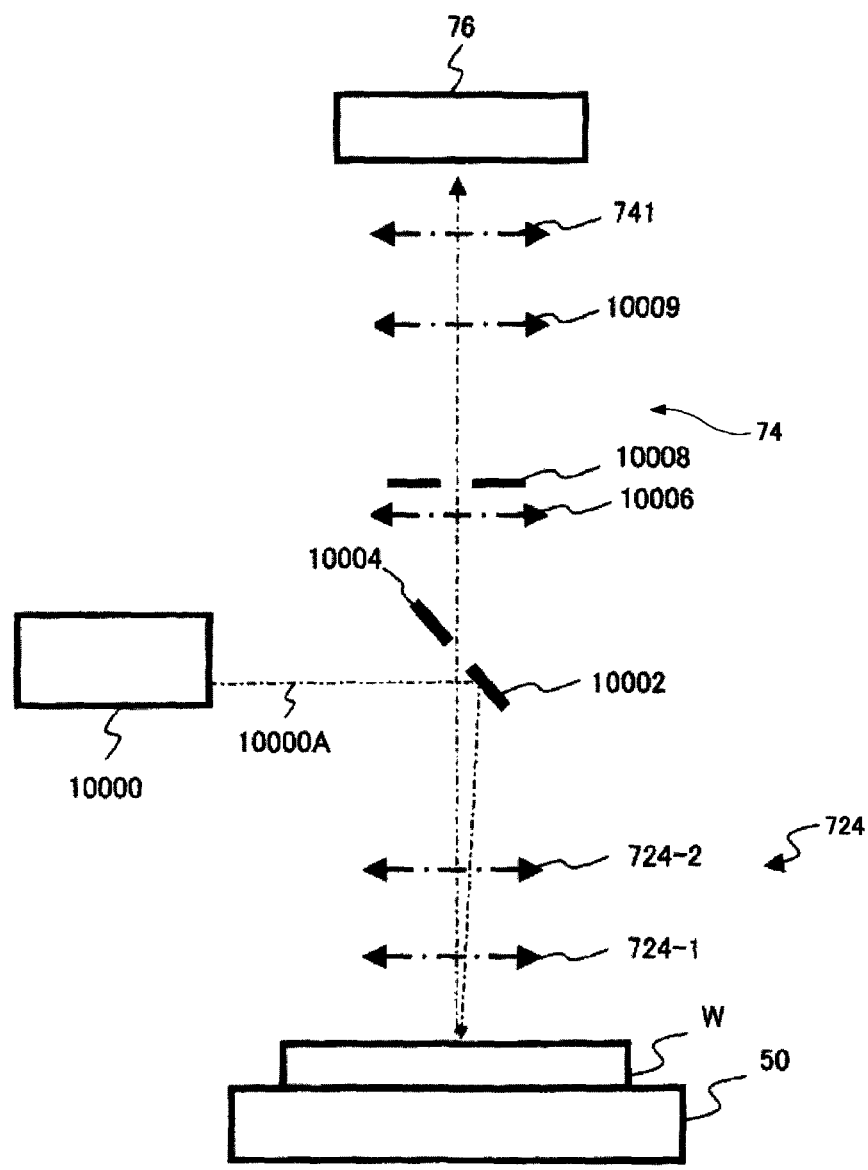
FIG. 26B is a diagram related to one embodiment of the present invention.
Figure 26C:
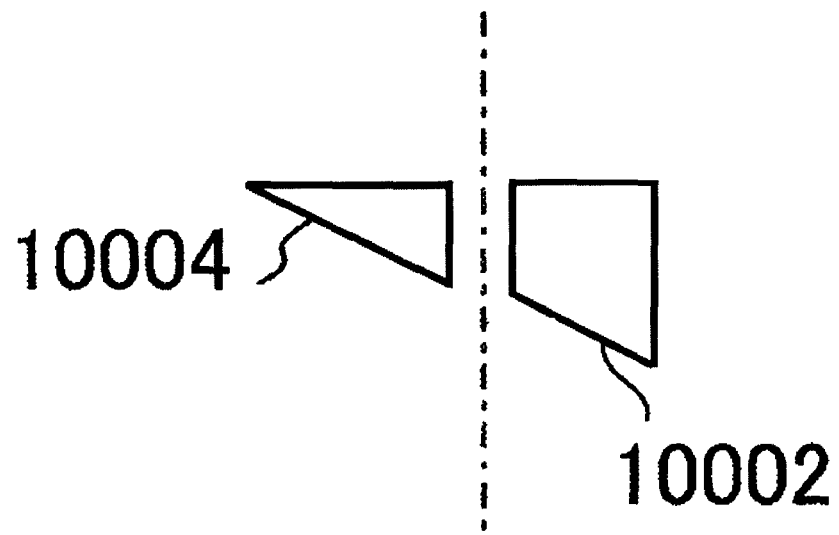
FIG. 26C is a diagram related to one embodiment of the present invention.
Figure 27A:
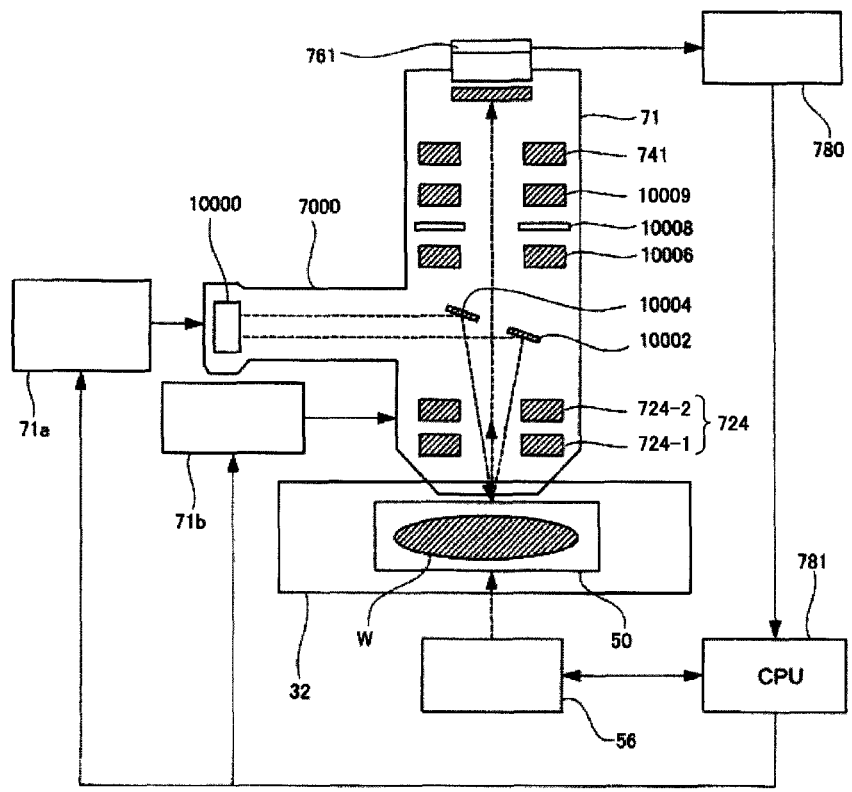
FIG. 27A is a diagram related to one embodiment of the present invention.
Figure 27B:
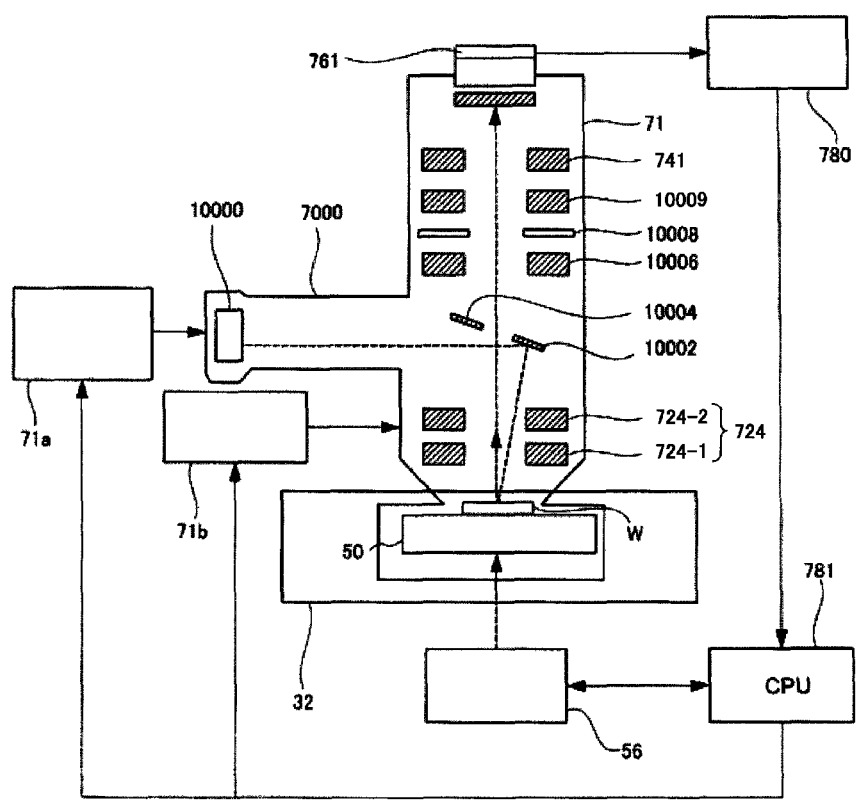
FIG. 27B is a diagram related to one embodiment of the present invention.

FIG. 27A is a schematic diagram of the electron-optical device 70 of the inspection device 1 of the present invention related to the present embodiment. In the present embodiment, apart from the structure of the primary lens system being different to the first embodiment, the remaining structure is the same and a reference may be made to the explanation of FIG. 9 in the first embodiment. In addition, in FIG. 26 and FIG. 27, an example of mentioned above uses the introduction of two laser beams being introduced, however, single laser beam may also be used. For example, in FIG. 26B, FIG. 27B, light or a laser is generated from the light source 10000, single laser beam 10000A is reflected by the mirror 10002 in the secondary optical system and arrives at the sample surface (there is no 10000B). At this time, for example, the mirror arranged within the secondary optical system is at position separate from the center axis of the secondary optical system of about 1~10 mm, and the reflection position of the mirror is also at a position separate from the center axis of the secondary optical system. Consequently, the irradiation angle to the sample is not perpendicular but is slanted. When the angle with respect to the secondary optical system axis (x axis) is θp, the irradiation light is irradiated onto the sample surface at this angle θp. With this method, light is irradiated onto a single edge of an uneven structure, and the other edge part falls into shadow and is difficult to irradiate. In this way, the contrast of one edge is increased and it is possible to take an image of an uneven structure pattern. In addition, not limited to two laser beams but a plurality of laser beams are possible. In the case of a plurality of laser beams, irradiation with more uniform beam can be performed because a laser with a different angle θp or light introduction image is possible. In addition, a beam with a strong bias can also be irradiated. A laser or light beams for example can have between 3~20 beams, and even more is possible. Uniformity improves when irradiation of an object at the center axis of the secondary optical system is performed, and an electron image having high uniformity can be obtained. Also, when a plurality of lasers or light beams are asymmetrically irradiated, a beam with a strong bias is irradiated. At this time, an image can be obtained having a locally high contrast. Alternatively, as is shown in FIG. 26C, the mirror has a single unit structure and it is possible to use the mirror with single laser beam or a plurality of laser beams. For example, a triangular unit structure with a hole at the center and an inclined surface has a mirror function. At this time, it is important to be able to coat the surface with a conductive material or be formed from a conductive material. Photoelectrons from the sample surface pass through the hole at the center. Consequently, when there is an insulation material bad effects are produced such as a change in trajectory or deterioration in aberration caused by a potential change due to charge up. The hole has a cross sectional shape but often has circular shape and may also have an angular shape. An axis object shape is preferred. A pentagon shape where all the surfaces are angular, or a shape in which the inclined surface and upper surface are planar and the side surfaces are curved is also possible. What is important is that surface roughness (for example, average surface roughness R) of the inclined surface having a mirror function is smaller than the wavelength of the irradiated laser or light. About ½~1/16 is preferred. When the surface roughness is larger than the wavelength, scattered light increases and reflection ratio decreases which leads to a drop in efficiency. In addition, in the structure of the mirror, even in two beams irradiation or a plurality of beams irradiation as shown in FIGS. 26, 27 and 29, the number of parts may be this single mirror. The mirror part 10002 and mirror part 10004 may be a single unit mirror. Specifically, it is possible to coat the mirror surface and other part with aluminum when the base material is a glass. At this time, the surface roughness of the mirror surface is a value smaller than the wavelength as mentioned above. In addition, either one of Au, Ru, Os, carbon, Pt, Ti or Cr may be coated or a plurality of materials may be coated in an electrode thin film state on the aluminum coat of the mirror surface.

(Third Embodiment)

In the present embodiment, the optical system for irradiating light generated from the light source 10000 to a substrate is different to the optical system used in the electron-optical device 70 of the inspection device 1 of the present invention related to the second embodiment. Other structural elements are the same as in the second embodiment and therefore their explanation is omitted here.

Figure 28:
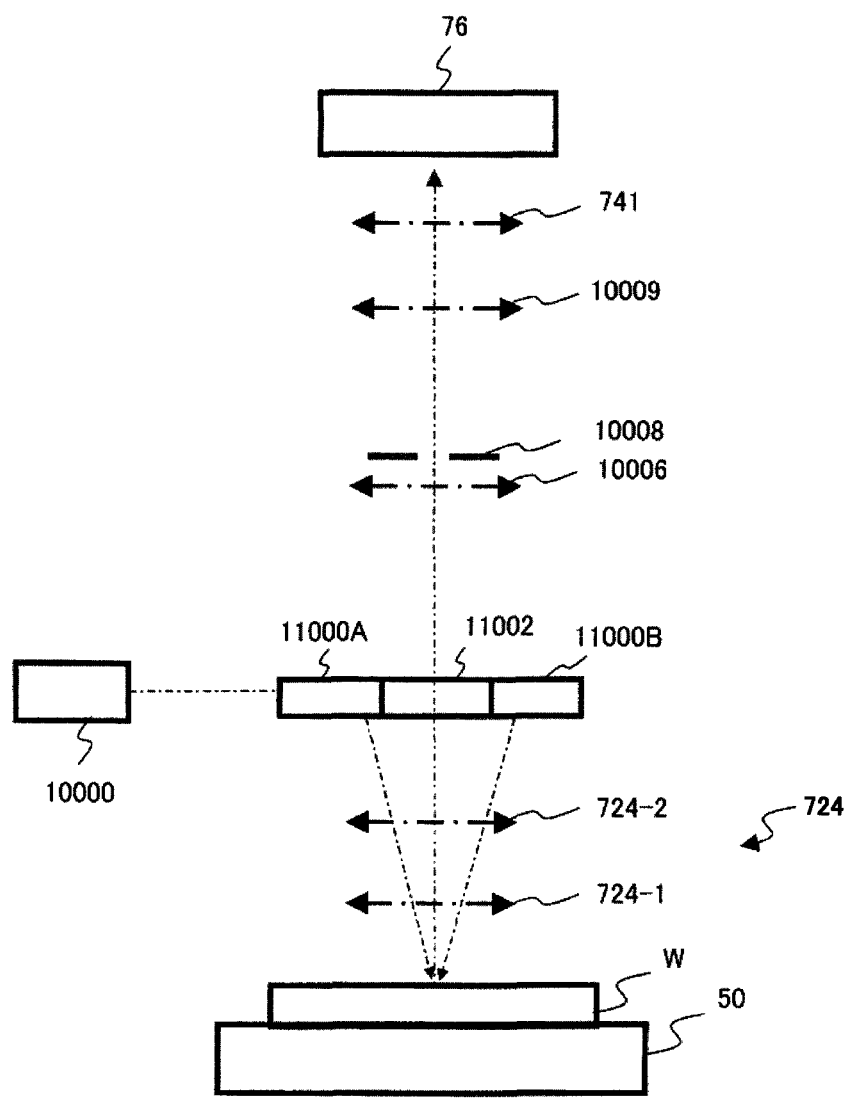
FIG. 28 is a diagram related to one embodiment of the present invention.

FIG. 28 is referred to. FIG. 28 is s a schematic diagram of an optical system used in the electron-optical device 70 of the inspection device 1 of the present invention related to the present embodiment. The electron-optical device 70 related to the present embodiment includes a light source 10000, a fiber plate 11000A and 11000B, a hole part 11002, a lens optical system 724 (lenses 724-1 and 724-2), electrostatic lenses 10006 and 10009, numerical aperture 10008, electrostatic lens optical system 741 and a detection system 76. In the present embodiment, a UV laser beam source may be used as the light source 10000, however, as in the first embodiment, other light sources may be used if a photoelectron beam is emitted from a substrate which is irradiated with a light from a light source such as UV, DUV, EUV light and laser, and X ray and X ray laser etc. Furthermore, the same reference symbols are used for the same structural components as the first embodiments.

Laser beam is generated from the light source 10000 and irradiated to each fiber plate 11000A and 11000B. The light irradiated to the fiber plates 11000A and 11000B is bent in a forward direction to a wafer WF on a stage device 50, passes through the lens optical system 724 and is irradiated as a primary beam onto the wafer WF on the stage 50. A two dimensional image produced by photoelectrons generated by the primary beam irradiated on the wafer is formed at a location of a field stop, after passing through the hole part 11002 and passing through numerical aperture 10008 via the electro-static lenses 10006, 10009 and magnified and projected by a subsequent stage of lens 741 and detected by the detection system 76.

(Fourth Embodiment)

In the present embodiment, the optical system which leads a two-dimensional secondary electron image generated by a primary beam irradiated onto a wafer is different to the optical system used in the electron-optical device 70 of the inspection device 1 of the present invention related to the second embodiment. Other structural elements are the same as in the second embodiment and therefore their explanation is omitted here.

Figure 29A:
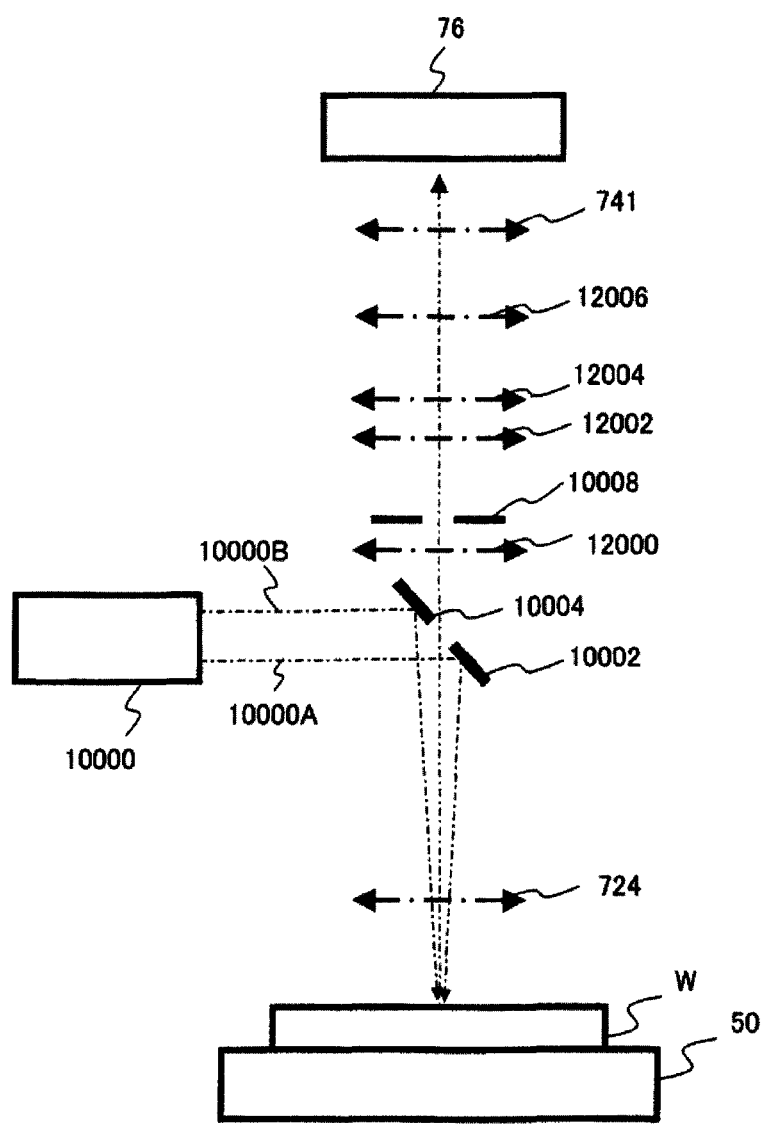
FIG. 29A is a diagram related to one embodiment of the present invention.

FIG. 29A is referred to. FIG. 29A is s a schematic diagram of an optical system used in the electron-optical device 70 of the inspection device 1 of the present invention related to the present embodiment. The electron-optical device 70 related to the present embodiment includes a light source 10000, mirrors 10002 and 10004, a lens optical system 724, a correction lens 12000, numerical aperture 10008, a fiber plate 11000A and 11000B, electrostatic lens optical system 741 and a detection system 76. In the present embodiment, a UV laser beam source may be used as the light source 10000, however, as in the first embodiment, other light sources may be used if a photoelectron beam is emitted from a substrate which is irradiated with a light from a light source such as UV, DUV, EUV light and laser, and X ray and X ray laser etc. Furthermore, the same reference symbols are used for the same structural components as the first embodiments.

Figure 29B:
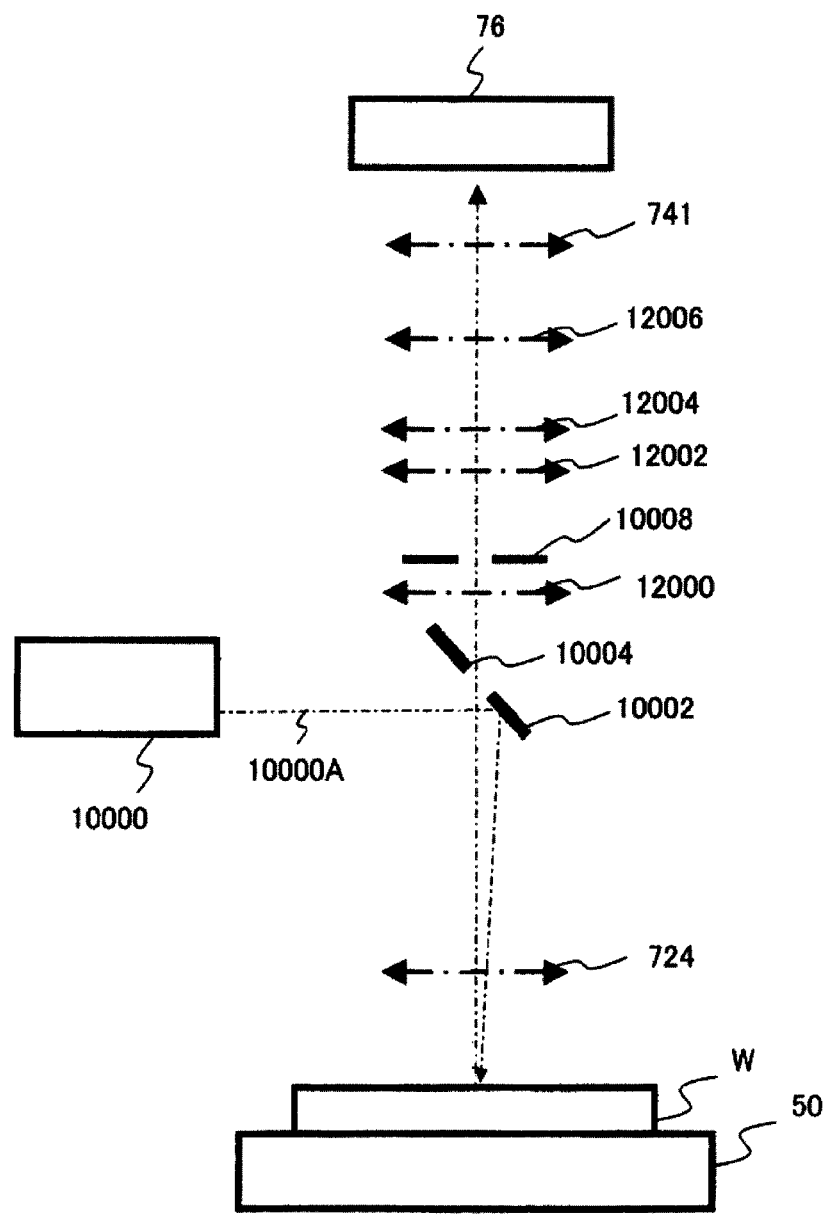

Two laser beams (10000A and 10000B) are generated from the light source 10000 and each are irradiated to the mirrors 10002 and 10004, reflected by the mirrors reflection surfaces, and bent in a forward direction to a wafer WF on a stage device 50. The laser beam reflected by the reflection surface of the mirrors 10002 and 10004 pass through the lens optical system 724 and is irradiated as a primary beam onto the wafer WF on the stage 50. A two-dimensional image produced by secondary emitting electrons generated by the primary beam irradiated on the wafer converges at a location of the numerical aperture (NA) 10008 via the correction lens 12000 after passing between the mirrors 10002 and 10004 and a cross over is formed. The image is magnified and projected by a subsequent stage field lens 12002, a zoom lens 12004, a zoom lens 12006 and the electro-static lens system 741 and detected by the detection system 76. Off-axis aberration is corrected by the field lens 12002, continuous magnification setting becomes possible using the zoom lenses and an image is formed in the detector by the electro static lenses 741, magnified and projected. Furthermore, in the present embodiment, 1 system laser may be introduced as is shown in FIG. 29B. The effects in this case are the same as the effects explained using FIG. 26B and FIG. 27B.

(Fifth Embodiment)

In the present embodiment, the optical system for irradiating light generated from the light source 10000 to a substrate is different to the optical system used in the electron-optical device 70 of the inspection device 1 of the present invention related to the second embodiment. Other structural elements are the same as in the second embodiment and therefore their explanation is omitted here.

Figure 30:
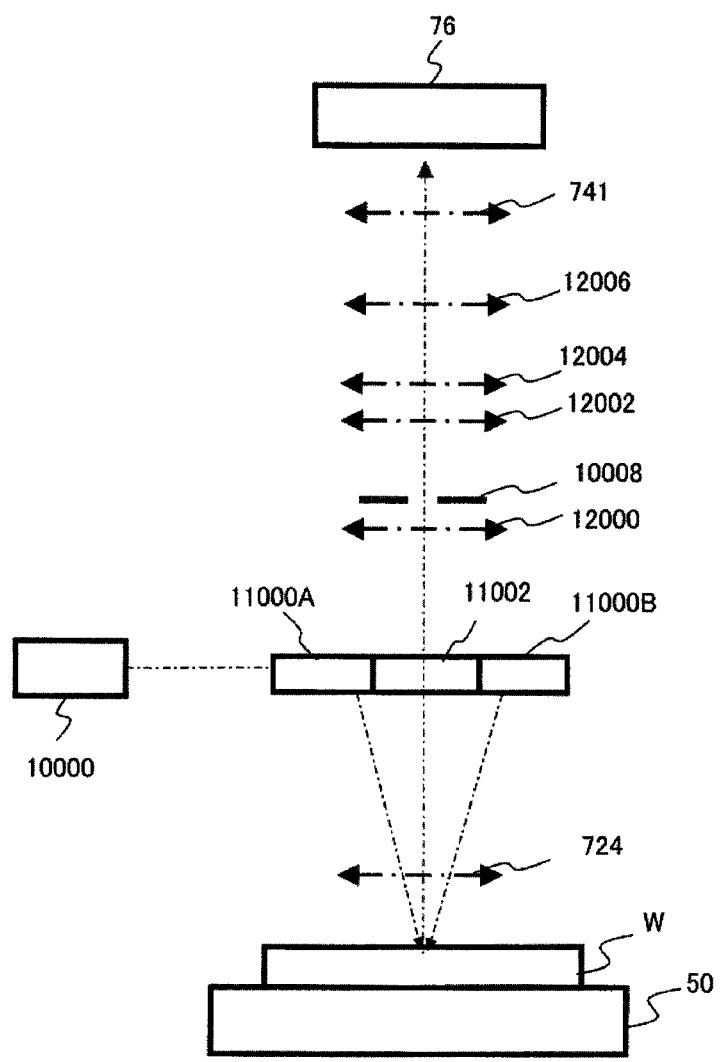
FIG. 30 is a diagram related to one embodiment of the present invention.

FIG. 30 is referred to. FIG. 30 is s a schematic diagram of an optical system used in the electron-optical device 70 of the inspection device 1 of the present invention related to the present embodiment. The electron-optical device 70 related to the present embodiment includes a light source 10000, a fiber plate 11000A and 11000B, a hole part 11002, a lens optical system 724 (cathode lenses 724-1 and 724-2 (not shown in the diagram)), correction lens 12000, numerical aperture (NA) 10008, field lens 12002, zoom lens 12004, zoom lens 12006, electrostatic lens optical system 741 and a detection system 76. In the present embodiment, a UV laser beam source may be used as the light source 10000, however, as in the first embodiment, other light sources may be used if a photoelectron beam is emitted from a substrate which is irradiated with a light from a light source such as UV, DUV, EUV light and laser, and X ray and X ray laser etc. Furthermore, the same reference symbols are used for the same structural components as the first embodiments.

Two laser beams is generated from the light source 10000 and irradiated to each fiber plate 11000A and 11000B. The light irradiated to the fiber plates 11000A and 11000B is irradiated as a primary beam onto the wafer WF on the stage 50 after passing through the lens optical system, 724. A two dimensional image produced by secondary emitting electrons generated by the primary beam irradiated on the wafer is formed at a location of a field stop via the correction lens 12000 and is magnified and projected by a subsequent stage field lens 12002, zoom lens 12004, zoom lens 12006 and the electro-static optical system 741 741 and detected by the detection system 76.

(Sixth Embodiment)

In the present embodiment, the optical system is different to the optical system used in the electron-optical device 70 of the inspection device 1 of the present invention related to the second embodiment in the point where a plurality of lights having different wavelengths are irradiated to a substrate. Other structural elements are the same as in the second embodiment and therefore their explanation is omitted here.

Figure 31:
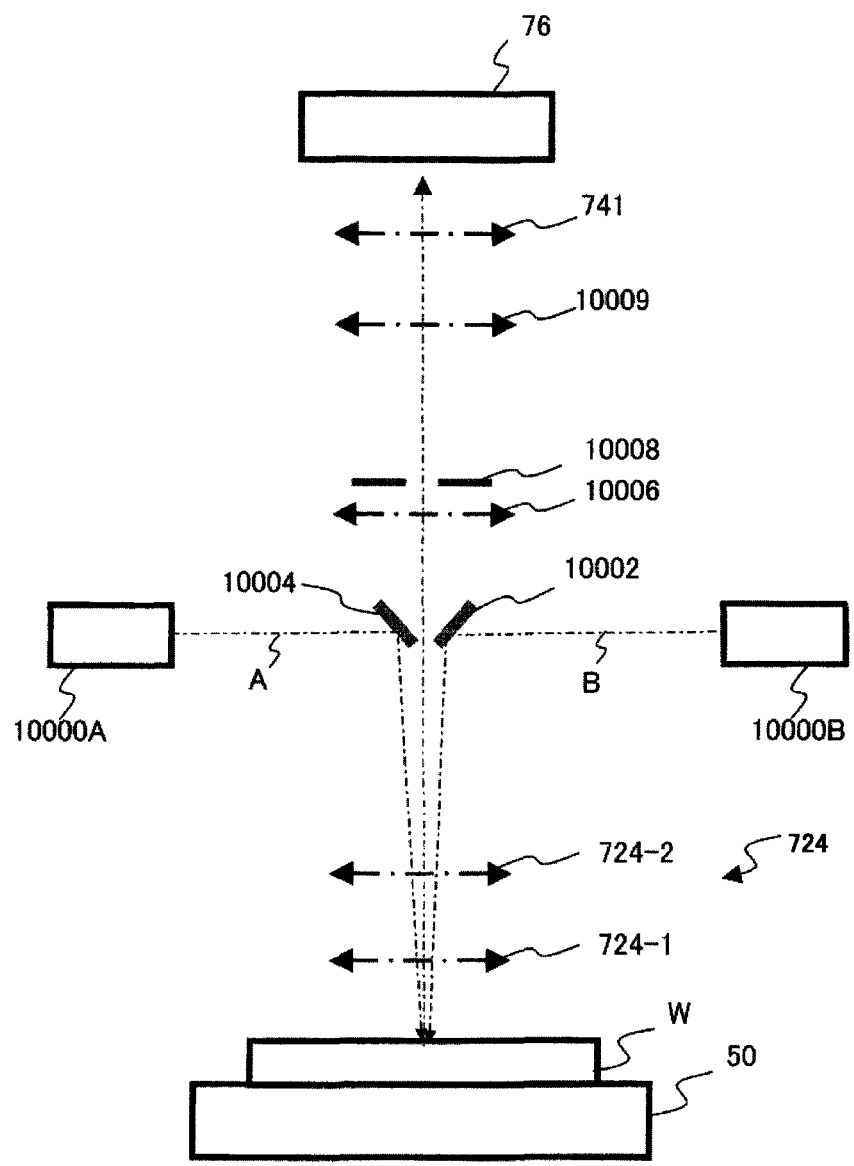
FIG. 31 is a diagram related to one embodiment of the present invention.

FIG. 31 is referred to. FIG. 31 is s a schematic diagram of an optical system used in the electron-optical device 70 of the inspection device 1 of the present invention related to the present embodiment. The electron-optical device 70 related to the present embodiment includes a light source 10000A (wavelength λ1) and 1000B (wavelength λ2), mirrors 10002 and 10004, a lens optical system 724 (cathode lenses 724-1 and 724-2), electrostatic lenses 10006, 10009, numerical aperture (NA) 10008, and electrostatic lens optical system 741 and a detection system 76. In the present embodiment, a DUV laser beam source may be used as the light source 10000A and light source 10000B, however, as in the first embodiment, other light sources may be used if an photoelectron beam is emitted from a substrate which is irradiated with a light from a light source such as UV, DUV, EUV light and laser, and X ray and X ray laser etc. Furthermore, the same reference symbols are used for the same structural components as the first embodiments.

Two laser beams having different wavelengths, A (wavelength λ1) and B (wavelength λ2) are generated from the light source 10000A and 10000B and each are irradiated to the mirrors 10002 and 10004, reflected by the mirrors reflection surfaces, and bent in a forward direction to a wafer WF on a stage device 50. The laser beam reflected by the reflection surface of the mirrors 10002 and 10004 pass through the lens optical system 724 and is irradiated as a primary beam onto the wafer WF on the stage 50. The laser beams having different wavelengths A (λ1) and B (λ2) may be irradiated onto the wafer simultaneously or alternately irradiated. A two dimensional secondary electron image generated by the primary beam irradiated on the wafer is formed at a location of a field spot after passing between the mirrors 10002 and 10004, passing through the numerical aperture 10008 via the electrostatic lenses 10006 and 10009, magnified and projected by the subsequent stage lens 741 and detected by the detector system 76.

Furthermore, in the present embodiment, a light source having two different wavelengths was used, however, a light source having more 2 or more different wavelengths may also be used.

(Seventh Embodiment)

In the present embodiment, the irradiation direction of light from a light source to a wafer substrate is different to the optical system used in the electron-optical device 70 of the inspection device 1 of the present invention related to the second embodiment. Other structural elements are the same as in the second embodiment and therefore their explanation is omitted here.

Figure 32A:
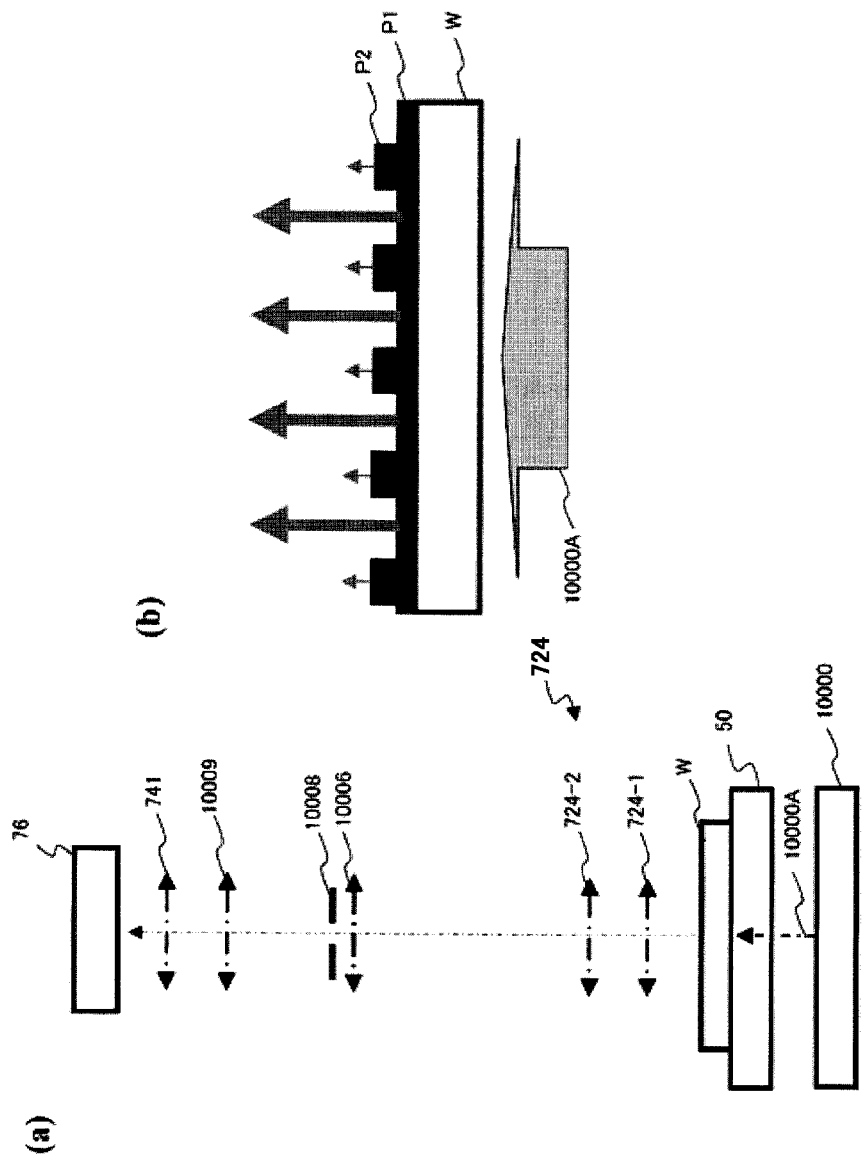
FIG. 32A is a diagram related to one embodiment of the present invention.

FIG. 32A is referred to. FIG. 32A is s a schematic diagram of an optical system used in the electron-optical device 70 of the inspection device 1 of the present invention related to the present embodiment. The electron-optical device 70 related to the present embodiment includes a light source 10000, a lens optical system 724 (cathode lenses 724-1 and 724-2), electrostatic lenses 10006, 10008, numerical aperture 10008, electrostatic lens optical system 741 and a detection system 76. In the present embodiment, a DUV laser beam source may be used as the light source 10000, however, as in the first embodiment, other light sources may be used if a photoelectron beam is emitted from a substrate which is irradiated with a light from a light source such as UV, DUV, EUV light and laser, and X ray and X ray laser etc. Furthermore, the same reference symbols are used for the same structural components as the first embodiments.

In FIG. 32A (a), laser 10000A is generated from the light source 10000 and irradiated as a primary beam on the back surface of the sample W on the stage device 50. When the laser 10000A irradiated as a primary beam is irradiated onto the sample W, a two dimensional secondary electron image which follows the pattern on the wafer is produced, and the two dimensional image of the photoelectron beam passes through the cathode lenses 724-1 and 724-2, is converged by the electrostatic lens 10006, a cross over is formed in the vicinity of a location of the numerical aperture (NA) 10008, and the electrostatic lenses 10006 and 10009 include a zoom function which can control the magnification. Following this, the image is magnified and projected by the subsequent stage lens 741 and detected by the detector system 76.

FIG. 32A (b) shows photoelectrons being emitted from the surface P1 and P2 of a wafer W. At this time, when P1 is a material which allows photoelectrons to be easily generated and P2 is a material which does not allow photoelectrons to be easily generated, many photoelectrons are generated from P1 by laser irradiation from the back surface, while only a few photoelectrons are generated from P2. Therefore, a pattern having a contrast due to photoelectrons can be obtained with respect to a pattern shape formed by P1 and P2.

The example shown in FIG. 32A above used irradiation of a laser or light from the back surface of a sample. However, an example of an embodiment where a laser or light is irradiated from the front surface is described in FIG. 32B, FIG. 32C,
FIG. 32D and FIG. 32E. The laser or light which is used is a DUV laser beam source, however, as in the first embodiment, other light sources may be used if an photoelectron beam is emitted from a substrate which is irradiated with a light from a light source such as UV, DUV, EUV light and laser, and X ray and X ray laser etc.

Figure 32C:
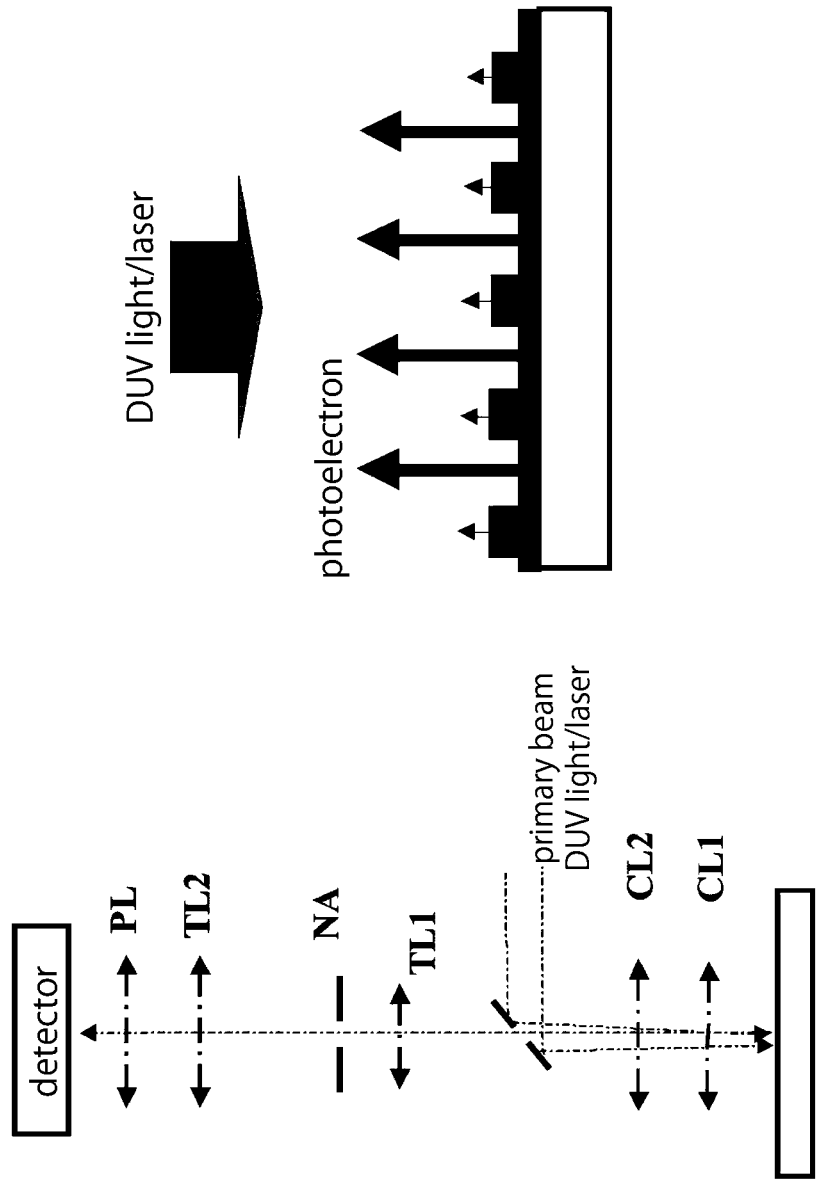
FIG. 32C is a diagram related to one embodiment of the present invention.

FIG. 32B and FIG. 32C include the same devices, irradiation system and secondary optical system as FIG. 8, 9, 26A, 27A and 29A. In addition, in FIG. 32B and FIG. 32C and example is shown whereby a contrast is formed when the sample has asperities, the amount of photoelectrons emitted from the hollow and bump parts is different, and an image having a high resolution is possible. When the material of the sample uneven structure parts is different, the amount of photoelectrons emitted from the hollow part is more than the bump part and the reverse is often true due to the wavelength of primary beam irradiation. While a more detailed example is explained below, this is an example where a high resolution can be achieved due to the difference in the amount of emitted photoelectrons.

Figure 32D:
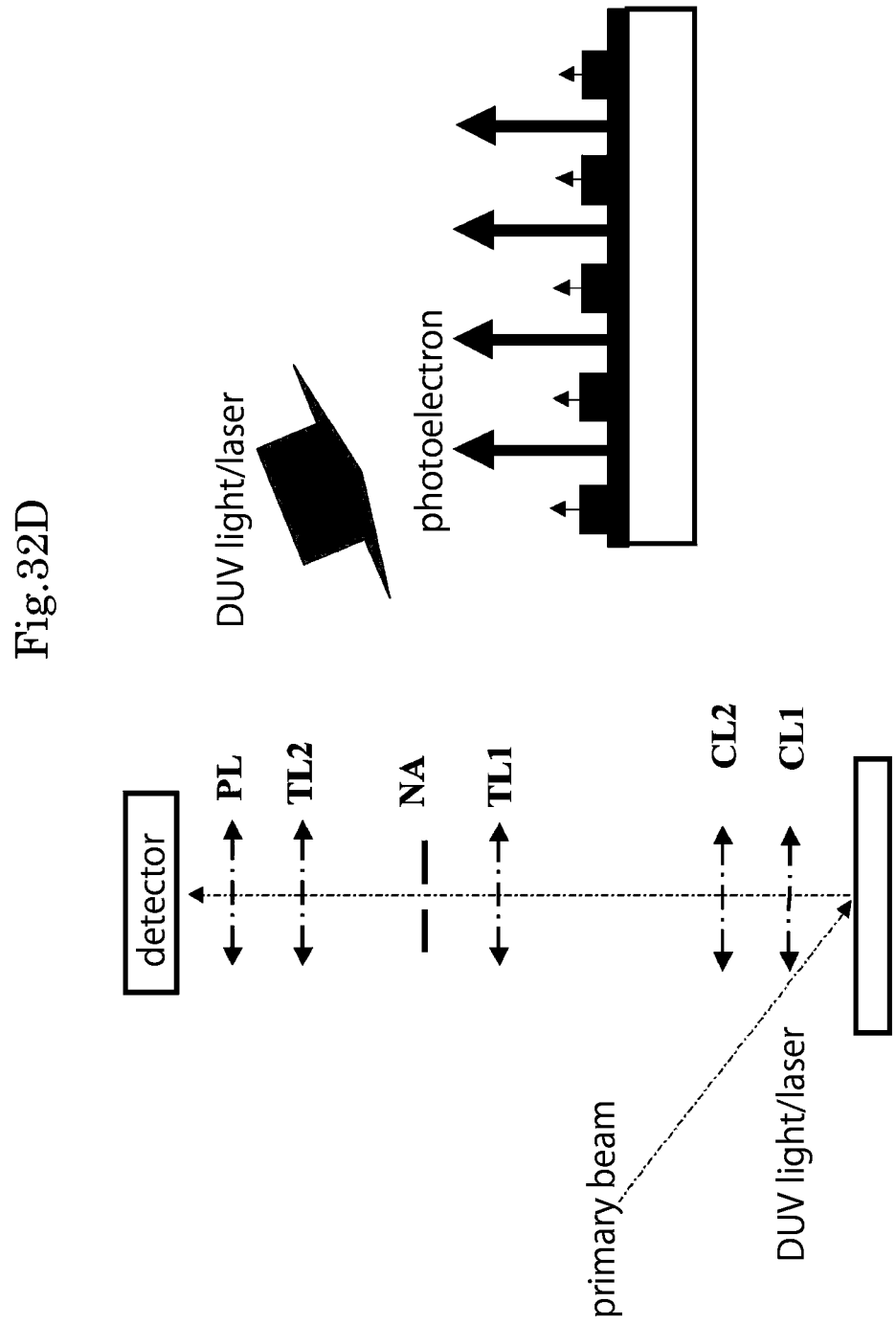
FIG. 32D is a diagram related to one embodiment of the present invention.
Figure 32E:
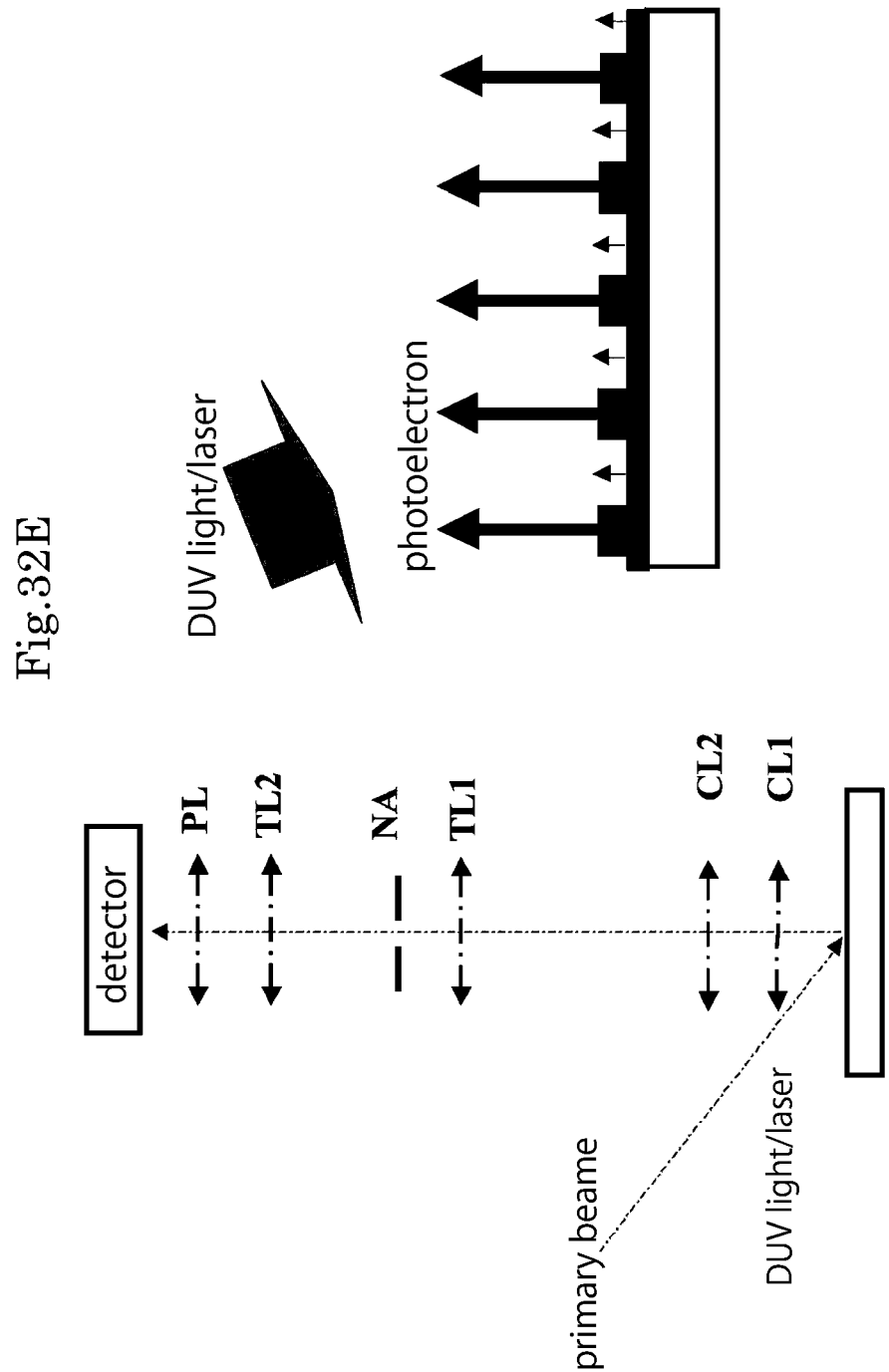
FIG. 32E is a diagram related to one embodiment of the present invention.

In addition, FIG. 32D and FIG. 32E show image formation by the difference in the amount of photoelectrons from the sample surface having asperities, and also shown an example in the case where a primary beam irradiation system irradiates at a different angle the same as is shown in FIG. 32B and FIG. 32C. While FIG. 32B and FIG. 32C show an example in the case where irradiation is performed at an angle almost perpendicular to the surface of the sample, FIG. 32D and FIG. 32E show an example in the case where irradiation is performed at a slanted angle. In this case, the primary beam is introduced using a laser, mirror and lens, however, it is also possible to irradiate the surface of a sample using fiber. In the case, of a short wavelength such as UV, DUV, EUV and X rays, the transmittance rate of a laser or light is sometimes poor in a usual silica fiber. Laser or light can be transmitted efficiently by using hollow fiber or a hollow pipe.

In addition, as described above, with respect to the irradiation angle of a primary beam, because a sample having a pattern sometimes receives the effects of an angle, at this time, optimization of the angle of light or laser angle which is irradiated, that is, the best S/N of a pattern defect or conditions with high contrast are selected and it is possible to select the angle at which to irradiate which us important (Eighth Embodiment)

Electron Optical Device arranged with a primary optical system using in electron irradiation instead of a primary system used in light irradiation.

Figure 33:
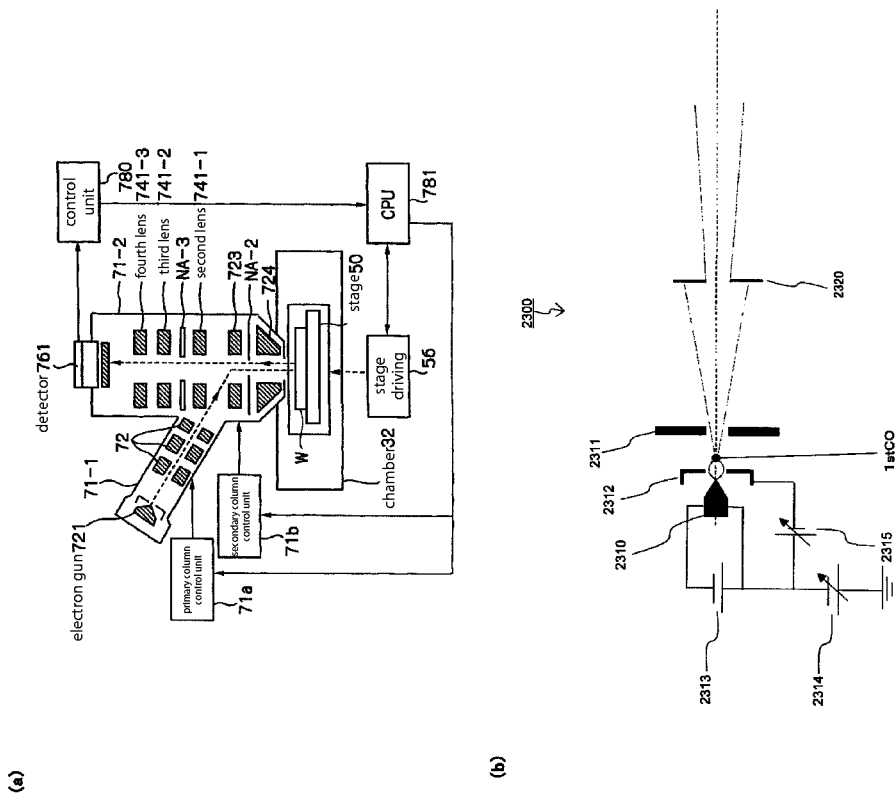
FIG. 33 is a diagram related to one embodiment of the present invention.

Irradiating a sample surface with light or a laser has been described up to this point, and the generation of photoelectrons from the sample surface. Here, instead of irradiating light, an embodiment of a primary system which irradiates an electron beam is described. First, an example of an inspection device arranged with a general electron gun (beam generator) is shown in FIG. 33. FIG. 33 (*a*) show the entire structure, FIG. 33 (*b*) is an exploded schematic diagram of an electron gun part. However, a partial structure has been omitted.

In FIG. 33 (*a*), the inspection apparatus has a primary column 71-1, a secondary column 71-2 and a chamber 32. An electron gun 721 (beam generator) is arranged on the inside of the primary column 71-1, and a primary optical system 72 is disposed along the optical axis of an electron beam (a primary electron beam) irradiated from the electron gun 721. Further a stage 50 is installed in the interior of the chamber 32 and a sample W is loaded on the stage 50. On the other hand, in the interior of the secondary column 71-2, a cathode lens 724, a numerical aperture NA-2, a Wien filter 723, a second lens 741-1, a field aperture NA-3, a third lens 741-2, a fourth lens 741-3 and a detector 761 are located on the optical axis of the secondary electron beam emanating from the sample W. It is to be noted that the numerical aperture NA-3 corresponds to an aperture diaphragm, which is a thin plate made of metal (Mo or the like) having a circular aperture formed therein. Herein, the numerical aperture NA-2 is arranged with an aperture section so as to be at a focused location of the primary electron beam and also at a focusing location of the cathode lens 724. Accordingly, the cathode lens 724 and the numerical aperture NA-2 construct a telecentric electronic optical system. In particular, the cathode lens 724 sometimes forms both telecentric electron optical systems in which a first intermediate image forming point is formed near the E×B center by a two stage tablet lens. Compared to a single telecentric or no telecentric it is possible to reduce aberration and achieve two dimensional electron image with a wide field and high resolution image forming. That is, it is possible to realize ½~⅓ the aberration.

On the other hand, the output from the detector 761 is input into a control unit 780, and the output from the control unit 780 is input into a CPU 781. A control signal from the CPU 781 is input into a primary column control unit 71a, a secondary column control unit 71b and a stage driving mechanism 56. The primary column control unit 71a controls a lens voltage in the primary optical system 72, and the secondary column control unit 71b controls lens voltages in the cathode lens 724 and the second lenses 741-1 to the fourth lens 741-3 and also an electromagnetic field applied to the Wien filter 723. Further, the stage driving mechanism 56 transmits position data of the stage to the CPU 781. Still further, the primary column 71-1, the secondary column 71-2 and the chamber 32 are connected to the vacuum exhausting system (not shown in the diagram) and exhausted by a turbo pump in the vacuum exhausting system so as for the interior thereof to be maintained in vacuum.

(Primary Beam)

The primary electron beam from the electron gun 721 (beam generator) enters into the Wien filter 723 while receiving a lens effect caused by the primary optical system 72. Herein, LaB6 may be used for a chip of the electron gun, which is a rectangular or elliptical flat, curved surface (for example about r=50 μm) and from which a high current can be emitted. Further, the primary optical system 72 may use an electrostatic (or electromagnetic) quadrupole or octopole lens, asymmetric with respect to a rotating axis. This lens, similar to what is called a cylindrical lens, can cause a focusing and a divergence in the X and the Y axes respectively. Such a configuration comprising two or three steps of these lenses to optimize respective lens conditions allows the beam irradiation region on the sample surface to be formed into a rectangular or elliptical shape as desired without any loss of irradiated electrons. Specifically, in the case of the electrostatic lenses being used, four cylindrical rods may be used. Each two opposite electrodes are made to be equal in potential and reverse voltage characteristics are given thereto. It is to be appreciated that a lens formed in the shape of a quarter of a circular plate used commonly in the electrostatic deflector, rather than the cylindrical shape, may be used for the quadrupole lens. That case allows for the miniaturization of the lens.

The primary electron beam after passing through the primary optical system 72 is forced by the deflecting effect from the Wien filter 723 so as to deflect the trajectory thereof. In the Wien filter 723, the magnetic field is crossed with the electric field at right angles, and only the charged particles satisfying the Wien condition of E=vB are advanced straight ahead, and the orbits of the other charged particles are deflected, where the electric field is E, the magnetic field B, and the velocity of the charged particle v. A force FB by the magnetic field and another force FE by the electric field may be generated against the primary beam, and consequently the primary beam is deflected. On the other hand, the force FB and the force FE are reversely applied to the secondary beam and those forces are cancelled to each other, so that the secondary beam is allowed to go directly forward. A lens voltage of the primary optical system 72 has been determined beforehand such that the primary beam is formed into an image at the aperture portion of the numerical aperture NA-2. That numerical aperture NA-2 prevents any excess electron beams to be dispersed in the apparatus from reaching to the sample surface and thus prevents charging or contamination in the sample W. Further, since the numerical aperture NA-2 and the cathode lens 724 together form the telecentric electronic optical system, the primary beams that have passed through the cathode lens 724 may turn to be parallel beams, which are irradiated uniformly and similarly against the sample W. That is to say, it accomplishes what is called in an optical microscope, the Koehler illumination.

(Secondary Beam)

When the primary bean is irradiated against the sample, secondary electrons, reflected electrons or back-scattering electrons are generated as the secondary beam from the beam irradiated surface of the sample. The secondary beam passes through the lens while receiving a lens effect from the cathode lens 724. It is to be noted that the cathode lens 724 is composed of three or four electrodes. Among those electrodes, the one at the lowest position is designed to form a positive electric field between the potentials in the sample W side and itself, and to take in electrons (particularly, secondary emitting electrons with smaller directivities and mirror electrons) so that the electrons may be efficiently introduced into the lens. Further, the lens effect takes place in such a way that voltages are applied to the first and the second electrodes of the cathode lens 724 and the third electrode is held to zero potential. Alternatively, a voltage is applied to the first, second and third electrodes and the fourth electrode is held to zero potential. The third electrode is used for focus adjustment when there are four electrodes. On the other hand, the numerical aperture NA-2 is disposed at the focal position of the cathode lens 724, that is, the back focal position with respect to the sample W. Accordingly, the trajectories of electron beams originating from the center of the field of view (off-axis) also become the parallel beams and pass through the central location in this numerical aperture NA-2 without being kicked out any further. It is to be appreciated that the numerical aperture NA-3 serves to reduce lens aberrations of the cathode lens 724, second lens 741-1 to the fourth lens 741-3 for the secondary beams. Those secondary beams having passed through the numerical aperture NA-2 may not affected by the deflecting effect from the Wien filter 723 but may keep on going straight through the filter. It is to be noted that varying the electromagnetic field applied to the Wien filter 723 may allow only electrons having specified energies (for example, secondary electrons, reflected electrons or back-scattering electrons) to be introduced into the detector 761. The cathode lens 724 is an important lens for determining aberration of the secondary emitting electrons generated form the sample surface. Consequently, a large magnification can not be expected. Therefore, a dual telecentric structure is formed as a cathode lens having a two stage tablet lens structure in order to reduce aberration. Furthermore, an intermediate image formation for reducing aberration (astigmatism etc) which is generated by the Wien filter formed by E×B, is set near the center location vicinity of E×B. In this way, the effect of controlling an increase in aberration is significant.

Also, beams are converged by the second lens 741-1 and a cross over if formed near the vicinity of the numerical aperture NA-3. A zoom lens function is obtained by the second lens 741-1 and third lens 741-2, a control of magnification becomes possible. The fourth lens 741-3 exists at this subsequent stage and a magnified image is formed on the surface of the detector. The fourth lens has a five stage lens structure with stages 1, 3, 5 being grounded. A positive high voltage is applied to the second and fourth stages and a lens is formed. At this time, the second stage includes a field lens function and second intermediate image forming is performed in this vicinity. At this time, it is possible to correct off-axis aberration using the field lens function. In this way, here, image forming is performed a total of three times. Furthermore, the cathode lens 724 may be combined with the second lens 741-1 to form an image on the detector surface (total of two times). In addition, each of the second lens 741-1 to the fourth lens 741-3 should be a lens symmetrical with respect to a rotating axis of the kind referred to as a uni-potential lens or Einzell lens. Each lens is composed of three electrodes, in which typically the outer two electrodes have zero potentials and a voltage applied to the center electrode is used to causes a controlling lens effect. Further, a field aperture FA-2 (not shown in the diagram) is located in the intermediate image forming point. This field aperture FA-2 is arranged near the second stage when the fourth lens 741-3 has five lens stages, and is arranged near the first stage when the fourth lens 741-3 has three lens stages. The field aperture FA-2 which constrains the field of view to be limited to a required range, similar to a field stop in an optical microscope, for the case of an electron beam, cooperatively blocks any excess beams so as to prevent charging and/or contamination of the detector 761. The secondary beam is magnified and projected by the secondary optical system and formed into an image on the detection plane of the detector 761. The detector 761 comprises a MCP for amplifying an electron, a fluorescent screen for converting the electrons into light, lenses and other optical elements for use as a relay and transmitting an optical image between the vacuum system and external components, and an image sensor (CCD or the like). The secondary beam is formed into an image on the MCP detection plane and amplified, and then the electrons are converted into light signals by the fluorescent screen, which are in turn converted into photoelectric signals by the image sensor. The control unit 780 reads out the image signal of the sample from the detector 761 and transmits it to the CPU 781. The CPU 781 performs a defect inspection of the pattern by template matching and so forth from the image signal. On the other hand, the stage 50 is adapted to be movable in the X and Y directions by a stage driving mechanism 56. The CPU 781 reads the position of the stage 50 and outputs a drive control signal to the stage driving mechanism 56 to drive the stage 50, allowing for sequential detection and inspection of the images.

Thus, in the inspection apparatus according to the present embodiment, since the numerical aperture NA-2 and the cathode lens 724 comprise the telecentric electron optical system, therefore the primary beam may be irradiated uniformly against the sample. That is, it accomplishes the Koehler illumination. Further, as to the secondary beam, since all of the principle beams from the sample W enter the cathode lens 724 at a right angle (parallel to the optical axis of the lens) and pass through the numerical aperture NA-2, therefore the peripheral beam would not be kicked out thus preventing deterioration of image brightness in the periphery of the sample. In addition, although a variation of the energy pertaining to the electrons gives a different focal position, which causes what is called a magnification chromatic aberration (especially for the secondary electrons, since the energies thereof are varied to a great extent, the magnification chromatic aberration is rather great), the arrangement of the numerical aperture NA-2 at the focal position of the cathode lens 724 makes it possible to control the magnification chromatic aberration so that it is kept low.

On the other hand, since a change of the magnification factor is executed after the beam has passed through the numerical aperture NA-2, any changes in the determined magnification factor in the lens condition for the third and the fourth lenses 741-2 and 741-3 can still bring a uniform image over the field of view to be obtained in the detection side. It should be appreciated that although an even and uniform image can be obtained in the present embodiment, typically, increasing the magnification may problematically cause deterioration in the brightness of the image. Accordingly, in order to improve this problematic condition, when the lens condition for the secondary optical system is changed to vary the magnification factor, the lens condition for the primary optical system should be controlled such that the effective field of view on the sample determined in association with the magnification and the electron beam to be irradiated on the sample may be equally sized.

That means, as the magnification is increased, consequently the field of view gets smaller, but when the irradiation beam current of the electron beam is increased at the same time, the signal density of the detected electron can be kept at a constant level and the brightness of the image may be prevented from deterioration even if the beam is magnified and projected in the secondary optical system. Further, although in the inspection apparatus according to the present embodiment, a Wien filter 723 has been employed, which deflects the trajectories of a primary beam but allows a secondary beam to go straight forward, the application is not limited to this and the apparatus may employ a Wien filter with another configuration in which the primary beam is allowed to go straight forward but the orbit of the secondary beam is deflected. Still further, although in the present embodiment, a rectangular cathode and a quadrupole element lens are used to form a rectangular beam, the application is not limited to this and, for example, a rectangular beam or elliptical beam may be formed from a circular beam, or the circular beam may be passed through a slit to extract the rectangular beam.

In this example, two numerical apertures, numerical aperture NA-2 and numerical aperture NA-3 are arranged. These can be used separately according to the amount of irradiated electrons. In the case where the amount of irradiated electrons to a sample is small, for example 0.1~10 nA, an appropriate beam diameter, for example, $\phi 30$~$\phi 300$ μm is used in order to reduce aberration of the primary beam and secondary beam using the numerical aperture NA-2. However, when the amount of irradiated electrons increases, charge up occurs due to contamination being attached to the numerical aperture NA-2 and reversely image quality sometimes degraded. At this time, the numerical aperture NA-2 with a comparatively large hole diameter, for example, $\phi 500$~$\phi 3000$ μm is used in the cut of periphery stray electrons. In addition, the numerical aperture NA-3 is used for determining stipulation of aberration and rate of transmittance of the secondary beam. Few contaminants are attached to the numerical aperture NA-3 because the primary beam is not irradiated and there is no deterioration in image quality due to charge up. Consequently, it is extremely effective to use a numerical aperture after selecting the numerical aperture diameter according to the size of the amount of irradiated electrons.

When this form of primary beam electron irradiation is performed, in the semiconductor inspection device 1 which uses an electron gun as the primary optical system 72 of the electron optical device 70, a problem occurs whereby the energy band of an electron becomes wider in the case of attempting to obtain a large irradiation current. This is explained in detail below using the diagrams. FIG. 33 (*b*) is an exemplary diagram of the primary optical system 72 of the electron optical device 70 arranged with a general electron gun 2300.

In the electron gun 2300 a heating current is passed through a cathode 2310 via a heating power supply 2313 for generating thermal electrons. In addition, an acceleration voltage Vacc is set to the cathode 2310 by an acceleration power supply 2314. On the other hand, a voltage is applied to an anode 2311 so that the cathode 2313 is made to have a relatively positive voltage, for example, a voltage difference of 3000~5000V. When the cathode 2310 is −5000V the anode 2311 may be 0V. At this time, the amount of emission is controlled by a voltage applied to a Wehnelt 2312. The Wehnelt 2312 is superimposed by the acceleration voltage Vacc, for example, a superimposed voltage of 0~−1000V. When the voltage difference with Vacc is large the amount of emission decreases, and when it is small the amount of emission increases. In addition, the cross over (first cross over: 1st CO) location which can be first set by a Wehnelt voltage is misaligned in an axis direction. In addition, if the center of the cathode and the center of the Wehnelt, anode are misaligned, a misalignment also occurs in a perpendicular x, y direction to the z axis, and the emitted emission becomes wider. Within this, a field aperture FA2320 selects an effective beam and beam shape. At this time, the transmittance of to the emission is a normal ratio of 0.1~0.5%. For example, an irradiation current is 5~25 nA when an emission is 5 μA. Consequently, for example, when attempting to obtain an irradiation current of 1 μA, an emission of 200 μA~1 mA is required. At this time, the energy band of an electron becomes wider due to the Boersch effect in an orbit from the cathode to the first cross over and from the first cross over to the field aperture when the emission becomes large. For example it widens to 10~50 eV from 1.2 eV at an FA position.

Energy band becomes problematic at a low LE in particular. This is because the widening of an orbit of an electron near the surface of a sample becomes larger in a z direction. FIG. 34 shows the intensity (amount) of an irradiation current of an electron beam irradiated to a sample surface, energy state and state of a beam irradiated to a sample surface. FIG. 34 (*a*) shows the intensity of an irradiation current of a beam irradiated to a sample surface and energy band, FIG. 34 (*b*) shows the state of a beam irradiated to the sample surface. A beam in which the energy of the irradiation current of a beam irradiated to the sample is optimized is given as beam c, a beam in which the energy of the irradiation current of a beam is low is given as beam a, and a beam in which the energy of the irradiation current of a beam is highest is given as beam b. Abeam in which the energy of the irradiation current of a beam is high is given as beam d. The relationship between the energy of an electron beam and intensity (amount) of irradiation current is shown as the distribution in FIG. 34 (*a*) according to Maxell distribution in a thermal electron shaping method such as LaB6. At this time, an electron beam having high and low energy characteristics as described above is given as beam a~beam d.

As one example, the case where a high energy beam d is collided directly into the sample surface is shown in FIG. 34 (*b*). At this time, the beam d collides into the surface but is not reflected (no mirror reflection shape). On the other hand, beam a, beam b and beam c are each reflected at reflection potential points. That is, mirror electrons are formed. In addition, the axis direction location at which beam c, beam b and beam a having different energies are reflected, that is, the Z position, is different. A difference ΔZ of this Z position occurs. The larger ΔZ becomes the greater image distortion becomes of an image formed by the secondary optical system. In other words, this is because misalignment of mirror electrons formed at the same surface position occurs in the image forming surface. In particular, the effects are significant because in mirror electrons, an energy misalignment causes reflection point misalignment and mid orbit misalignment. The same can also be said for an image forming using mirror electrons or image formation using mirror electrons and secondary emitting electrons. Also, these bad effects become large (ΔZ becomes larger) when the energy band of an irradiated electron beam is larger. Consequently, a primary beam which can irradiate a sample surface in a narrow energy band state is particularly effective. In order to achieve this, the electron generator supply and primary optical system is explained below using FIGS. 35~41. Because it is not only possible to narrow the energy band of an electron beam and dramatically increase the transmittance of a primary system beam compared to a conventional type, it is possible to irradiate a large current at a narrow energy band to a sample surface. That is, because it is possible to reduce ΔZ as described above, misalignment on an image formation surface in the secondary optical system becomes smaller and it is possible to realize low aberration, high resolution, a large current and high throughput. Normally, a thermal electron type gun such as LaB6 includes an electron generation part with an energy band of about 2 eV. In addition, as the amount of current generated increases, the energy band increase further due to the Boersch effect caused by a Coulomb repulsion etc. For example, when an emission current of an electron supply is change from 5 μA to 50 μA, the energy band widens to 8.7 eV from 0.6 eV for example, that is, when the current value is increased 10 times, the energy band becomes wider by about 15 times. The energy band widens due to a space charge effect etc while passing through the primary optical system. In order to make an electron beam with a low energy band reach the sample surface it is very important to reduce the energy band at the electron generator, increase the transmittance of the primary optical system and reduce the emission current at the electron generator. Although there was no means for achieving this previously, the present invention realized these effects. These effects are explained using the examples shown in FIGS. 35~41.

In addition, the intensity (when the amount if high, beam b) of an electron beam is not always optimized for imaging. For example, when an energy distribution conforming to Maxell distribution is included, the beam intensity (amount) at the part where energy is low is often the highest (beam b). At this time, because there are many beams with a higher energy than beam b, a different image quality to that of an image formed by these beams is often produced. That is, when a beam d collides into a sample and secondary emitting electron image is formed, because the energy of beam d is relatively low, the effects on the uneven structure of the sample surface are small, and mirror electrons are easily formed, that is, the effect on uneven structure of the surface or potential difference is small and mirror electrons are formed, thereby an image with an overall low contrast and free from glare is easily produced. From experience, an image with a high resolution is difficult to obtain. In particular, because the effects an amount of current which collides with the surface becomes larger when there is an oxide film on the uppermost part of a surface, compared to when the emission current is small, for example, the energy band widens by 10 times or more when emission becomes larger (for example 10 times). At this time, when an electron beam is irradiated to a sample surface with the same landing energy LE, the absolute amount of a part, beam d for example, with a higher energy than beam b which collides with the sample surface increases and charge up of the oxide film becomes larger as a result. The orbit of mirror electrons or image forming conditions becomes disordered due to the effect of this charge up and normal imaging is sometimes no longer possible. This is one cause of not being able to increase an irradiation current. Given this state, the amount of beam d which is collided with the sample surface is reduced and it is possible to use beam c which has an energy which can reduce a potential change in the oxide film (optimized energy beam). In this way, it is possible to control the amount of a beam which is collided with a sample and obtain a stable image. However, as can be seen from FIG. 34 (a) beam c has a lower intensity (amount) than beam b. When it is possible to bring the optimized energy beam c closer to beam b which has the highest intensity, the amount of electrons which contribute to image formation increases by this amount and it is possible to increase throughput. In order to achieve this it is important to obtain a narrow energy band and reduce the electrons which are collided with a sample surface. The present invention realizes this and this is explained using the examples in FIGS. 35~41.

In addition, in FIG. 34 (b) when LE is gradually increased beam d is collided with the sample surface, next beam c is collided and when the colliding electron beam increases the secondary emitting electrons which are thereby generated increase. A region in which mirror electrons and secondary emitting electrons are mixed is called a transition region. When all the primary beams are collided onto a sample surface, the mirror electrons disappear and only secondary emitting electrons remain. In addition, when there are no colliding electrons all the electrons become mirror electrons.

Furthermore, because the first cross over position changes when an emission changes by changing a Wehnelt voltage, it is necessary to adjust the aligner and lens in the lower side by this amount.

In addition, in an inspection of a semiconductor device, a 10 nm level defect inspection such as EUV mask inspection (extreme ultraviolet lithography mask inspection) or NIL inspection (nano imprint lithography mask inspection) compatible with new technology is necessary. In order to achieve this, a decrease in aberration and an increase in resolution are being demanded in semiconductor inspection devices.

In order to reduce aberration and increase resolution, it is important to reduce aberration of the secondary optical system in particular. However, a cause of deterioration in a mapping system is what is called energy aberration (also called color aberration) and coulomb blur. Thus, in order to improve aberration in the secondary optical system an increase in acceleration energy in a short amount of time is demanded.

Therefore, in order to solve this problem, the inventors invented an electron optical device which includes a primary optical system, said primary optical system being arranged with a new electron beam generation device (beam generator). This primary optical system uses DUV light or a DUV laser as a light source. However, the light source is not limited to this, UV, EUV or X rays may also be used. These are explained in detail below based on FIG. 35.

Figure 35:
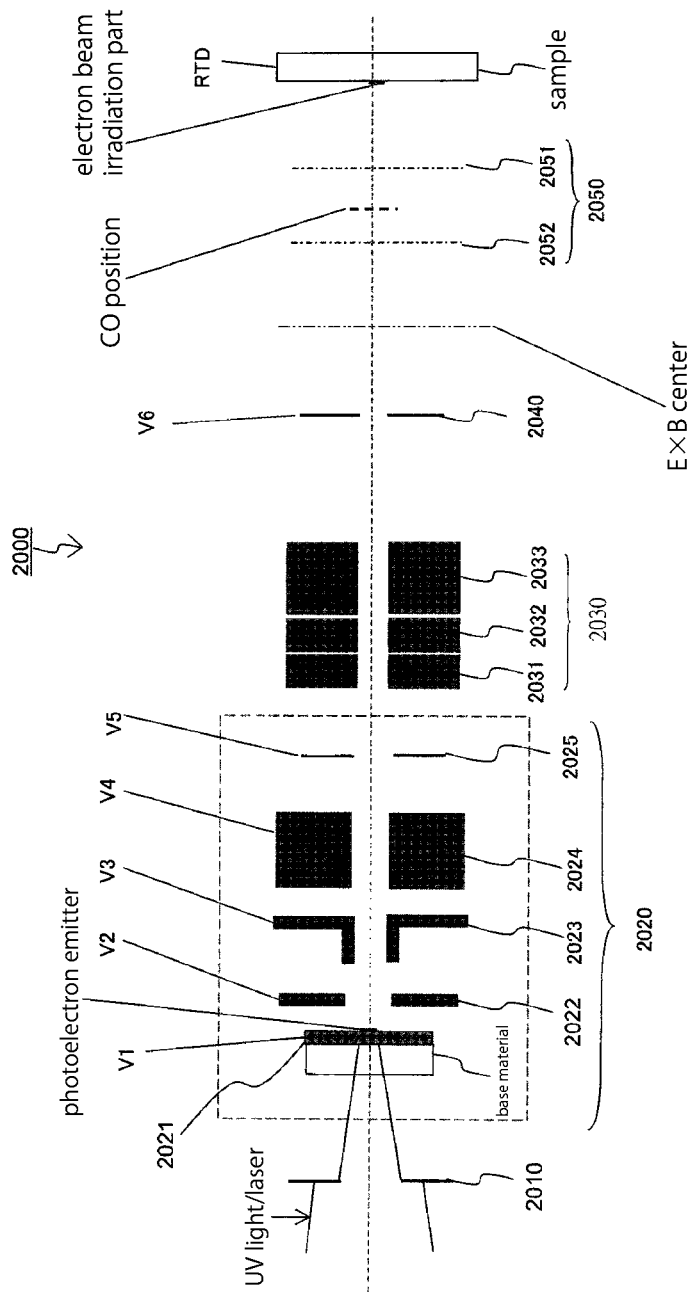
FIG. 35 is a diagram related to one embodiment of the present invention.

As is shown in FIG. 35, the present primary optical system 2000 is arranged with a light source (not shown in the diagram), a field aperture (FA) 2010, a photoelectron generation device 2020 (beam generator), an aligner 2030, an EXB deflector (Wien filter) (not shown in the diagram), an aperture 2040 and a cathode lens (CL) 2050.

The field aperture 2010 is disposed between a photoelectron surface 2021 of the photoelectron generation device 2020 described herein, and a light source, and is arranged with a hole including a predetermined shape. Light or a laser which is irradiated from the light source towards the field aperture 2010 passed through the hole of the field aperture 2010 and is irradiated as light or a laser having the shape of the hole of the photoelectron surface 2021. That is, the light or laser which is irradiated from the light source generates a beam having the same shape as the hole shape of the photoelectron surface 2021. Furthermore, light or a laser such as DUV (Deep ultraviolet), UV (ultraviolet), EUV (extreme ultraviolet) or X rays which have a wavelength which generated a photoelectron beam is used as a light source.

The photoelectron generation device 2020 is arranged with a photoelectron surface 2021, and one extraction lens comprised from a three stage extraction lens, first lens 2022, second lens 2023 and third lens 2024. In addition, a numerical aperture 2025 is also arranged. A magnetic field lens or electrostatic lens is used as the extraction lens. However, in the case where a magnetic lens is used, a magnetic field corrector is arranged near the numerical aperture 2025 described below. In addition, it is effective to arrange the lens near the lower side of the field lens (not shown in the diagram) or object lens (not shown in the diagram) in the secondary optical system. An image sometimes bends to the effects of a magnetic field and in the lens is arranged to correct this. Also, the number of extraction lenses is not limited to the number described above.

The surface 2021 for generating photoelectrons is a base material coated with material for generating photoelectrons. The base material is comprised of a light transmitting material such as quartz, silica glass, colts glass, magnesium fluoride glass etc and includes a planar surface part. A material having a low work function (a material having efficient photoelectron generation) such as ruthenium, gold etc is preferably used as the photoelectron material. In the present embodiment, a photoelectron material such as ruthenium, gold etc is coated onto the base material with a thickness of 1~10 nm. The shape of the photoelectron surface 2021 may be a 10 μm~50 nm elliptical or rectangular shape for example but not limited to this. Light or a laser is introduced by transmittance through the viewport of the base material, reaches the electron surface and photoelectrons are produced in the photoelectron surface.

The extraction lens (extraction electrode) comprised form the first lens 2022, second lens 2023, and third lens 2024 extract the electrons generated from the photoelectron surface 2021 in the opposite direction from the light source and the extracted electrons are accelerated. An electrostatic lens is used as these extraction lenses. In addition, a Wehnelt is not used in the extraction lenses 2022, 2023 and 2024 and an extraction electric field is held constant. Furthermore, it is preferable to use a single side telecentric or dual side telecentric structure in the first extraction lens 2022, second extraction lens 2023, and third extraction lens 2024. This is because it is possible to form an extremely uniform extraction electric field region and transport the generated photoelectrons at low loss.

With respect to the voltage which is applied to each extraction lens, when a voltage V1 is applied to the electron surface, and V2, V3 and V4 to the first extraction lens 2022, second extraction lens 2023, and third extraction lens 2024 respectively, V2 and V4 are set at V1+3000~30000V and V3 is set at V4+10000~30000V as an example. However, the voltages are not limited to these.

A numerical aperture 2025 is arranged between the third extraction electrode 2024 of the photoelectron generation device 2020 and an aligner 2030 described below. The numerical aperture 2025 selects a formation location of a cross over, and an effective beam such as the beam amount and aberration.

The aligner 2030 includes a first aligner 2031, second aligner 2032 and third aligner 2033 and is used for adjustment of light axis conditions. The first aligner 2031, second aligner 2032 and third aligner 2033 perform quiet operations, and fulfill the role of tilt and shift used when adjusting the light axis conditions. On the other hand, the third aligner 2033 is used when performing a high speed operation with a dynamic deflector and is used for example for a dynamic blanking operation.

An aperture 2040 is arranged on the lower side of the aligner 2030 (sample side. In the positional relationship between each part, the beam side is referred to as upper side and sample side as lower side herein). The aperture 2040 receives a beam during a blanking operation and is used in stray electron cut and beam centering. In addition, electron beam amount measurement is possible by measurement of the absorption current of the aperture 2040.

An E×B region which is a region which intersects the secondary optical system exists on the lower side of the aperture 2040 and an E×B deflector (Wein filter) is arranged here. The E×B deflector deflects a primary electron beam so that its optical axis is perpendicular to the surface of the sample.

A cathode lens 2050 is arranged on the lower side of the E×B region. The cathode lens 2050 is shared by the primary optical system and secondary optical system. The cathode lens 2050 may be comprised from a two stages, a first cathode lens 2051 and second cathode lens 2052, or may be a single cathode. When the cathode lens 2050 is comprised form two stages, a cross over is formed between the first cathode lens 2051 and second cathode lens 2052, and a cross over is formed between the cathode lens 2050 and the sample in the case of a single cathode.

Furthermore, the amount of photoelectrons is determined by the intensity of the light or laser which is irradiated onto the photoelectron surface. Therefore, a method for performing adjustment of the output of a light source or laser beam source may be applied in the present primary optical system 2000. In addition, although not shown in the diagram, an output adjustment mechanism may be arranged between the light source or laser beam source and the base material, for example, an attenuator or beam separator etc.

Figure 36:
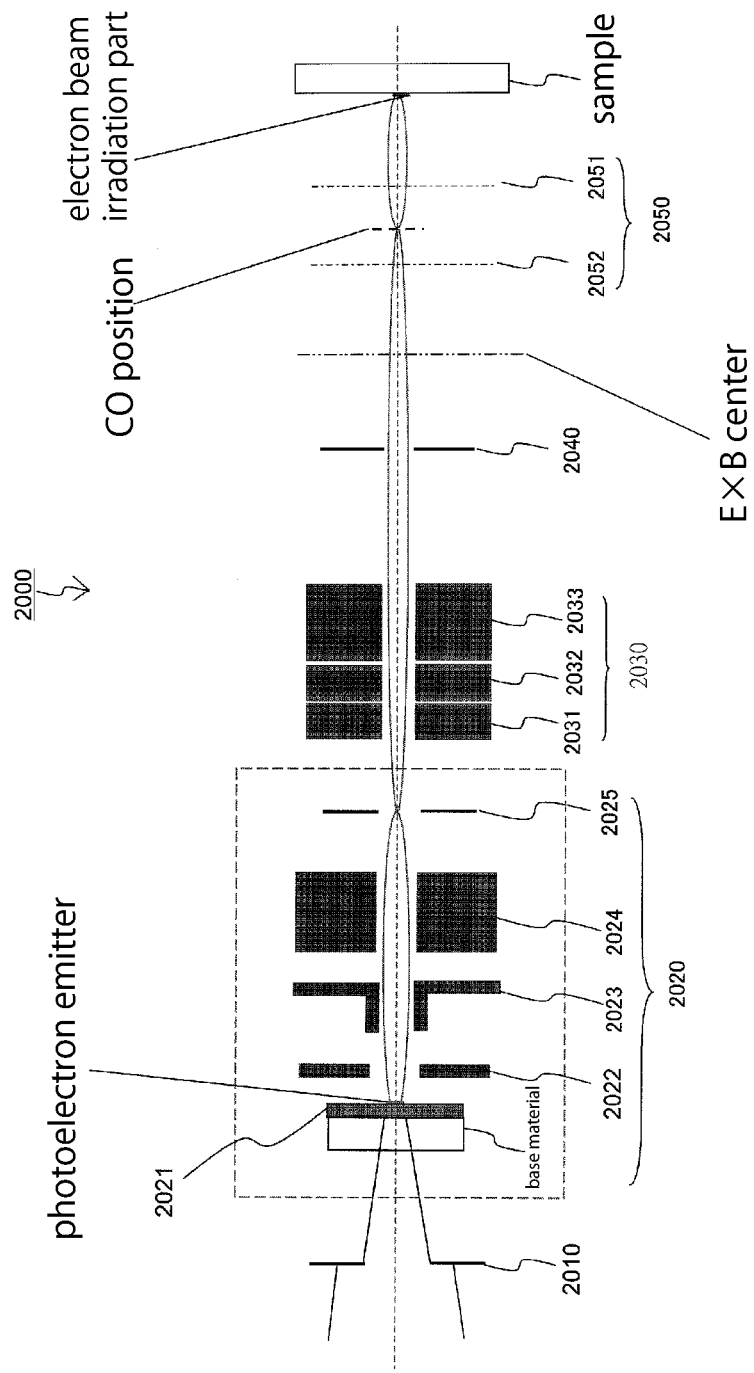
FIG. 36 is a diagram related to one embodiment of the present invention.

Here, the formation of a cross over in the primary optical system 2000 related to present invention is described using the diagrams. FIG. 36 is an exemplary diagram of a formation of a cross over in the primary optical system 2000 related to present invention. FIG. 36 is exemplary expressed to illustrate that photoelectrons generated in the photoelectron surface are irradiated perpendicular to the sample, however, actually the photoelectrons are deflector by the E×B deflector.

As is shown in FIG. 36, light or a laser is irradiated from a light beam or laser beam to a photoelectron surface 2021 after passing through the field aperture 2010. The photoelectrons which are generated at the photoelectron surface 2021 in this way form a cross over at the location of the numerical aperture 2025, are deflected perpendicularly to the sample by the an E×B deflector via an aperture 2040 and a cross over is formed between the first cathode lens 2051 and the second cathode lens 2052. Then the photoelectrons which formed this cross over are irradiated into the sample surface as an area beam. Therefore, the shape of the electron emission of the photoelectron surface and the shape of the electron beam irradiated to the sample surface are conjugate. On the other hand, in the primary optical system arranged with a general electron gun, the photoelectrons generated from the cathode 2310 as is shown in FIG. 33 (b) form a first cross over between the cathode 2310 and the anode 2311 and are irradiated into the sample surface via the anode 2311 and the field aperture 2320. Therefore, the shape of the field aperture 2320 and the shape of the electron beam irradiated to the sample surface are conjugate.

Setting an application voltage in the primary optical system 2000 related to the present invention is explained. The present invention is different to a general electron gun and structure whereby light or a laser is irradiated to a photoelectron surface and the photoelectrons which are generated are extracted by a subsequent extraction lens and accelerated. Because there is no Wehnelt or suppressor, the photoelectrons are accelerated by a uniform electrical field and the setting of an application voltage to each structural element is also different to a general electron gun.

The explanation below is made using FIG. 35. Each voltage which is applied to each structural element is as follows. V1 is applied to the photoelectron surface 2021, V2, V3, and V4 are applied to the first extraction electrode 2022, second extraction electrode 2023 and third extraction electrode 2024 which form the extraction lens respectively, V5 is applied to the numerical aperture 2025 and V6 is applied to the aperture 2040. In addition, a voltage RTD is applied to a wafer surface (also called a retarding voltage). In the primary optical system 2000 of the present invention, the following voltages are applied to each structural element when based on voltage V1 of the photoelectron surface 2021. That is, in the case of a low LE, V1=RTD−10V~RTD+5V. Y2, T4=V1+3000~30000V. V3=V4+1000~30000V. V5. V6=a reference potential. In addition, in the present embodiment of the primary optical system related to the present invention, the following settings are made, RTD=5000V, V1=5005V, V2, V4=GND, V3=+20000V. It is possible to realize high resolution and high throughput with a low LE using these voltage applications. However, this is only an example and the voltages applied to each structural element are not limited to these.

Furthermore, when a reference potential is expressed as V0 and the voltage of a surface where electrons of a detector entre is expressed as DV, the settings expressed in Table 1 below can be preferably used in the voltage application relationship with RTD in the primary optical system 2000 related to the present invention.

TABLE 1

|  | RTD | V0 | DV |
| --- | --- | --- | --- |
| Example 1 | −30 kV | 0 V | −25 kV |
| Example 2 | −5 kV | −25 kV | 0 V |
| Example 3 | 0 V | −30 kV | +5 kV |

The electron optical device arranged with the primary optical system 2000 related to the present invention having the above described structure can obtain the following effects.

First, the primary optical system 2000 of the present invention can realize a very high transmittance. A transmittance of 5~50% can be secured which is 10~100 times the transmittance of 0.1~0.5% of a primary optical system arranged with a general electron gun. This is because first, since it is possible to form a very uniform extraction electric field region with a structure comprising a planar cathode surface and new extraction lens, it is possible to transport the formed electrons at a low loss rate. This structure can also maintain a constant extraction electric field distribution depending on the increase or decrease in the amount of generated electrons and thereby a stable operation can be realized at a high transmittance. Since a primary optical system arranged with a general electron gun requires a Wehnelt or suppressor mechanism, and since an electric field distribution changes due to the amount of generated electrons, that is, amount of emission, and since a uniform extraction electric field part becomes smaller and an effective beam region becomes narrower, it is difficult to increase the transmittance. However, because the primary optical system 2000 related to the present invention does not require a Wehnelt or suppressor mechanism, it is possible to increase the transmittance. In addition, secondly, in the primary optical system 2000 related to the present invention, because the location of a first cross over is on the lower side of the lens, it is easy to arrange a numerical aperture etc and therefore, it is possible realize an optical system where it is easy to reduce lens aberration and reduce Boersch effects. In a primary optical system arranged with a general electron gun, because the location of the first cross over is situated in the vicinity of the Wehnelt, it is difficult to arrange a numerical aperture at this location. In addition, because the location is misaligned due to emission, even if it is possible to arrange a numerical aperture etc at this location for example, it is difficult to be used effectively. In the primary optical system 2000 related to the present invention, because it is possible to place the location of the first cross over on the lower side of the lens, it is possible to remove this problem.

Second, the primary optical system 2000 related to the present invention can realize high throughput at a high resolution. Since a high transmittance can be realized as described above, a very small amount of cathode emitting current of 2~10 µA is sufficient in order to obtain a high throughput, for example, an electron irradiation amount of 1 µA, Therefore, the Boersch effect can be minimized. For example, the energy band at the location of the numerical aperture is 0.5~1.2 eV. Consequently, because it is possible to increase the amount of electron irradiation with a small energy band, misalignment of a beam formed in the secondary optical system can be reduced and it is possible to maintain a high resolution. These effects can realize high throughput at a high resolution.

Thirdly, the primary optical system 2000 related to the present invention can constantly maintain an optical system in a stable state. This is because misalignment of a first cross over in the primary optical system 2000 related to the present invention does not occur.

Next, the effects of the electron optical device arranged with the primary optical system 2000 related to the present invention are explained in detail.

First, because the primary optical system 2000 is used with the structure described above it is possible to make the shape of an electron beam irradiated to a sample surface 10 times to 0.1 times the magnification with respect to the electron emission shape of a photoelectron surface. In particular, because it is possible to use the primary optical system 2000 with reduction in magnification of ×1 or less, it is not necessary to reduce the size of the photoelectron surface and the density of photoelectrons which are generated can be reduced and controlled. In this way, the electron optical device arranged with the primary optical system 2000 of the present invention can reduce the Boersch effect and control the widening of an energy band.

Secondly, with respect to a center axis of an electron generation part of the photoelectron surface it is possible to form a photoelectron generation part at a center location formed at the extraction lens. This can be achieved by irradiating light or a laser at this center axis location. The location of a light source is shown in FIG. 35 and FIG. 36 however it is possible to achieve the above simply by using a laser or mirror etc regardless of the location of the light source. The primary optical system 2000 related to the present invention is arranged within a column fixed to a main housing, however, by using light or a laser for the generation of photoelectrons it is not necessary to always arrange a light source within the column, for example, it is possible to arrange the light source on the exterior of the column and guide the light to the center axis of the electron generation part on the photoelectron surface using a mirror lens etc. Therefore, since it is possible on the atmosphere side, adjustment of the center location of the electron optical device which uses the primary optical system 2000 related to the present invention is easy. In the inspection device which uses a general electron gun shown in FIG. 33 (*b*), the center locations of the cathode 2310, Wehnelt 2312, anode 2311 and field aperture 2320 are misaligned due to assembly. In addition, misalignment due to baking which is performed after the atmosphere is released, that is, location variation after assembly, also occurs due to undergoing a thermal expansion and cooling process due to temperature change. In order to correct these misalignments, a general aligner is arranged on the upper side of the field aperture 2320 and correction is performed using the aligner. In the case where misalignment is significantly bad, it is necessary to repeat breakdown, assembly, adjustment and baking. On the other hand, in the electron optical device which uses the primary optical system 2000 related to the present invention, it is possible to easily form a photoelectron generation part at a center position formed by an electro static lens simply by irradiating light or a laser at the center axis location and thereby it is possible to easily make adjustments even if misalignment occurs due to assembly. In addition, because it is possible to arrange a light source on the atmosphere side, variations in location after assembly do not occur easily and it is possible to make adjustments easily even when they do occur after assembly. Therefore, it is possible to significantly reduce operational processes and costs. Furthermore, because it is possible to arrange the field aperture 2010 which determines the electron generation shape of the photoelectron surface on the atmosphere side, the field aperture 2010 can easily be replaced, which also reduces operational processes and costs. When the field aperture is arranged on the vacuum side, operations such as vacuum damage, column breakdown, assembly, adjustment, vacuum disposal, baking and optical axis adjustment are necessary for replacement, however, this process is no longer required.

Third, the electron optical device arranged with the primary optical system 2000 related to the present invention improves the level of freedom in the size of a beam. Since the electron generation shape of the photoelectron surface is determined by the field aperture 2010, not just an elliptic or square shape but a rectangular shape or asymmetric shape with respect to its axis are also possible. In the inspection device arranged with the primary optical system 2000 related to the present invention, as an example a φ100 µm elliptical shape at the photoelectron surface and a φ50 µm~100 µm elliptical shape at the sample surface are possible, and a 100×100 µm square shape at the photoelectron surface and a 50×50 µm~100×100 µm square shape at the sample surface are possible.

Fourth, in the electron optical device arranged with the primary optical system 2000 related to the present embodiment, it is possible to significantly reduce the number of parts within a vacuum. In an electron optical device arranged with a general electron gun, an aligner on the front side of the field aperture 2320 shown in FIG. 33 (b) is required for correcting misalignment of the center of the cathode, Wehnelt, anode and field aperture center. In addition, 1 to 3 stage lenses are required for forming a beam shape formed by field aperture 2320 on the sample surface. Since the electron optical device arranged with the primary optical system 2000 related to the present invention does not require these parts, it is possible to significantly reduce the number of parts within the vacuum.

If the electron optical device arranged with the primary optical system related to the present invention explained above is applied to a semiconductor inspection device, it is possible to achieve high resolution and high throughput and thereby is suitable for a EUV mask inspection or NIL mask inspection. In addition, it is also possible to achieve high resolution even in the case of a low LE (landing energy).

(Ninth Embodiment)
Second Embodiment of the Primary Optical System

Figure 37:
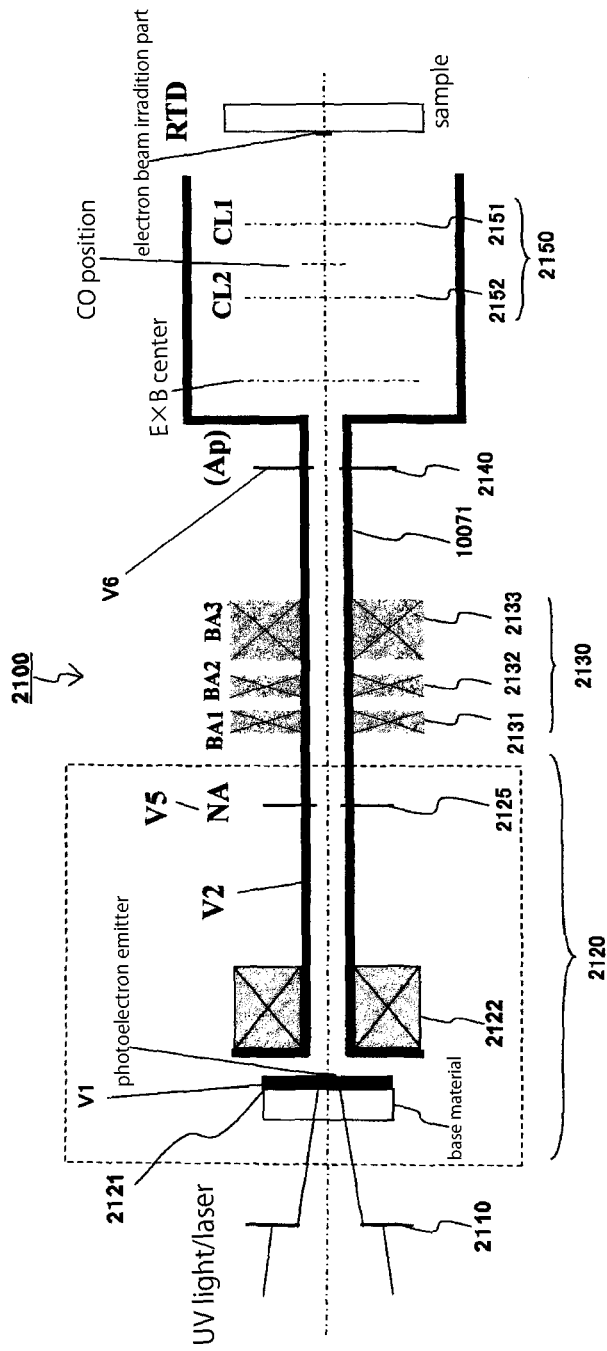
FIG. 37 is a diagram related to one embodiment of the present invention.

A second embodiment of the primary optical system related to the present invention is explained. FIG. 37 is a diagram which shows a second embodiment of the primary optical system related to the present invention. This primary optical system 2100 is arranged with a light source (not shown in the diagram), a field aperture (FA) 2110, a photo-electron generation device 2120 (beam generator), an aligner 2130, an ExB deflector (Wehnelt) (not shown in the diagram), an aperture 2140, a cathode lens (CL) 2150, a first tube 10071 and a second tube (not shown in the diagram) which houses the primary optical system. The second embodiment of the primary optical system related to the present invention is characterized by making a reference potential a high voltage. An explanation is given below focusing on the different points from the primary optical system related to the present invention described above.

The present embodiment includes a dual structure comprising a first tube 10071 and a second tube and the photo-electron generation device 2120 is arranged with a photoelectron surface 2121, one extraction lens 2122 and a numerical aperture 2125.

The first tube 10071 is a tube for creating a reference voltage when the reference voltage is a high voltage and a high voltage is applied to the first tube. The first tube 10071 is arranged on so as to contact with a hole on the inner side of the hole which allows a primary beam to pass through arranged on each of an extraction lens 2122, numerical aperture 2125 and aligner 2130, the diameter of the first tube is formed larger on a latter part of the aperture 2140 and a cathode lens 2150 is arranged on the inner side of the spot where the diameter of the first tube is formed large.

The material of the first tube 10071 is not particularly limited as long as it is not magnetic. However, a tube having the thickness of copper or a tube having the thickness of titanium, or a plastic tube which is copper plated or titanium plated is preferred. In this way, a magnetic field is formed on the interior of the first tube 10071 when a high voltage is applied to the first tube 10071 and a primary beam generated at the photoelectron surface 2121 irradiated with light or a laser is accelerated at a high speed.

On the other hand, although not shown in FIG. 37, the second tube covers the field aperture (FA) 2110, the photo-electron generation device 2120, the aligner 2130, the ExB deflector (Wehnelt) (not shown in the diagram), the aperture 2140, the cathode (CL) 2150 and the first tube 10071 and is set to GND. This becomes the outermost structure of a column device and therefore, this part is maintained at GND for preventing a conduction connection with other device parts and electric shocks etc.

The extraction lens is a single lens and is an electromagnetic lens in the second embodiment of the primary optical system related to the present invention. The remaining structure is the same as the first embodiment described above and thus an explanation is omitted here.

By adopting this type of dual structure pipe in the primary optical system 2100 related to the present embodiment it is possible to accelerate at a high speed the electron beam which is generated at the photoelectron surface 2121 by setting the sample surface voltage to GND, and adding a high voltage to the first tube 10071 which is the pipe on the inner side of the dual pipe structure. Therefore, it is possible to call the primary optical system related to the present invention a high acceleration column.

The voltages which are applied to each structural element in the primary optical system 2100 related to the present invention (refer to FIG. 37), are as follows. V1 is applied to the photoelectron surface 2121, V2 is applied to the first tube 10071, V5 is applied to the numerical aperture NA 2225 and V6 is applied to the aperture 2140. In addition, a voltage RTD is applied to a wafer surface (also called a retarding voltage). At low LE conditions, V1=RTD−10V~RTD+5V. V2, V5. V6=a reference potential. In addition, in the first embodiment of the present invention, the following settings were made, RTD=0, V1=5V, reference potential=40000V. It is possible to realize high resolution and high throughput with a low LE using these voltage applications.

At this time, when a magnetic field lens is used, a beam rotates due to a longitudinal magnetic field (remaining magnetic field in the optical axis direction which is generated. Consequently, the two dimensional shape of generated photo-toelectrons formed at the photoelectron surface sometimes rotate after passing through the generation part and magnetic field lens. In order to correct this, a rotation correction lens is arranged near the NA or at a location on the lower side of the magnetic field lens and the effects are corrected. The correction lens located on the lower side of the magnetic field lens is preferred to be arranged at a location (directly after) as near as possible to the magnetic field lens and correct the rotation.

In addition, in the primary optical system 2000 of the electrostatic lens of the present invention (refer to FIG. 35) when describing the example of a dual tube structure based on the voltage V1 of the photoelectron surface 2021 each of the structural elements is applied with a voltage as follows. That is, in the case of a low LE V1=RTD−10V~RTD+5V. V2, V5, V6 are reference potentials, and V3=reference voltage+10~100 kV. In addition, in one example of the present invention, the settings are as follows; RTD=0, V1=−5V, V2=reference potential+40000V, and V3=65000V. Also, there is a first tube installed with these lenses so that a reference voltage becomes a reference space voltage and the lens, aperture and aligner of FIG. 35 are installed within the first pipe in which the reference voltage is applied. In addition, a second tube which includes a GND potential is arranged on the exterior. An insulation part is fixed between the first and second tubes. (The first and second tubes are not shows in the diagram). A high resolution and high throughput at a low LE can be realized by the voltage applications described above.

The primary optical system 2100 related to the present invention can obtain the effect of being able to perform an inspection while a sample surface voltage RTD remains at 0V. Furthermore, the primary optical system 2100 related to the present invention can also obtain the same effects as the primary optical system 2000 related to the present invention described above. In addition, because the effects of the electron optical device arranged with the primary optical system related to the present invention are also the same an explanation is omitted.

Figure 38:
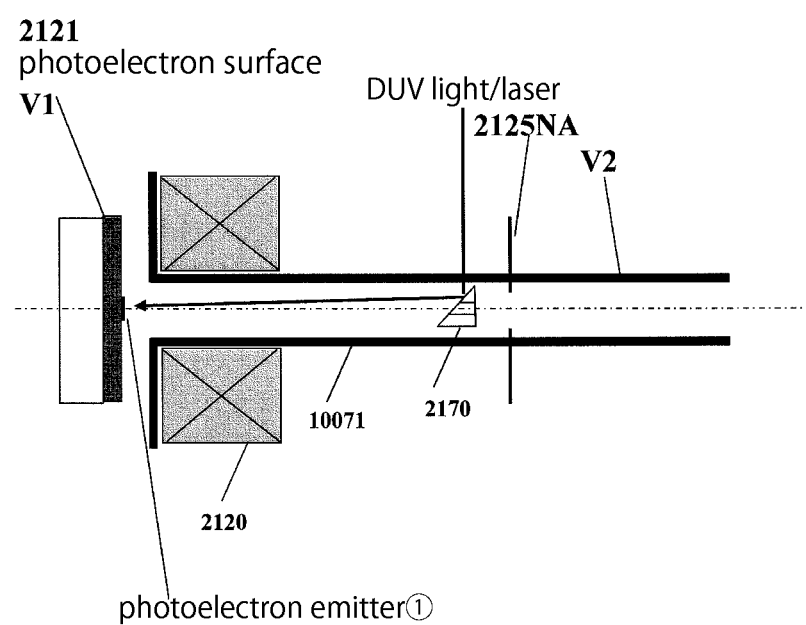
FIG. 38 is a diagram related to one embodiment of the present invention.
Figure 39:
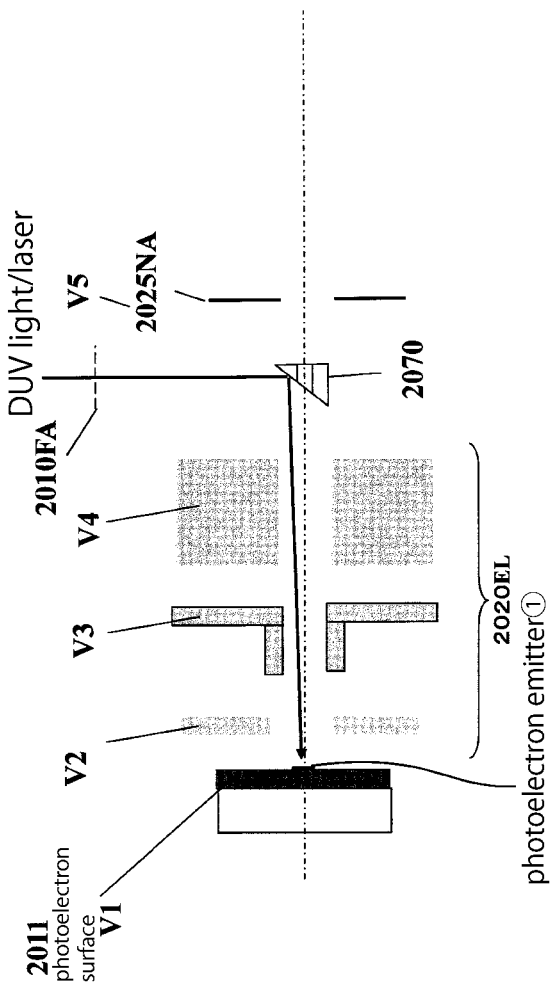
FIG. 39 is a diagram related to one embodiment of the present invention.

Modified Example of a Photoelectron Generation Device in the Primary Optical System Another example of a photoelectron generation device in the primary optical system related to the present invention is shown. FIG. 38 and FIG. 39 are examples when light or a laser is guided to a photoelectron surface from a midpoint device of the primary system by a mirror arranged within a column.

FIG. 38 is an example when a reference voltage is a high voltage, for example, 40 kV. That is, an example applied to a second embodiment of the primary optical system 2000 related to the present invention. At this time, a voltage of V2=40 kV is applied to a tube 10071 which is applied with a high voltage for forming a reference voltage. The interior of the tube 10071 has the same voltage space. Therefore, in this example, DUV light or a UV laser is introduced by passing through the hole arranged in the tube 10071 which is not shown in the diagram using a mirror with a hole at a center part through which photoelectrons pass, for example, a triangular mirror 2170, reflected by the triangular mirror 2170 and irradiated to the photoelectron surface 2121. In addition, photoelectrons are generated from the surface which is irradiated, and these photoelectrons pass through an EX lens 2120 and the NA 2125 and an aligner located the lower side are irradiated to the sample surface. At this time a voltage having a specified value is applied to the photoelectron surface 2121 in order for the photoelectrons to form an orbit around the primary system, which is determined by LE=RTD voltage−V1.

On the other hand, FIG. 39 shows an example where light or a laser which generated photoelectrons is irradiated to a photoelectron surface via a triangular mirror 2070 the same as the example shown in FIG. 38, and is an example of a reference voltage GND. That is, an example applied to the first embodiment of the primary optical system 2000 related to the present invention. At this time, for example, V2, V4 and V5 are set to GND and the area in this vicinity is a reference voltage space. In addition, it is possible to arrange a mirror similar to FIG. 38 and introduce light or a laser. At this time, the amount of photoelectrons which are generated is determined by the irradiation intensity of the light or laser and therefore control of the irradiation intensity is performed. The intensity control method previously mentioned is used for this. At this time, the mirror surface and entire structure is a conductor or coated with a conductor. Also, the potential is the same as a reference potential so that the space potential is not distorted. In addition, so that a primary beam can pass through without being affected by the mirror, a hole is opened at the optical axis center part of the mirror and the primary beam passes through this hole. A conducting material or conductor is coated on the interior of the hole and connected to a reference voltage part so that the interior of the hole is also maintained the same potential as a reference voltage.

In addition, two methods for the shape of photoelectron generation are explained using FIG. 39. One method uses an FA aperture 2010 which specifies a beam system shape before being irradiated to a mirror with the column. The beam shape is formed using the field aperture (FA) 2010, the beam is irradiated to the photoelectron surface and photoelectrons having this shape are generated. At this time, the projection size of the field aperture (FA) 2010 is controlled by the lens location on the upper side of the field aperture (FA) 2010.

Figure 40:
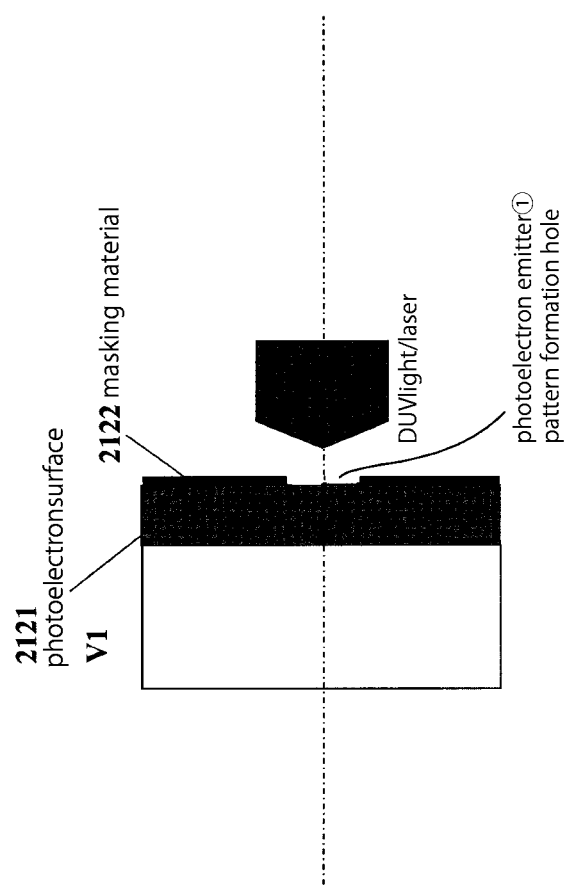
FIG. 40 is a diagram related to one embodiment of the present invention.

The other method is for coating a masking material of a pattern onto a photoelectron surface. FIG. 40 shows an example which uses the an example of coating a masking material of a pattern onto a photoelectron surface in the primary optical system 2100 related to the second embodiment of the primary optical system related to the present invention. As is shown in FIG. 40 a masking material 2122 is coated onto the photoelectron surface 2122. This masking material 2122 has a pattern shape hole and the hole part is not coated with the masking material. Due to the coating, photoelectrons are not generated from this part but from the part which is not coated with the masking material. That is, when DUV light is irradiated, pattern shaped photoelectrons are generated from the photoelectron surface part of the pattern shape which is not masked. At this time, a material in which photoelectrons are not generated can be coated in advance as the masking material. Also, a material which a high work function, or a material with a low generation efficiency can be used. For example, carbon, Pt or Cr. However, a conducting material is used because potential non-uniformity is formed when charging up which brings bad effects such as curving of the orbit of emitting electrons.

Figure 41:
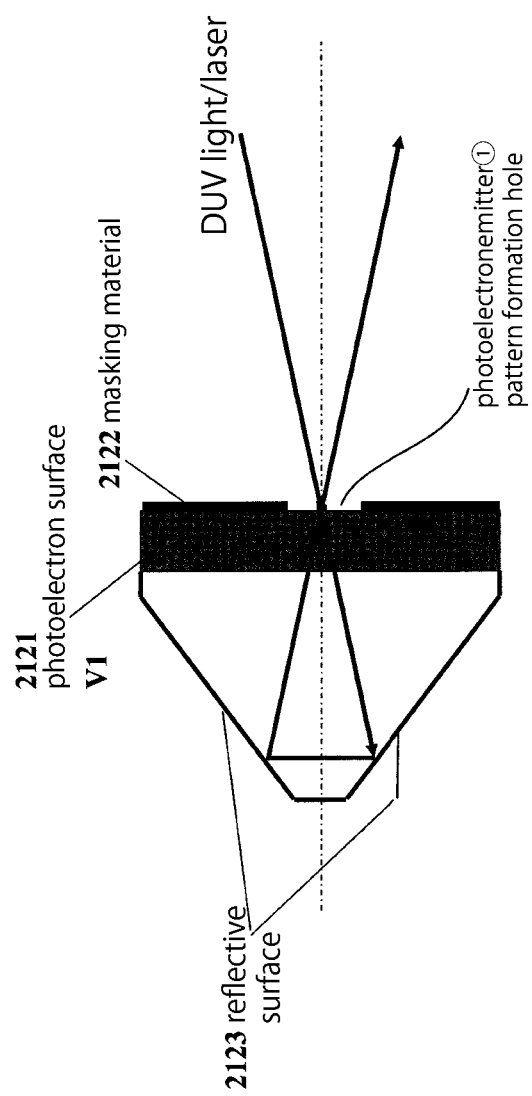
FIG. 41 is a diagram related to one embodiment of the present invention.

FIG. 41 shows a method of reflecting light or laser which has transmitted through and re-irradiating onto a photoelectron surface in order to further improve efficiency. The light or laser which is irradiated from the photoelectron surface 2121 side is reflected within a light, laser transmittance part which includes a reflection surface structure (reflection surface 2123), returned to the photoelectron surface 2121 and re-irradiated. Efficiency is improved since light or a laser is irradiated a plurality of times onto the photoelectron surface 2021 in this method. For example, when the light or laser transmittance of the photoelectron surface 2021 is 60%, an increase in the amount of photoelectrons generated corresponding to the number of times the light or laser is irradiated is increased by re-irradiating the transmitted 60% of the light or laser. A method of irradiating a plurality of times is effective and not limited to this example. In particular, this level of efficiency can be obtained by irradiating 2~5 times. Irradiating more than this can reduce the intensity of the light or laser and therefore effectiveness is significantly reduced. In this way, when irradiating a plurality of times is possible, the intensity of the irradiated light or laser can expect to obtain the effect of ½~⅕ the case of a single irradiation. In particular, in the case where a large output light source is required, when there is not light source at all or in the case where operational management costs are high. At this time, since it is possible to reduce costs, improve efficiency, reduce the effects of heat and the effects of element deterioration of a light introduction system, it is very effective to use a low output light source.

Furthermore, the examples explained in FIG. 40 and FIG. 41 are applied to the primary optical system 2100 related to the second embodiment of the primary optical system related to the present invention. However, these examples are not limited to the embodiment and can be applied to the primary optical system 2000 related to other embodiments.

(Tenth Embodiment)

Semiconductor Inspection Device Having a Double Tube Structure Column

As described above, the electron optical device 70 which is arranged with the primary optical system 2100 shown in the second embodiment of the primary optical system related to the present invention has different settings of voltage applied to each element from a general electron gun. That is, a reference potential V2 is set as a high voltage (as an example, +40000V). Thus, the semiconductor inspection device 1 arranged with the electron optical device 70 related to the present invention first has a double tube structure.

Figure 42:
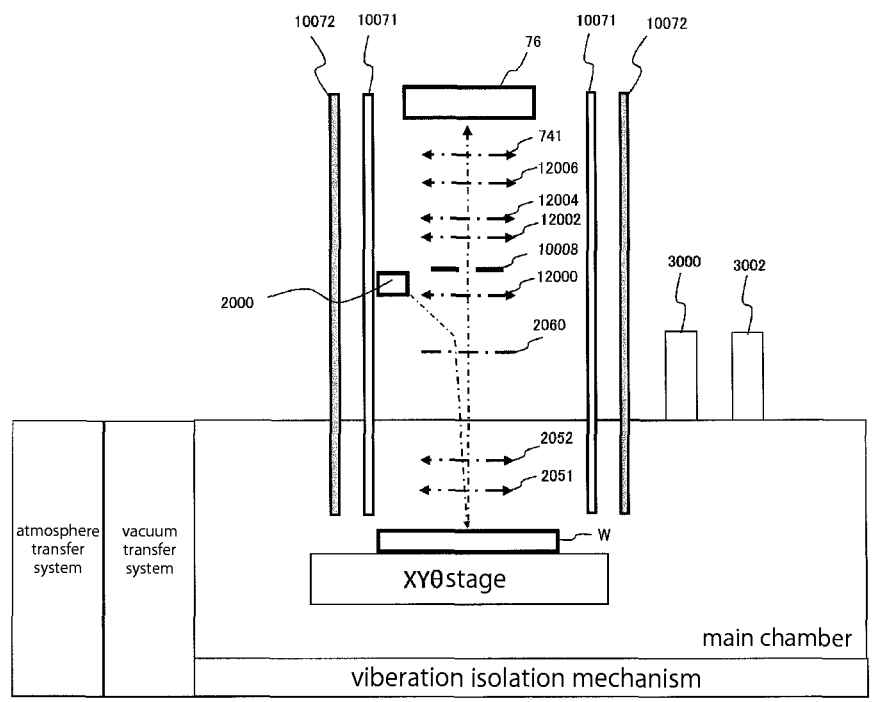
FIG. 42 is a diagram related to one embodiment of the present invention.

FIG. 42 shows an exemplary view of a double tube structure of a semiconductor inspection device related to one embodiment of the present invention. In FIG. 42, the first and second tubes are shown highlighted, however, the cross sections of the actual first and second tubes are different to this. As is shown in FIG. 42, the electron optical device 70 arranged with the primary optical system 2000 related to the present invention is comprised from two tubes, a first tube 10071 and a second tube 10072 arranged on an exterior part of the first tube 10071, in other words, a double tube structure. In addition, a light source, primary optical system, secondary optical system and detector are housed on the interior of the dual tube structure. Also, a high voltage (as an example, +40000V) is applied to the first tube 10017 and the second tube 10072 is set to GND. A high potential space reference voltage V0 is secured at the first tube 10071 and keeps the second tube at GND. In this way, a GND connection of the device arrangement and electron shocks are prevented. The tube 10071 is fixed to the tube 10072 by insulation parts. The second tube 10072 is at GND and is attached to a main housing 30. The primary optical system 2000, or the second optical system and detector system 76 etc are arranged on the interior of the first tube 10071.

The interval wall on the interior between the first tube 10071 and the second tube 10072 is formed with a non-magnetic part including a part such as a screw so that a magnetic field is not affected and so that a magnetic field does not affect an electron beam. Furthermore, although not shown in FIG. 42, a side surface of the second tube 10072 is arranged with a space and a projecting part arranged with a part of the first primary optical system 2000 such as a light source and photoelectron generation part is connected to the interior. Similarly, a similar space to the space arranged in the second tube 10072 is also arranged in the first tube 10071, and the photoelectrons which are generated in the photoelectron generation part pass through this these spaces and are irradiated to the sample. Furthermore, the light source does not always need to be arranged on the interior of the second tube 10072, it can be arranged on the atmosphere side and introduced to the photoelectron generation part housed within the second tube 10072 on the vacuum side. However, the first and second primary systems must be housed on the interior of the double tube structure. The detector may be arranged within the first tube 10071 or may be arranged at an independent potential which is not related to the first and second tube. The potential of the detector surface of the detector is arbitrarily set and the energy of the electrons irradiated to the detector may be controlled to an appropriate value. It is possible to operate the detector by applying an arbitrary voltage as the detection sensor surface potential of the detector in a state in which the potential is divided by insulation parts with respect to the first and second tube. At this time, when the sensor surface potential is set at VD, the energy irradiated to the sensor surface is determined by VD-RTD. In the case where EB-CDD, or EB-TDI is used for detector, it is effective to use an irradiation energy at 1~7 keV in order to reduce damage to the sensor and use the sensor for long periods of time.

Figure 43:
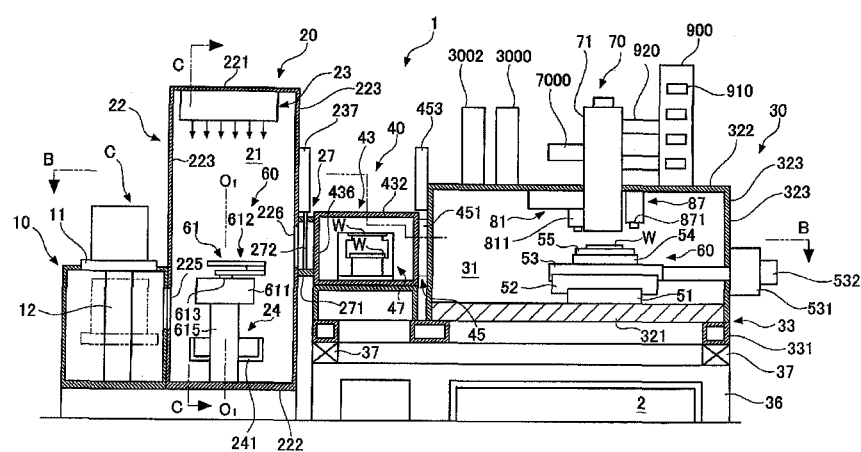
FIG. 43 is a diagram related to one embodiment of the present invention.

Furthermore, another structure of the semiconductor inspection device 1 arranged with the electron optical system 70 related to the present invention is explained below. FIG. 43 shows the entire structure of the semiconductor inspection device 1 related to one embodiment of the present invention. As is shown in FIG. 43 the semiconductor inspection device 1 related to one embodiment of the present invention includes a second vacuum chamber 900. That is, a second vacuum chamber 900 is arranged in the semiconductor inspection device 1 and together with arranging a power supply source 910 for generating a high voltage within the second chamber 900, a lens column 71 in which the first tube and second tube are housed, and the second vacuum chamber 900 are connected by a connection tube 920 and wires are arranged within the connection tube 920. This is because in the electron optical device 70 related to the present invention described above, a reference potential V0 is set to a high voltage unlike a conventional device. In order to set a reference potential V0 to a high voltage, the semiconductor inspection device 1 arranged with the electron optical device 70 related to the present invention is given a double tube structure. In addition, a high voltage is applied to interior side first tube 10071. In the case where a high voltage is applied, the vacuum feed through must be a large feed through in order to secure a creeping dielectric strength voltage on the atmosphere side which is low compared to a creeping dielectric strength voltage on the vacuum side. For example, an insulation part which includes an insulation creeping distance of 40 mm or more and a large connector with respect to insulation part is required at 40 kV with a creeping dielectric strength voltage of 1 kV/mm. The parts which are arranged in the lens column occupy a larger place and the column size and costs are significantly increased when there are many large connectors. Consequently, a power supply vacuum chamber is arranged in the present invention. Since feed through from an output is not required by arranged a power supply vacuum chamber it is sufficient to simply connect wires to an electrode. At this time, since generated gas from the power supply can cause contamination, it is effective to insulate the space between the power supply vacuum chamber and lens column using an insulation part in order to cut a vacuum conduction at the middle of a wire. In addition, the wire must be thick in the case of a high voltage. In the semiconductor inspection device 1, when a sample application voltage is set high is becomes necessary to arrange many thick wires on the periphery of a stage. When a wire with a large diameter is arranged on the interior of a working chamber a large torque is required due to movement of a wire when a stage is operated, for example, the force with which a wire rubs against a side surface becomes larger which generates particles which is a problem. Therefore, a method of setting the sample potential to GND and the reference voltage to a high voltage is very effective. At this time, it is even more effective to control the voltage of the detector surface and reduce sensor damage. The sample potential, the reference space potential and sensor surface potential are all set to different values. At this time, for example, it is very effective to set the sample potential to GND, the reference voltage to 10~50 kV and the sensor surface potential to 3~7 kV. In addition, as described above, the power supply 910 is housed by arranging the second vacuum chamber 900, connected to a lens column etc by the connection tube 920 and a vacuum wire is realized by arranged wires within the connection tube 920. A supply power (AC100V or DC24V etc) is introduced from an external source to the power supply and an optical communication method is used for communication. Connection from the atmosphere side is easy since a small feed through is sufficient at this level of supply power.

In addition, as described above, because the invention includes a double tube structure the interior side tube (tube 1) has a high vacuum and atmospheric pressure state is possible between the exterior side tube (tube 2) and the interior side tube 100 tube 1). At this time, it is not practical to arrange an electrostatic electrode within the tube 1 since the number of wires connected by the tube 1 is large and the feed through of the vacuum/atmosphere is large. A lens, aligner and corrector which use a magnetic field are used for the lens, aligner and corrector at this time. In this way, it is no longer necessary to arrange a feed through on the tube 1 and it is effective in the case of forming a high voltage reference space. Use of such a structure can be applied to the first to ninth embodiments previously described.

The semiconductor inspection device 1 arranged with the primary optical system 2000 related to the present invention described above is provided by making each structure of the lens column, power supply second vacuum chamber and connection tube of the vacuum wire which connects the lens column and second vacuum chamber described above a double structure. However, this is just an example and the semiconductor inspection device 1 arranged with the primary optical system 2000 related to the present invention is not limited to this example. In addition, it is also possible to perform the embodiments described thus far, for example, the embodiments of the primary and secondary systems shown in the first to ninth embodiments, using the double tube structure of the present embodiment.

(Eleventh Embodiment)

A beam measurement method at a cross over location, and a primary irradiation electron beam which uses this method, and a NA location adjustment method and a semiconductor inspection device which uses this adjustment method.

A semiconductor inspection method which uses an electron optical device arranged with the primary electron system related to the present invention described above is explained below. Furthermore, the methods described below can be applied to a semiconductor inspection device which uses an electron optical device arranged with a general electron gun.

In the embodiment, a projection-type observation device (an electron beam observation device having a projection optical system) is used to observe a sample. An electron beam observation device of this type comprises a primary optical system and a secondary optical system. The primary optical system 2000 irradiates a sample with an electron beam emitted from a photoelectron generation part to generate electrons which have obtained information on the structure or the like of the sample. The secondary optical system has a detector, and generates an image of the electrons generated by the electron beam irradiation. A projection-type observation device uses an electron beam of a large diameter and provides an image over a wide area. That is, irradiation is performed using an area beam not a spot beam such as general SEM.

When a sample is irradiated with an electron beam, electrons of a plurality of types are detected by the secondary optical system. The electrons of a plurality of types are mirror electrons, secondary electrons, reflected electrons, and backscattered electrons. In the embodiment, secondary electrons, reflected electrons and backscattered electrons are called secondary emission electrons. In addition, a sample is observed by using mainly the characteristics of mirror electrons. Mirror electrons refer to electrons that do not collide with a sample but bounce back immediately in front of the sample. The mirror electron phenomenon is caused by the effect of an electric field on the surface of a sample.

As described above, secondary electrons, reflected electrons, and backscattered electrons are referred to as secondary emission electrons. The term secondary emission electron is also used when these three types of electrons are mixed. Secondary electrons are typical among the secondary emission electrons. Secondary electrons are thus sometimes described as typical secondary emission electrons. Expressions such as "be emitted from a sample," "be reflected from a sample," and "be generated by an electron beam irradiation" may be used for both mirror electrons and secondary emission electrons.

Figure 44:
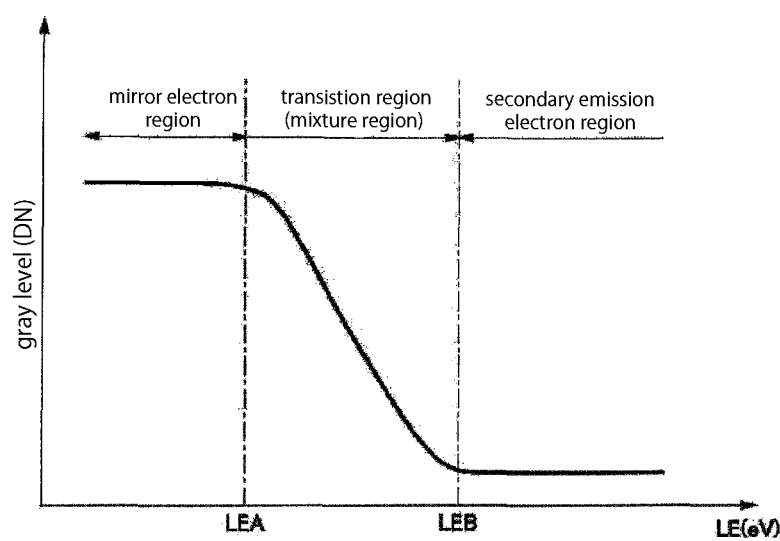
FIG. 44 is a diagram related to one embodiment of the present invention.

FIG. 44 shows a relation between the landing energy LE and gray level DN of a sample irradiated with an electron beam. The landing energy LE is energy given to the electron beam with which the sample is irradiated. Suppose that an acceleration voltage Vacc is applied to an electron gun and a retarding voltage Vrtd is applied to the sample. In this case, the landing energy LE is expressed by the difference between the acceleration voltage and the retarding voltage.

In FIG. 44, the gray level DN on the vertical axis represents the brightness of an image generated from electrons detected by the detector of the secondary optical system. That is, the gray level DN represents the number of detected electrons. The more electrons are detected, the larger the gray level DN becomes.

FIG. 44 shows a gray-level characteristic in an energy region of small energy near 0 [eV]. As illustrated, in a region in which LE is larger than LEB (LEB<LE), the gray level DN stands at a relatively small constant value. In a region in which LE is LEB or less but not less than LEA (LEA≦LE≦LEB), the gray level DN increases as LE decreases. In a region in which LE is less than LEA (LE<LEA), the gray level DN stands at a relatively large constant value.

The above-described gray-level characteristic is related to the type of electrons to be detected. In the region LEB<LE, almost all electrons to be detected are secondary emission electrons. This region can be referred to as the secondary emission electron region. On the other hand, in the region LE<LEA, almost all electrons to be detected are mirror electrons. This region can be referred to as the mirror electron region. As illustrated, the gray level in the mirror electron region is larger than that in the secondary emission electron region. This is because the distribution area of mirror electrons is smaller than that of secondary emission electrons. Since the distribution area is small, more electrons can reach the detector and the gray level increases.

In addition, the region LEA≦LE≦LEB is a transition region from the secondary emission electron region to the mirror electron region (or vice versa). This region is a region in which mirror electrons and secondary emission electrons are mixed, and can also be referred to as the mixture region. In the transition region (mixture region), the yield of mirror electrons increases and the gray level increases as LE decreases.

LEA and LEB denote minimum and maximum landing energy of the transition region. Specific values of LEA and LEB will be described. Study results of the inventors show that LEA is −5 [eV] or more and LEB is 5 [eV] or less (that is, −5 [eV]≦LEA≦LEB≦5 [eV]).

The merits of the transition region are as follows. In the mirror electron region (LE LEA), all electrons generated by the beam irradiation become mirror electrons. For this reason, all detected electrons would be mirror electrons regardless of the shape of the sample; the difference in gray level both at hollows and at bumps of the sample would be small; and the S/N ratio and contrast of patterns and defects would be small. It is therefore sometimes difficult to use the mirror electron region for inspection. In the transition region, on the other hand, mirror electrons are characteristically and specifically generated at edge-shaped parts, and secondary emission electrons are generated at the other parts. The S/N ratio and contrast of edges can therefore be increased. The transition region is thus very effective for inspection. This will be described in detail below.

Figure 45:
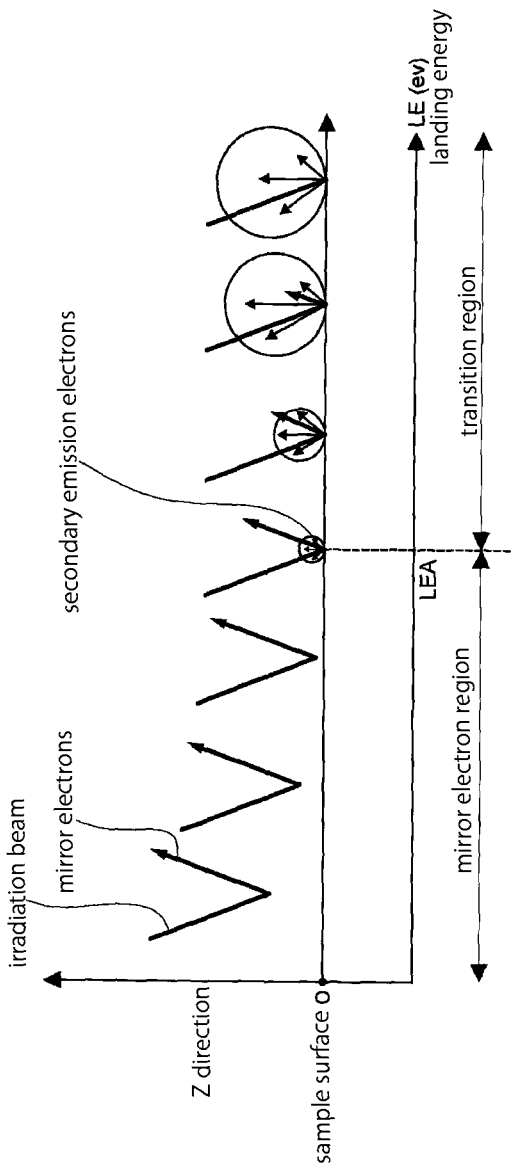
FIG. 45 is a diagram related to one embodiment of the present invention.

FIG. 45 shows the above-described phenomenon in the transition region. In FIG. 45, all electrons become mirror electrons without colliding with the sample in the mirror electron region (LE<LEA). In the transition region, on the other hand, some electrons collide with the sample, which emits secondary electrons. The ratio of the secondary electors becomes high as LE becomes larger. Though not shown in the figure, only secondary electrons are detected if LE exceeds LEB.

In the present invention, is a method of creating and adjusting conditions of an electron beam of a secondary optical system for forming an irradiation electron beam and image, including secondary emission electron region, a transition region and mirror electron region, and also including a pattern having an uneven structure and a pattern with no asperities. The present invention can achieve dramatic efficiency, high accuracy adjustment and condition creation which are described below.

The present invention has a significant feature of measuring the location and formation of a beam at a cross over location (below referred to as CO location) at a midpoint of the secondary optical system. Conventionally, an NA was moved, and image taken and the contrast of the image was evaluated without measuring the beam at a CO location. This took a considerable amount of time. The conventional sequence is as follows.
a) Form image forming conditions at a lens between the CO location and detector.
b) Use a large diameter in the case where an NA is present. Alternatively, remove the NA. It is preferable to be able to observe the entire CO. For example, $\phi 1000 \sim \phi 5000$ μm.
c) Image a beam of the CO location.

In the present invention, the structure of the apparatus are described herein in order to efficiently perform this type of imaging and adjustment and improve deterioration due to contamination and replacement and maintenance, however, characteristically, a movable type numerical aperture (NA) 10008 is arranged.

Figure 46:
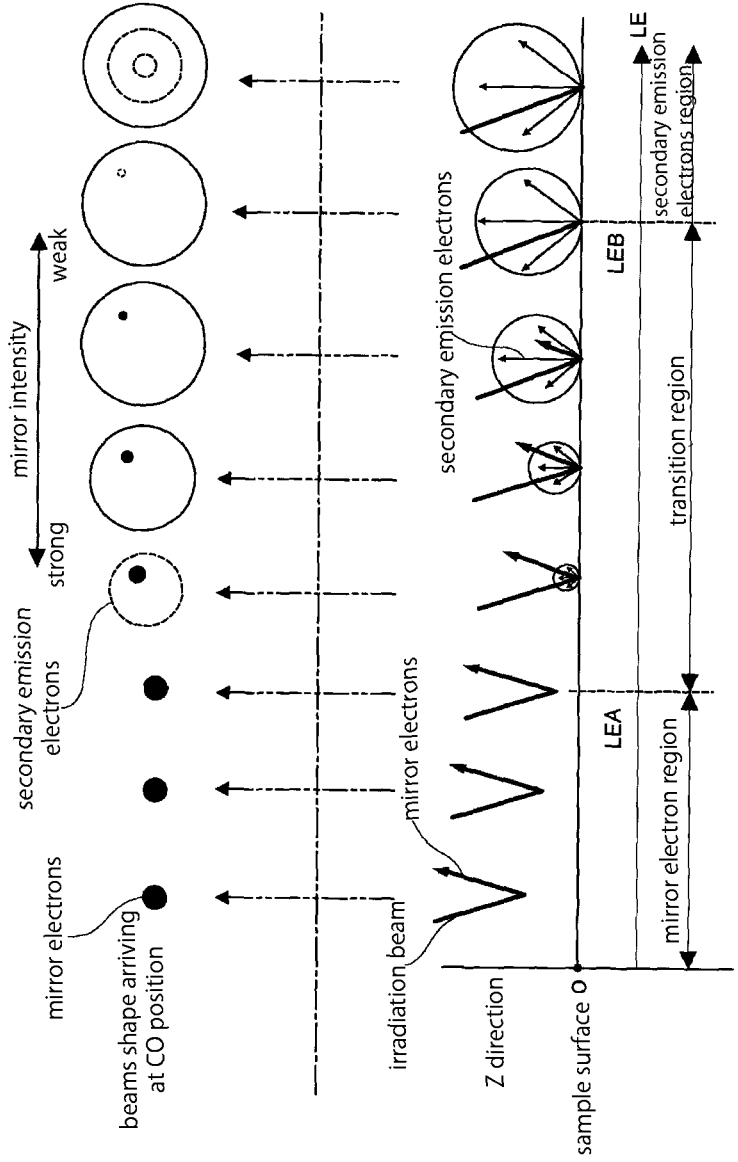
FIG. 46 is a diagram related to one embodiment of the present invention.

In this way, a measurement example of a beam shape at a CO location with respect to LE is shown in FIG. 46. FIG. 46 shows a measurement example of a beam shape at a CO location with respect to LE. In FIG. 46 shows formation of a beam arriving at a CO location on the upper stage and phenomena in a mirror region, transition region and secondary emission electron region of a beam irradiated to a sample surface on the lower stage. In addition, in the upper stage, mirror electrons are shown by black dots and the secondary emission electrons are shown by circles. Only the mirror electrons are observed with respect to LE in the mirror electron region. The mirror electrons and secondary emission electrons are observed in the transition region. Only the secondary emission electrons are observed in the secondary emission electron region, and the mirror electrons are not observed. The location, size, intensity of the mirror electrons and size and intensity of the secondary emission electrons are measured using image data obtained from this imaging.

In addition, with this observation it is possible to rapidly determine which state among three states the sample is in when an irradiation electron beam is made to impact the subject sample. Conventionally, a vague prediction was performed from the irradiation conditions and the obtained image. An accurate determination of the state could not be made. In addition, errors due to power supply setting accuracy and the effects of optical axis conditions also could not be determined. This was because formation of a mirror electron region, transition region is sensitive to optical axis conditions and apparatus for controlling this would be affected by condition errors. For example, the setting accuracy of a power supply is generally has an accuracy of 0.1%. Setting errors of a 5000V setting power supply would become 5V. When a variation of 5V occurs, a transition region would often become a mirror region and a transition region would often become a secondary emission electron region. Since this could not be confirmed, only a vague prediction stating a region might be a mirror electron region or a transition region due to setting values could be made.

Furthermore, in the present invention, a setting method of an NA location for adjustment of a primary irradiation electron beam and image formation is described using a method for performing this measurement. It is assumed that the direction of a sample such as a mask or wafer and coordinates of a secondary optical system (column) and location adjustment have been performed.

Figure 48:
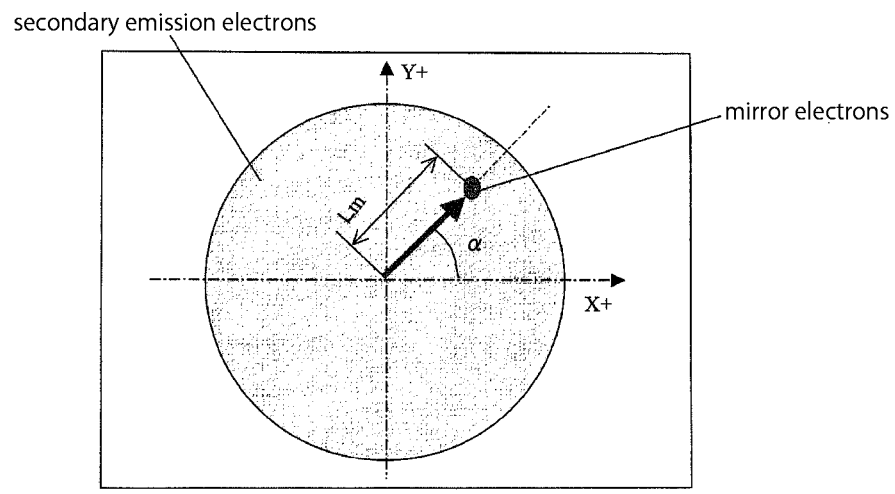
FIG. 48 is a diagram related to one embodiment of the present invention.

FIG. 47 shows an irradiation angle of a primary beam to a sample in an inspection method related to one embodiment of the present invention. As is shown in FIG. 47, an irradiation angle of an irradiation electron beam is given as θ and an irradiation direction with respect to a sample (or column coordinates) is given as α. That is, and angle from a perpendicular direction (Z direction, same as the optical axis direction of a secondary optical system) with respect to a sample surface is given as θ. For example, when θ=0, the sample surface is irradiation from a perpendicular direction. When θ=90°, the sample surface is irradiated from a horizontal direction. When θ=45°, which is an oblique direction, the sample surface is irradiation from an angle of 45°. In addition, θ may be displayed as an absolute value from the Z axis. θ has the same value if it has the same angle on the right side or on the left side with respect to the Z axis. Usually, θ is used within a range of 0~45°. As an example of α in the sample (or column coordinates) X, Y directions are given as Y direction for the E direction in E×B and the B direction is given as X direction. For example, an E+ side of E×B (direction in which a primary optical system exists) is given as Y+ and the E− side is given as Y−. At this time, a right 90° angle direction with respect to Y+ becomes X+ when the sample is seen from the detector side, and X− becomes a left 90° angle direction. In addition, for example, when a sample includes a pattern region with vertical line/space (L/S) and a horizontal line/space (L/S), the sample is arranged so that the vertical line becomes a Y direction and the horizontal line becomes the X direction. At this time, for example as is shown in FIG. 47 (*a*), it is possible to determine the sample irradiation angle in which the X+ direction is assume to be 0° as α. When α=0°, the irradiation angle of a primary electron beam becomes the X+ direction. When α=45° which one example of an oblique direction, the irradiation angle becomes an oblique 45° angle in an intermediate direction between X+, Y+. It is also possible to form the same irradiation direction of a primary electron beam with respect to a vertical L/S and horizontal L/S. When the values of θ and α mentioned above are adjusted, an observation is made of the beam at the CO location when an NA aperture of the secondary optical system is present as in FIG. 48. FIG. 48 shows an example of a CO location beam observation and is an adjustment example in a transition region.

A secondary emission electron beam becomes circular at a CO location. Since these are emission electrons from the surface when the electron beam collides with a sample, the emission direction from the surface becomes isotropic and therefore circular at the CO location. However, because mirror electrons are reflected in the vicinity of a surface in the direction affected by θ and α mentioned above, mirror electrons are formed at a location which reflects θ and α.

For example, when the irradiation angle to a sample is α, a mirror location is formed at the angle direction of α at the CO location with respect to the circular shape of secondary emission electrons. In addition, a perpendicular direction of the sample surface is given as Z, the detector direction is given as Z+ and an irradiation angle with respect to Z is given as θ. The mirror location of CO location is affected depending on the size of θ. That is, as is shown in FIG. 48, when θ (absolute value) is large, the distance LM from the center of CO of the secondary emission electrons becomes larger. That is, in the case of oblique irradiation, when the irradiation θ is large, the mirror electrons location us formed at location away from the CO center of the secondary emission electrons. In addition, when a primary electron beam is irradiated at a perpendicular angle, a mirror location is formed at the CO center location of the secondary emission electrons.

Figure 49:
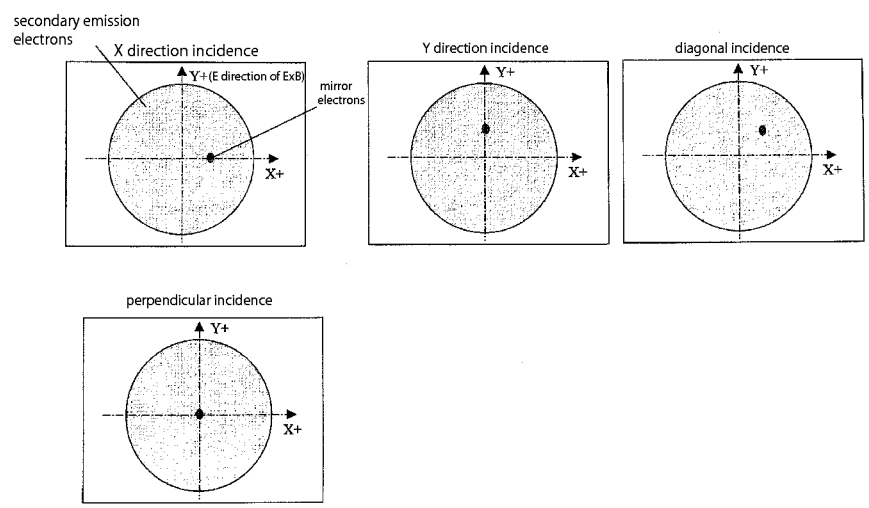
FIG. 49 is a diagram related to one embodiment of the present invention.

This example is described in FIG. 49. FIG. 49 shows a mirror location according to the irradiation angle of a primary electron beam. In the case of an electron beam irradiated in the X direction, the mirror electron location is formed on the X axis with respect to the CO of the secondary emission electrons. In the case of an electron beam irradiated in the Y direction, the mirror electron location is formed on the Y axis with respect to the CO of the secondary emission electrons. In the case of irradiation from an oblique angle α, a mirror electron location is formed in the α direction with respect to the CO of the secondary emission electrons. Often used α are 0°, 30°, 45°, 60°, 90°, 120°, 150°, 180°, 210°, 240° and 270°. In addition, θ is often used in the range of 0~45°. Also, in a sample which has an uneven structure surface in which high contrast and S/N are obtained, for example, an EUV mask, nano-print mask or semiconductor wafer, θ is often used in the range of 0~20°.

It is possible to control an irradiation angle of this primary system using the primary system beam aligner. In addition, it is also possible to perform an adjustment using a primary system beam aligner as the X direction and EXB as the Y direction. Also, a beam aligner may also be used instead of EXB in the Y direction.

In the present embodiment, an NA adjustment is performed is order to form electron image conditions with a high contrast and S/N. This is because the image data obtained is different due to the relationship between a mirror electron location and NA location and image quality varies significantly. For example:

a) An image including many mirror electrons: arrange an NA in the vicinity of a mirror electron location
b) An white hollow/black bump image with many mirror electrons in the hollow parts in the case of a uneven structure pattern
c) An black hollow/white bump image with few mirror electrons in the hollow parts in the case of a uneven structure pattern
d) An image, vertical/horizontal pattern etc with an asymmetric contrast
e) An image etc formed with mirror electrons on the edge part of asperities Consequently, in order to obtain a demanded image it is necessary to calculate and set the relationship between a mirror location and NA location. Conventionally, because understanding of the phenomena that occurred was insufficient and an adjustment method as not understood, conditions was determined by blindly moving the NA and obtaining an image. Using the present invention, it is possible to improve work efficiency and significantly reduce time and costs. An NA movable mechanism is required in order to adjust and set the NA location. In addition, it is more preferable if this is a two dimensional moving mechanism. This is because in a one dimensional moving mechanism, when an MC (mirror electron location) is in an oblique direction or axial direction which from which it can not be moved (for example, can not move in a y direction when it can only be moved in an x direction) with respect to the CO center of a secondary emission electron, an NA can not be arranged between the center locations of an MC and CO.

Figure 50:
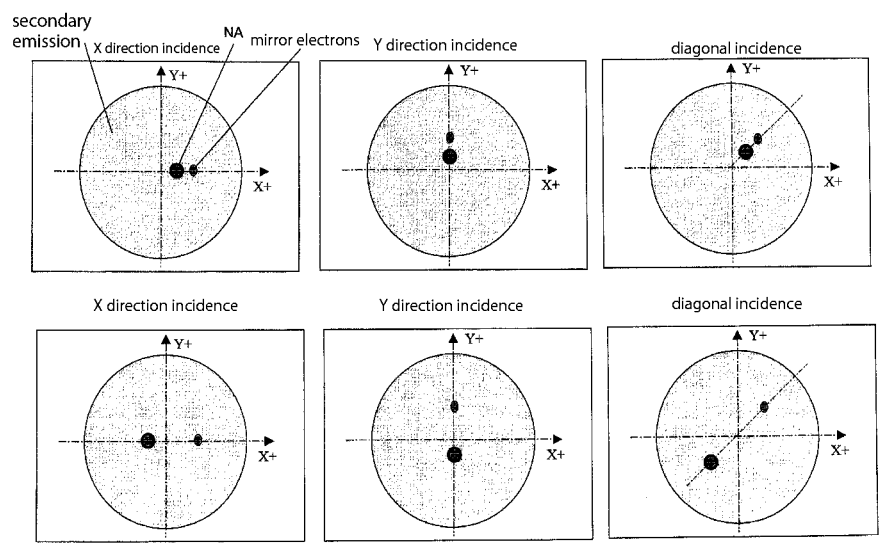
FIG. 50 is a diagram related to one embodiment of the present invention.
Figure 51:
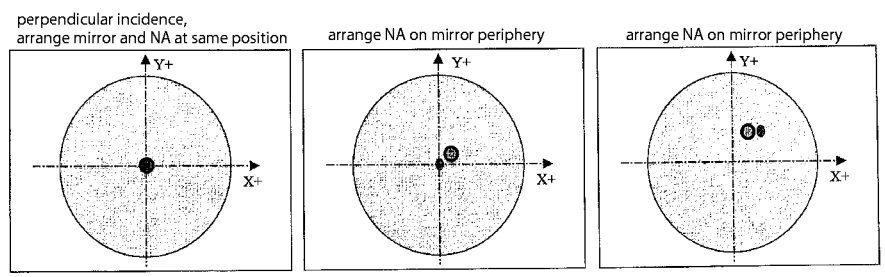
FIG. 51 is a diagram related to one embodiment of the present invention.

FIG. 50 and FIG. 51 show examples of a mirror electron location and NA location. The same condition adjustment method may be applied also to a planar surface sample as well as a sample having an uneven structure pattern. In the case where it is desired to form an image which takes into account changes in the potential or changes in the material of a planar sample, it is possible to calculate and create conditions for easy removal of such changes using the present invention. For example, the present invention can be applied in the detection of small foreign materials, the remains of cleaning, contamination etc or to detection in a mixed pattern of a conductive material and insulation material. In this case it is also possible as stated above to use a condition creation method in order to calculate conditions of defects or a pattern with a high contrast and S/N. In addition, it is also possible to realize highly sensitive detection which was not conventionally possible. By being able to perform this type of adjustment it was confirmed that a contrast of ×1.2~2, S/N×1.5~5 can be obtained compared to a method performed while looking an image which is very effective for adjustment time Tc and reproducibility, for example, Tc=½~⅒ can be obtained compared to conventional examples.

There are two categories of an NA setting location, arranging on the periphery of a mirror electron location and arranging the NA in a location away from the mirror electron location. The effects of a mirror electron decrease the further away the NA location is set.

An example of image formation is shown below.

1) Hollow white part/bump black part signal image in an uneven pattern

An example where high contrast, high S/N is obtained by an increase in the amount of electrons where localized mirror formation occurs.

Figure 52:
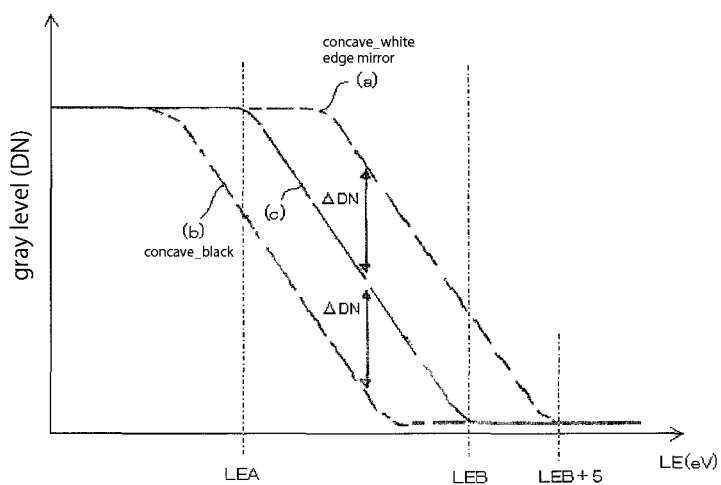
FIG. 52 is a diagram related to one embodiment of the present invention.

FIG. 52 shows a relation between the landing energy LE and the gray level DN at an edge part of an uneven structure on a sample surface. The edge part refers to a part which is located at both edges of a hollow and in which the height of the sample changes. In FIG. 52, the dotted line represents the gray-level characteristic of the edge part, and the solid line represents that of the other part. The characteristic of the other part corresponds to that in FIG. 44.

As shown in FIG. 52, the characteristic line is different between the edge part and the other part. The characteristic line of the edge part is shifted in a direction in which the landing energy increases. That is, at the edge part, the upper and lower limits of the transition region are large, and the upper limit of the transition region is LEB+5 [eV], where LEB is the upper limit of the transition region for the part other than the edge part. Such a shift in the characteristic line occurs because the shape, structure, material, or the like is different between the edge part and the other part. The shift in the characteristic line causes a gray-level difference ΔDN between the edge part and the other part.

The reason why the characteristic of the edge part is different from that of the other part as shown in FIG. 52 and the reason why the gray-level difference ΔDN occurs will next be discussed.

Figure 53:
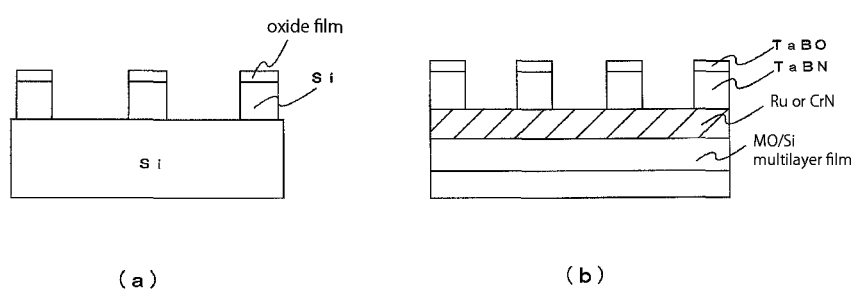
FIG. 53 is a diagram related to one embodiment of the present invention.

FIG. 53 is an example of the uneven structure of a sample, showing a cross section of a fine line/space shape. For example, the bump is a line and the hollow is a space. The line width and the space width are 100 μm or less. In the shape in FIG. 53 (*a*), a conductor (Si) has the uneven structure. An oxide film (SiO$_2$ or the like) is formed on top of the bumps. Similarly, in the shape in FIG. 53 (b), TaBO is formed on the top of the bumps.

Figure 54:
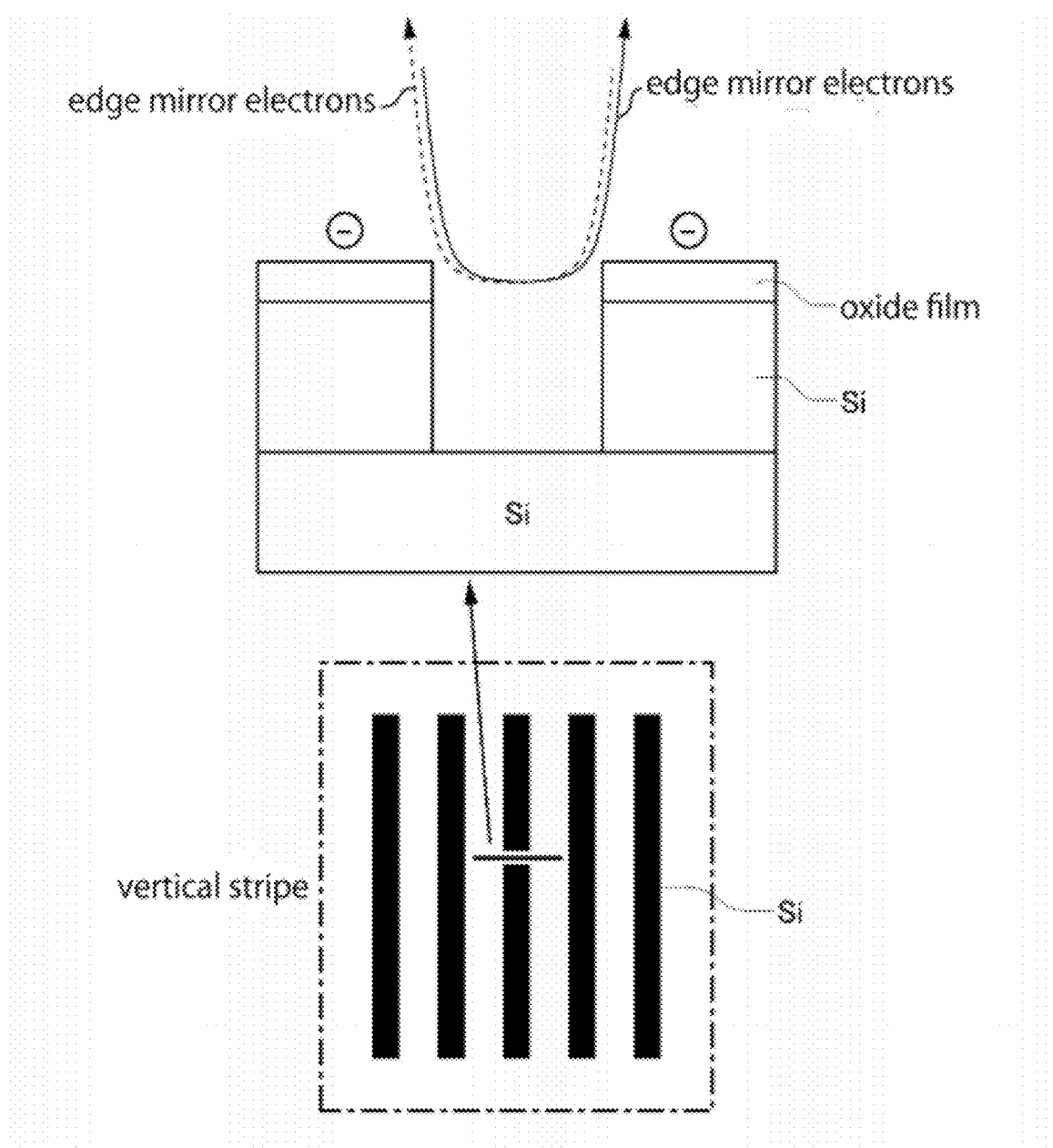
FIG. 54 is a diagram related to one embodiment of the present invention.
Figure 55:
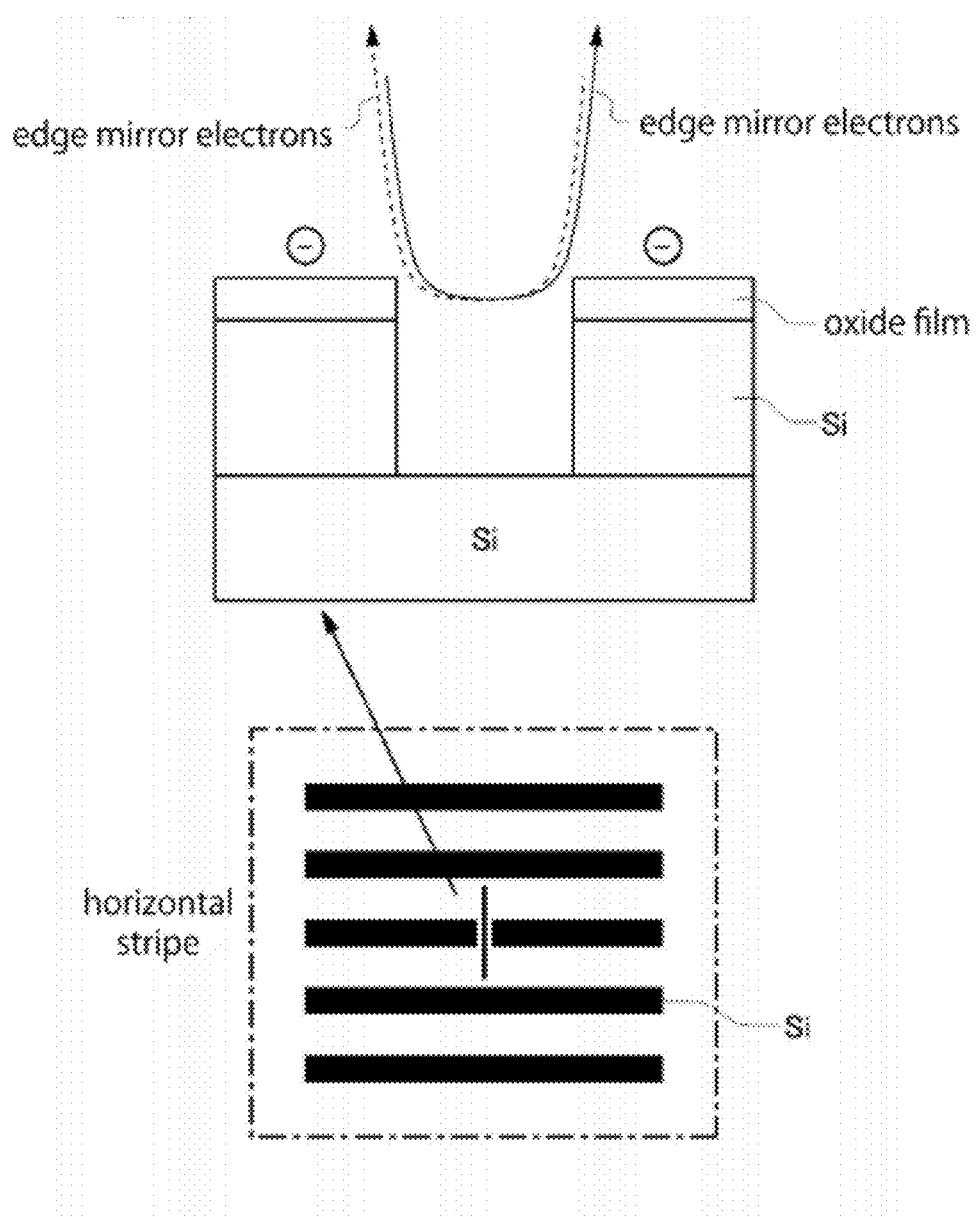
FIG. 55 is a diagram related to one embodiment of the present invention.

FIG. 54 shows a phenomenon in which mirror electrons are generated at the edge part of the uneven structure when the structure in FIG. 53 (a) is irradiated with an electron beam. A vertically-striped pattern is formed in FIG. 54. When irradiation is made with an electron beam, irradiation electrons change their path near one edge of a hollow (groove), turn sideways, and move toward the opposite edge of the groove. The irradiation electrons then change their path again near the opposite edge and return upward. Irradiation electrons thus become mirror electrons without colliding with the sample. The mirror electrons generated at edges in this way can be referred to as edge mirror electrons. Edge mirror electrons are generated symmetrically from both edges. FIG. 55, like FIG. 54, also shows edge mirror electrons generated in the structure in FIG. 53 (a). A horizontally-striped pattern is formed in FIG. 55. At this time, because this takes place in a transition region, electrons other than edge mirror generation part collide with the surface and secondary emission electrons are generated. As a result, for example, a pattern contrast and S/N are determined by mirror electrons at the edge part and secondary emission electrons at other parts. Because the transmittance of the mirror electrons is high, it is possible to obtain a high contrast and S/N. In addition, sometimes an image can not be formed by completely resolving an edge mirror depending on a pattern shape and capabilities of a secondary optical system. For example, because the reduction of secondary optical system aberration is insufficient, edge mirror electrons are observed as one unit. Consequently, observation is sometimes made by a white signal where a space part is an edge mirror and a black signal where a line part is a secondary emission electron. In addition, depending on the irradiation direction of a primary electron beam, edge mirrors are sometimes generated only in a one direction of an edge part. At this time, observation is sometimes made by a white signal where a space is an edge mirror and a black signal where a line part is a secondary emission electron.

Figure 56:
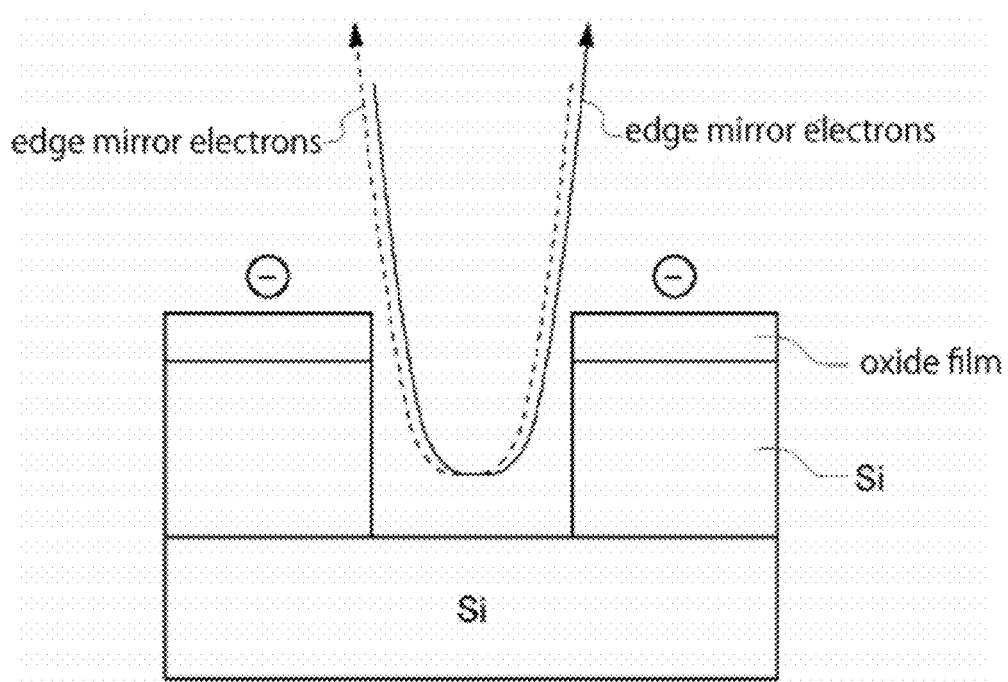
FIG. 56 is a diagram related to one embodiment of the present invention.

In addition, FIG. 56 is another example of the electron path along which the irradiation electrons change into edge mirror electrons. In this example, the irradiation electrons enter toward one edge of a hollow, go inside the hollow along a curved path near the one edge, turn around without colliding with the bottom of the hollow, and go near the other edge of the hollow to become mirror electrons. Such mirror electrons are also edge mirror electrons. In the edge structure, each irradiation electron is considered to go through the path in FIG. 54 or 56, or go through a path intermediate between the paths in FIGS. 54 and 56, to become an edge mirror electron.

The reason why the path of electrons easily bends near an edge will next be described. In the structure in FIG. 53, the oxide film is formed on the surface of the bumps of the conductor. In this structure, the oxide film on the sample surface is negatively charged. The potential of the conductor within the hollow is relatively higher than that of the oxide film. Since the potential changes near an edge, the path of electrons easily bends as described above, and consequently edge mirror electrons are generated.

Precharge is also preferable in the embodiment. Precharge is electron beam irradiation to be made before sample observation. An insulating area on a sample is negatively charged by precharge (the oxide film on the sample surface is negatively charged in the example in FIG. 54 and the like). Precharge stabilizes the potential of the insulating area. Consequently, edge mirror electrons are stably generated, and the characteristic in FIG. 52 is stably obtained. Sample observation can thus be satisfactorily carried out, and the precision of inspection using the sample observation result can also be improved.

Irradiation with the electron beam for precharge may be made by using the electron optical system for sample observation. Alternatively, another electron gun may be provided for precharge.

Figure 57:
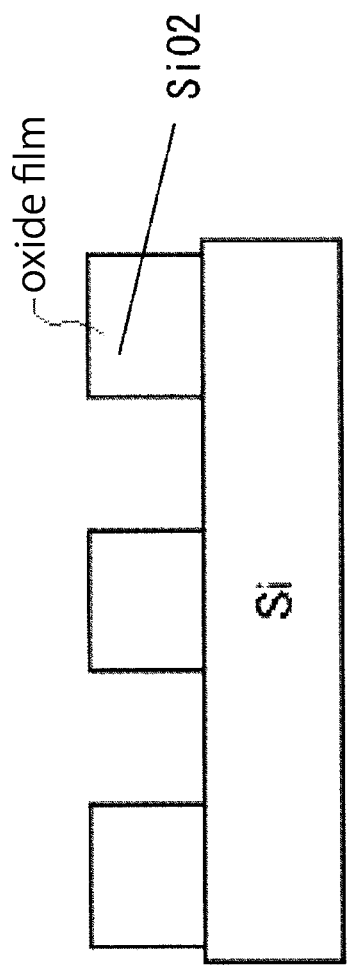
FIG. 57 is a diagram related to one embodiment of the present invention.

FIG. 57 shows another example related to the uneven structure of a sample. FIG. 57 is also a cross section of a line/space shape. In FIG. 57, a bump of an oxide film (SiO$_2$ or the like) is formed on a Si surface. In such structure, an equipotential surface bends at both edges of a hollow. The path of irradiation electrons bends due to the bend of the equipotential surface. As a result, irradiation electrons go through the paths shown in FIGS. 54 to 56 to become edge mirror electrons also in the structure in FIG. 57. Precharge is also suitably performed in the structure in FIG. 57, thereby allowing the potential of the oxide film on the bump to be stabilized.

Sometimes the uneven structure is formed only of a conductive material. In this case also, an equipotential surface is formed along the bumps and hollows. The equipotential surface bends at both edges of a hollow. The path of irradiation electrons bends due to the bend of the equipotential surface. As a result, irradiation electrons go through the above-described paths to become edge mirror electrons. In addition, in the structure in FIG. 53 (b) the same can be considered with respect to a structure mask which does not include TaBO. This may also be a EUV mask.

There is a natural oxide film on the surface of the conductive film also when the uneven surface is formed only of a conductive material. Precharge is therefore preferable and can stabilize the potential.

As described in detail above, electrons at a hollow of a sample go near both edges and turn around to become edge mirror electrons. Edge mirror electrons are therefore more easily generated than mirror electrons generated by a normal part. As a result, the transition region for the edge part, compared to that for the part other than the edge part, extends more in a direction in which the energy increases, as shown in FIG. 52.

In addition, mirror electrons and secondary emission electrons are mixed in the above-mentioned region. Secondary emission electrons are secondary electrons, reflected electrons, or backscattered electrons (or a mixture thereof), as described before. Secondary emission electrons are emitted in an isotropically-spread manner. For this reason, at most only several percent of the electrons reach the detector. On the other hand, edge mirror electrons are generated by irradiation electrons being reflected as-is. The transmittance (the rate of reaching the detector) of edge mirror electrons is therefore almost 100%. Consequently, a high brightness (gray level) is obtained, and the gray-level difference ΔDN with the surroundings increases.

At the edge part, as described above, mirror electrons are easily generated and the transmittance of mirror electrons is high. Consequently, as shown in FIG. 52, the gray-level characteristic line of the edge part is shifted in a direction in which the landing energy LE increases, and a gray-level difference ΔDN occurs between the edge part and the other part.

Using the above-described phenomenon, the embodiment generates a high-resolution and high-contrast pattern image. The hollow structure described above corresponds to the hollow pattern of the invention. In the embodiment, the landing energy is set so that edge mirror electrons are efficiently generated at the hollow pattern. The landing energy LE will be set to a very low value as compared to conventional common observation techniques, as illustrated. Such an energy setting increases the gray-level difference ΔDN between a pattern and the surroundings, allowing a high-resolution and high-contrast image to be obtained.

Specifically, the landing energy LE is set so that LEA≦LE≦LEB or LEA≦LE≦LEB+5 [eV] is achieved. This allows the landing energy LE to be set in a region in which mirror electrons and secondary electrons are mixed.

As described before, study results of the invention show −5 [eV]≦LEA≦LEB≦5 [eV]. For example, suppose that LEA=−5 [eV] and LEB=5 [eV]. In this case, the landing energy LE is set as −5 [eV]≦LE≦5+5 [eV]=10 [eV]. More specifically, the state of mixture of mirror electrons and secondary emission electrons varies depending on the landing energy LE, and the gray-level difference also varies. A great advantage may be obtained by setting the landing energy LE in a region in which the yield of mirror electrons is relatively small.

2) Hollow black part/bump white part signal image in an uneven pattern

An example where high contrast, high S/N is obtained by a black signal due to a mirror not reaching a detector where localized mirror formation occurs.

Mirror electrons which are formed at a hollow part collide into a side wall etc. Alternatively, their trajectory is misaligned and because they do not reach the upper CO location or detector location, the hollow part signal is reduced and detected as a black signal.

At this time, in FIG. 52 the signal characteristics of a hollow part are b and other parts are c. The signal of a bump part is obtained by mirror electrons, mirror electrons+secondary emission electrons or secondary emission electrons reaching the detector. At this time, when hollow part mirror electrons collide with a side wall surface, secondary emission electrons are generated from the side wall material. In addition, the bump part mirror electrons form an image as a white signal due to the large amount of electrons arriving at the detector. At this time, secondary emission electrons form a black signal. It is possible to obtain an uneven pattern, that is, conditions of a high contrast and S/N of a line/space structure using this hollow black signal and bump part white signal, and a defect inspection with a level of sensitivity is possible. In addition, electrons from the bump part, are sometimes included mirror electrons and secondary emission electrons generated by colliding one part of a primary electron bean into a sample surface. At this time also, because the amount of electrons arriving at the electron detector from the bump part is large, it is possible to obtain an uneven pattern, that is, conditions of a high contrast and S/N of a line/space structure using this hollow black signal and bump part white signal, and a defect inspection with a level of sensitivity is possible. At this time, effects are received from the material of the outermost layer. There are sometimes more secondary emission electrons in an oxide film of SiO2 or TaBO than a side wall material. At this time, it is possible to obtain an even higher contrast and S/N. In addition, the trajectory of the mirror electrons formed at the hollow parts is greatly misaligned, or misaligned from a location whereby they can not pass through the NA, or many collide with a side wall. At this time, the electrons from the hollow part change into secondary emission electrons when a part of a primary beam irradiated to the hollow part collide with the side wall, and become a black signal due to the low amount of secondary emission electrons. However, because the entire primary beam which is irradiated to a bump part and generates mirror electrons, a mix of mirror electrons and secondary emission electrons or secondary emission electrons from a bump part has an effect on the formation of the image, therefore it is possible to obtain a relatively larger amount of bump electrons than the hollow part and thereby obtain a high contrast and S/N.

In this case also, the relationship between the irradiation angle θ of a first irradiation electron beam and α, and the relative relationship between the mirror location of a secondary optical system and the NA location has a significant effect on the formation of the image. It is also possible to cut the hollow part mirror electrons using the conditions of the NA location. Such adjustment is performed and the conditions which can obtain a high contrast and S/N of an uneven pattern are measured and set.

(Beam Measurement Mechanism at a CO Location: Second Detector)

It is possible to create conditions and adjust high accuracy of an electron beam with respect to various patterns by measuring the location and formation of a beam at a CO location. It is effective to arrange a movable numerical aperture for performing this type of adjustment. In particular, an aperture movable in a biaxial (x, y directions) direction is required. In addition, because the CO location sometimes changes in a z direction due to lens conditions, an aperture movable in an x, y, z tri-axial direction is more preferable.

However, even if a movable type numerical aperture is arranged, only one detector is used each time adjustment is performed. An electron image from a mask or wafer, which is formed into an image by the secondary optical system, is primarily amplified in the micro-channel plate (MCP) of a detector and then impinges against a fluorescent screen to be converted into an optical image. The image that has been converted into the light by the detector is projected on the TDI-CCD by the FOP system disposed in the atmosphere through a vacuum permeable window on a one-to-one basis. When a detector is frequently used whenever adjustment is performed, damage to the micro channel plate (MCP) etc becomes worse, and frequent replacement of the detector is required. Because a still image is used for optical axis adjustment of a secondary optical system or for adjusting an electron image, an electron intensity distribution within the still image is maintained for a long time. In other words, imaging is performed in a state where whereby a part with many electrons and a part with few electrons are maintained for more than a fixed period of time. At this time, because element deterioration is different for parts with many electrons and parts with few electrons, a localized gain differential occurs which produces variations in gain in the detector itself. This causes an increase in the amount of artificial defects when the next stage inspection is performed and deteriorates detection capabilities. Consequently, it is preferable to include another detector when imaging a still image. At the time of an inspection, because imaging is performed while continuously changing parts having different obtained electron distributions during a short period of time while moving a stage, there is little deterioration of a detector due to variations is gain.

Figure 58:
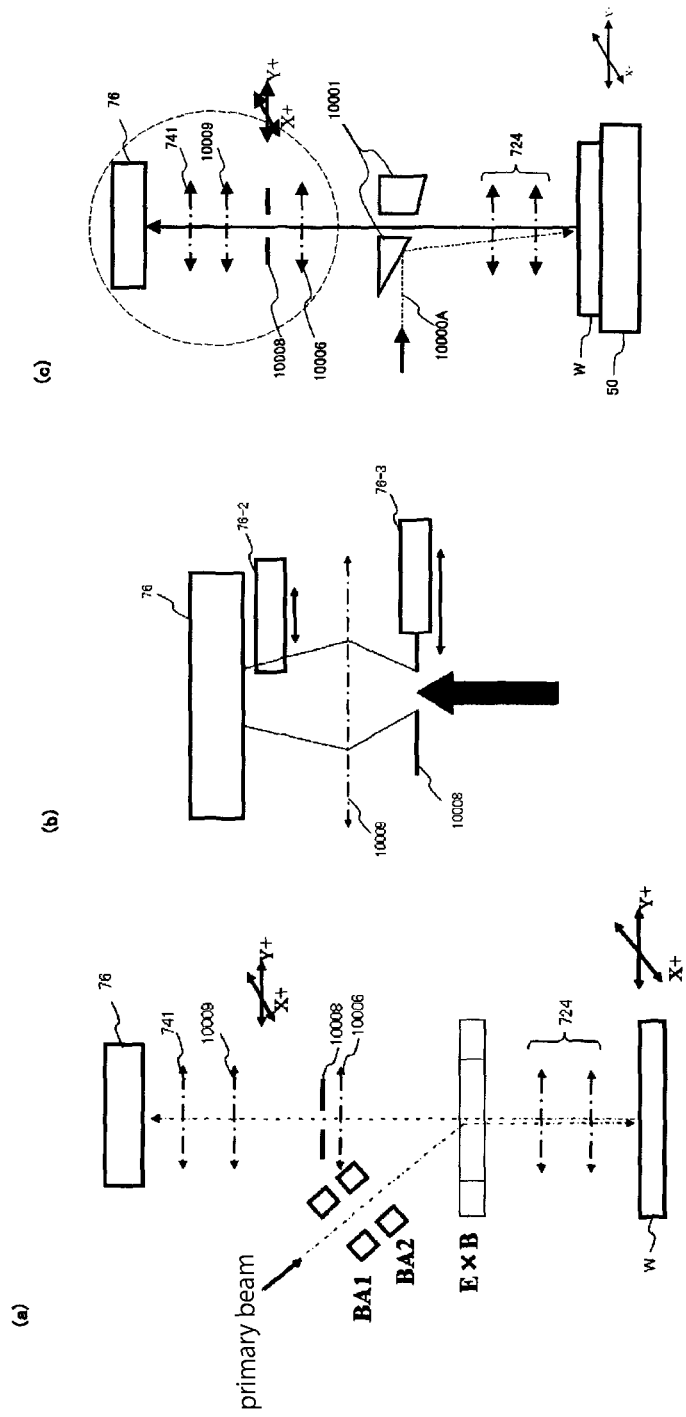
FIG. 58 is a diagram related to one embodiment of the present invention.

A second detector is arranged immediately anterior to the inspection detector as a means of measuring the location and formation of a beam at a CO location where frequent replacement of this type of detector is not required and an optical adjustment and as a detector for measuring a beam at a CO location. FIG. 58 shows the principle of the second detector related to the present invention. FIG. 58 (*a*) shows a secondary optical system of the present invention, and FIG. 58 (*b*) shows an electron beam of secondary emission electrons or mirror electrons at a numerical aperture (NA) 10008 location, passing through a lens and forming an image at a detector 76-2. The second detector 76-2 related to one embodiment of the present invention is arranged between the numerical aperture 10008 and detector 76 shown in FIG. 58 (*b*), the movable type numerical aperture (NA) 10008 is moved thereby imaging of the location and formation of a beam of the CO location at the second detector is performed. Here, it is sufficient that it is possible to take a still image of the formation and location of a beam of the CO location (or NA location). Adjustment is repeatedly performed based on the data imaged by the second detector 76-2 and an inspection is performed after adjustment.

The secondary emission electrons or mirror electrons form an image on the sensor surface of the detector via the numerical aperture (NA) 10008. This two dimensional electron image is obtained by the second detector 76-2, converted to an electric image and sent to an image processing unit. A transfer lens or magnification projection electrostatic lens may be used between the numerical aperture 10008 and the second detector 76-2 so that an electron beam image of the CO location can be imaged by the second detector 76-2.

It is possible to use an EB-CCD or C-MOS type EB-CCD as the second detector 76-2. A pixel size may be ½ to ⅓ of the pixel size of an EB-TDI which is the first detector (detector 761). In this way, imaging with a smaller Px size than the first detector is possible. Px size is a value whereby a pixel size is divided by optical magnification, and the size of image partitions on a sample surface. For example, Px size=10 um/1000 magnification=10 nm when each side of the pixel size is 10 μm and magnification is 1000 times. Using a second detector which has a smaller pixel size than the first detector it is possible to perform a surface observation with a smaller Px size than the first detector. The EB-TDI of the first detector, and the EB-CCD or C-MOS type EB-CCD of the second detector do not require a photoelectric conversion mechanism and a light transmission mechanism. Electrons directly enter the sensor surface of an EB-TDI. Consequently, the resolution does not deteriorate, so that a high MTF (modulation transfer function) and high contrast can be obtained. The C-MOS type EB-CDD can significantly reduce background noise compared to a conventional EB-CDD and therefore is very effective for noise reduction caused by a detector, and it is possible to improve contrast and S/N compared to a conventional example when performing imaging using the same conditions. In particular, it is effective when the number of obtained electrons is small. It is about ⅓~1/20 more effective in noise reduction than a conventional type EB-CCD.

A beam which passes through the numerical aperture (NA) 10008 and forms an image at the detector surface is detected by the second detector 76-2, condition creation of the electron beam and the location of the numerical aperture (NA) 10008 are adjusted using the location and formation of the detected beam. A sample is inspected using the detection system 76 after performing various adjustments using the detection results of the second detector 76-2. Therefore, because the detection system 76 is used only when performing an inspection, it is possible to control the frequency of replacing the detection system 76. In addition, because the second detector 76-2 only images a still image, there is no influence on an inspection even if deterioration occurs. In order to achieve this type of image forming conditions, for example, conditions for forming an electron image in the first detector, conditions for forming an image in the second detector, conditions for forming a beam an image in the second detector using the shape of a beam which arrives at a CO location for observing a beam at a CO location etc, referring to the example in FIG. 33 (*a*), the lens intensity of the transfer lens 10009 is adjusted and certain image formation conditions are used by measuring the optimum conditions for the first detector and second detector. In addition, a lens 741 may be used instead of the transfer lens 10009. Because the distance between the center of a lens and a detector changes, the magnification changes between using the transfer lens 10009 and the lens 741, therefore, a suitable lens and magnification should be selected.

It is effective to use the second detector 76-2 described above together with an adjustment method related to the present invention for performing measurement of the location and shape of a beam at the CO location described above, conditions creation of an electron beam and adjustment of high accuracy. In addition, the second detector 76-2 may also be applied to an electron optical device arranged with the general electron gun as well as an electron optical device arranged with the new electron generation part related to the present invention. The present embodiment can also be applied to the devices described in the first to eleventh embodiments described above. An electron beam was used as an example of a primary beam in the example of a beam, NA location adjustment method described above, however, an irradiation system can also be applied in the case of light or a laser. It can also be applied when a laser or light is irradiated to generate electrons from a sample surface and appropriately setting a cross over size of these electrons or a relationship between a center location and NA setting location. In this way, electron image formation with a good level of resolution is possible.

In addition, as another example, it is also possible to include a third detector which can move with the NA in an x, y direction as is shown in FIG. 58 (*c*), at an NA location. For example, a third detector 76-3 maybe arranged as set as one unit to a setting plate of the NA. At this time, it is possible to move the plate for observing the shape and location of a beam which arrives at the NA location, move to coordinates where the center of the third detector 76-3 arrives at the optical axis center, and directly observe the arriving beam using the third detector 76-3. In this way, it is no longer necessary to perform adjustment of subsequent lenses.

(Twelfth Embodiment)

Figure 59:
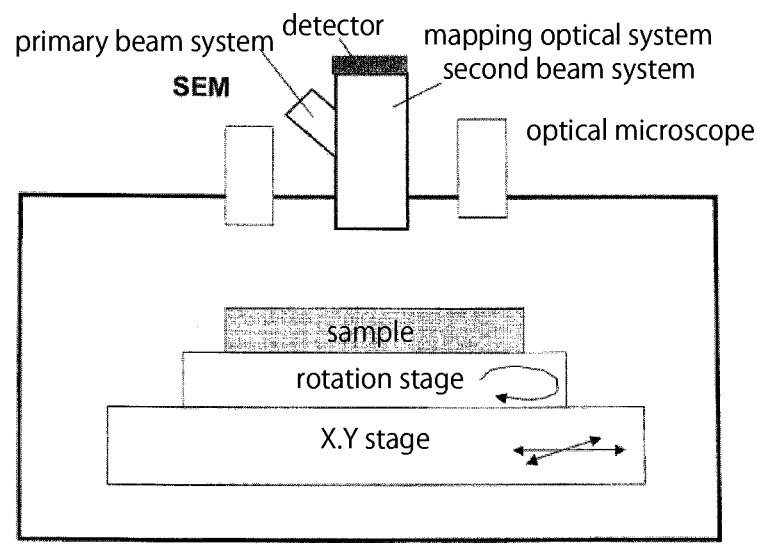
FIG. 59 is a diagram related to one embodiment of the present invention.
Figure 61:
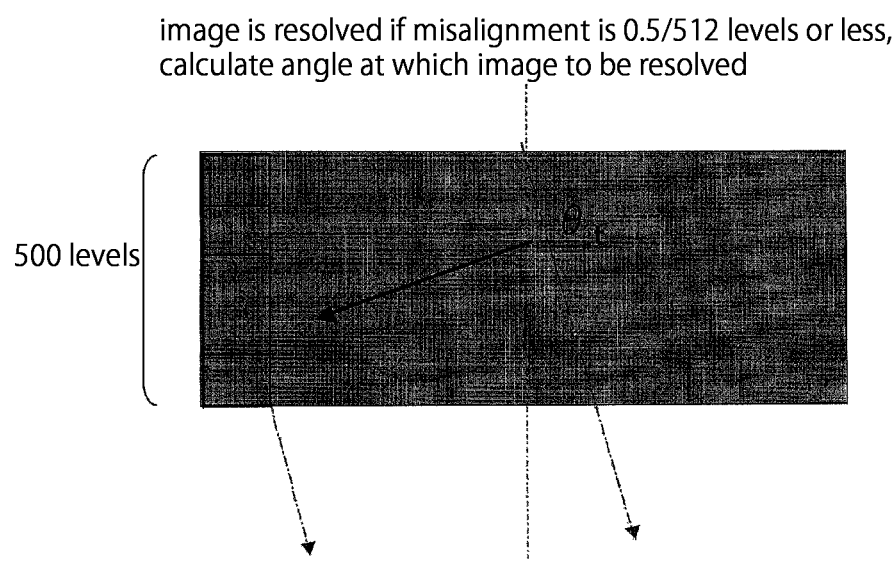
FIG. 61 is a diagram related to one embodiment of the present invention.

Inspection Device Arranged with an Optical Microscope and SEM in the Same Chamber Furthermore, observation using a SEM is sometimes necessary when performing an inspection of a sample using the above described detector. Thus it is very effective to arrange a projection type optical inspection device and a SEM within the same chamber (refer to FIG. 59). For example, in an inspection of a fine pattern such as a EUV mask or NIL (nanoprint lithography) mask, inspection of an ultrafine pattern with a high level of sensitivity using imaging conditions of a projection type optical pattern and a pattern defect is demanded. In the case where a projection type optical inspection device and a SEM are arranged within the same chamber, it is possible to load a sample onto the same stage and perform observation and an inspection of the sample using both a projection optical method and a SEM. The usage method and its merits are as follows.

First, because a sample is loaded onto the same stage, a coordinate relationship is unambiguously measured when moving the sample between the projection type and the SEM thereby it is possible to easily specify the same parts with a high level of accuracy. When a sample is moved between separated devices, it is necessary to align each of the samples respectively for arranging on different stages, and thus separately performed alignment of the sample would cause a location error of 5 to 10 μm for one and the same position. Due to this type of location misalignment, a place which is misaligned with a defect spot is reviewed, and a place with no defects is mistakenly imaged, and mistakenly judged to have no defects. In particular, in the case of a sample with no pattern, a location reference can not be specified and therefore such error becomes even larger, about 2~10 times compared to a sample having a pattern.

Secondly, a sample is arranged on the same stage and the same chamber, the same position can be precisely located even if the stage moves between the projection type the SEM, therefore, a location can be specified with a high level of accuracy, for example, it is possible to move a location of a foreign material or defect within a range of 0.05~1 μm with an accuracy 1 μm or less. In this way, it is effective when the inspection of the sample is first performed by the projection method to inspect a pattern and pattern defect. After that, location and detailed observation (reviewing) of the detected defect is performed by the SEM. Since the position can be located accurately, not only the presence or absence of a defect (false detection if absent) can be determined, but also detailed observation of the size and shape of the defect can be performed quickly. The separate installation of a device wastes a considerable amount of time for detecting and specifying a pattern defect.

In the embodiment, as described above, an ultrafine pattern can be inspected with high sensitivity by using conditions for imaging a pattern and with the projection-type optical method. In addition, the projection-type optical method and the SEM-type inspection device are mounted in the same chamber. Consequently, in particular, inspection of an ultrafine pattern of 100 nm or less and determination and classification of a pattern can be carried out with great efficiency and speed. Examples are described in detail below.

EXAMPLE 1

The invention includes the following functions and apparatus when the optical microscope, projection type optical system and SEM explained above are arranged within one chamber.

The optical system center of the optical microscope, projection type optical system and SEM are each calculated in advance, the coordinate relationship of the these centers are stored in a memory etc, and it is important to be able to move these stored optical system center coordinates. An apparatus for achieving this may be installed in the present example. When the same spot is observed with respect to a sample loaded on the same stage with the same chamber, it is possible to easily move between the stored optical centers using a button or click operation on a PC control screen. Because the sample is arranged on the same stage, it is possible to move or stop the location of the sample with a high level of accuracy, for example, 0.05~0.1 μm. In addition, if control is improved when the sample is stationary, a level of accuracy of 0.05~0.1 μm is possible. As an example of this control, stopping a sample using a plurality of stop allowable values can be given, for example, using two types of allowable values such as $A \leq 1$ μm or $B \leq 0.1$ μm. In this way, it is possible to stop a sample smoothly and efficiently using a plurality of allowable values and using small allowable values step by step.

(Alignment Sequence)

The relationship between sample alignment in each optical system, that is, optical microscope, projection type optical system and SEM, sensor alignment in a detector in a projection type optical system and image formation alignment is required for making the above described operation possible. Depending on how these are measured, the capabilities of operation processes, required time and location accuracy, false determination and categorization of defect types are affected. In the present case, the following sequence is performed in order to obtain efficiency and accuracy.

a) Determining a sample alignment using an optical microscope (refer to FIG. 60)

This involves matching the movement direction of a stage and the direction of a sample and determining the direction of the sample. For example, the sample is rotated using a rotation stage etc, and a rotation angle θs of the sample is determined so that the y direction of the sample is matched with the movement direction (y direction) of the stage. For example, in the case where there are 2 or more representative pattern marks in the y direction of the sample, 2 patterns or marks separated in the y direction by 10~300 mm are used. At this time, the rotation angle θs of the sample is measured and determined so that these two patterns or marks arrive on the optical center of the optical microscope. At this time, it is possible to obtain an alignment accuracy of 1/10~1/100 Px by performing image processing such as pattern matching.

b) Determining a rotation angle θt of a detector which detects an electron image of a projection type optical system.

Figure 62:
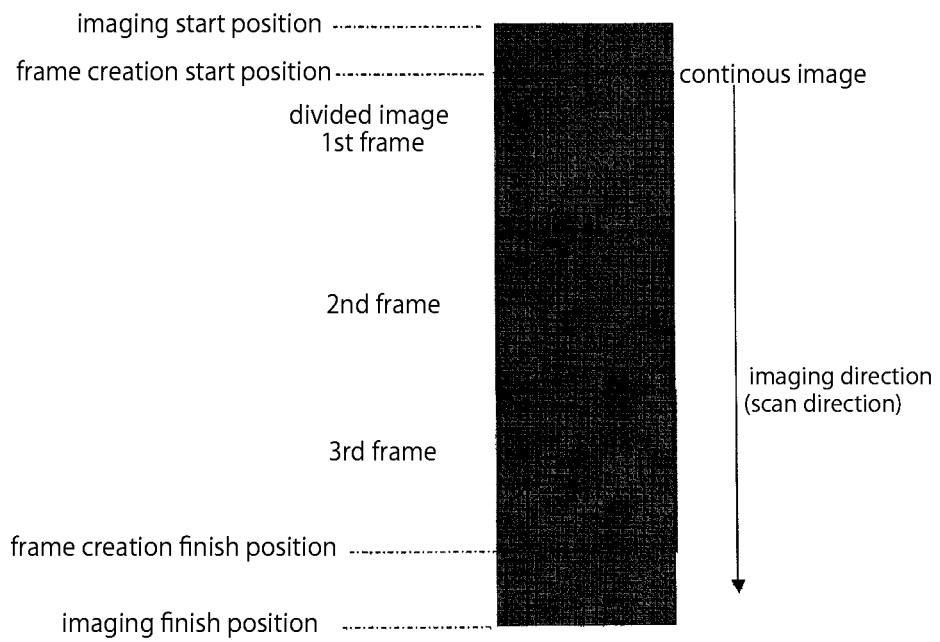
FIG. 62 is a diagram related to one embodiment of the present invention.
Figure 63:
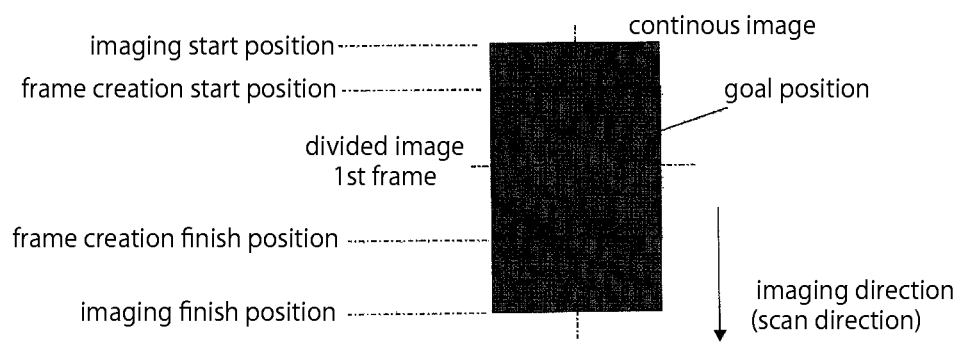
FIG. 63 is a diagram related to one embodiment of the present invention.

This angle adjusts and determines the rotation angle θt for matching the y direction (direction in which each pixel lines up in a y direction) of a TDI sensor (time delay integration CCD-TDI sensor) or CCD sensor with the movement direction of a stage. Specifically, the following operation is performed. Patterns or marks separated by a distance of around 10~300 mm are used. The stage movement direction and rotation angle θs of the sample are adjusted using a) described above, and the stage movement direction y and y direction of the sample are adjusted at a high level of accuracy, for example, adjusted to within 1/1000~1/100000 rad, or within 1/10000~1/100000 rad. In this state, the stage is moved in a y direction and an image is simultaneously obtained, and the rotation angle θt where resolution of a TDI image of a pattern or mark is at maximum, for example, where contrast is at its maximum, is calculated. A one dimensional L.S pattern etch in a Y direction may be used as the pattern. The L/S pattern becomes distorted and contrast decreases when the rotation angle θt is misaligned. Contrast increases when the rotation angle θt is an appropriate value, and the most optimum value can be calculated. A misalignment of 1/1000~1/100000 rad is possible in the stage movement direction y and in a Y direction of a TDI or CCD sensor when this operation is performed. In addition, a misalignment of 1/10000~1/100000 rad is possible by adjusting at a high level of accuracy.

c) Next, center coordinates of a TDI image frame are calculated (see FIG. 62, FIG. 63)

Because a TDI image is a two dimensional continuous image, a continuous image is divided into frames by image processing. For example, 1000×10000 Px, 2000×2000 Px, 4000×4000 Px etc are created as one frame. Adjustment and determination are performed so that the center of each of these frames matches the desired location. Here, an example of a method for determining desired coordinates is given.

A) For example, a pattern part of mark part that has a characteristic is used. These are arranged at the optical center location of the optical microscope and their coordinate values are stored. In addition, the obtained start location and finish end location of the TDI image is determined so that the pattern part or mark part become the frame center of a TDI image. Adjustment of the y direction location may be performed by image processing, that is, adjusting the parameters of the start location which divided a frame. Adjustment can easily be performed by adjusting the start location which divides a frame in 1 Px units. For example, adjustment is possible with an accuracy of 50 nm at 1 Px 50 nm, and 10~500 nm/Px is usually used.

B) Adjustment of a location in an x direction is performed by fine adjusting the coordinate location relationship of the optical centers so that the desired pattern or mark move to the center location in an x direction of the sensor. Alternatively, it is also possible to perform fine adjustment using a last stage deflector. In this case, adjustment with an accuracy of $1/10$ Px~10Px is possible. In addition, adjustment with an accuracy of $1/10$~1 Px is often used.

C) Next, whether the desired pattern or mark has moved to the optical center of a SEM (scanning type electron microscope) is confirmed. If there is a misalignment, the coordinate relationship between the optical centers is corrected. That is, it is confirmed whether the desired pattern or mark is at the center of the optical microscope, the frame center of a TDI image and center of an SEM image and confirmed and determined that this is within an allowable value range. If it is confirmed that the desired pattern or mark is within an allowable value range from the center of the optical microscope, TDI image frame of a projection type optical system and SEM image, the distance between each optical center location is determined and stored in a memory etc. An allowable value of 1 μm or less is possible. In addition, an allowable value of 0.1 μm or less is possible by a high level of accurate adjustment.

D) Other than this, in the case where a detector used in a projector type optical system is a CCD or an EB-CCD which forms an image by directly irradiating electrons to a sensor surface, because an image is obtained while the stage is in a stationary state, adjustment and determination is made so that the optical center arrives at the center of the still image and a pattern or mark arrives at the optical center of an optical microscope, projection type optical system EB-CCD image or SEM image within an allowable value range. This procedure and allowable value is the same as described above.

As described above, the present invention includes the features of A) a step of performing alignment using an optical microscope B) performing alignment in a direction of a detector sensor (y direction: calculation direction of a sensor) using a projection type optical system C) a step of calculating the optical center of an optical microscope, projection type optical system and SEM and storing correlated coordinates. In addition, in the case where a TDI image of a projection type optical system is used, it is necessary to include a step of calculating a frame center of a TDI image in step B).

In addition, in step C) it is possible to perform the following procedures when calculating accuracy with respect to a SEM image. The x direction and y direction which form the image frame of a SEM image are calculated and determined. The desired direction is obtained by obtaining a SEM image of a pattern or mark when step A) and B) described above are completed and misalignment of the x, y directions is extracted and corrected. The corrections means includes matching the direction while finely adjusting the misaligned x and y directions. In order to achieve this, 8 deflectors for forming a SEM image, that is, for scanning, are used. In this way, control of a deflection angle with an angle adjustment within $1/1000$~$1/100000$ rad is possible. It is possible to perform this operation in step C).

In the example used in the devices of the present invention, a defect inspection is performed using a TDI image in a projection type optical system after the operational steps pre-inspection described above are completed. In addition, a patch image and coordinate values of the inspection result are output and stored in a memory etc. Next, if a review is carried out using a SEM, review imaging is performed using a SEM of the parts in which defects are detected using a TDI image and defect or false determination is performed.

At this time, it is possible to perform a defect determination or false determination using a SEM image by an image processing device. The following methods can be used.

First, comparison of a pair of SEM images: Comparison with a reference part image using a SEM Second, comparison of a SEM image and TDI image (patch image). A patch image is a defect image obtained during an inspection and is formed by cutting out the vicinity of a defect part detected from a TDI scan image and stored in a memory. Usually, this is performed at around 50200 Px. It is preferable that the short side of an image is 1 ~$1/3$ when this value is the long side of an image.

In particular, in the second method, because image processing such as pattern matching is not performed sufficiently when the x, y direction of a SEM image are misaligned, it is necessary to perform adjustment and determination of the SEM x, y directions in advance. For example, pattern mismatching occurs due pattern location misalignment.

In addition, there is a method for correcting the x, y directions of a SEM image by image processing. A method of comparison is also possible by calculating in advance the amount of correction of x. y of the SEM image and making corrections when an image comparison with a TDI image.

EXAMPLE 2

In the present example it is possible to clean adhered contamination when performing a review using a SEM.

It is known that contamination such as carbon is adhered when performing a SEM observation. Because contamination is adhered when a SEM review observation is performed, the contamination itself sometimes occurs as a defect. In particular, considerable contamination is generated in an end part region of a beam scan.

Two methods are used in the present invention in order to solve this type of problem.

First, a method of introducing a contamination reaction gas a simultaneously cleaning a sample surface while performing a SEM observation.

Second, a method of cleaning using a projection type optical system after a SEM observation. A gas which has reactivity with contamination is sometimes introduced and sometimes not introduced.

In the first method, a SEM review observation is performed while introducing an inert gas such as oxygen or oxygen+Ar, or a fluoride group gas such as SF6. In this way, although contamination occurs during the SEM observation, it is possible to remove the contamination by introducing the gases described above which react with the contamination and thereby causing a sublime gas state. At this time, it is important to adjust the amount gas introduced to a level which does not affect the level of resolution of an SEM image. The effects are as follows. The remaining gas particles within a vacuum chamber are excited by an electron beam, polymerize with C or H to become contamination such as carbon or DLC and adhere to the sample surface. The amount grows due in proportion to the amount of the irradiated beam and time. At this time, when the above described gases such as oxygen having reactivity with contamination are introduced, the gas particles are excited by irradiation of an electron beam, become active gas particles and gas particles having reactivity with contamination such as an oxygen radical are formed. In addition, the active gas particles react with the contamination, become gas particles such as CO, $CO_2$ etc and are removed. As a result, a SEM observation in a state where there is small amount of adhered contamination is possible.

The second method described above is a cleaning method which can rapidly remove contamination after a SEM review observation is performed. An irradiation beam of a projection type optical system which irradiates a surface beam is used as the electron beam irradiation. At this time, the above described inert gas is introduced, gas particles such as an oxygen radical are formed as an active gas by irradiating the surface beam onto the gas particles and contamination is removed. The contamination removal effects are the same as described above. The merit of using the surface beam is that it can be performed rapidly. Cleaning can be performed by moving a stage at a speed of 30 mm/s with a 200×200 μm beam, and irradiating an area region of about 100 mm for around 30 minutes. A contamination removal process can be performed at a speed of 2~3 times that of a SEM type. At this time, in order to remove contamination efficiently, it is preferable to remove contamination of a boundary region where a SEM review is performed. Since a considerable amount of contamination is generated in this region, it is possible to significantly reduce contamination defects by removing the contamination in this region and thereby, cleaning of this region is practical and often sufficient.

As explained above, an entire structural view of a semiconductor inspection device in which an electron microscope, projection type optical system and SEM are arranged in one chamber is shown in FIG. 43 already explained above. Since this structure has been explained in detail above, an explanation is omitted here. However, by adopting this structure, a spot can be specified with a high level of accuracy and alignment adjustment becomes easy. In addition, determination and classification of an inspection of an ultrafine pattern of 100 nm or less can be performed efficiently and rapidly. Furthermore, the present embodiment can be applied to the device in the first to eleventh embodiments described above. Providing the SEM and optical microscope of the present embodiment to a device including the same projection type optical system to the same device system and performing an inspection and review is very effective.

(Thirteenth Embodiment)
Particle Measures

Figure 64:
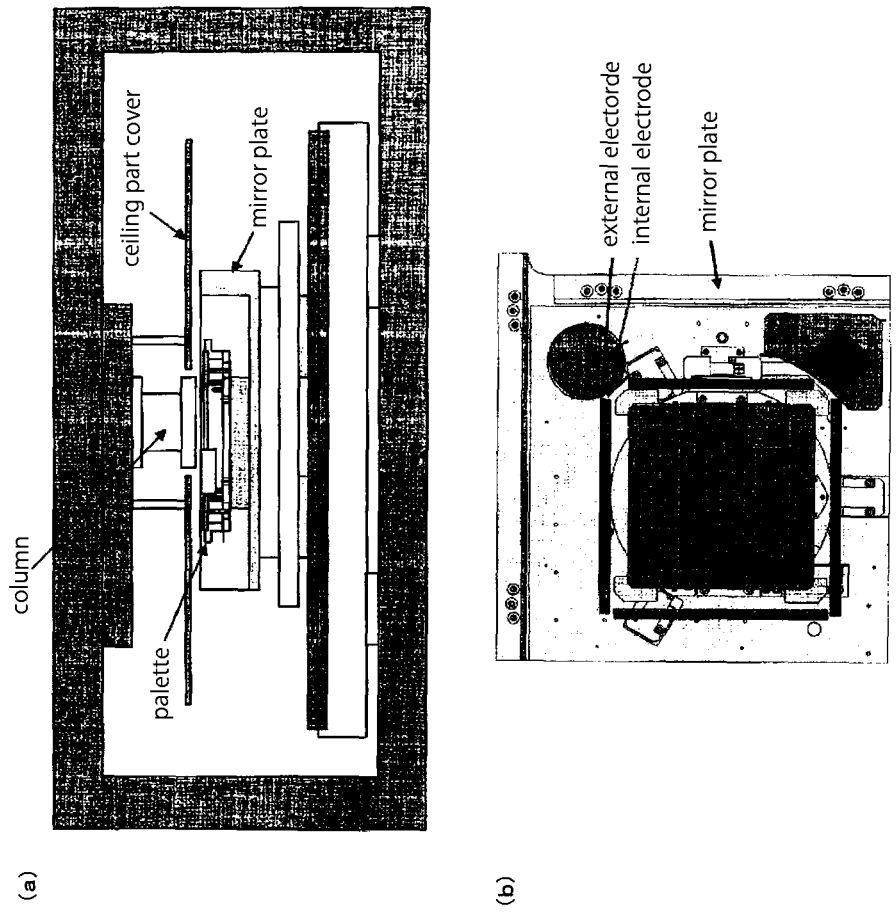
FIG. 64 is a diagram related to one embodiment of the present invention.

Because the effect of particles increases together with miniaturization technology the demand for measures to prevent particle adhering is becoming stronger. When a device is realized for performing a defect inspection of foreign materials of 5~30 nm or a pattern size as in the present technology, prevention of particles and prevention of particles a size of the same level is required. While such prevention was sufficient in all conventional devices it is possible in the present invention. Particle prevention measures used in the inspection device and inspection method of the present invention are explained while referring to FIG. 64 and FIG. 65. Only the points of difference from conventional measures are described.

Ceiling Cover Attachment
(Effects)
Protection from Particles Falling from a Ceiling A ceiling cover is attached so that a region of a sample which moves with a stage is covered. In this way, an effect which prevents particles which fall from the top part of a column onto a main chamber including a sample from being adhered to the sample is obtained. In addition, a conductor cover is arranged on the periphery of a sample surface such as a mask and becomes the same potential as the mask surface. In addition, the tip end part of the conductor cover has a thickness of around 10 um~300 um, a back surface contacts with a region having a conduction film of the sample surface and conducts. The thickness described here is provided so that the effects of a change in a mask surface potential near the conductor cover are as small as possible. The width of the conductor cover extends in an exterior direction from the sample by around 10~130 mm. By reducing the distance between the conductor cover and ceiling cover the likelihood that particles which fall into this space collide or adhere the conductor cover and ceiling cover increase and thereby it is possible to prevent particles from entering the sample surface. In addition, by covering the sample surface to which a RTD voltage is applied with the ceiling cover which has a GND potential, it is possible to prevent upper particles being attracted by an electric field from the ceiling cover.

Dust Collector
(Effects)

A dust collector is arranged which can suck and absorb particles which are attracted from the periphery by arranging an electrode with the same voltage on the periphery of a sample applied with a RTD voltage. This dust collector may be formed using one electrode or a plurality of electrodes. For example, in the case of two electrodes, it is possible to increase dust collecting effects by providing different voltages between the inner and outer electrodes. For example, by applying either a higher or lower voltage than the potential of the sample surface, particles which have a positive charge are absorbed by the dust collecting electrode which is applied with a low voltage and particles which have a negative charge are absorbed by the dust collecting electrode which is applied with a high voltage. In this way, it is possible to prevent particles from reaching the sample surface.

Ultrasound Motor Cover
(Features)

Movable parts used with a vacuum chamber such as an ultrasound motor etc which are a source of dust generation within the vacuum chamber are covered with a cover. Furthermore, particles are actively sucked and absorbed by the cover by applying a voltage to the cover.

It is possible to capture particles adhered to a travel plate by arranging a travel plate cover on a travel plate movable part.

Stage Cable
(Features)

Particles which are generated by the friction between cables are reduced by using single unit flat cables (Teflon (registered trademark)) for stage cables which move within the vacuum chamber.

A flat cable contact surface is arranged on a cable base (Teflon (registered trademark)) and friction between the cable and metal is removed. In a usual cable, a resin usually covers the core which has around cross section. When there is a plurality of these, a plurality of cables are bunched together and tied using an insulation lock. At this time, particles are generated by friction between cables due to movement or transformation of the bunched cables together with movement of the stage. Furthermore, in the present invention, it is possible to apply a stage cable to the device in the first to twelfth embodiments described above.

(Fourteenth Embodiment)
(Axial Correction Inherent to an Electron Image)

Axial correction inherent to an electron image in an inspection device and inspection method of the present invention is explained.

It is possible to apply FIG. 26, FIG. 27 and their embodiments as an example or as a reference. A DUV laser is irradiated to a sample surface, photoelectrons are generated from the sample surface, a magnified image is formed at a detector by a secondary optical system and a two dimensional photoelectron image is imaged. The RTD conditions of the secondary optical system, for example, a surface potential is positively charged due to photoelectron emission with respect to −4000V by the setting of the photoelectron image formation conditions. Because misalignment occurs from RTD −4000V due to this surface potential, the amount of misalignment is corrected by changing the RTD potential.
(Simultaneous Irradiation of Light with Different Wavelengths)

An example of simultaneous irradiation of light having different wavelengths to a sample W in an inspection device and inspection method of the present invention is explained.

In the case of a sample such as a EUV mask having a pattern with an uneven structure, when the outermost surface layer which are the bump parts are TaBO and the hollow parts are Ru, the contract between TaBO and Ru is sometimes TaBO>Ru ($\lambda$=266 nm), and sometimes TaBO<Ru ($\lambda$=244 nm) due to the wavelength. That is, when a sample surface having a pattern structure with TaBO and Ru is simultaneously irradiated with light of two types of wavelength, the pattern disappears and the parts (for example, foreign materials) other than the material which forms the pattern are detected. This can improve particle inspection or detection sensitivity of defects (foreign materials) of a pattern hollow part (Ru).

In the case of simultaneously irradiating light having different wavelengths, because the quantum efficiency is each is different, it is necessary to adjust the DUV light intensity or DUV laser intensity so that the contrast between TaBO and Ru disappears. At this time, in the case of laser irradiation, the laser irradiation intensity to a sample surface is adjusted using a polarization filter by adjusting the angle between the polarization surface of the laser and polarization surface of the filter. Because the quantum efficiency is different due to the wavelength of the light, the amount of variation in the surface potential is different due to the material of the sample surface.

The energy of a photoelectron becomes 4000V in the case of a detector surface potential GND at RTD −4000V mentioned above. When the secondary optical system lens conditions are optimized by adjusting RTD, it is possible increase a contrast difference and increase signal intensity by irradiating a light (laser) with a different wavelength to a wavelength used in an inspection in order to match in advance the material to be seen as a white signal (the amount of electrons generated is relatively high) and greatly displace other materials from the lens conditions. FIG. 33 (a) and FIG. 35~FIG. 42 are examples of this. A laser is irradiated to a photoelectron surface chip, photoelectrons generated from the surface are guided to a sample surface by a primary optical system, photoelectron irradiation is performed on the sample surface as a primary beam, and secondary emission electrons from the sample surface are magnified and an image is formed at a detector by a secondary optical system. At this time, the wavelength of the laser irradiated to the photoelectron surface chip may be larger than the work function of a material which forms the photoelectron surface and light with an energy as close as possible to the work function is preferred. In this way, it is possible to significantly reduce the dispersion of work energy held by a photoelectron. That is, it is possible to reduce the energy band of a primary electron beam compared to a conventional method. In this way, the energy dispersion of secondary emission electrons or mirror electrons which are generated by irradiating a primary beam (electrons) to a sample surface is also reduced and it is possible to obtain a sharp image with few aberrations when forming an image. The photoelectron surface chip structure includes coating a photoelectron material onto a single surface of a base material having good laser transmittance, for example, Ru, Au or Ag etc. A laser is irradiated from the rear side of a coating surface, photoelectrons are generated from the coating surface and photoelectrons are emitted in a direction opposite to the laser irradiation. In this way, it is possible to make the structure of a gun more compact with the need for adding an angle between the irradiation axis of a laser and the axis of a photoelectron.

(Fifteenth Embodiment)
Atmosphere carrier which carries a double POD

Figure 66:
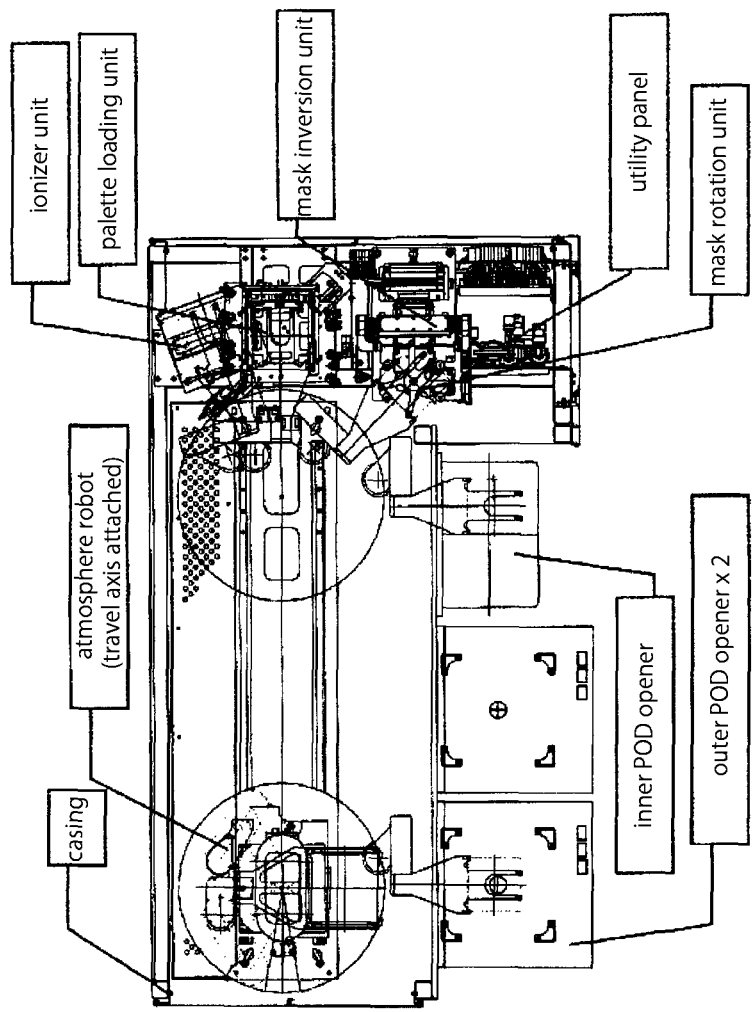
FIG. 66 is a diagram related to one embodiment of the present invention.

An atmosphere carrier which carries a double POD in the inspection device and inspection method of the present invention is explained while referring to FIG. 66.
(Operation/Conditions)

A double POD is a box having a double structure which encloses a sample such as mask. An inner POD includes a gap or a hole and the outer POD should be open during load lock. At this time, the inner POD is structured by a lower plate and an upper plate. A EUV mask pattern surface is arranged in proximity to the lower plate. At this time, the operation flow is as follows. Outer POD opener→inner POD opener→rotation unit b→inversion unit→neutralization unit→palette loading unit→load lock chamber.
(Operation/Effects/Merits)

Figure 67:
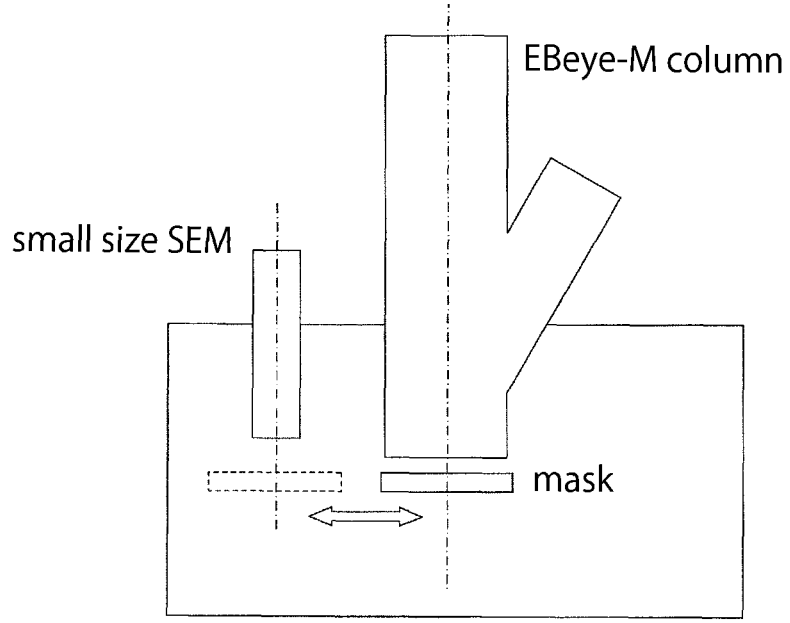
FIG. 67 is a diagram related to one embodiment of the present invention.

While the present invention is double POD compatible, it is possible to use a single and double POD together because the operation flow extracts a single mask using an inner POD opener. Furthermore, the present embodiment can also be applied to the first to fourteenth embodiments.
(Sixteenth Embodiment)
Compact SEM A compact SEM used in the inspection device and inspection method of the present invention is explained while referring to FIG. 67.

A feature of the present invention is reviewing a detected defect within the same chamber as a defect inspection device (projection type electron beam inspection device) at a higher magnification using a scanning electron microscope (herein referred to as SEM).
(Effects)

Because it is possible to perform a review within the same chamber, a sample is not moved between devices and thereby the sample is not contaminated and time efficiency is improved.

A feature of the present invention is determining whether a detected defect is an actual defect or a false defect based on a review result using the SEM described above.

Automatic defect categorization (ADC) is performed using reviewed image data and the reliability of a defect detection result is increased.

A feature of the present invention is that the all the electron lenses in the SEM used for performing a review described above are formed by electrostatic lenses.

A SEM structure using electrostatic lenses can also be used for observation of an alignment mark since distortion of an image is small in a low magnification observation.
(Effects)

In the case of an electromagnetic lens, a system for correcting the scanning shape of a beam is required in order to obtain an image with low distortion at a low magnification. However, this is not required when using an electrostatic lens and thereby a simple system is sufficient. In addition, in an electromagnetic lens a current is applied to a coil in a lens structure, a magnetic field is generated and a lens field is formed. As a result, 1~5 hours is usually required until a stable temperature and stable resistance state is reached after a device is started, that is, until an operation state of a lens is stable. However, an electrostatic lens reaches a stable state in a few minutes when certain voltage output setting is performed because a constant voltage power supply is used. In this way, an electrostatic lens has excellent compatibility with condition setting or condition variation. Furthermore, this embodiment can also be applied to the first to fifteenth embodiments explained above.

(Seventeenth Embodiment)

Adjustment Method of a Laser Beam

An adjustment method of a laser beam used in the inspection device and inspection method of the present invention is explained. The method can be applied to FIG. 26~FIG. 31 and related embodiments and are examples of this method.

It is necessary to set a voltage of a secondary system lens etc to an optimum value in order to increase of resolution of photoelectrons emitted from a sample surface, what is called optical axis adjustment. A usual procedure of optical axis adjustment entails observing an image with an initial low magnification and performing a broad axis adjustment in advance, then the magnification is gradually increased and an axis adjustment is performed at a high level of accuracy.

The amount of photoelectrons that contribute to image observation decreases as the magnification increases. That is, if the photoelectron density is constant the magnification increases and when the Px size decreases the amount of photoelectrons per 1 Px decreases as the Px size decreases. Therefore, when a low magnification is changed to a high magnification without changing power, the signal amount is insufficient and only a dark image can be obtained. In contrast, when an observation is made at a low magnification while maintaining an optimum laser power at a high magnification, the amount of photoelectrons become saturated and a required contrast can not be obtained. As a result, it is necessary to adjust the power of a laser beam. However, it is often impossible to adjust the power of a laser itself. In this case, it is possible to adjust the power or a laser beam which reaches a sample surface using an optical element such as a variable beam splitter, an attenuator, a polarization element or lens etc.

A variable beam splitter changes the proportion of transmitted light by adjusting the angle with respect to a laser beam using a plate shaped optical element.

An attenuator is an integrated unit of a plurality of optical elements such as a variable beam splitter and can easily be operated.

A polarization element changes the transmittance due to the polarization state of a beam and changes the polarization state by changing the phase. A polarization element includes a polarization plate, wavelength plate or depolarization plate and by combining these it is possible to transmit only a specified polarization state and control the power of light.

For example, the focal distance of a lens is changed by changing the location of a plane-convex lens for collecting light, localized power density of an observation range is changed by changing a power profile and the amount of photoelectrons can be controlled. Other than this, the thickness or number of transmittance substances such as a lens, or silica glass etc may be adjusted and power may be adjusted by increasing the number of mirror reflections.

Methods for adjusting the power of a laser other than the method using an element such as described above are as follows. For example, power density of an observation surface changes by changing the angle of a mirror and changing the irradiation location of a beam. It is possible to obtain a large amount of photoelectrons when a part with a high power density is irradiated as the observation part and a small amount of photoelectrons are obtained when a part with a low power density is irradiated as the observation part.

A method which uses two or more types of light source with different power is also possible. For example, in the case of a low magnification observation, it is possible to use a mercury xenon lamp which has ultraviolet regions with little power, and it is possible to use a gas laser has twice the harmonics of a YAG4 harmonic solid state laser or Ar ion laser in the case of observation at a high magnification. At this time, it is possible to guide the mercury xenon lamp within a vacuum using a fiber, and irradiate directly from the fiber exit or via an optical element such as a mirror.

The laser beam irradiated from a laser transmits through a synthetic silica view port via a first mirror, light collecting lens, second mirror, and is guided to the inside of a vacuum chamber. After passing through the view port, the beam is reflected by a triangular mirror arranged in the vicinity of a column axis center and is irradiated to a sample surface at an angle misaligned about 0.1~30° from the axis center of an electron beam.

The triangular mirror has a hole having a diameter of 0.5~5.0 mm so that an electron beam can pass through the axis center and has a synthetic silica or phosphor bronze surface which is coated with aluminum. The potential of the triangular mirror is made the same as a space potential such as an earth potential so that the electron beam which passes through the triangular mirror hole is not bent by an electric field. In the case of manufacturing the mirror using a synthetic silica, it is also necessary to coat the inside of the hole with aluminum in order to secure conductivity.

A polarization element, beam splitter or attenuator may be arranged after a lens for example in order to adjust the power of a laser.

Although a method of arranging a mirror or lens on the atmosphere side was explained above, these lenses or mirrors may all be arranged within a vacuum chamber.

(Eighteenth Embodiment)

Inspection Device for Controlling an Irradiation Angle $\theta$ and Irradiation Direction $\alpha$ of a Beam to a Sample Surface A method for controlling the irradiation angle $\theta$ and irradiation direction $\alpha$ of a primary electron beam to a sample surface used in the inspection device and inspection method of the present invention is explained.

(Difference from Conventional Technology)

A projection type electron beam device is disclosed in International Publication WO2009/125603 in which the LE energy of an electron beam is given as a transfer region which includes both mirror electrons and secondary emission electrons, an NA location is optimized, electrons emitted from a conductive material are extracted and a line and space pattern or contact plug are observed at a high contrast.

In addition, a method of optimizing an NA location while observing an electron distribution at an NA surface under lens conditions for image forming an NA surface at a detector is disclosed in paragraph (0205) of Patent Application 2010-091297. In this application, a method was discovered for obtaining an image with an even higher contrast by controlling the irradiation angle and irradiation direction of a primary beam to a sample surface.

Figure 68:
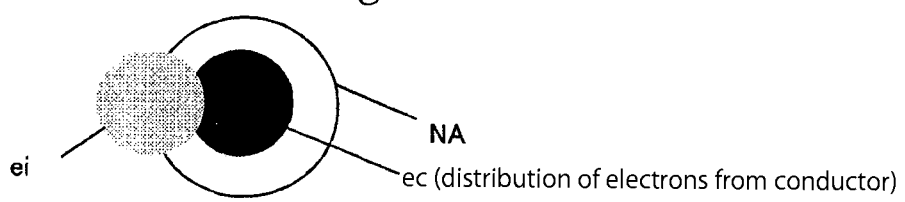
FIG. 68 is a diagram related to one embodiment of the present invention.

FIG. 6 (B) of Patent Application 2010-091297 shows an exemplary diagram of an NA surface observation (FIG. 68).

Figure 69:
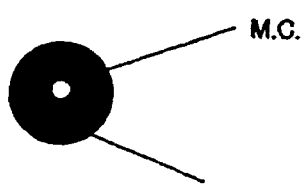
FIG. 69 is a diagram related to one embodiment of the present invention.

The inventors found that in a cross over (CO) image in the NA image forming optical conditions, a separate distribution (MC) of mirror electrons which rebound without hitting a sample to the distribution (CO) of secondary electrons which hit a sample within an ec distribution exists even if the LE of a primary beam is changed into a transfer region of secondary electrons and mirror electrons (FIG. 69).

Figure 70:
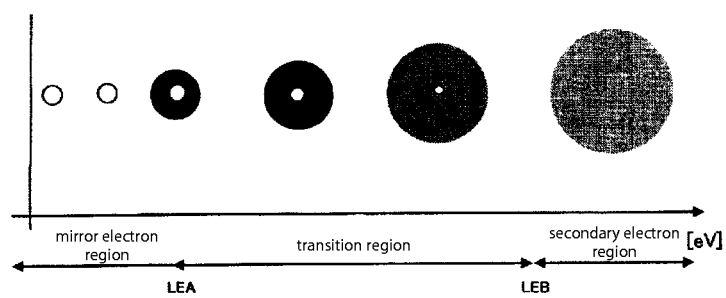
FIG. 70 is a diagram related to one embodiment of the present invention.

An NA image formation exemplary view which corresponds to the exemplary view in FIG. 3 of Patent Application 2010-091297 in which an image in which the image conditions LE which link NA stated above is shown in FIG. 70. At this time, a mirror electron region is defined when a landing energy is lower than LEA, a transfer region in which mirror electrons and secondary emission electrons are mixed is defined when LEA≦LE≦LEB and a secondary emission electron region is defined when LEB<LE. In addition, the following is an example when LEA=0.

Because about 2 eV exists in the case where an energy distribution for a primary beam is a LaB6 chip, more than a few negative LE electrons exist when a landing energy LE=0eV. For example, CO and MC are sometimes expressed simultaneously in FIG. 70.

This example is shown in FIG. 70. The furthest right diagram is a CO cross section of secondary emission electrons and moving to the left, CO decreases because of an increase in the emission amount of mirror electrons and a decrease in secondary emission electrons, MC appears and its intensity gradually increases. When LE becomes negative only MC exists. The size of this electron distribution sometimes represents the emission angle distribution of mirror electrons or secondary emission electrons.

The trajectory of mirror electrons is changed in an opposite direction when a parabola is drawn due to the potential of a sample surface and a primary beam forms an MC at an NA surface. That is, the location of MC can be controlled by the irradiation angle of a beam.

On the other hand, because the secondary emission electrons which hit the sample and are emitted are different to the primary beam (electrons) no effect is received from the irradiation angle.

Figure 71:
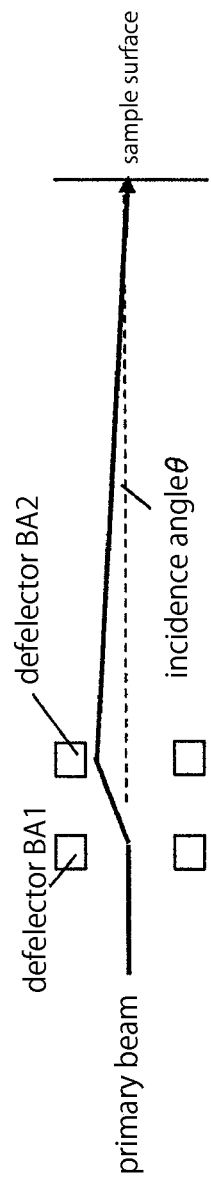
FIG. 71 is a diagram related to one embodiment of the present invention.

A method for changing only the irradiation angle without changing an irradiation location can be realized by using a two stage deflector (BA1, 2) mounted on a primary column (FIG. 71).

Figure 72:
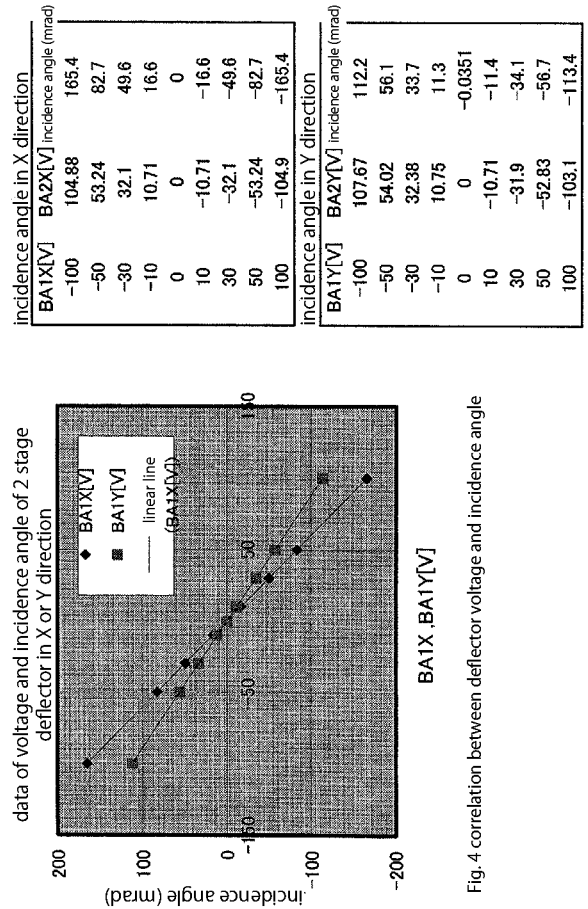
FIG. 72 is a diagram related to one embodiment of the present invention.

The voltage and irradiation angle data of a two stage deflector in a X direction or Y direction is shown in FIG. 72.

The MC location is important with respect to CO in the case of attempting to reduce the NA diameter in order to achieve high resolution.

Figure 73:
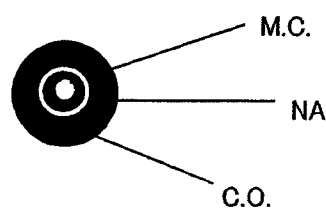
FIG. 73 is a diagram related to one embodiment of the present invention.

When the NA is arranged at the CO center in an attempt to obtain a high resolution, MC mainly passes through the NA and an image is formed in the case where a primary beam is irradiated at a perpendicular angle (FIG. 73). A good image can not be obtained since the MC does not include sample surface data.

Thus, a method was examined for obtaining a high resolution image by changing the irradiation angle of a primary beam and offsetting an MC vertically and horizontally.

In the case of observing an L&S pattern, the bump (line) part of the horizontal pattern becomes brighter due to the effect of an MC light in the case of arranging an MC vertically, and the electron density in the bump (line) part of the vertical pattern becomes higher when an MC is arranged horizontally. In addition, the contrast of the vertical and horizontal pattern can easily become non-uniform. In the case of shifting the beam irradiation angle θ in the X direction and Y direction and making the irradiation direction to a 45° direction, the MC location also changes in a 45° direction within the NA surface. An image with a good contrast where the vertical and horizontal pattern are the same can be obtained.

In the example in FIG. 74, the irradiation direction is defined as the X+ direction at 0° and an angle in an anticlockwise direction is defined.

A voltage may be set to the voltage of the deflector which becomes a desired irradiation angle. An exemplary view of NA image formation is shown in FIG. 74 and a trajectory exemplary view of a mirror electron is shown by the trajectory A.

As MC approaches NA, the SN of a pattern improves. However, contrast deteriorates and when MC moves further away from NA, SN deteriorates and the contrast sometimes decreases. It could be experimentally confirmed that an optimum location relationship exists when MC is at a distance 2~3 times the NA diameter from the center.

A method for adjusting an MC location can be easily realized while observing an NA image formation.

On the other hand, in the case of observing particles on a sample, it was experimentally confirmed that a higher sensitivity can sometimes be obtained when observing in a vertical direction (X direction) than a horizontal direction (Y direction).

In addition, in the case where the MC is arranged on the left or right (X direction), the left and right side of an image becomes brighter, and in the case of scan imaging in a Y direction either the left or right side becomes brighter. In this case it is preferred to place the MC about 2~3 times the NA diameter form the CO center.

The merits of using an EB-CDD or EB-TDI in these observations and inspections can be referred to in paragraphs (0403) and (0404) of International Publication WO2009/125603. Furthermore, the present embodiment can also be applied to the first to seventeenth embodiments described above.

EXAMPLE 1

First Step

Sample: Cu/SiO$_2$ wire pattern (refer to FIG. 75)
Acceleration Voltage: −4005 [V]
Sample Surface Potential: −4002.6 [V]
LE=2.4 [eV]
Current Density: 1 [mA/cm$^2$]
Secondary Optical System NA image formation TL2-2; 5550 [V]

Figures 75, 76, 77:
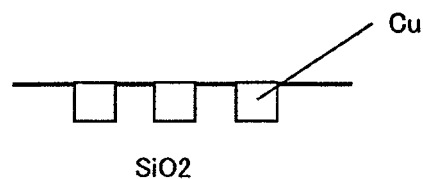
FIG. 75 is a diagram related to one embodiment of the present invention.
FIG. 76 is a diagram related to one embodiment of the present invention.
FIG. 77 is a diagram related to one embodiment of the present invention.

An EB-CCD camera was used for a detector and an MC and CO were observe using NA image formation conditions. Values of aligners BA1, 2 were set so that a sample surface was irradiated from an irradiation direction α=45[°] and irradiation angle θ=100 [mrad] (FIG. 76).

Second Step

Magnification setting of an electron optical system, square of 29 nm (pixel) A 25 nm L&S pattern on a wafer was observed with an NA hole diameter of 30~100 μm. BA1, 2 and an NA location were adjusted and the L&S (line and space) pattern became the same vertically and horizontally.

Third Step

MC location was 45° above the sample surface, an irradiation angle was changed with a range of 20~200 [mrad] and the contrast and S/N of the L&S pattern was measured. S/N was defined by dividing the contrast by a standard deviation σ of an average grey level of a W surface.

The relative location of MC with respect to the NA diameter is shown in FIG. 77. From FIG. 77 a good image together with a contrast and S/N around a relative location of 2.5 was obtained.

The relative location of MC and contrast and S/N correlation is shown in FIG. 78.

Fourth Step

Stage Speed: 1~20 mm/s
Data Rate: 50~100 MPPS
When an inspection was performed on a wafer while scanning using a TDI camera, a defect detection of about 25 nm could be performed.

EXAMPLE 2

First Step

Figure 7:
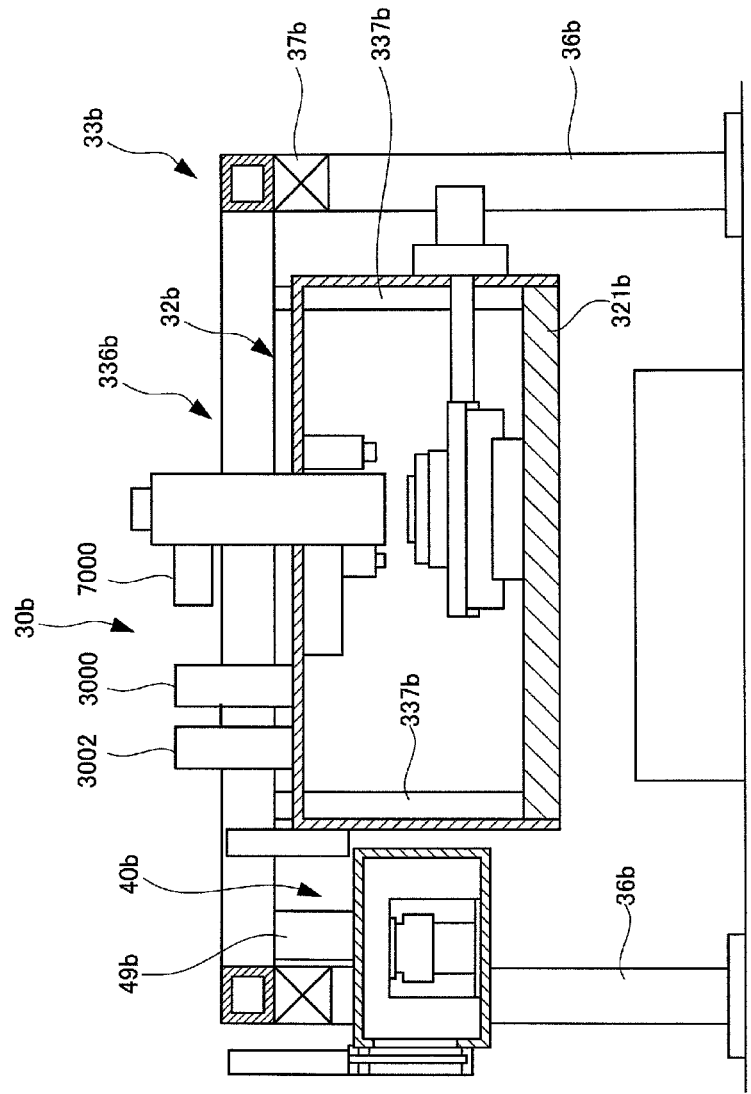
FIG. 7 is a diagram which shows modifications of a method for supporting a main housing.

Sample: Refer to FIG. 7 of Patent Application 2010-091287 regarding φ30 nm φW contact plug/SiO2 structure.
Acceleration Voltage: −4005 [V]
Sample Surface Potential: −4002 [V]
LE=2.4 [eV]
Current Density: 1 [mA/cm$^2$]
Optical System NA image formation TL2-2; 5550 [V]
A mirror electron (MC) and cross over (CO) at NA image formation were confirmed using an EB-CCD camera and a two stage deflector BA1, 2 was arranged as follow (refer to FIG. 79). The values of BA1, 2 were adjusted and a sample surface was irradiated from a 0[°] Y direction and an irradiation angle 100 [mrad] (refer to FIG. 80).

Second Step

Magnification setting of an electron optical system, square of 29 nm (pixel)
A W plug on a wafer was observed with an NA hole diameter of 30~100 μm, and the contrast and SN correlation in [Third Step] described above were measured. In this case also, an optimum image was obtained around a relative location of 2.5.

Third Step

Stage Speed: 1~20 mm/s
Data Rate: 50~100 MPPS
When an inspection was performed of a plug on a wafer while scan imaging using a TDI camera, a defect inspection of a φ30 nm plug structure could be performed. An even higher contrast inspection can be informed by applying the principle of a beam dose in FIG. 19 and contrast inversion in FIG. 22 in Patent Application 2010-091297.

EXAMPLE 3

First Step

Sample: particles on Si
Adjustment of an irradiation angle with the same conditions as in [First Step] in Example 2 was performed.

Second Step

Magnification setting of an electron optical system, square of 100 nm (pixel)
Particles on a wafer were observed with an NA hole diameter of 30~100 μm, and the contrast and SN correlation in [Third Step] described above were measured. In this case also, an optimum image was obtained around a relative location of 2.5.

Third Step

Stage Speed: 1~20 mm/s
Data Rate: 50~100 MPPS
When an inspection was performed of particles on a wafer while image scanning using a TDI camera with these conditions, an inspection at a size of φ10~30 nm could be performed.

(Nineteenth Embodiment)

A high voltage power supply used in the inspection device and inspection method of the present invention is shown in FIG. 81.

A superimposed type high voltage generation device and application example are shown in FIG. 81 (a) and FIG. 81 (b). The high voltage generation part in FIG. 81 (a) receives a 20 kHz alternating current signal and superimposition of different potentials becomes possible. The output side of an insulation transistor is converted to a direct current by a rectifier circuit. The 20 kHz alternating current signal is preferred to have a sine wave or rectangular wave which is not steep at start up in consideration of preventing excess noise. The direct current output is an energy source for obtaining a high voltage output, and is converted to an alternating current signal by an inverter. Here too, a sine wave or rectangular wave which is not steep at start up in consideration of preventing excess noise is preferred. After converting to an alternating current signal it is converted to several kV by a boosting transistor and converted to a direct current voltage which is boosted to a desired voltage by a boost rectifier circuit. The boost rectifier circuit is a usual Cockcroft Walton circuit. The boosted direct current high voltage output is divided, compared with a voltage command value within a block of a voltage control function, the comparison value is controlled to be minimally fed back and a constant output voltage is maintained. The voltage command value and a monitor output are converted to photoelectrons and are input or output by optical fiber. The photoelectron conversion procedure includes a method of converting the photoelectrons to a frequency proportional to a voltage value, sending as a two value signal of light, reverse converting on the receiving side and returning to a voltage value which is method conventionally performed. However, because this method broadly belongs to A/D, D/A conversion, other known methods can also be applied.

When a high voltage power supply is separated from a column, a high voltage connector, high voltage cable and high voltage vacuum introduction terminal is required for a connection. Because these require a resistance voltage in an atmosphere, a large element is essential in proportion to the voltage used considering the necessity of maintain a sufficient creeping distance. Therefore, this becomes a large obstacle to the miniaturization of devices. A commercially available connector with a resistance of 30 kV, length of 200 mm and diameter of 50 mm is required. On the other hand, in a vacuum pressure of $1 \times 10^{-4}$ Pa or less, the density of a gas molecule as a medium becomes sparse and the resistance pressure of space significantly improves compared to atmosphere. In the present embodiment this point is utilized by arranging a high voltage generation block within the space adjacent to an optical system, and generation of a high voltage and supply are realized within a high vacuum. Because an optical system requires a high vacuum and contamination is significantly detested, an optical system and high voltage generation part are divided by a separation wall, a high voltage is supplied by passing through this separation wall, and both are discharged by separate discharge systems. A light or a communication cable of a control communication system for supplying a low voltage alternating current or direct current voltage from the high voltage generation atmosphere side and controlling a voltage is required for connecting to this high voltage generation unit. However, since the potential is significantly low and around several V or less, it is possible to achieve a small scale device with a small scale vacuum introduction terminal. Furthermore, the present embodiment can be applied to the first to eighteenth embodiments described above.

(Twentieth Embodiment)

EO Correction

An example of EO correction in an inspection device and inspection method of the present invention is explained.

(Outline)

A wafer is explained as an example of a sample. An exposure mask, EUV mask, nano-imprint mask and template can also be similarly used as well as a wafer.

When imaging a beam from a wafer using a TDI, the location of the wafer requires accurate positioning. However, actually, the wafer exists on an X-Y stage and because positioning is mechanically determined, several 100 μm to several tens of nm and a response speed of several seconds to several ms are practical accuracy values.

On the other hand, since design rules are miniaturized approaching several 10 mm, imaging relying only on the mechanical positioning described above, the order of response time and positioning accuracy become separated from the order of design rules and imaging accuracy which is a significant obstacle to obtaining an accurate image.

The imaging sequence is performed by combining a step (x axis) and a constant speed scan (y axis), and the (y axis) which performs comparatively dynamic control is has a control residual error which is generally large and considering prevention of image distortion, a greater level of control is being demanded.

An X-Y stage which is highly accurate and has excellent responsiveness is included for solving these issues. However, an EO correction function was devises for realizing control accuracy and speed of a beam to an imaging part which are issues that can not be solved by a stage.

A basic method includes accurately confirming the location of a wafer on a stage with a delay of within several microseconds at a sub nm order by a laser interferometer system and a bar mirror arranged on an x-y axis, a mechanical aperture is driven by an automatic control loop, and positioning is performed while considering time delay and residual error from a target position. A control residual error of a positioning result performed using this control is calculated from the difference between a target position generated within a control device and an actual position obtained by a laser interferometer system. On the other hand, a beam is guided to an imaging device via several electrodes and a correction deflecting electrode. A correction deflecting electrode has a sensitivity in which deflection is possible of around several tens of μm which is converted to distance on a wafer, and two dimensional deflection of a beam to an arbitrary location is possible by applying a voltage to the electrode. After a control residual error is calculated by a calculation device, it is converted to a voltage using a D/A convertor, and applied to the correction deflecting electrode for cancelling the control residual error. It is possible to perform correction close to the resolution of a laser interferometer using this structure.

A method in which the above procedure is used for the X axis (step direction) and synchronizing a transfer lock of a TDI which is an imaging element with the movement speed of a stage and transferring for the Y axis (scan direction) was also invented an alternative method.

Figure 82:
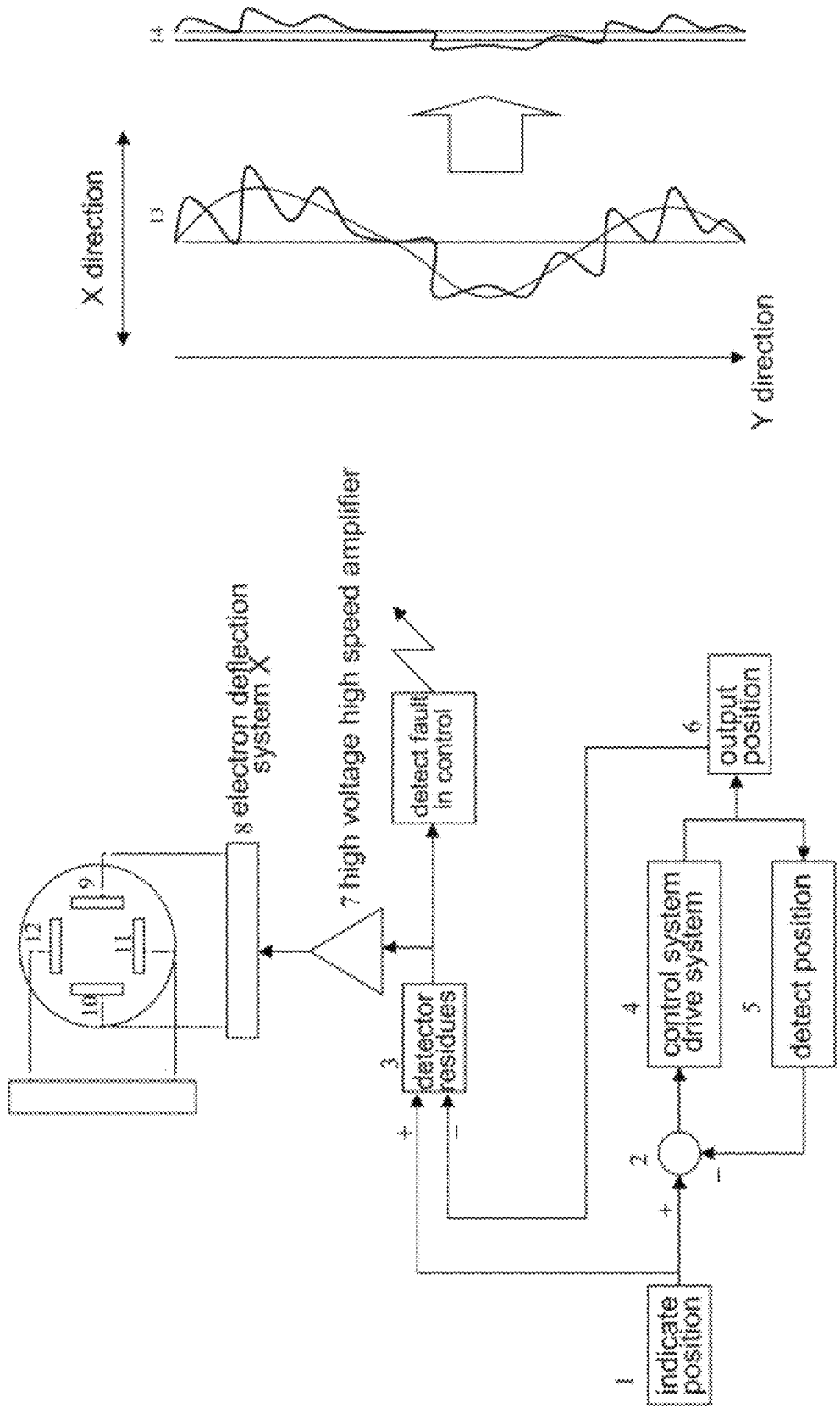
FIG. 82 is a diagram related to one embodiment of the present invention.

The concept of EO correction is shown in FIG. 82. A command is output to a target position from 1, and provided to control feedback loops 2, 4, 5 which include a mechanical actuator. This part equates to a stage. Feedback is performed via a position detector 5 as a result of a position displacement which is driven and the position displacement of a drive system gradually converges to the target position from the position command, however, a residual error is produced due to the benefit limits of the control system. The actual position is detected with an order of sub nm by a position output system 6 (the laser interferometer is used here), a difference with the position command device 1 is detected by a residual error detector, then applied to deflector electrodes 9, 10 using a high voltage high speed amplifier 7, a voltage is applied to cancel the residual error. In the case where this function is not present, a function such as 14 is included for reducing a variation which is produced as in 13.

Figure 83:
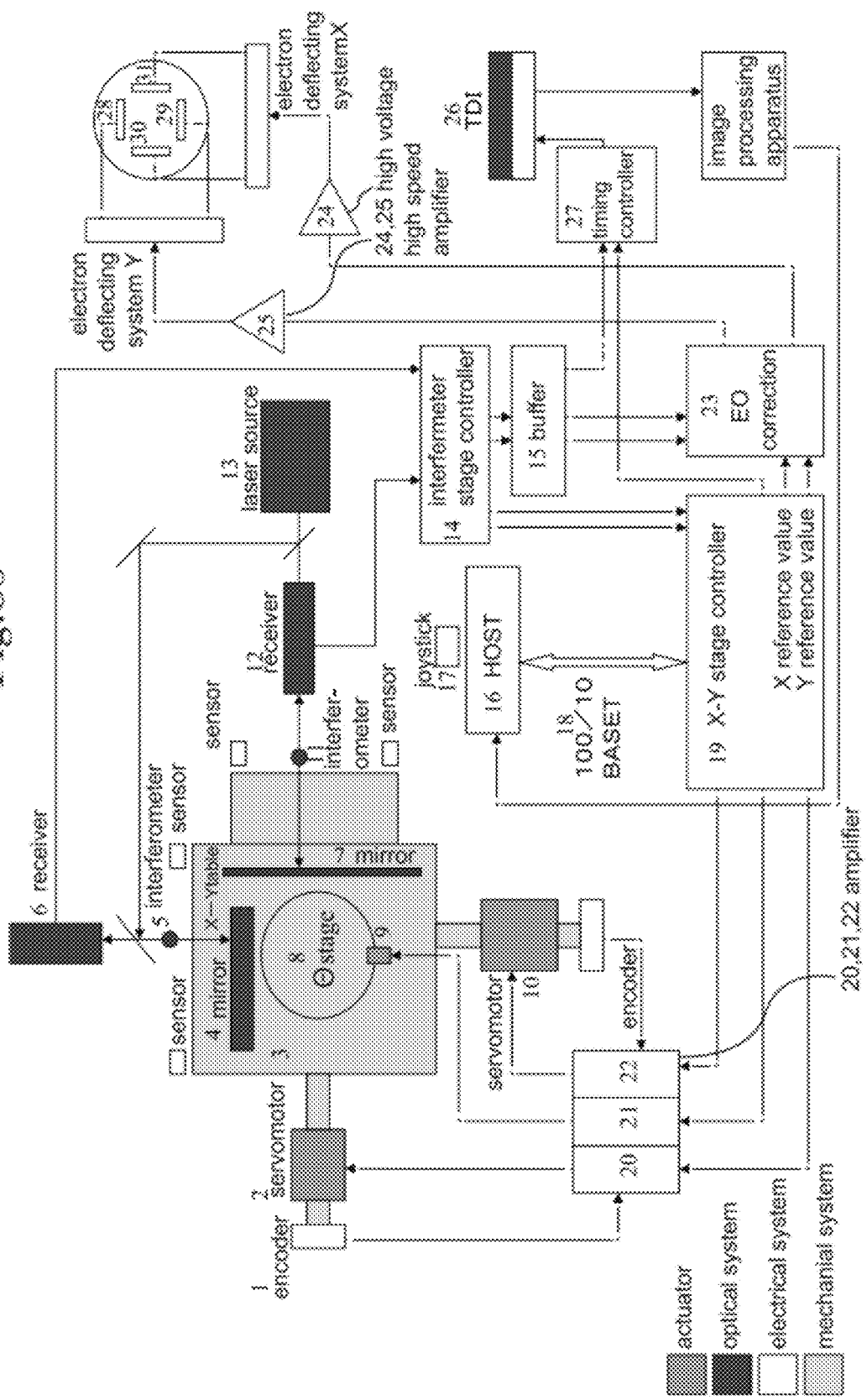
FIG. 83 is a diagram related to one embodiment of the present invention.

A detailed apparatus structure is shown in FIG. 83.

An X-Y stage can be provided with smooth servo characteristics by driving an X axis using a servomotor 2 for an X axis drive and encoder 1 and detecting a rough position and speed. A servomotor is used in the present example, however, a similar structure in an actuator such as a linear motor or ultrasound motor is possible. 20 is an output amplifier which drives a motor. Accurate position data of an X axis can realize a position detection function which includes sub nm a resolution by combining a mirror 7, interferometer 11, receiver 12, laser source 13, and interferometer board 14.

Each function related to the X axis described above are the same functions for the intersecting Y direction and are realized by 10, 22, 4, 5 and 6.

An X-Y stage controller 19 performs overall control of these devices and thereby it is possible to two dimensionally operate a stage and realize capabilities with an accuracy of several hundreds of μm to several tens of nm and a response speed of several seconds to several microseconds. On the other hand, an X reference value and Y reference value are output from 19 to an EO corrector, position data output in 32 bit binary form from 14 passes a high speed buffer board 15 and an actual position is received by an EO corrector 23. After an internal calculation is performed, and after voltage amplification by a high voltage high speed amplifier 25, 24, a voltage is applied to deflection electrodes formed from 28, 29, 30, 31, and deflection for correcting a residual error part is performed and an image data electron beam in which a position misalignment is minimized is guided to a TDI 26 (imaging element). 27 is a part for generating a timing signal for determining a transfer speed of 26 described below.

A function for generating a target position in a scan direction in the present device is described next.

EO correction is a function for correcting a position by calculating a difference between a target position and actual position and deflecting an electron beam in order to cancel this difference. However, the correction range is limited to a range of several tens of μm.

This electrode sensitivity is determined by a dynamic range, noise level, the number of bits of D/A converter of a high voltage high speed amplifier. However, a significant misalignment between the actual position of a stage when scanning with respect to the target position is produced compared to when stationary due to the gain of a control loop being limited. A divergence from the target position is around 400 μm in the case of travelling at 20 mm/s, and even if the difference is calculated and output as it is, the correction range is significantly exceeded which saturates the system.

In order to prevent this phenomenon and avoid this problem, the following procedure in performed in the present device.

Figure 84:
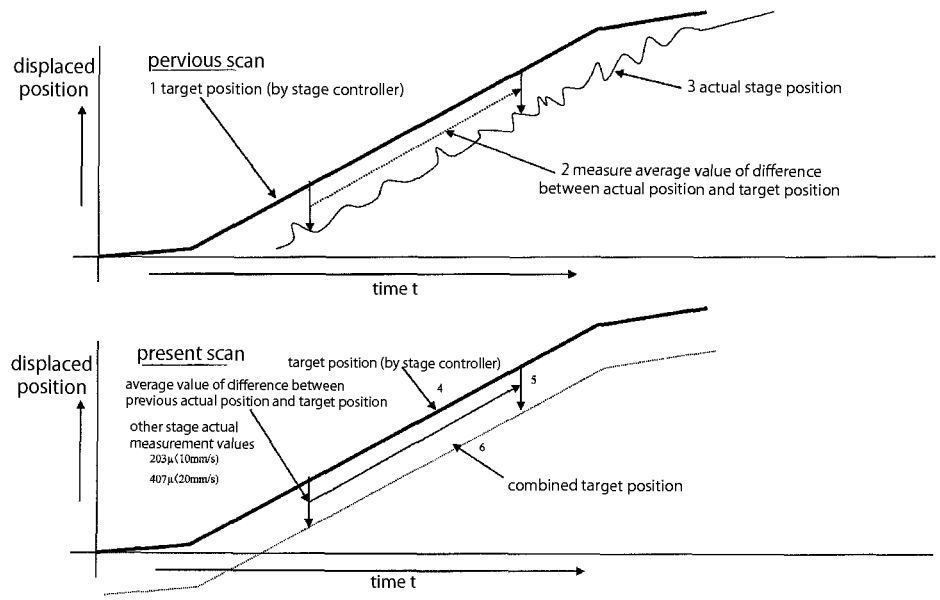
FIG. 84 is a diagram related to one embodiment of the present invention.
Figure 85:
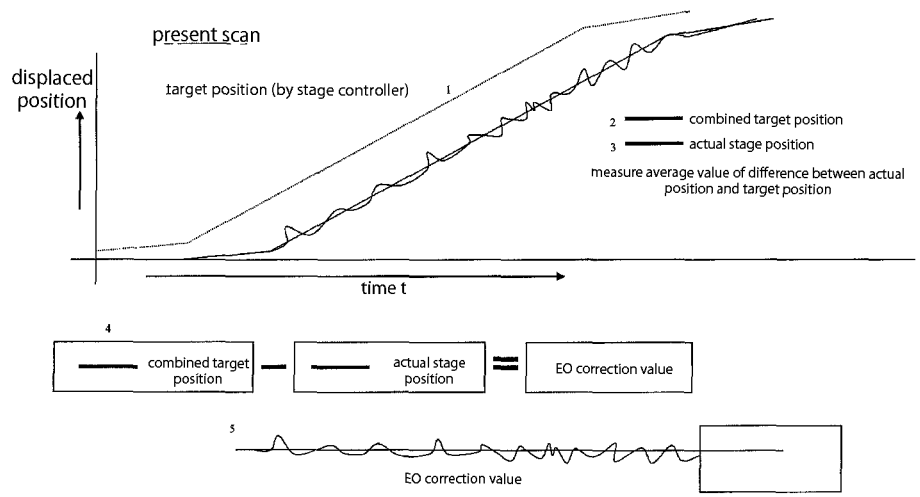
FIG. 85 is a diagram related to one embodiment of the present invention.

This concept is shown in FIG. 84. 1 is a target position on a stage which moves at a constant speed during a scan and therefore increases in a direction line with time. On the other hand, a mechanical position 3 of a stage as a result of actual control includes a mechanical vibration of several microns and a stationary deviation 2 of around 400 μm. While it is possible to smooth position data when actually travelling using a filter as a means for removing this stationary deviation, a delay is always produced due to a time constant of a filter, and when a time constant in which a ripple can be ignored is provided, a measurement start area is significantly limited which leads to a significant increase in the total amount of measurement time. Thus, in the present invention, at least the following calculation is performed in order to detect the stationary deviation. A difference between the actual position and target position at the time of the previous scan is calculated by accumulating at least 2 to the 16th power the number of samples. An average value 5 of the stationary deviation between the target position and the actual position is calculated by dividing this accumulation result by the number of samples. The combined target position 6 is calculated by subtracting the average value 5 of the stationary deviation from the target position 4 at the time of a present scan. In this way, a structure is realized in which EO correction within a dynamic range such as the EO correction value 5 shown in FIG. 85 is possible.

Figure 86:
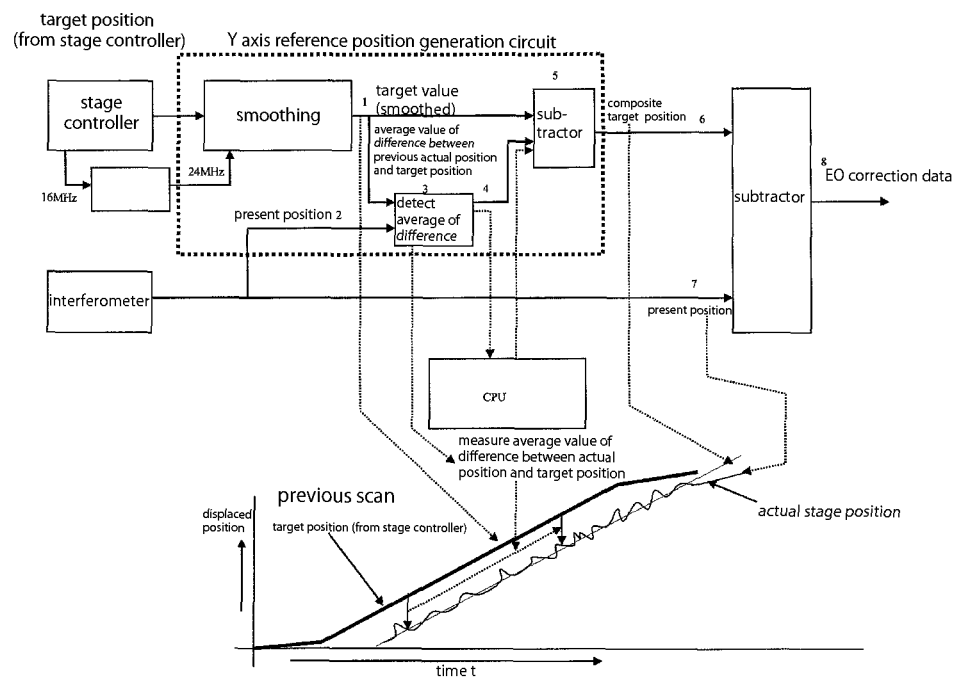
FIG. 86 is a diagram related to one embodiment of the present invention.

A block view is shown in FIG. 86. A target value 1 is subtracted from the actual position 2 and the previous accumulation is performed within the block 3 at the time of a scan. On the other hand, an average value of a stationary deviation calculated the same as the previous time is output from 4. EO correction data 8 with no response delay or ripple is realized by a combined target position 6 calculated by subtracting 4 from 1 using a subtractor 5 and subtracting this value and the actual position 7 from an interferometer.

Figure 87:
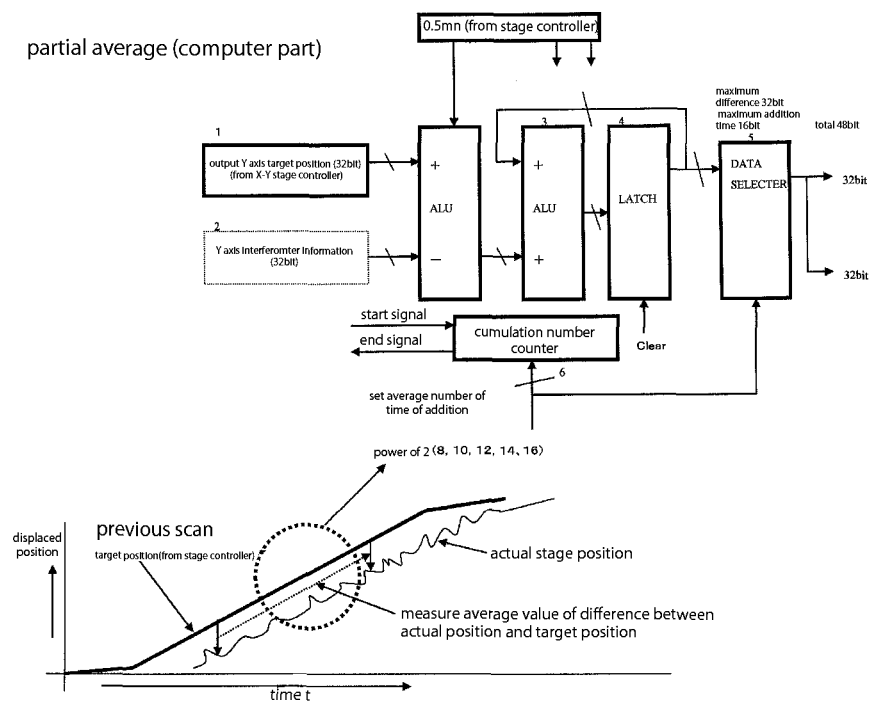
FIG. 87 is a diagram related to one embodiment of the present invention.

The structure of a block difference average detection 3 in FIG. 86 is shown in FIG. 87. A calculation is performed in 3, 4, a word of a data selector 5 is selected by the value of an accumulation counter 6, a division quality calculation is performed and an average value of a stationary deviation is output.

Figure 88:
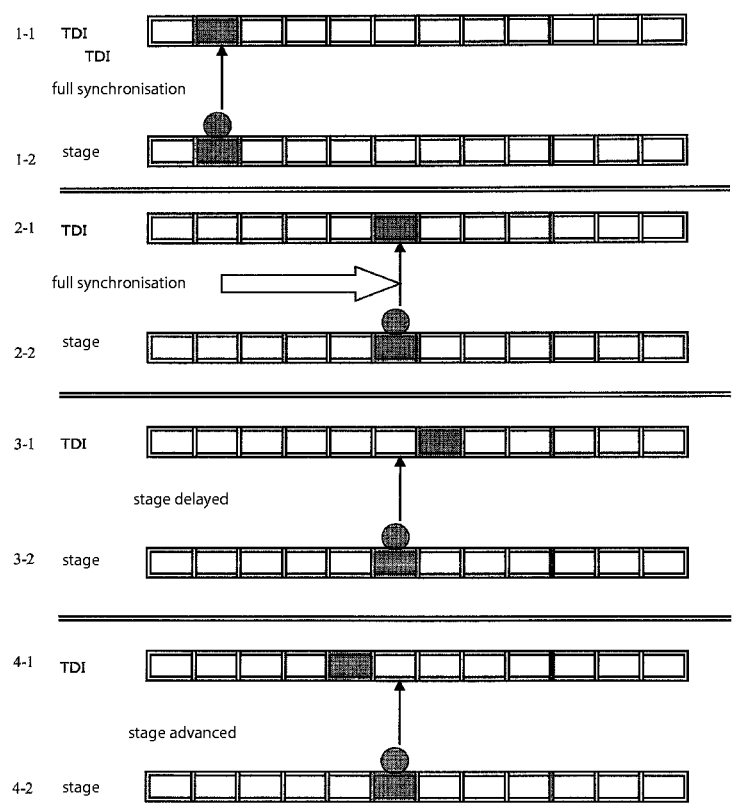
FIG. 88 is a diagram related to one embodiment of the present invention.

An example of a transfer clock of a TDI shown in FIG. 88 is described. A TDI is an imaging element which aims to improve sensitivity and reduce random noise by connecting several photoelectron elements in stacks in a scan direction and transferring the charge of each imaging element to a following element. However, as is shown in FIG. 88, it is important that the imaging object on a stage and an a pixel on the TDI correspond one to one and when this relationship is broken, image distortions occur. In FIG. 88, the relationship between 1-1 and 1-2 and the relationship between 2-1 and 2-2 show the case where each are in a synchronized relationship respectively, and the relationship between 3-1 and 3-2 and the relationship between 4-1 and 4-2 show the case where synchronization of is misaligned respectively. TDI transfer is synchronized with an external pulse and transferred to the next stage, thereby when a stage is moved one pixel at a time, this can be realized when a transfer pulse is generated.

However, since the position data output of a currently mainstream laser interferometer is in a form which synchronizes a 32 bit binary output with 10 MHz internal block and outputs, it is not easy to realize as it is. In addition, the accuracy of a transfer pulse is also important given a resolution of several nm, and high speed highly accurate digital processing is required. The method invented in the present example is shown in H-1.

Figure 89:
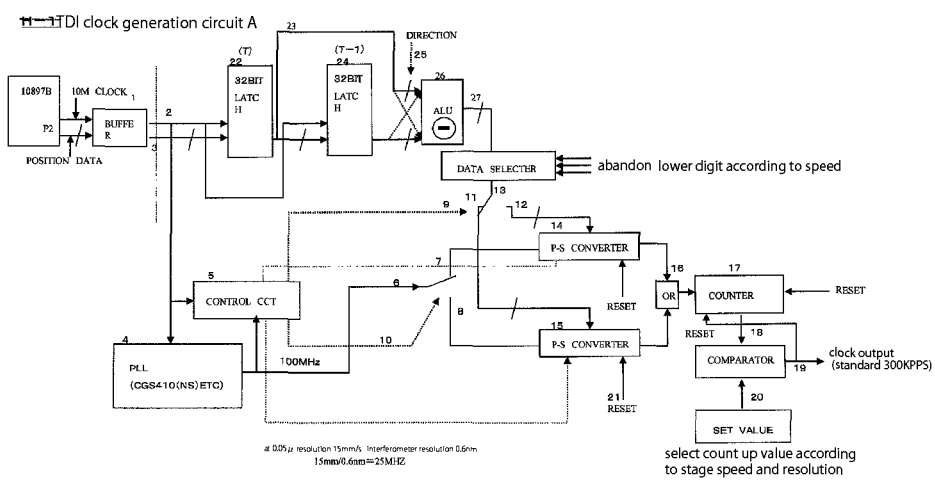
FIG. 89 is a diagram related to one embodiment of the present invention.

FIG. 89 is explained. Information data of a laser interferometer and a 10M synchronized signal are introduced to this circuit. The 10M clock 2 generates a 100 MHz clock synchronized by PLL 4, and is supplied to each circuit. A calculation process is performed each time this synchronization signal generates a 10 state. The actual position data is held in 22 and the previous value us held in 24. The difference between these two is calculated by 26, and the position difference for each 10 state is output from 27. This difference value is loaded as a parallel value to a parallel serial convertor 14, synchronized with a 100 MHz clock and the difference is output as the number of serial pulses from 16. 15 also has the same function, however, a structure where operation is possible without rest at each 10 state is possible by combining 11, 12, 13, 6, 7 and 8. As a result, a serial pulse corresponding to a position difference is output for each 10M to a counter 17 by a summation circuit 16. If a comparator 18 is offset in advance when the resolution of the laser interferometer is 0.6 nm and 1 pixel is 48 nm, the counter outputs a pulse 19 at a timing equivalent to 1 pixel. An operation synchronized with the variation in speed of a stage is possible by changing this signal into an external pulse from a TDI and it is possible to prevent distortions or blurring.

Figure 90:
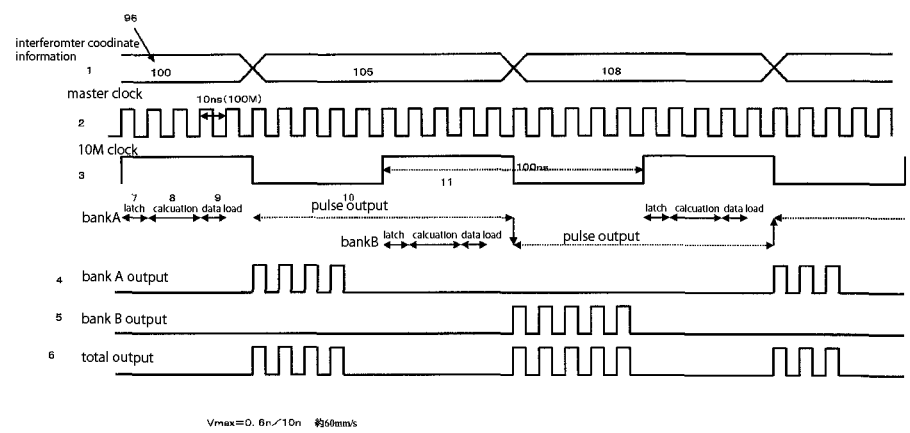
FIG. 90 is a diagram related to one embodiment of the present invention.

A timing chart is shown in FIG. 90.

1 is interferometer coordinate (position) data and the numerals are shown as examples of a position. 2 is a 100 MHz synchronized signal created by PLL. Bank A is an operation timing of a parallel serial converter group (14 in FIG. 89) and bank B is 15 shown in FIG. 89. A difference calculation timing 8 is performed after a latch timing 7 for storing position data, a value is loaded to the parallel serial converter (14 in FIG. 89), and 4 is output using a 1 cycle pulse of the next 10M clock 3. Bank B performs the same operation at a timing delayed by 1 cycle of the 10M clock 3, and pulse generation 6 is easily realized. Furthermore, the present embodiment can also be applied to the first to nineteenth embodiments described above.

(Twenty First Embodiment)

Figure 91:
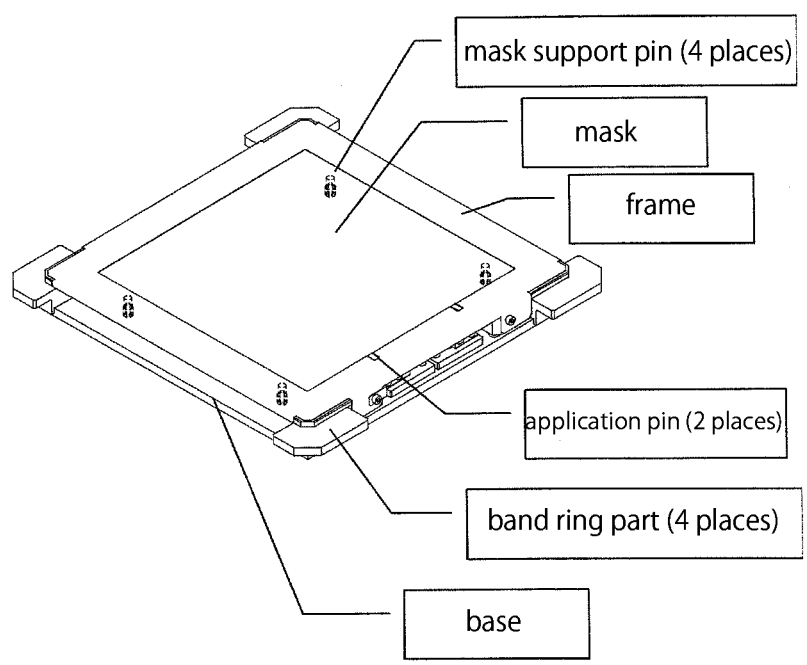
FIG. 91 is a diagram related to one embodiment of the present invention.

An example of a palette used in the inspection device and inspection method of the present invention is explained while referring to FIG. 91.

(Formation, Structure)

[Base] manufactured from aluminum or titanium. Electrostatic chuck adsorption surface (requires a flat surface). Arrange a RTD contact part. Arrange a pin for supporting a mask.

[Handling part] manufactured from aluminum or titanium. Handling device in atmosphere and vacuum robot.

[Frame] manufactured from phosphorous or titanium. Covers the mask upper surface 1.2 mm from an end.

[Application Pin] manufactured from phosphor bronze. RTD is applied to the mask upper surface. Wire is drawn around the application pin from an application part of the base.

(Operation, Conditions)

Frame is moved vertically by using a separate drive mechanism which arranging a mask within the palette.

(Effects, Merits)

The following effects can be obtained when a palette is used and not a mask single unit.

When the palette of the present invention is used, a part of the rear surface of a mask is supported. There is no contact with a pattern formation part. Consequently, damage by an electrostatic chuck and the attachment of foreign materials to the mask can be prevented. That is, when the mask is directly arranged on the electrostatic chuck mechanism, the rear surface of the mask is sometimes scratched and bad effects due to the attachment of foreign materials are produced. In particular, because high accuracy and setting conditions are demanded in the case of an EUV mask or nano-print mask, prevention of the attachment of small sized particles is necessary. For example, prevention of 30~50 nm foreign materials is necessary on the rear surface of an EUV mask and prevention of 3~20 nm foreign materials is necessary on a nano-print mask is necessary due to poor exposure.

The palette of the present invention includes a contact mechanism on a part of the interior periphery part of the frame for applying a voltage to the mask rear surface. As a result, since the frame is set to the same potential as the mask application voltage, it is possible to achieve potential uniformity at the end part of the mask and apply a voltage to the rear surface (surface conductive mask) of the mask which is stabilized by the frame arrangement. That is, it is possible to apply a RTD voltage from the upper part of a stable mask.

A movement part within a vacuum could be removed by providing the frame with the effects of a correction ring. That is, since the mask moves in a vacuum due to the arrangement of a palette, there is no movement between the mask and these arrangement parts. Consequently, it is effective in prevent the attachment of foreign materials since there is no friction. Furthermore, the present embodiment can also be applied to the first to twentieth embodiments described above.

(Twenty Second Embodiment)

Method of applying a high voltage to a vacuum movable part

Figure 92:
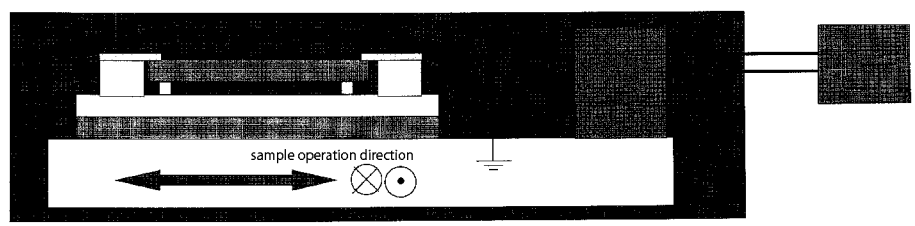
FIG. 92 is a diagram related to one embodiment of the present invention.

A method of applying a high voltage to a vacuum movable part used in the inspection device and inspection method of the present invention is explained while referring to FIG. 92. Application In a device where a sample is transferred to the inside of a vacuum chamber and demonstrates functions by applying a voltage to the sample, a high voltage power source such as the voltage applied to a sample in a projection type optical electron inspection device, which is −4000 [V]+ or −5 [V] and the voltage applied to a sample in the example in FIG. 42 previously described, which is −20~−50 [kV] are sometimes applied to a movable part. At this time, a high voltage power source is arranged on the stage (for example, on an x, y stage) of a vacuum chamber and the use of a high voltage line as a movable cable us avoided, that is, a high voltage is applied to a sample with a cable wire that does not move. Furthermore, by limiting an electrical lead wire from the atmosphere side to a low voltage signal, it is possible to easily use a high voltage. The wire cable from the high voltage power supply becomes thicker and therefore it is possible to not only reduce the generation of particles by using a cable which does not move, but also remove the need for a large feed through, improve the efficiency of design and manufacture and reduce costs.

In addition, the high voltage power source which is applied to a sample as described above is arranged on a movable part such as a stage and a high voltage wire does not exist on the movable part. In addition, an external low voltage power source is superimposed on the high voltage applied to the sample, and it is possible to control a high voltage value. Furthermore, the present embodiment can also be applied to the first to twenty first embodiments described above.

(Twenty Third Embodiment)

Figure 93:
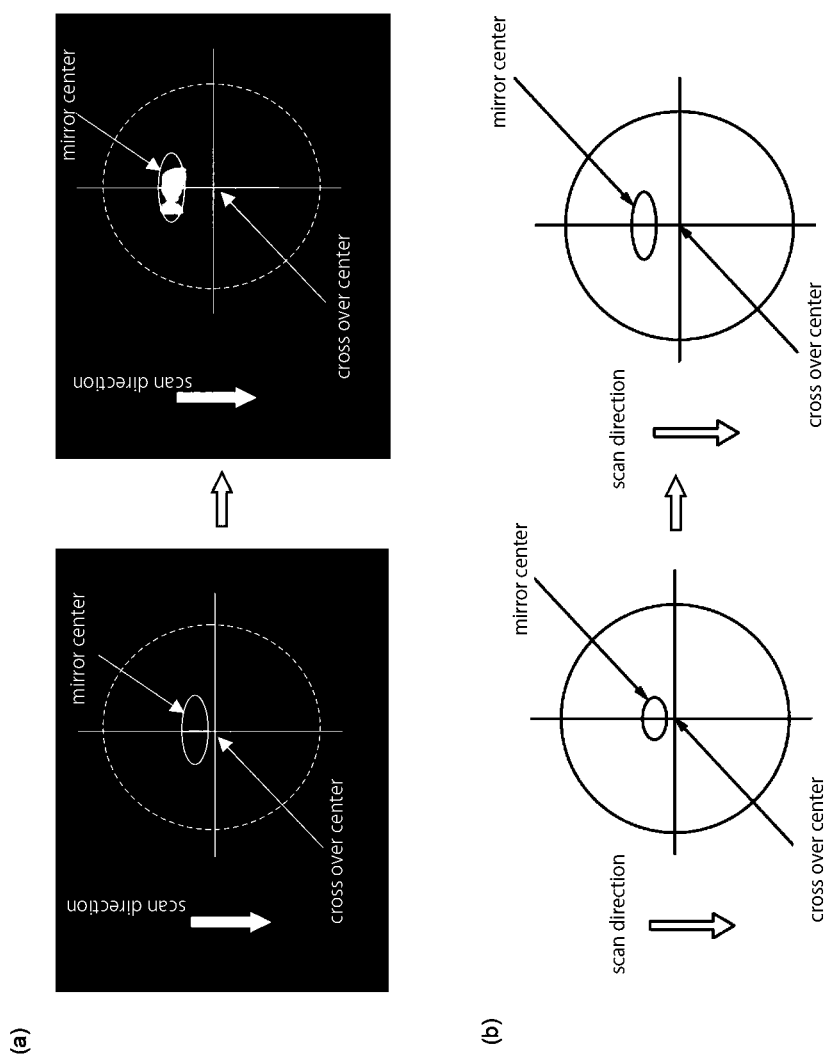
FIG. 93 is a diagram related to one embodiment of the present invention.
Figure 94:
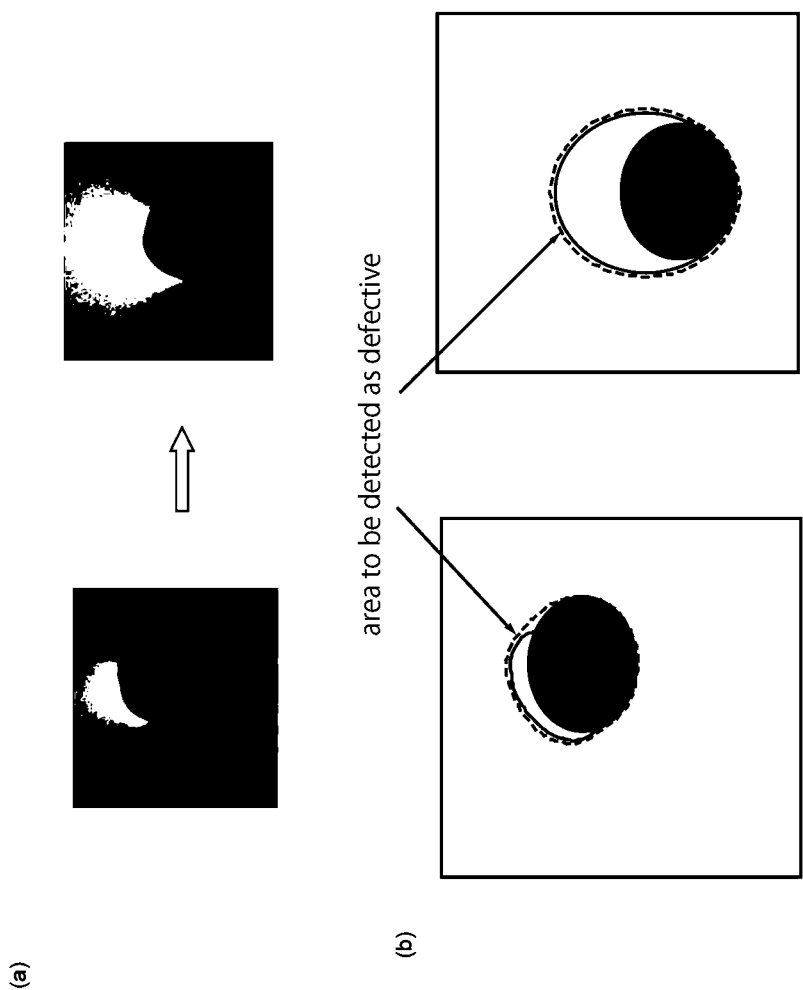
FIG. 94 is a diagram related to one embodiment of the present invention.

Method of improving the detection efficiency of a defect in a defect inspection device A method of improving the detection efficiency of a defect in a defect inspection device used in the inspection device and inspection method of the present invention is explained while referring to FIG. 93 and FIG. 94. In each of the diagrams, (a) shows an electron microscope, (b) is an exemplary diagram of the electron microscope. The electron microscope images the shape of a beam at an NA location in a projection type method. Conditions for forming an image in the shape of a beam of an NA location on a detector surface using a lens between the NA and detector are formed and imaging is performed. In this way, data such as the shape of the beam, profile, and center location etc is obtained, and it is possible to adjust the desired beam location (mirror electron) to a desired location, and set the NA to an optimum location.

This method is a method for improving the defect detection sensitivity of a defect inspection device using a projection type method by changing the irradiation angle of a primary electron beam which is irradiated at a perpendicular angle in the conditions for obtaining an image using both secondary emission electrons and mirror electrons.

In the device described above, this method is a method for improving defect detection sensitivity by projecting detects on a detector larger than the actual defect size by changing the irradiation angle of a primary electron beam which is irradiated at a perpendicular angle.

The location of a mirror center which is the center of a beam of mirror electrons is adjusted within a range of 100~800 μm in the scan direction side with respect to the center of a cross over when an NA image is obtained.

By adjusting the mirror center location in a direction further away from the cross over center in a scan direction than adjusting the mirror center location to the center of a cross over, a very bright region which appears from a defect is expanded.

In the case where secondary emission electrons are generated in a part where there are no defects and mirror electrons are formed in a part with defects, the region of mirror electrons is expanded by performing the adjustment described above, thereby, the detection sensitivity of ultrafine defects is improved by utilizing the expansion of a very bright region.

(Twenty Fourth Embodiment)

Uniform Stable Supply of a Sample Surface Potential

An example of uniform stable supply of a sample surface potential in the inspection device and inspection method of the present invention is explained while referring to FIG. 95, FIG. 96 (A) and FIG. 96 (B).

It is necessary to apply a voltage to a sample surface in a defect inspection device using a projection type method.

The appearance of a surface state and defect is adjusted by changing the voltage applied to a sample surface.

That is, when the voltage distribution of a sample surface is not uniform, conditions change due to the differences in the voltage distribution and problems of reproducibility arise.

Therefore, an application method is proposed so that a voltage distribution of a sample surface becomes uniform.

A high voltage is applied to a sample surface by connecting an output from a high voltage power source to a part which contacts with the mask surface.

The area which contacts with sample is broadened.

The part attached with a sample application electrode is called a frame and it is possible to transfer the sample to the interior by moving the frame vertically.

Figure 96A:
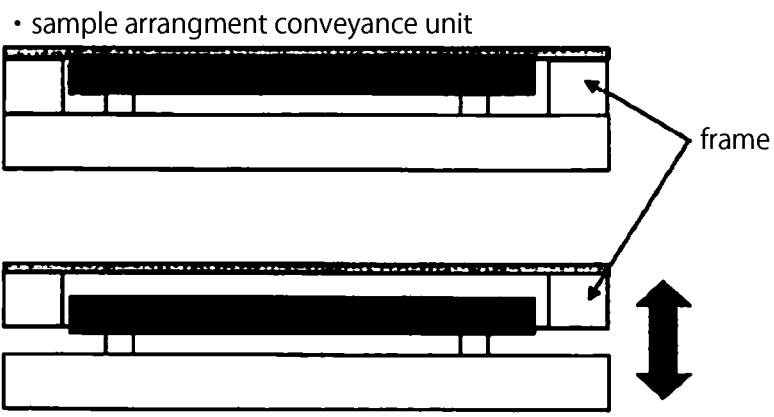
FIG. 96A is a diagram related to one embodiment of the present invention.

When the frame is in a lowered state, the sample application electrode contacts with the sample surface and it is possible to supply a uniform voltage to the sample (refer to FIG. 96A).

Furthermore, using a separate frame structure is effective for applying a uniform and stable voltage. An example of this is shown in FIG. 96 (B). Referring to the lower surface diagram (FIG. 96 (b)) and upper surface diagram (FIG. 96 (C)) of the frame shown in FIG. 96 B, the upper surface forms a smooth finished surface of a frame structure with no bumps, for example, a 195×195 mm titanium or phosphor bronze plate, and a 146×146 mm hole is opened at the interior. In addition, there are bumps at 3 places as shown on the rear surface. These bumps have a height of 10~200 μm. The tips of these bumps may be sharp. A voltage having a defined value is applied to a rear surface layer of a mask using the frame (cover). In the present invention, the mask is arranged on a palette. The palette includes a mask support pin and above this an exposure mask such as a EUV mask is arranged. A material in which few particles are produced is used for the mask support pin. A metal material coated with a resin such as polyimide, Teflon (registered trademark) or fluororesin or a part made of resin can be used. The mask setting location of the support pin contacts further to the exterior than the 142×142 mm mask interior. When a mask is arranged internally on an exposure device, the mask leans diagonally when foreign materials or particles become attached and therefore the support pin prevents the attachment of foreign materials or particles on this region. In addition, it is also possible to contact and fix the support pin to corner part of a side surface and bottom surface of a mask. In this case, a surface structure is adopted whereby the contact part becomes diagonal to a defined angle. In addition, in order to prevent location variation of a mask when moving a stage, it is possible to arrange a mask fixing guide pin for location fixing.

Figure 96B:
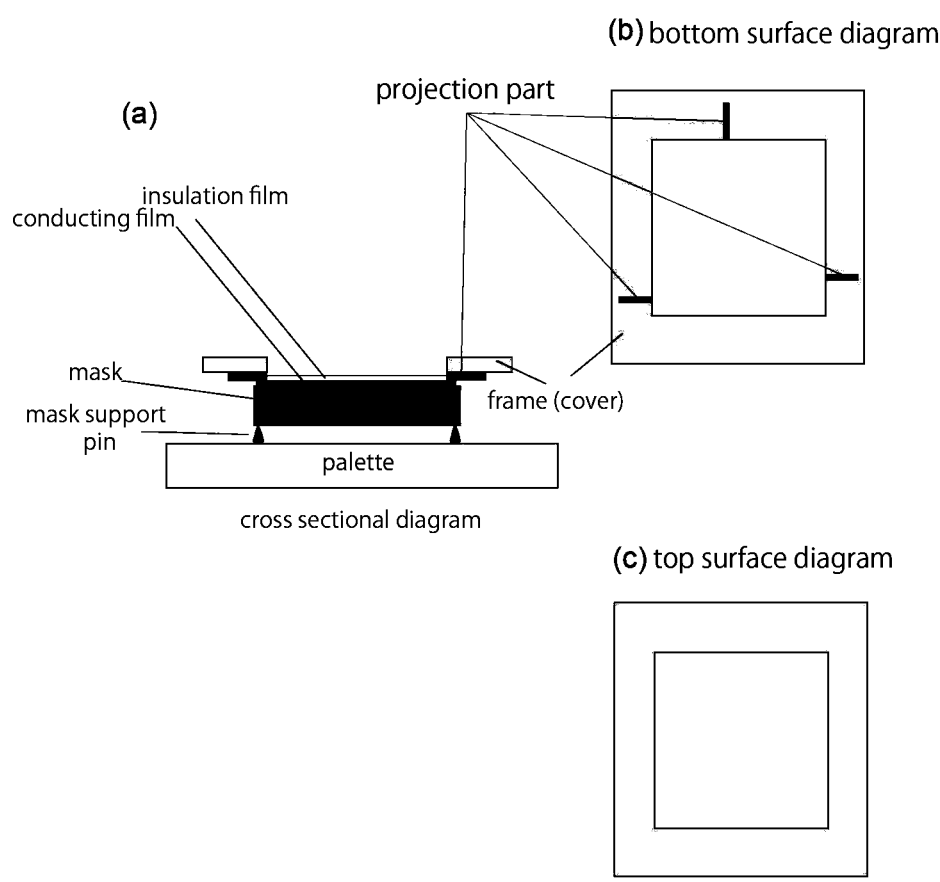
FIG. 96B is a diagram related to one embodiment of the present invention.

A EUV mask is arranged as described above. A usual EUV mask has an insulation film on the uppermost surface and below this a conducting film. Therefore, it is necessary to break the insulation film of the uppermost surface and ignite the conducting film in order to apply a uniform and stable voltage to the mask surface. At this time, a frame (cover) which includes bumps as shown in FIG. 96B is effective. A defined voltage which is to be applied to the mask surface is applied to the frame. In addition, as is shown in FIG. 96B, the frame is arranged from above the mask. At this time, the bump parts break the insulation film and reach the lower conducting film making it is possible to apply a stable voltage. When these bump parts are present they become parts for applying a voltage to the mask and therefore it is possible to specify a voltage application part, that is, it is possible to apply a voltage by controlling these parts. In addition, since these parts are three contacts points, it is possible to arrange the mask upper surface and frame with a good level of parallelism. In an arrangement with two contact points, the frame begins to lean and in an arrangement with four or more contact points it becomes difficult to specify which bump actually breaks the insulation film and applies the voltage to the conducting film. In addition, similarly, in the case where there are no bumps, it is difficult to specify which part is in contact with a mask. This is because it is likely that a different contact state is produced each time a mask is replaced. At this time, since a usual thickness of an insulation film of a EUV mask is 10~20 nm, it is preferred to arrange a frame weight suitable for breaking the insulation film.

In addition, when the frame makes contact it is necessary to reduce a difference in level between the mask surface and frame. This is because a non-uniform electric field distribution is produced due to this difference. When an inspection is performed on a mask end part, that is, on a part near the frame, the trajectory of electrons become misaligned due to the non-uniform electric field distribution, and a misalignment between coordinates and center location of an electron image is sometimes produced. As a result, it is necessary to reduce the difference in level between the frame and mask surface to a minimum. The present embodiment adopts a structure reduced to 10~200 μm. A level difference of 10~100 μm is more preferable. In addition, a method for reducing the plate thickness near the mask contact surface of the frame is also possible. Furthermore, the present embodiment can also be applied to the first to twenty third embodiments described above.

(Twenty Fifth Embodiment)

Photoelectron Image Formation Using Light/Laser Irradiation

Photoelectron image formation using light/laser irradiation in the inspection device and inspection method of the present invention is explained. The sample having an uneven surface such as in FIG. 53 (a), (b) and FIG. 57 is an example of the object sample. An exposure mask, EUV mask, nanoimprint mask and template and semiconductor wafer can be used.

(Irradiation of a Sample Using Feed Through and a Triangular Mirror)

The embodiments in FIG. 26~FIG. 32 are example which can be applied.

An explanation of a triangular mirror in a vacuum and other lenses in an atmosphere was given above. There are also embodiments which can be arranged in a vacuum other than a light source. Light scattering or vibration occurs when there is an atmosphere, rubbish or dust in the path of a irradiated light with a large energy such as UV, DUV, EUV and X rays, and instability of a an irradiation system is increased which leads to a deterioration of optical elements such as a lens or mirror. In other words, oxide film formation of an element surface and film quality of parts impacted with light deteriorates and surface deterioration occurs due to the attachment of dust or rubbish. A device and method can significantly reducing this problem by arranging engineering components in a vacuum. In this case, after arranging a separate chamber which contacts with a main column and adjusting an optical axis in an atmosphere, a vacuum exhaust of the optical system is performed. It is possible to easily perform an atmosphere release/vacuum exhaust in the case of a separate chamber of only the optical system. When there is a column and vacuum conduction in an electron engineering system, since both the main column and main chamber must be released of an atmosphere together, vacuum exhaust and atmosphere release must also be performed on unrelated parts. This leads to significant costs and time loss.

(Optical Axis Adjustment Via an Atmosphere Side Mirror/Lens, Irradiation Size Adjustment Via a Lens Location)

It is possible to adjust the location and size of an optical axis and optical irradiation within a main column in a mirror lens system on the exterior side of a main column. Adjustment of an optical axis, that is, shirt and tilt, is performed using two or more mirrors before introducing a light to the main column. In this way, adjustment is performed so that the center of an irradiation light arrives at the irradiation location of a sample. At this time, it is also possible to adjust the angle in a perpendicular direction of the sample surface, that is, an irradiation angle.

In addition, adjustment of the size of an irradiation light is possible by changing the lens location in an optical axis direction. For example, it is possible to adjust the size of an irradiation light by reducing or increasing the distance from the lens location to the location of the sample surface shorter or longer than f in the case where the focal distance of f300 mm. ϕ5~1000 μm, about $\frac{1}{200}$~×1 magnification of a laser output light diameter.

(Adjustment of Light Output Compatible with a Secondary System Magnification Using an Attenuator, Secondary System Optical Adjustment)

In optical axis adjustment of a main column, that is, axis adjustment of a photoelectron, when photoelectrons are used in light irradiation it is necessary to control the amount irradiation light according to the magnification of an optical axis of a main column. If the same light irradiation density (amount) is used, in the case of low magnification, the amount of electrons which reach the detector becomes large and in the case of a high magnification, too many electrons are detected and the detector becomes saturated. As a result, an attenuator or beam splitter is arranged on the optical path of the exterior side of the main column in order to change the density of light which is irradiated and it is possible to adjust the power of the irradiated light. It is preferred not to change the output of the light source itself in order to maintain stable operation. In addition, this is particularly effective when the irradiation size is left unchanged. It is also possible to change the light irradiation size by changing the density of light irradiated. In the case of a low magnification, adjustment is performed by reducing the density of the irradiation light and in the case of a high magnification, the size which is irradiated is reduced light density is increased and image adjustment is performed. In addition, it is also possible to adjust an image by combining adjustment of the output light which is introduced and control of the size of the light which is irradiated.

($\lambda$<264 nm: Ru white signal, TaBO black signal, $\lambda$>264 nm: Ru black signal, TaBO white signal)

A work function WF of a material is a value inherent to a material which outputs light when a large energy is irradiated than the energy of the work function value. An optical wavelength corresponding to the WF is given as $\lambda$WF. There is a method for imaging in a state where there are few photoelectrons by selecting a wavelength with a higher energy than the WF of a sample and selecting a wavelength with a lower energy than an image which generates many photoelectrons and WF.

In addition, in a sample where a plurality of materials are mixed, the imaging method which has the following characteristics is possible in the present invention. At this time, for example in the case where there two materials 1 and 2, each are given as WF1, $\lambda$WF1, WF2, AWF2. The wavelength of the light which is irradiated is given as $\lambda$.

A: in the case where $\lambda$<$\lambda$WF1<WF2

Observation is made with a contrast where a higher emission efficiency of photoelectrons is a white signal and a lower efficiency is a black material between the materials 1, 2.

B: in the case where $\lambda$WF1<$\lambda$<WF2

Because the material 1 has the relationship light energy <WF1, the amount of photoelectrons from the material 1 is significantly reduced. Consequently, an observation is made where the material 1 is black and the material 2 is white (material with a relatively larger amount of photoelectrons is called a white signal and the material with a smaller amount of photoelectrons is called a black signal).

C: in the case where $\lambda$WF1<AWF2<$\lambda$

Since both materials have the relationship light energy<WF1, WF2, the amount of photoelectrons of both material 1 and material 2 is significantly reduced. Therefore, it is difficult to determine which is white and which is black.

In this way, it is possible to obtain a contrast is the cause of a difference in the amount of photoelectrons by selecting a light wavelength, and irradiating a light or laser with a higher energy than the work function of a plurality of materials, and since the energy band of a photoelectron is small compared to a secondary electron etc (for example, $\frac{1}{5}$~$\frac{1}{20}$)), aberrations are small and a high resolution can be achieved.

In the case of A described above, when a material is selected with a high photoelectron emission efficiency for the material 1, and a material is selected with a low photoelectron emission efficiency for the material 2, imaging with a high contrast is possible (contrast 0.5~1.0).

In the case of B described above, since the material 1 provides a lower energy wavelength than $\lambda$WF1, the amount of photoelectrons in material 1 is low, however, since the material 2 is irradiated with light (or a laser) having a higher energy wavelength then WF2, many photoelectrons are generated in material 2. Consequently, it is possible to image a pattern with a relatively high contrast using material 2 as a white signal and material 1 as a black signal.

In the case of C described above, since the material 1 is also irradiated with a lower energy wavelength than the work function of the material 2, the material 1 is in a state with few photoelectrons. At this time, when there are defects such as foreign materials with a low work function, these defects generated photoelectrons and the defects can be detected.

In this way, it is very effective for imaging to select the wavelength of an irradiated light or laser (energy of a laser is selected) to a sample formed from a plurality of materials such as a mask, EUV mask, semiconductor wafer, nano-imprint mask etc with respect to the work function of each material, and the wavelength which generated many photoelectrons is selected, and it is possible to image a pattern with a high resolution and foreign materials with a level of sensitivity. At this time, in the case of two of more materials, it is effective to use a method for forming a relatively large/small amount of photoelectrons. In addition, in the case of three of more materials, it is effective to form a state where only one material generates a large amount of photoelectrons. At this time, a sample such as a mask, EUV mask, semiconductor wafer or nano-imprint mask etc is often formed with an uneven structure which is particularly effective. It is possible to form conditions where only the top layer generates many photoelectrons and perform imaging or defect inspection. Because a pattern shape can be clearly imaged, this is effective for pattern defect imaging or inspection. In addition, it is effective for an observation or inspection of a hollow part defect to select conditions in which there are many photoelectrons generated from a material of a bottom surface of a hollow part. At this time, it is particularly effective when a pattern size, for example, line/space, half pitch (hp) size, or hole shape size is smaller than the light wavelength. For example, in an optical inspection device defects of a pattern etc are observed or inspected using scattered light of a light which is irradiated, however, when the size is smaller than the wavelength, the resolution drops significantly due to a wavelength limit, the resolution of a pattern decreases due to scattered light and observation or inspection of a pattern becomes difficult. In order to overcome this, the method which uses photoelectrons in the present invention can perform an observation or inspection of a pattern at a high resolution even in the case where a pattern size is smaller than a light wavelength. As stated above, 1) It is possible to increase contrast by selecting a wavelength with respect to the work function of a material, and 2) it is possible to generate photoelectrons by forming a near field in the case of a pattern smaller than a wavelength, thereby, it is possible to generate photoelectrons which reflects the shape of a pattern, and thus achieve high contrast and high resolution. For example, if a state is formed where only the amount of photoelectrons in the top layer is high, it is possible to form a pattern where the top, that is, line part (bump parts) is white. In addition, if a state a condition is formed where only the bottom surface of a hollow part has a large amount of photoelectrons, it is possible to perform an observation or inspection with a high resolution where the hollow part (space part) is a white signal. When forming these conditions, the methods A, B, C stated above are selected and performed. In addition, in the case of three of more materials, for example, in the case of a top layer, hollow part and wall part, a condition is formed where only the top layer generates a large amount of photoelectrons. It is also possible to form a state where only the hollow part (space part) generates a large amount of photoelectrons and form a state where only the wall part generates a large amount of photoelectrons.

In addition, it is more effective to combine these states for use in imaging and inspection. For example, when an observation or inspection is performed in a state where only a top layer (bump part) generates a large amount of photoelectrons and a state where only a hollow part (space) generates a large amount of photoelectrons, each defect is extracted from the result of both, and it is possible to detect a pattern shape defect, ultrafine foreign material defect in a hollow part or film defect etc and therefore, an observation or inspection can be thoroughly performed. In addition, it is also possible to perform an observation or inspection by simultaneously forming a state where a large amount of photoelectrons are generated in a top layer and a state where a large amount of photoelectrons are generated in a hollow part. At this time, the pattern resolution becomes poor resulting in a grey state (an intermediate color between white, black) due to a combined image. In addition, because parts which include defects are significantly misaligned from this color, that is, become white or black, it is preferred to detect only foreign materials or pattern defects. In particular, detection is easily performed in the case of foreign materials on the top layer of a pattern, however, this is particularly effective for detecting ultrafine foreign materials in the hollow parts of an uneven pattern. Only these ultrafine foreign materials become white or black and therefore it is possible to perform detection with a high contrast. As a result the amount of photoelectrons being different due to a difference in work functions of different materials or in the case where the potential distribution within a hollow part changes due to ultrafine foreign materials in the case of same materials, the trajectory of the photoelectrons changes and the amount of photoelectrons reaching the hollow part is large an observation is performed with a relatively white signal and with a black signal when they are few. In addition, it is possible to perform an observation with a black signal when the amount of photoelectrons of ultrafine foreign materials is few and with a white signal when the amount is large. In addition, an inspection is performed using these methods.

For example, in the case of an EUV mask, a structure where a top layer is formed from TaBO and a hollow part is formed from Ru is often used. In addition, the work function of Ru is 4.7 eV and relative wavelength is 264 nm.

At this time, by selecting or combining a wavelength $\lambda$ of a light or laser which is irradiated as in the conditions A, B, C above, it is possible to perform an observation or inspection where a top layer is a white signal and a hollow part is a black signal.

For example, a state where there are many Ru light signals of a hollow part where $\lambda<264$ nm, that is, observation or inspection is possible with a white signal. In addition, in the case where $\lambda>264$ nm, an observation and inspection is possible where TaBO of a top layer is a white signal.

At this time, it is possible to form an image having symmetry in a vertical, horizontal, diagonal line/space pattern by irradiating a light and/or laser from many directions. It is possible to perform irradiation from 4 or 8 directions. In addition, it is effective to perform irradiation of a light or laser by selecting or combing T/M directions.

Because the distribution of a near field (energy field transmitted to a pattern size region smaller than a wavelength) formed on the pattern surface is significantly different due to a pattern direction, light or laser irradiation direction to the pattern and polarization direction, it is possible to select and use conditions for obtaining a high contrast.

That is, it is possible to perform an observation or inspection by selecting conditions for obtaining a strong near field in a top layer or strong near field in a hollow part.

At this time, the effects of interference or diffraction are sometimes received when using a single wavelength laser. An unnecessary white/black pattern is sometimes formed due to these effects. The wavelength width may be broadened in order to avoid these effects, for example, + or $-1\sim2$ nm. In addition, it is effective to simultaneously irradiate lasers having different wavelengths.

In addition, it is effective to make a polarization direction multidirectional instead of one direction, so that the effects of interference or diffraction are significantly reduced. In addition, it also effective to perform imaging while continuously changing the polarization direction. An image which can be obtained within an exposure time by changing a polarization direction within the time for imaging one frame becomes an integrated image and an image with few effects from diffraction or interference can be obtained. Furthermore, the present embodiment can also be applied to the first to twenty fourth embodiments.

Inspection method/device using scattered light from EUV light irradiation

It is possible to perform an inspection of a EUV mask using the same method and device as in FIG. 1~FIG. 25 which describe a device system. In this example, EUV light is irradiated to a sample. A pattern image is formed by the light (or EUV light) reflected from an uneven pattern of an EUV mask using a mirror system and detection is performed by a detector. Following this, it is possible to detect a defect using signal processing. An inspection can be performed using cell/cell, die/die or die/database etc. A wavelength of 13.5 nm is used in EUV exposure. However, it is also possible to use a similar method and device system for a wavelength in a soft X ray region.

Loss in transfer and irradiation within an atmosphere and in inspection image formation is large because the wavelength of EUV is short and contamination and noise increases due to ion formation of atmosphere particles which is inefficient. Consequently, light transfer, irradiation and image formation is required in a vacuum device system. At this time, it is possible to apply the vacuum device system of the present invention.

EUV irradiation is the same as the examples described in relation to FIG. 8, 9 and FIG. 26~FIG. 32. The difference between the examples described above is that a pattern is formed using light or EUV light which is reflected or scatted from a EUV mask in a primary optical system. A secondary system is a magnification optical system in which mirror electrons and secondary emission electrons are not used but EUV reflection mirrors are used instead of an electron electrostatic lens or magnetic lens. An image is formed, magnified and projected in a detector using this optical system. The optical magnification is 500~3000 and 3~4 Px/line is achieved for a L/S pattern for example. The advantage of EUV light irradiation is that the reflectance ratio of a hollow part of an uneven pattern is high. In addition, the reflectance intensity of a hollow part is high and low for a bump part since a side wall part or bump part become an adsorption layer with respect to EUV light, and therefore a high contrast and S/N can be achieved. At this time, it is possible to use EB-TDI or EB-CCD as a detector. This is because EUV has sensitivity even if electrons are not irradiated since the energy of EUV light is high. In addition, it is possible to adjust the optical system or image formation conditions using an EB-CCD.

In addition, it is possible to form a continuous inspection image using an EB-TDI and perform an inspection at high speeds. At this time, a linked operation between a stage and the EB-TDI is performed, the obtained amount of light is increased by a calculation of an image and it is possible to obtain an image with a high S/N and perform an inspection at high speeds. An EB-TDI, EB-CCD have a sensor part arranged in a vacuum. Not only these detectors but detectors which have sensors that can be arranged in a vacuum or elements which can form a two dimensional image can also be applied. For example, a scintillator+TDI etc. In addition, in a primary optical system which an optical system of EUV reflected light, it is possible to coat a thin film of TaBN or carbon on a surface of a part other than a column surface or mirror in order to reduce reflectance due to EUV or noise due to the generation of photoelectrons.

Figure 192:
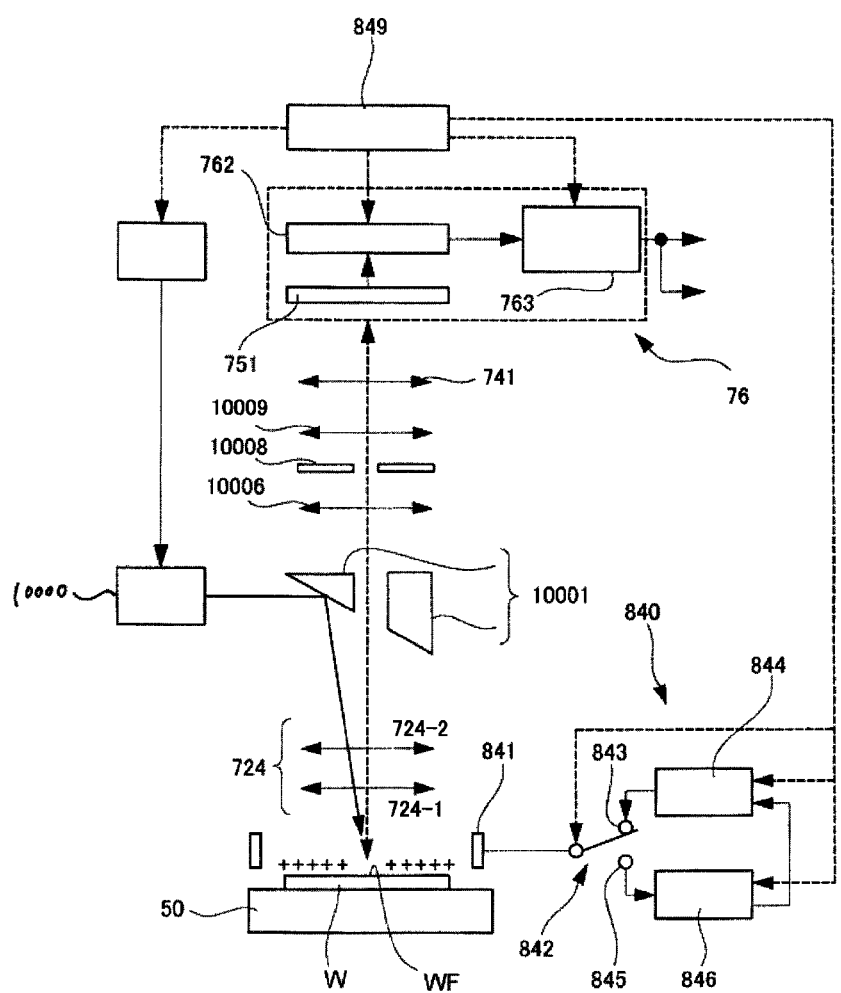
FIG. 192 is a diagram related to one embodiment of the present invention.

In addition, when a EUV mask top layer includes an oxide film, a control electrode is arranged near the sample as in FIG. 192 in order to control charge up of the EUV mask surface due to EUV light irradiation, thereby, the sample surface potential can be controlled.

For example, when a EUV mask itself is connected to GND, photoelectrons are emitted from a top layer oxide film when irradiated with EUV light and the oxide film is positively charged. In order to control this, a negative electric field is generated near a mask surface, that is, the mask surface is set to a relatively positive potential. In this way, it is possible to control to charge up when the generated photoelectrons return to the oxide film. Other than this, a method for applying a potential of about 3~10V to the EUV mask surface and applying a negative potential in advance is effective. Furthermore, the present example can similarly be applied to the first to twenty fifth embodiments other than the secondary optical system.

(Axis Adjustment Method of Irradiation Light Using a Jig)

The present invention is characterized by an irradiation mechanism of a light or a laser of the first embodiment which is used when performing imaging or an inspection and a method of using light or a laser of the second embodiment for use in adjustment. The light or laser of the second embodiment may also be used for adjustment. At this time, the light of the second embodiment is included in a lens or column and an irradiation location is fixed, the irradiation location is measured in advance, and irradiation is positioned almost at a center location of an electron optical system. This location is for example within + or −100 μm depending on the mechanical assembly accuracy of the introduction mechanism. At this time, the size of the light or laser beam is larger than an arrangement error, for example, about assembly accuracy +200~2000 μm, or ϕ1 mm (a 1×1.5 mm ellipse may also be used) in the example used. At this time, it is possible to use an introduction mechanism using fiber or a lens. In this way, because the irradiation location is determined by the accuracy of the apparatus which is arranged, handling becomes easy and reproducibility of an arrangement location is good. It is also very effective when using the optical introduction system of the second embodiment for adjustment.

Adjustment 1: used in an optical axis adjustment of an electron optical system. Photoelectrons are emitted from a sample surface and are guided to a detector by a secondary electron optical system. In this case, light of a laser surface beam is irradiated and two dimensional surface shape photoelectrons are emitted and guided to a detector by the secondary optical system. The surface photoelectrons form a two dimensional photoelectron image which is magnified and projected at the detector by the secondary optical system. At this time, a photoelectron image is formed using the light introduction system of the second embodiment and it is possible to calculate the optical axis center conditions of the secondary optical system. The optical axis conditions calculated in advance and the center location of an object lens (object surface location) is calculated in advance. In this way, a mark (a characteristic pattern or faraday cup is used) is arranged at this location. Thereby, the object lens center location is determined. Next, the light or laser introduction system of the first embodiment is adjusted so that a beam is irradiated at the location of this mark. At this time, a structure of a mirror, lens and light source is adopted whereby adjustment of the irradiation location and size are adjusted using two or mirrors and lenses. Light or laser of the second embodiment may be irradiated at the mark at the object lens center calculated in the first embodiment. It is possible to efficiently adjust the optical axis of a light or laser introduction system of the first embodiment using this mark. If there is no secondary optical system, optical axis adjustment must be performed in the first optical introduction system after assembling the first optical system and therefore the location of the center of the object lens must be initially searched while it is still unclear. That is, a situation where a photoelectron image can be roughly seen is formed, the secondary optical system is adjusted, that is, the center location of an object lens is calculated while in this state, a mark is arranged at this location, and then optical axis adjustment of the first optical introduction system is performed. As a result, extraction of a center of an object lens from this rough situation and a rough optical axis adjustment of the optical introduction system of the first embodiment must be performed alternately while performing final axis adjustment of the secondary optical system and axis adjustment of the optical introduction system of the first embodiment. Consequently, it is effective to form a state in advance where axis adjustment of the secondary optical system is always complete using the optical introduction system of the second embodiment.

In addition, it is possible to perform axis adjustment of a first optical introduction system using a jig. A power meter is arranged below a guide plate with a hole and optical axis adjustment of the first optical introduction system is performed so that a maximum amount passes through the hole of the guide plate. At this time, the coordinates where the hole location of the guide plate meet the center location of the object lens are calculated in advance.

(Light+EB Irradiation Method)

Explanation of an embodiment in the case of primary systems of two types exist.

It is effective to form an image by combining a photoelectron image obtained using light or laser irradiation and secondary emission electrons and/or mirror electrons (also includes cases where there are mirror electrons and where there are no mirror electrons). Here, secondary emission electrons refer to a partial or mixed state of secondary electrons, reflecting electrons or back scattered electrons. In particular, it is difficult to distinguish between these in the case of a low LE.

Figure 196:
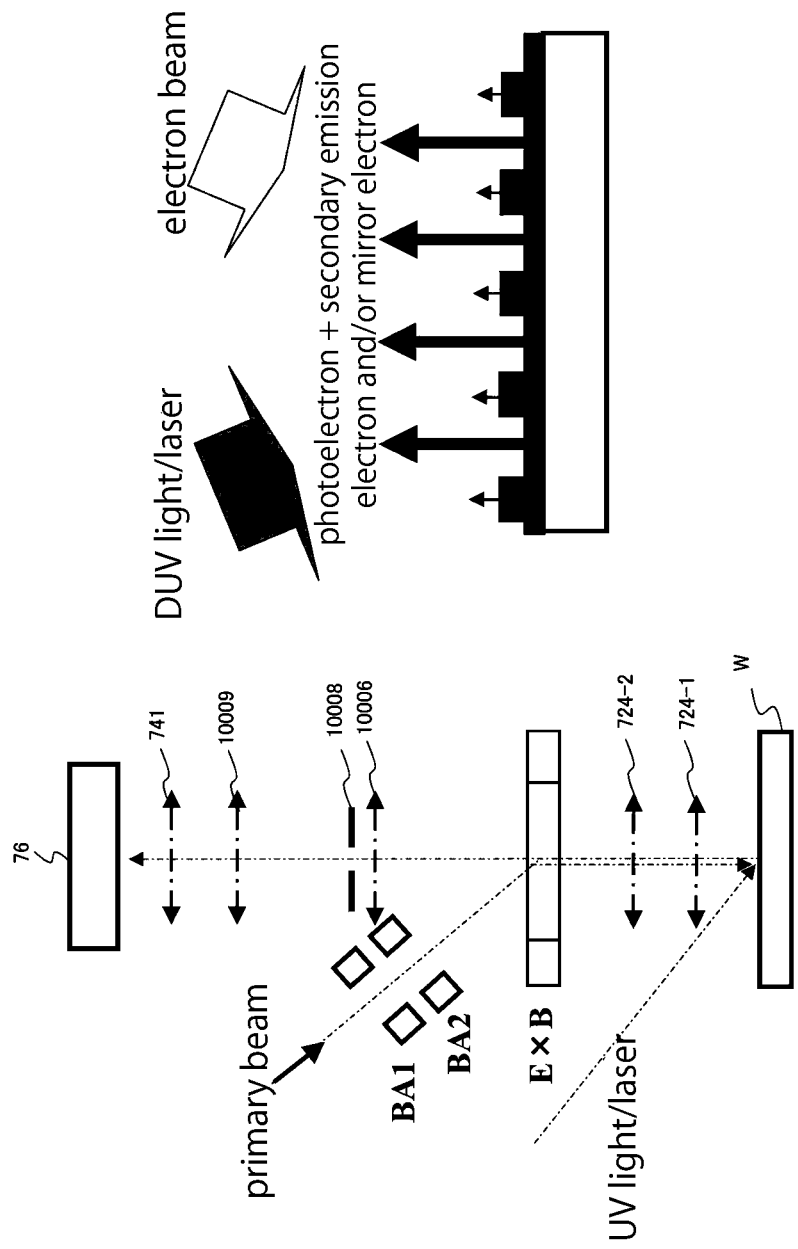
FIG. 196 is a diagram related to one embodiment of the present invention.
Figure 197:
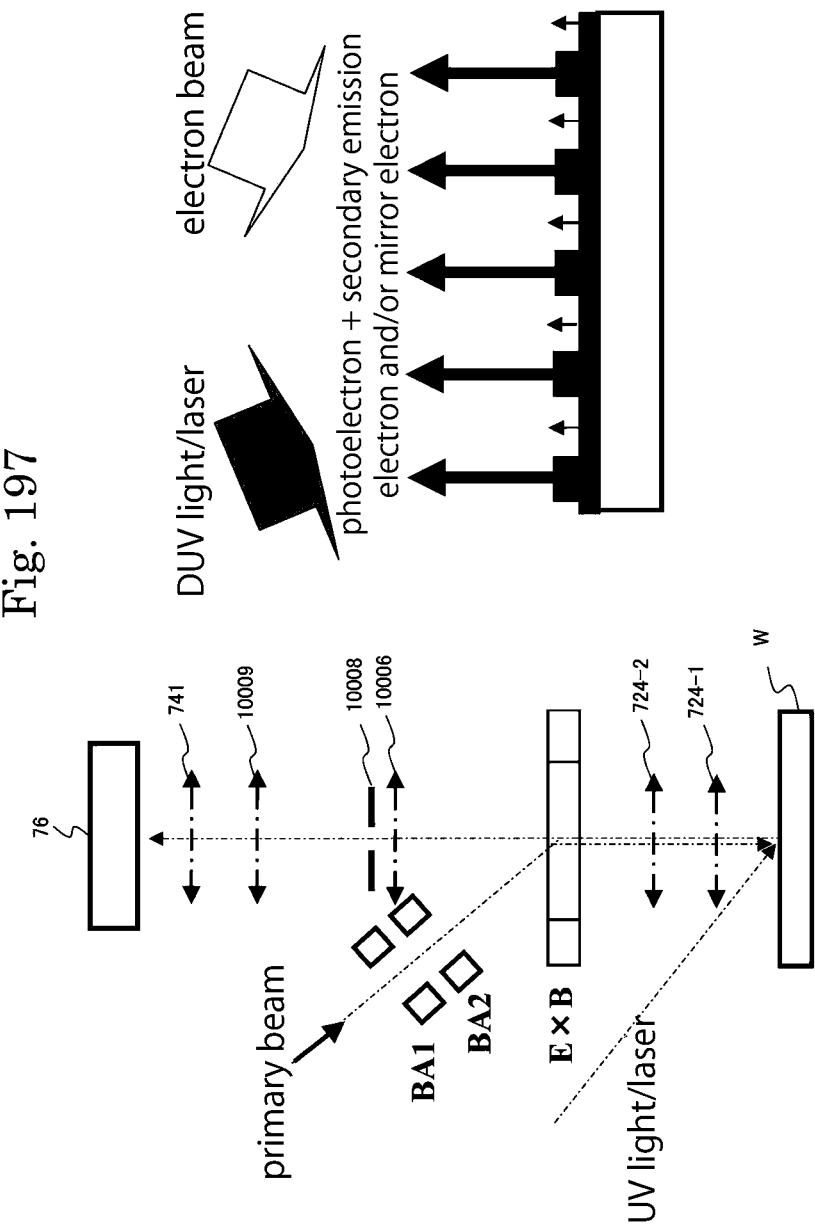
FIG. 197 is a diagram related to one embodiment of the present invention.
Figure 198:
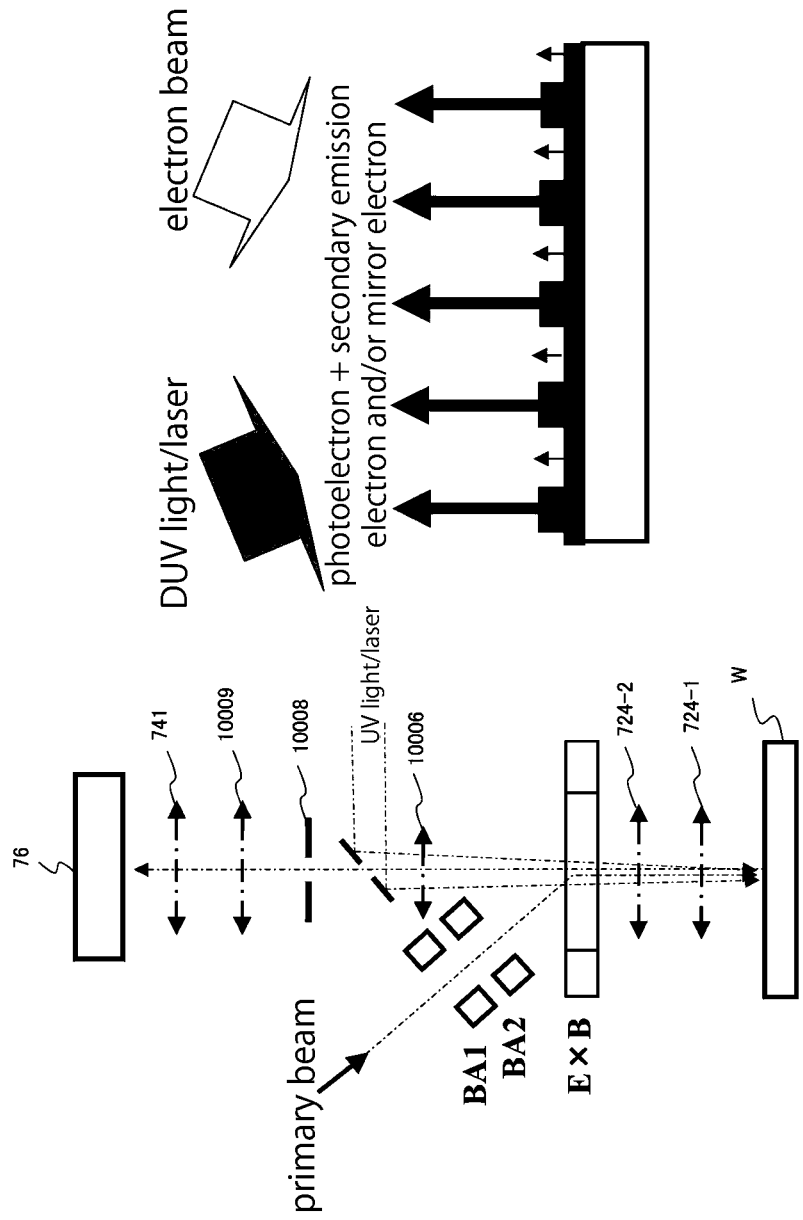
FIG. 198 is a diagram related to one embodiment of the present invention.

An embodiment in which the light or laser in FIG. 7~9, FIG. 26~31 is irradiated to a sample is combined with an embodiment for irradiating a sample using an electron beam in a primary system in FIG. 33a–FIG. 42. The examples of the embodiments are shown in FIG. 196, FIG. 197, FIG. 198. An example whereby a sample has an uneven shape is described below.

In this example, laser (or light) irradiation and electron beam irradiation are simultaneously performed as a primary beam. As an irradiation method, it is possible to perform irradiation simultaneously or alternately. At this time, the characteristics of performing laser irradiation and electron beam irradiation are described below and the effects where these are combined are also described.

By combining a photoelectron image and a secondary emission electron image in the case of a white signal where there is a large amount of photoelectrons in a top layer (bump part) when performing laser irradiation, and a white signal where there is a large amount of secondary emission electrons in a top layer when performing irradiation using an electron beam, the amount of electrons are increase in the top layer (photoelectrons white+secondary emission electrons and/or mirror electrons), that is, an image can be formed where the top layer (bump part) is white and hollow part is black and an increase in contrast and S/N is possible.

In contrast, in the case of performing an observation where a hollow part with many photoelectrons is a white signal and a where a hollow part of has many secondary emission electrons is a white signal, it is possible to increase contrast and S/N of an image formed by a white hollow part (photoelectrons+secondary emission electrons and/or mirror electrons white) and a black top layer (bump part) when laser irradiation and electron beam irradiation are performed simultaneously (combined). At this time, a white signal refers to a large amount of electrons are detected compared to other parts and brightness is relatively high, that is, white imaging is possible.

As is shown in FIG. 33 (a), in the case of using an electron beam, an electron beam splitter such as E×B is always required in order to separate from a secondary beam (using a Wien filter condition for allowing the secondary beam to travel straight). Therefore, this type of electron beam splitter is also required in an embodiment for combining an electron beam and laser or light beam. An example of this is shown in FIG. 196, FIG. 197, FIG. 198.

The difference between FIG. 196, FIG. 197 and FIG. 198 is as follows. FIG. 196 and FIG. 197 include a mechanism for introducing a laser (or light) further to the sample side than an E×B. FIG. 198 includes a mechanism for introducing a laser (or light) further to a detector side than an E×B. For example, in FIG. 196 and FIG. 197 a method is shown in which a lens introduction hole is arranged on a cathode lens and a sample is irradiated with a laser after alignment adjustment is performed using a mirror etc on the exterior of a chamber, and it is possible to introduce fiber and a lens etc to the cathode lens and perform laser irradiation. In addition, FIG. 198 shows that is possible to arrange a mirror similar to that explained in FIG. 26 within a secondary system column, introduce a laser from the exterior of the column and irradiate a laser (or light) to a sample. FIG. 198 shows a case where an amount of electrons emitted from a bump part by laser irradiation and electron beam irradiation is large (white signal). However, the reverse may also be performed the same as in FIG. 196 in the case where an amount of electrons from a hollow part is large (white signal).

In addition, with regards to a primary system electron beam, it is even more effective to use the electron beam explained in the embodiments shown in FIG. 35–41. Because an electron beam with a narrow band energy and a large current is irradiated, the energy of the secondary emission electrons or mirror electrons which are formed also becomes narrow band and it is possible to realize an image with few aberrations and distortions and a high resolution. In addition, because the energy of photoelectrons generated by a laser irradiation have a narrower band than secondary emission electrons, it is possible to maintain an energy narrow band state even when combination is performed and therefore, although the amount of photoelectrons increases the energy width does not broaden. This is particularly effective and useful since it is possible to be realized when increasing a laser or electron beam to be irradiated for raising throughput without deteriorating image quality.

In addition, the reverse case in also possible whereby the photoelectrons which are white and the secondary emission electrons which are black are combined. In this case, a combined image becomes grey, that is, an intermediate color between white and black, and pattern resolution and contrast decreases. At this time, for example, the white signal of only a defect becomes stronger. Alternatively it is also possible to perform an observation where black becomes stronger. At this time, for example, in the case of a defect which is highly sensitive to light irradiation, it is possible to form a white or black signal shape by an increase or decrease in the amount of photoelectrons. In addition, in the case of a defect which is highly sensitive to electron irradiation, it is possible to form a white or black signal by an increase or decrease in the amount of secondary emission electrons.

In addition, a combination is also similarly possible in the case where photoelectrons are black and secondary emission electrons are white. In a EUV mask example, it is possible to form the combination described below with respect to a TaBO top layer and Ru hollow part.
(Combination of an Image Formed from Ru White/TaBO Black Photoelectrons and Secondary Emission Electrons and/or Mirror Electrons, Combination of an Image Formed from Ru Black/TaBO White Photoelectrons and Secondary Emission Electrons and/or Mirror Electrons)

In this way, it is possible to realize a high contrast and S/N and perform an inspection of a pattern defect and foreign materials with high sensitivity.

Oxide film potential stabilization is performed using light irradiation with respect to a low LE image. The electron irradiation energy is −5 eV<LE<10 eV. It is particularly effective when the material of the top layer is an oxide film with respect to a low LE image. When the top layer is an oxide film, the oxide film is charged to a negative potential by a low LE electron beam irradiation which deteriorates image quality. In addition, current density can not be increased. At this time, irradiation is performed using a light such UV, DUV, EUV or X rays or a laser and the potential of the oxide film can be controlled. It is possible to positively charge the oxide film when photoelectrons are generated by irradiating these lights. Consequently, it is possible to control the potential of the oxide film to a constant by simultaneously or intermittently irradiating a low LE and these lights or a laser. Image quality becomes stable and even if current density is increased it is possible to form a stable image which can increase throughput.
(Photoelectron Cathode Primary System)

FIG. 37 shows an example used in a case where a reference voltage is a high voltage instead of GND. In this example the reference voltage is +40000V. A cylindrical shaped tube is used so that this reference voltage is uniform within a column to produce an electric field. This tube is given as tube 1. In addition, 40000V is applied and a reference voltage is formed. Also, areas near a photoelectron are parallel with an equipotential line (distribution) photoelectron surface. As a result, a magnetic field lens is used as a lens and an electromagnetic aligner is used as an aligner. NA or a different aperture becomes a reference potential and arranged in a tube structure. The tube 1 also includes another tube 2 arranged on the exterior since a high voltage is applied. The tube 2 is set to GND and the device can be GND connected. The tube 1 and tube 2 are insulated by an insulation material having a voltage resistance and a required application voltage is maintained. Although not described here, the reference voltage of the primary system is controlled in order to set the reference voltage of the secondary optical system to a high voltage. Therefore, the secondary optical system also has a column with a double tube structure the same as the primary optical system. A high voltage is applied to the inner tube and the exterior tube is set to GND. Thus voltage differential is maintained the same as the primary system. In addition, the tube 1 is a conductor and a resin material such as polyimide or epoxy may be coated on the exterior periphery of the tube 1. A conductive material may be further coated on the exterior periphery of the resin material and may be set to GND. In this way, the inner side of the resin material becomes a high voltage reference voltage and the exterior side is set to GND so that other GND connections and parts which can be set to GND can be combined. In addition, the tube 2 may be a conductor shield tube on this exterior. The tube 2 may be a magnetic body made from permalloy or pure iron and can shut out an exterior magnetic field. Furthermore, the present invention can also be applied to embodiments 1~25 described above and embodiments not attached with a number.

(Twenty Sixth Embodiment)
EO correction

An example of EO correction used in the inspection device and inspection method of the present invention is explained.

A. Summary

When imaging a beam from a wafer using a TDI, the location of the wafer requires accurate positioning. However, actually, the wafer exists on an X-Y stage and because positioning is mechanically determined, several 100 µm to several tens of nm and a response speed of several seconds to several ms are practical accuracy values.

On the other hand, since design rules are miniaturized approaching several tens of nm, performing an inspection of a wire having a wire width of several tens of nm or a via with a diameter of several tens of nm is necessary and detection of a defect having these shapes or an electrical defect and rubbish with a diameter of several tens of nm is necessary. Imaging depending only on the mechanical positioning described above, the order of response time and positioning accuracy become separated from the order of design rules and imaging accuracy which is a significant obstacle to obtaining an accurate image.

The imaging sequence is performed by combining a step (x axis) and a constant speed scan (y axis), and the (y axis) which performs comparatively dynamic control is has a control residual error which is generally large and considering prevention of image distortion, a greater level of control is being demanded.

An X-Y stage which is highly accurate and has excellent responsiveness is included for solving these issues. However, an EO correction function was devises for realizing control accuracy and speed of a beam to an imaging part which are issues that can not be solved by a stage.

A basic method includes accurately confirming the position of a wafer on a stage with a delay of within several microseconds at a sub nm order by a laser interferometer system and a bar mirror arranged on an x-y axis, a mechanical aperture is driven by an automatic control loop, and positioning is performed while considering time delay and residual error from a target position. A control residual error of a positioning result performed using this control is calculated from the difference between a target position generated within a control device and an actual position obtained by a laser interferometer system. On the other hand, a beam is guided to an imaging device via several electrodes and a correction deflecting electrode. A correction deflecting electrode has a sensitivity in which deflection is possible of around several hundreds of µm or less or more preferably a hundred µm or less which is converted to distance on a wafer, and two dimensional deflection of a beam to an arbitrary position is possible by applying a voltage to the electrode. After a control residual error is calculated by a calculation device, it is converted to a voltage using a D/A convertor, and applied to the correction deflecting electrode for cancelling the control residual error. It is possible to perform correction close to the resolution of a laser interferometer using this structure.

A method in which the above procedure is used for the X axis (step direction) and synchronizing a transfer lock of a TDI which is an imaging element with the movement speed of a stage and transferring for the Y axis (scan direction) was also invented an alternative method.

The concept of EO correction is shown in FIG. 97. A command 95.1 is output to a target position and provided to a control feedback loop 95.2 which includes a mechanical actuator. This part equates to a stage. Feedback is performed via a position detector 95.3 as a result of a position displacement which is driven and the position displacement of a drive system gradually converges to the target position from the position command, however, a residual error is produced due to the benefit limits of the control system. The actual position is detected with an order of sub nm by a position output system 95.4 (the laser interferometer is used here), a difference with the position command device 95.1 is detected by a residual error detector 95.5, then applied to a deflector electrode 95.7 using a high voltage high speed amplifier 95.6, a voltage is applied to cancel the residual error. In the case where this function is not present, a function such as 95.9 is included for reducing a variation which is produced as in 95.8.

Figure 98:
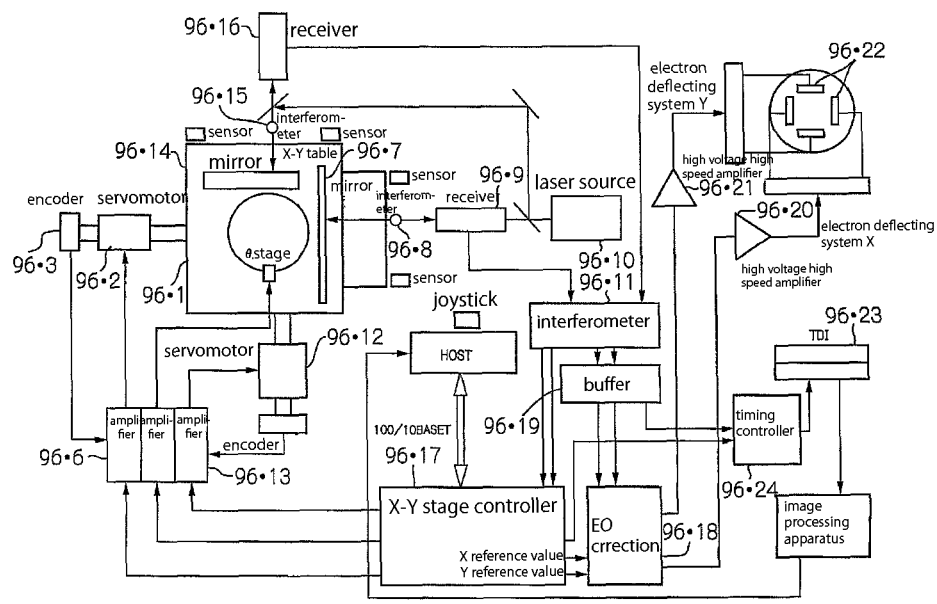
FIG. 98 is a diagram related to one embodiment of the present invention.

A detailed apparatus structure is shown in FIG. 98. An X-Y stage 96.1 can be provided with smooth servo characteristics by driving an X axis using a servomotor 96.2 for an X axis drive and encoder 96.3 and detecting a rough position and speed. A servomotor is used in the present example, however, a similar structure in an actuator such as a linear motor or ultrasound motor is possible. 96.6 is an output amplifier which drives a motor. Accurate position data of an X axis can realize a position detection function which includes sub nm a resolution by combining a mirror 96.7, interferometer 96.8, receiver 96.9, laser source 96.10, and interferometer board 96.11.

Each function related to the X axis described above are the same functions for the intersecting Y direction and are realized by a servomotor 96.12, an amplifier 96.13, a mirror 96.14, an interferometer 9.5, and a receiver 96.16 An X-Y stage controller 96.17 performs overall control of these devices and thereby it is possible to two dimensionally operate a stage and realize capabilities with an accuracy of 1000 µm to 1 nm, or preferably 100 µm to 2 nm and more preferably 1 µm to 2 nm and even more preferably 0.1 µm to 2 nm and a response speed of several thousands of ms or less, or more preferably several tens of ms or less and even more preferably several ms or less. On the other hand, an X reference value and Y reference value are output from X-Y stage controller 96.17 to an EO corrector 96.18, position data output in 32 bit binary form from the interferometer 96.11 passes a high speed buffer board 96.19 and an actual position is received by an EO corrector 96.18. After an internal calculation is performed, and after voltage amplification by high voltage high speed amplifiers 96.20, 96.21, a voltage is applied to deflection electrodes 96.22 and deflection for correcting a residual error part is performed and an image data electron beam in which a position misalignment is minimized is guided to a TDI 96.23 (imaging element). TDI 96.23 is a part for generating a timing signal for determining a transfer speed of 26 described below.

Figure 99:
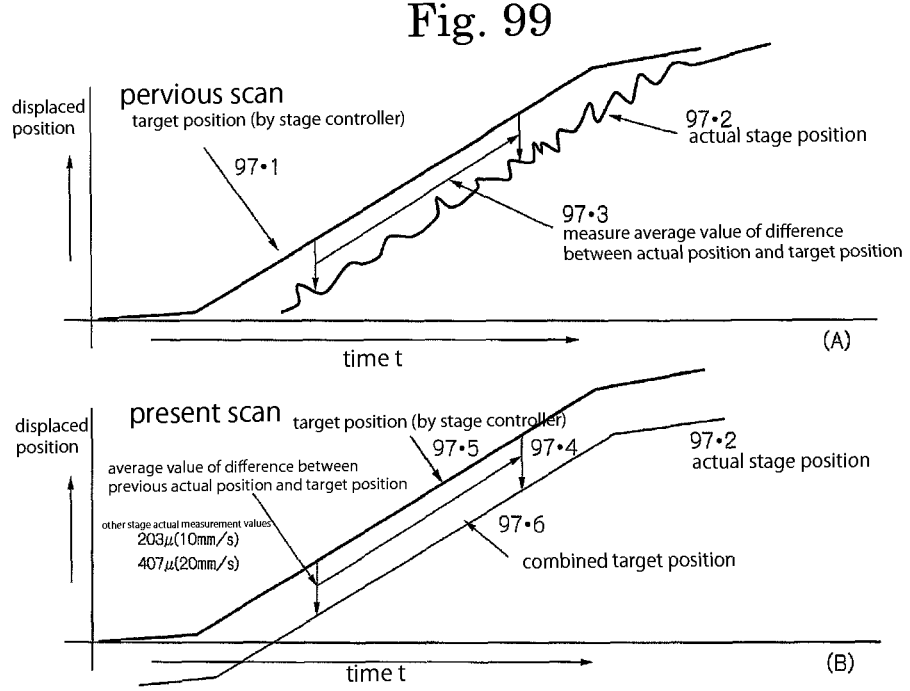
FIG. 99 is a diagram related to one embodiment of the present invention.

A function for generating a target position in a scan direction in the present device is described next. EO correction is a function for correcting a position by calculating a difference between a target position and actual position and deflecting an electron beam in order to cancel this difference. However, the correction range is limited to a range of several tens of μm. This electrode sensitivity is determined by a dynamic range, noise level, the number of bits of D/A converter of a high voltage high speed amplifier. However, a significant misalignment between the actual position of a stage when scanning with respect to the target position is produced compared to when stationary due to the gain of a control loop being limited. A divergence from the target position is around 400 μm in the case of travelling at 20 mm/s, and even if the difference is calculated and output as it is, the correction range is significantly exceeded which saturates the system. In order to prevent this phenomenon and avoid this problem, the following procedure in performed in the present device. This concept is shown in FIG. 99.

Figure 100:
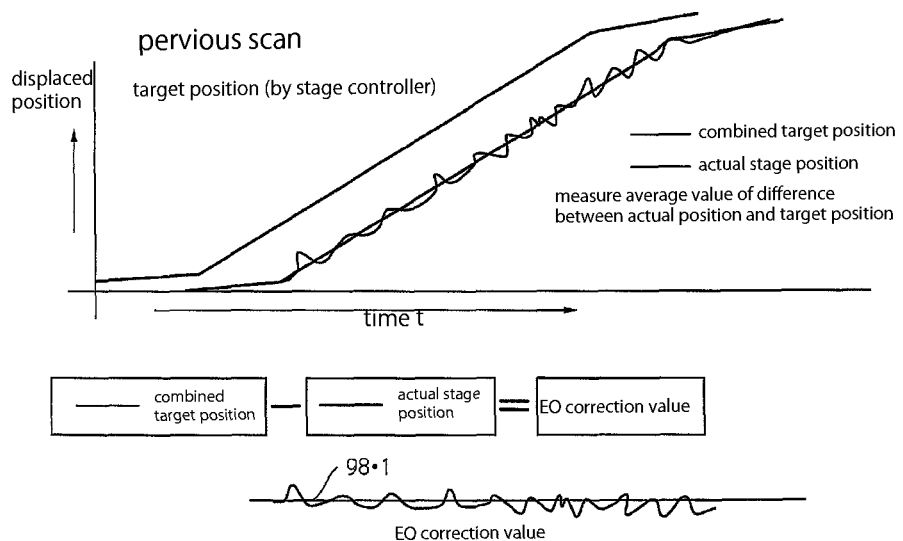
FIG. 100 is a diagram related to one embodiment of the present invention.

97.11 is a target position on a stage which moves at a constant speed during a scan and therefore increases in a direction line with time. On the other hand, a mechanical position 97.2 of a stage as a result of actual control includes a mechanical vibration of several microns and a stationary deviation 97.3 of around 400 μm. While it is possible to smooth position data when actually travelling using a filter as a means for removing this stationary deviation, a delay is always produced due to a time constant of a filter, and when a time constant in which a ripple (voltage variation which becomes noise) can be ignored is provided, a measurement start area is significantly limited which leads to a significant increase in the total amount of measurement time. Thus, in the present invention, at least the following calculation is performed in order to detect the stationary deviation. A difference between the actual position and target position at the time of the previous scan is calculated by accumulating at least 2 to the 16th power the number of samples. An average value 97.4 of the stationary deviation between the target position and the actual position is calculated by dividing this accumulation result by the number of samples. The combined target position 97.6 is calculated by subtracting the average value 97.4 of the stationary deviation from the target position 97.5 at the time of a present scan. In this way, a structure is realized in which EO correction within a dynamic range such as the EO correction value 98.1 shown in FIG. 100 is possible. Furthermore, since a desired accuracy may be obtained the number of accumulation may be fewer the value shown here.

Figure 101:
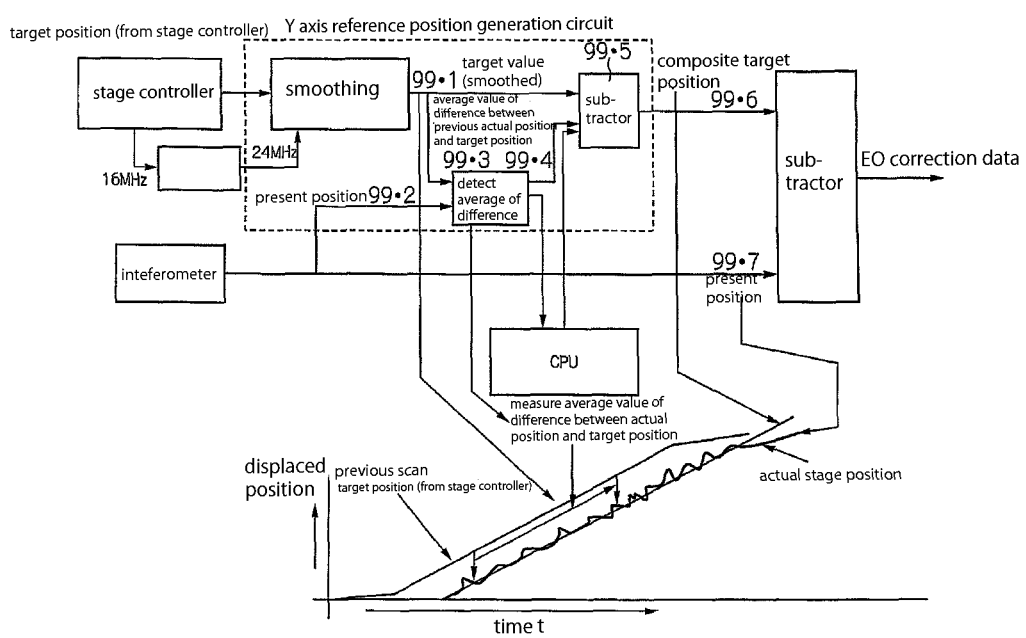
FIG. 101 is a diagram related to one embodiment of the present invention.

A block view is shown in FIG. 101. A target value 99.1 is subtracted from the actual position 99.2 and the previous accumulation is performed within the block 99.3 at the time of a scan. On the other hand, an average value of a stationary deviation calculated the same as the previous time in 99.3 is output from 99.4. EO correction data with no response delay or ripple is realized by a combined target position 99.6 calculated by subtracting 99.4 from 99.1 using a subtractor 99.5 and subtracting this value and the actual position 99.77 from an interferometer.

Figure 102:
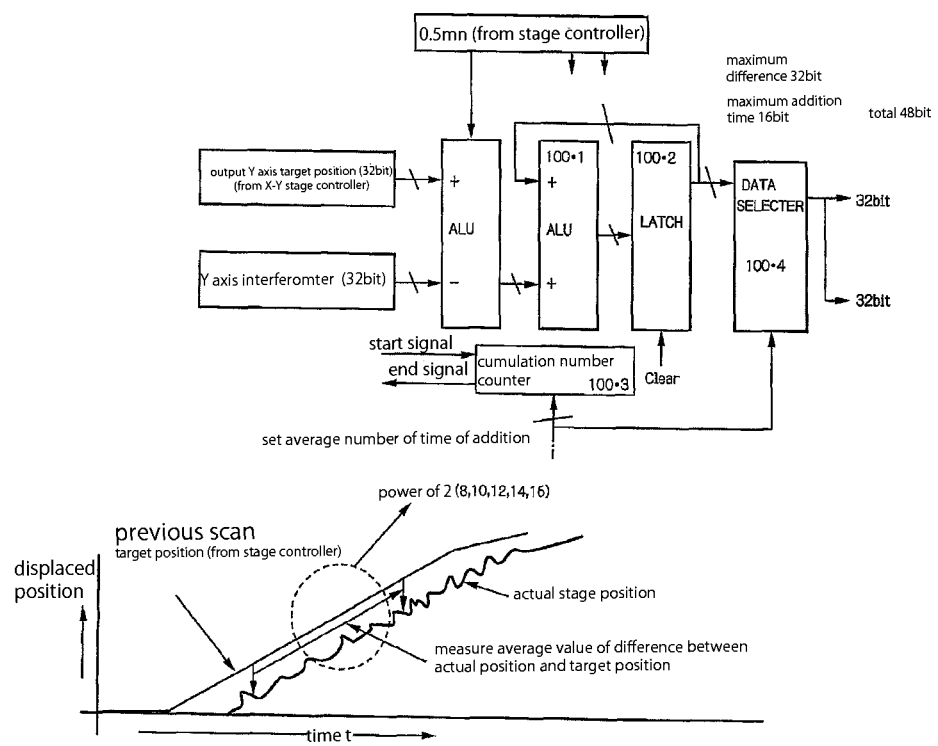
FIG. 102 is a diagram related to one embodiment of the present invention.

The structure of a block difference average detection 99.3 in FIG. 101 is shown in FIG. 102. A calculation is performed in 100.1, 100.2, a word of a data selector 100.4 is selected by the value of an accumulation counter 100.3, a division quality calculation is performed and an average value of a stationary deviation is output.

Figure 103:
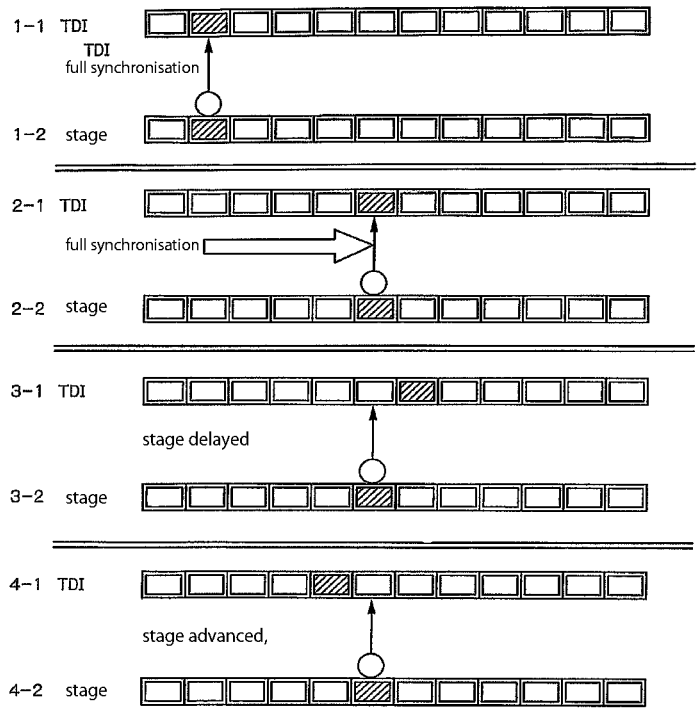
FIG. 103 is a diagram related to one embodiment of the present invention.

The idea of a transfer clock of a TDI shown in FIG. 103 is described. A TDI is an imaging element which aims to improve sensitivity and reduce random noise by connecting several photoelectron elements in stacks in a scan direction and transferring the charge of each imaging element to a following element. However, as is shown in FIG. 101, it is important that the imaging object on a stage and a pixel on the TDI correspond one to one and when this relationship is broken, image distortions occur. In FIG. 101, the relationship between 1-1 and 1-2 and the relationship between 2-1 and 2-2 show the case where each are in a synchronized relationship respectively, and the relationship between 3-1 and 3-2 and the relationship between 4-1 and 4-2 show the case where synchronization of is misaligned respectively. TDI transfer is synchronized with an external pulse and transferred to the next stage, thereby when a stage is moved one pixel at a time, this can be realized when a transfer pulse is generated.

Figure 104:
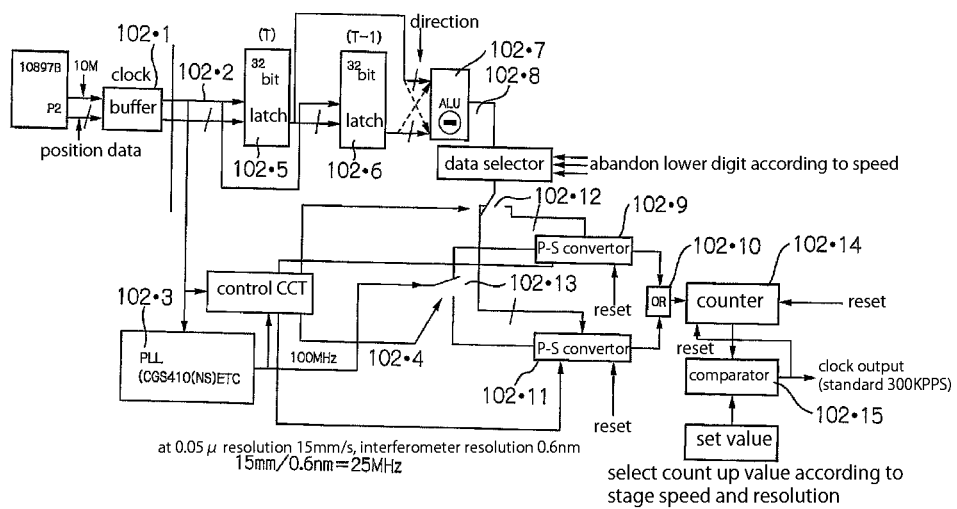
FIG. 104 is a diagram related to one embodiment of the present invention.

However, since the position data output of a currently mainstream laser interferometer is in a form which synchronizes a 32 bit binary output with 10 MHz internal block and outputs, it is not easy to realize as it is. In addition, the accuracy of a transfer pulse is also important given a resolution of several nm, and high speed highly accurate digital processing is required. The method invented in the present example is shown in FIG. 104. Information data of a laser interferometer and a 10M synchronized signal are introduced to this circuit by a buffer 102.1. The 10M clock 102.2 generates a 100 MHz clock synchronized by PLL 102.3, and is supplied to each circuit. A calculation process is performed each time this synchronization signal 102.4 generates a 10 state. The actual position data is held in 102.5 and the previous value is held in 102.6. The difference between these two is calculated by 102.7, and the position difference for each 10 start is output from 102.8. This difference value is loaded as a parallel value to a parallel serial convertor 102.9, synchronized with a 100 MHz clock and the difference is output as the number of serial pulses from 102.10. 102.11 also has the same function, however, a structure where operation is possible without rest at each 10 state is possible by combining 102.12, 102.13. As a result, a serial pulse corresponding to a position difference is output for each 10 MHz to a counter 102.14 by a summation circuit 102.10. If a comparator 102.15 is set in advance when the resolution of the laser interferometer is 0.6 nm and 1 pixel is 48 nm, the counter outputs a pulse 19 at a timing equivalent to 1 pixel. An operation synchronized with the variation in speed of a stage is possible by changing this signal into an external pulse from a TDI and it is possible to prevent distortions or blurring.

Figure 105:
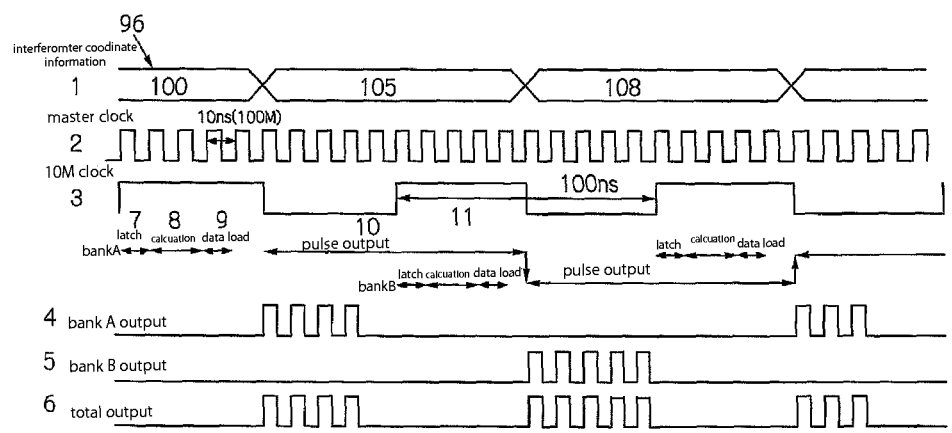
FIG. 105 is a diagram related to one embodiment of the present invention.

A timing chart is shown in FIG. 105. 1 is interferometer coordinate (position) data and the numerals are shown as examples of a position. 2 is a 100 MHz synchronized signal created by PLL. Bank A is an operation timing of a parallel serial converter 102.9 and bank B is 102.11. A difference calculation timing 8 is performed after a latch timing 7 for storing position data, a value is loaded to the parallel serial converter 102.9, and 4 is output using a 1 cycle pulse of the next 10M clock 3. Bank B performs the same operation at a timing delayed by 1 cycle of the 10M clock 3, and pulse generation 6 is easily realized. Furthermore, the present embodiment can also be applied to embodiments 1~26 described above and also to embodiments with no number attached.

(Twenty Seventh Embodiment)

A foreign material attachment prevention method and electron beam inspection device A foreign material (particle) attachment prevention method in the inspection device and inspection method of the present invention is explained.

Figure 106:
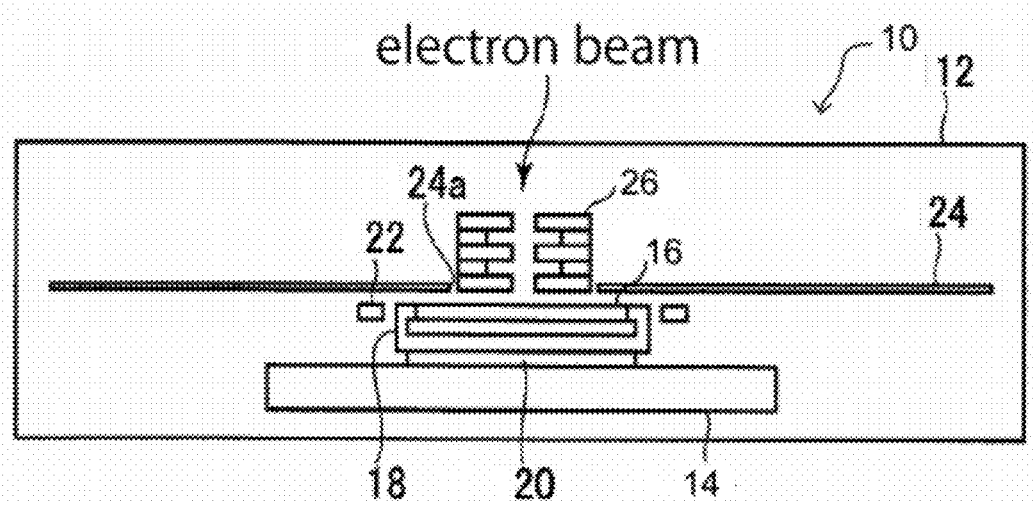
FIG. 106 is a diagram related to one embodiment of the present invention.
Figure 107:
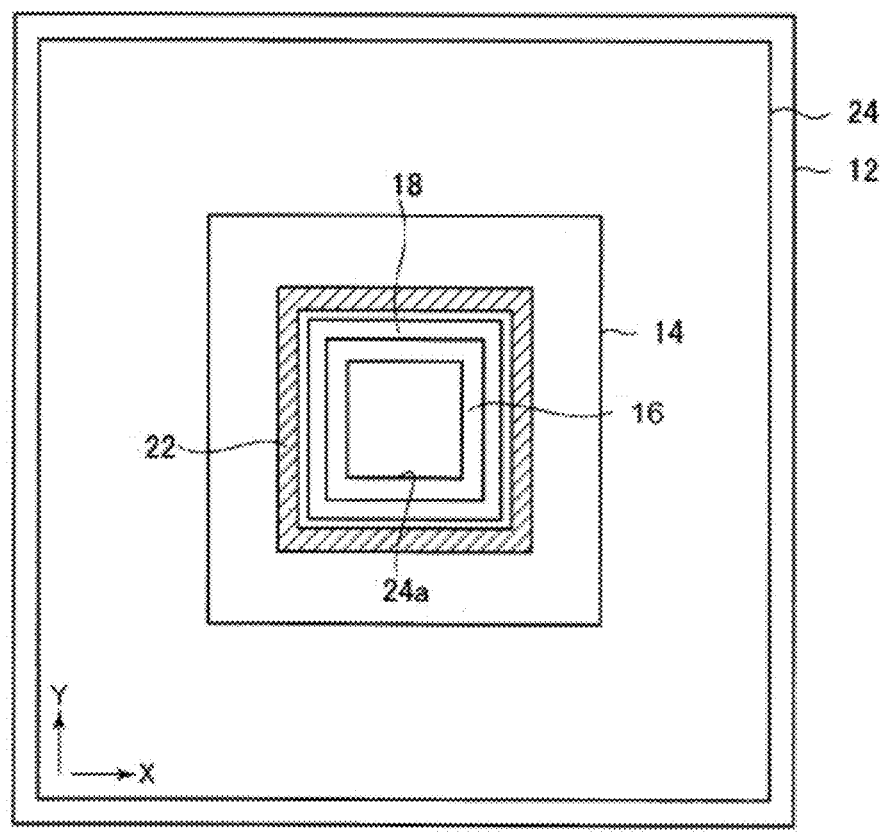
FIG. 107 is a diagram related to one embodiment of the present invention.

The present embodiment of the present invention is explained in detail below while referring to the diagrams (FIG. 106 and FIG. 107). In the example below, foreign materials such as particles are prevented from being attached to a sample surface using a rectangular mask or circular semiconductor wafer including a thin film, for example, Si (including dopants), Cr, TaN, TaBN, CrM, Ru, Ta, W or Cu etc on a surface layer as a sample. The uppermost layer of the thin film may be an insulation film of TaBO, TaO or $SiO_2$ etc. A material on which a thin film formed on a silica or quartz substrate or a circuit pattern thin film structure for an LSI formed on a Si wafer may be used for a mask. Furthermore, in each example described below, the same reference symbols are attached to the same or equivalent parts and thus overlapping explanations are omitted here.

FIG. 106 is a longitudinal front elevation diagram which shows a summary of the main parts of an electron beam inspection device of the embodiments of the present invention. FIG. 107 is a lateral palne view of FIG. 106. As is shown in FIG. 106 and FIG. 107, a vacuum chamber 12 which can exhaust a vacuum is arranged in an electron beam inspection device 10, and an X-Y stage 14 movable in an X direction and Y direction is arranged within the vacuum chamber 12. In addition, a holder 18 which supports a sample 16 comprised from a rectangular mask is arranged via an electrostatic chuck 20 on the upper surface of the X-Y stage 14.

The X-Y stage 14 includes a movement region of a stroke of effective distance+entrance distance (inspection maximum speed*speed stabilization time) so that imaging of an effective region and defect inspection of a sample 16 (mask) is possible. For example, the X-Y stage 14 includes a 400 mm stroke movement region when the entrance distance is 100 mm/c×0.5s=50 mm at an effective distance of 300 mm of the sample 16 in an X direction and Y direction.

A dust collecting electrode 22 which has a cross sectional rectangular shape and extends continuously in a rectangular frame shape is arranged at a location which encloses the entire periphery of the sample 16 separated by a predetermined interval from the sample 16 arranged on the X-Y stage 14. Furthermore, a gap control plate 24 which includes a through hole 24a at a center and is arranged on the upper side of the sample 16 (mask) arranged on the X-Y stage 14 and the dust collector 22, is arranged parallel with an internal periphery surface of the vacuum chamber 12 with a small gap therebetween. An optical system main element 26 of the electron beam inspection device is located within the through hole 24a, and an electron beam is irradiated through the optical system main element 26 onto a surface of the sample 16 arranged on the X-Y stage 14. The size of the through hole 24a is set to a slightly larger size than the exterior shape of the optical system main element 26.

The dust collector 22 is formed by a non-magnetic material such as phosphor bronze or Ti etc in order to prevent bending or a change in the trajectory of an electron beam due to a magnetic field. The electron beam includes an irradiation electron beam of a primary system, a secondary emission electron beam and a mirror electron beam reflected near the sample 16 which are emitted from the sample 16.

The gap control plate 24 is formed from a flat plate with a thickness of 0.3~5 mm for example from a material such as phosphor bronze, Ti or SUS material etc. A material coated with Au, Pt, Ru or Os etc is used as the gap control plate 24 in order to stabilize a potential or prevent contamination. In addition, the gap control plate 24 is set to a size to cover a region in which the dust collector does not extend to the exterior of a gap control plate 21 even when the X-Y stage 14 moves within a movement region. In this way, the X-Y stage 14 moves and when the sample 16 arranged on the X-Y stage 14 moves to the most slanted location within the vacuum chamber 12, an electric field distribution breaks up, the trajectory of particles is prevented from changing and it is possible to prevent the attachment of particles which fly to the surface of the sample 16. Furthermore, the gap control plate 24 is not always necessary. This is also the case for each example described below.

In this example, as is shown in FIG. 107, the dust collector 22 which continues in a rectangular frame shape encloses as one unit the entire periphery of the sample 16 which is arranged on the X-Y stage 14, and a gap is produced at a location along the length direction of the dust collector 22, parts with a non-uniform electrical field are generated, and particles are prevented from entering the interior which is enclosed by the dust collector 22 from so called gaps in the electric field.

Figure 108:
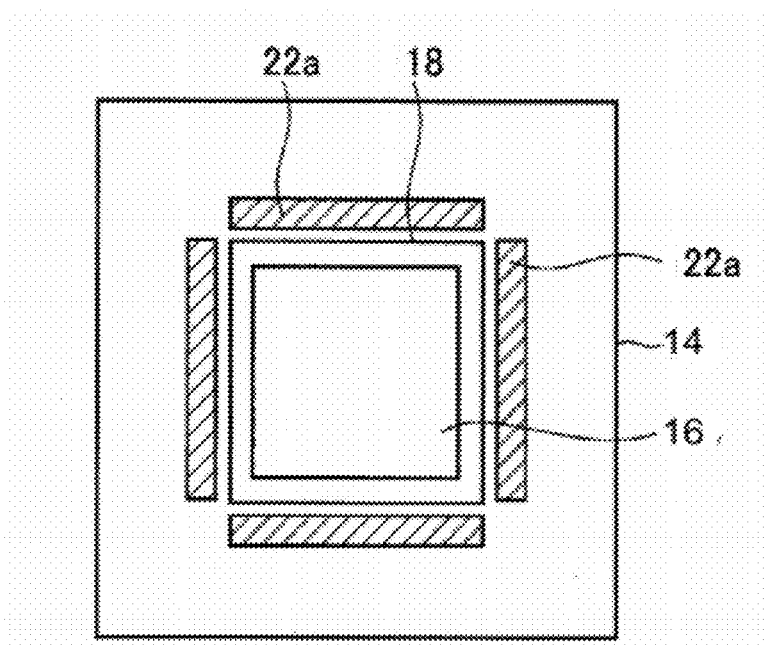
FIG. 108 is a diagram related to one embodiment of the present invention.

The dust collector 22 does not always enclose the entire periphery of the sample 16, it is sufficient that the electric field formed by the dust collector be able to enclose the periphery of the sample 16. For example, as is shown in FIG. 108, the dust collector 22 which extends in a straight line shape is arranged so that it extends almost the entire length of each side of the sample 16, and may be arranged to enclose almost the entire exterior periphery of the sample 16. In addition, although not shown in the diagram, the dust collector electrodes which extend in a straight line may be alternately separated midway. In this case, distortion in the electric field occurs between adjacent dust collector electrodes, however, it is sufficient that a distribution of a required potential be obtained by the dust collector electrodes. For example, thinking in a two dimensional manner, when the width of a dust collector is given as D, and the distance between electrodes of the dust collector electrodes given as L, then as long as $D/L \geq 4$ there is no problem. This is also the same for each example described below.

Figure 109:
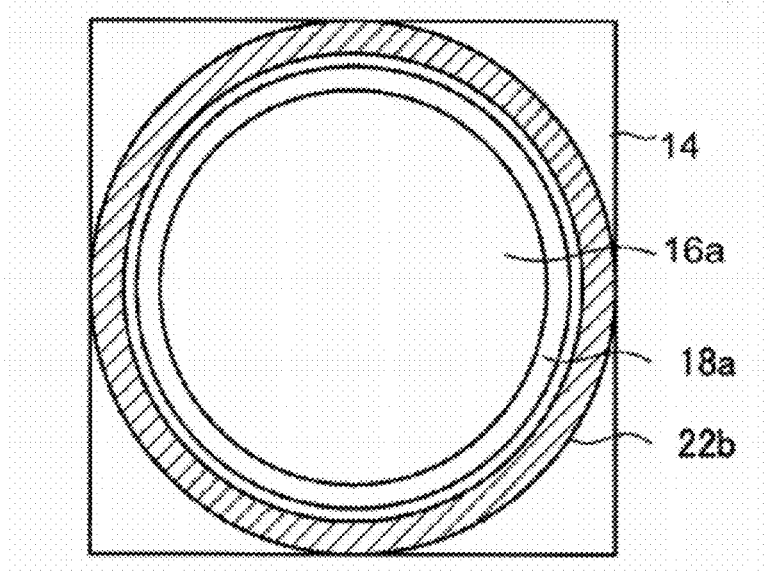
FIG. 109 is a diagram related to one embodiment of the present invention.
Figure 110:
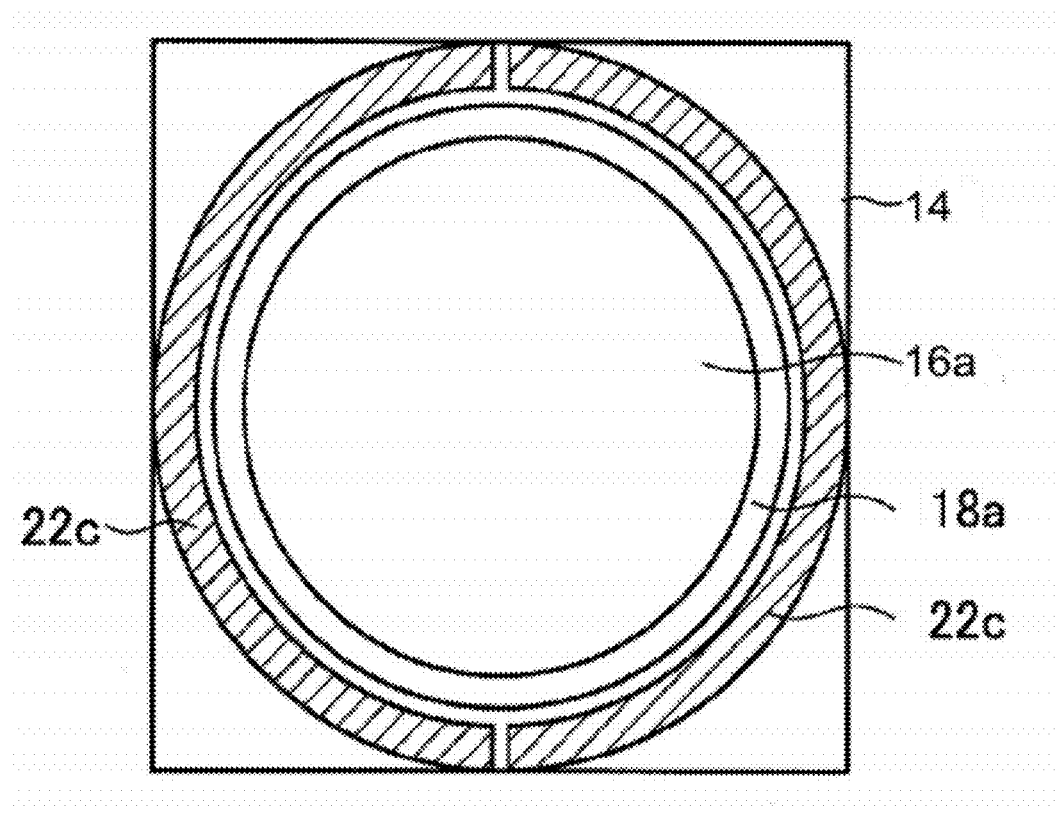
FIG. 110 is a diagram related to one embodiment of the present invention.

In the example described above, a rectangular mask is used as the sample 16. When a circular semiconductor wafer is used as the sample 16a, as is shown in FIG. 109, the sample (semiconductor wafer) 16a which is supported by a circular holder 18a is arranged on the X-Y stage 14, and by arranging the dust collector electrodes 22b which continues in a circular ring shape around the periphery of the sample 16a, it is possible to enclose the entire periphery of the sample 16a as one integrated unit. In this case, as is shown in FIG. 110, a pair of semicircular dust collector electrodes 22c is arranged to mutually oppose each other to form a full circle, and enclose almost the entire periphery of the sample 16a (semiconductor wafer) arranged on the X-Y stage 14. In addition, although not shown in the diagram, a plurality of dust collector electrodes may be arranged separated from each other extending along a circular periphery direction.

Figure 111:
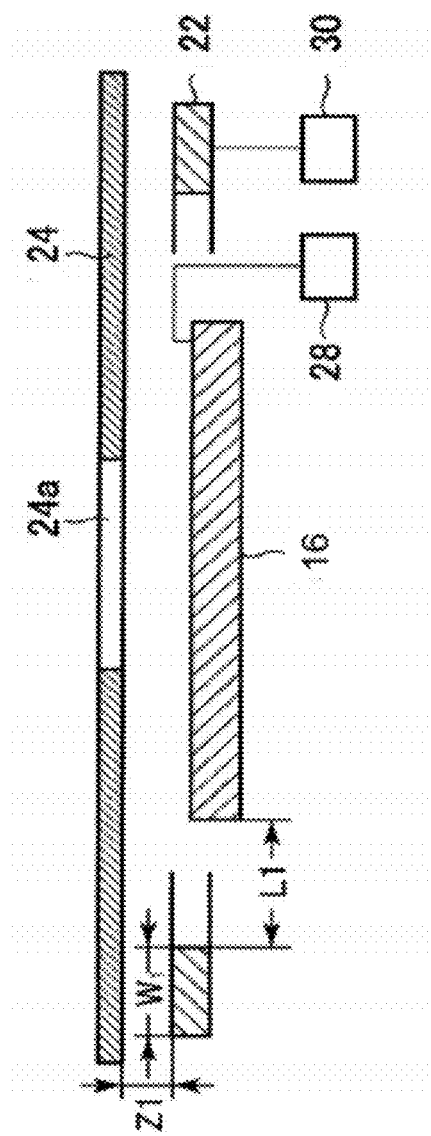
FIG. 111 is a diagram related to one embodiment of the present invention.

FIG. 111 shows an expanded view of the sample 16, dust collector electrodes 22 and gap control plate 24. As is shown in FIG. 111, a first power source 28 which applies a predetermined voltage to the surface of the sample 16 is connected to the sample 16, and a second power source 30 which applies predetermined voltage to the dust collector electrode 22 is connected to the duct collector electrode 22. The thickness of the dust collector 22 is 0.1~5 mm for example. The wider a width W1 of the dust collector electrode 22 the better, although the wider this width becomes, the size occupied by the dust collector electrode 22 inside the vacuum chamber 12 increases and therefore generally 5~50 mm is preferred. The distance L1 between the sample 16 and the dust electrode 22 is preferred to be in a range which satisfies the relationship with the width W1 of the dust collector electrode 22 which is 0.5L1<W1<5L1 for example.

In this example, a voltage of −1~−5 kV is applied through the first power source 28 to the surface of the sample 16, and a large voltage having an more absolute value than the voltage applied to the sample 16, for example, 0.5~5 kV is applied through the second power source 30 to the sample 16 with the same polarity as a voltage applied to the sample 16. That is, for example, when a voltage of −3 kV is applied to the sample 16, a voltage of −3.5~8 kV, for example, −5 kV is applied to the dust collector electrode 22.

The vacuum chamber 12 is set to an earth potential and manufactured from a metal material such as iron or aluminum. In addition, when a foreign material such as particle which exists with the vacuum chamber 12 is charged by static electricity etc, in the case where the potential of the sample 16 is negative, foreign materials such as a positively charged particle are attracted by an electric field and fly towards the sample 16.

According to this example, by enclosing the entire periphery of the sample 16 which is applied with a negative potential with the dust collector electrode 22 and applying a larger negative voltage than the voltage applied to the sample 16 to the dust collector electrode 22, the majority of foreign materials such as particles which are attracted by an electric field are captured by a dust collector electrode 18 and it is possible to significantly reduce the possibility of foreign materials such as particles from attaching to the surface of the sample 16. In this way, it is possible to prevent foreign materials from being attached to the surface of the sample 16.

In this example, a gap control plate 24 which prevents the attachment of foreign materials such as particles to the surface of the sample 16 after following a trajectory away from the dust collector electrode 22 is arranged. In this way, when the gap control plate 24 is arranged, the suction power of the dust collector electrode 22 towards foreign materials such as particles which pass a trajectory away from the dust collector electrode 22 decreases, and thereby the possibility of foreign materials such as particles being captured by the dust collector electrode 22 decrease in proportion to distance. As a result, when a negative voltage is applied to the sample 16, by making sure the electric field strength A between the sample 16 and the dust collector electrode 22 becomes negative (A<0), it is possible to increase the suction power of the dust collector electrode 22 and increase the possibility of foreign materials such as particles being captured by the dust collector electrode 22. In addition, by ensuring that electric field strength B (absolute value) between the gap control plate 24 and the dust collector electrode 22 has the relationship $0.1 \leq B$ (absolute value) $\leq 10$ kV/mm, it is possible to increase the possibility of foreign materials such as particles being captured by the dust collector electrode 22.

For example, a negative voltage of −1~−5 kV is applied to the sample 16, and a large negative voltage of −5~−10 kV which is −0.5~−5 kV larger than the negative voltage applied to the sample 16 is applied to the dust collector electrode 22. When the gap control plate 24 is set to an earth potential, the distance between the sample 16 and the dust collector electrode 22 is L1=10 mm, and the distance between the gap control plate 24 and the dust collector electrode 22 is Z1=8 mm, the electric field strength A between the sample 16 and the dust collector electrode 22 becomes negative (A<0), and the electric field strength (absolute value) between the gap control plate 24 and the dust collector electrode 22 becomes B=0.19~1.25 kV/mm (=1.5~10 kV/8 mm), and in particular, when a voltage of −5 kV is applied to the dust collector electrode 22, the electric field strength (absolute value) becomes B=0.625 kV/mm (=5 kV/8 mm), which is an effective condition. At this time, it is possible to prevent electrical discharge in space occurring by making sure the voltage resistance of space does not exceed 10 kV/mm.

Figure 112:
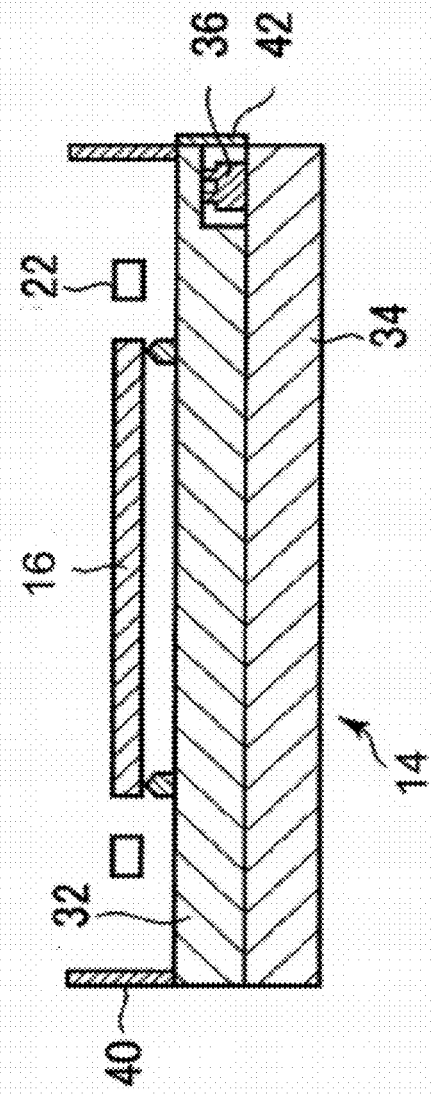
FIG. 112 is a diagram related to one embodiment of the present invention.

FIG. 112 shows the details of the X-Y stage 14. As is shown in FIG. 112 the X-Y stage 14 is formed by alternately stacking an X stage 32 and Y stage 34 and an ultrasound motor 36 is arranged between the X stage 32 and Y stage 34. In addition, an upper end of a first dust control cover 40 which reaches the upper side of the dust collector electrode 22, is arranged at a location which encloses the exterior side of the dust collector electrode 22 on the upper surface of the X-Y stage 14, and a second dust control cover 42 which blocks off an aperture end of a housing part of the ultrasound motor is arranged on the exterior side of the ultrasound motor 36.

In this way, it is possible to prevent foreign materials such as particles heading towards the sample 16 from attaching to the surface of the sample 16 by arranged the first dust control cover 40. In addition, it is also possible to prevent foreign materials such as particles flying from the ultrasound motor 36 from flying into the vacuum chamber 12 by arranging the second dust control cover 42 on the exterior side of the ultrasound motor 36 which is a source of particles. In this way, preventing foreign materials such as particles flying from a particle source into the vacuum chamber 12 is particularly effective in the case of using a motor which is driven by friction with a side surface of a piezo actuator etc.

Figure 113:
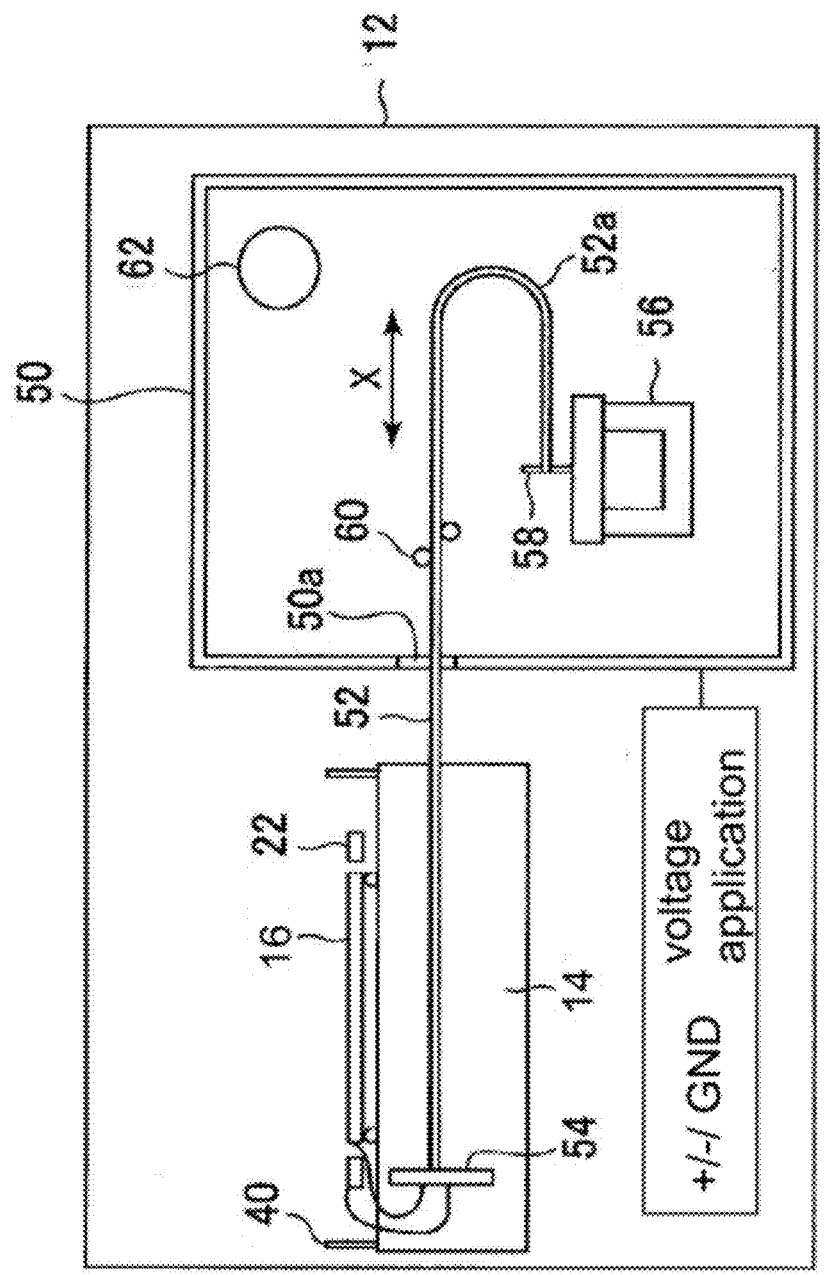
FIG. 113 is a diagram related to one embodiment of the present invention.

In this example, as is shown in detail in FIG. 113, a sealed structure wire box 50 is arranged within the vacuum chamber 12. The wire box 50 is for preventing foreign materials such as particles which are generated from a cable by bending or friction of the cable from flying into the vacuum chamber 12. In this example, all the parts of a cable 52 which bends with the movement of the X-Y stage 14 are enclosed within the wire box 50. That is, one end of the cable 52 extends in a straight line towards the wire box 50 from the X-Y stage 14, passes through a slit 50a arranged on the wire box 50, reaches the inside of the wire box 50 and curves and is inverted 180° towards the bottom. In addition, the other end of the cable 52 is connected to a movement plate 58 which is arranged on a terminal base 56b arranged within the wire box 50. In this way, when the X-Y stage 14 moves in an X direction, only a curved part 52a of the cable 52 within the wire box 50 curves.

A guide roller 60 which acts as guide of the cable 52 and extends along a Y direction is arranged within the wire box 50, and when the X-Y stage 14 moves in a Y direction, the movement plate 58 moves in a Y direction along the guide roller 60 and thus stress in a Y direction is not applied to the cable 52 up to the movement plate 58. Although not shown in the diagram, a cable which extends from the terminal base 56, passes through a wire hole arranged in the wire box 50 and connects to a feed through which is arranged in the vacuum chamber 12.

In this way, when all of the curved parts of the cable 52 are within the wire box 50, it is possible to significantly reduce the possibility of foreign materials such as particles generated within the wire box 50 from escaping to the exterior of the wire box 50 because a hole which passes through to the exterior of the wire box 50 is small, and the majority of these particles become attached to an inner wall of the wire box 50. Furthermore, in this example, by arranging a wire box dust collector electrode 62 within the wire box 50 and applying a voltage for capturing foreign materials such as particles to the wire box dust collector electrode 62, it is possible to significantly reduce the possibility of foreign materials such as particles from flying from the wire box 50 to the exterior.

Furthermore, by applying measures such as 1) aligning the length of cables 2) correcting cables by fixing a cable tie (tie band) and 3) using a flat cable, it is possible to reduce the generation of particles due to friction between a plurality of cables. That is, when the lengths of a plurality of cables are aligned and fixed, a cable bunch is integrated but bends when the X-Y stage moves. However, by reducing friction between each of these cables it is possible to reduce the generation of foreign materials such as particles. In addition, by using a flat cable, it is possible to turn a plurality of wires into one cable and remove friction between cables. Furthermore, when a flat cable having a plurality of wire can not be used immediately it is possible to combine 1) and 2) described above.

Figure 114:
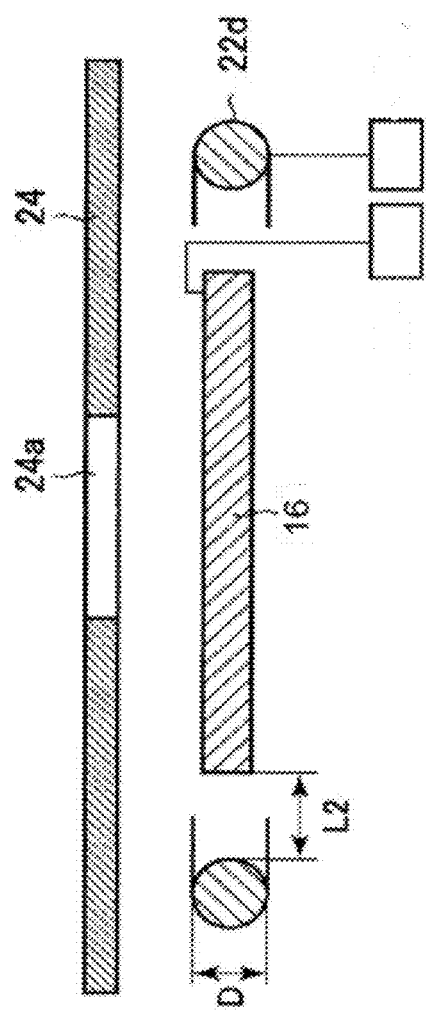
FIG. 114 is a diagram related to one embodiment of the present invention.

In the example described above, a lateral profile rectangular shaped dust collector electrode 22 was used. However, as is shown in FIG. 114, a lateral profile circular dust collector electrode 22 may also be used. The diameter D of the dust collector electrode 22 is preferably within a range which satisfies the relationship 5L2<D<5L2 for example with the relationship distance L2 between the sample 16 and the dust collector electrode 22d. When the diameter D of the dust collector electrode 22d is smaller than this, the capturing possibility of the dust collector electrode 22d decreases, and in the case where D is larger than this, the capturing possibility of the dust collector electrode 22d does not change, rather it attracts the capture of excessive foreign materials such as particles.

Figure 115:
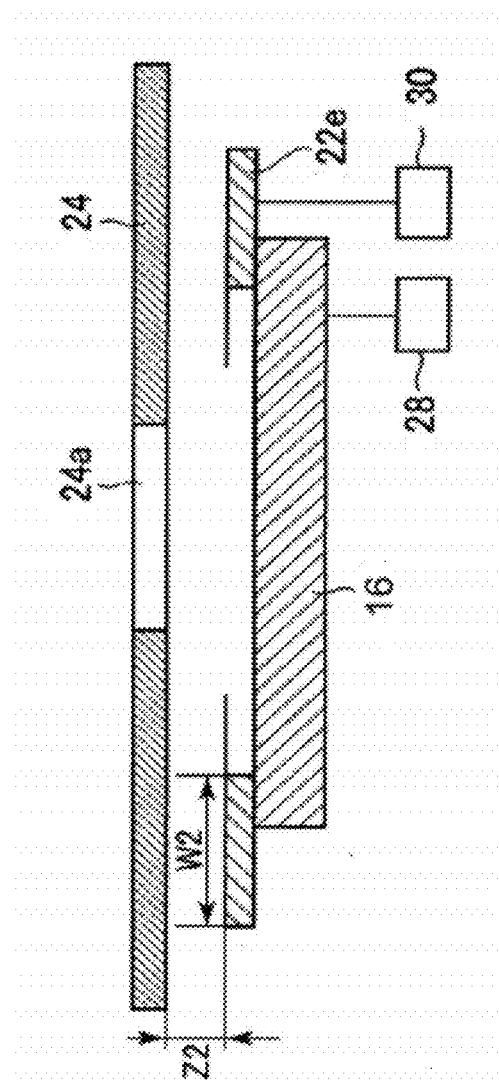
FIG. 115 is a diagram related to one embodiment of the present invention.

In addition, in the example described above, the dust collector electrode 22 is arranged at a location separated by a predetermined interval from the sample 16, and a voltage with a larger absolute value than the voltage applied to the sample 16 with the same polarity as the voltage applied to the sample 16 is applied to the dust collector electrode 22. However, as is shown in FIG. 115, it is possible to arrange a lateral profile rectangular shaped dust collector electrode 22e which continues in a rectangular frame shape so as to contact the interior periphery edge part to the exterior periphery edge part of the sample 16 and enclose the entire periphery of the sample 16, and apply the same voltage as the voltage applied to the sample 16 via a first power source 28 to the dust collector electrode 22e via the second power source. The thickness of the dust collector electrode 22e is for example 0.1~5 mm and the width W2 may be the same as the dust collector electrode 22 previously described, for example, 5~50 mm.

Figure 116:
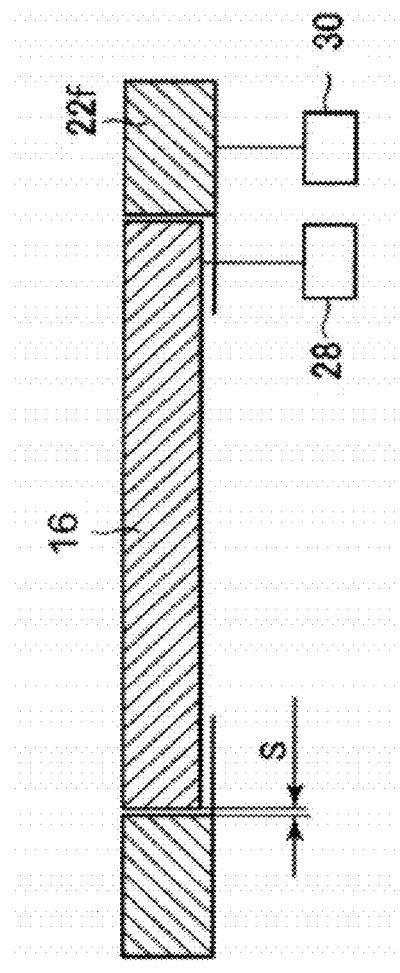
FIG. 116 is a diagram related to one embodiment of the present invention.

In the example above, a dust collector electrode 22e which includes an interior shape which is smaller than the exterior shape of the sample 16 and the interior periphery edge part of the dust collector electrode 22e is made to contact the exterior periphery edge part of the sample 16. However, as is shown in FIG. 116, for example, it is possible to use a dust collector electrode 22f which has a rectangular frame shape and a slightly larger interior shape than the exterior shape of the sample 16, and arranged the dust collector electrode 22f so that it encloses the entire periphery of the sample 16 with a small gap S arranged therebetween. This gap S is for example 1~500 μm.

In the example described above, for example, a −1~−5 kV negative voltage is applied via a first power source 28 to the sample 16, and when a voltage the same as the voltage applied to the sample 16 via the second power source 30 is also applied to the dust collector electrode 22e, for example when −3 kV is applied to the sample 16, the voltage applied to the dust collector electrode 22e is −3 kV.

As stated previously, when the potential of the sample 16 is negative, foreign materials such as particles which are positively charged are attracted by an electric field, and fly towards the sample 16. According to this example, when the dust collector electrode 22e which is the same potential as the sample 16 is arranged at a location which encloses the entire periphery of the sample 16, the majority of foreign materials such as particles which are attracted by the electric field, are captured by the dust collector electrode 22e. In this way, by capturing a majority of foreign materials such as particles using the dust collector electrode 22e which is arranged on the periphery of the sample 16, it is possible to reduce the amount of foreign materials such as particle which fly towards and become attached to a sample 16 surface, and in this way it is possible to prevent foreign materials from becoming attached to the surface of the sample 16.

In the example described above, when the distance between the dust collector electrode 22e and the gap control plate 24 is given as Z2, and given the relationship with the width W2 of dust collector electrode 22e, it is particularly effective when W2>4Z2. In addition, when the size (absolute value) of a voltage density B between the dust collector electrode 22e and the gap control plate 24 is increase more than 0.1 kV/mm, it is more effective when (B(absolute value)>0.1 kV/mm).

Figure 117:
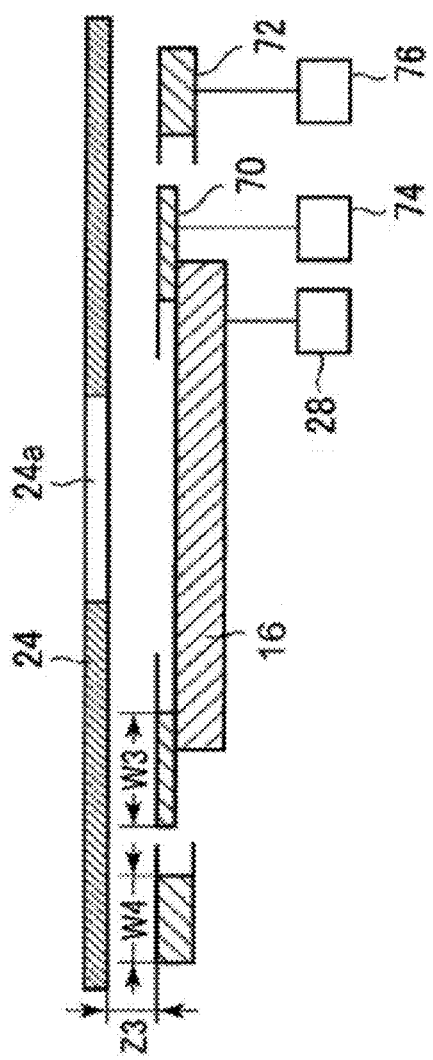
FIG. 117 is a diagram related to one embodiment of the present invention.

FIG. 117 shows another example which combines the example which is mainly shown in FIG. 111 and the example shown in FIG. 115. In this example, a first dust collector electrode 70 is arranged which contacts an interior periphery edge part with an exterior periphery edge part of the sample 16, and has a lateral profile rectangular shape which continues in a rectangular frame shape so as to enclose the entire periphery of the sample 16, and a second dust collector electrode 72 is arranged which has a lateral profile rectangular shape which continues in a rectangular frame shape so as to enclose the entire periphery of the first dust collector electrode 70. In addition, a second power source 74 is connected to first dust collector electrode 70 and a third power source 76 is connected to the second dust collector electrode 72.

Furthermore, as stated previously, the second dust collector electrode which extends in a straight line is arranged to extend along almost the entire length of each side of the first dust collector electrode, and the second dust collector electrode may be arranged so as to enclose almost the entire exterior periphery of the first dust collector electrode or the second dust collector electrode which extends in a straight line may be arranged to be separate from the first dust collector electrode at a midway point.

In this example, as stated previously, for example, a −1~−5 kV voltage is applied to the sample 16 via the first power source 28, and when a voltage the same as the voltage applied to the sample 16, for example is −3 eV, the voltage applied to the first dust collector electrode 70 is −3 eV. Furthermore, a larger voltage having an absolute value, for example, 0.5~5 kV, than the voltage applied to the sample 16 with the same polarity as the voltage applied to the sample 16 is applied to the second dust collector electrode 72. That is, for example, when a −3 kV voltage is applied to the sample 16, −3.5~−8 kV, for example, a −5 kV voltage is applied to the second dust collector electrode 72.

In this example also, almost the same as the example shown in FIG. 111 etc described above, when a negative voltage is applied to the sample 16, by ensuring that the electric field strength A between the sample 16 and the second dust collector electrode 72 becomes negative (A<0), the suction power of the second dust collector electrode 72 is increased, and the possibility of the second dust collector electrode 72 capturing foreign materials such as particles is increased. Furthermore, by ensuring that the electric field strength (absolute value) B between the gap control plate 24 and the second dust collector electrode 72 has the relationship $0.1 \leq B$ (absolute value)$\leq 10$ kV/mm, it is possible to further increase the possibility of the second dust collector electrode 72 capturing foreign materials such as particles.

The first dust collector electrode 70 has a thickness, for example of 0.1~5 mm and a width W3 of 5~50 mm the same as the dust collector electrode 22e shown in FIG. 115 described above. In addition, the second dust collector electrode 72 has a thickness, for example of 0.1~50 mm and a width W4 of 5~50 mm the same as the dust collector electrode 22 shown in FIG. 111 described above.

In addition, for example, a negative voltage −1~−5 kV is applied to the sample 16 and the first dust collector electrode 70, and a negative voltage of −1.5~−10 kV which is −0.5~5 kV larger than the negative voltage applied to the sample 16 and first dust collector electrode 70, is applied to the second dust collector electrode 72. When the gap control plate 24 is set to an earth potential and when the distance Z between the gap control plate 24 and the second dust collector electrode 72 is given as Z8=8 mm, the electric field strength A between the sample 16 and the second dust collector electrode 72 becomes negative (A<0), and the electric field strength (absolute value) between the gap control plate 24 and the second dust collector electrode 72 becomes B=0.19~1.25 kV/mm (=1.5~10 kV/8 mm), and in particular, when a −5 kv voltage is applied to the dust collector electrode 22, the electric field strength (absolute value) becomes B=0.625 kV/mm (=5 kV/8 mm) which is an effective condition. At this time, by ensuring that a space voltage resistance does not exceed 10 kV/mm, it is possible to prevent electric discharge of a space.

Figure 118:
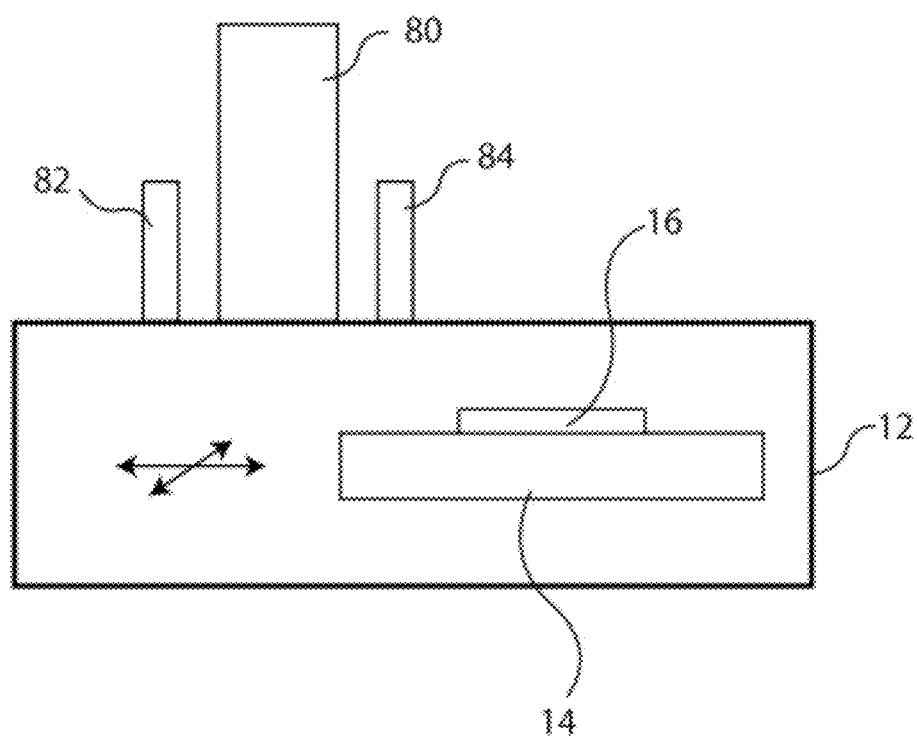
FIG. 118 is a diagram related to one embodiment of the present invention.

FIG. 118 is a concept view which shows another embodiment of an electron beam inspection device. In this example, a projection type optical inspection device 80, SEM type inspection device 82 and optical microscope 84 are arranged in a vacuum chamber 12 which is arranged with an X-Y stage 14 in its interior, the X-Y stage 14 having a sample 16, and an observation and inspection can be performed on the sample 16 arranged on the X-Y stage 14 within the vacuum chamber 12 using both the projection type optical inspection device 80 and SEM type inspection device 82.

According to this example, because the sample 16 is mounted on the X-Y stage 14 which is common to both the projection type optical inspection device 80 and SEM type inspection device 82, when the sample moves between the projection type optical inspection device 80 and SEM type inspection device 82, a coordinate relationship is unambiguously calculated and it is possible to easily and accurately specify the same potential.

That is, when a sample moves between separated devices, it is necessary to arrange a sample on separate stages, and therefore it is necessary to align the sample on each stage which results in a specification error of 5~10 μm or more for the same place. In particular, in the case where a sample does not include a pattern, a location reference can not be specified and therefore this error is further increased, According to this example, because it is possible to specify the same place with a high level of accuracy even when a sample 16 is moved between the projection type optical inspection device 80 and SEM type inspection device 82, specification of a place can be performed with an accuracy of 1 μm or less for example. In this way, when an inspection of a pattern and pattern defect is performed using the projection type optical inspection device 80, it is effective to perform a specification and detailed observation (review) of the detected defect using the SEM type inspection device 82. That is, because a place can be specified it is possible to not only determine the present of a defect (or detection of a false defect) but also accurately and rapidly determine the shape and size of the defect. When there are separate devices, a large amount of time is waster on a pattern defect and its specification.

As described herein, while preventing the attachment of foreign materials such as particles to a surface of the sample 16, by using a device system in which the projection type optical inspection device and SEM type inspection device are mounted within the same chamber, in particular, it is possible to perform an inspection, specification and classification of an ultrafine pattern of 100 nm of less efficiently and rapidly.

Figure 119:
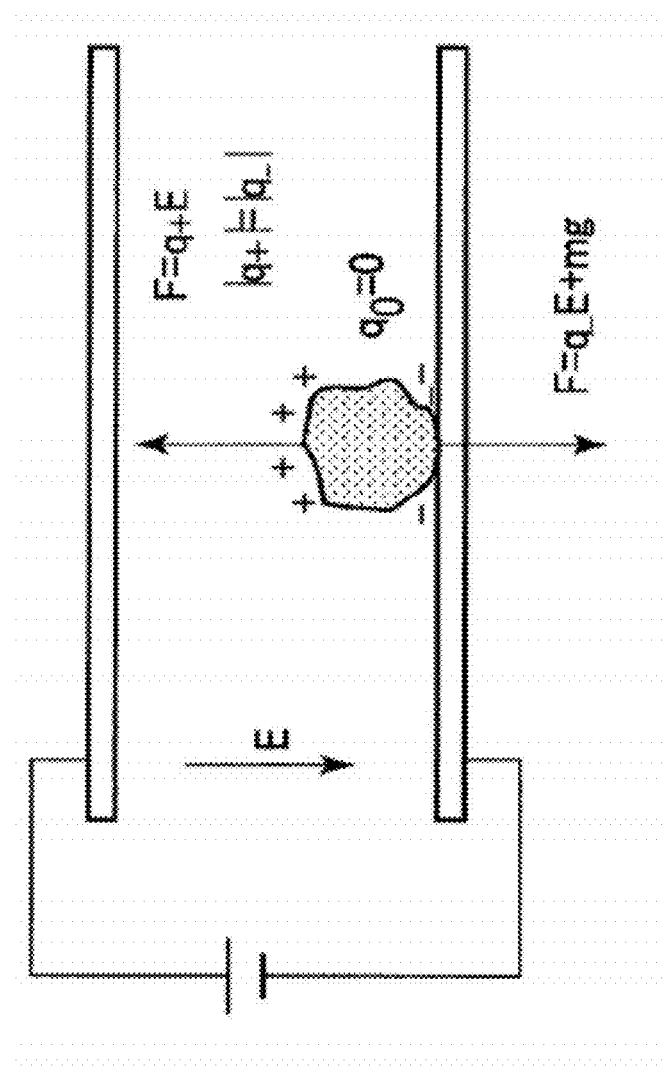
FIG. 119 is a diagram related to one embodiment of the present invention.
Figure 120:
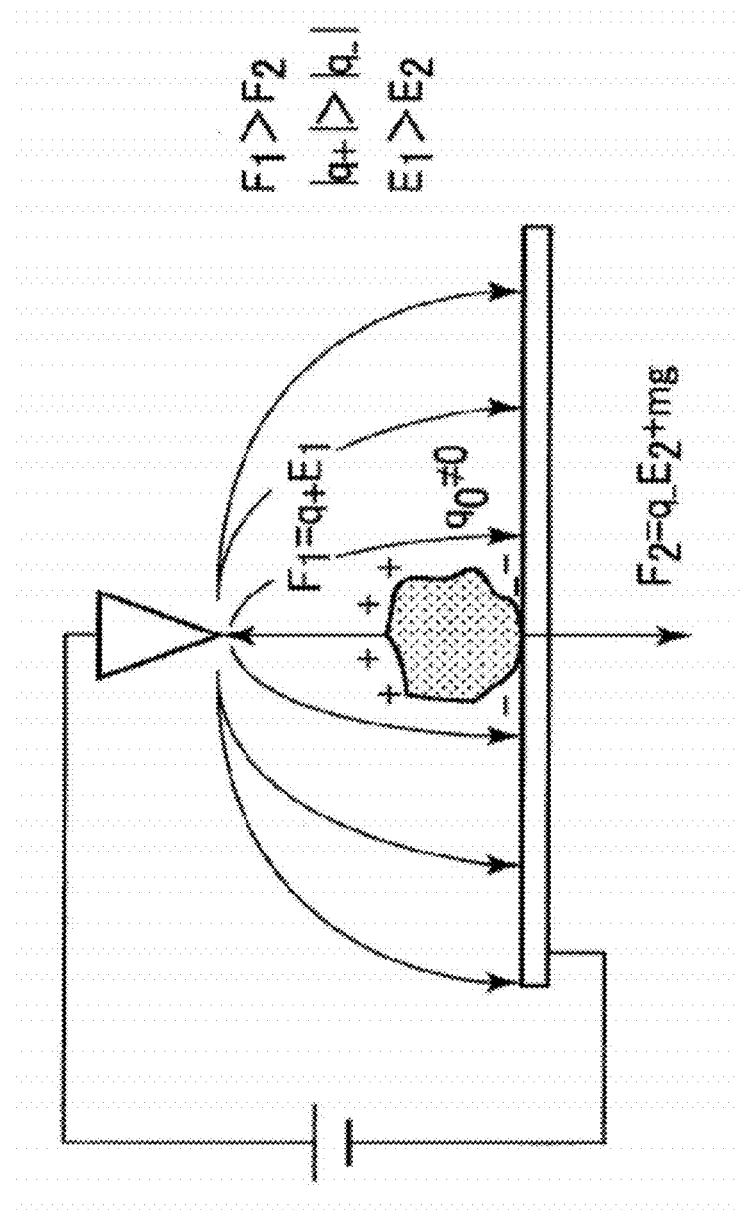
FIG. 120 is a diagram related to one embodiment of the present invention.

As is shown in FIG. 119, even if a particles comprised form an insulation material exists within a uniform electric field ($q_+=q_-$) between electrodes comprised from parallel plates, although the particle is polarized due to electrostatic induction from the electric field it does not fly. However, when the electric field is a non-uniform electric field, the particles fly due to a charge produced by induced polarization. Similarly, as is shown in FIG. 120, when a particle comprised form an insulation material exists in a non-uniform electric field ($q_+ \neq q_-$) between a pair of electrodes where one is a plate, the particle is polarized due to electrostatic induction from the electric field and flies. However, as is shown in FIG. 121, when a particle comprised form an insulation material exists in a uniform electric field ($q_+=q_-$) between a pair of electrodes where one is a plate, although the particle is polarized due to electrostatic induction from the electric field it does not fly.

Figure 121:
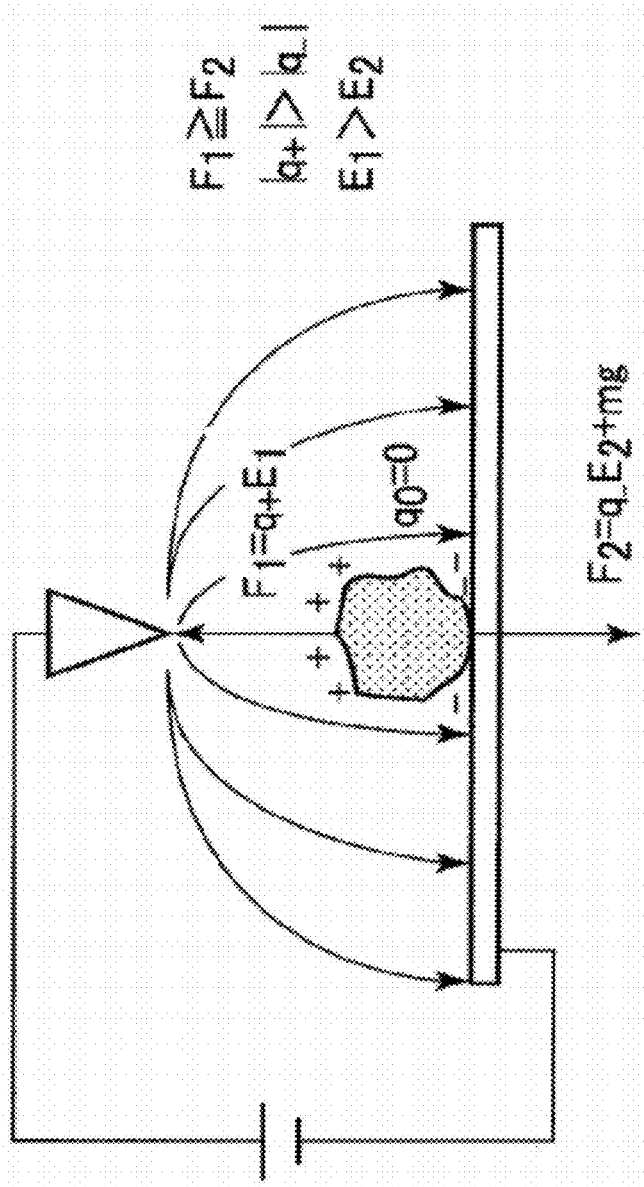
FIG. 121 is a diagram related to one embodiment of the present invention.

That is, as is shown in FIG. 120 and FIG. 121, it is considered that the possibility that a foreign material such as a particle will fly is controlled to the initial charge $q_0$ of a particle controlled before the foreign material such as a particle is induced polarization. The initial charge $q_0$ held by a residual substance is thought to be provided with static electricity produced by the flow of air mainly during a vacuum discharge.

Figure 122:
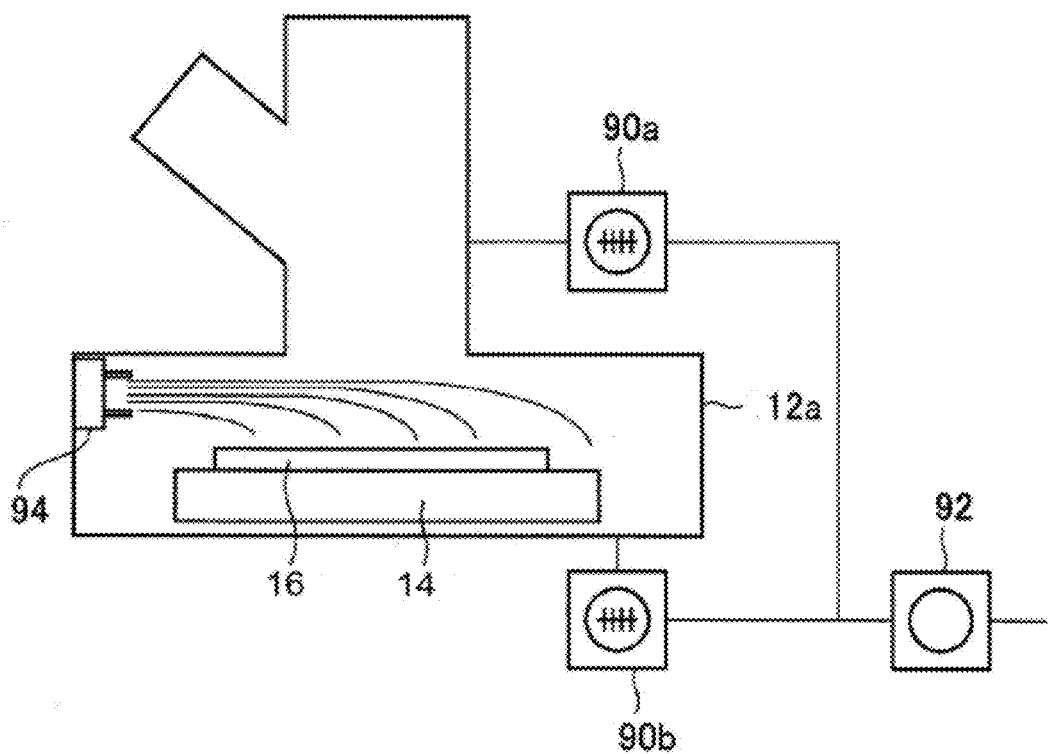
FIG. 122 is a diagram related to one embodiment of the present invention.

FIG. 122 shows another vacuum chamber 12a arranged in an electron beam inspection device. An X-Y stage 14 arranged with a sample 16 is arranged within the vacuum chamber 12a. Two vacuum pumps 90a, 90b are connected to the vacuum chamber 12a, and a common dry pump 92 is connected to the two vacuum pumps 90a, 90b. In addition, a gas is ionized using a soft X ray or UV ray in order not to charge foreign materials (residual materials) such as particles which can not be removed by cleaning the vacuum chamber 12a, and a neutralization device 94 for removing static electricity on the surface of a substance within an ionized gas by the ionized gas is arranged.

According to the present example, the neutralization device 94 is operated at the same time as when a vacuum discharge begins within the vacuum chamber or before a vacuum exhaust begins, and the neutralization device 94 is continuously operated during the vacuum discharge process which is performed with the vacuum chamber 12a. That is, the flow of within the vacuum chamber 12a is removed, and the neutralization device 94 is continuously operated until static electricity is no longer generated by the flow or air. In this way, by preventing charging of a foreign material (residual material) such as particles within the vacuum chamber 12a and when this initial charge is given as $q_0=0$ (refer to FIG.

121), it is possible to reduce the possibility of flying caused by induction polarization due to a non-uniform electric field.

In addition, even if foreign materials such as particles which remain within a vacuum chamber since they can not be removed by cleaning are ultrafine and few, they are deposited on the surface of a planar surface structure within the vacuum chamber due to gravity.

Figure 123:
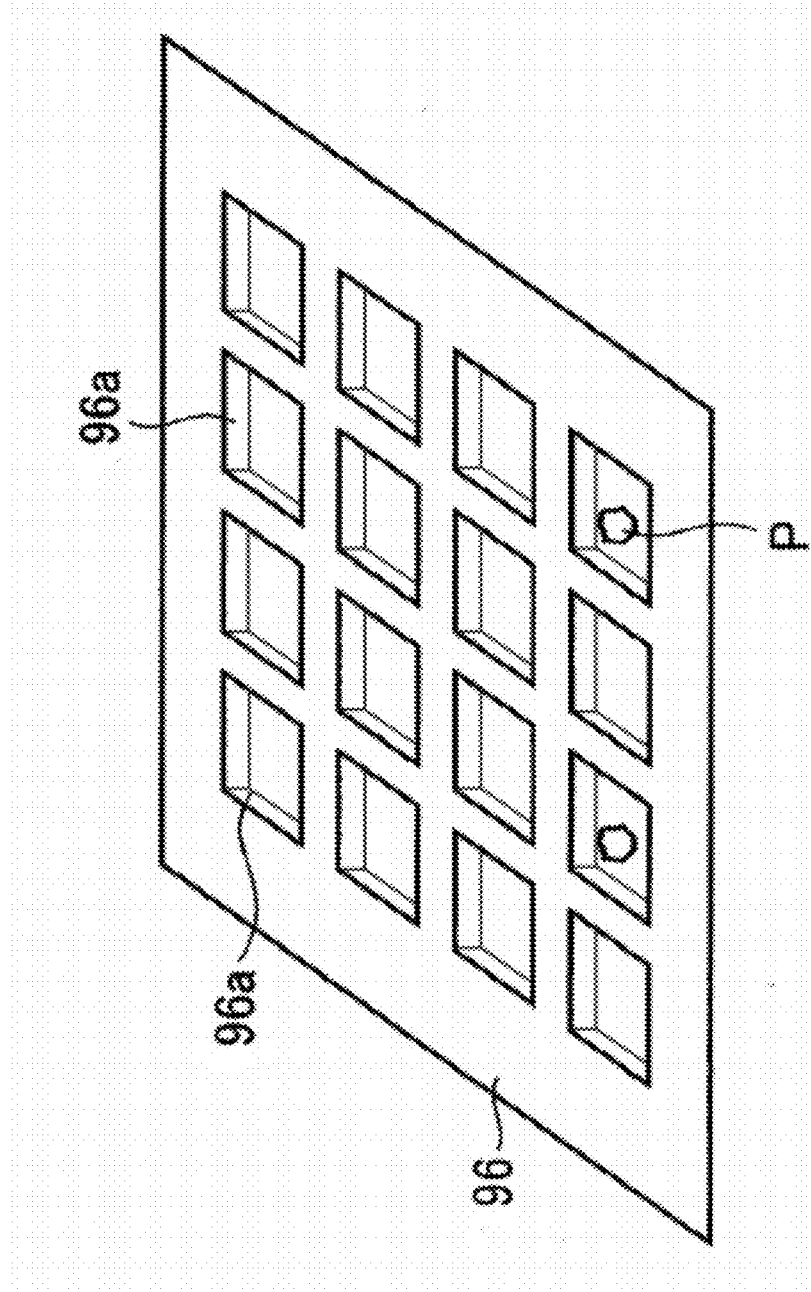
FIG. 123 is a diagram related to one embodiment of the present invention.
Figure 124:
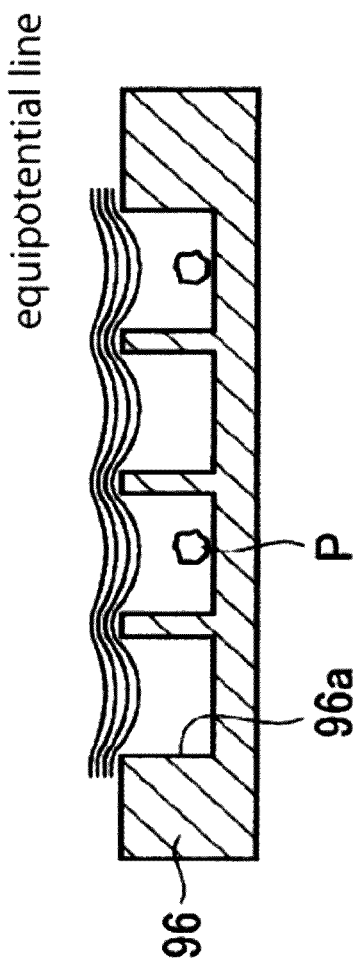
FIG. 124 is a diagram related to one embodiment of the present invention.

FIG. 123 is a perspective view which shows one example of a wall which forms a planar structure of the vacuum chamber shown in FIG. 106 for example or the vacuum chamber 12a shown in Fig, FIG. 122, and FIG. 124 is a cross section view of FIG. 123. As is shown in FIG. 123 and FIG. 124, for example, a wall which forms a planar structure in the vacuum chamber 12 or 12a (refer to FIG. 106 and FIG. 122 etc) is formed by a wall unit 96 arranged with a plurality of lattice shaped holes 96a on an inner surface. In this way, by arranging a plurality of lattice shaped holes 96a on an inner surface of the wall unit 96, foreign materials P such as particles which remain within the vacuum chamber are deposited on the bottom part of the holes 96a due to gravity. An electric field does not enter to the bottom of the lattice shaped holes 96a due to an static electric shield effect of the lattice shaped holes 96a and as a result, the foreign materials (residual materials) P which are deposited on the bottom part of the lattice shaped holes 96a do not receive a pulling force by static electricity and do not fly. In this way, it is possible to prevent foreign materials such as particles which remain within the vacuum chamber 12 or 12a from attaching to the surface of a sample 16 which is arranged within the vacuum chamber 12 or 12a.

Figure 125:
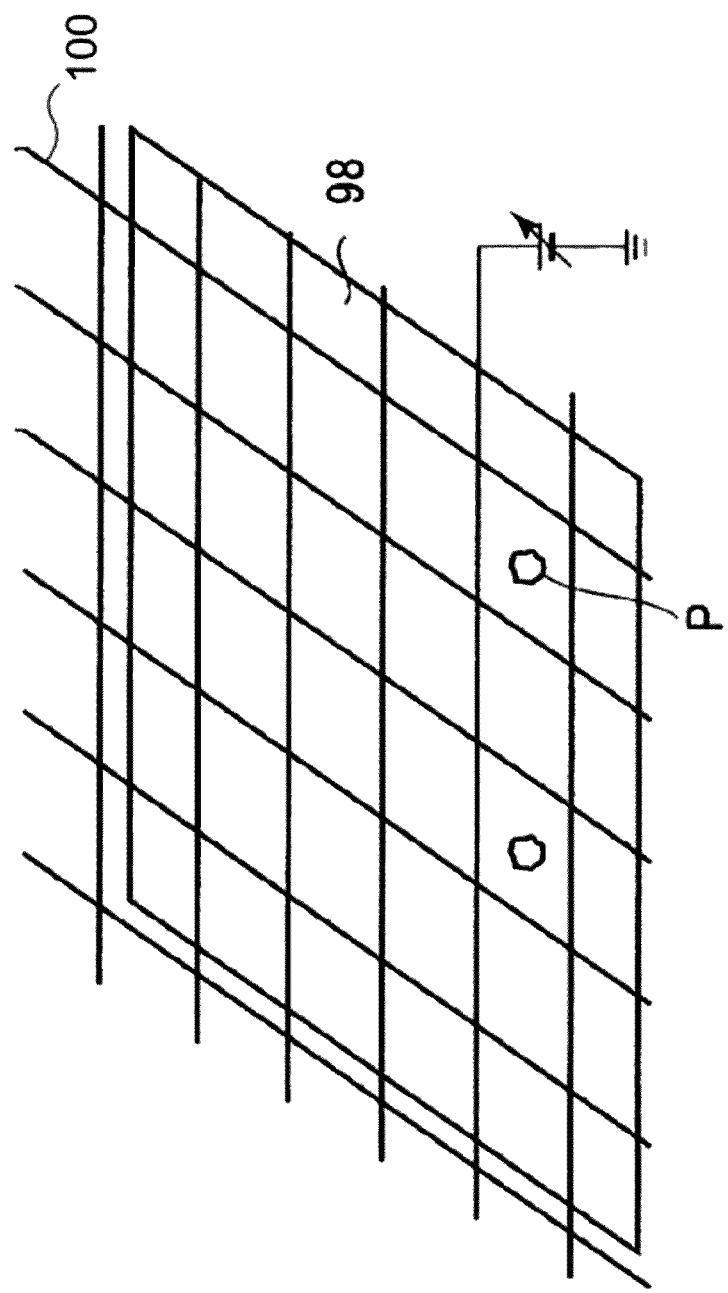
FIG. 125 is a diagram related to one embodiment of the present invention.
Figure 126:
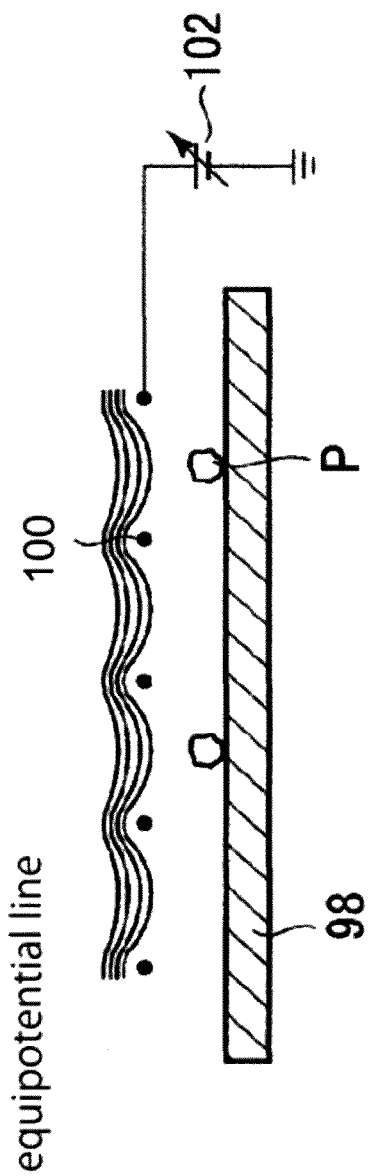
FIG. 126 is a diagram related to one embodiment of the present invention.

FIG. 125 is a perspective view which shows another example of a wall which forms a planar structure of the vacuum chamber 12 shown in FIG. 106, or vacuum chamber 12a shown in FIG. 122 for example, and FIG. 126 is a cross section view of FIG. 125. As is shown in FIG. 125 and FIG. 126, a wall which forms a planar structure of the vacuum chamber 12 or 12a (refer to FIG. 106 and FIG. 122 etc) is formed from a plate shaped wall unit 98 and a plate 100 having a mesh structure which is laid parallel to the wall unit 98 separated by a predetermined interval, and the mesh structured plate 100 is connected to an independent power source 102.

In this way, for example, foreign materials P such as particles which remain within the vacuum chamber 12 or 12a are made to pass through the mesh structure plate 100 by gravity and reach the surface of the wall unit 98. Because the wall unit 98 is covered by the mesh structure plate 100, an electric field is blocked by the mesh structure plate 100, and does not reach the surface of the wall unit 98. As a result, foreign materials (residual materials) P which reach the surface of the wall unit 98 do not receive a pulling force by static electricity and do not fly. In this way, it is possible to prevent foreign materials such as particles which remain within the vacuum chamber 12 or 12a from attaching to the surface of a sample 16 which is arranged within the vacuum chamber 12 or 12a.

In particular, by being able to independently apply a voltage to the mesh structured plate 100, foreign materials P such as particles which remain within a vacuum chamber are actively attracted to the mesh structured plate 100, become interdependent with the effects of gravity of the foreign materials P and it is possible to deposit the foreign materials P on the surface of the wall unit 98 which forms a planar structure of the vacuum chamber 12 or 12a.

The present invention is not limited to the embodiments of the present invention explained herein. Various modifications are possible with the scope of the technical idea of the invention. Furthermore, the present invention can also be applied to the embodiments 1~27 described above and to embodiments that are not attached with numbers.

(Twenty Eighth Embodiment)

Substrate mounting device which mounts a substrate on a tray and method of positioning the substrate with respect to the tray A substrate mounting device which mounts a substrate on a tray and a method of positioning the substrate with respect to the tray are explained in a method of the inspection device and inspection method of the present invention.

The substrate mounting device of the embodiment of the present invention is explained below using the diagrams.

In the present embodiment, a substrate is a mask for example used in a EUV exposure device. In addition, the substrate mounting device is for example, arranged with a substrate inspection device for a mask.

Figure 127:
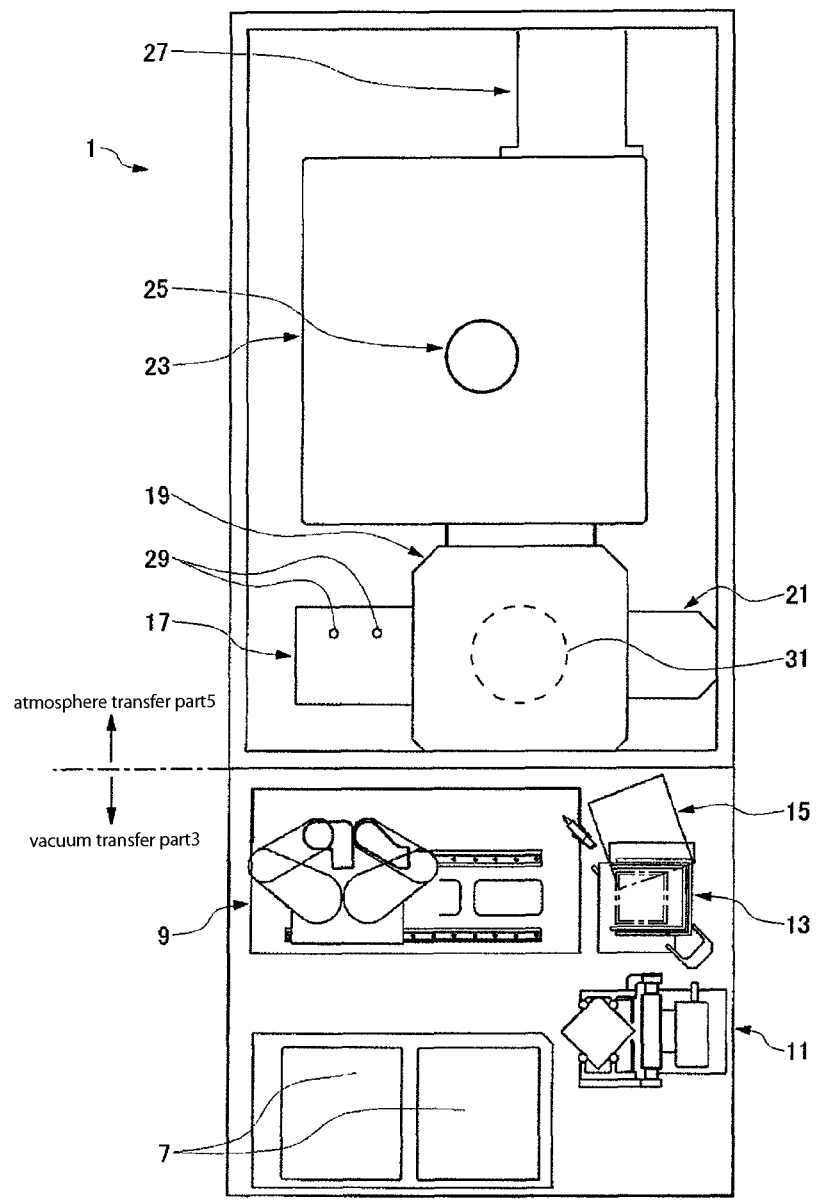
FIG. 127 is a diagram related to one embodiment of the present invention.
Figure 128:
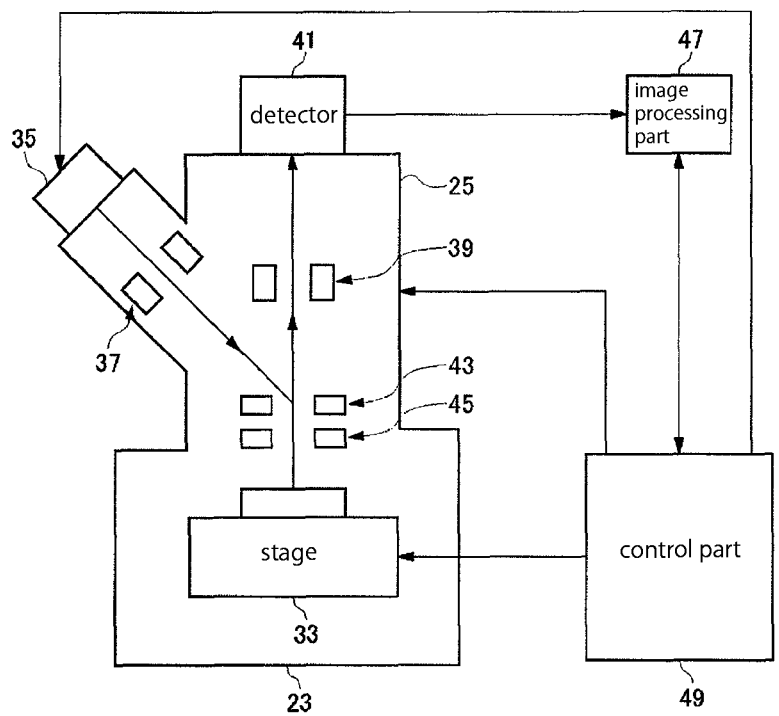
FIG. 128 is a diagram related to one embodiment of the present invention.

FIG. 127 and FIG. 128 show an inspection device arranged with the substrate mounting device. The concept of the inspection device is explained before explaining in detail the substrate mounting device.

FIG. 127 is a diagram seen from above the inspection device 1. As is shown in FIG. 127, the inspection device 1 is largely divided into an atmosphere transfer part 3 and vacuum transfer part 5. The atmosphere transfer part 3 handles a substrate within an atmosphere and the vacuum transfer part 5 handles a substrate within a vacuum. The atmosphere transfer part 3 and vacuum transfer part 5 are sectioned by an interval wall which can be opened and closed.

The atmosphere transfer part 3 is called a mini-environment chamber. A SMIF pod 7 is arranged adjacent to the atmosphere transfer part 3. In addition, an atmosphere transfer robot 9, substrate rotation invention unit 11, substrate mounting unit 13, neutralization unit 15 and fan filter unit (FFU) are arranged in the atmosphere transfer part 3.

The SMIFF pod 7 is a structure for supporting a substrate (mask) before or after an inspection. The atmosphere transfer robot 9 is a robot which transfers a substrate in an atmosphere. The substrate rotation inversion unit 11 receives a substrate from the atmosphere robot 9 and can rotate and invert the substrate. The substrate mounting unit 13 mounts a substrate onto a tray. The substrate mounting unit 13 is the substrate mounting device of the present embodiment. The neutralization unit 15 performs a neutralization process of a substrate before or after an inspection. The fan filter unit (FFU), although not shown in the diagram, is arranged on an upper part within the mini-environment chamber of the atmosphere transfer part 3. Specifically, the FFU forms the upper part of the atmosphere transfer robot 9, the substrate rotation inversion unit 11, substrate mounting unit 13 and neutralization unit 14 and is arranged or near the ceiling.

In addition, a load lock chuck 17, transfer chamber 19, first turbo pump 21, main chamber 23, inspection column 25 and second turbo pump 27 are arranged on the vacuum transfer part 5.

Two CCD cameras 29 are arranged in the load lock chamber 17. The CCD cameras 29 are used in positing of a substrate as described below. The transfer chamber 19 is a chamber for transferring a substrate to the main chamber 23 from the load lock chamber 17. The transfer chamber 19 is arranged with a vacuum transfer robot 31. The vacuum transfer robot 31 transfers a substrate within a vacuum. In addition, the first turbo pump 21 maintains the load lock chamber 17 and the transfer chamber 19 in vacuum state. The main chamber 23 and the inspection column 25 have a structure which irradiates a charged particle beam onto a substrate and inspects the substrate. The second turbo pump 27 maintains the main chamber 23 and the inspection column 25 in a vacuum state.

FIG. 128 is a diagram seen from a side direction of the main chamber 23 and the inspection column 25. The main chamber 23 is arranged with a stage 33. The stage 33 is mounted with a tray which supports a substrate. The stage 33 has a structure which moves the tray in a horizontal direction, that is, X, Y θ directions. The X, Y directions are along a mutually intersecting axis and the θ direction is an able around a rotation axis, that is, rotation movement is also performed.

The inspection column 25 is connected to the upper side of the main chamber 23. The inspection column 25 is arranged with an electron gun 35, primary lens system 37, secondary lens system 39 and detector 41. The electron gun 35 is a charged particle beam source. The electron gun 35 and the primary lens system 37 are electron beam irradiation systems and irradiate a substrate with an electron beam. The electron beam is deflected by a Wien filter 43, passes through an object lens system 45, and is irradiated to the substrate. When an electron beam is irradiated to a substrate, the substrate emits a signal having a substrate data. The signal is comprised of for example, secondary emission electrons (secondary electrons, reflected electrons, back scattered electrons) and mirror electrons. This signal passes through the object lens system 45, Wien filter 43, and secondary lens system 39, reaches the detector 41 and is detected by the detector 41.

The detector 41 is connected to an image processing part 47 and the detected signal is supplied to the image processing part 47. The image processing part 47 has a structure formed from a computer having an image processing function and processes a defect inspection. That is, the image processing part 47 forms an image of the sample from a signal detected by the detector 41, processes the image of the sample and performs detection and determination of a defect.

In addition, as is shown in FIG. 128, the inspection device 1 is arranged with a control part 49. The control part 49 is a computer which controls the entire inspection device 1 and carries out an inspection. The control part 49, as shown in the diagram, controls the main chamber 23, the inspection column 25 and the image processing part 47. In this way, the control part 49 moves a substrate (tray), irradiates an electron beam onto the substrate and produces an image of the substrate in the image processing part 47.

The control part 49 can control inspection conditions. Specifically, the control part 49 controls the beam energy, magnification and dose amount of an electron beam. Specifically, the beam energy is the landing energy when the electron beam is irradiated to a substrate.

In the present embodiment, the inspection device 1 is a projection type inspection device. In a projection type inspection device an electron beam includes a beam size (beam diameter) corresponding to a two dimensional pixel group, that is, includes a certain size. An irradiation region on a sample also includes an area corresponding to a two dimensional pixel group. A signal detected by a detector 41 also corresponds to a two dimensional pixel group. In addition, the detector 41 includes a detection capability corresponding to a two dimensional pixel group, for example, a CCD camera including a two dimensional detection surface.

A projection type inspection device is compare with a SEM type inspection device. In a SEM an electron beam narrowly corresponds to one pixel. In a SEM, the electron beam is scanned, a 1 pixel measurement is repeated, the measurement values are accumulated and a sample image is obtained. In a SEM type inspection device, an electron beam has a beam size of 1 pixel, however, in a projection type inspection device the electron beam has a beam size corresponding to a plurality of pixel groups. The projection type inspection device can inspect a fine particle. In addition, the projection type inspection device can also perform several types of inspection. For example, the projection type inspection device can also be used for inspection of foreign materials such as particles, and can also be used in a multilayer film defect inspection.

Returning to FIG. 127, the entire operation of the inspection device 1 is explained. The atmosphere transfer robot 9 extracts a substrate from the SMIF pod 7, and transfers it to the neutralization unit 15. The neutralization unit 15 neutralizes the substrate. In addition, the substrate is transferred to the substrate rotation inversion unit 11 from the atmosphere transfer robot 9, and rotation and inversion of the substrate is performed according to necessity. Furthermore, the atmosphere transfer robot 9 transfers the substrate to the substrate mounting unit 13. In the substrate mounting unit 13, the substrate is mounted onto a tray prepared in advance.

When a substrate is mounted on a tray, the atmosphere transfer robot 9 transfers the substrate to the load lock chamber 17 while supporting the tray. At this time, an interval wall between the atmosphere transfer part 3 and the vacuum transfer part 5 is opened. In the load lock chamber 17, a CCD camera 29 images a mark on the substrate. In this way, a mark location is detected. The vacuum transfer robot 31 transfers the tray from the load lock chamber 17 to the main chamber 23 and mounts the tray on the stage 33 of the main chamber 23. At this time, positing of the substrate is carried out based on the mark detection result.

The substrate is positioned by the substrate mounting unit 13 when mounting to the tray. Then, when mounting on the stage 33 as described above, the substrate is positioned based on the detection result of the CCD camera 29. The former positioning can be called "temporary positioning" and the later positioning can be called "actual positioning". In an actual substrate inspection process, further positioning may be performed using an optical microscope after actual positioning is performed. An optical microscope is arranged in the electron beam inspection device and the main chamber 23. The substrate and the tray are positioned using an optical image of the optical microscope, and from there the substrate is inspected using an electron beam. Here, for example, the substrate is positioned so that an electron beam is irradiated to a defect location detected by the optical microscope.

An inspection is performed using electron beam irradiation in the main chamber 23 as explained using FIG. 128. A substrate which has been inspected is transferred to the load lock chamber 17 from the main chamber 23 via the transfer chamber 19 by the vacuum transfer robot 31.

In addition, the atmosphere transfer robot 9 transfers the substrate to the substrate mounting unit 13 from the load lock chamber 17. The substrate is released from the tray in the substrate mounting unit 13. The substrate is transferred to the substrate rotation inversion unit 11, and rotated and inverted according to necessity. Then, the substrate is transferred to the neutralization unit 15 and neutralization is performed. In addition, the substrate is returned to the SMIFF pod 7 by the atmosphere transfer robot 9.

The entire structure and operation of the inspection device 1 is described above. The structure described above is a typical system structural example, and the operations described above are typical examples of an operation pattern. As a result, the inspection device part explained above may be replaced by an inspection device which utilizes light of a primary beam and photoelectrons of a secondary beam as in FIG. 9, and the structure and operations of the inspection device in the scope of the present invention are not limited to the examples described above.

(Substrate Mounting Device)

Next, a substrate mounting device of the present embodiment is explained in detail. The substrate mounting device is equivalent to the substrate mounting unit 13 of FIG. 127 already described and functions together with the atmosphere transfer robot 9 and mounts a substrate onto a tray. The substrate may be a mask for example and more specifically may be a glass mask having a square shape with each side being 6 inches and a thickness of 6.35 mm.

Figure 129:
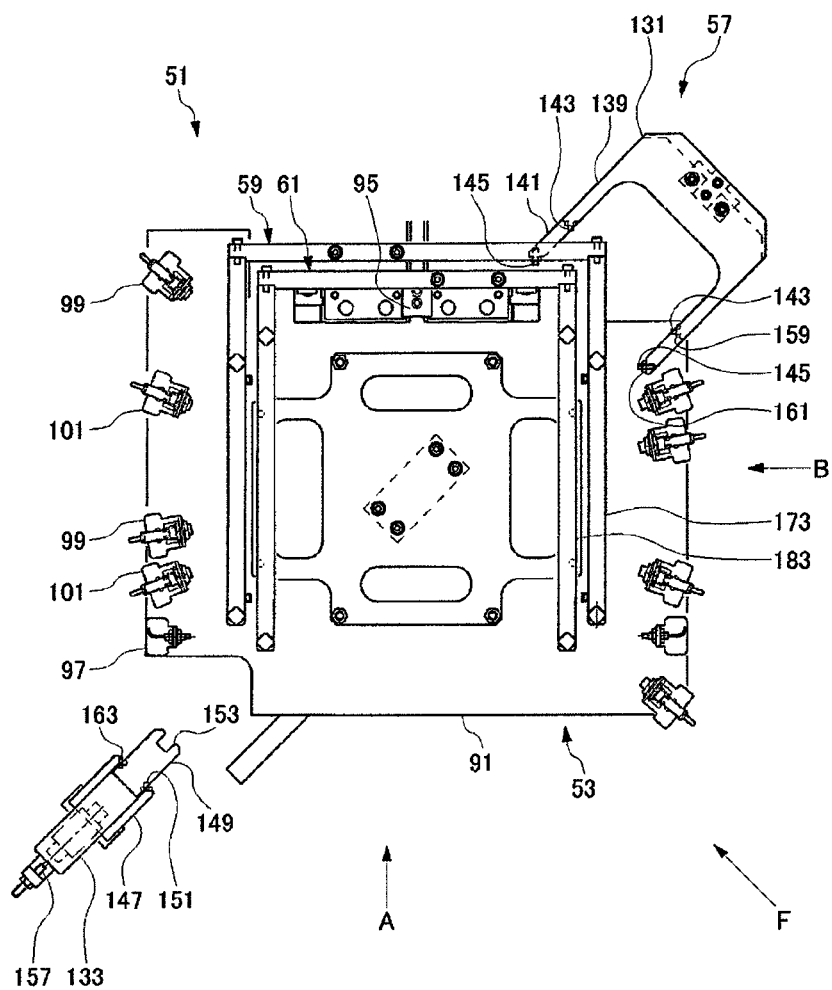
FIG. 129 is a diagram related to one embodiment of the present invention.
Figure 130:
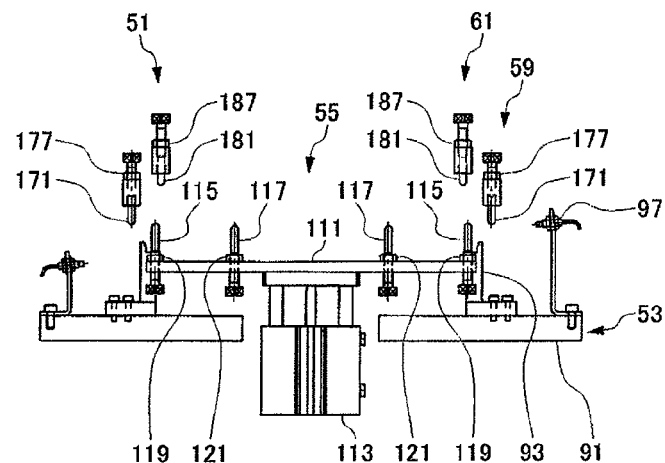
FIG. 130 is a diagram related to one embodiment of the present invention.
Figure 131:
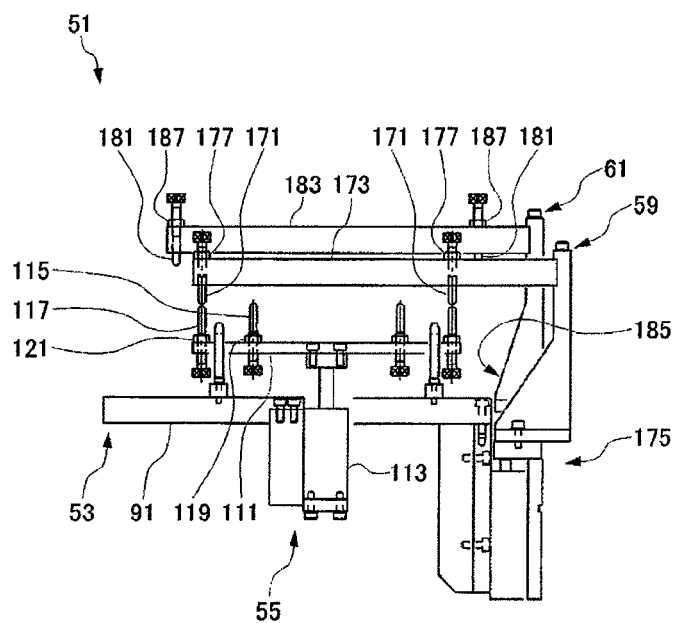
FIG. 131 is a diagram related to one embodiment of the present invention.
Figure 132:
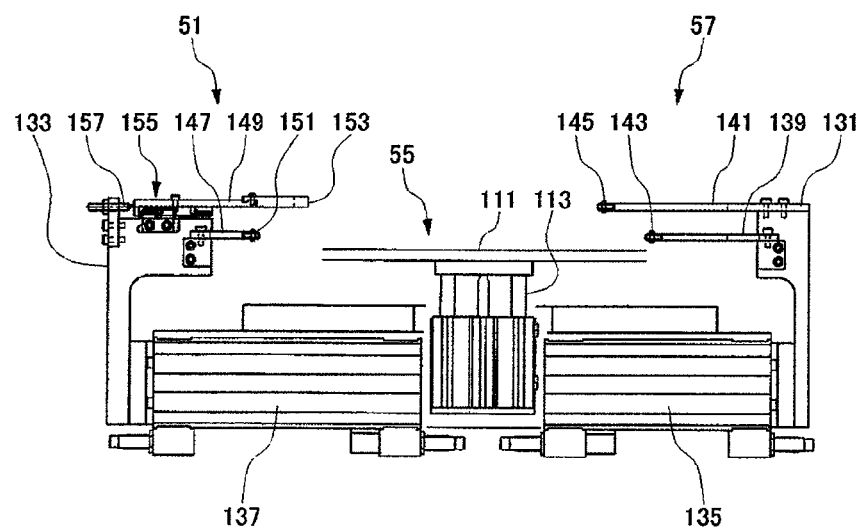
FIG. 132 is a diagram related to one embodiment of the present invention.
Figure 133:
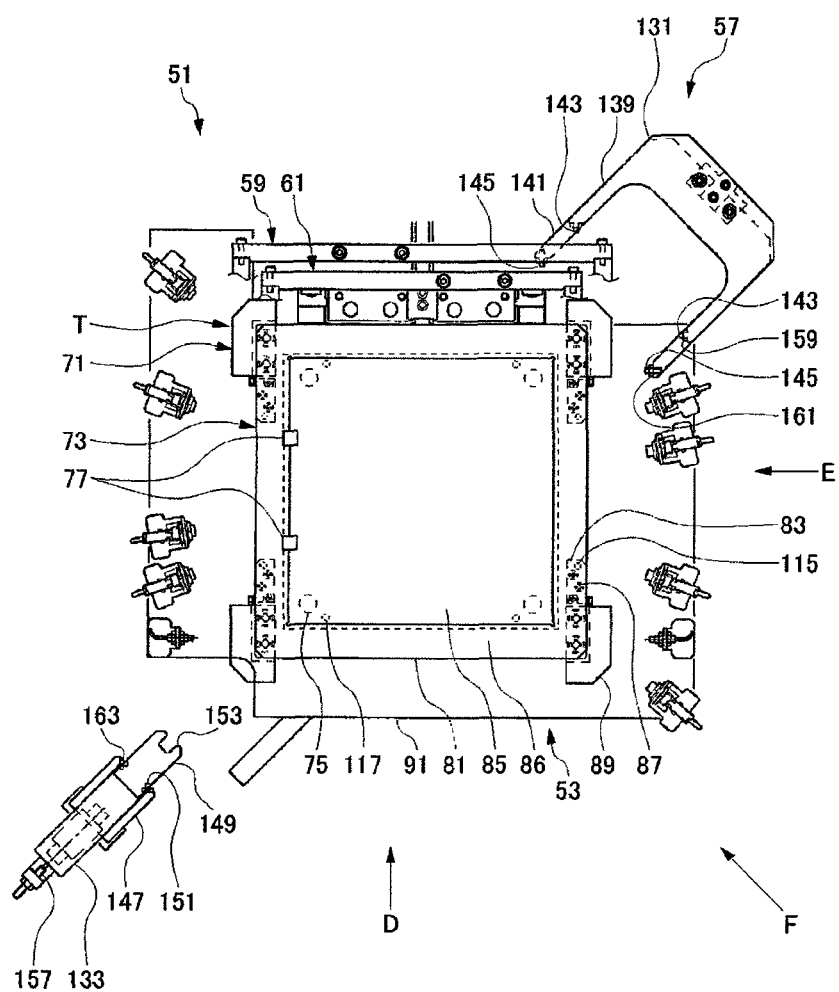
FIG. 133 is a diagram related to one embodiment of the present invention.
Figure 134:
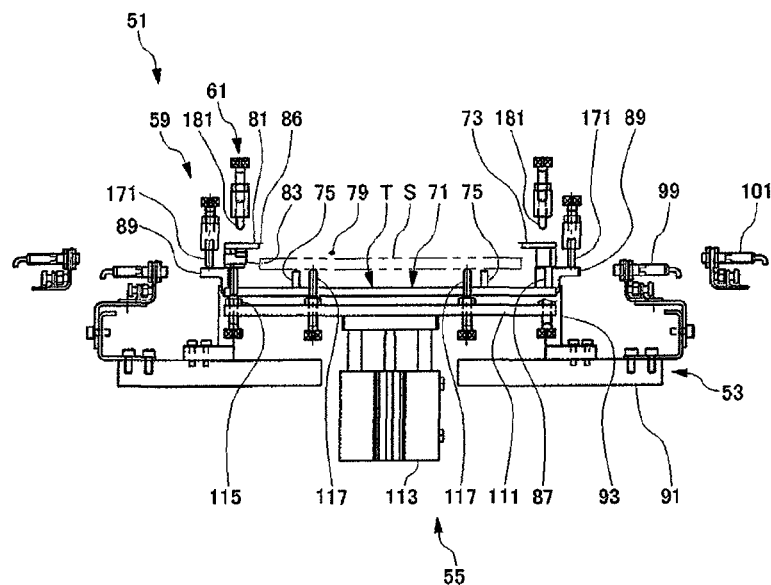
FIG. 134 is a diagram related to one embodiment of the present invention.
Figure 135:
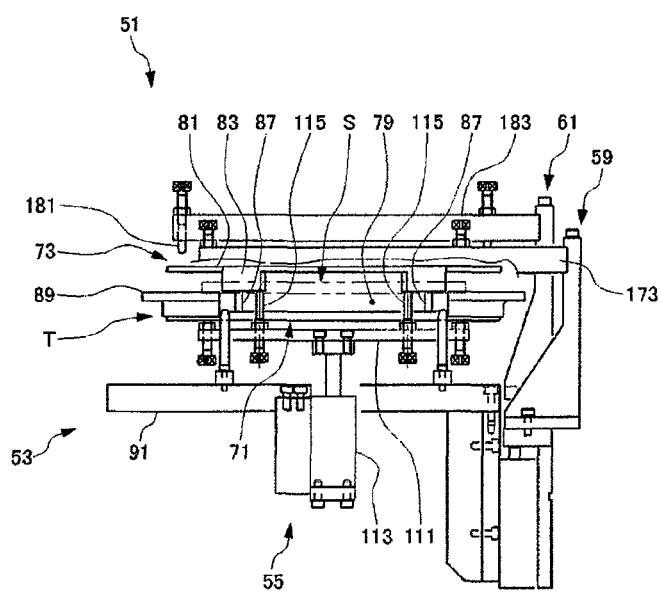
FIG. 135 is a diagram related to one embodiment of the present invention.
Figure 136:
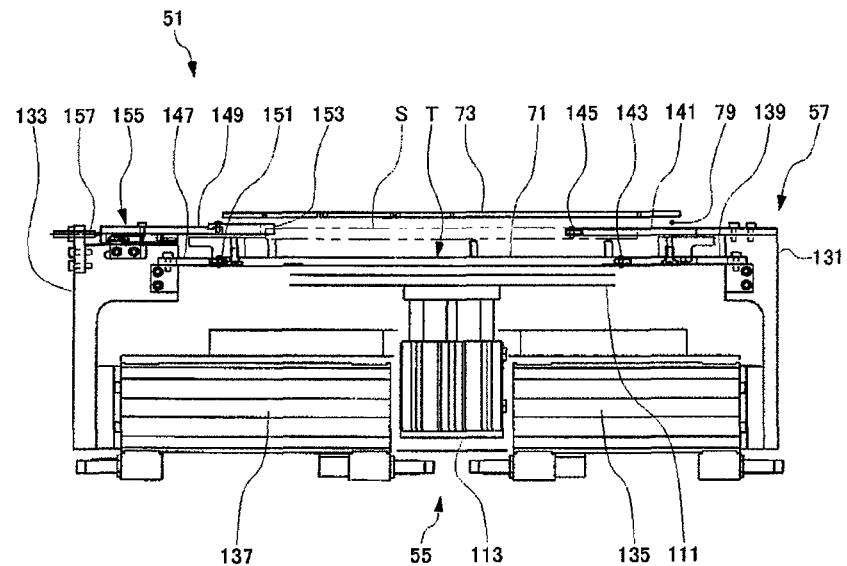
FIG. 136 is a diagram related to one embodiment of the present invention.
Figure 137:
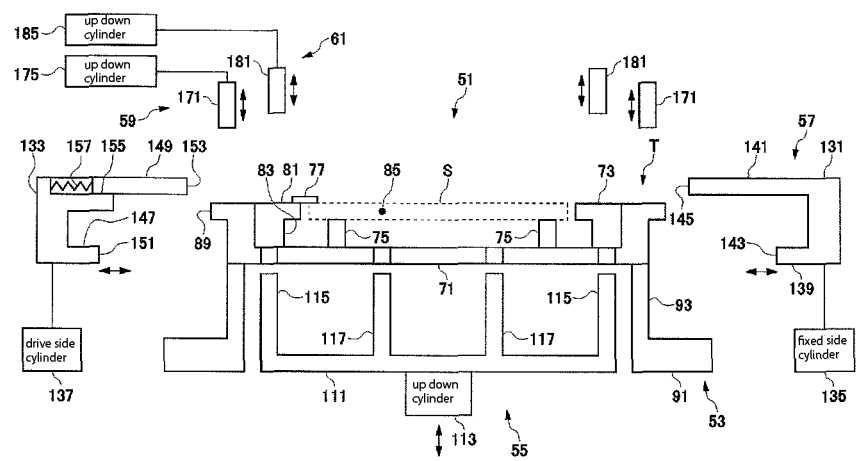
FIG. 137 is a diagram related to one embodiment of the present invention.
Figure 138:
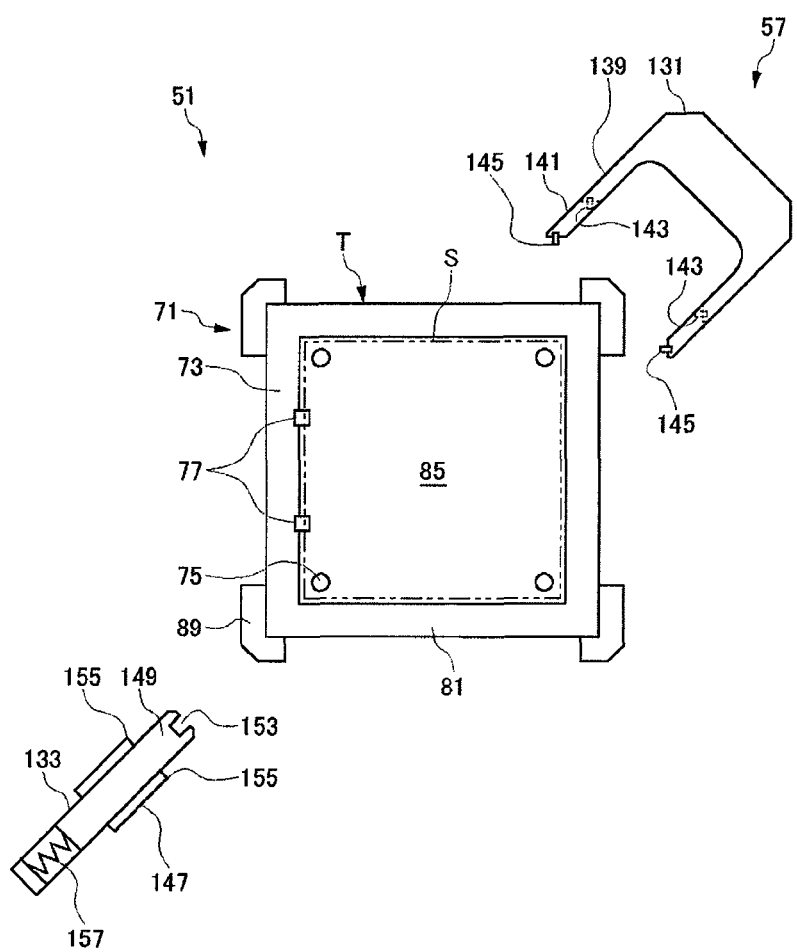
FIG. 138 is a diagram related to one embodiment of the present invention.

FIG. 129~FIG. 138 show the substrate mounting device of the present embodiment. FIG. 129~FIG. 132 shows the substrate mounting device 51 with no tray. FIG. 133~FIG. 136 shows the substrate mounting device 51 together with a tray. FIG. 129 is a planar view of the substrate mounting device 51, FIG. 130 is a diagram of the substrate mounting device 51 seen from the arrow A direction, FIG. 131 is a diagram of the substrate mounting device 51 in FIG. 129 seen from the arrow B direction, FIG. 132 is a diagram of the substrate mounting device 51 in FIG. 129 seen from the arrow C direction cut along diagonal lines of the tray T and substrate S. Similarly, FIG. 133 is a planar view of the substrate mounting device 51, FIG. 134 is a diagram of the substrate mounting device 51 in FIG. 133 seen from the arrow D direction, FIG. 135 is a diagram of the substrate mounting device 51 in FIG. 133 seen from the arrow E direction, FIG. 136 is a diagram of the substrate mounting device 51 in FIG. 133 seen from the arrow F direction cut along diagonal lines of the tray T and substrate S. In addition, FIG. 137 and FIG. 138 are abbreviated diagrams which exemplary show the substrate mounting device 51 for the purposes of explanation.

The substrate mounting device 51 is a device for mounting a substrate S on a tray T. The substrate mounting device 51 is broadly formed by a stage 53, a lift mechanism 55, a clamp mechanism 57, a tray support mechanism 59 and a frame dropping mechanism 61. Below, the structure is explained first and then each structure of the substrate mounting mechanism.

(Tray T)

The structure of the tray T is explained while referring to FIG. 133~FIG. 138. As is shown in FIG. 137 etc, the tray T is formed from a tray body 71 and a frame 73. The tray T for example is made from a ceramic.

The tray body 71 has a plate shape and has a roughly square shape with respect to the square shaped substrate S. A plurality of substrate mounting pins 75 protrude from the tray body 71 and the substrate S is supported by the substrate mounting pins 75. There are four substrate mounting pins 75. By adopting this structure, the substrate contacts with the substrate mounting pins at a small contact area and does not directly contact with the tray body 71 and is thereby maintained in a floating state. In addition, the substrate mounting pins 75 include a surface which makes it difficult for the substrate S to slide and thus misalignment of the substrate S during transfer is prevented.

The frame 73 is supported by the tray body 71 and encloses the substrate S. The frame 73 has a structure for providing a potential to the upper surface of the substrate S during an inspection, and this potential is provided via a terminal part 77. In addition, the frame 73 functions as a dummy by enclosing the substrate S. Bending of an equipotential surface at a part of the substrate S is reduced and it is possible to make the potential near the end part uniform, thereby the potential of the entire substrate which includes the end part can be made uniform and inspection accuracy can be improved. In addition, the frame 73 can be lifted vertically with respect to the tray body 71. As is shown in FIG. 137, when the frame is lowered, the frame surface and substrate surface are at the same height, and the frame 73 encloses the substrate S. As is shown in FIG. 134 and FIG. 135, when the frame 73 is raised, an insertion opening 70 is formed between the tray body 71 and the frame 73. The insertion opening 79 is a gap or aperture between the tray body 71 and the frame 73 and may also be called an insertion gap. The insertion opening 79 allows insertion or extraction of the substrate S and allows access for positioning the substrate S.

Next, the frame 73 is explained in more detail. The frame 73 includes a frame body 81 and a plurality of frame leg parts 83 which extend below the frame body 81.

As is shown in FIG. 133 and FIG. 138, the frame body 81 is a square shaped plate including a square shaped aperture 85. The material of the frame body 81 may be an insulator, for example a ceramic. The aperture 85 has a size corresponding to the substrate S. The substrate S is arranged within the aperture 85 and thereby the substrate S is enclosed by the frame 73. The frame body 71 and the substrate S do not have direct contact. An almost constant gap is formed between the entire frame body 81 and the substrate S.

Figure 143:
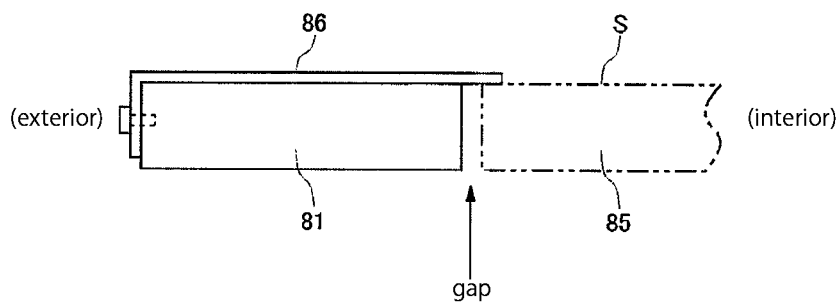
FIG. 143 is a diagram related to one embodiment of the present invention.

A frame cover 86 is arranged on the upper surface of the frame 73. Referring to FIG. 134, the width of the upper end of the frame 73 is a little wider than the frame body 81, and the upper end part of the frame 73 protrudes a little to the interior and the upper end part is equivalent to the frame cover 86. FIG. 143 exemplary shows the frame cover 86. As is shown in FIG. 143, the frame cover 86 is a thin plate. The frame cover 86 is bent downwards in an L shape at an exterior end part and is fixed by a screw etc to the side surface of the frame body 81 as shown in the diagram (the frame cover 86 may also be fixed to other places such as the upper surface of the frame body 81). The material of the frame cover 86 may be a conductor, for example, copper. The exterior periphery shape of the frame cover 86 is almost the same as the frame body 81. However, the aperture of the frame cover 86 is smaller than the aperture 85 of the frame body 81 and therefore, the frame cover 86 protrudes more to the interior than the frame body 81. When the substrate S is mounted, the interior periphery edge of the frame cover 86 overlaps the exterior periphery edge of the substrate S and makes contact. The aperture size of the frame cover 86 is fixed so that this overlapping is produced. Therefore, seen from above, the frame cover 86 covers a gap between the frame 73 (frame body 81) and the substrate S. By arranging this frame cover 86 it is possible to prevent bending of an equipotential surface on an edge part of the substrate S. The frame cover 86 is omitted from FIG. 137 and FIG. 138.

Two terminal parts 77 are arranged on the frame body 81. The terminal parts 77 protrude from the aperture 85. In addition, when the substrate S is mounted within the aperture 85, the terminal parts 77 contact the upper surface of the substrate S. As described above, the terminal parts 77 are used to provide a potential to the upper surface of the substrate S during a substrate inspection. In addition, the frame cover 86 described above covers a gap between the substrate S and frame 73 around the entire frame except the terminal parts 77.

There are four frame legs parts 83 which are each arranged near the corners of the frame boy 81. As is shown in FIG. 137, when lowered, the frame leg parts 83 are supported by the tray body 71 and the frame body 81 is located above the tray body 71. In addition, the upper surface of the frame is located at almost the same height as the upper surface of the substrate S on the substrate mounting pins 75 (as is shown in FIG. 143, specifically, the upper surface of the frame body 81 is located at the same height as the upper surface of the substrate. The upper surface of the frame cover 86 is located at almost the same height as the substrate upper surface. However, specifically, the cover is a little higher than the substrate surface by the thickness of the cover. The same is true below). When the frame 73 is raised, an insertion opening 79 is formed between the tray body 71 and the frame body 81 and insertion and extraction of and access to the substrate S is made possible.

In addition, as is shown in FIG. 134 and FIG. 135, a lift guide 87 is arranged in order to guide the lifting operation of the frame 73. The lift guide 87 is a guide rod which protrudes from the tray body 71. The lift guide 87 is inserted into a guide hole in the frame leg parts 83. In this way, the frame 73 can only be moved in a perpendicular direction with respect to the tray surface.

In addition, as is shown in FIG. 133 etc, the tray body 71 includes a plurality of protruding edge parts 89. In the present embodiment, four protruding edge parts 89 are each arranged at each corner of the tray body 71. The protruding edge parts 89 are the parts which protrude more to the exterior than the frame 73. Specifically, a wall part is arranged at each corner of the tray body 71 and the protruding edge parts 89 protrude to the exterior from the upper end of the wall parts. The protruding edge parts 89 are used for supporting the tray T by a transfer robot described below, and are used for supporting the tray body 71 when raising the frame 73.

(Stage)

A stage 53 is a structure for supporting a tray T. As is shown in FIG. 129 and FIG. 130, the stage 53 includes a stage base 91. A plurality of stage columns 93 are arranged on the stage base 91. In the present embodiment, four stage columns 93 are arranged in locations corresponding to the four corners of the tray T. In addition, the four corner of the tray body 71 are supported by the four stage columns 93. The tray T is movably supported in a horizontal direction and can be moved when positioning by a clamp mechanism 57 described below.

As is shown in FIG. 129 etc, a substrate presence detection sensor 95, tray presence detection sensor 97, and substrate tilted placement detection sensor 99 and tray diagonal placement detection sensor 101 are arranged on the stage 53. These sensors are attached to the stage base 91.

(Lift Mechanism)

A lift mechanism 55 moves the frame 73 and substrate S in a perpendicular direction with respect to the tray planar surface, and lifts and lowers the frame 73 and substrate S.

As is shown in FIG. 130, FIG. 134, FIG. 137 etc, the lift mechanism 55 includes a lift plate 111 which is plate shaped lift part. The lift plate 111 is driven by a lift cylinder 113 for the lift mechanism 55 and moves vertically within a predetermined range in a downwards direction from the tray T.

A plurality of frame support pins 115 and a plurality of substrate support pins 117 protrude upwards from the lift plate 111. The frame support pins 115 and substrate support pins 117 are almost the same height.

The frame support pins 115 are equivalent to a frame support part of the present invention and are arranged at a location corresponding to the lower surface of the frame 73, and move vertically together with the lift plate 111. In the present embodiment, four frame support pins 115 are arranged at a location corresponding to each of the four frame leg parts 83 of the frame 73. As is shown in FIG. 135, when the lift mechanism 55 rises, the frame support pins 115 pass through a hole in the tray body 71, contact with the lower surface of the frame leg parts 83, lift up the frame 83 and the insertion opening 79 is formed between the tray body 71 and the frame 73.

In addition, the substrate supports pins 117 are equivalent to a substrate support part of the present invention and are arranged at a location corresponding to the lower surface of the substrate S3 when positioning, and move vertically together with the lift plate 111. As is shown in FIG. 133, in the present embodiment, the four substrate support pins 117 are arranged slightly misaligned from the four substrate mounting pins 75 of the tray T. In addition, as is shown in FIG. 134 and FIG. 135, when the lift mechanism is raised, the substrate support pins 117 pass through a hole in tray body 71 the same as the frame support pins 115 and are raised. The tip end parts of the substrate support pins 117 reach a position slightly above the tip end parts of the substrate mounting pins 75 of the tray T. In this way, the substrate S is supported by the substrate support pins 117 before mounting on the substrate mounting pins 75.

Here, the location of the substrate S in a height direction when mounting on the substrate mounting pins 75 of the tray T is called a substrate mounting height. In addition, the location of the substrate S in a height direction when being supported by the substrate supporting pins 117 of the lift mechanism 55 described above is called a substrate support height. The substrate support height is above the substrate mounting height as described above.

Furthermore, the substrate support height is at a height corresponding to the insertion opening 79 described above. The substrate supporting pins 117 reach the substrate support height, the substrate S is supported at the substrate supporting height by the substrate supporting pins 117 before being mounted to the substrate mounting pins 75, and the substrate S is clamped as described below.

In addition, the substrate supporting pins 117 are formed from a material which is difficult to slide such as polychlorotrifluoroethylene (PCTFE, registered trademark). In this way, it is easy to position the substrate S.

In addition, as is shown in FIG. 130 etc, the lift mechanism includes a frame support height adjustment mechanism 119 for adjusting the height of the frame supporting pins 115 and a substrate support height adjustment mechanism 121 for adjusting the height of the substrate supporting pins 117. The frame support height adjustment mechanism 119 includes a screw structure. An external thread is arranged on the exterior periphery of the frame supporting pins 115, and the external thread joins with the internal thread of the lift plate 111 to enable adjustment of the pin height by rotating the frame support pins 115. The substrate support height adjustment mechanism 121 includes the same screw structure. With this structure the frame support height adjustment mechanism 119 and the substrate support height adjustment mechanism 121 can independently adjust the frame support pins 115 and the substrate supporting pins 117.

(Clamp Mechanism)

The clamp mechanism 57 is a structure for positioning the substrate S with respect to the tray T. In the present embodiment the clamp mechanism 57 moves in a direction parallel to the tray planar surface and clamps both the substrate S and tray T in one clamp operation. The clamp mechanism 57 is described in more detail below.

As is shown in FIG. 133, 136, 137 and FIG. 138 etc, the clamp mechanism 57 is formed by a plurality of clamp bodies. In the example of the present embodiment, two clamp bodies, fixing side clamp body 131 and driven side clamp body 133 are provided. The fixing side clamp body 131 and driven side clamp body 133 are arranged facing each other along diagonal lines of the substrate S and tray T.

The fixing side clamp body 131 and driven side clamp body 133 are each linked respectively to a fixing side cylinder 135 and driven side cylinder 137. The fixing side clamp body 131 is driven in a straight line by the fixing side cylinder 135 and the driven side clamp body 133 is driven in a straight line by the driven side cylinder 137. In this way, the clamp mechanism 75 is opened and closed. The fixing side cylinder 135 and driven side cylinder 137 are equivalent to clamp movement mechanisms in the present invention.

The fixing side clamp body 131 includes two fixing side tray clamp arms 139 and two substrate clamp arms 141. The tray clamp arms 139 and substrate clamp arms 141 extend towards the tray T. The height of the tray clamp arms 139 corresponds to the height of the tray body 71 and the height of the substrate clamp arms 141 corresponds to the substrate support height when supported by the substrate support pins 117 of the lift mechanism 55, and therefore, the substrate clamp arms 141 move vertically higher than the tray clamp arms 139.

The two ray clamp arms 139 are separated in a horizontal direction as shown in the diagram and each tray clamp arm 139 includes a tray clamp part 143 near a tip end part. The tray clamp part 143 is formed by a support pin and contacts with the tray T when clamping for positioning. The movement direction of the clamp mechanism 57 is along the diagonal line of the tray T, therefore, diagonally with respect to a contact surface. Thus, a pin of the tray clamp part 143 protrudes diagonally towards a tray diagonal line from the tray clamp arm 139.

The substrate clamp arm 141 includes the same structure as the tray clamp arm 139, that is, the two substrate clamp arm 141 are separated in a horizontal direction and each substrate clamp arm 141 includes a substrate clamp part 145 near a tip end part. The substrate clamp part 145 is formed by a support pin and contacts with the tray T when clamping for positioning. The movement direction of the clamp mechanism 57 is along the diagonal line of the substrate S, therefore, diagonally with respect to a contact surface. Thus, a pin of the substrate clamp part 145 protrudes diagonally towards a substrate diagonal line from the substrate clamp arm 141.

In addition, the exterior shape of the substrate S is smaller than the tray T. As a result, as is shown in FIG. 132, the substrate clamp arm 141 protrudes considerably further than the tray clamp arm 139.

Next, the driven side clamp body 133 is explained. The driven side clamp body 133 has a narrower shape compared to the fixing side clamp body 131.

The driven side clamp body 133 includes a tray clamp arm 147 and substrate clamp arm 149 which protrude towards the tray T the same as the fixing side clamp body 131, the height of the tray clamp arm 147 corresponds to the height of the tray body 71 and the height of the substrate clamp arm 149 corresponds to the height of the substrate S when supported by the substrate supporting pins 117 of the lift mechanism 55. There are two tray clamp arms 147 the same as the fixing side. However, unlike the fixing side there is only one substrate clamp arm 149.

The two tray clamp arms 147 have the same structure as the fixing side apart from having a narrower arm interval and shorter arm length. That is, the two tray clamp arms 147 are separated in a horizontal direction and each tray clamp arm 147 includes a tray clamp part 151 in near a tip end. The tray clamp part 151 has a support pin structure and contacts the tray T when clamping. The pin of the tray clamp part 151 protrudes diagonally towards the diagonal line of the tray.

There is one substrate clamp arm 149 as stated above. A substrate clamp part 153 is arranged at the arm end tip. The substrate clamp part 153 is a hollow part formed by cutting out the arm tip part. The substrate clamp part 153 contacts with two spots on end surface of the substrate S at an edge part of both side of the hollow part when clamping.

In the present embodiment, the tray clamp arm 147 and the substrate clamp arm 149 are arranged so that the substrate clamp part 153 contacts the substrate S before the driven side tray clamp part 151 contacts the tray T. In addition, as is shown in FIG. 132, the substrate clamp arm 149 is arranged above a direct movement guide 155, and can move in a straight line along the clamp movement direction. In addition, a spring pusher 157 is arranged to the rear of the substrate clamp arm 149. The spring pusher 157 is equivalent to a bias part in the present invention. The substrate clamp arm 149 and substrate clamp part 153 are flexibly biased towards the substrate S by the spring pusher 157. In addition, when the substrate clamp part 153 is pushed by the substrate S by the rebound force of the clamp of the substrate S, the substrate clamp part 153 continues to be flexibly biased towards the substrate S and can be retracted above the driven side clamp body 133. The function of the flexible structure described above is explained below.

In addition, a tray clamp location adjustment mechanism 159 and substrate clamp location adjustment mechanism 161 are arranged on the fixing side clamp body 131 in the clamp mechanism 57.

The tray clamp location adjustment mechanism 159 is arranged on each tray clamp part 143 and has a structure for adjusting the amount of protrusion of the tray clamp 143 towards the tray T. The tray clamp location adjustment mechanism 159 includes a screw structure. An external thread is arranged on the exterior periphery of a support pin of the tray clamp part 143, and the external thread joins with the internal thread of the tray clamp arm 139 to enable adjustment of the pin height by rotating the support pin. The substrate clamp location adjustment mechanism 161 is arranged on each substrate clamp part 145 and has a structure for adjusting the amount of protrusion of the substrate clamp 145 towards the substrate S. The tray clamp location adjustment mechanism 159 and the substrate clamp location adjustment mechanism 161 both include the same screw structure. With this structure the amount of protrusion of the tray clamp body 143 and the substrate clamp part 145 of the fixing side clamp body 131 can independently be adjusted.

In addition, the driven side clamp body 133 also includes a tray clamp location adjustment mechanism 163 the same as the fixing side clamp body 131. The tray clamp location adjustment mechanism 163 is arranged on each tray clamp part 151 and has the same screw structure as the fixing side.

In addition, in the examples of the present embodiment, the tray T is clamped at four locations, and the substrate is also clamped at four locations. However, the number of clamp locations is not limited to four. The required minimum number of clamp locations is different according to the shape of the tray and substrate. For example, in the case where the substrate is round, the substrate may be clamped at 3 locations.

(Tray Support Mechanism)

As is shown in FIG. 130, 131, 134 and FIG. 137 etc, the tray support mechanism 59 is a drive mechanism in a perpendicular direction with respect to the tray planar surface. The tray support mechanism 59 includes a plurality of tray support pins 171 which move down toward the tray body 71 and contact with the tray body 71. The tray support pins 171 are equivalent to tray support parts in the present invention. As is shown in FIG. 131, the tray support pins 171 are attached to a pin attachment arm 173, links with a lift cylinder 175 for the tray support mechanism 59 and the tray support pins 171 are moved vertically by the lift cylinder 175.

The tray support mechanism 59 has a function for preventing the tray body 71 from rising when raising the frame 73.

That is, the tray support mechanism 59 lowers the tray support pins 171 when the lift mechanism 55 raises the frame 73 and the tray support pins 171 contacts with the tray body 71 thereby the tray body 71 is restrained and prevented from being raised.

In the present embodiment, there are four tray support pins 171. The four tray support pins 171 are each arranged to correspond with the protrusion edge part 89 of the four corners of the tray body 71, and contact and press the protrusion edge parts 89 when lowering. In this way, the upper surface of the protrusion edge parts 89 function as contact parts of the tray support pins 171. Furthermore, the lower surface of the protrusion edge parts 89 function as support surfaces for the robot when transferring the tray.

In addition, as is shown in FIG. 131, the tray support mechanism 59 includes a height adjustment mechanism 177 for adjusting the height of the tray support pins 171. The height adjustment mechanism 177 has the same adjustment structure and screw structure as the lift mechanism 55. That is, an external thread is arranged on the exterior periphery of the tray support pins 171, and the external thread joins with the internal thread of the pin attachment arm 173 to enable adjustment of the pin height by rotating the tray support pins 171.

(Frame prop Mechanism)

As is shown in FIG. 130, 131, 134 and FIG. 137, the frame drop mechanism 61 is a drive mechanism in a perpendicular direction with respect to the tray planar surface. The frame drop mechanism 61 includes a plurality of frame drop pins 181 which move down toward the frame 73 and press the frame 73. The frame drop pins 181 are equivalent to frame drop parts in the present invention. As is shown in FIG. 131, the frame drop pins 181 are attached to a pin attachment arm 183, links with a lift cylinder 185 for the frame drop mechanism 61 and the frame drop pins 181 are moved vertically by the lift cylinder 185.

In the present embodiment, there are four frame drop pins 181 and each are arranged above the frame 73. The frame drop mechanism 61 lowers the frame drop pins 181 when releasing the frame lift after positioning is compete by the clamp mechanism 57, presses the frame 73 and the frame 73 is made to lands securely on the tray body 71. The landing of the frame 73 may be detected and in this way a certain lowering operation can be guaranteed.

In addition, as shown in FIG. 131, the frame drop mechanism 61 includes a height adjustment mechanism 187 for adjusting the height of the frame drop 181. The height adjustment mechanism 187 has the same adjustment structure and screw structure as the lift mechanism 55. That is, an external thread is arranged on the exterior periphery of the frame drop pins 181, and the external thread joins with the internal thread of the pin attachment arm 183 to enable adjustment of the pin height by rotating the frame drop pins 181.

The structure of each part in the substrate mounting device 51 related to the present embodiment was explained above. Next, the operations of the substrate mounting device 51 are explained.

Figure 139:
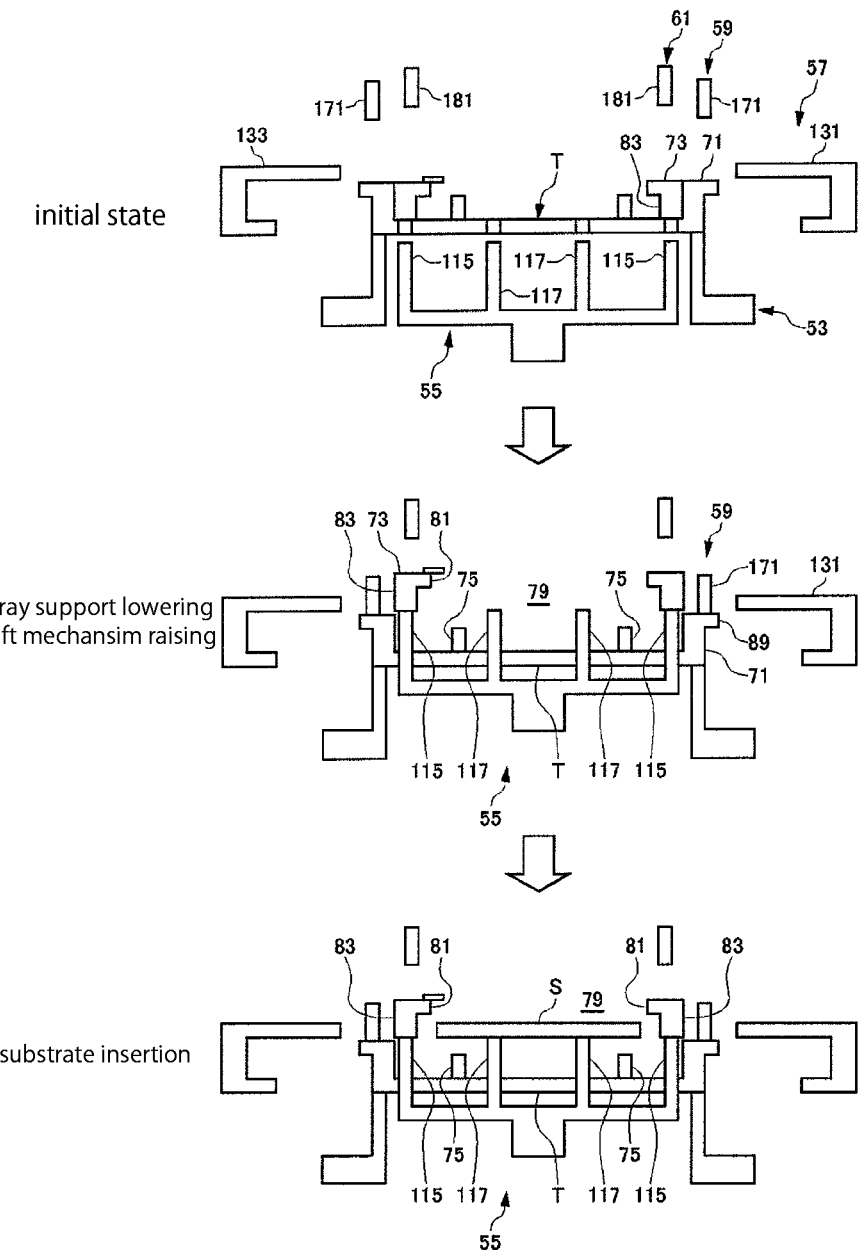
FIG. 139 is a diagram related to one embodiment of the present invention.
Figure 140:
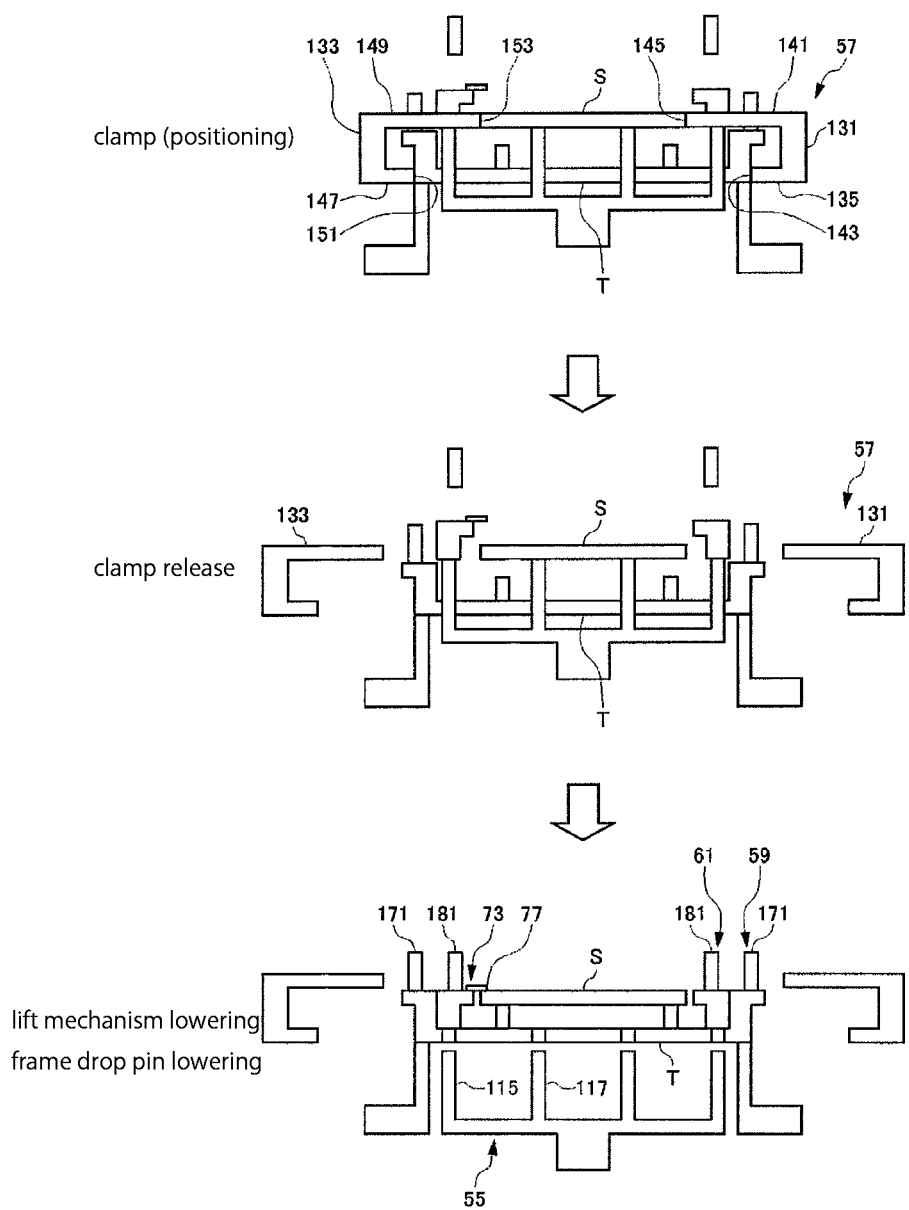
FIG. 140 is a diagram related to one embodiment of the present invention.

FIG. 139 and FIG. 140 exemplary show an outline of the substrate mounting device 51. As is shown in FIG. 139, the tray T is already arranged on the stage 53 before the substrate S is mounted. The frame 73 is lowered and the tray body 71 is supported by the frame leg parts 83.

The lift mechanism 55 is lowered and the frame support pins 115 and substrate support pins 117 are located at a lower position. The clamp mechanism 57 is open, the fixing side clamp part 131 and the driven side clamp part 133 are retracted to a predetermined waiting position. Furthermore, the tray support mechanism 59 and the drop mechanism 61 are raised and the tray support pins 171 and the frame drop pins 181 are located above the tray T.

When a mounting operation begins, first, the tray support mechanism 59 lowers the tray support pins 171. The tray support pins 171 contact with the protrusion edge part 89 of the tray body 71 and the tray body 71 is pressed.

Then, the lift mechanism 55 raises the frame support pins 115 and the substrate support pins 117. The frame support pins 115 pass through the hole in the tray body 71, contact with the lower surface of the frame leg parts 83, and the frame 73 is raised. At this time, the frame 73 is guided by the direct movement lift guide 87 (FIG. 135) arranged on the frame leg parts 83 and is raised in a vertical direction.

In addition, the substrate support pins 117 also pass through the hole of the tray body 71 and are raised the same as the frame support pins 115. The tip ends of the substrate support pins 117 reach a slightly higher position than the substrate mounting pins 75 of the tray T.

The frame support pins 115 raise the frame 73 and thereby the insertion opening 79 is formed between the tray body 71 and the frame body 81. The substrate S is inserted from the insertion opening 79 by a robot which is a substrate transfer part (substrate transfer means), and set on the substrate support pins 117 having a substrate support height. The substrate S is inserted from the arrow D direction in FIG. 133. Because the substrate support pins 117 protrude further than the substrate mounting pins 75 of the tray T, the substrate S is supported not by the substrate mounting pins 75 but by the substrate support pins 117. The robot described above is the atmosphere transfer robot 9 in FIG. 127. For example, the transfer robot includes a fork shaped arm which supports the lower surface of the substrate S at the arm end part and the substrate is inserted by extending the arm.

Here, in the present embodiment the height of the end tip of the frame support pins 115 and the height of the end tip of the substrate support pins 117 is almost the same. However, the lower surface of the frame leg parts 83 is located lower than the lower surface of the substrate S. The frame support pins 115 contact the lower surface of the frame leg parts 83 quicker than when the substrate support pins 117 contact with the lower surface of the substrate S. In addition, the lift mechanism 55 can raise the frame 73 by height amount of the frame leg parts 83. As a result, the frame body 81 reaches a higher position than the substrate support height of the end tip of the substrate support pins 117 and it is possible to form a sufficiently large insertion opening 79.

Next, as is shown in FIG. 140, the clamp mechanism 57 positions the substrate S with respect to the tray T. In the present embodiment, the clamp mechanism 57 accurately positions the substrate S by clamping the tray T and substrate S in one operation.

Figure 141:
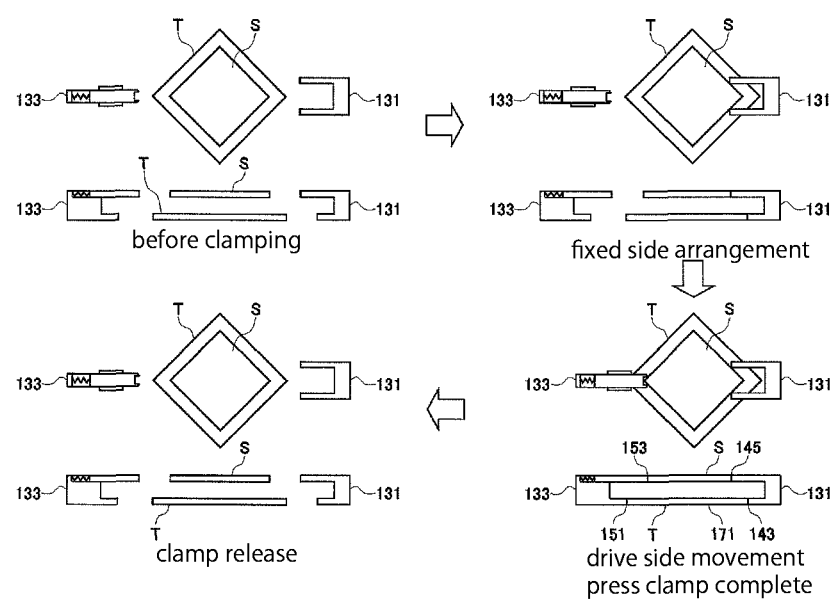
FIG. 141 is a diagram related to one embodiment of the present invention.

FIG. 141 is a diagram which explained the operations of a clamp. As is shown in the diagram, before the clamp is initiated, the fixing side clamp body 131 and the driven side clamp body 133 are separated from the tray T and substrate S. When the clamp is initiated (when positioning begins), first, the fixing side clamp body 131 is driven by the fixing side cylinder 135 (FIG. 136), moved up to a predetermined fixing side clamp location and stopped.

Next, the driven side clamp body 133 is driven by the driven side cylinder 137, contacts with the end part of the tray T and the end part of the substrate S and the tray T and substrate S are pressed towards the fixing side clamp body 131. The driven side tray clamp part 151 presses the tray body 71 towards the fixing side tray clamp part 143, and the driven side substrate clamp part 153 presses the substrate S towards the fixing side substrate clamp part 145.

In this way, the tray body 71 and the substrate S are clamped by one clamp operation. The tray body 71 and the substrate S are positioned at a location which contacts with the fixing side clamp body 131. In this way, the relative location relationship between the substrate S and the tray T is determined, and therefore, the substrate S is positioned with respect to the tray T.

When clamping is complete, the driven side clamp body 133 is retracted and the substrate S and tray T are separated, then, the fixing side clamp body 131 is retracted and the substrate S and tray T are separated and thereby the clamp is released.

According to the present embodiment, the tray T and substrate S are simultaneously positioned using a single clamping operation. The fixing side clamp body 131 includes a structure whereby the tray clamp part 143 and the substrate clamp part 145 are arranged as a single unit, and their locational relationship is fixed. The tray T and substrate S are pressed to this fixing side clamp body 131. As a result, the locations of the tray T and substrate S and the location of the substrate S with respect to the tray T are determined corresponding to the locational relationship between the tray clamp part 143 and the substrate clamp part 145. Therefore, a high positioning accuracy can be obtained.

In addition, in the present embodiment, the fixing side clamp body 131 advances forward as described above followed by the driven side clamp body 133. By providing the clamp mechanism 57 with this type of structure it is possible to obtain the merit whereby the amount of tray movement can be reduced.

In addition, in the clamp operation, the fixing side cylinder 135 and the driven side cylinder 137 are controlled so that the clamp force of the driven side clamp is less than the clamp force of the fixing side clamp. The fixing side clamp force is the force when the fixing side cylinder 135 fixes the fixing side clamp body 131, and the driven side clamp force is the force when the driven side cylinder 137 moves the driven side clamp body 133. By adopting such clamp force settings, it is possible to prevent misalignment of the fixing side clamp body 131 and obtained high positioning accuracy.

In addition, in the present embodiment, as already explained, the substrate support pins 117 protrude above the substrate mounting pins 75 of the tray T. Therefore, as is shown in FIG. 140, when positioning, the substrate S is supported not by the substrate mounting pins 75 but by the substrate support pins 117. The substrate mounting pins 75 include a difficult to slide surface considering a later stage transfer, while the substrate support pins 117 include a surface on which it is easy to slide. Therefore, the substrate S is places in a state whereby it easy to move in a horizontal direction. In this way, it is possible to prevent damage to the substrate S when positioning. In addition, because the substrate S securely moved to an appropriate location it is possible to improve positioning accuracy.

In addition, as stated previously, in the present embodiment, the driven side clamp body 133 includes the substrate clamp arm 149 above a direct movement guide 155, and a spring type pusher 157 is arranged on the rear side of the substrate clamp arm 149. This structure functions as described below when clamping.

Figure 142:
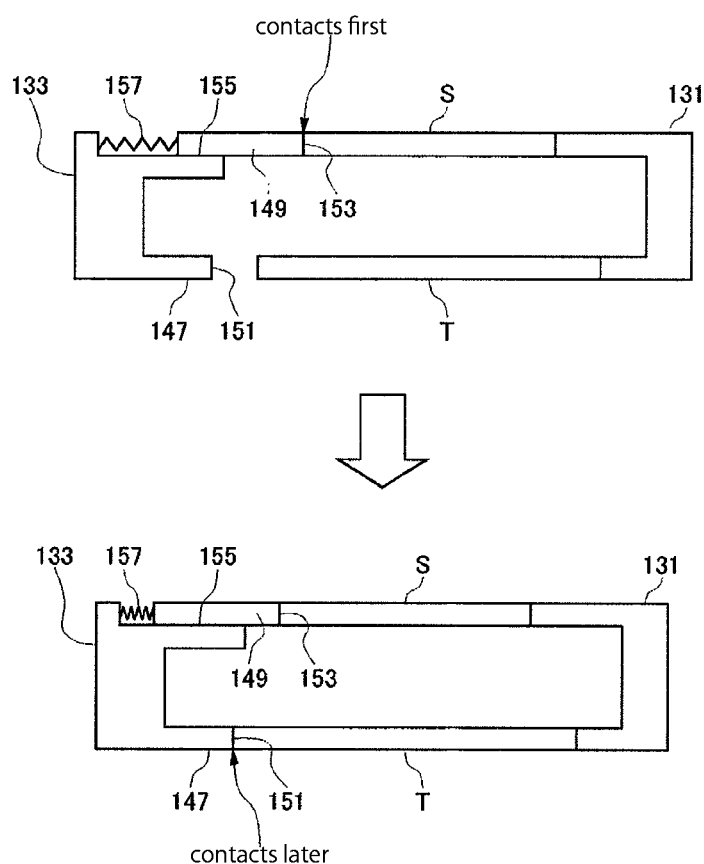
FIG. 142 is a diagram related to one embodiment of the present invention.

Referring to FIG. 142, in the present embodiment, the tray clamp arm 147 and the substrate clamp arm 149 are arranged so that the substrate clamp part 153 contacts the substrate S before the driven side tray clamp part 151 contacts the tray T.

Therefore, when the driven side clamp body 133 moves, first the substrate clamp part 153 contacts and presses the substrate S. The opposite side of the substrate S contacts the fixing side clamp body 131, the spring type pusher 157 contracts due to the rebound force from the substrate S and the substrate clamp arm 149 is retracted on the direct movement guide 155. At this point, the substrate S is clamped by the spring force of the spring type pusher 157. Then, the tray clamp part 151 contacts and presses the tray T. In addition, the substrate S and the tray T are both clamped and positioned.

Here, the case where the direct movement guide 155 and the spring type pusher 157 are not arranged is explained temporarily. In this case, either the tray clamp part 151 or the substrate clamp part 153 can not contact the object due to a dimension error and as a result, positioning accuracy decreases. In the present embodiment, using the above described structure, the tray clamp part 151 and the substrate clamp part 153 securely contact the tray T and substrate S and positioning accuracy can be improved.

In addition, in the present embodiment, a flexible structure is applied not to the tray T but to the substrate S. The substrate S is lighter than the tray T and furthermore, the substrate S is supported by the substrate support pins 117 of the lift mechanism 55 when positioning. Therefore, the substrate S can move easily and even in the case when the substrate is pressed via a spring etc, it is possible to move the substrate for positioning more securely. In this way, positioning accuracy can be further improved.

Returning to FIG. 140, when positioning is complete, after a clamp is released, the lift mechanism 55 is lowered and the frame support pins 115 and the substrate support pins 117 are lowered. The frame 73 is lowered, the frame leg parts 83 are supported by the tray body 71 and the frame 73 returns to its original location. In addition, the substrate S is lowered and supported by the substrate mounting pins 75. The upper surface of the substrate S and the upper surface of the frame 73 become the same height (as described above, specifically, the upper surface of the frame body 81 is located at the same height as the substrate upper surface, and the upper surface of the frame cover 86 is located slightly higher than the substrate upper surface). The terminal part 77 of the frame 73 contacts the upper surface of the substrate S. In addition, the frame cover 86 covers the gap between the frame 73 and the substrate S across the entire periphery of the substrate S (except the two terminal parts 77).

When the lift mechanism 55 is lowered, the frame drop mechanism 61 lowers the frame drop pins 181. The frame drop pins 181 contact and press the upper surface of the frame 73. In this way, the frame drop mechanism 61 supports the lowering of the frame 73. The frame 73 receives the effects of the frame drop pins 181 in addition to its own weight and can be lowered securely to its original location.

Next, the frame drop mechanism 61 raises the frame drop pins 181 and the tray support mechanism 59 raises the tray support pins 171. In this way, a series of mounting operations is complete. When the mounting operation is complete, a robot transfers the tray on which the substrate S is mounted. The robot includes an arm and the arm supports the lower surface of the protrusion edge parts 89 of the tray body 71. The robot is the atmosphere transfer robot 9 in FIG. 127 as stated above and transfers the tray T to the load lock chamber 17.

An operation for mounting while positioning a substrate S on a tray T was explained above. Next, an operation for removing a substrate S from a tray T is explained.

In the present embodiment, the substrate mounting device 51 is arranged in an inspection device. When an inspection is complete, a tray T is transferred by a robot, and placed on a stage 53 of the substrate mounting device 51. At this time, the substrate mounting device 51 is in the same state as the when mounting is complete described above. That is, in the substrate mounting device 51, the lift mechanism 55 is lowered and the frame support pins 115 and the substrate support pins 117 are located in a lower position. The clamp mechanism 57 is open, and the fixing side clamp body 131 and the driven side clamp body 133 are retracted to a predetermined waiting location. In addition, the tray support mechanism 59 and the drop mechanism 61 are raised and the tray support pins 171 and the frame drop pins 181 are located above the tray T.

First, the tray support mechanism 59 lowers the tray support pins 117 and pushed against the tray body 71. Then, the lift mechanism 55 raises the frame support pins 115 and the substrate support pine 117. The frame 73 is raised and the insertion opening 70 is formed between the tray body 71 and the frame body 81. The terminal part 77 of the frame 73 is separated from the upper surface of the substrate S. The frame cover 86 also moves to above the substrate S. In addition, the substrate S is raised by the substrate support pins 117 of the lift mechanism 55. In this way, the substrate S is separated from the substrate mounting pins 75 and floats above the tray.

Then, the robot extends its arm, the substrate S is accessed from the insertion opening 79, the lower surface of the substrate S is supported and the substrate S is removed from the insertion opening 79. The substrate S is removed in the opposite direction to the arrow D in FIG. 133.

Here, positioning may be performed again before the substrate removal operation. Specifically, after the frame is raised, positioning is performed by the clamp mechanism 57. The positioning operation may be the same as the positioning operation in the substrate mounting process. Following this, the substrate is removed by the robot. In this way, positioning may be performed again and secure transfer can be improved.

When the substrate S is removed, the lift mechanism 55 is lowered, and the frame 73 returns to its original location. At this time, the frame drop mechanism 61 lowers the frame drop pins 181 and supports the lowering of the frame 73. Then, the frame drop mechanism 61 raises the frame drop pins 181 and the tray support mechanism 59 raises the tray support pins 171. In this way, a series of substrate removal operation is complete. Furthermore, the present embodiment can also be applied to the embodiments 1~28 and to embodiments that do not have numbers attached.

(Other Embodiments)

The substrate mounting device of the present invention was explained above. Examples of other embodiments of the present invention are as follows.

A mask inspection device or method for inspecting a mask by irradiating a charged particle beam onto a mask mounted on a tray using the substrate mounting device or method described above.

A mask manufacturing device or method for inspecting a mask manufacturing process by irradiating a charged particle beam onto a mask mounted on a tray using the substrate mounting device or method described above.

A mask inspected by the mask inspection device or method described above.

A mask manufactured by the mask manufacturing device or method described above.

A semiconductor manufacturing device or method for manufacturing a semiconductor device using the mask described above.

A semiconductor device manufactured using the mask described above. A semiconductor device manufactured by the semiconductor manufacturing device or method described above.

For example, a Cr mask, EUV mask or nano-imprint mask can be given as a type of a mask. A Cr mask is used for light exposure, and the EUV mask is used for EUV exposure, the nano-imprint mask is used for forming a resist pattern by a nano-imprint. With regards to each of these masks, a mask formed with a pattern may be the object of an inspection. In addition, a mask formed with a film before a pattern is formed may also be the object of an inspection.

Next, a manufacturing method of a semiconductor device which can apply a mask obtained by the above described embodiments is described. The manufacturing method includes the following processes (1)~(5).
(1) a wafer manufacturing process for manufacturing a wafer (or a wafer preparing process for preparing a wafer
(2) a mask manufacturing process for manufacturing masks to be used during the exposure (or mask preparing process for preparing masks)
(3) a wafer processing process for performing any processing treatment necessary for the wafer
(4) a chip assembling process for cutting out those chips formed on the wafer one by one to make them operable
(5) a chip inspection process for inspecting finished chips Among these main processes, the wafer processing process set forth in (3) exerts a critical effect on the performance of resultant semiconductor devices. This process involves sequentially laminating designed circuit patterns on the wafer to form a large number of chips which operate as memories, MPUs and so on. The wafer processing process includes the following sub-processes:
(A) a thin film forming sub-process for forming dielectric thin films serving as insulating layers and/or metal thin films for forming wirings or electrodes, and the like (by using CVD, sputtering and so on);
(B) an oxidization sub-process for oxidizing the thin film layers and the wafer substrate;
(C) a lithography sub-process for forming a resist pattern by using masks (reticles) for selectively processing the thin film layers and/or the wafer substrate;
(D) an etching sub-process for processing the thin film layers and/or the wafer substrate in accordance with the resist pattern (by using, for example, dry etching techniques);
(E) an ion/impurity injection/diffusion sub-process;
(F) a resist striping sub-process; and
(G) a sub-process for inspecting the processed wafer;

The wafer processing process is repeated a number of times depending on the number of required layers. The lithography sub-process in (C) includes the following steps:
(a) a resist coating step for coating a resist on the wafer on which circuit patterns have been formed in the previous process
(b) an exposing step for exposing the resist
(c) a developing step for developing the exposed resist to produce a resist pattern
(d) an annealing step for stabilizing the developed resist pattern The preferred embodiments of the present invention are explained above. As described above, according to the present invention, the clamp mechanism clamps both the tray and substrate in one clamp operation. This clamp operation is for pressing a tray and substrate from different directions using a plurality of clamps pieces. Because a clamp mechanism which moves parallel to a substrate planar surface is used, it is possible to position the substrate without inclining the substrate. In addition, because the tray and substrate are clamped in one operation using a clamp body arranged with a tray clamp part and substrate clamp part as one unit, the substrate is positioned with respect to the tray corresponding to a location relationship between the tray clamp part and substrate clamp part and the location relationship between the tray and substrate can be accurately determined. Therefore, the substrate can be accurately positioned with respect to the tray.

In addition, according to the present invention, because the substrate and tray are clamped in one operation, it is possible to obtain the merit of being able to simultaneously position the tray as well as the substrate.

In addition, according to the present invention, because contact with a substrate is made using a clamp it is possible to avoid contact with the substrate. It is preferred that the clamp is related after positioning is completed, and therefore, contact time can be reduced. Therefore, according to the present invention, it is possible to preferably perform positioning while avoiding as much contact as possible with the substrate.

In particular, in the examples of the embodiments described above, a substrate is a mask and the substrate mounting device is arranged on a charged particle type inspection device (in particular, projection type inspection device). In this case, both surfaces of the mask are sometimes inspected in sequence and it is necessary to avoid as much contact with both surfaces of the mask as possible. Therefore, performing highly accurate substrate mounting, mask positioning without contact with a mask is being demanded. According to the present invention, it is possible to preferably meet the requests for such a mask inspection.

In addition, the mask which is applied in the present invention is a glass manufactured mask having a square shape with 6 inch sides and a thickness of 6.35 mm, which is heavy compared to a wafer. However, this type of mask can also be preferably positioned with the substrate mounting device of described above.

In addition, the inspection device applied with the present invention performs a mask inspection inside a vacuum chamber for example as is shown in the embodiments described above. However, the present invention can also preferably position a mask in this case.

In addition, in the example of the embodiments described above, the substrate mounting device performs temporary positioning of a substrate when viewed from the entire inspection device. Actual positioning is performed at a later stage. That is, a mark on a substrate is detected by a CCD camera in a load lock chamber, tray set location is controlled in a main chamber based on the mark location, and actual positioning is performed. The accuracy of this actual positioning is affected by the accuracy of the temporary positioning. For example, when the field of view of the CCD camera is broadened due to a low temporary positioning accuracy, the magnification of the CCD camera decreases and accuracy of the actual positioning decreases. According to the present invention, it is possible to prevent a decrease in the accuracy of the actual positioning and therefore improve inspection accuracy.

Other merits of the present invention are explained below. According to the present invention, a fixing side clamp body and a driven side clamp body are arranged as a plurality of clamp bodies. First, the fixing side clamp body may be arranged at a predetermined fixing side clamp location, then, the driven side clamp body moves and the tray and substrate may be pressed towards the fixing side clamp body. The location relationship between a tray clamp part and substrate clamp part of the fixing side clamp body may be fixed at the time of clamping. In this way, the fixing side clamp body and driven side clamp body become linked, and it is possible to accurately position the substrate to a predetermined location defined by the location relationship between the tray clamp part and substrate clamp part of the fixing side clamp body. In addition, because the driven side clamp body advances after the fixing side clamp body has advance, it is possible to obtain the merit whereby it is possible to reduce the amount of tray movement in a positioning process.

In addition, in the driven side clamp body, the tray clamp part and substrate clamp part may be arranged so that the substrate clamp part contacts the substrate before the tray clamp part contacts the tray, and a bias part may be arranged which flexibly biases the substrate clamp part towards the substrate when clamping. The bias part may be able to retract the substrate clamp part when the driven side substrate clamp part is pressed from the substrate due to the rebound force of the substrate clamp. The bias part may be a flexible part and may be arranged on the rear of the driven side substrate clamp part. The flexible part may be a spring for example. By adopting this structure, it is possible to avoid a decrease in positioning accuracy due a dimension error of the tray clamp part and substrate clamp part, and a substrate can be positioned with a high level of accuracy. In addition, it is possible to further improve positioning accuracy by applying a flexible structure to the substrate which is lighter than the tray and can move easily.

In addition, according to the present invention, the clamp body may include a tray clamp location adjustment mechanism for adjusting the amount of protrusion by the tray clamp towards the tray and a substrate clamp location adjustment mechanism for adjusting the amount of protrusion by the substrate clamp towards the substrate. The amount of protrusion of the tray clamp part and the amount of protrusion of the substrate clamp part may be independently adjusted. By adopting this type of structure, it is possible to adjust the amount of protrusion of a tray clamp part and substrate part of the clamp body and further improve positioning accuracy.

In addition, according to the present invention, the substrate mounting device may be arranged at a location corresponding to the substrate at the time of positioning and may include a plurality of substrate support parts which can be moved vertically. The clamp mechanism may clamp the substrate while the substrate is in a state supported at a substrate support height which is higher than a substrate mounting height of a tray by the plurality of substrate support parts. In this way, because the substrate is clamped while in a state separated from the tray, it is possible to avoid friction between the tray and substrate when positioning. Therefore, it is possible to perform positioning with as little contact with the substrate as possible, prevent a decrease in positioning accuracy due to friction and further prevent substrate damage due to friction.

In addition, according to the present invention, the tray may include a tray body and a frame which can be raised from the tray body and encloses the substrate. The substrate mounting mechanism may be arranged at a location corresponding to the frame and include a plurality of frame support parts which can be moved vertically. It is possible to form an insertion opening between the frame and tray body for inserting the substrate and clamp body when the frame support part raises the frame. In this way, it is possible to provide a potential to the substrate upper surface from the frame on the substrate periphery. In addition, by enclosing the substrate with a frame, it is possible to make a potential near the substrate end parts uniform. It is preferable of the frame contacts the substrate end part and thus it is possible to preferably make a potential uniform. In the embodiments described above, a frame cover is arranged so as to cover a gap between the frame and substrate, and the frame cover contacts the substrate end parts. Furthermore, in the present invention, because the frame is raised, it is possible to prevent interference between the clamp mechanism and frame, and preferably perform positioning using the clamp even when a frame is arranged in order to provide a potential to the substrate upper surface.

More specifically, at lift mechanism may be arranged as explained in the embodiments described above. The lift mechanism may include a plurality of frame support parts arranged at a location corresponding to a frame, and a plurality of substrate support parts arranged at a location corresponding to the substrate, and the plurality of frame support parts and plurality of substrate support parts may be linked and moved vertically. In addition, an insertion opening may be formed between the frame and tray body for inserting a substrate and clamp body when the lift mechanism raises the frame support parts and raises the frame. Furthermore, the lift mechanism raises the substrate support parts and may protrude the substrate support parts to a substrate support height which a height corresponding to the insertion opening which is higher than the substrate mounting height of the tray. The substrate can be inserted by passing through the insertion opening and is supported by the substrate supporting parts at a substrate support height. The clamp body can also be inserted through the insertion opening without interference.

By adopting such a structure, it is possible to suitably raise a frame in order to form an insertion opening. In addition, it is also possible to support the substrate at a location above and separated from the tray when positioning. Therefore, it is possible to preferably obtain the merits of the present invention described above. Furthermore, by arranging the frame support parts and substrate supports parts on a common lift mechanism, it is possible to form a simple structure.

In addition, according to the present invention, the frame may also include a frame body which encloses a substrate and frame leg parts which extend downwards from the frame body. The lower surface of the frame leg parts may be located lower than the lower surface of the substrate. The frame support parts may be arranged at a location corresponding to the frame leg parts and by supporting the frame leg parts, the frame body may be located higher than the substrate support height by the substrate support parts and an insertion opening may be formed. With this structure, it is possible to raise the frame body to a location higher than a substrate support height even when the substrate support parts and frame support parts are simultaneously raised by the same distance, and it is possible to preferably form an insertion opening for the substrate and clamp between the frame body and tray body. Therefore, the structure of the lift mechanism can be made simple.

In addition, according to the present invention, a substrate mounting mechanism may include a frame support height adjustment mechanism for adjusting the height of a frame supporting part and a substrate support height adjustment mechanism for adjusting the height of a substrate supporting part. The height of the frame support parts and the height of the substrate support parts may be adjusted independently. With this structure, it is possible to adjust the height of the frame support parts and the height of the substrate support parts, and preferably adjust the location relationship between the frame and substrate.

In addition, according to the present invention, a tray support mechanism may be arranged. The tray support mechanism may include a tray support part arranged at a location corresponding to the tray body and may move the tray support parts vertically. The tray support mechanism lowers the tray support parts to contact with the tray body when the lift mechanism raises the frame and thereby the tray body may be prevented from being raised. With this structure, it is possible to prevent the tray body rising with the frame, and it is possible to preferably perform simultaneously positioning of the tray and substrate using the clamp.

In addition, according to the present invention, the tray body may include a protrusion edge part which protrudes further to the exterior than the frame, and the upper surface of the protrusion edge part may be a contact surface of the tray support part and the lower surface of the protrusion edge part may be a support surface of the transfer robot which transfers a tray. With this structure, it is possible to use the protrusion edge part of the tray body for tray support when mounting the substrate and tray transfer when mounting is complete. It is possible to realize these two functions with a simple structure.

In addition, according to the present invention, a frame drop mechanism may be arranged. The frame drop mechanism may include a frame drop part arranged at a location corresponding to the frame, and may move the frame drop part vertically. The frame drop mechanism may lower the frame drop part when releasing the frame lift to press the frame. With this structure, the frame which is raised in order to prevent interference between the substrate and clamp may be securely returned to a location which encloses the substrate.

Figure 144:
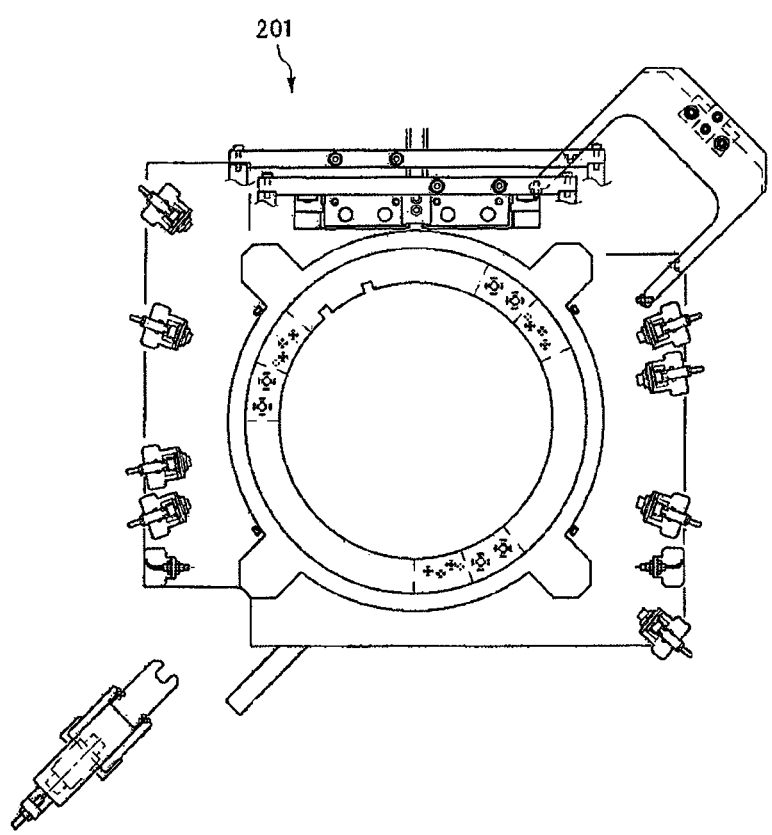
FIG. 144 is a diagram related to one embodiment of the present invention.

In addition, in the present invention, the substrate may be mask for manufacturing semiconductors. In addition, the substrate may have a square shape. Conventionally, a positioning mechanism of a round shaped substrate is generally used, however, this can not be applied to square shaped mask positioning. According to the present invention, square shaped mask positioning can be preferably performed. However, within the scope of the present invention, the substrate is not limited to a mask and may also be a wafer. In addition, the substrate shape may round as well as square. FIG. 144 shows an example of a substrate mounting device in the case of a round shaped substrate. The round shaped substrate may be a wafer for example. As is shown in the diagram, the shape of the tray is changed to a round shape to match the shape of the substrate. Except for changing the shape of the substrate and tray, the substrate mounting device 201 in FIG. 144 includes almost the same structure as the embodiments described above. The substrate mounting device 201 in FIG. 144 may be arranged with each structure of the present invention described above, that is, stage, lift mechanism, clamp mechanism, tray support mechanism and drop mechanism etc. A structure view from a horizontal direction (including a cross sectional structure) may be almost the same as the embodiments described above with respect to a square substrate.

The preferred embodiments of the present invention are explained above. However, the present invention is not limited to these embodiments. A person with ordinary skill in the field may make various modifications of the embodiments described above within the scope of the present invention. Furthermore, the present embodiment can be applied to embodiments 1~28 as well as embodiments with no number attached.

As stated above, the present invention is effective as a substrate mounting technology which can position a substrate with respect to a tray at a high level of accuracy.

(Twenty Ninth Embodiment)

Sample observation method and device, and an inspection method and device using the sample observation method and device.

An example of a sample observation method and device in the inspection device and method of the present invention is explained.

[First Point of View]

The first point of view relates to observation of foreign materials, and in particular to a technique for inspecting foreign materials.

A purpose of the invention is to provide an electron beam inspection method and an electron beam inspection device capable of quickly and reliably detecting a foreign material on a sample surface.

An electron beam inspection method according to the invention is for irradiating a sample surface with an imaging electron beam having a predetermined irradiation area, detecting reflected electrons by means of a detector, and thereby acquiring an image of the sample surface and of a foreign material on the sample surface, and the electron beam inspection method has: a foreign material charging step of charging the foreign material by irradiation with a charging electron beam and forming around the foreign material a potential distribution different from that of the sample surface; and a magnified image acquisition step of detecting the electrons which are reflected from the foreign material by the imaging electron beam irradiation and reach the detector through a path bent by the effect of the potential distribution, and acquiring a magnified image of the foreign material in which the magnification for the foreign material is increased more than the magnification for the sample surface.

Since this allows an electron beam inspection to be carried out by using the electron beam having a predetermined irradiation area, a wide area can be inspected quickly. Since the magnified image in which the foreign material is magnified more than the surrounding sample surface is acquired, the foreign material can be detected reliably.

In the invention, the foreign material charging step may comprise negatively charging up the foreign material by the charging electron beam irradiation, and the magnified image acquisition step may comprise setting the landing energy of the imaging electron beam to 10 eV or less, detecting mirror electrons reflected immediately in front of the foreign material, and acquiring the magnified image of the foreign material.

This allows the magnified image of the foreign material to be reliably detected by using mirror electrons which are easily generated in a low landing energy range.

In the invention, the foreign material charging step may comprise increasing the absolute value of the potential of the foreign material by the charging electron beam irradiation.

Consequently, the potential difference between the background sample surface and the foreign material can be increased, the contrast of the magnified image of the foreign material can be increased, and the electron beam inspection can be facilitated.

In the invention, the landing energy of the charging electron beam may be larger than that of the imaging electron beam.

Consequently, the absolute value of the negative potential of the foreign material can be increased by the charging electron beam irradiation with a high landing energy. As a result, mirror electrons can easily be generated when the imaging electron beam irradiation is performed.

In the invention, the landing energy of the charging electron beam may be smaller than that of the imaging electron beam.

This configuration is suitable when an appropriate landing energy of the imaging electron beam is known. The above configuration can prevent a potential shift of the surface of the foreign material from increasing when the magnified image of the foreign material is acquired by using the imaging electron beam. Consequently, the magnified image can be detected reliably.

In the invention, the charging electron beam and the imaging electron beam may have the same landing energy and dose amounts different from each other.

This allows the charging of the foreign material to be controlled by the dose amount without changing the landing energy of the electron beam. Consequently, the magnified image of the foreign material can be detected by easy control.

In the invention, the imaging electron beam may be made to enter the sample surface not perpendicularly thereto.

Consequently, the angle of incidence of the imaging electron beam can be adjusted appropriately, and the magnified image of the foreign material can be acquired at a higher resolution.

In the invention, the magnified image acquisition step may comprise setting the landing energy of the imaging electron beam to 10 eV or more, detecting secondary emission electrons reflected by being emitted from the foreign material, and acquiring the magnified image of the foreign material.

This allows secondary emission electrons to be generated from the foreign material to acquire the magnified image of the foreign material based on the secondary emission electrons, so that the electron beam inspection can be carried out.

In the invention, the landing energy of the imaging electron beam may be equal to or more than a maximum landing energy which causes all electrons reflected from the sample surface to be mirror electrons and be equal to or less than a value of a minimum landing energy, which causes all electrons reflected from the sample surface to be secondary emission electrons, added with 5 eV.

In other words, in the invention, the landing energy LE of the imaging electron beam may be set as LEA≦LE≦(LEB+5 eV), where LEA is the maximum landing energy which causes all electrons reflected from the sample surface to be mirror electrons, and LEB is the minimum landing energy which causes all electrons reflected from the sample surface to be secondary emission electrons.

This allows the electron beam inspection to be carried out by using a landing energy range in which the difference in gray level is large between the foreign material and the surrounding sample surface. Consequently, the electron beam inspection can be carried out easily and reliably with the acquisition of a high-contrast image. Here the gray level means the brightness of an image, and the difference in gray level means the difference in brightness.

In the invention, the landing energy of the imaging electron beam may be set to a landing energy which: is in a landing energy range in which electrons reflected from the sample surface are a mixture of mirror electrons and secondary emission electrons, or only secondary emission electrons; is in a landing energy range in which electrons reflected from the foreign material are a mixture of mirror electrons and secondary emission electrons; and maximizes the difference in gray level between the image of the sample surface and the magnified image of the foreign material.

This maximizes the difference in gray level between the surrounding background and the foreign material. Consequently, the foreign material can be detected in a state where the foreign material is easily detected.

An electron beam inspection device according to the invention comprises: a stage for placing a sample thereon; a primary optical system for generating an electron beam having a predetermined irradiation area and for emitting the electron beam toward the sample; and a secondary optical system, having a detector for detecting electrons reflected from the sample, for acquiring an image of a predetermined visual field area on the sample, where the primary optical system charges the foreign material by irradiation with a charging electron beam to cause the potential distribution of the foreign material to be different from that of a sample surface, and then irradiates the sample with an imaging electron beam, and where the secondary optical system detects electrons which are reflected from the foreign material and reach the detector through a path bent by the effect of the potential distribution, and acquires a magnified image of the foreign material in which the magnification for the foreign material is increased more than the magnification for the sample surface.

This allows the whole sample surface to be inspected quickly by the electron beam having an irradiation area of a predetermined size. The foreign material can be detected reliably by magnifying the image of the foreign material larger than that of the surroundings.

In the invention, the primary optical system may charge up the foreign material by irradiation with the charging electron beam and then irradiate the sample with the imaging electron beam with a landing energy of 10 eV or less, and the secondary optical system may detect mirror electrons reflected immediately in front of the foreign material by means of the detector and acquire the magnified image of the foreign material.

With the use of a low landing energy, this allows the foreign material to be in a state where it easily generates mirror electrons. The use of mirror electrons makes it easy to acquire the magnified image of the foreign material. Consequently, the foreign material can be detected more reliably.

In the invention, at least one of a Faraday cup, a reference sample chip, and an EB-CCD may be placed on the stage.

This allows the profile of the electron beam to be detected directly, so that the electron beam can be adjusted appropriately.

In the invention, a reference sample chip may be placed on the stage, and the reference sample chip may have a circular, crisscross, or rectangular shape pattern.

This allows the beam profile of the electron beam to be adjusted so that mirror electrons are suitably generated. Mirror electrons are suited to detect the magnified image of the foreign material, and the above configuration can generate mirror electrons appropriately.

In the invention, the primary optical system may set the landing energy of the imaging electron beam to 10 eV or more, and the secondary optical system may detect secondary emission electrons which are emitted from the foreign material and reach the detector and acquire the magnified image of the foreign material.

This allows the foreign material to be detected also by causing secondary emission electrons to be generated from the foreign material.

In the invention, the secondary optical system may have an EB-CCD interchangeable with an NA aperture.

This allows the profile of a secondary electron beam going through the secondary optical system to be directly measured. Consequently, an appropriate adjustment can be made.

In the invention, the secondary optical system may have an NA aperture, which may be placed so that the center of the intensity distribution of the mirror electrons coincides with the center position of the aperture.

This allows the NA aperture to be appropriately positioned to detect the mirror electron signal satisfactorily and to cause the detection amount of secondary emission electrons to be relatively small. Consequently, a high-contrast image can be acquired.

In the invention, the secondary optical system may have an NA aperture, and the shape of the NA aperture may be an elliptical shape having the major axis in a direction corresponding to the longitudinal direction of the intensity distribution of the mirror electrons.

Consequently, the aperture of an elliptical shape adapted to the intensity distribution of the mirror electrons can be used. As a result, more mirror electron signals can be detected and a high-contrast image can be acquired.

In the invention, the secondary optical system may have an NA aperture having a plurality of apertures, and the NA aperture may be placed so that the plurality of apertures are located around the center of the intensity distribution of the mirror electrons.

Here the NA aperture is an aperture member, and the plurality of apertures are a plurality of openings provided on the aperture member. In the above-described configuration, the aperture can be placed according to the scattering direction of the mirror electrons, and the mirror electrons can be appropriately detected depending on the intended use and property.

In the invention, the secondary optical system may comprise an NA aperture having a plurality of apertures, and the NA aperture may be placed so that any one of the plurality of apertures coincides with the center of the intensity distribution of the mirror electrons.

Here the NA aperture is an aperture member, and the plurality of apertures are a plurality of openings provided on the aperture member. In the above-described configuration, an effective inspection can be carried out for a foreign material distinctive in the scattering direction. An inspection useful in classifying foreign materials can also be carried out.

In the invention, the secondary optical system may further comprise a moving mechanism for moving the NA aperture.

This allows the NA aperture to be positioned easily by using the moving mechanism.

In the invention, the primary and secondary optical systems may be optical systems whose sensitivity is calibrated by using microspheres of a known size scattered on the sample.

This allows the sensitivity calibration to be carried out precisely. Consequently, image acquisition can be carried out under good conditions.

The electron beam inspection device of the invention may have: a chamber for containing the stage; and an SEM-type inspection device provided in the chamber, where based on positional information on the magnified image of the foreign material acquired by the detector the stage may be moved and the foreign material may be inspected in detail by the SEM-type inspection device.

Consequently, review inspection for the foreign material can be carried out quickly and precisely, and the foreign material inspection can be carried out quickly and precisely.

[Effects of the Invention]

As described above, the invention allows the foreign material inspection to be carried out quickly and allows the foreign material to be detected reliably and easily.

[Embodiment of the Invention]

Now, the invention will be described in detail. The following detailed description and appended drawings are not intended to limit the invention. Rather, the scope of the invention is defined by the appended claims.

Figure 145A:
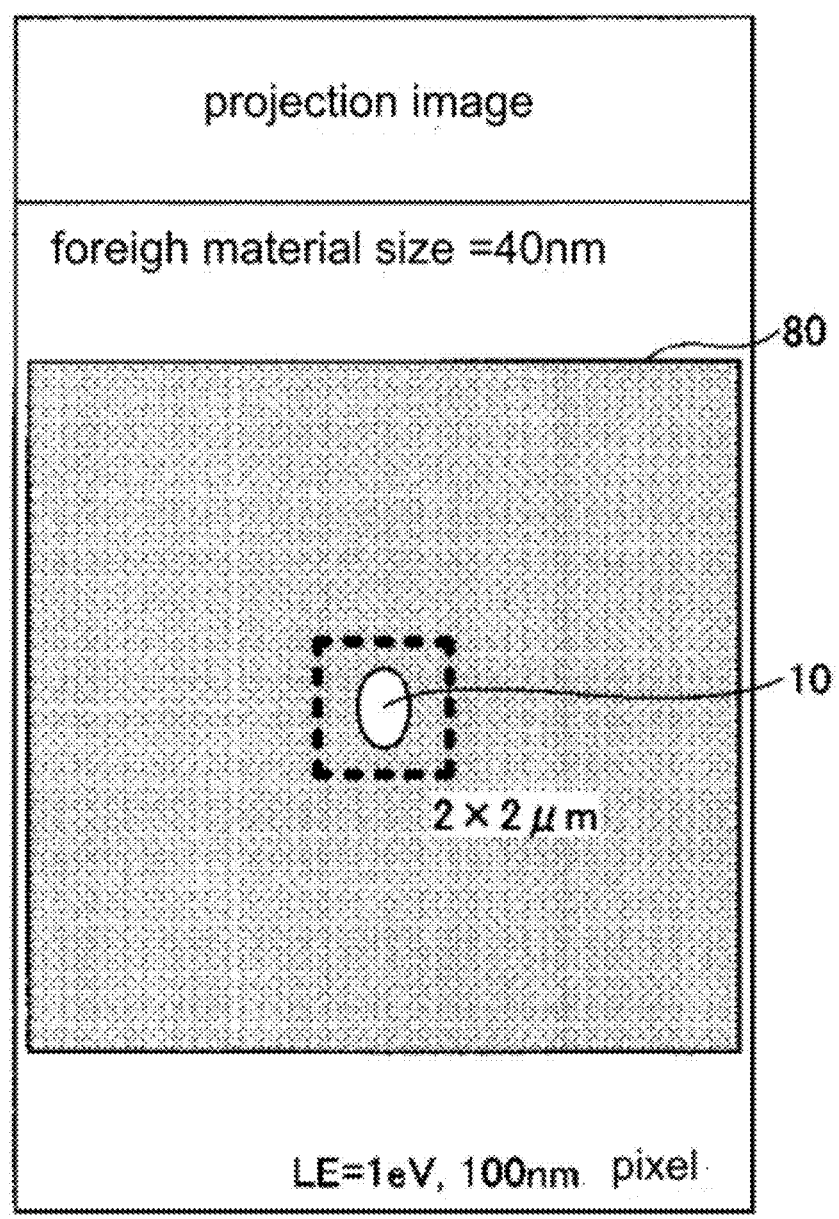
FIG. 145A is a diagram related to one embodiment of the present invention.

FIG. 145A shows an image to be obtained by an electron beam inspection method according to an embodiment. An outline of the principles of the invention will be described with reference to FIG. 145.

FIG. 145A shows an image 80 of a foreign material 10 obtained by a projection method according to the embodiment. The size of the foreign material is 40 nm. In the image in FIG. 145A, the size of the foreign material 10 mostly covers an area of a pixel size of 2×2 [μm]. Here the pixel size is an actual size on a sample corresponding to one pixel of a detector. The pixel size means a minimum unit of the size of a sample that can be observed. Hence in FIG. 145A the displayed image 80 is magnified to almost as large as 2×2 [μm] despite the actual size of the foreign material being 40 nm. This means that the foreign material 10 of about 40 nm can be found even if the pixel size is about 1 μm or 1.5 μm large for example.

In FIG. 145A, the landing energy of an imaging electron beam is 1 [eV]. The pixel size is 100 nm. Conventionally, the pixel size is required to be less than 40 nm when the actual size of a foreign material is 40 nm. In contrast to this, the embodiment can acquire the magnified image of the foreign material 10 that is magnified more than the optical magnification.

Figure 145B:
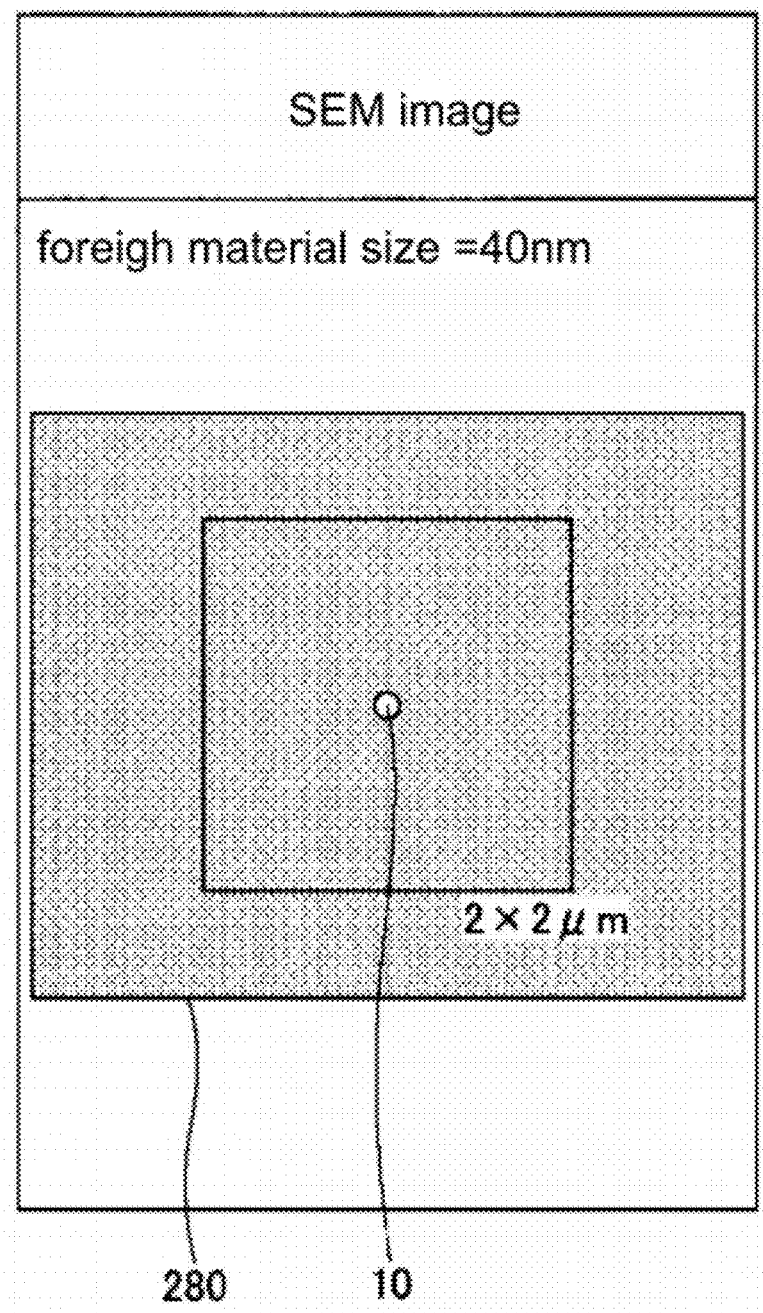
FIG. 145B is a diagram related to one embodiment of the present invention.

FIG. 145B shows an image 280 of the foreign material 10 to be obtained by a conventional foreign material inspection device of an SEM (scanning electron microscope) type. The size of the foreign material is 40 nm. In FIG. 145B, the pixel size is 2×2 [μm] as in FIG. 145A. It can be seen, however, that the size of the image of the foreign material 10 is considerably small in FIG. 145B compared to that in FIG. 145A.

As seen above, the electron beam inspection method according to the embodiment can acquire an image in which the size of the foreign material 10 is significantly increased, compared to the conventional SEM method. That is, a detection signal from the foreign material 10 is magnified more than the optical magnification. High sensitivity can be achieved even for a foreign material of an ultra-micro size. Furthermore, a foreign material can be detected by using a pixel size that is larger than the actual foreign material.

Figure 145C:
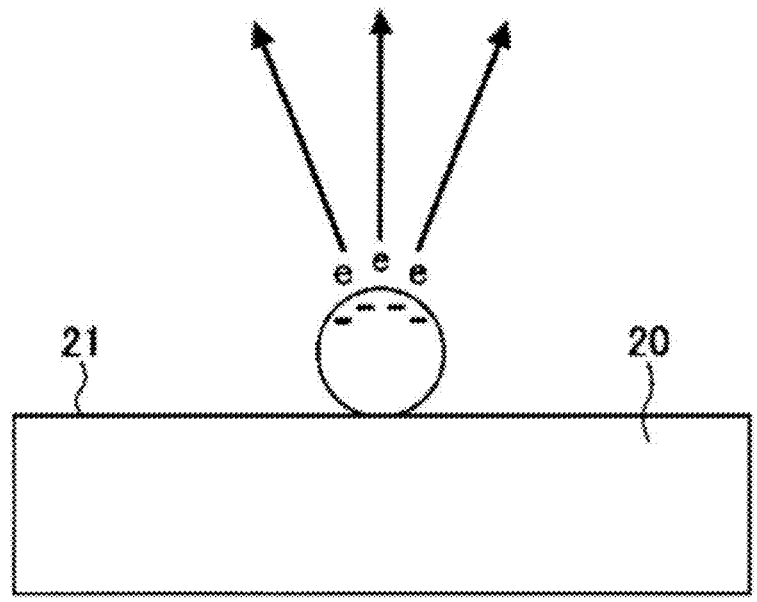
FIG. 145C is a diagram related to one embodiment of the present invention.

FIG. 145C is a side view showing a state where the foreign material 10 is present on a sample 20. In FIG. 145C, the surface of the foreign material 10 is spherical. For this reason, electrons reflected from the surface do not go through a vertical path, but change the path and spread out. This is for the following reason: since the foreign material 10 has a spherical surface, the potential distribution of the foreign material 10 is different from that of a sample surface 21; so, if the sample surface 21 is seen macroscopically, the potential distribution of its part where the foreign material 10 is present is distorted; and therefore the electron path changes. This will be described in detail later.

Figure 146A:
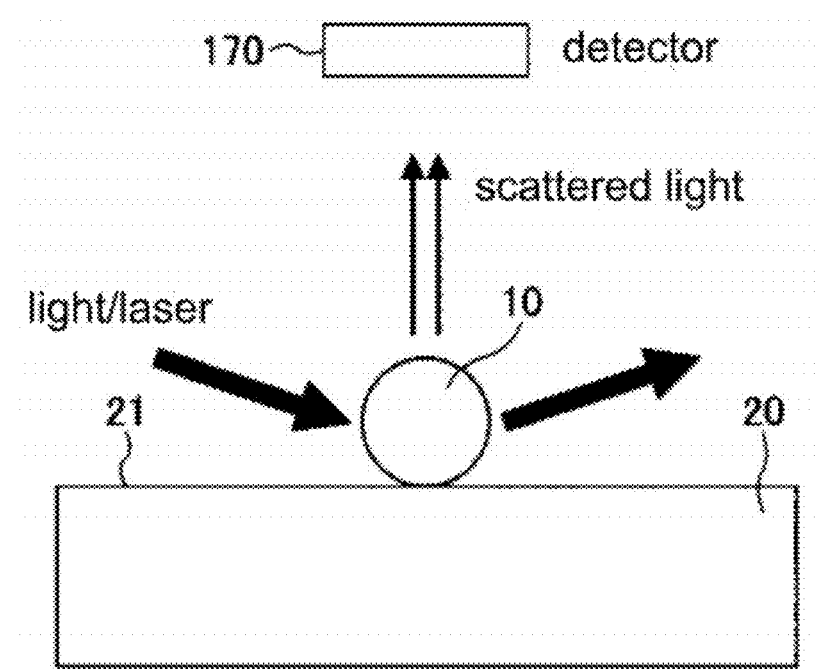
FIG. 146A is a diagram related to one embodiment of the present invention.
Figure 146B:
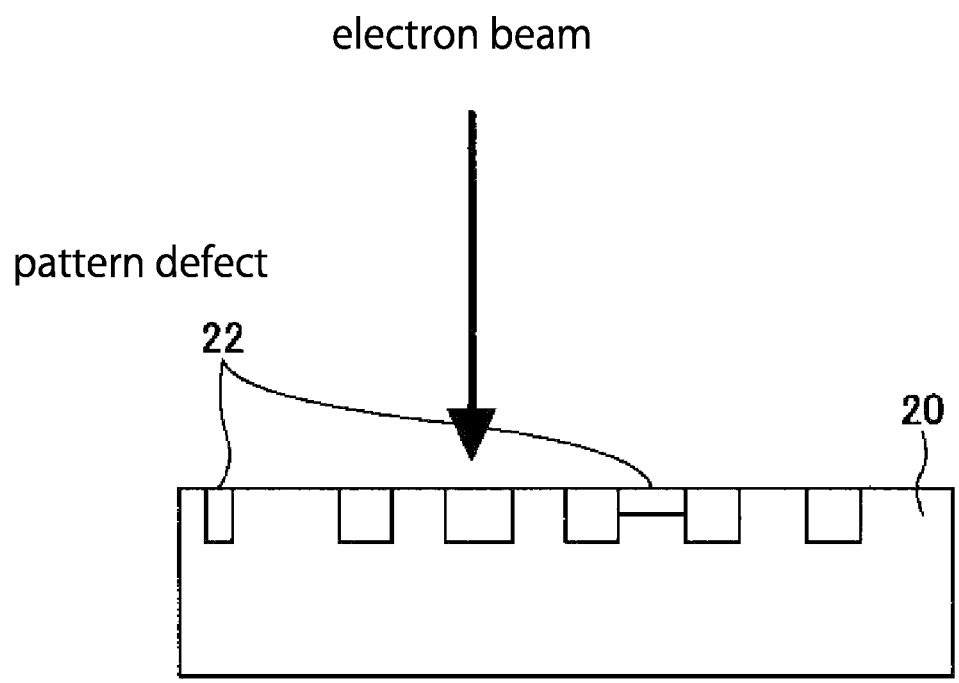
FIG. 146B is a diagram related to one embodiment of the present invention.

FIG. 146A and FIG. 146B show conventional electron beam inspection methods for comparison. FIG. 2A shows a conventional optical-type electron beam inspection method. In the optical method, the foreign material 10 is detected by a so-called dark-field scattering method. That is, the sample surface 21 of the sample 20 is irradiated with light or a laser, and the scattered light is detected by a detector 170. In the conventional optical method, however, the detection sensitivity decreases for ultra-micro foreign materials of a size between 50 and 100 nm or less, organic deposits, or the like. It would therefore be difficult to apply the conventional optical method. A major cause for the sensitivity decrease is considered to be a decrease in S/N ratio due to the foreign material 10 being smaller than the wavelength of light.

FIG. 146B shows a conventional SEM-type electron beam inspection method. In the SEM method, an ultra-micro pattern defect 22 or the like can be detected by condensing the electron beam to reduce the pixel size. For example, a pixel size smaller than the size of an object foreign material can be used, and therefore the foreign material 10 can be inspected for at a high resolution. However, since the pixel size is small, the inspection requires an immense amount of time and is difficult to carry out within a realistic time frame, so the SEM method is not practical.

As seen above, there has been conventionally no foreign material inspection method and foreign material inspection device that realizes high sensitivity, high speed, and high throughput in the inspection for foreign materials of an ultra-micro size between 50 and 100 nm or less.

Figure 147A:
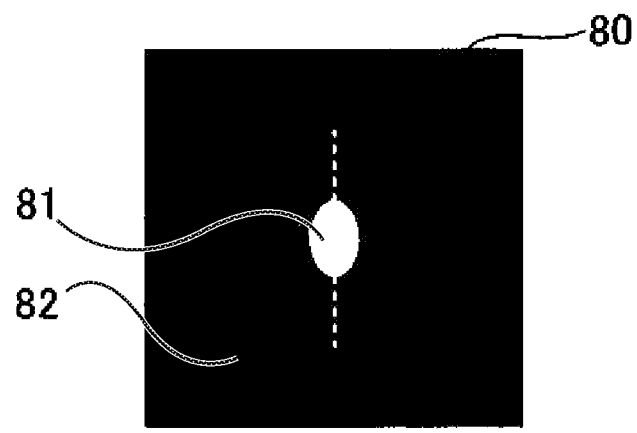
FIG. 147A is a diagram related to one embodiment of the present invention.
Figure 147B:
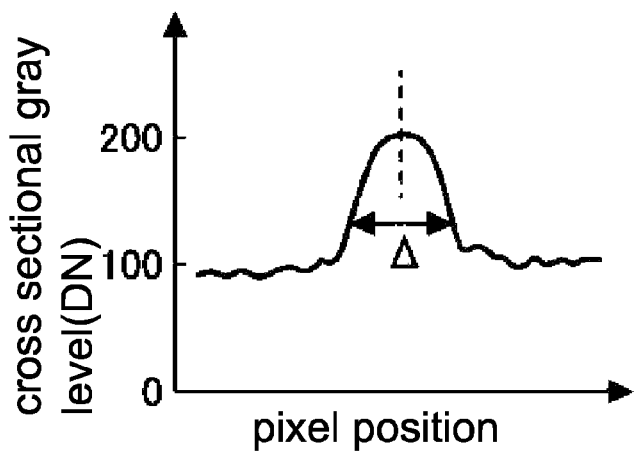
FIG. 147B is a diagram related to one embodiment of the present invention.

FIG. 147A and FIG. 147B show an example of a magnified image 80 of the foreign material 10 to be acquired by the foreign material inspection method and a cross-sectional gray level of the magnified image. Here the gray level means the brightness of an image, and the difference in gray level is the difference in brightness. The higher the gray level is, the higher the brightness is. FIG. 147A is an example of the magnified image 80; more particularly, the white area in the center is a magnified image 81 of the foreign material 10, and the black area shows a surface image 82 of the sample 20. Here the size (diameter) of the foreign material is 40 nm and the optical magnification is 300 times. In this case, the size of an image of the foreign material 10 would be 40 nm×the optical magnification 300=12 μm according to the conventional foreign material inspection method. In the embodiment in FIG. 147A, the size of the magnified image 81 of the foreign material 10 is 190 μm. The pixel size of the detector is 15 μm.

FIG. 147B shows the cross-sectional gray level versus pixel position. The horizontal axis represents the pixel position coordinate, and the vertical axis represents the cross-sectional gray level. In FIG. 147B the triangular mark (A) indicates the mountain shape (protrusion shape) part. This part is an area in which the gray level is high, and corresponds to the white magnified image part 81 in FIG. 147A. That means that the horizontal width (the triangular mark A) of the magnified image 81 on the image 80 is 190 μm.

Here the pixel size of the detector 170 is 15 μm. The size of the foreign material would be displayed as 12 μm on the image 80 by the conventional method, and therefore an image of the foreign material 10 would be a signal corresponding to one pixel or less. One pixel would not be able to accurately represent the foreign material 10.

On the other hand, the magnified image 81 of the foreign material 10 can be detected as an image whose number of pixels is 12.7 by the foreign material inspection method according to the embodiment. The imaging can therefore be carried out with a larger pixel size at a lower magnification. If the imaging can be carried out with a large pixel size, the whole sample surface 21 can be inspected quickly. Accordingly, the foreign material inspection can be carried out at high speed and high throughput. For example, the pixel size may be 100 to 1000 nm if the size of the foreign material is 10 to 30 nm. A pixel size larger than the size of the foreign material can thus be used, and a quick foreign material inspection can be carried out.

An electron beam inspection device applied to the electron beam inspection method according to the embodiment has an electron beam column (a primary optical system) of a projection type. In the SEM method, the electron beam is condensed. The spot size of the electron beam is the pixel size corresponding to one pixel. In the projection method, on the other hand, the electron beam has a predetermined area including a plurality of pixels. The sample 20 is irradiated with such an electron beam. A detector simultaneously detects electrons corresponding to the plurality of pixels. An image corresponding to the plurality of pixels is formed, and is acquired as an image signal. As seen above, the projection optical system has: the electron irradiation system which irradiates the sample surface 21 with electrons; the optical system for forming an image of electrons reflected from the sample surface 21 in a magnified manner; the detector 70; and the image processing device system for processing the signal from the detector 70.

Figure 148A:
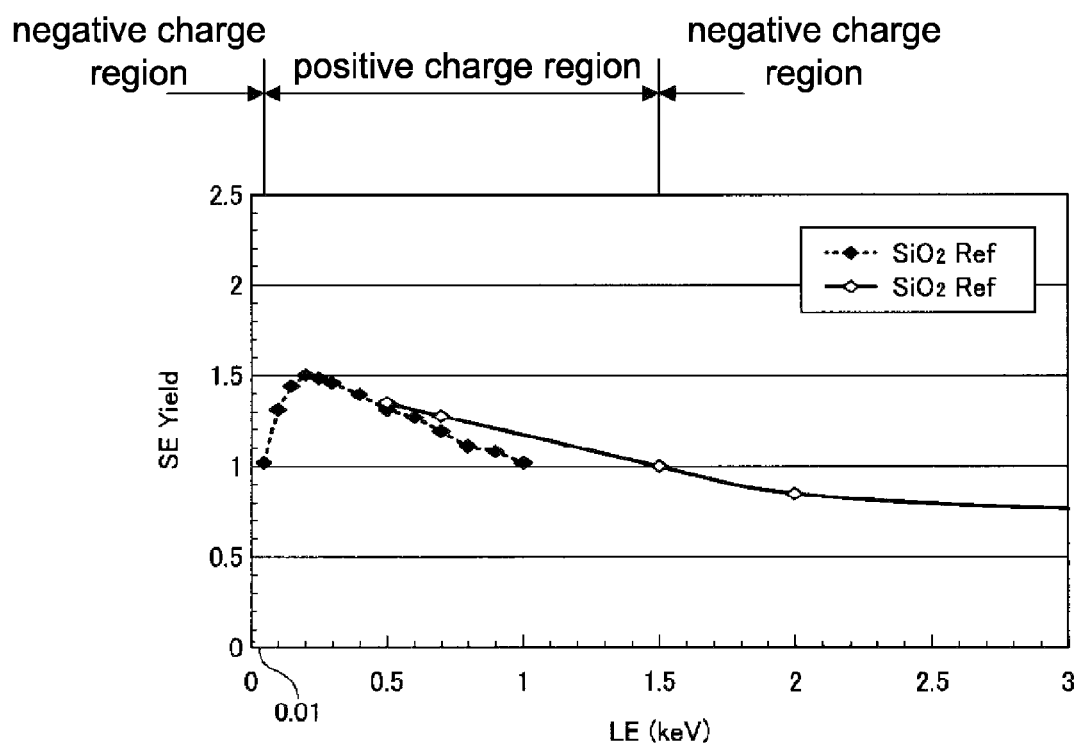
FIG. 148A is a diagram related to one embodiment of the present invention.

FIG. 148A shows a relation between the landing energy of the electron beam with which the sample is irradiated and electrons emitted from the sample. More specifically, FIG. 148A shows the yield of secondary emission electrons observed when the sample 20 is irradiated with the electron beam with the landing energy being varied.

In FIG. 148A, the horizontal axis represents the landing energy LE (keV), and the vertical axis represents the ratio of the yield of secondary emission electrons to the amount of incident electrons.

In FIG. 148A, when the yield of secondary emission electrons is larger than 1, the amount of emitted electrons is larger than the amount of incident electrons. The sample therefore becomes positively charged. In FIG. 148A, the positive charge region is a region in which the landing energy LE is 10 eV or more but not exceeding 1.5 keV.

In contrast, when the amount of secondary electron emissions is smaller than 1, the amount of electrons incident on the sample 20 is larger than the amount of electrons emitted from the sample 20. The sample 20 therefore becomes negatively charged. In FIG. 148A, the negative charge region is a region in which the landing energy LE is 10 eV or less and a region in which the landing energy LE is 1.5 keV or more.

Figure 148B:
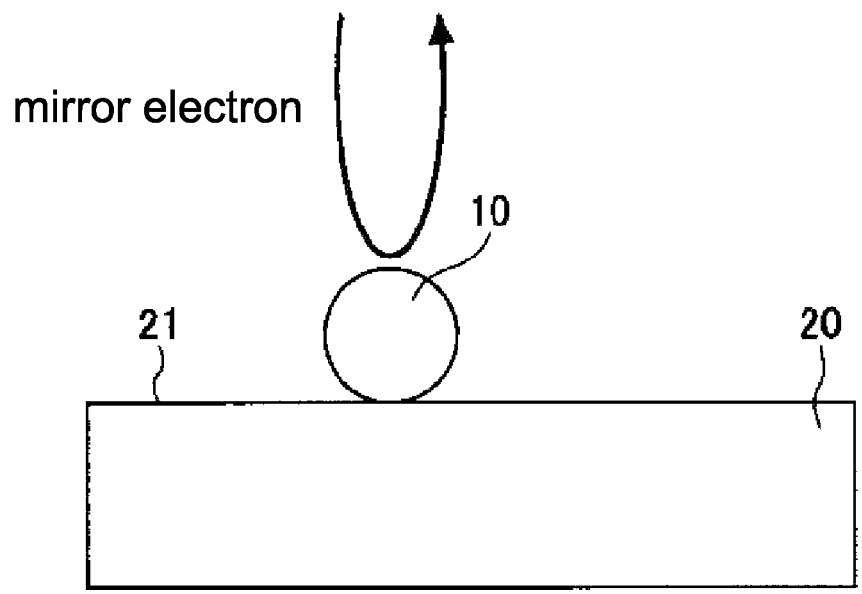
FIG. 148B is a diagram related to one embodiment of the present invention.

FIG. 148B shows mirror electrons. In FIG. 148B, the foreign material 10 is present on the sample surface 21, and the foreign material 10 is negatively charged. If the sample 20 is irradiated with an electron beam under certain conditions, electrons in the electron beam do not collide with the foreign material 10, but turn and are reflected immediately in front of it. Electrons that do not collide with an object to be irradiated but bounce back immediately in front of it like this are called mirror electrons. Whether electrons with which an object is irradiated become mirror electrons or not depends on the potential distribution (the state of charge) of the foreign material 10 and on the landing energy of the electron beam with which the foreign material 10 is irradiated. For example, if the foreign material 10 is negatively charged up and the landing energy is not very high, the electron beam is bounced back by the negative electric field of the foreign material 10, is reflected without colliding with the foreign material 10, and becomes mirror electrons.

Figure 148C:
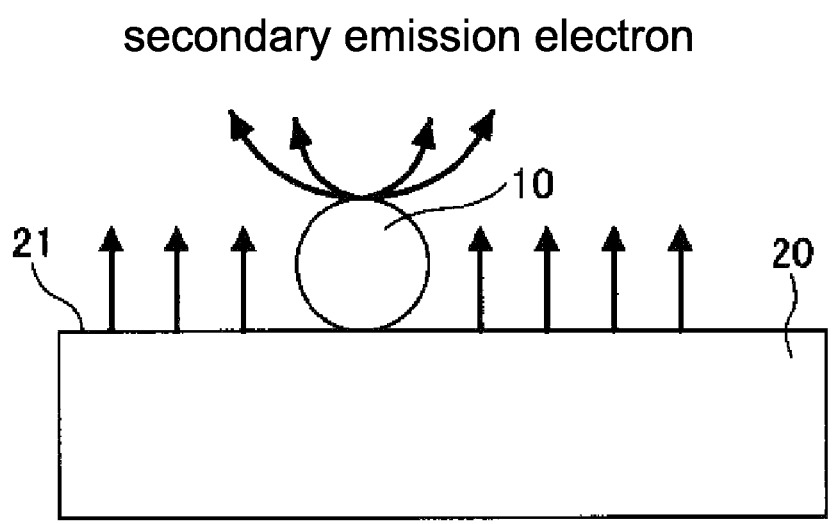
FIG. 148C is a diagram related to one embodiment of the present invention.

FIG. 148C shows secondary emission electrons. In FIG. 148C, the sample 20 is irradiated with an electron beam, which collides with the sample surface 21, and consequently secondary emission electrons are emitted from the sample. This is similar on the foreign material 10, where the electron beam collides with the foreign material 10 and secondary emission electrons are emitted from the foreign material 10.

In the electron beam inspection method according to the embodiment, the foreign material 10 present of the sample surface 21 is detected by using mirror electrons and secondary emission electrons.

Figure 149A:
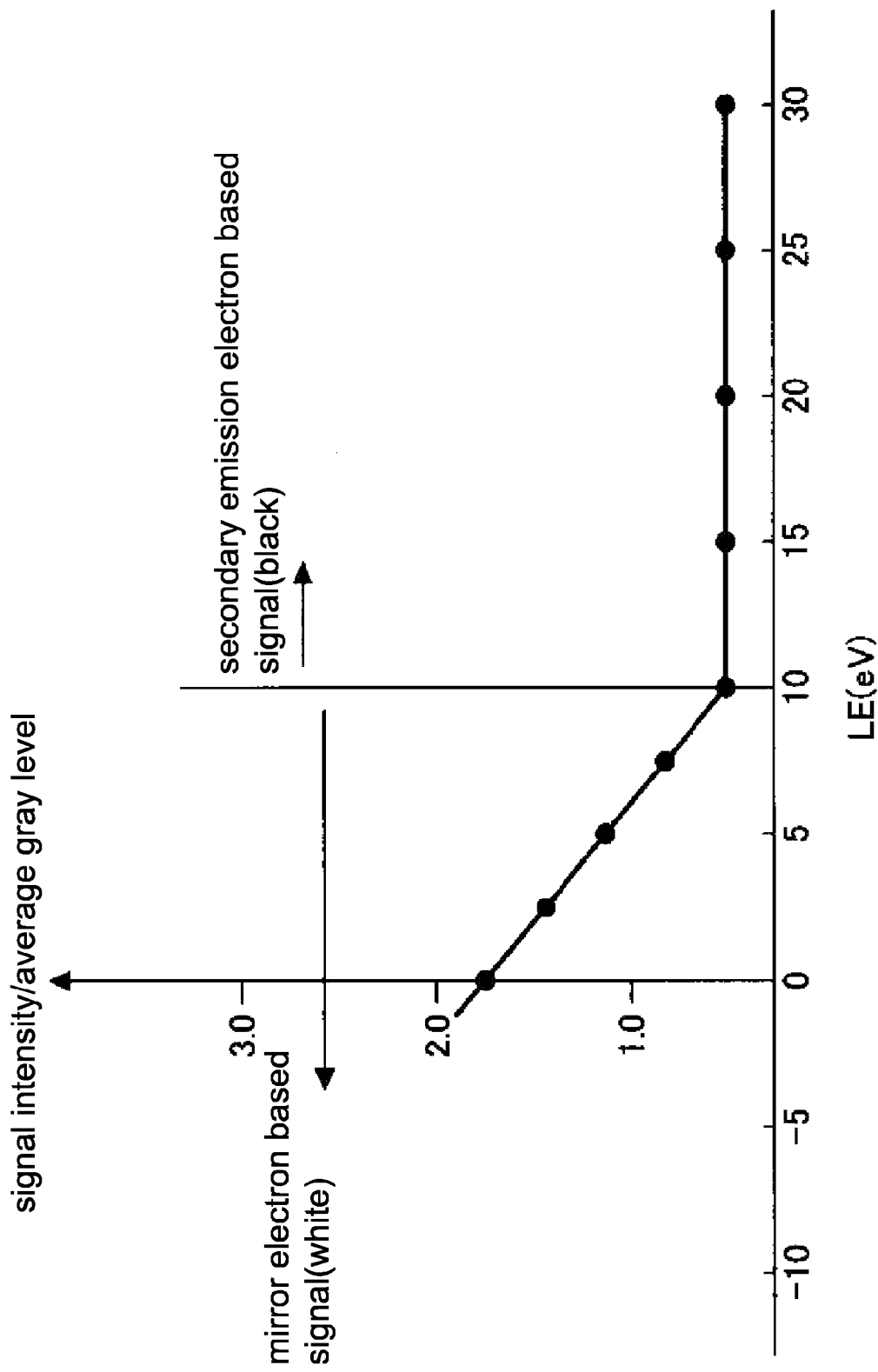
FIG. 149A is a diagram related to one embodiment of the present invention.
Figure 149B:
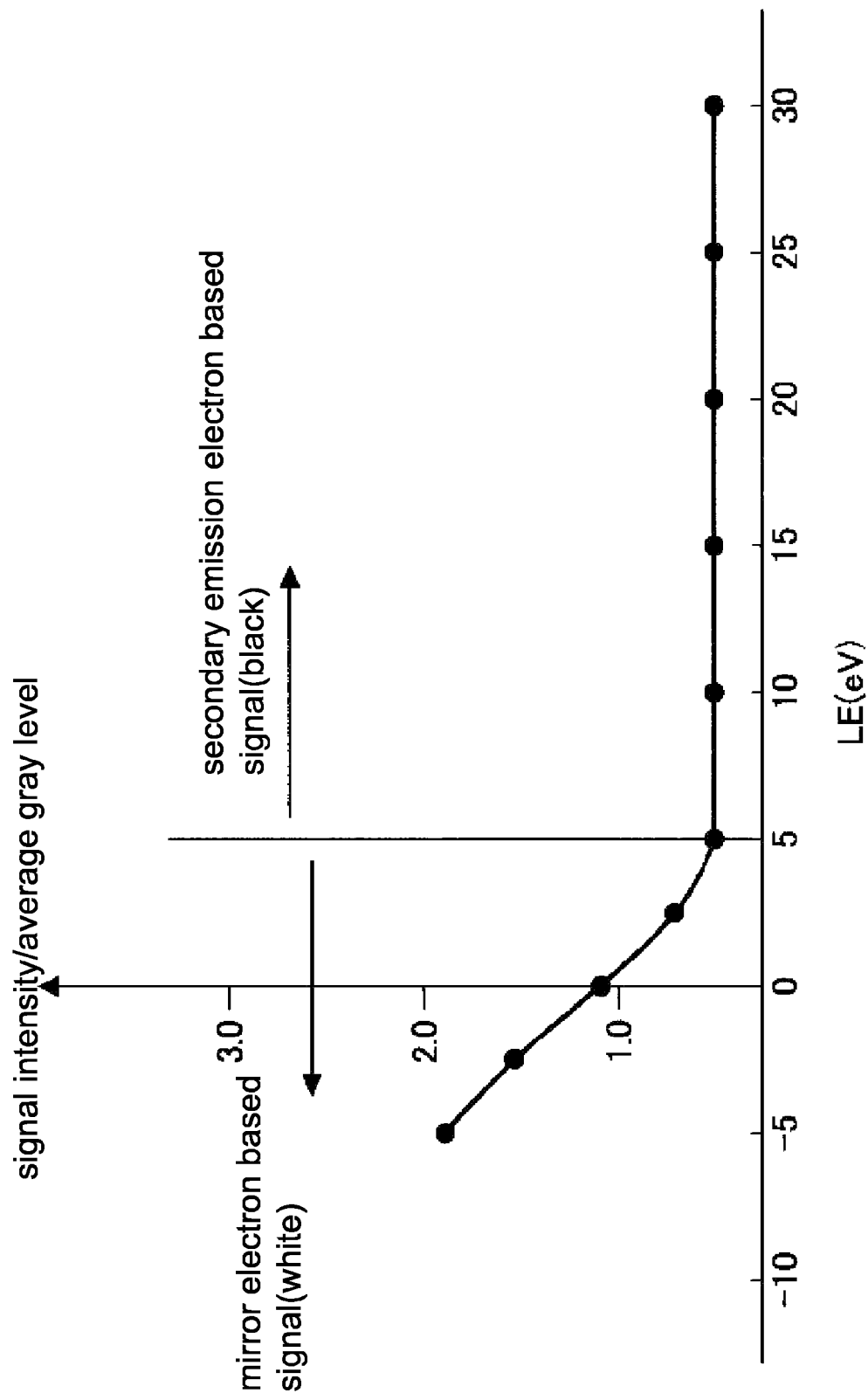
FIG. 149B is a diagram related to one embodiment of the present invention.

FIG. 149A and FIG. 149B show examples of a relation between the landing energy LE of the electron beam with which the sample 20 and the foreign material 10 are irradiated and "signal intensity/average gray level" of electrons reflected from the sample 20. Here "to be reflected" means that electrons oriented approximately opposite to the electron beam return from the sample 20 or foreign material 10 by the electron beam irradiation. Accordingly, "to be reflected" includes both of electrons that are reflected without colliding with the sample 20 or foreign material 10 and secondary emission electrons that are reflected by colliding with the sample 20 or foreign material 10 and then being emitted therefrom.

FIG. 149A is an example of a relation between the landing energy LE of the electron beam for the irradiation and "signal intensity/average gray level" of reflected electrons. In FIG. 149A, the horizontal axis represents the landing energy LE of the electron beam, and the vertical axis represents the "signal intensity/average gray level." The average gray level represents the brightness of an image and corresponds to the signal intensity. FIG. 149 is the characteristic around the landing energy LE being near 0 eV showing the characteristic in an energy range which is far lower than that in FIG. 148. In FIG. 149A, the region in which the landing energy LE is 10 eV or less is a region in which a mirror-electron-based signal (white) is acquired. On the other hand, the region in which the landing energy LE is 10 eV or more is a region in which a secondary emission-electron-based signal (black) is acquired. It can be seen that, in the mirror electron region, the lower the landing energy LE is, the more the signal intensity increases.

FIG. 149B shows an example different from that in FIG. 149A, and FIG. 149B also shows a relation between the landing energy of the electron beam for the irradiation and "signal intensity/average gray level" of reflected electrons. In FIG. 149B, the region in which the landing energy LE is 5 eV or less is a region in which a mirror-electron-based signal (white) is acquired, and the region in which the landing energy LE is 5 eV or more is a region in which a secondary emission-electron-based signal (black) is acquired.

The characteristic line in FIG. 149B is different from that in FIG. 149A in that the landing energy LE at the boundary between the mirror-electron-based signal and the secondary emission-electron-based signal is 5 eV. The boundary of the landing energy LE between mirror electrons and secondary emission electrons varies depending on the properties of the sample 20, the profile of the electron beam, and the like, and can take on various values. The electron beam inspection method and electron beam inspection device according to the embodiment will hereinafter be described based on the example in FIG. 149A (the example in which the landing energy LE at the boundary is 10 eV). The invention is not limited to this, however. As shown in FIG. 149B, the invention may be applied when the landing energy at the boundary is 10 eV or less and, for example, the landing energy at the boundary may be 5 eV.

In FIG. 149A and FIG. 149B, the region in which the landing energy is the boundary or less corresponds to the transition region of the invention, where mirror electrons and secondary emission electrons are mixed. The region in which the landing energy is the boundary or more corresponds to the secondary emission electron region of the invention. As described above, the boundary landing energy is 10 eV in the example in FIG. 149A, and 5 eV in the example in FIG. 149A.

Figure 150:
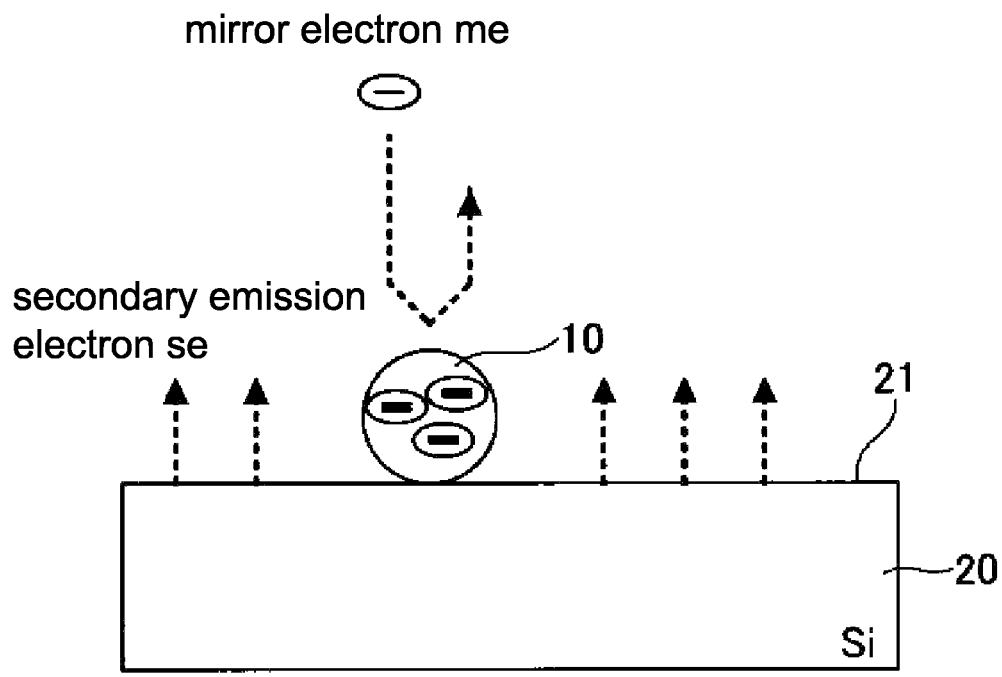
FIG. 150 is a diagram related to one embodiment of the present invention.

FIG. 150 shows a state where the foreign material 10 is present on the sample surface 21 of the sample 20. As illustrated, electrons are generated by irradiation with an electron beam. When the landing energy LE$\leqq$10 eV; the foreign material 10 is negatively charged up. If an electron beam enters the foreign material 10, an electron of the electron beam becomes a mirror electron me. The electron is therefore reflected from the foreign material 10 without colliding therewith, and reaches the detector 70. Meanwhile, in the normal part where the foreign material 10 is not present (the sample surface 21), a secondary emission electron se is generated by the irradiation with the primary electron beam.

Here the "secondary emission electron se" means a secondary electron, a reflected electron, or a backscattered electron. A mixture of them also corresponds to the "secondary emission electron se."

The emission coefficient 11 of such secondary emission electrons is generally low. In particular when the landing energy LE is approximately 50 eV or less, the emission coefficient 11<1.0. The closer the landing energy LE comes to zero, the lower the emission coefficient becomes; and the emission coefficient is almost zero when the landing energy LE=0.

There is also a distribution in the emission angle of electrons. For example, secondary electrons are distributed according to the cosine law. The transmittance of electrons that reach the detector 70 is therefore several percent or less in the projection optical system.

On the other hand, the mirror electron me is generated by an incident electron reflecting just before colliding with the foreign material 10. The mirror electron me is reflected from the foreign material 10 and enters a lens system of a secondary system at an angle approximately symmetrical to the angle of the incident primary electron beam. The scattering and emission distribution are therefore small, and the mirror electron me reaches the detector 70 at a transmittance of approximately 100 percent.

Figure 151A:
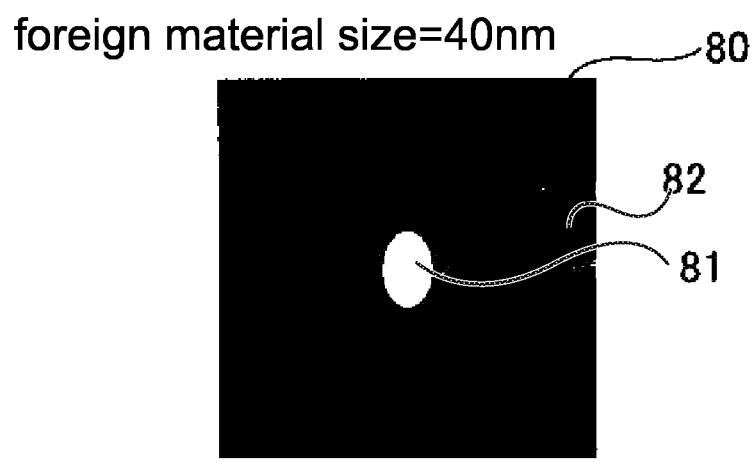
FIG. 151A is a diagram related to one embodiment of the present invention.

FIG. 151A shows the image 80 of the foreign material 10 on the sample surface 21 to be acquired when the landing energy LE is 10 eV or less, and FIG. 151B shows the gray-level value of the image 80.

Referring to FIG. 151A, in the image of the sample surface 21 and foreign material 10, the magnified image 81 of the foreign material 10 is shown as a white area, and the surface image 82 of the sample surface 21 is shown as a black area. In this case, the brightness (the gray level) is very high in a part where the mirror electron me is obtained.

FIG. 151B is an example of a relation between the y-direction cross-sectional position on the image 80 in the detector 70 and the gray-level value. The range in the y direction includes the magnified image 81 of the foreign material 10. As shown in FIG. 151B, for example, the gray level of the mirror electron part is about three times as high as the part where the mirror electron me is not obtained. As a result, high brightness and a high S/N ratio can be achieved.

In the example in FIG. 151B, the part where the mirror electron me is obtained exhibits about three times as high gray-level value DN as the part where the mirror electron me is not obtained. The relation of the gray-level value, however, varies depending on conditions or the like. The gray-level value of the mirror electron part may take on an about two to ten times higher value.

Figure 152:
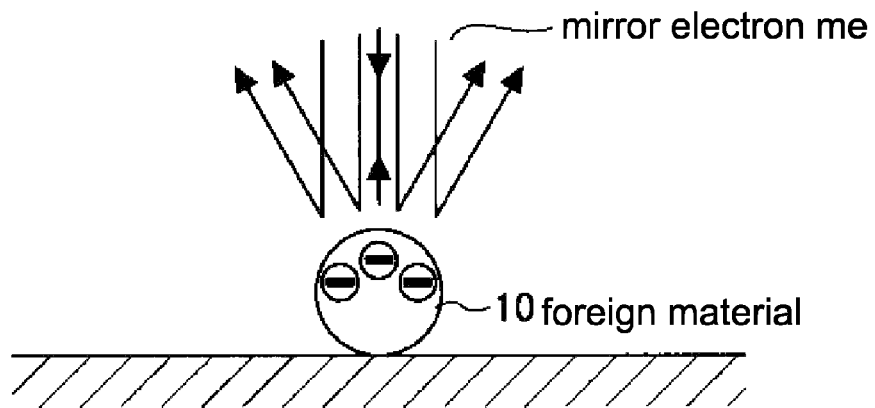
FIG. 152 is a diagram related to one embodiment of the present invention.

FIG. 152 shows a state where the mirror electron me is generated from the foreign material 10 by the irradiation of the foreign material 10 with the electron beam. The shape of the foreign material 10 causes a shift in the reflection point of the mirror electron me and the nonuniformity of the chargeup voltage. For this reason, the path and energy of the mirror electron me are slightly shifted. Consequently, when the mirror electron me goes through a lens, beam filter, and the like of the secondary system, the size of the signal area becomes large.

FIG. 152, the reflection direction of the mirror electron me radially spreads out from the effect of the surface potential of the foreign material 10. Consequently, in a signal from the foreign material 10 that has reached the detector 70, the signal size is magnified more than the optical magnification of the electron optical system. The magnification is, for example, 5 to 50 times.

For example, suppose that there is a secondary system with 100 times optical magnification. The signal size in the detector 70 for secondary electrons from the foreign material 10 is 100 times×0.1 µm=10 µm, according to a theoretical calculation.

On the other hand, the signal size of the mirror electron me from the foreign material 10 is magnified, for example, 30 times. Accordingly, the size of a signal entering the detector 70 is 300 µm. This phenomenon is equivalent to a magnification optical system that simply magnifies 100 nm (0.1 µm) to 300 um. That is, a 3000 times magnification optical system is achieved. This means that a pixel size larger than the foreign material 10 can be used. If the foreign material 10 is 100 nm, the pixel size may be larger than 100 nm. A pixel size of 300 to 1000 nm can be used.

By using a pixel size larger than an object foreign material, a large area on the sample surface 21 of the sample 20 can be inspected at a time. This is therefore very effective in terms of quick inspection. For example, the inspection rate for a pixel size of 300 nm can be nine times faster than for a pixel size of 100 nm. The inspection rate can be 25 times faster for a pixel size of 500 nm. That is, if one inspection would conventionally take 25 hours, the embodiment requires one hour for the inspection. In contrast to this, imaging by the SEM method has to be performed with a pixel size smaller than the size of the foreign material, since the SEM method comprises forming a precise shape image, comparing it with an image of a normal part, and thereby detecting the foreign material.

As described above, the projection optical system not only can enhance the difference in brightness between the mirror electron me and the secondary emission electron se, but also can achieve speedups.

When the landing energy LE≦10 eV, precharge can be used suitably. Precharge is carried out by irradiating with a charging electron beam before imaging.

Precharge may be carried out in order to increase the charge-up voltage of the foreign material 10. Precharge may also be carried out in order to reduce the change in potential of the foreign material 10 during imaging. In the foreign material inspection method, the amount of change in the charge-up voltage is controlled by a landing energy LE1 of a charging beam. For example, there are foreign materials 10 of various sizes and various capacities. In this case, foreign materials 10 that are charged to a certain charge-up voltage or less are detected by using mirror electrons. The path of the mirror electrons is adapted by the difference between the surrounding sample voltage and the charge-up voltage, and consequently a state can be formed in which the transmittance of the mirror electrons is 11 igh. This will be described in detail later.

Methods for precharge will next be described. There are three methods for precharge.

[Precharge-1]

Figure 153A:
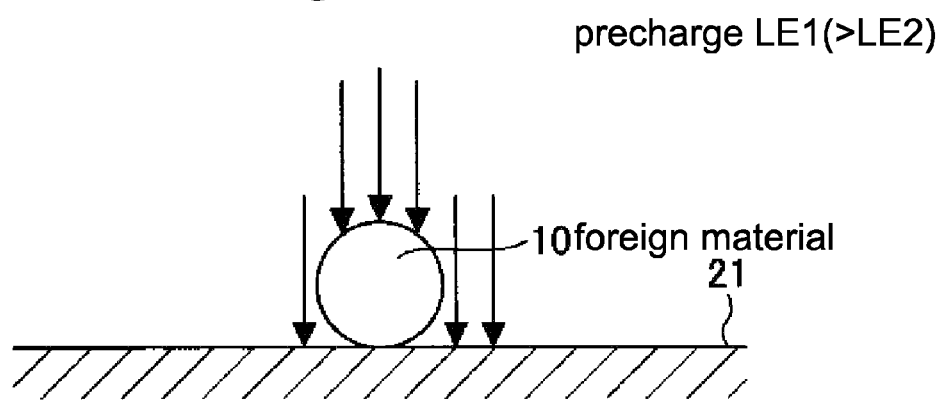
FIG. 153A is a diagram related to one embodiment of the present invention.
Figure 153B:
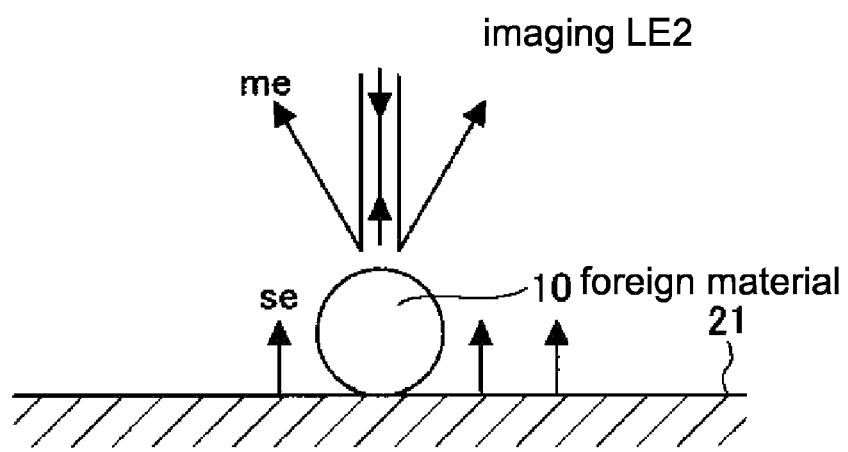
FIG. 153B is a diagram related to one embodiment of the present invention.

FIG. 153A and FIG. 153B illustrate a first precharge mode (Precharge-1). Here the landing energy of the charging electron beam is LE1, and the landing energy of the imaging electron beam is LE2. In Precharge-1, the landing energy is set as LE2<LE1, which facilitates generation of mirror electrons.

In FIG. 153A, the foreign material 10 is present on the sample surface 21, which is irradiated with the charging electron beam with the landing energy LE1, and precharge is thus performed. The landing energy LE1 for the precharge is larger than the landing energy LE2 of the imaging electron beam. This increases the charge-up voltage of the foreign material 10, causing electrons to become mirror electrons easily during imaging. That is, by increasing the absolute value of the negative potential of the foreign material 10, a reflection point in the potential distribution created by the charge up is formed in front of the foreign material 10. Consequently, the incident imaging electron beam is reflected, becoming the mirror electron me, before colliding with the foreign material 10.

FIG. 153B shows a state where the foreign material 10 on the sample surface 21 is irradiated with the imaging electron beam. In FIG. 153B, the foreign material 10 is negatively charged up and has a negative-voltage potential distribution. The imaging electron beam has the landing energy LE2 as described above. Under the effect of the surface potential of the foreign material 10, an incident electron is reflected, becoming the mirror electron me, in front of the foreign material 10 without colliding therewith. Meanwhile, the secondary emission electron se is reflected from the sample surface 21 by being emitted therefrom.

As seen above, in the configuration shown in FIG. 153A and FIG. 153B, the landing energy LE1 of the charging electron beam is set larger than the landing energy LE2 of the imaging electron beam. This allows the mirror electron me to be suitably generated from the imaging electron beam with which the foreign material 10 is irradiated, so that the magnified image 81 of the foreign material 10 can be acquired.

[Precharge-2]

FIG. 154 illustrates a second precharge mode (Precharge-2). In Precharge-2, the landing energy LE2 of the imaging electron beam is set larger than the landing energy LE1 of the charging electron beam. In the foreign material inspection method, imaging can be carried out with an appropriate potential variation being made during the imaging.

In FIG. 154, the horizontal axis represents the landing energy of electron beams, and the vertical axis represents the surface potential of the foreign material 10. The landing energy LE1 of the charging electron beam is smaller than the landing energy LE2 of the imaging electron beam. The surface potential of the foreign material 10 varies between LE1 and LE2. The potential difference $\Delta V$ is small as illustrated.

Precharge-2 in FIG. 154 is suitable when the landing energy LE2 of the imaging electron beam appropriate to imaging is known in advance. Simply imaging with the imaging electron beam with the appropriate landing energy LE2 would cause variations in the surface potential of the foreign material 10 during imaging and might be incapable of obtaining the accurate magnified image 81. Precharge-2 avoids such a situation. In the configuration of Precharge-2, the surface potential of the foreign material 10 is controlled by the precharge to reach close to the optimum value. This allows the potential change $\Delta V$ in the surface potential of the foreign material 10 to be reduced during imaging.

[Precharge-3]

Figure 155:
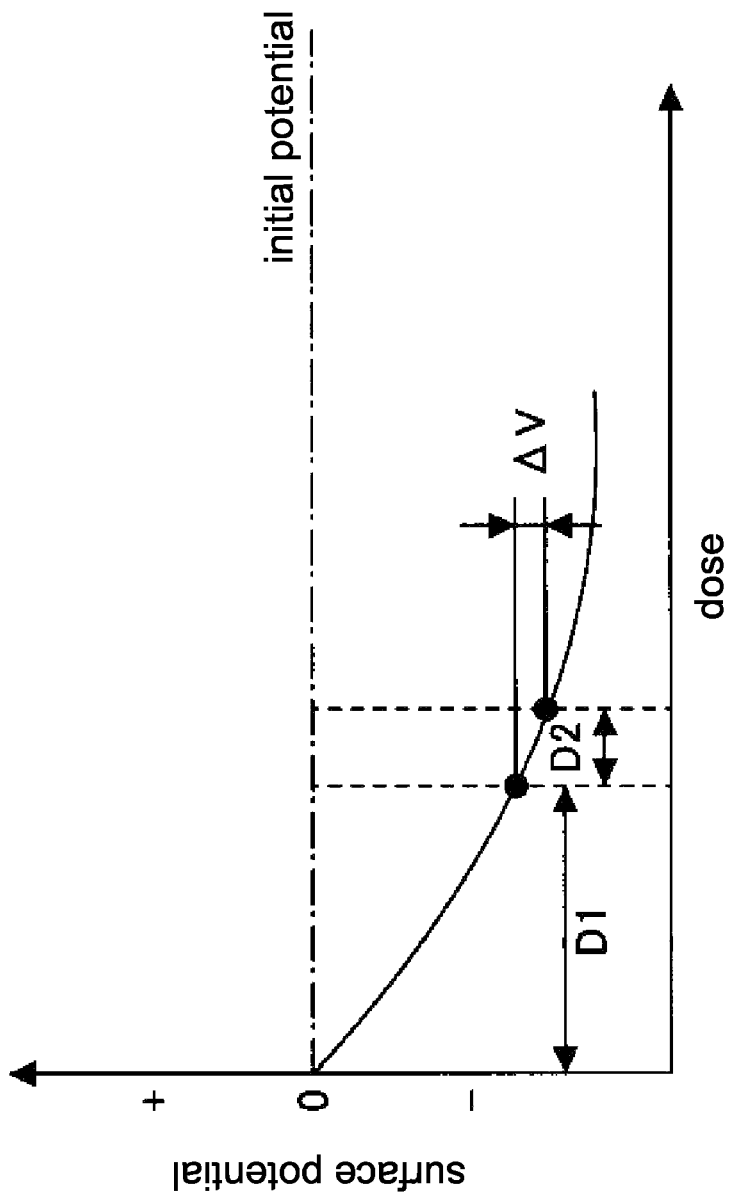
FIG. 155 is a diagram related to one embodiment of the present invention.

FIG. 155 illustrates a third precharge mode (Precharge-3). In Precharge-3, the landing energy LE1 of the charging electron beam is set equal to the landing energy LE2 of the imaging electron beam. The dose amount is then made to differ between the charging electron beam and the imaging electron beam. In FIG. 155, the horizontal axis represents the dose amount, and the vertical axis represents the surface potential of the foreign material 10.

Precharge-3 is effective for stabilizing the chargeup voltage of the foreign material 10 to achieve stable imaging and sensitivity. In FIG. 155, a change in the dose amount causes variation in the surface potential of the foreign material 10. The precharge is carried out so as to give a dose D1 close to the required dose amount. A dose D2 is then given to perform imaging. Such a configuration is effective, and can reduce the potential variation $\Delta V$ of the surface of the foreign material during the imaging with the dose D2. Stable image quality (shape, focus, and the like) can therefore be achieved.

In the three types of precharges in FIG. 153 to FIG. 155, the beam source of the charging electron beam for precharge may be the same as that of the imaging electron beam, and the conditions of the beam source may be controlled so as to carry out the above-described precharges. A precharge unit for precharge may also be provided separately. This can improve the throughput.

The precharge unit may use a cathode comprising, for example, LaB6, a W filament, a hollow cathode, a carbon nanotube, or the like. The precharge unit may also use a Wehnelt for extracting the electron beam, an extraction electrode, a lens for controlling the irradiation area, and the like. The beam size of the precharge unit may be equal to or a little larger than the beam size for regular irradiation by the column system. The landing energy of the electron beam is determined by the voltage difference between the cathode and the sample. For example, suppose that a negative voltage −3000 V is applied to the sample 20. Suppose also that the landing energy of the electron beam is set to 10 eV. In this case, a cathode voltage −3010 V is applied to the cathode to generate the electron beam.

(Another Inspection Method (for LE>10 eV))

Figure 156:
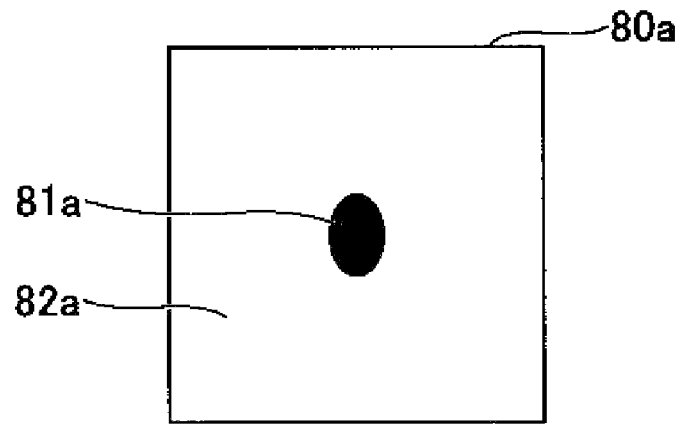
FIG. 156 is a diagram related to one embodiment of the present invention.

FIG. 156 shows an image 80a acquired by the detector 70 when the landing energy LE of the electron beam is larger than 10 eV. In FIG. 156, a magnified image 81a of the foreign material 10 is represented by a black signal, and a surface image 82a of the sample 20 is represented by a white signal.

Figure 157C:
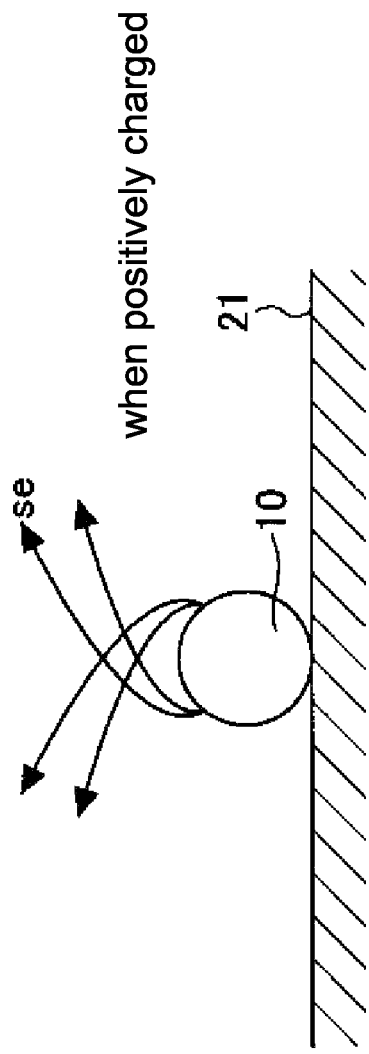
FIG. 157C is a diagram related to one embodiment of the present invention.

FIG. 157A to FIG. 157C show the secondary emission electron se being emitted from the foreign material 10 by irradiation with the imaging electron beam.

FIG. 157A shows a behavior of the secondary emission electron se in a state where the foreign material 10 is charged up and the potential difference between the foreign material 10 and the surrounding sample surface 21 is large. In FIG. 157A, the foreign material 10 is negatively charged up, and the path of the secondary emission electron se from the foreign material 10 is bent. For this reason, the transmittance (the ratio of electrons that reach the detector 70) extremely decreases. As a result, the brightness of the foreign material part in the observed image decreases as compared to the surroundings. This means that the foreign material 10 is detected as a black signal.

FIG. 157B shows a behavior of the secondary emission electron se in a state where the potential difference between the foreign material 10 and the surrounding sample surface 21 is small. In FIG. 157B, since the potential difference between the foreign material 10 and the surroundings is small, electrons are generated from the foreign material 10 and from the sample surface 21 in almost the same manner. For this reason, it is difficult to distinguish the foreign material 10 from the surroundings. That is, it is difficult to detect the foreign material 10 from an acquired image. It is desired to avoid such a situation. So, even when the secondary emission electron se is to be detected from the foreign material 10, it is suitable to charge up the foreign material 10 by irradiation with the charging electron beam. Applying the imaging electron beam after the charge up facilitates detection of the foreign material 10 as described above.

FIG. 157C shows a behavior of the secondary emission electron se in the positive charge region. In the positive charge region, the secondary emission electron se follows a path through which it is drawn by the foreign material 10 for a moment and then rises. As illustrated, the path of the secondary emission electron se is bent by the effect of the potential distribution of the foreign material 10, and the number of electrons that reach the detector 70 decreases. This phenomenon is the same as FIG. 156A. Consequently, the same phenomenon is observed and the magnified image 81a of the foreign material 10 is obtained as an image of a black signal also in the positive charge.

In a foreign material inspection method and foreign material inspection device according to the embodiment, an electron beam projection method is used in order to further enhance the throughput. The use of a projection system allows the secondary emission electron se or mirror electron me from the sample surface 21 to be used to detect foreign materials such as wafers and masks at high speed and high throughput, so that, for example, foreign material inspection after sample cleaning is suitably carried out. As described above, since a detection signal from the foreign material 10 is magnified more than the optical magnification, a signal of the foreign material 10 of an ultra-micro size can be obtained with a large pixel size, so that high speed and high throughput is achieved.

For example, the size of the foreign material signal can be magnified 5 to 50 times the actual size. A pixel size which is three times or more the size of a foreign material to be detected can be applied. This is particularly effective for the foreign material 10 of a size of 50 to 100 nm or less. The optical method has difficulty detecting the foreign material 10 of such size. The SEM method is required to use a pixel size smaller than the foreign material size. The throughput therefore significantly decreases if a small foreign material is to be detected. In the electron beam inspection method according to the embodiment, the foreign material 10 on a wafer in process can be quickly detected by using the projection method. The acquisition of the magnified images 81 and 81a allows the foreign material 80 to be detected reliably.

(The Electron Beam Inspection Device)

FIG. 43 shows the structure of the electron beam inspection device applied to one embodiment of the present invention. A foreign material inspection device applied to carry out the above-described foreign material inspection methods will be described here. Accordingly, all the foreign material inspection methods described above can be applied to the foreign material inspection device described below.

The electron beam inspection device is to inspect the sample 20. The sample 20 is a silicon wafer, a glass mask, a semiconductor substrate, a semiconductor pattern substrate, a substrate having a metal film, or the like. The electron beam inspection device according to the embodiment detects the presence of the foreign material 10 on a surface of the sample 20 comprising such a substrate. The foreign material 10 is an insulating material, a conductive material, a semiconductor material, a composite thereof, or the like. The type of the foreign material is particle, noncleaned residue (organic matter), reaction product on the surface, or the like. The electron beam inspection device may be an SEM-type device or a projection-type device. In this example, the invention is applied to a projection-type inspection device.

The projection-type electron beam inspection device comprises: a primary optical system 40 for generating an electron beam; the sample 20; a stage 30 for placing the sample thereon; a secondary optical system 60 for forming a magnified image of secondary emission electrons or mirror electrons from the sample; the detector 70 for detecting those electrons; an image processing device 90 (an image processing system) for processing a signal from the detector 70; an optical microscope 110 for positioning; and an SEM 120 for reviewing. In the invention, the detector 70 may be included in the secondary optical system 60. The image processing device 90 may be included in the image processor of the invention.

The primary optical system 40 is configured to generate an electron beam and emit it toward the sample 20. The primary optical system 40 has: an electron gun 41; lenses 42 and 45; apertures 43 and 44; an E×B filter 46; lenses 47, 49, and 50; and an aperture 48. The electron gun 41 generates the electron beam. The lenses 42 and 45 and the apertures 43 and 44 shape the electron beam and control the direction thereof. The electron beam is then affected by a Lorentz force caused by the magnetic and electric fields in the E×B filter 46. The electron beam obliquely enters the E×B filter 46, and is deflected vertically downward toward the sample 20. The lenses 47, 49, and 50 control the direction of the electron beam and appropriately reduce the speed thereof to adjust the landing energy LE.

The primary optical system 40 irradiates the sample 20 with the electron beam. As described before, the primary optical system 40 carries out both the charging electron beam irradiation for precharge and the imaging electron beam irradiation. According to an experimental result, the difference between the landing energy LE1 for the precharge and the landing energy LE2 of the imaging electron beam is preferably 5 to 20 eV.

Suppose in this regard that the irradiation for the precharge is carried out with the landing energy LE1 in the negative charge region when there is a potential difference between the foreign material 10 and the surroundings. The charge-up voltage varies depending on the value of LE1, since the relative ratio between LE1 and LE2 varies (LE2 is the landing energy of the imaging electron beam as described above). A large LE1 increases the charge-up voltage, causing a reflection point to be formed at a position above the foreign material 10 (a position closer to the detector 70). The path and transmittance of mirror electrons vary depending on the position of this reflection point. An optimum charge-up voltage condition is therefore determined according to the reflection point. A too low LE1 decreases the efficiency of the mirror electron formation. In the invention, it has been found that this difference between LE1 and LE2 is desirably 5 to 20 eV. The value of LE1 is preferably 0 to 40 eV, and more preferably 5 to 20 eV.

The E×B filter 46 is especially important in the primary optical system 40 which is a projection optical system. The angle of the primary electron beam can be determined by adjusting electric and magnetic field conditions of the E×B filter 46. For example, conditions of the E×B filter 46 can be set so that the irradiation electron beam of the primary system and the electron beam of the secondary system make approximately a right angle with the sample 20. It is effective for further increasing the sensitivity, for example, to tilt the incident angle of the electron beam of the primary system upon the sample 20. An appropriate tilt angle is 0.05 to 10 degrees, and preferably about 0.1 to 3 degrees.

Figure 159:
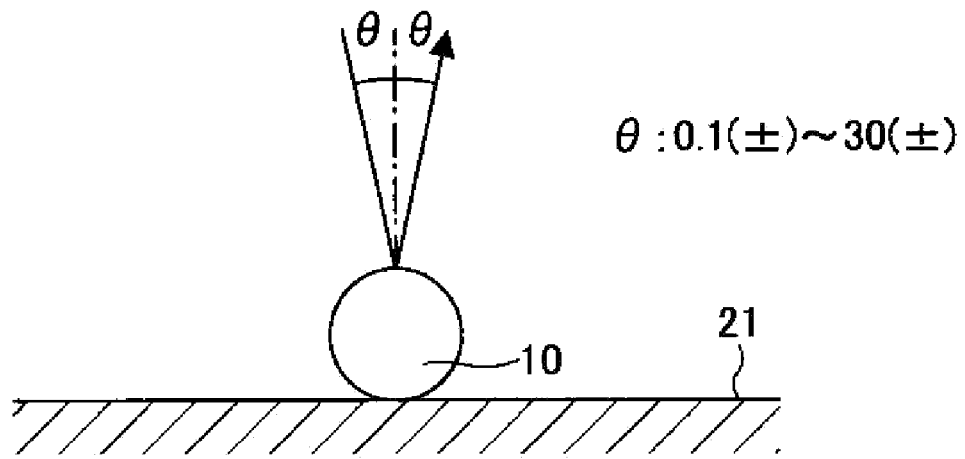
FIG. 159 is a diagram related to one embodiment of the present invention.

In FIG. 159, the foreign material 10 present on the sample surface 21 is irradiated with the primary electron beam. The tilt angle of the electron beam is θ. The angle θ may be, for example, within a range of ±0.05 to 10 degrees, and preferably within a range of ±0.1 to 3 degrees.

As seen above, irradiating the foreign material 10 with an electron beam tilted at a certain angle θ can enhance the signal from the foreign material 10. This can create a condition in which the path of mirror electrons does not deviate from the center of the optical axis of the secondary system, and can therefore increase the transmittance of the mirror electrons.

The tilted electron beam is thus very advantageously used when the foreign material 10 is charged up and the mirror electrons are guided.

Returning to FIG. 158, the stage 30 is a means of placing the sample 20 thereon, and can move in the x-y horizontal directions and in the θ direction. The stage 30 may also be movable in the z direction as required. On the surface of the stage 30 may be provided a sample fixing mechanism such as an electrostatic chuck.

On the stage 30 is present the sample 20, on which the foreign material 10 is present. The primary optical system 40 irradiates the sample surface 21 with an electron beam with a landing energy LE of −5 to −10 eV. The foreign material 10 is charged up, and incident electrons from the primary optical system 40 are bounced back without coming into contact with the foreign material 10. This allows the mirror electrons to be guided through the secondary optical system 60 to the detector 70. At the same time, secondary emission electrons are emitted in spreading directions from the sample surface 21. The transmittance of the secondary emission electrons therefore takes on a low value, for example, of about 0.5% to 4.0%. In contrast to this, since the mirror electrons are not scattered in directions, a high transmittance of approximately 100% can be achieved for the mirror electrons. The mirror electrons are formed by the foreign material 10. Only the signal from the foreign material 10 can therefore cause a high brightness (a state where the number of electrons is large). The difference in brightness from and the brightness ratio to the surrounding secondary emission electrons increase, allowing a high contrast to be obtained.

As described above, an image of the mirror electrons is magnified at a magnification larger than the optical magnification. The magnification reaches 5 to 50 times. Under typical conditions, the magnification is often 20 to 30 times. In such a case, a foreign material can be detected even if the pixel size is three times or more larger than the size of the foreign material. High speed and high throughput can therefore be achieved.

For example, when the size of the foreign material 10 is 20 nm in diameter, the pixel size may be 60 nm, 100 nm, 500 nm, or the like. Like this example, a foreign material can be imaged and inspected for by using a pixel size three times or more larger than the foreign material. This is a characteristic significantly superior to the SEM method and the like in achieving high throughput.

The secondary optical system 60 is a means of guiding electrons reflected from the sample 20 to the detector 70. The secondary optical system 60 has: lenses 61 and 63; an NA aperture 62; an aligner 64; and the detector 70. Electrons are reflected from the sample 20 and go through the objective lens 50, lens 49, aperture 48, lens 47, and E×B filter 46 again. The electrons are then guided to the secondary optical system 60. In the secondary optical system 60, the electrons go through the lens 61, NA aperture 62, and lens 63 to be collected. The electrons are aligned by the aligner 64, and are detected by the detector 70.

The NA aperture 62 has a function of defining the transmittance and aberration of the secondary system. The size and position of the NA aperture 62 are selected so as to widen the difference between the signal (mirror electrons etc.) from the foreign material 10 and the signal from the surroundings (the normal part). Alternatively, the size and position of the NA aperture 62 are selected so as to increase the ratio of the signal from the foreign material 10 to the signal from the surroundings. Consequently, the S/N ratio can be increased.

For example, suppose that the NA aperture 62 can be selected in a range from φ50 to φ3000 μm. Suppose also that mirror electrons and secondary emission electrons are mixed in detected electrons. In order to improve the S/N ratio of a mirror electron image under such conditions, the selection of the aperture size is advantageous. In this case, the size of the NA aperture 62 is preferably selected so that the transmittance of the secondary emission electrons can be reduced to maintain the transmittance of the mirror electrons.

For example, when the incident angle of the primary electron beam is 3 degrees, the angle of reflection of the mirror electrons is almost 3 degrees. In this case, it is preferable to select a size of the NA aperture 62 large enough to be able to let the path of the mirror electrons through. An appropriate size is φ250 μm, for example. The transmittance of the secondary emission electrons decreases since they are limited by the NA aperture (φ250 μm in diameter). Consequently, the S/N ratio of a mirror electron image can be improved. For example, if the aperture diameter is changed from φ2000 to φ250 μm, the background gray level (noise level) can be reduced to ½ or less.

Figure 160A:
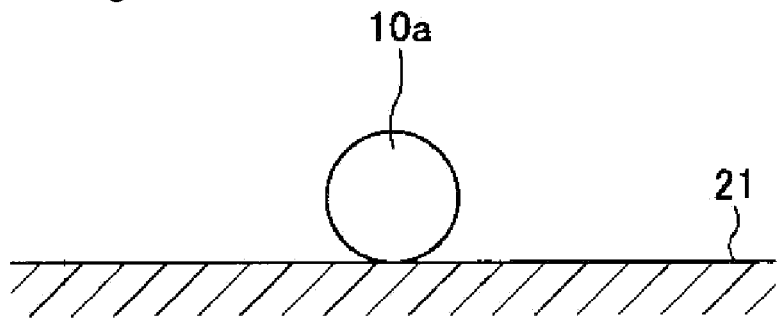
FIG. 160A is a diagram related to one embodiment of the present invention.
Figure 160B:
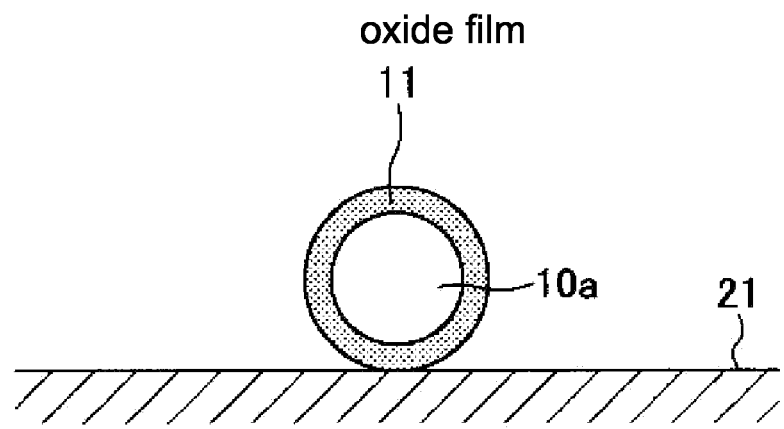
FIG. 160B is a diagram related to one embodiment of the present invention.

The foreign material 10 may be formed of a material of any type, and may be, for example, a semiconductor, an insulating material, a metal, or the like. FIG. 160A and FIG. 160B show a foreign material 10a made of a metallic material, present on the sample surface 21. FIG. 160B is an enlarged view of the foreign material 10a made of a metallic material. In FIG. 160B, the foreign material 10a may be a metal, a semiconductor, or the like, or a mixture thereof. As illustrated, a natural oxide film 11 or the like is formed on the surface of the foreign material, and therefore the foreign material 10 is covered by an insulating material. Accordingly, even if the material of the foreign material 10 is a metal, the charge up occurs on the oxide film 11. This charge up is suitably used in the invention.

Returning to FIG. 158, the detector 70 is a means of detecting the electrons guided by the secondary optical system 60. The detector 70 has a plurality of pixels on its surface. Various two-dimensional sensors can be applied to the detector 70. For example, a CCD (charge coupled device) and a TDI (time delay integration)-CCD may be applied to the detector 70. These are sensors for detecting a signal after converting electrons to light, and therefore require a means of photoelectric conversion or the like. Photoelectric conversion or a scintillator is therefore used to convert the electrons to light. Image information of the light is transmitted to the TDI that detects light. The electrons are thus detected.

An example where an EB-TDI is applied to the detector 70 will be described here. An EB-TDI does not require a photoelectric conversion mechanism and a light transmission mechanism. Electrons directly enter the sensor surface of an EB-TDI. Consequently, the resolution does not deteriorate, so that a high MTF (modulation transfer function) and high contrast can be obtained. Conventionally, detection of the foreign material 10 of a small size would be unstable. In contrast to this, the use of an EB-TDI can increase the S/N ratio of a weak signal of the small foreign material 10. A higher sensitivity can therefore be obtained. The S/N ratio improves up to 1.2 to 2 times.

An EB-CCD may also be provided in addition to the EB-TDI. The EB-TDI and the EB-CCD may be interchangeable, and may be arbitrarily interchanged. It is also effective to use such a configuration. For example, a method of use shown in FIG. 161 is applied.

Figure 161:
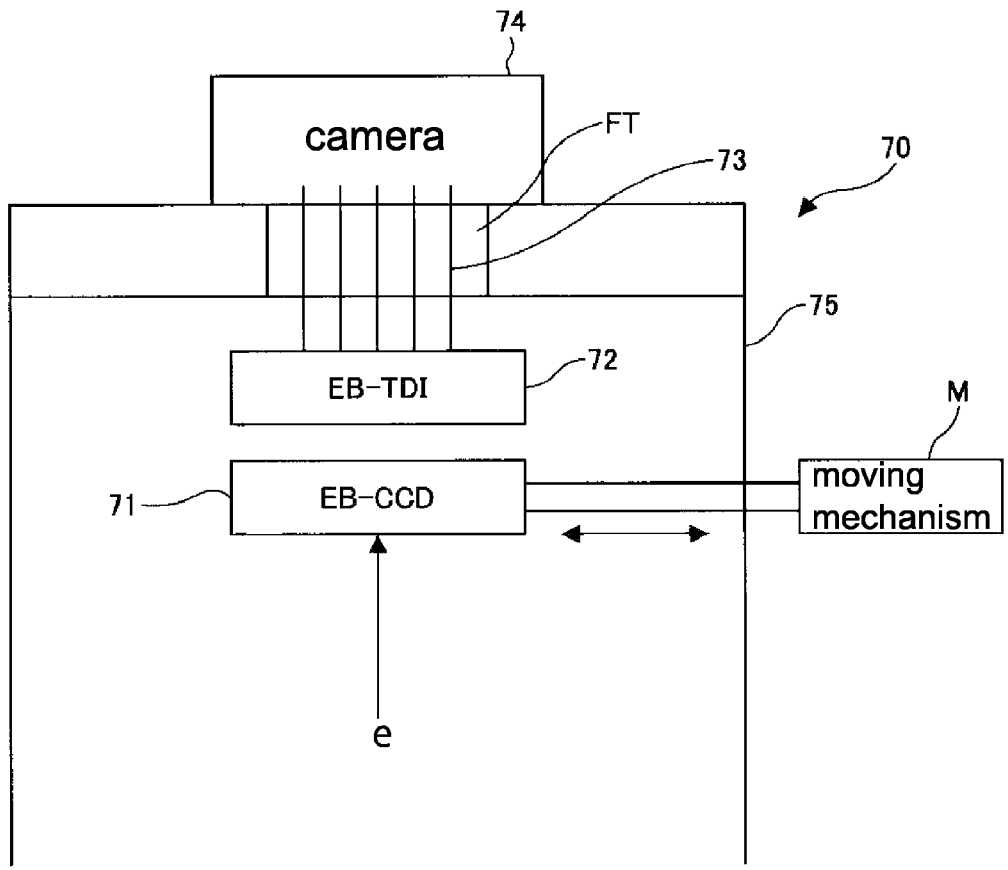
FIG. 161 is a diagram related to one embodiment of the present invention.

FIG. 161 shows the detector 70 in which an EB-TDI 72 and an EB-CCD 71 can be interchanged. The two sensors can be interchanged depending on the intended use, and both sensors can be used.

In FIG. 161, the detector 70 comprises the EB-CCD 71 and the EB-TDI 72. The EB-CCD 71 and the EB-TDI 72 are electron sensors for receiving an electron beam. The electron beam e is made to enter the detection surface directly. In this configuration, the EB-CCD 71 is used to adjust the optical axis of the electron beam, and is also used to adjust and optimize imaging conditions. On the other hand, when the EB-TDI 72 is to be used, the EB-CCD 71 is moved by a moving mechanism M to a position away from the optical axis. A condition determined by using the EB-CCD 71 is then used or referred to, to image using the EB-TDI 72. The image is used to carry out evaluation or measurement. Furthermore, the movement mechanism M is formed to be able to move the EB-CCD 71 not only in an X direction but tri-axially (for example, X, Y, Z directions) and may be formed so to be able to adjust the center of the EB-CDD with respect to the optical axis of the electron optical system.

With the detector 70, an electron optical condition determined by using the EB-CCD 71 can be used or referred to, to detect foreign materials on a semiconductor wafer using the EB-TDI 72.

After the foreign material inspection using the EBTDI 72, the EB-CCD 71 may be used to carry out review imaging and make a defect evaluation of the type and size of foreign materials or the like. The EB-CCD 71 can integrate images. The integration can reduce noise. Consequently, review imaging of an area where a defect has been detected can be carried out with a high S/N ratio. In addition, it is effective for pixels of the EB-CCD 71 to be smaller than those of the EB-TDI 72. This means that the number of pixels of the imaging device can be large relative to the size of a signal magnified by the projection optical system. As a result, an image with a higher resolution can be obtained. This image is used for inspection, and for classification and determination of the type of defect or the like.

The EB-TDI 72 has a configuration in which pixels are arranged two-dimensionally, and has, for example, a rectangular shape. This allows the EB-TDI 72 to directly receive the electron beam e to form an electron image. The pixel size is, for example, 12 to 16 µm. On the other hand, the pixel size of the EB-CCD 71 is, for example, 6 to 8 µm.

The EB-TDI 72 is formed into a package 75. The package 75 itself functions as a feed through. Pins 73 of the package are connected to a camera 74 on the atmosphere side.

The configuration shown in FIG. 161 can eliminate various faults. Faults to be eliminated are: optical conversion loss caused by an FOP, a hermetic optical glass, an optical lens, and the like; aberration and distortion during light transmission; and the resulting deterioration in image resolution, detection errors, high cost, growth in size, and the like.

Figure 162A:
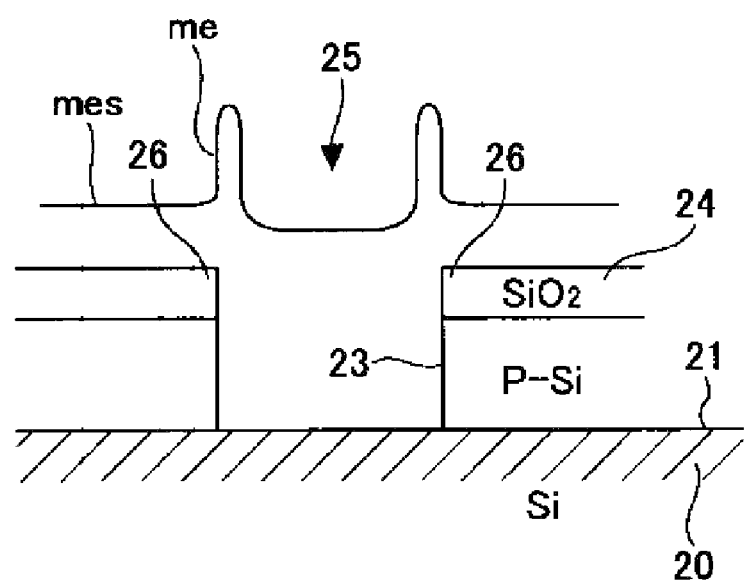
FIG. 162A is a diagram related to one embodiment of the present invention.
Figure 162B:
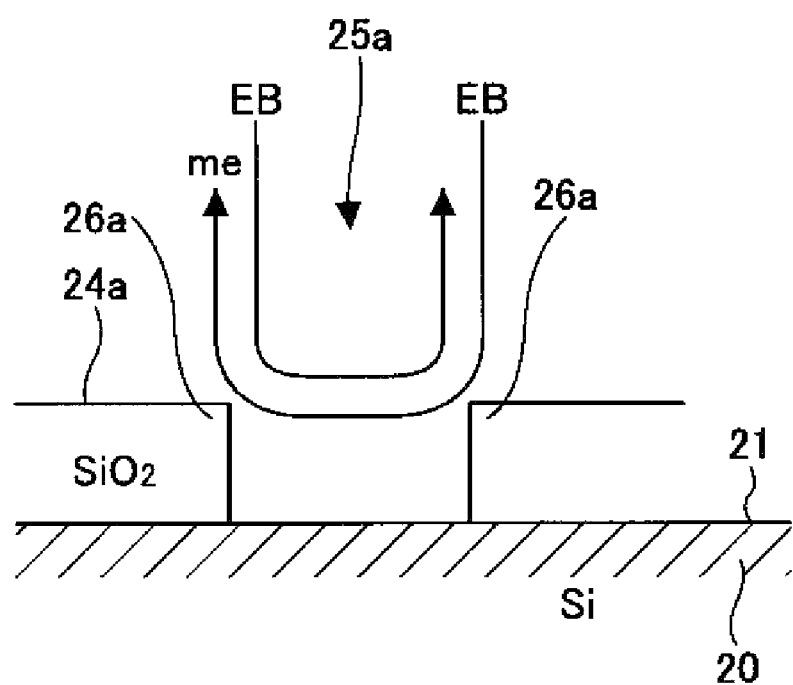
FIG. 162B is a diagram related to one embodiment of the present invention.

FIG. 162A and FIG. 162B illustrate a method of efficiently determining electron beam path conditions, the method being effective when a mirror electron image is to be obtained. The electron beam path conditions are: lens conditions of the lenses 42, 45, 47, 49, 50, 61, and 63 of the primary optical system 40 and secondary optical system 60; and an aligner condition of the aligner 64.

FIG. 162A shows a configuration in which a layered structure of a polysilicon layer 23 and a silicon dioxide film 24 is provided on the sample surface 21 of the sample 20 of a silicon substrate. A hollow groove 25 is formed in a cut in the layered structure. In FIG. 162B, a silicon dioxide layer 24a is formed on the sample surface 21 of the sample 20 of a silicon substrate. A hollow groove 25a is formed in a cut in the layer.

FIG. 162A shows a signal intensity distribution diagram mes of the mirror electron me. A landing energy set in an area where the mirror electron me is generated causes the path of incident electrons to bend easily, causes the mirror electron me to be generated easily at edge parts 26 of the pattern, and causes the signal intensity at the edge parts 26 of the hollow groove 25 to increase.

FIG. 162B shows a path through which an electron beam EB enters and the mirror electron me is reflected. Electrons enter the sample 20, are reflected from an edge part 26a on one side to travel approximately horizontally, move to the opposite side of the hollow groove 25a, and are reflected from an edge part 26a on the opposite side to rise. In this way, mirror electrons are easily generated at the edge parts of the hollow groove 25a.

Such a phenomenon is particularly noticeable in a hollow symmetrical structure. The symmetrical structure is, for example, a Faraday cup, a cross-shaped groove structure, or the like. Here the symmetry of mirror electrons generated at the edge parts 26 and 26a has an effect on the resolution of the image. It is desired to achieve the symmetry of the gray level so that the difference in gray level between both edges in the image is 15% or less. The gray level is the brightness of the image, and the difference in gray level is the difference in the brightness. Adjusting the lens conditions and the aligner condition so as to be able to obtain such symmetry allows the lens and aligner conditions to be optimized for mirror electrons. A mirror electron image with a high resolution can thus be achieved. The S/N ratio can be improved by 10 to 30% and the adjustment time can be reduced by about 10 to 50%, as compared to when this adjustment method is not used.

Figure 163:
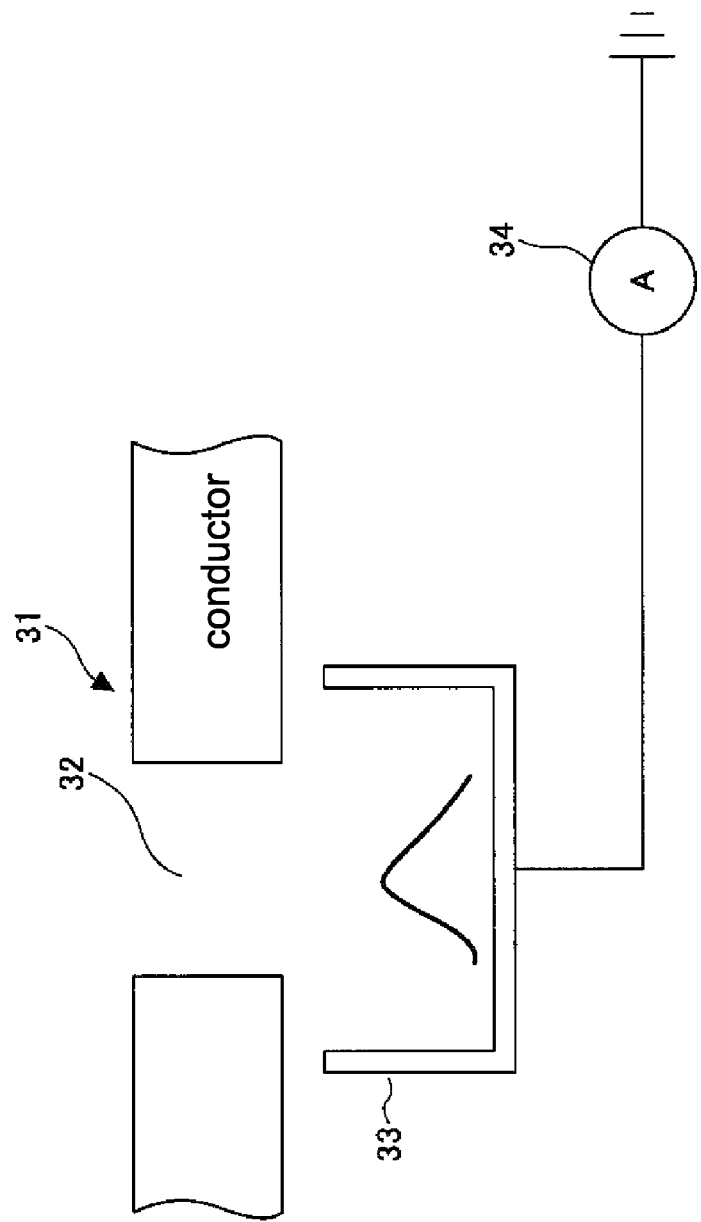
FIG. 163 is a diagram related to one embodiment of the present invention.

FIG. 163 is a cross-sectional side view showing a Faraday cup 31. The Faraday cup 31 comprises an opening 32 in a conductor, and a cupped metal electrode 33. The Faraday cup 31 measures the amount of electrons that have gone through the opening 32 by means of an ammeter 34. The opening 32 may be, for example, about 30 µm in diameter. Since the Faraday cup 31 has a hollow groove shape, mirror electrons are easily generated at the edge parts as described above. The Faraday cup 31 can therefore be used for adjustment.

Figure 158:
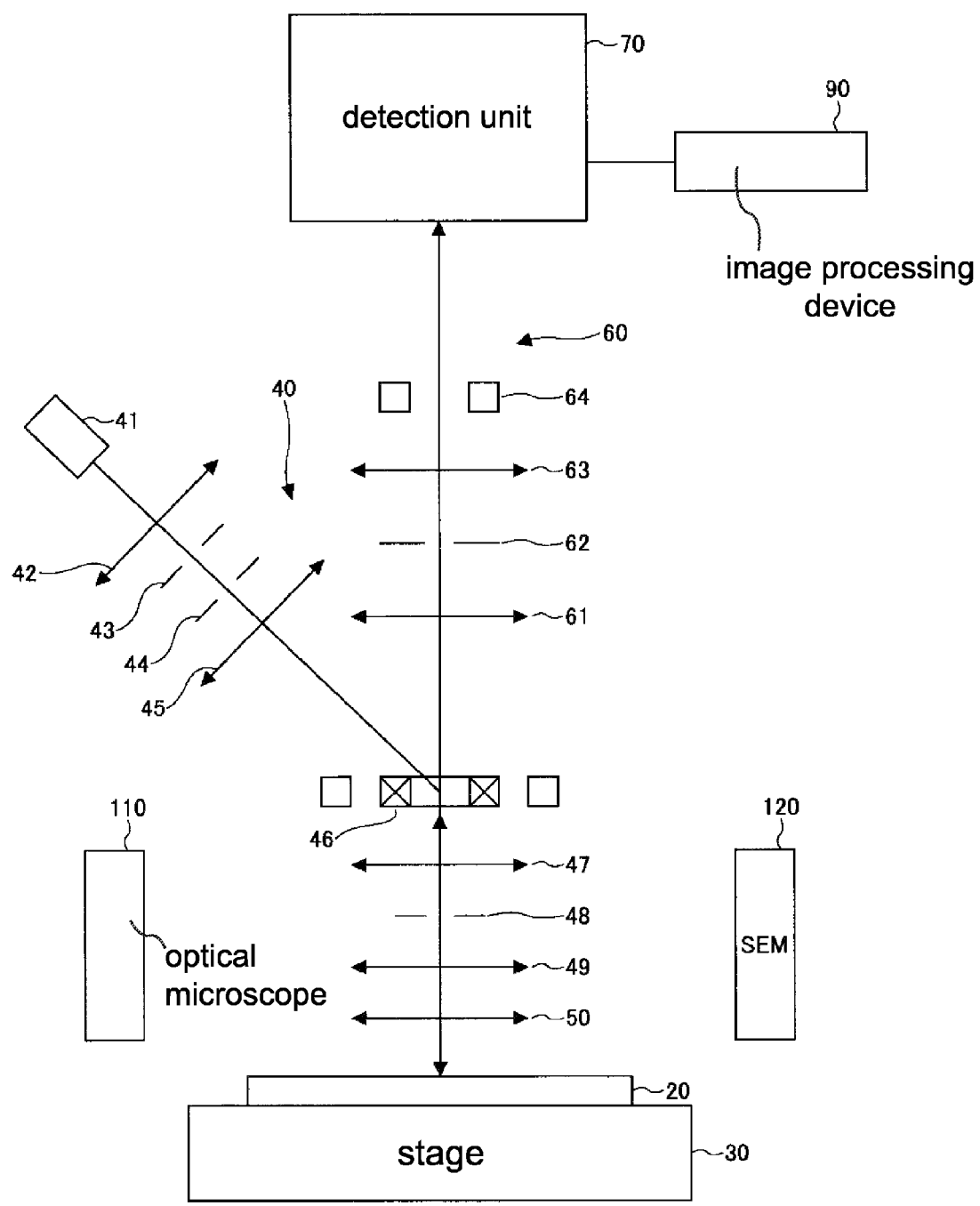
FIG. 158 is a diagram related to one embodiment of the present invention.

An example where the foreign material inspection method according to the invention is applied to the foreign material inspection device in FIG. 158 will next be described.

The aforementioned FIG. 148A shows a correlation between the "secondary electron yield" and the "landing energy LE." This correlation suggests a mechanism for detecting the foreign material 10 using an electron beam with LE>10 eV. The secondary electron emission coefficient varies depending on the landing energy LE with which the foreign material 10 is irradiated. For this reason, a negative charge state and a positive charge state are formed. For example, when the insulating material is SiO2, the following charge states can be seen:

50 eV$\geq$LE: negative charge;
50<LE$\leq$1500 eV: positive charge; and
1500 eV<LE: negative charge.

In each case, the foreign material 10 is charged up, causing the foreign material and the surroundings to be different from each other in the value of the potential, so that the potential distribution around the foreign material is distorted. This distorted electric field significantly bends the path of secondary electrons emitted from the foreign material 10 and reduces the transmittance thereof. Accordingly, electrons that reach the detector from the foreign material are extremely small in number as compared to those from the surroundings of the foreign material. As a result, the brightness for the foreign material becomes lower (black signal) than that for the surroundings, and the foreign material 10 can be detected with a high contrast. The black signal of the foreign material is magnified in size more than the optical magnification. A signal of the foreign material magnified 5 to 20 times can be captured. These phenomenon and detection can be similarly achieved in the above-described three energy regions.

An example of a projection-type electron beam column using an electron beam will next be given. The sample 20 may be a wafer, a mask for exposure, a recording medium, or the like. If it is a wafer, a circuit pattern in process of LSI manufacture may be formed on a silicon wafer of 8 to 12 inches. The wafer may also have no pattern. The wafer may be in a state where it has no pattern after film formation. The wafer may be in a state where it has been subjected to a planarization process, such as grinding and CMP, after film formation. The wafer may be an Si substrate or the like before film formation or other process.

This sample 20 is placed on the x-y-θ control stage 30. The electron beam is emitted from the electron gun 41. The beam irradiation area and the irradiation energy are controlled by the lens 42, the apertures 43 and 44, the quadrupole lens 45, the E×B filter 46, and the like, and the sample surface is irradiated with the electron beam. For example, the beam diameter is φ300 μm (or an ellipse of about 270 μm×80 μm). The projection optical system forms on the detector 70 an image of emission electrons emitted from the sample surface 21 at a magnification of 50 to 500 times. A negative voltage is applied to the sample 20. The potential of the principal plane of the first lens 50 of the primary optical system 40 is positive. Accordingly, a positive electric field is formed near the sample 20. For example, the positive electric field may be 1 to 3 kV/mm. The detector 70 comprises an MCP (micro channel plate), a fluorescent plate, an FOP (fiber optical plate), and a TDI (the internal configuration is not illustrated). The MCP multiplies the amount of electrons to be detected, and the fluorescent plate converts the electrons to an optical signal. This two-dimensional optical signal is transmitted by the FOP, and the TDI sensor forms the image and detects the signal. When the TDI is used, the two-dimensional image signal is acquired with the sample being continuously moved. Consequently, the image signal acquisition can be carried out quickly. The image processing mechanism processes the signal transmitted from the TDI to carry out electron image formation, foreign material detection, and foreign material classification and distinction.

An example where the foreign material 10 on the sample 20 is inspected for by using such an electron beam column will be described. The landing energy LE of the primary electron beam with which the sample 20 is irradiated is set to 2 eV. The landing energy LE is the difference between the cathode voltage of the electron gun 41 of the primary optical system 40 and the voltage (applied voltage) of the sample. Irradiation with this electron beam causes the foreign material 10 to be charged up. Then, only the beam with which the foreign material 10 is irradiated becomes mirror electrons. The mirror electrons are guided by the secondary optical system 60 to the detector 70. From the normal part where the foreign material 10 is not present, secondary emission electrons caused by the beam irradiation are guided to the detector 70. The secondary emission electrons are secondary electrons, reflected electrons, or backscattered electrons. These electrons may be mixed.

Here the closer LE is to zero, the lower the emission coefficient 11 of the secondary emission electrons becomes. In addition, directions of the emission from the surface show a divergent distribution (for example, the distribution of secondary electrons follows the cosine law). For this reason, a design calculation of the secondary emission electrons that reach the detector 70 in the secondary optical system 60 indicates that the arrival rate of the secondary emission electrons is about several percent. As seen above, the arrival rate of the mirror electrons is high, and the arrival rate and emission coefficient of the electrons from the surrounding part are low. Accordingly, there occurs a relatively large ratio between the numbers of electrons, that is, a difference in brightness. Consequently, a large contrast and S/N ratio can be obtained. For example, if the pixel size is 100 nm and the diameter of the foreign material is φ20 nm, the S/N ratio is between 5 and 10. Generally, $S/N \geqq 3$ is sufficient to carry out the detection and inspection. The invention therefore allows inspection for the extremely small foreign material 10 like the above example to be achieved with a pixel size larger than the size of the foreign material.

An example where the charging electron beam for precharge is used in the above-described device system will be described.

LE1 is the landing energy of the charging electron beam for precharge, and LE2 is the landing energy of the electron beam for the imaging and inspection. The insulating foreign material 10 can be efficiently inspected for under conditions LE1: 14 eV and LE2: 1 eV. The foreign material 10 on the surface of Si, an SiO$_2$ film, a metal film, an SOI, a glass mask, or the like can be inspected for. In this process, the whole surface of the inspection area is irradiated with the charging electron beam with LE1=14 eV. Irradiation with the imaging electron beam is then performed with LE2=1 eV to carry out the imaging and inspection for the foreign material 10. The execution of this process depends on how long the effect of the precharge can be maintained. Under normal conditions, the effect of the precharge can be maintained for about 10 to 30 hours, and for 150 hours or more in some cases, if no charge removal process or the like is applied.

As compared to when no precharge is performed, performing such precharge can enhance the effect of the mirror electron formation, and can improve the S/N ratio about three to ten times.

If the landing energy is $LE \leqq 10$ eV, and particularly if it is in a region $LE \leqq 0$ eV, mirror electrons can be formed in the normal part. Even if this condition is set, the invention can create the conditions in which the mirror electrons from the foreign material 10 reach the detector 70 and the mirror electrons from the normal part do not reach the detector 70, and can carry out the inspection for the foreign material 10 with a high S/N ratio. More specifically, the sample surface 21 is flat, and the electron beam enters almost perpendicularly. The incident beam on the normal part is slowed down on the sample surface 21. For this reason, the path of the electrons is bent, and deviates from the center of the secondary optical system 60. As a result, this phenomenon reduces the number of electrons guided from the normal part to the detector 70. On the other hand, the mirror electrons from the foreign material 10 rise from a curved surface or an inclined surface of the foreign material 10, and is guided through a path near the center of the secondary optical system 60 to the detector 70. Consequently, the mirror electron signal from the foreign material 10 is guided to the detector with a high transmittance. A high S/N ratio can thus be achieved. This will be described in detail with reference to FIG. 164.

Figure 164:
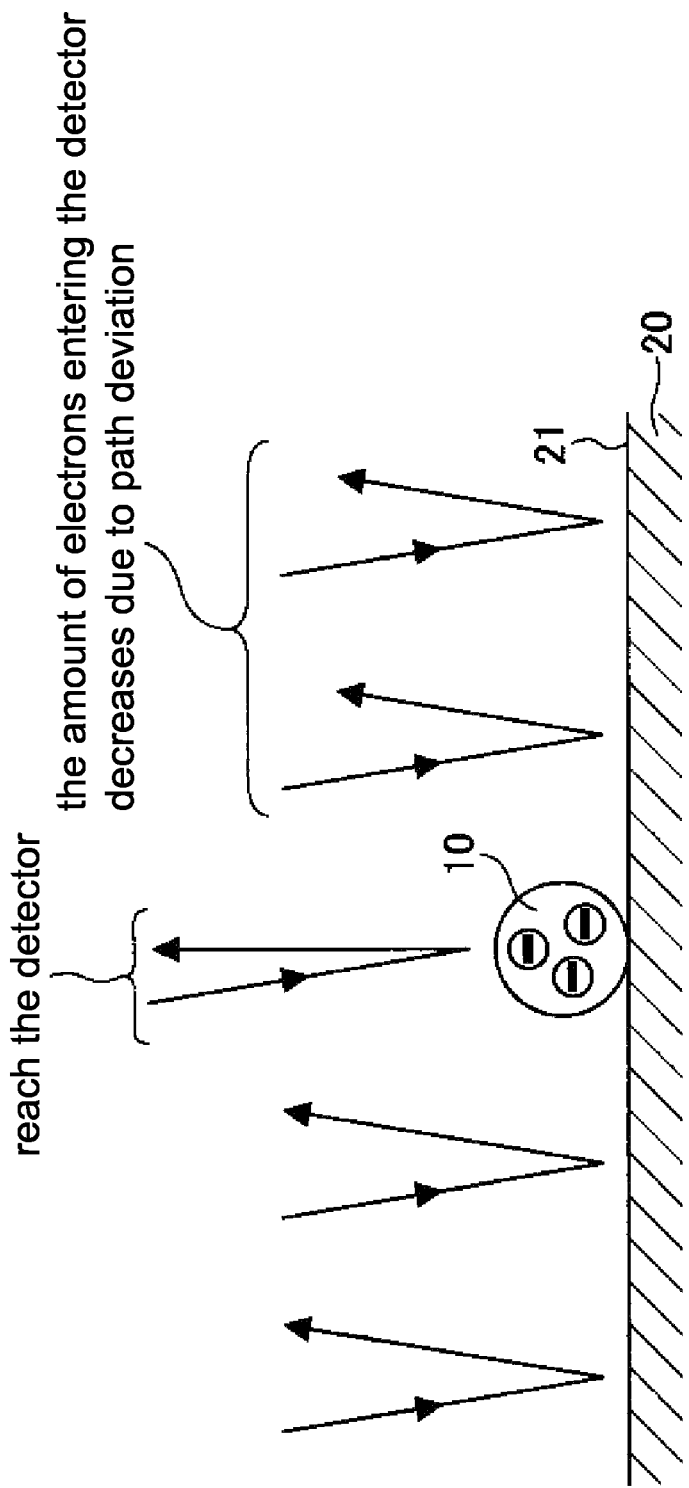
FIG. 164 is a diagram related to one embodiment of the present invention.

FIG. 164 illustrates filtering for when mirror electrons are emitted from the foreign material 10 and the surrounding normal part. In FIG. 164, the sample 20 with the foreign material 10 being present thereon is irradiated with an electron beam, and mirror electrons are reflected from both the foreign material 10 and the sample surface 21. In such a case, the invention causes a phenomenon in which the mirror electrons reflected from the foreign material 10 reach the detector 70 and the mirror electrons from the sample surface 21 of the normal part do not reach the detector 70. That is, the foreign material 10 is charged up, causing a potential difference between the foreign material and the surrounding normal part (the sample surface 21), and this allows for separation of the mirror electrons from the foreign material 10 and the mirror electrons from the sample surface 21 of the surrounding normal part.

For example, as described with reference to FIG. 159, the angle of incidence of the primary electron beam is slightly tilted to the vertical and is caused to deviate from the center. This can create a condition where the path of the mirror electrons goes near the center of the secondary optical system 60. The path of the mirror electrons deviates on the flat normal part. The path of the mirror electrons from the normal part deviates from the central part of the secondary optical system 60, thereby reducing the amount and probability of electrons reaching the detector 70. The mirror electrons from the normal part also become stray electrons or the like due to their collision with the column of the secondary optical system 60. Consequently, there occurs a difference in the amount or density of electrons that reach the detector 70 between the foreign material 10 and the surrounding sample surface 21. This allows a large gray-level difference, i.e. contrast, to be created.

Here the factors that have an effect on the deviation of the path are the intensity and focus of the lenses 47, 49, 50, 61, and 63, the E×B filter 46, and the NA aperture 62. The focus and intensity of the lenses 47, 49, 50, 61, and 63 are adjusted so as to obtain a condition in which the path of the mirror electrons from the foreign material 10 goes through the center of the secondary optical system 60. The angle of incidence and focus of the lenses are different between the mirror electrons from the surrounding normal part (the sample surface 21) and those from the foreign material 10. The mirror electrons from the normal part therefore go through paths that are off the center of the secondary optical system 60. The NA aperture 62 blocks the mirror electrons going through paths that are off the center, and reduces the amount and probability of them reaching the detector 70. Additionally, the E×B filter 46 is adjusted so that when the mirror electrons go through the E×B filter 46, the mirror electrons from the foreign material 10 go through the path that reaches the subsequent NA aperture 62 and detector 70. This allows the mirror electrons to be appropriately adjusted when they go through the E×B filter 46. The angle of incidence on the E×B filter 46 and the energy in the axial direction (the z-axis direction) are different between the mirror electrons from the foreign material 10 and those from the surrounding normal part (the sample surface 21). Accordingly, the mirror electrons reflected from the sample surface 21 of the normal part deviate from the center of the subsequent NA aperture 62 and lenses 61 and 63. As a result, their probability of incidence on the detector 70 decreases.

Generally, the LE region that can be used effectively is between −30 and 0 eV. However, when the optical axis of the secondary optical system 60 is not perpendicular to the sample surface, mirror electrons are sometimes formed even if LE is 0 eV or more. Also in a sample with microscopic unevenness on the surface such as a wafer with a pattern, mirror electrons are sometimes formed even if LE is 0 eV or more. For example, such a condition may be created in an LE region from −30 to 10 eV.

The electron beam inspection method according to the invention can also be applied to the SEM by using the precharge effectively. For example, the foreign material inspection can be carried out with the SEM by imaging and inspecting after the precharge under the following condition: Precharge LE1: 0 to 30 eV; and Imaging LE2: −5 to 20 eV.

For example, imaging is performed under conditions Precharge LE1=25 eV and Imaging LE2=5 eV. In this case, the foreign material (an insulating material or an object including an insulating material) is charged up, and the surface potential becomes negatively charged (e.g. −7 V). Irradiation is then performed with the imaging electron beam (LE2=5 eV). Consequently, mirror electrons are formed only in the charged-up foreign material part, and the mirror electrons are acquired by the detector 70. The normal part without the foreign material 10 generates secondary emission electrons (the secondary emission electrons are secondary electrons, reflected electrons, or backscattered electrons, or these may be mixed). Since the emission coefficient of the secondary emission electrons is low, the brightness of the normal part is low. The brightness difference (the contrast) between the mirror electrons from the foreign material 10 and the secondary emission electrons from the normal part is large, and therefore the foreign material 10 can be detected with high sensitivity.

A precharge device may be provided in front of the imaging unit for an efficient precharge.

If no precharge is performed in the SEM method, there may be the following faults. Generally in the SEM method, the spot size of the electron beam is set smaller than the size of the object such as a pattern defect and foreign material to be detected in order to appropriately perform image formation and shape recognition of the pattern or foreign material 10. Consequently, the difference between the beam spot size and the foreign material size causes a local and temporal change in the charge-up potential of the foreign material 10. As a result, no stable signal can be obtained, or it is difficult to obtain stable mirror electrons. It is thus important to perform imaging after stabilizing the surface potential condition of the foreign material 10 or stabilizing the chargeup condition and potential of the foreign material 10 using the precharge.

In conventional SEM methods, since beam scanning is performed, the angle of incidence of the beam relative to the sample 20 considerably varies depending on the scan position. When a beam of mirror electrons is formed, the angle of reflection of the beam varies depending on the angle of incidence. Consequently, the probability of the electrons entering the detector 70 considerably varies depending on the scan position, and this is a fault. For this reason, it is difficult to acquire a uniform and precise image. In order to overcome this fault, the aligner and the lens voltage are suitably adjusted in conjunction with each other so that the angle of incidence of the electron beam relative to the sample will be almost a right angle.

As seen above, the electron beam inspection method according to the invention can also be applied to the SEM method by establishing appropriate conditions.

Figure 165:
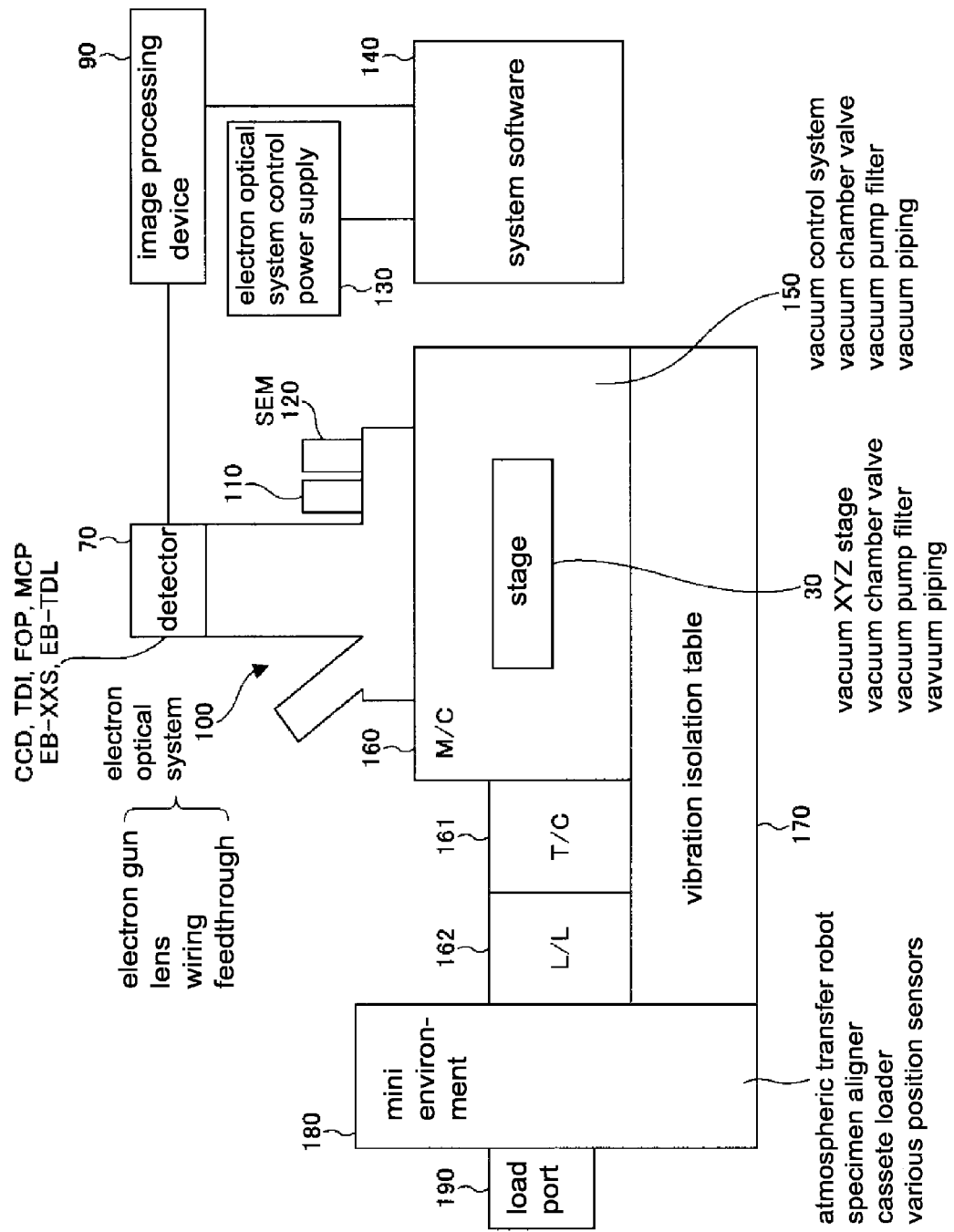
FIG. 165 is a diagram related to one embodiment of the present invention.

FIG. 165 shows an electron beam inspection device to which the invention is applied. Here an example of a general system configuration will be described.

In FIG. 165, the foreign material inspection device has a sample carrier 190, a minienvironment 180, a load lock 162, a transfer chamber 161, a main chamber 160, an electron beam column system 100, and an image processing device 90. The minienvironment 180 is provided with an atmospheric transfer robot, a sample alignment device, a clean air supply mechanism, and the like. The transfer chamber 161 is provided with a vacuum transfer robot. Since the robot is placed in the transfer chamber 161 which is always in a vacuum state, the generation of particles or the like caused by pressure fluctuations can be suppressed to a minimum.

The main chamber 160 is provided with a stage 30 that moves in the x direction, y direction, and θ (rotation) direction, and an electrostatic chuck is installed on the stage 30. On the electrostatic chuck is placed the sample 20 itself. Alternatively, the sample 20 set in a pallet or jig is held by the electrostatic chuck.

The main chamber 160 is controlled by a vacuum control system 150 so as to maintain a vacuum in the chamber. The main chamber 160, the transfer chamber 161, and the load lock 162 are mounted on a vibration isolation table 170, and they are configured so that no vibration is transmitted from the floor.

The electron column 100 is installed on the main chamber 160. The electron column 100 comprises columns of the primary optical system 40 and secondary optical system 60, and the detector 70 for detecting secondary emission electrons, mirror electrons, or the like transmitted from the sample 20. A signal from the detector 70 is transmitted to and processed by the image processing device 90. Real-time signal processing and delayed signal processing can both be performed. The real-time signal processing is performed during inspection. When the delayed signal processing is performed, simply an image is acquired, and the signal processing is performed later. Data processed by the image processing device 90 is saved to a hard disk, memory, or other recording medium. The data can be displayed on a monitor on a console as required. The data to be displayed is, for example, an inspection area, a map of the number of foreign materials, the distribution and a map of the foreign material size, foreign material classification, a patch image, or the like. System software 140 is provided to perform such signal processing. An electron optical system control power supply 130 is provided to supply the electron column system with power. The main chamber 160 may be provided with the optical microscope 110 and the SEM-type inspection device 120.

Figure 166:
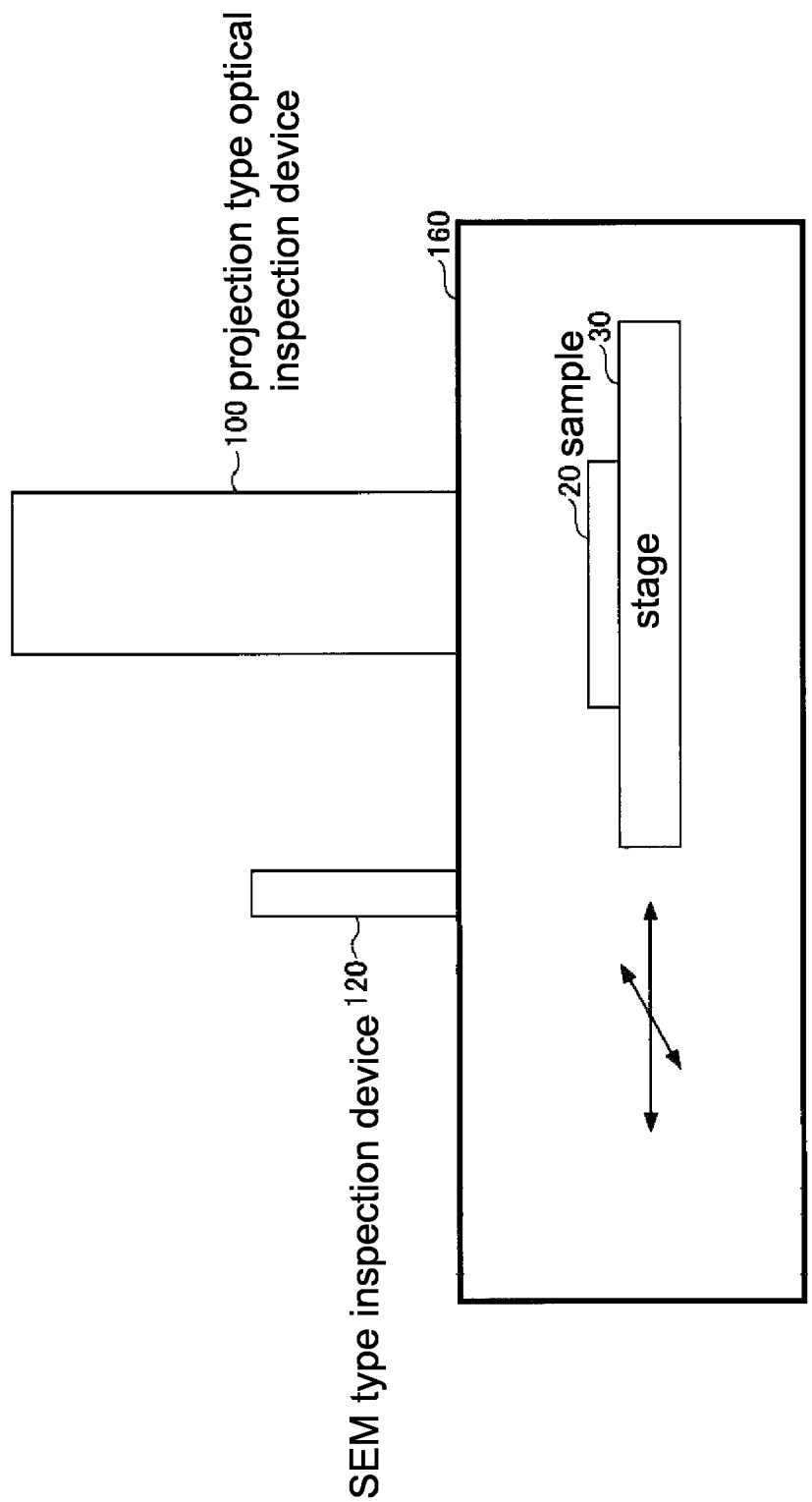
FIG. 166 is a diagram related to one embodiment of the present invention.

FIG. 166 shows an example of a configuration in which the electron column 100 which is a projection-type optical inspection device and the SEM-type inspection device 120 are installed in the one and the same main chamber 160. As shown in FIG. 166, it is very advantageous if the projection type optical inspection device and the SEM-type inspection device 120 are installed in the one and the same chamber 160. The sample 20 is placed on the one and the same stage 30, and the sample 20 can be observed or inspected by both the projection method and the SEM method. A method of use and advantages of this configuration are as follows.

First, since the sample 20 is placed on the one and the same stage 30, the coordinates are uniquely determined when the sample 20 moves between the projection-type electron column 100 and the SEM-type inspection device 120. Accordingly, when a detection point of the foreign material or the like is to be located, the two inspection devices can precisely and easily locate one and the same part.

Suppose that the above-described configuration is not applied. For example, the projection-type optical inspection device and the SEM-type inspection device 120 are separately configured as different devices. The sample 20 is moved between the separate different devices. In this case, since it is required to place the sample 20 on different stages 30, the two devices are required to align the sample 20 separately. The separately performed alignment of the sample 20 would cause a location error of 5 to 10 µm for one and the same position. In particular, the error further increases if the sample 20 does not have any pattern, since the positional reference cannot be located.

In the embodiment, on the other hand, the sample 20 is placed on the stage 30 in the one and the same chamber 160 for the two types of inspection as shown in FIG. 166. One and the same position can be precisely located even if the stage 30 moves between the projection-type electron column 100 and the SEM-type inspection device 120. Consequently, a position can be precisely located even if the sample 20 does not have any pattern. For example, a position can be located with a precision of 1 µm or less.

Such precise location is significantly advantageous in the following case. The foreign material inspection of the sample 20 having no pattern is first performed by the projection method. After that, location and detailed observation (reviewing) of the detected foreign material 10 is performed by the SEM-type inspection device 120. Since the position can be located accurately, not only the presence or absence of the foreign material 10 (false detection if absent) can be determined, but also detailed observation of the size and shape of the foreign material 10 can be performed quickly.

As mentioned above, the separate installation of the electron column 100 for foreign material detection and the SEM-type inspection device 120 for reviewing would require a great deal of time to locate the foreign material 10. The sample having no pattern would increase the difficulty. Such problems are solved by the embodiment.

In the embodiment, as described above, the foreign material 10 of an ultra-micro size can be inspected for with high sensitivity by using conditions for imaging the foreign material 10 with the projection-type optical method. In addition, the projection-type optical electron column 100 and the SEM-type inspection device 120 are mounted in the one and the same chamber 160. Consequently, in particular, inspection for the foreign material 10 of an ultra-micro size of 30 nm or less and determination and classification of the foreign material 10 can be carried out with great efficiency and speed. Furthermore, the present embodiment can be applied to embodiments 1~28 as well as embodiments with no number attached.

Another example of the inspection using both projection-type inspection device and SEM will next be described.

In the above description, the projection-type inspection device detects the foreign material, and the SEM performs review inspection. However, the invention is not limited to this. The two inspection devices may be applied to another inspection method. Effective inspection can be carried out by combining the characteristics of each inspection device. Another inspection method, for example, is as follows.

In this inspection method, the projection-type inspection device and the SEM inspect different areas. In addition, "cell to cell" inspection is applied to the projection type inspection device, and "die to die" inspection is applied to the SEM, so that precise inspection is achieved with great overall efficiency.

More specifically, the projection-type inspection device performs the "cell to cell" inspection on an area in a die where there are many repetitive patterns. The SEM then performs the "die to die" inspection on an area where there are not many repetitive patterns. Both inspection results are combined and one inspection result is obtained. The "die to die" is an inspection for comparing successively obtained images of two dies. The "cell to cell" is an inspection for comparing successively obtained images of two cells. A cell is a part of a die.

In the above-described inspection method, the repetitive pattern part is quickly inspected by using the projection method and, on the other hand, the area where there are not many repetitive patterns is inspected by the SEM with precision and less faults. The SEM is not suited to quick inspection. However, since the area where there are not many repetitive patterns is relatively small, the SEM does not require too much time for inspection. Consequently, overall inspection time can be reduced. This inspection method can thus maximize the merits of the two inspection methods to carry out precise inspection in a short inspection time.

Returning now to FIG. 165, a transfer mechanism for the sample 20 will be described.

The sample 20 such as a wafer and mask is transferred from the load port into the minienvironment 180, where alignment work is performed. The sample 20 is transferred to the load lock 162 by the atmospheric transfer robot. The load lock 162 is evacuated from atmospheric pressure to a vacuum by a vacuum pump. When the pressure becomes a certain value (about 1 Pa) or less, the sample 20 is transferred from the load lock 162 to the main chamber 160 by the vacuum transfer robot placed in the transfer chamber 161. The sample 20 is then placed on the electrostatic chuck mechanism on the stage 30.

Figure 167:
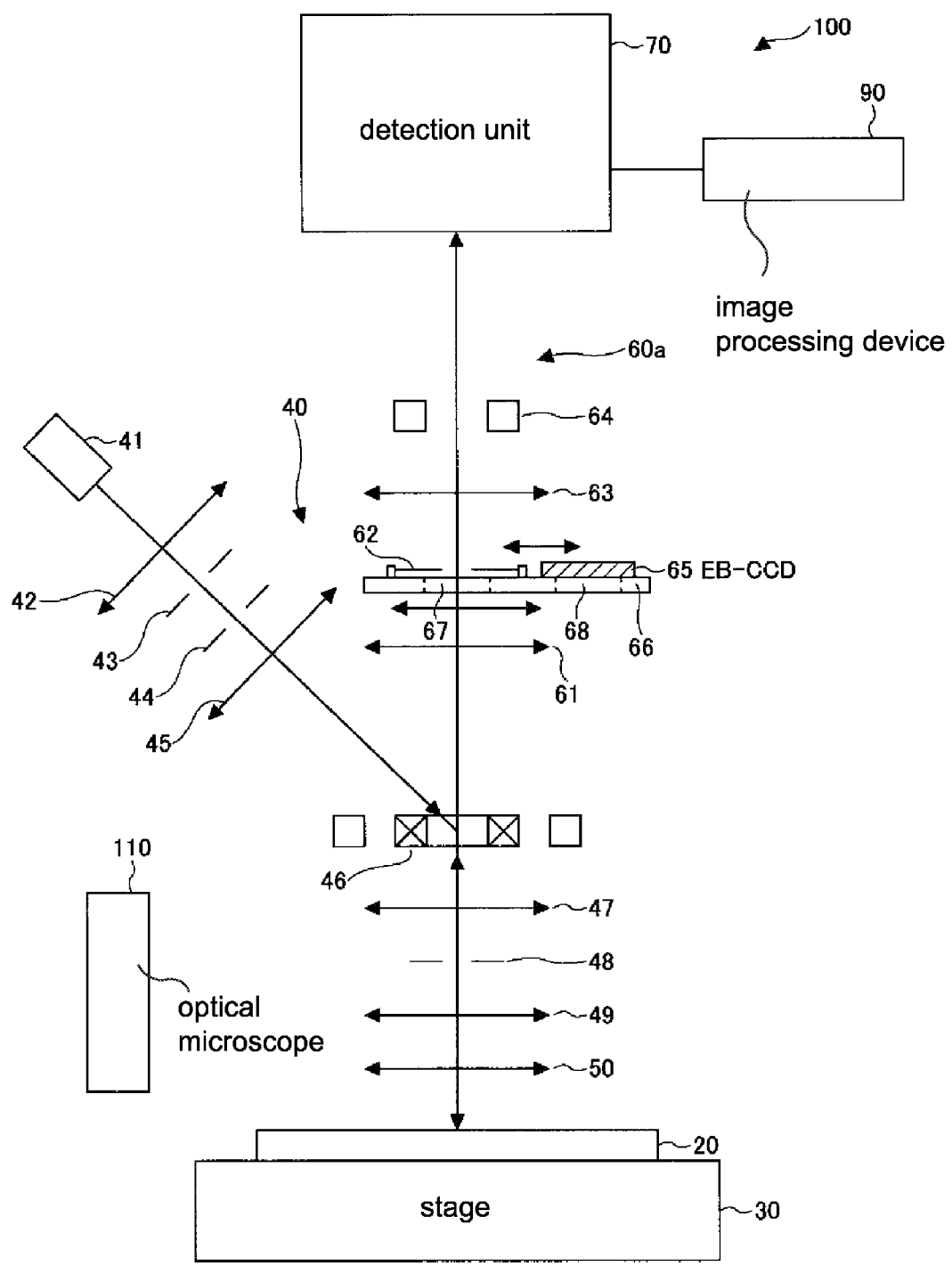
FIG. 167 is a diagram related to one embodiment of the present invention.

FIG. 167 shows the inside of the main chamber 160, and the electron column system 100 placed in an upper part of the main chamber 160. The same components as those in FIG. 158 are given the same reference numerals as in FIG. 158 and therefore, an explanation of those components is omitted.

The sample 20 is placed on the stage 30 that can move in the x, y, z, and θ directions. The stage 30 and the optical microscope 110 perform precise alignment. The projection optical system then uses the electron beam to perform the foreign material inspection and pattern defect inspection of the sample 20. Here the potential of the sample surface 21 is important. A surface potential measurement device that can measure in vacuum is installed in the main chamber 160 in order to measure the surface potential. This surface potential measurement device measures the two-dimensional surface potential distribution on the sample 20. Based on the measurement result, focus control is performed in a secondary optical system 60a that forms an electron image. A focus map of two-dimensional positions in the sample 20 is created based on the potential distribution. By using this map, the inspection is carried out with the focus being changed and controlled during the inspection. This can reduce the defocus and distortion of the image caused by a change in the surface potential according to location, so that a precise and stable image acquisition and inspection can be carried out.

Here the secondary optical system 60a is configured to be able to measure the detection current of electrons entering the NA aperture 62 and the detector 70, and further to be able to place an EB-CCD in the position of the NA aperture 62. Such a configuration is significantly advantageous and efficient. In FIG. 23, the NA aperture 62 and the EB-CCD 65 are mounted on a one-body holding member 66 having openings 67 and 68. The secondary optical system 60a has a mechanism that can separately and independently perform current absorption with the NA aperture 62 and image acquisition with the EB-CCD 65. In order to realize this mechanism, the NA aperture 62 and the EB-CCD 65 are mounted on the x-y stage 66 that operates in vacuum. Accordingly, position control and positioning of the NA aperture 62 and the EB-CCD 65 can be performed. Since the stage 66 is provided with the openings 67 and 68, the mirror electrons and the secondary electrons can go through the NA aperture 62 or the EB-CCD 65.

An operation of the secondary optical system 60a with such a configuration will be described. First, the EBCCD 65 detects the spot shape of the secondary electron beam and the center position of the spot shape. Voltage adjustment is then performed on a stigmator, the lenses 61 and 63, and the aligner 64 so that the spot shape becomes circular and minimum. In terms of this point, conventionally the spot shape and astigmatism at the position of the NA aperture 62 could not be directly adjusted. The embodiment allows such a direct adjustment to be made, allowing the astigmatism to be corrected precisely.

The center position of the beam spot can also be detected easily. Accordingly, the position of the NA aperture 62 can be adjusted so that the center of the opening in the NA aperture 62 is placed in the beam spot position. In terms of this, conventionally the position of the NA aperture 62 could not be directly adjusted. In the embodiment, the position of the NA aperture 62 can be directly adjusted. Consequently, the NA aperture can be precisely positioned, the aberration in the electron image decreases, and the uniformity improves. The uniformity of the transmittance improves, and an electron image can be acquired with a high resolution and uniform gray level.

In the inspection for the foreign material 10, it is important to efficiently acquire a mirror signal from the foreign material 10. The position of the NA aperture 62 is very important since it defines the transmittance and aberration of the signal. Secondary electrons are emitted from the sample surface in a wide angle range following the cosine law, and reach the NA position uniformly with a wide area (e.g. ϕ3 mm). For this reason, the secondary electrons are insensitive to the position of the NA aperture 62. In contrast, the reflection angle of mirror electrons on the sample surface is about the same as the incident angle of the primary electron beam. The mirror electrons therefore exhibit a small spread, and reach the NA aperture 62 with a small beam diameter. For example, the spread area of the mirror electrons is 1/20 or less of the spread area of the secondary electrons. For this reason, the mirror electrons are very sensitive to the position of the NA aperture 62. The spread area of the mirror electrons at the NA position is generally an area of ϕ10 to ϕ100 μm. Because of this, it is very advantageous and important to determine a position where the intensity of the mirror electrons is the highest and place the center position of the NA aperture 62 in the determined position.

In order to achieve such placement of the NA aperture 62 in an appropriate position, the NA aperture 62 in a preferred embodiment is moved in the x and y directions in the vacuum electron column 100 with a precision of about 1 μm. The signal intensity is measured with the NA aperture 62 being moved. A position where the signal intensity is the highest is then determined, and the center of the NA aperture 62 is placed in the position of the determined coordinates.

The EB-CCD 65 is very advantageously used for the measurement of the signal intensity. This is because it can get two-dimensional information on the beam and determine the number of electrons that enter the detector 70, thereby allowing the signal intensity to be evaluated quantitatively.

Alternatively, the placement of the aperture may be determined and a condition of the lens 63 existing between the aperture and the detector may be established so that a conjugate relation between the position of the NA aperture 62 and the position of the detection surface of the detector 70 is achieved. This configuration is also very advantageous. This allows an image of the beam at the position of the NA aperture 62 to be formed on the detection surface of the detector 70. The beam profile at the position of the NA aperture 62 can thus be observed by using the detector 70.

The NA size (aperture diameter) of the NA aperture 62 is also important. Since the signal area of the mirror electrons is small as described above, an effective NA size is about 10 to 200 μm. In addition, the NA size is preferably a size 10% to 100% larger than the beam diameter.

Discussing in relation to this, the image of the electrons is formed from the mirror electrons and the secondary emission electrons. The above-mentioned setting of the aperture size can increase the ratio of the mirror electrons more. This can increase the contrast of the mirror electrons, that is, increase the contrast of the foreign material 10.

Describing in more detail, when the opening in the aperture is small, the secondary emission electrons decrease inversely with the area of the aperture. This reduces the gray level of the normal part. However, the mirror signal does not change, and the gray level of the foreign material 10 does not change. Consequently, the contrast of the foreign material 10 can be increased by the amount of decrease in the gray level of the surroundings, and a higher S/N ratio can be obtained.

The aperture and the like may be configured so that the position of the aperture can be adjusted in the z-axis directions as well as in the x and y directions. This configuration is also advantageous. The aperture is suitably placed in a position where the mirror electrons are most condensed. This very effectively reduces the aberration of the mirror electrons and cuts down the secondary emission electrons. Consequently, a higher S/N ratio can be obtained.

As described above, the mirror electrons are very sensitive to the NA size and shape. It is therefore very important to appropriately select the NA size and shape in order to obtain a high S/N ratio. An example of a configuration for such appropriate selection of the NA size and shape will next be described. The shape of the aperture (opening) of the NA aperture 62 will also be mentioned in the description.

Here the NA aperture 62 is a member (component) having an opening. Generally, the member is sometimes called an aperture, or the opening is sometimes called an aperture. In the following aperture-related description, the member is called an NA aperture in order to distinguish the member (component) from its opening, when FIG. 168 to FIG. 172 are referred to. An opening in the member is called an aperture. In the following description, symbols 62 and 62a to 62d denote NA apertures. Symbols 169, 69, 69a, and 69b denote apertures (openings). The aperture shape generally means the shape of an opening.

Figure 168:
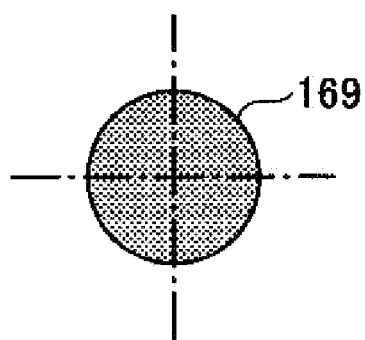
FIG. 168 is a diagram related to one embodiment of the present invention.

FIG. 168 is a reference example, showing a conventional aperture 169. As shown in FIG. 168, the circular aperture 169 would conventionally be placed in a fixed position. Consequently, the above-described appropriate selection of the NA size and shape could not be made.

On the other hand, the sample inspection apparatus according to the embodiment is configured to be able to move the position of the NA aperture 62 two-dimensionally or three-dimensionally to set the position. The movement of the NA aperture 62 may be performed by using the x-y stage 66 described in FIG. 167. A suitable aperture may be selected as appropriate from a plurality of apertures and the positioning may be performed. The one NA aperture 62 may be provided with a plurality of aperture openings 69, and the NA aperture 62 may be moved in order to select one of those (this configuration also corresponds to the selection from a plurality of apertures). Another moving mechanism may be used. For example, the NA aperture 62 may be moved by a linear motor instead of by the x-y stage 66. A rotation support member may support the NA aperture 62, and a common rotary motor may move the position of the NA aperture 62. A specific example of the shape of the opening in the NA aperture 62 will next be described.

Figure 169:
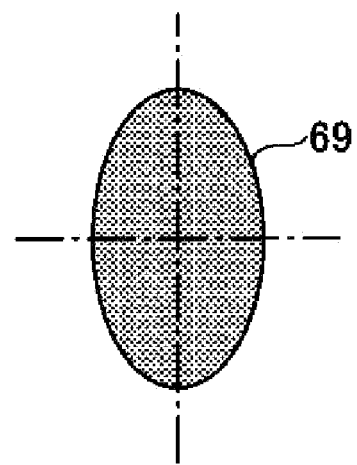
FIG. 169 is a diagram related to one embodiment of the present invention.

FIG. 169 shows an example of the shape of the aperture 69. In FIG. 168, the aperture 69 has an elliptical opening shape. This opening shape is created so as to match the intensity distribution of the mirror electron signal. In this example, the intensity distribution has an elliptical shape elongated in the y direction according to a measurement result of the intensity distribution of the mirror electrons in the aperture. Here the y direction is the direction in which the deflection is made by the E×B filter 46. The y direction corresponds to the direction of the optical axis of the primary electron beam. This means that the elliptical shape elongated in the y direction is considered to be caused by a deflection component of the E×B filter 46. The aperture shape having the major axis in the y direction is therefore very advantageous in order to capture the mirror electrons efficiently. This can increase the yield of the mirror electrons more than ever before and obtain a higher S/N ratio (e.g. two times or more). For example, suppose that the intensity distribution of the secondary electron beam extends 100 μm in the y direction and 50 μm in the x direction (these values are full widths at half maximum). The elliptical aperture 69 is selected in a range from 10% to 100% more than the secondary electron beam diameter. For example, the aperture may be selected so that the aperture size is 150 μm in the y direction and 75 μm in the x direction.

Configurations of the NA aperture 62 having a plurality of apertures 69 will next be described with reference to FIG. 170 to FIG. 173. Here NA apertures 62a to 62c are the aperture members, and apertures 69a are the openings provided in the aperture members.

Figure 170:
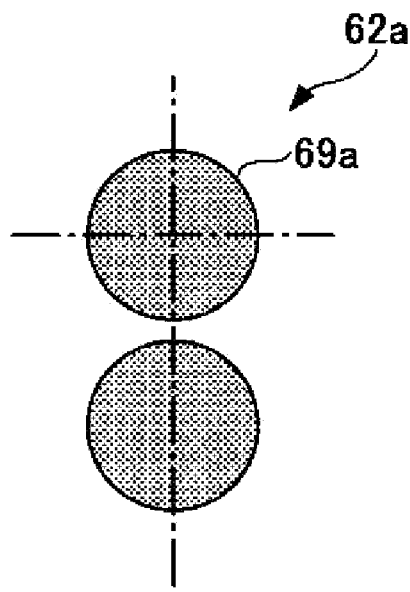
FIG. 170 is a diagram related to one embodiment of the present invention.

FIG. 170 shows an example of a configuration of an NA aperture 62a having a plurality of apertures 69a. In FIG. 170, the NA aperture 62a has two circular apertures 69a. In this example, the two openings are placed in positions displaced in ±y directions with respect to the center of the intensity of the mirror electrons. The amount of displacement is, for example, about 50 um. This configuration can capture both mirror electrons scattered on the +y and −y sides from the foreign material 10. This configuration can therefore increase the difference in the amount of the signal between the scattered mirror electrons and the background secondary emission electrons, allowing a high S/N ratio to be obtained. The reason of this is that the amount of the secondary emission electrons flying in the scattering direction is limited to a small amount. The background therefore decreases, and the S/N ratio can be improved relatively.

Figure 171:
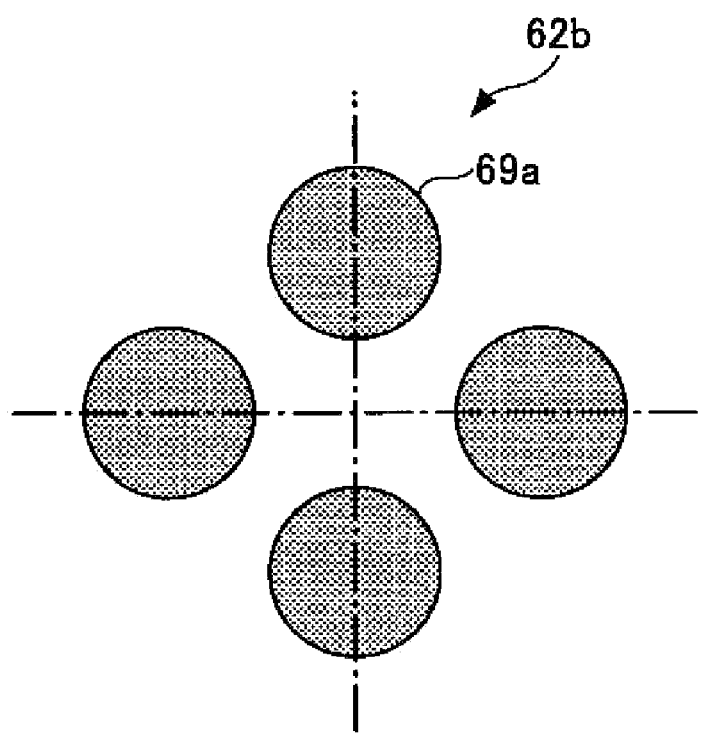
FIG. 171 is a diagram related to one embodiment of the present invention.

FIG. 171 shows an example of a configuration of an NA aperture 62b having four apertures 69a. In FIG. 171, the four circular apertures 69a are placed symmetrically with respect to the x and y axes. That is, two of the apertures 69a are placed on the x axis; two of the apertures 69a are placed on the y axis; and the four apertures 69a are positioned at the same distance from the center (the origin). In other words, the four apertures 69a are placed at regular intervals around the origin. More simply put, the four apertures 69a are placed in a rhombus shape. Consequently, even when there are mirror electrons scattered in both x and y directions from the foreign material 10, the electrons can be acquired with a high S/N ratio.

Figure 172:
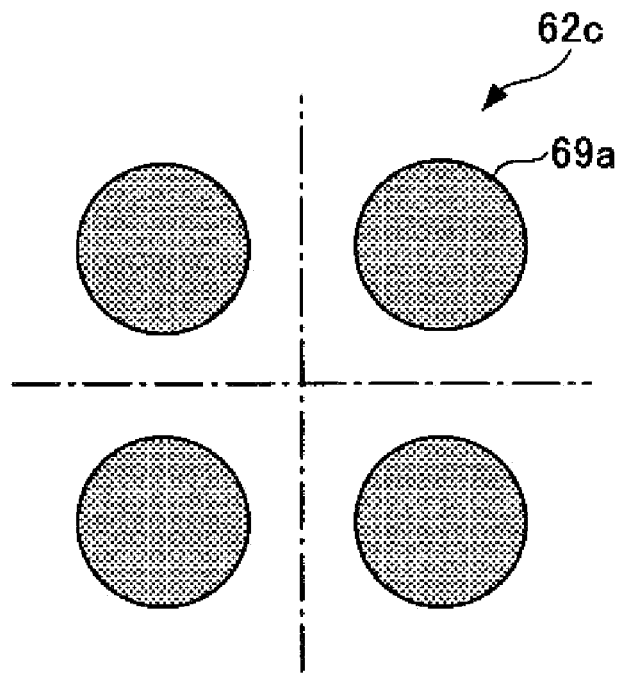
FIG. 172 is a diagram related to one embodiment of the present invention.

FIG. 172 shows an NA aperture 62c having four apertures 69a. The configuration in FIG. 172 is an example different from the configuration in FIG. 171. In FIG. 172, the four circular apertures 69a are separately placed in the first to fourth quadrants in the xy plane. Also in this example, the four apertures 69a are placed symmetrically with respect to the x and y axes, and are placed at the same distance from the center (the origin). In other words, the four apertures 69a are placed at regular intervals around the origin. Even in the NA aperture 62c of such a shape, the apertures 69a can be provided in a position where the signal intensity of the mirror electrons is high, and a signal with a high S/N ratio can be acquired.

As shown in FIG. 171 and FIG. 172, there may be configurations which are the same in the number of the apertures 69a but are different in their arrangement. This allows the appropriate NA aperture 62b or 62c to be used depending on the intended use. Consequently, a high S/N ratio can be acquired in each use.

Figure 173:
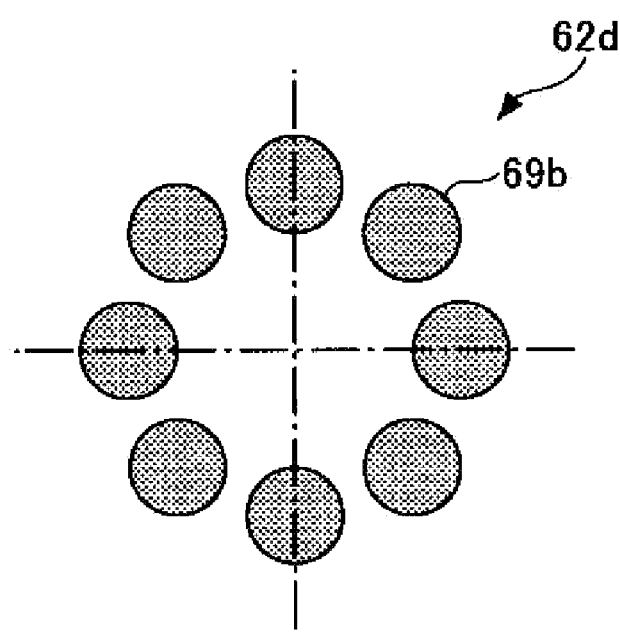
FIG. 173 is a diagram related to one embodiment of the present invention.

FIG. 173 shows an example of a configuration of an NA aperture 62d having eight apertures 69b. As shown in FIG. 173, the number of the apertures 69b may be more than four. In the NA aperture 62d shown in FIG. 173, the plurality of apertures 69b are placed at regular intervals on a circumference around the center of the intensity of the mirror electrons. This configuration is advantageous when there are mirror electrons scattering specifically and significantly on the position of one of the apertures 69b on the circumference. Such mirror electrons can be captured appropriately.

In FIG. 170 to FIG. 173, in terms of the relation between the center of the intensity of the mirror electron signal and the apertures 69a and 69b, the positions of the apertures are off the center of the intensity. However, the invention is not limited to this, and the positions of the apertures may coincide with the center of the intensity. That is, one of the apertures 69a or 69b may be placed so as to coincide with the center of the intensity of the mirror electrons. In this case, the other apertures 69a or 69b capture scattered mirror electrons. They will be included in an electron image together with the mirror electrons in the center of the intensity. Such a composite image is obtained by the detector 70. In this way, a composite image of the intense mirror electrons and the specifically scattered mirror electrons can be acquired. Consequently, a high S/N ratio can be obtained, and the foreign material 10 distinctive in the scattering direction can be detected effectively. Additionally, the characteristic in the scattering direction can be used to classify the foreign material 10.

Furthermore, in the embodiment, the apertures 69, 69a, and 69b of an appropriate shape can also be selected for the landing energy LE to be used. This selection also provides a very advantageous effect. The intensity distribution of the mirror electrons varies depending on the landing energy LE. Accordingly, the inspection device of the embodiment may be configured to use the apertures 69, 69a, and 69b having a size and shape according to the landing energy LE to be used. This allows the aperture to be adjusted in accordance with the intensity distribution, which is very advantageous. For example, suppose that the mirror electrons have an intensity distribution of an elliptical shape elongated in the y direction, and then the imaging or inspection is carried out under two different conditions. For example, suppose that the landing energy is a first value, i.e. LE=3 eV, in a first imaging or inspection condition. Suppose that the landing energy is a second value, i.e. LE=2 eV, in a second imaging or inspection condition. Here the smaller the landing energy LE is, the larger the intensity distribution of the mirror electrons becomes at the position of the NA apertures 62 and 62a to 62d. The NA apertures 62 and 62a to 62d are suitably selected so as to match such a change in the distribution. For example, when the first landing energy is used, the aperture 69 of an ellipse extending 100 μm in the y direction and 50 μm in the x direction may be selected. When the second landing energy is used, the intensity distribution of the mirror electrons is about two times larger. Accordingly, the aperture 69 of an elliptical shape extending 200 μm in the y direction and 100 μm in the x direction may be used. Selecting the apertures in this way allows the mirror electrons to be detected very effectively.

The Faraday cup and other components described in FIG. 162 will be described again. These components may be installed in the electron beam inspection device in FIG. 167.

Figure 174:
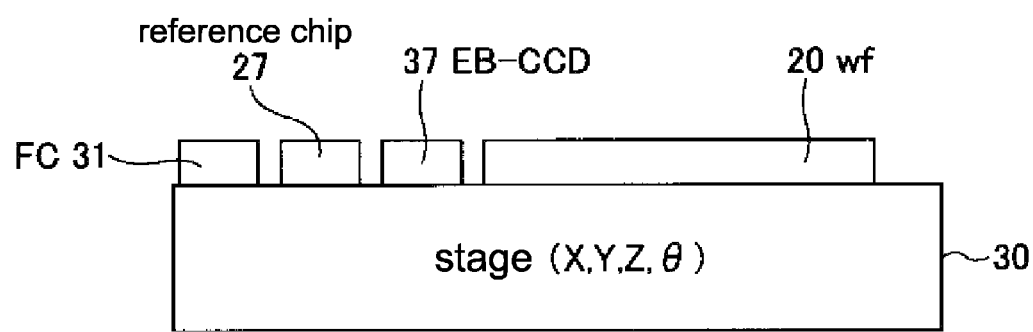
FIG. 174 is a diagram related to one embodiment of the present invention.

FIG. 174 shows the stage 30 in FIG. 167. On the stage 30 are mounted the Faraday cup 31, a reference sample chip 27 having the hollow grooves 25 and 25a, and an EB-CCD 37. Consequently, the uniformity and irradiation position of the primary electron beam can be precisely monitored, and a temporal variation of the primary electron beam can be precisely monitored.

In terms of this, there has been conventionally no means to directly monitor the primary electron beam. For that reason, conventionally the Faraday cup 31 would be placed in a plurality of points on one and the same sample 20 and an image of the electron beam irradiation would be acquired by means of the Faraday cup 31, on a regular basis. This image has been used for an evaluation and adjustment of the beam. Conventional techniques, however, could obtain only an image onto which variations of the primary optical system 40 and secondary optical system 60a are superimposed. It would be complicated to separate, evaluate, and adjust the factors of those two optical systems, and the precision would be low. The embodiment can solve these problems.

In the embodiment, the distribution of the current density of the primary electron beam can also be measured precisely. A precise feedback can be performed on the electron emission control system comprising the lenses 42 and 45, aligner, and electron gun 41 of the primary optical system. Consequently, a more uniform beam profile can be formed. In a conventional measurement of the distribution of the current density, for example, a Faraday cup of about φ30 μm in diameter would be used. The measurement would then be performed on about five points at 30 μm intervals. In such measurement, the resolution would be limited by the size of the opening in the Faraday cup 31. The measurement would take time since the measurement would be performed on a point-by-point basis. As a result, the distribution at the moment of irradiation with the electron beam could not be measured.

The foreign material inspection device according to the embodiment can directly measure the beam profile of the primary electron beam and, based on the measurement result, can appropriately adjust the primary electron beam.

In such adjustment of the primary electron beam in the embodiment, a standardized sample may be manufactured and used in order to determine the relation between the size of the foreign material 10 and the signal intensity or S/N ratio. The use of such a sample provides a great advantage. For example, standardized microspheres of a known size are scattered on a single film of a sample. Such a sample is preferably used to calibrate the sensitivity.

Figure 175:
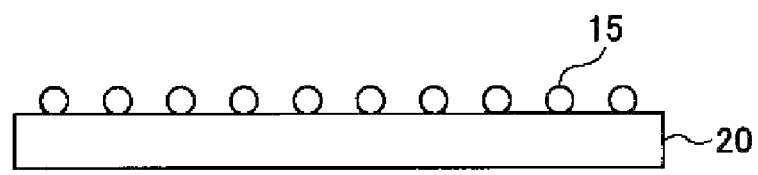
FIG. 175 is a diagram related to one embodiment of the present invention.

FIG. 175 shows the sample 20 on which samples 15 are scattered. The samples 15 typically substitute for the foreign material 10. It is therefore preferred to use a sample of a size close to that of the foreign material 10 and of a material close to that of the foreign material 10. For example, the samples 15 are standardized microspheres, whose material is PSL (polystyrene latex). Ultra-fine particles may also be used. The sample 20 may be a semiconductor wafer of Si or the like. A film may be formed on the semiconductor wafer. The sample 20 may also be a glass substrate on which a film is formed. The film on the sample 20 may be either of a conductive film or an insulating film. For example, the film on the semiconductor wafer may be a film of $SiO_2$, Ta, Cu, Al, W, or the like. The film on the glass substrate may be, for example, a film of Cr, CrN, Ta, TaN, TaBN, TaBO, Si, Al, Mo, or the like.

In FIG. 175, the size of the samples 15 is known. The relation between the size of the samples 15 and the signal intensity or S/N ratio can therefore be determined by acquiring an image of the samples 15.

Figure 176:
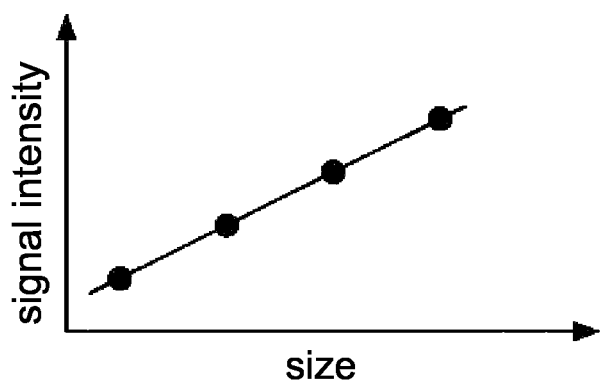
FIG. 176 is a diagram related to one embodiment of the present invention.

FIG. 176 shows a measurement result to be obtained when an image of the samples 15 shown in FIG. 175 is acquired.

FIG. 176 is an example of the relation between the samples 15 and the signal intensity. In FIG. 176, the horizontal axis represents the size of the samples 15, and the vertical axis represents the signal intensity. The vertical axis may also represent the S/N ratio. The signal intensity corresponding to the sample size is determined by varying the size of the samples 15 in various ways. A graph is created from the signal intensity as shown in FIG. 176. Consequently, the relation between the size of the foreign material 10 and the signal intensity or S/N ratio can be grasped.

In the above description, microspheres are used as the samples 15. An appropriate size of the spheres is particularly 100 nm or less. That is, microspheres o φ1 to φ100 nm are used advantageously.

As described up to this point, the electron beam inspection device and electron beam inspection method according to the embodiment are sensitive even to the ultramicro foreign material 10 of the order of nanometers. The above-described microscopic samples 15 are advantageously used particularly for the inspection for the microscopic foreign material 10.

In terms of this, conventional optical-type foreign material inspection methods would have a difficulty in detecting the foreign material 10 of a size smaller than 100 nm since the resolution would be limited by the wavelength of light. The electron beam inspection device and electron beam inspection method according to the embodiment can provide an adequate sensitivity and can detect the microscopic foreign material 10.

Figure 177:
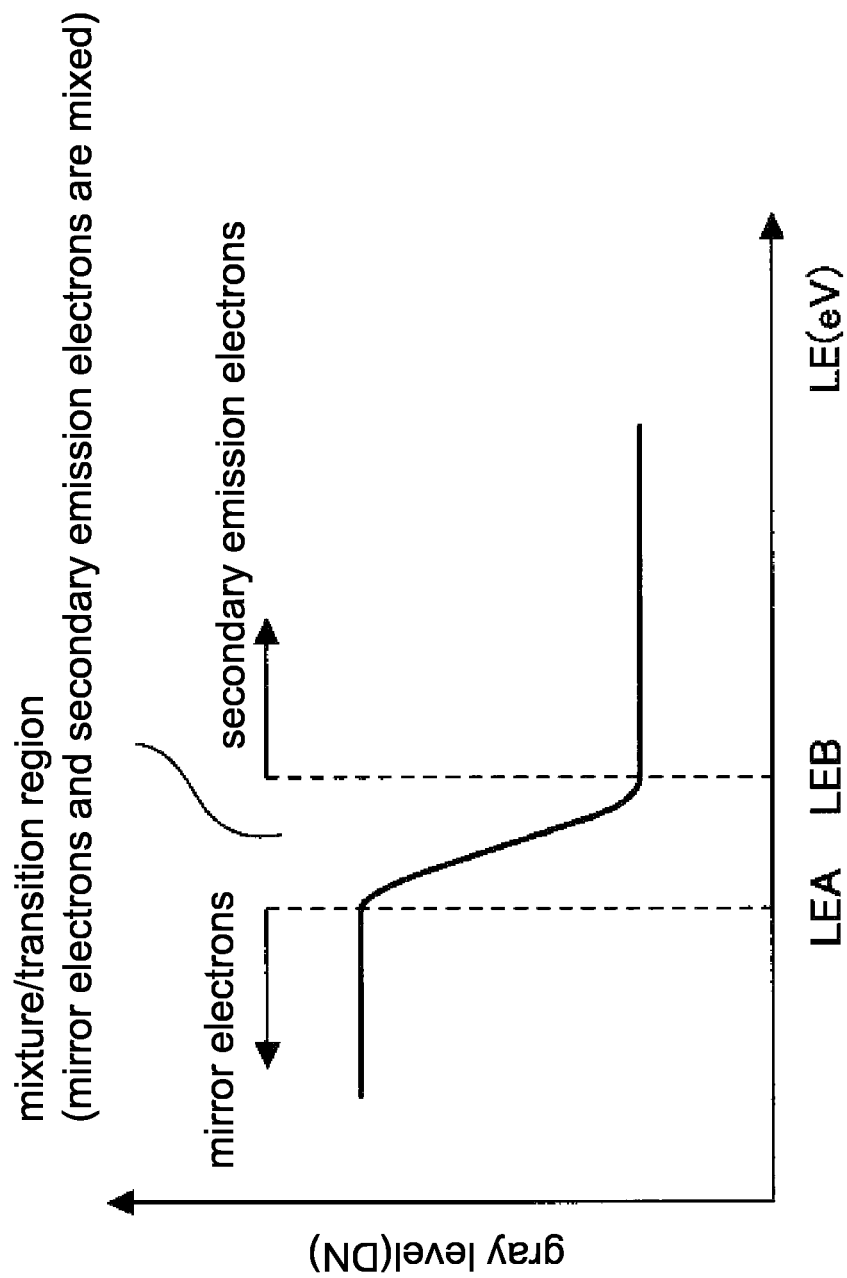
FIG. 177 is a diagram related to one embodiment of the present invention.

Referring now to FIG. 177, an embodiment that achieves an appropriate setting of the landing energy will be described further.

FIG. 177 shows a gray-level characteristic versus beam landing energy in the electron beam inspection method according to the embodiment. This foreign material inspection method may be applied to the sample 20 having a solid surface or patterned surface (the solid surface means a surface without a pattern; hereinafter the same shall apply). The embodiment is characterized in that the characteristic shown in FIG. 177 is acquired and the characteristic in FIG. 33 is used to select a region of the landing energy LE. The gray-level characteristic (the change in the gray-level value versus the landing energy LE) relates to the types of electrons to be detected. The types of electrons are shown below:
LE<LEA: mirror electrons;
LEA≦LE≦LEB: a mixture of secondary emission electrons and mirror electrons; and
LEB≦LE: secondary emission electrons.

Here, setting LE in a region LEA≦LE≦LEB+5 eV allows an image of a high S/N ratio to be acquired, so that a high-sensitivity defect inspection and foreign material inspection can be carried out. The reason of this setting will be described. Suppose, for example, that the foreign material 10 is present on a solid surface such as Si, W, or the like. In the embodiment, the foreign material 10 is charged up and forms mirror electrons. At this time, it is desired that a background solid surface (a surface without a pattern) has a low gray level, because this increases the S/N ratio. In order to reduce the gray level of the solid surface, the energy conditions for the secondary electron emission region and for the mixture region are appropriate. The mixture region is a region in which the mirror electrons and the secondary emission electrons are mixed. The mixture region is between the secondary emission electron region and the mirror electron region, and corresponds to the transition region.

The mixture region is LEA≦LE≦LEB in FIG. 33. It is considered that the foreign material 10 generates mirror electrons and the background sample 20 generates secondary emission electrons in this region. In the mirror electron region LE<LEA, the background also generates mirror electrons. The gray level of the background therefore increases, so that the difference in gray level between the foreign material 10 and the background decreases. That is, the S/N ratio decreases. In an energy region in which LE is much larger than LEB, the foreign material 10 also generates secondary emission electrons. The S/N ratio also decreases in this case.

In order to facilitate the detection of the foreign material 10, it is preferable to maximize the difference in gray level between the magnified image 81 of the foreign material 10 and the surface image 82 of the background sample surface 21. The difference in gray level depends on the gray level characteristic versus the landing energy LE shown in FIG. 177. One characteristic curve is shown in FIG. 33. In contrast, for example, two characteristic curves, a characteristic curve of the foreign material 10 and a characteristic curve of the sample 20 in a pure state, are suitably used in the embodiment. In the embodiment, the two characteristics may be compared, and a landing energy LE in a range in which the difference in gray level is the largest may be used. This allows the landing energy to be determined appropriately.

Discussing in relation to the above description, the energy range in which the difference in gray level is large varies depending on the combination of the characteristic curve of the foreign material 10 and that of the sample surface 21. Accordingly, the landing energy is suitably set by using the characteristic curves of an object to be detected.

According to past experimental experiences, LE in the region LEA≦LE≦LEB+5 eV is very advantageously used and provides a great advantage. The method and configuration that employs this energy region may be applied to any method and configuration described up to this point to the extent possible. Consequently, a high S/N ratio can be acquired, and high sensitivity and high speed defect inspection and foreign material inspection can be carried out.

Figure 178:
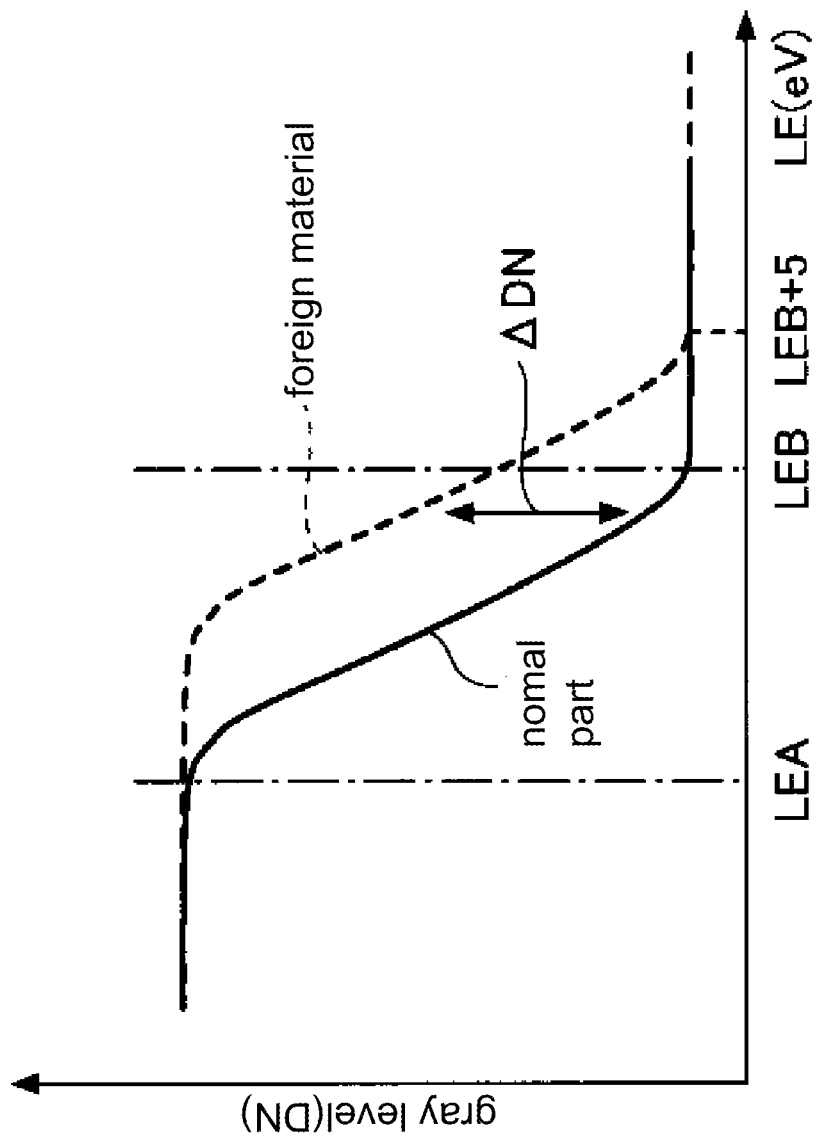
FIG. 178 is a diagram related to one embodiment of the present invention.

Referring now to FIG. 178, the landing energy LE of the primary electron beam efficient in detection of or inspection for the foreign material 10 will be described in further detail. FIG. 178 shows a relation between the landing energy LE of the electron beam of the primary system and the gray level of an image. In FIG. 178, the gray-level characteristic of the sample 20 and that of the foreign material 10 are shown as the relation between the sample 20 and the foreign material 10.

As referred to in the description of FIG. 177, the region in which the landing energy LE is smaller than LEA indicates the mirror electron region. The mirror electron region is an energy region in which almost only mirror electrons are detected from the normal part where the foreign material 10 is not present on the sample 20.

The region in which the landing energy LE is larger than LEB indicates the secondary electron region. The secondary electron region is a region in which almost only secondary electrons are detected from the normal part of the sample 20. Here, for the sake of simplicity, secondary electrons are given attention and the term secondary electron region is used. More specifically, the region is the secondary emission electron region, and secondary emission electrons are generated. As previously described, the secondary emission electrons may include secondary electrons, reflected electrons, and backscattered electrons.

The region in which the landing energy LE is LEA or more but not exceeding LEB is the mixture region. The mixture region means a mixture region in which both mirror electrons and secondary electrons are detected from the normal part of the sample 20. The mixture region is the transition region between the mirror electron region and the secondary electron region.

As described above, the landing energy LE of the electron beam of the primary system with which irradiation is performed is preferably set in the energy region LEA≦LE≦LEB or LEA≦LE≦LEB+5 eV. This will be described in more detail with reference to FIG. 178.

FIG. 178 shows a change in the gray-level DN versus the landing energy LE of the primary electron beam, for each of the foreign material 10 and the normal part on the sample 20. The gray-level DN (digital number) corresponds to the number of electrons to be detected by the detector 70. If the contact resistance between the foreign material 10 and the sample 20 is high or if the foreign material 10 is charged, the foreign material 10 exhibits a change in gray level different from that of the surrounding normal part. This is because a potential change occurs in the foreign material 10, allowing mirror electrons to be generated easily. According to the findings made by the inventors, the range from LEA to LEB has often been seen to be from −5 eV to +5 eV. As described above, the foreign material 10 generates mirror electrons even when the landing energy LE of the primary electron beam is high, as compared to the normal part (here the mirror electrons may be mixed with the secondary electrons). The range from LEA to LEB+5 eV is therefore suitable as the region of the landing energy LE to be used when the imaging of or inspection for the foreign material 10 is carried out. For example, suppose that LEA to LEB is −5 eV to +5 eV. In this case, the region of the landing energy LE is very preferably from −5 eV to +10 (:5+5) eV.

The landing energy range "from LEA to LEB+5 eV" is effective for substrates of all types, regardless of the material of the substrate. For example, the landing energy range "from LEA to LEB+5 eV" is effective for a substrate on which a pattern or the like is formed, and also for a substrate or the like on the surface of which a foreign material is present. Moreover, this LE range is effective regardless of the material of the substrate and foreign material. For example, the landing energy range "from LEA to LEB+5 eV" is also suitably applied to observation of a glass substrate. This allows a good image to be obtained.

Here the reason why the foreign material 10 can be imaged with a high contrast is clear from FIG. 178. As shown in FIG. 178, the change in brightness is different between the foreign material 10 and the surrounding normal part. The foreign material 10 generates mirror electrons at a higher landing energy LE (=LEB+5 eV) than the normal part. For this reason, the difference in gray level between the foreign material 10 and the normal part, ΔDN, can be secured large as illustrated. For example, suppose that the gray-level DN of the normal part is 50 DN and the variation in brightness (the noise) of the normal part is 3 DN. Suppose also that the gray-level DN of the foreign material 10 is 100 DN. In this case, the difference in gray level is ΔDN=50 DN (=100 DN−50 DN). The S/N ratio is therefore 50/3:16.7. In this way, a high S/N ratio can be obtained. This is exactly the above-described phenomenon that occurs in the region of the landing energy LE, from LEA to LEB+5 eV. The use of this phenomenon allows the imaging and inspection to be carried out with a high contrast. Other regions of the landing energy LE can not achieve the state where only the foreign material 10 generates mirror electrons, and therefore also cannot achieve a high contrast between the foreign material 10 and the surrounding normal part as described above. The foreign material 10 is therefore preferably detected in the range LEA≦LE≦LEB+5 eV. In addition, with regards to the descriptions in the present example, an adjustment method, that is, a method for adjusting, controlling and determining the relative relationship between mirror electrons (mirror center MC) and the NA aperture position (x, y direction) with respect to the center position of a crossover of secondary emission electrons at an NA location described in the embodiments related to FIGS. 44~50 is used. In this way, it is possible to efficiently and effectively obtain a high contrast and S/N of a defect.

While there have been described what are at present considered to be preferred embodiments of the invention, it will be understood that various modifications and variations may be made thereto, and it is intended that appended claims cover all such modifications and variations as fall within the true spirit and scope of the invention.

The present invention can inspect for the presence of foreign materials on a sample such as a semiconductor wafer using an electron beam, or be used in an electron beam inspection device which inspects for presence of a defect. Furthermore, the present embodiment can be applied to the embodiments 1~28 and also to embodiments with no number attached.

(Thirtieth Embodiment)

Platform

An example of platform used in the inspection device and inspection method of the present invention is explained.

In the present embodiment, an example which uses an inspection device and inspection method of the present invention for a mask (EUV mask, NIL), and parts (inversion unit, rotation unit, palette loading unit, neutralization unit) which are different to the inspection device and inspection method used for a wafer in the embodiments described are mainly explained.

Figure 179:
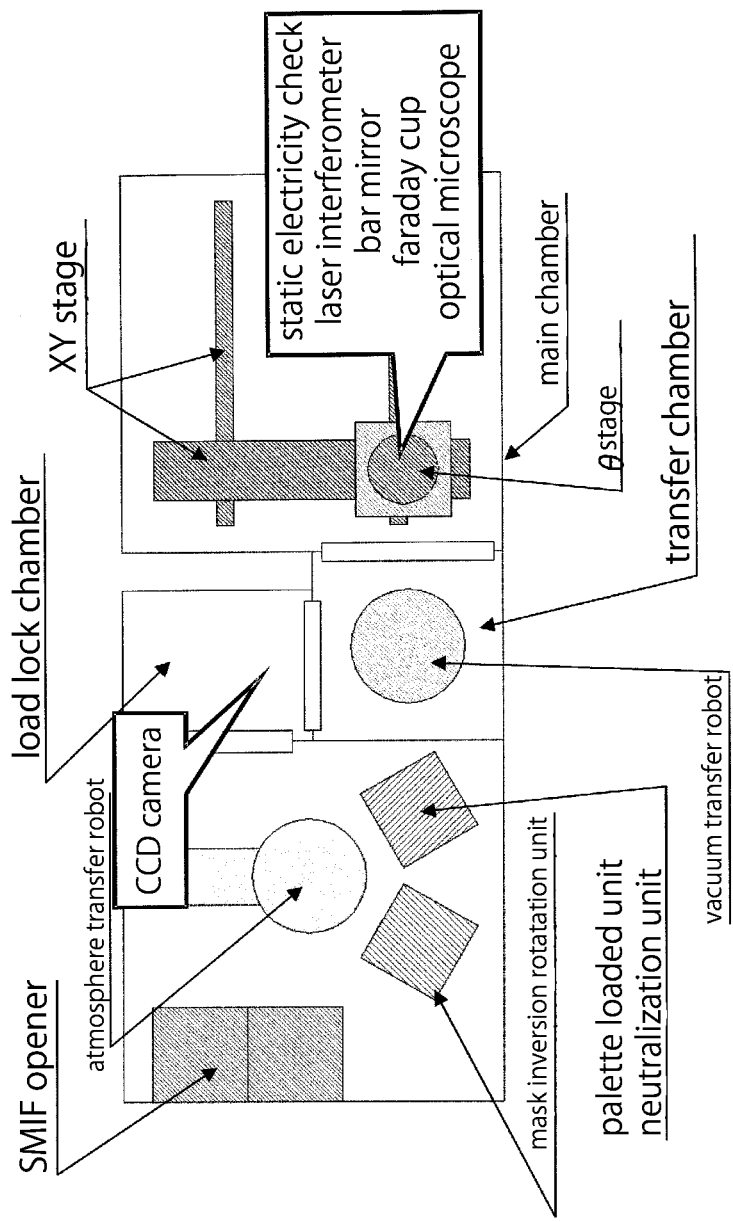
FIG. 179 is a diagram related to one embodiment of the present invention.
Figure 180:
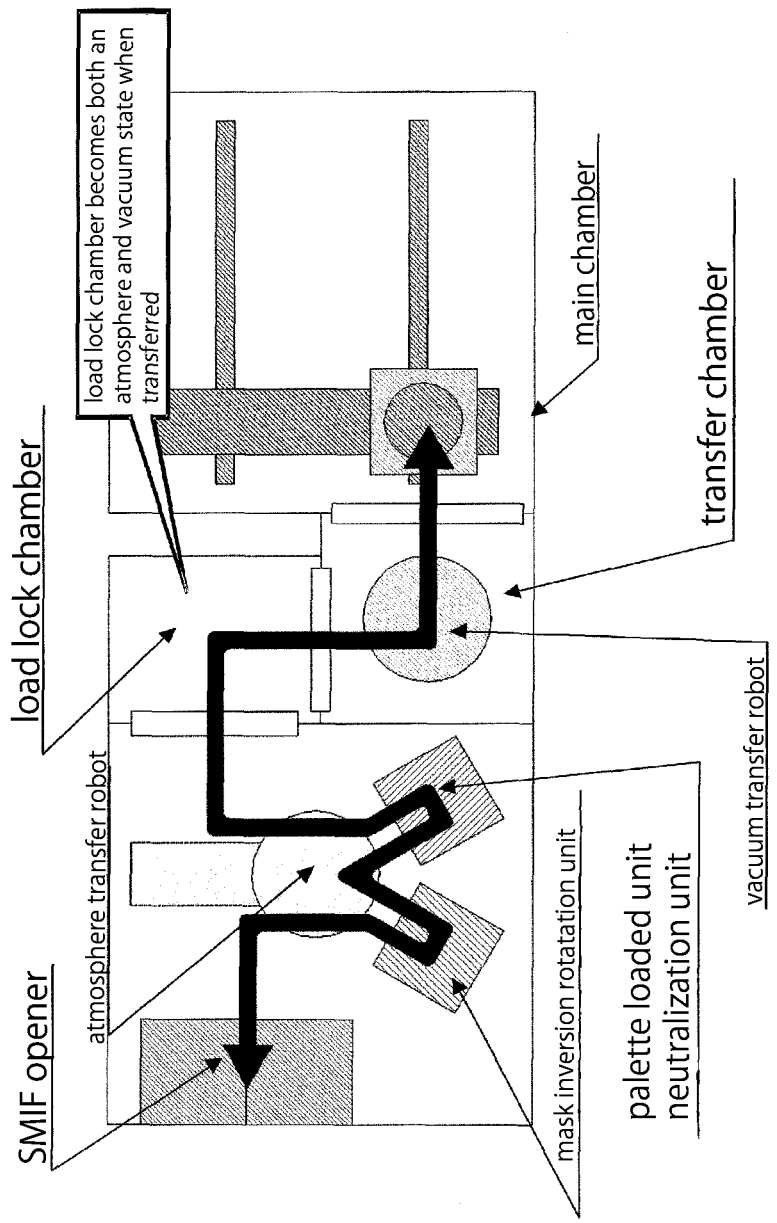
FIG. 180 is a diagram related to one embodiment of the present invention.

Referring to FIG. 179 and FIG. 180, a mask in a cassette such as a SMIF is transferred by an atmosphere transfer robot. Either the surface and rear surface of the mask is inspected. In addition, the direction for setting the mask is selected and inspection is performed. If the mask is in the same state as in the cassette then inversion is not necessary. In the case of changing the mask direction 90° or 180° for example, and performing an inspection, a direction in the rotation unit is selected as and set. If the mask is in the same state as in the cassette then this process is not necessary. Following this, the mask is arranged in the palette loading unit by the robot. The mask is mounted on the palette and the palette mounted with the mask is transferred. When mounting on the palette, a positioning mechanism is used for example, a direction adapter which determines the direction for arranging the mask at opposite corners. In this way, a rough direction is determined, for example, ±1~10 mrad (radian). The neutralization unit neutralizes a charge in the mask. When there is static electricity or when the mask is affected by light or electron or electrical effects in a previous process or inspection, a charge up remains on the mask surface. Neutralization is performed in the atmosphere transfer part in order to remove this charge, maintain a homogeneous surface potential state and perform a stable inspection. X ray irradiation, UV irradiation or ion irradiation are used for neutralization. Following this, the mask is transferred to an LL chamber. In the LL chamber a vacuum exhaust is performed to obtain a vacuum state. At this time, a slow exhaust is initially performed, and by raising the exhaust speed any attached particles are reduced and the time for forming a vacuum state is reduced. A CCD camera is arranged in the LL chamber in order to calculate the amount of alignment correction of the mask. In this way, the extent of any rotation direction misalignment is measured, and a correction amount of stage rotation is determined. If this is an amount which exceeds a correction amount, the mask is again returned to the palette loading unit, and the mask is reset. A vacuum, transfer robot is located in a transfer chamber. By arranging the mask in a vacuum state chamber, the attachment of particles to the robot is prevented and the production of dust from the robot is prevented. When the LL chamber reaches a defined vacuum level, a gate valve is opened and the palette and mask are transferred by the vacuum transfer robot to a stage in the main chamber. The stage can perform triaxial control x, y, θ. In order to maintain accuracy, the θ stage rotation angle is small, at maximum ±1~3°. This may be within a range achievable by pre-alignment. In this way, the θ stage accuracy and rigidity can be increased. A large clearance is required when a rotation angle is large, and angle control accuracy and rigidity deteriorate. The palette arranged in the stage is an electrostatic chuck and is fixed. A Faraday cup, correction sample and reference sample are located on the stage. A stage location detector performs location detection and control with a laser interferometer the same as in the case of a wafer. Furthermore, the present embodiment can be applied to the embodiments 1~29 and also to embodiments with no number attached.

(Thirty First Embodiment)

Another example in foreign material inspection in the inspection device and inspection method of the present invention is explained.

(EO Adjustment Method)

As described in the EO adjustment method of a pattern above, by measuring the EO conditions used in foreign material inspection, the distribution of a beam which arrives at an NA location and controlling the location of mirror electrons it is possible to realize a foreign material inspection with a high level of sensitivity. In an example of a pattern inspection, FIG. 181 is referred to which can adjust and determine an observation of a beam at an NA location and irradiation angles θ, α. In the case of foreign material inspection, the surface of an object to be inspected is often solid (flat), that is, the surface often does not have a pattern. Consequently, accuracy is not requested with respect to α. However, it is necessary to align the coordinates of a detected defect. At this time, it is possible to similar determine the correlation with an NA and pattern inspection.

In particular it is effective to distance the mirror electron location from the CO center of secondary emission electrons in order to increase sensitivity to an ultrafine foreign material with a size of 5~30 nm. That is, it is effective to increase the irradiation electron angle θ. (when a perpendicular axis from a sample is given as z axis, 0°). This is because when irradiating with a larger angle than a perpendicular angle, it is easy to be affected by the non-uniformity of a surface potential. That is, a potential difference of a surface with respect to an energy in a z direction provides an influence, however, the closer irradiation is performed in a horizontal direction rather than perpendicular direction the greater are the effects on the speed component of a z direction and therefore a large difference is produced with the trajectory of an electron in a periphery normal part. Another cause is that it is easy for a non-uniform charge to be produced in a foreign material. Simply speaking, a shadow of an irradiated beam can easily be formed, the potential difference between a part which is irradiated and parts which is not irradiated becomes larger, and a rapid potential distribution change is formed in the vicinity of a foreign material. Therefore, a trajectory may easily be changed due to these effects. Sensitivity is improved due to these effects. This concept is shown in FIG. 182. An experimental result shows that an irradiation angle of about 10~30° is effective when inspecting with a high sensitivity in a detection of a foreign material with a size of 5~30 nm. Alternatively, at this time, as much as possible a mirror electron signal from a normal part is not obtained. An NA location is determined so that only mirror electrons from the foreign material are obtained. Specifically, an NA is arranged between the CO center of the secondary emission electrons and the MC location. In addition, preferably, the NA is set at a location slightly away so that the MC location (mirror electron location) is not affected. In addition, more preferably, the distance between the MC end part and NA end part is set to 1~100 μm and more preferably, 10~50 μm. This is because when performing an inspection of a large area, the MC location varies for various reasons and therefore it is important to maintain the above described distance in order to achieve a stable and high S/N foreign material detection. In addition, although any direction may be the MC direction a signal can easily by produced from that direction. That is, when a foreign material is a sphere, an elliptical signal in that direction is obtained. This means that an enlarged signal is obtained. That is, since a signal is obtained with a larger size than the size of a foreign material, it is possible to perform detection with a Px size larger than the size of a foreign material. This is very effective for throughput of an ultrafine foreign material inspection in particular. For example, when the foreign material size is 10 nm, it is possible to perform a detection at 100 nm Px in the present invention. A throughput difference of ×100 times is produced compared to the case where 10 nm Px is used. In the present invention, it is possible to use a pixel size of ×5~50 times the minimum size of the foreign material to be detected. In addition, in particular, it is effective to use ×2~×10 in the case of a difficult ultrafine foreign material size of 5~30 nm. Because a Px size of ⅓~ 1/10 the size of a foreign material is necessary in the case of detecting a foreign material using a SEM method, a difference with the present invention of ×6~×100 is produced just in terms of Px size which is a significant throughput difference. In addition, since there is a limit to detecting foreign materials of a ½ wavelength size using a light method, detection of ultrafine foreign materials which is the object of this invention can not be performed.

In addition, with regards to direction, when the MC and NA are arranged in a Y direction or X direction, a symmetrical signal can be obtained with respect to the x and y axis, and asymmetric when diagonal. These are used separately by selecting the better sensitivity according to the object sample or foreign material. Furthermore, the present embodiment can be applied to the embodiments 1~30 and also to embodiments with no number attached.

(Thirty Second Embodiment)

In the present embodiment, an example of an NA (numerical aperture) used in the inspection device and inspection method of the present invention is explained.

(NA Shape)

Figure 183:
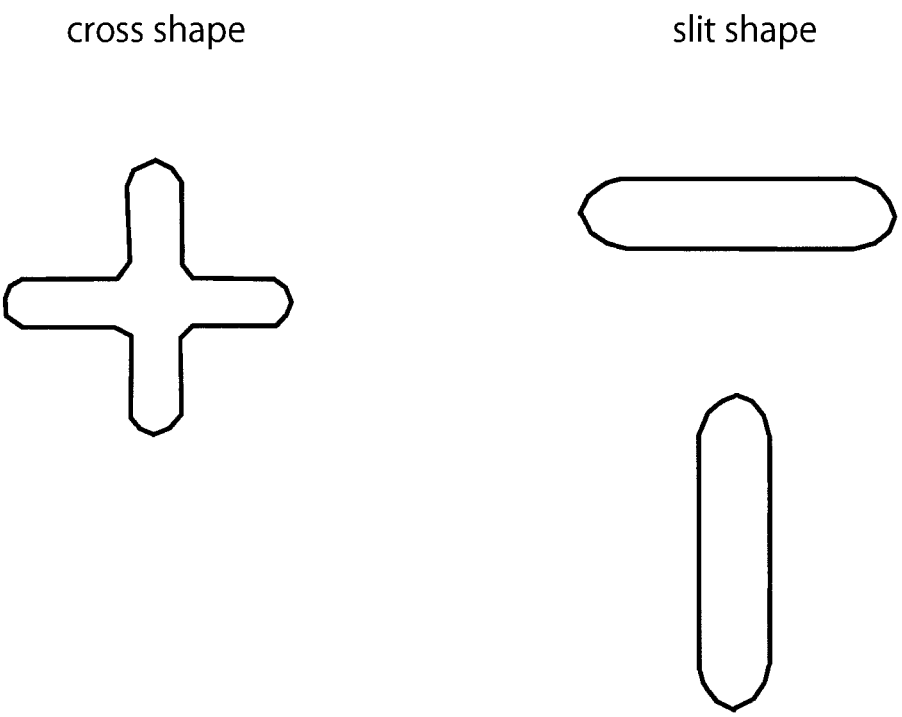
FIG. 183 is a diagram related to one embodiment of the present invention.
Figure 184:
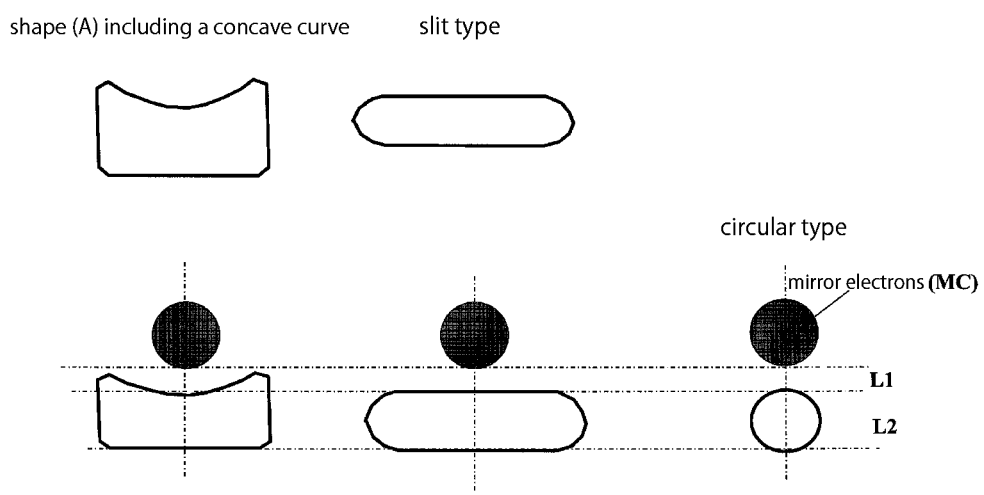
FIG. 184 is a diagram related to one embodiment of the present invention.

In a pattern inspection and foreign material inspection, it is more effective to use an NA with the shape shown in FIG. 183 and FIG. 184 compared with a normally used NA having a round shaped hole. A high contrast and S/N and electron amount can be obtained as well as an increase in sensitivity and throughput.

In a pattern inspection, a vertical and horizontal pattern sometimes has a different contrast in a y direction and x direction. When a + shaped hole is used in this case, it is possible to combine data of an electron signal with a strong vertical contrast and an electron signal with a strong horizontal contrast, increase the amount of electrons at a high contrast and obtained a high S/N.

A data of a stronger vertical signal is obtained using a slit. Alternatively, it is effective when obtaining electron data having characteristic due to a direction such as obtaining a lot of data in a horizontal direction. In the case of a pattern, for example, a misalignment is sometimes produced at a cross over point (Cox, Coy) in an x and y direction such as E×B. At this time, the amount of electron data and aberration in an y direction is measured, using a slit in which has a hole is longer in the y direction at a COx in the x direction, and the amount of electron data and aberration in an x direction is measured using a slit in which has a hole is longer in the x direction at a COy in the y direction. In this way, the amount of electrons and aberration is controlled, a high contrast and S/N can be obtained, and because the amount of electrons can be increased, sensitivity and throughput can be improved compared to a round shaped hole.

A sensitivity improvement of ×1.4~×5 and an increase in the amount of electrons of ×1.5~10 can be obtained with the NA described above.

In addition, the NA shape shown in FIG. 184 is particularly effective when used in a foreign material inspection, a shape A having a hollow part and a slit. When inspecting a foreign material, it is effective to arrange an NA at a location which does not affect a mirror electron. However, when arranging the NA at a location near the MC location where the mirror electron has a strong intensity, an S/N having a high foreign material signal can sometimes be obtained. At this time, it is effective to use the NA as shown in FIG. 184. Because a round shaped hole is a bump shaped hole, a lot of electron data near an MC can not be obtained and when the location of an MC varies the effects are soon received. The shape shown in FIG. 184 is provided as a method of solving this problem. It is easy to bring closer to an MC if this shape has a hollow part and it is possible to obtain a lot of electron data near the MC. In addition, because a hollow shape along the MC shape or the hole shape of a slit (line shape) is on the side close to an MC, even if the MC location varies it is possible to set the hole at a distance where no effects are received. It is also possible to obtain more periphery electron data than a round shape of a bump shaped hole. The fact that the brightness of only a foreign material increases by a mirror electron is used within electron data with a mixture of a mirror electron signal of a foreign material and a secondary emission electron signal of a normal periphery part. At this time, when MC electron data is mixed, mirror electrons are added to the entire image region, the grey level (same as a difference in brightness, difference in amount of electrons) between a foreign material and periphery decreases and an S/N also decreases.

A conceptual view of this state is shown at the bottom FIG. 184 which shows an example of the MC and NA arrangement. The MC is normally a round shape. At this time, each NA is arranged so that a hole end part is located at the same distance L1 from the end part of the MC. In addition, the width and diameter (L2) of the hole are the same. At this time, because the hollow type and slit type holes have a large area and because the area at a location near an MC is also large it is possible to obtain an electron signal near the MC.

Figure 185:
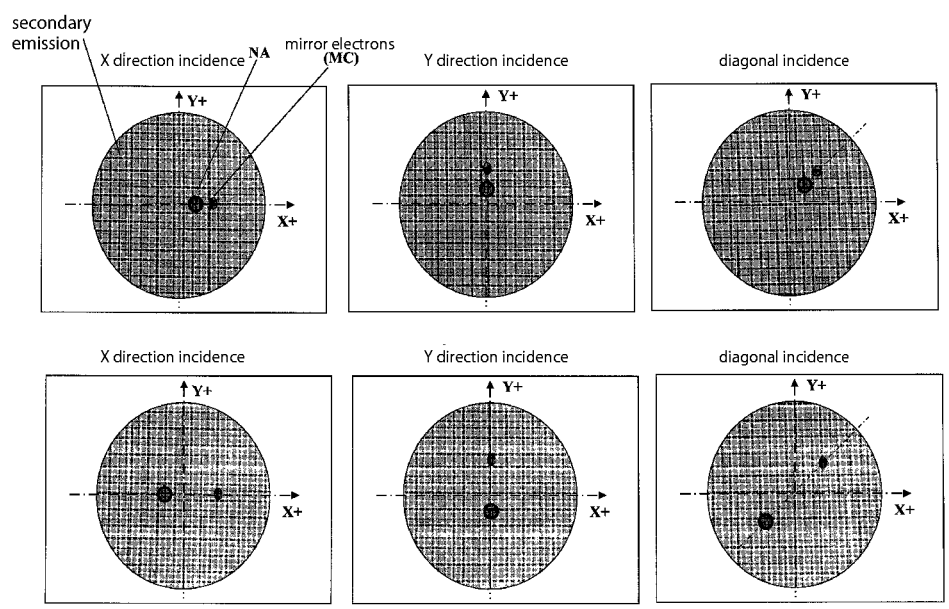
FIG. 185 is a diagram related to one embodiment of the present invention.
Figure 186:
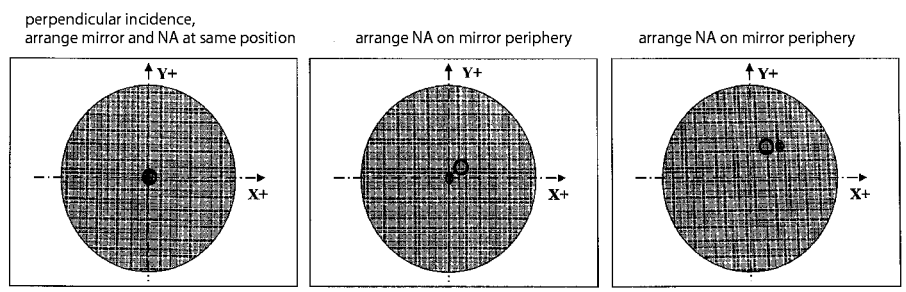
FIG. 186 is a diagram related to one embodiment of the present invention.

In addition, FIG. 185 and FIG. 186 are examples of the location relationship for arranging an MC and NA. It is possible to use this example in a pattern observation and foreign material inspection using this type of location relationship. In addition, it is possible and effective to use the examples in embodiment 29 described above with regards to the conditions of an irradiated electron beam and precharge conditions.

(Thirty Third Embodiment)

Figure 8:
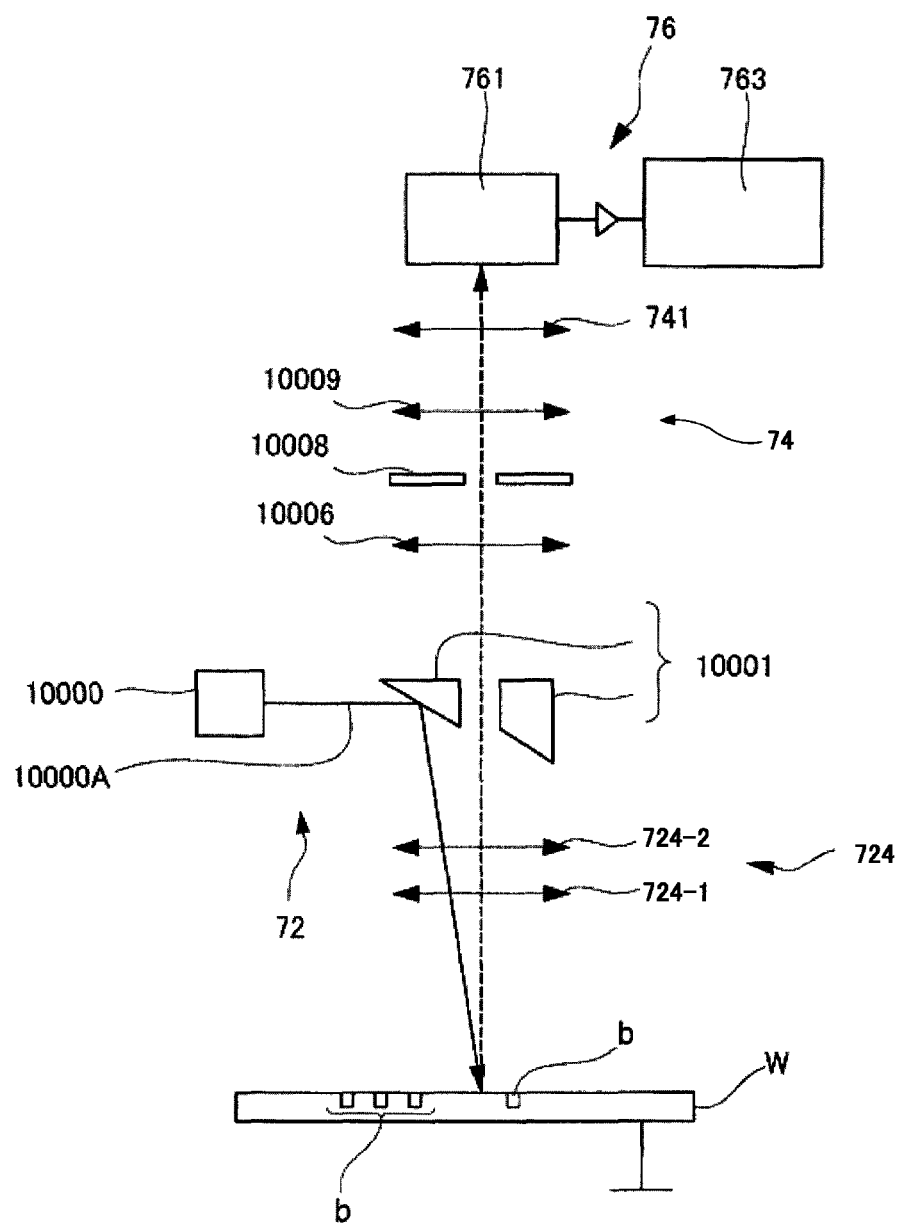
FIG. 8 is a schematic diagram which shows an approximate structure of an electron optical device of the inspection device in FIG. 1.
Figure 187:
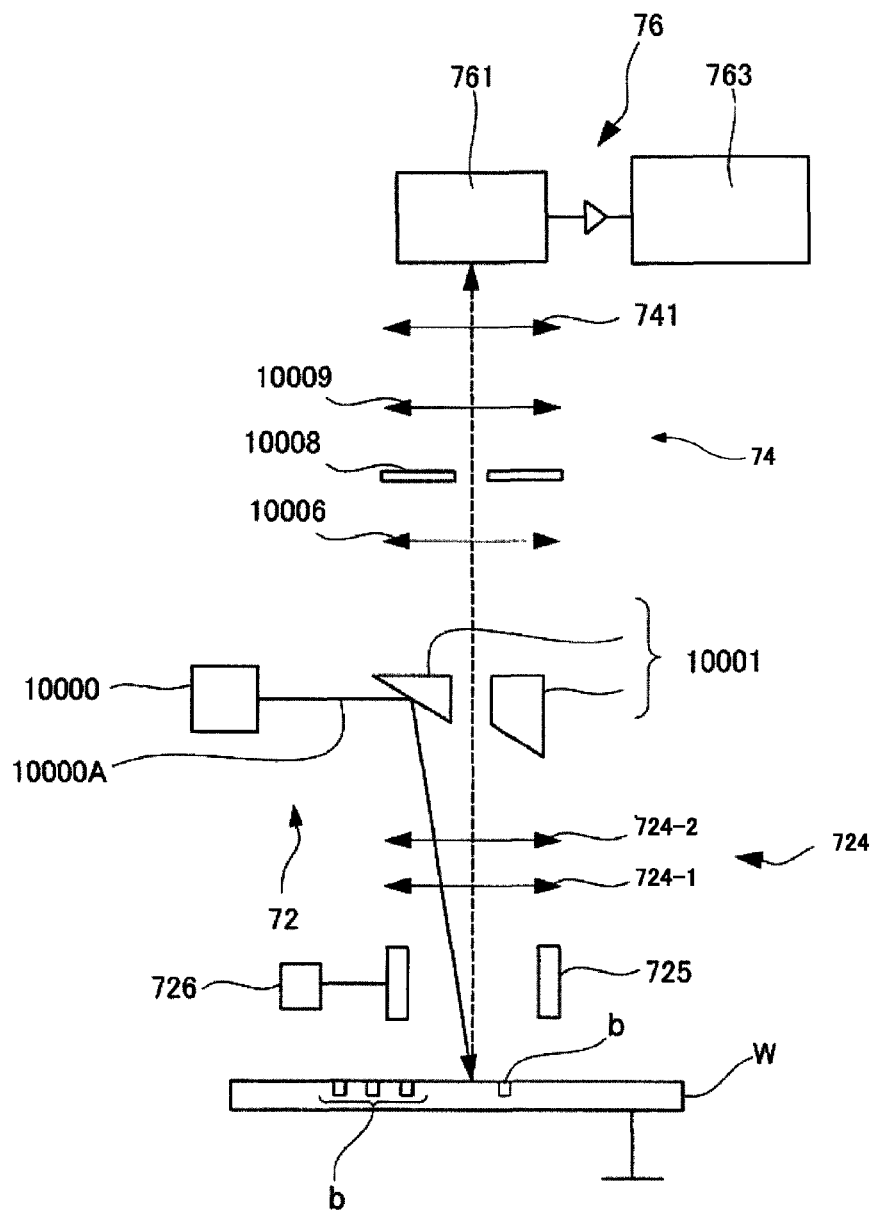
FIG. 187 is a diagram related to one embodiment of the present invention.

In the present embodiment, modified embodiments of the inspection device of the present invention shown in FIG. 8 are explained. Apart from arranging an electrode 725, the modified embodiment is the same as the inspection device of the present invention shown in FIG. 8 and therefore, repeated explanations are omitted. As is shown in FIG. 187, when a voltage applied to an electrode 725 is 4000V~−400V when there is a via b on a wafer, it is possible to obtain an electric field of the electron beam irradiation surface of a wafer of 2.0 kV~−0.2 kV/mm (− shows that the wafer side is a high potential). In this way it is possible to increase or decrease the electrical field intensity (perpendicular direction, Z direction from the surface) of a sample surface. That is, it is possible to reduce the electrical field intensity in the case of a sample which is easily discharged so that it does not discharge. In this state, discharge does not occur between an object lens system 724 and a wafer W, and a defect inspection of the wafer W can be performed. However, the emission efficiency of electrons slightly decreases. Therefore, a predetermined detection sensitivity is obtained by an accumulation calculation or averaging process of a detection result comprised of four detection results obtained by performing a series of four operations for detecting a photoelectron which is irradiated.

In addition, it is possible to use a relatively high electrical field intensity in the case where the wafer does not include a via b. It is possible to perform a defect inspection of a wafer W without discharge occurring between an object lens system 724 and the wafer W even when a voltage provided to the electrode 725 is +3000V. In this case, it is possible to increase a pickup electric field increases due to the voltage provided to the electrode 725 and reduce aberrations in the object lens, and therefore, it is possible to improve resolution and achieve a high contrast and S/N. Consequently, an inspection can be performed with a high sensitivity and throughput.

(Electrode)

A roughly symmetrically shaped electrode 725 with respect to the irradiation optical axis of an electron beam is arranged between the object lens 724 and wafer W. An example of the shape of the electrode 725 is shown in FIG. 188 and FIG. 189.

Figure 188:
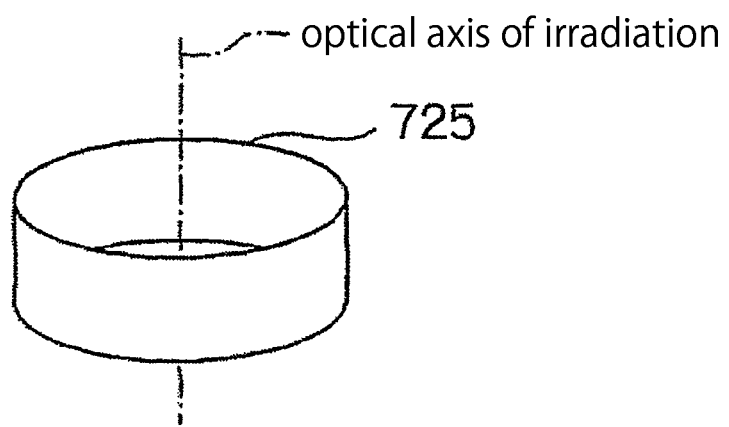
FIG. 188 is a diagram related to one embodiment of the present invention.
Figure 189:
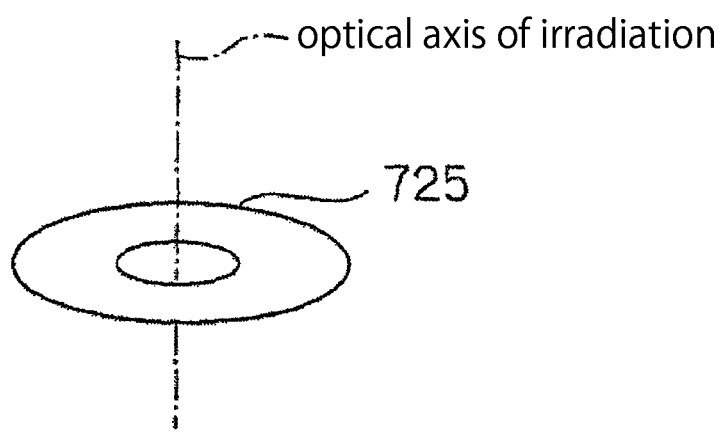
FIG. 189 is a diagram related to one embodiment of the present invention.

FIG. 188 and FIG. 189 are perspective views of the electrode 725, FIG. 188 is a perspective view showing the case where the electrode has an axisymmetrically cylinder shape, and FIG. 189 is a perspective view showing the case where the electrode 725 has an axisymmetrically disc shape.

In the present embodiment, as is shown in FIG. 188, the electrode 725 is explained with a cylinder shape. However, the disc shape shown in FIG. 189 may also be used if it is roughly symmetrical with respect to the irradiation optical axis of an electron beam.

Furthermore, a lower predetermined voltage (negative potential) than the voltage (since the voltage in the present embodiment is grounded the potential is 0) applied to the wafer W is applied by the power supply 726 in order to generate an electric field for preventing discharge between the object lens 724 and the wafer W. The potential distribution between the wafer W and the object lens 724 is explained referring to FIG. 190.

Figure 190:
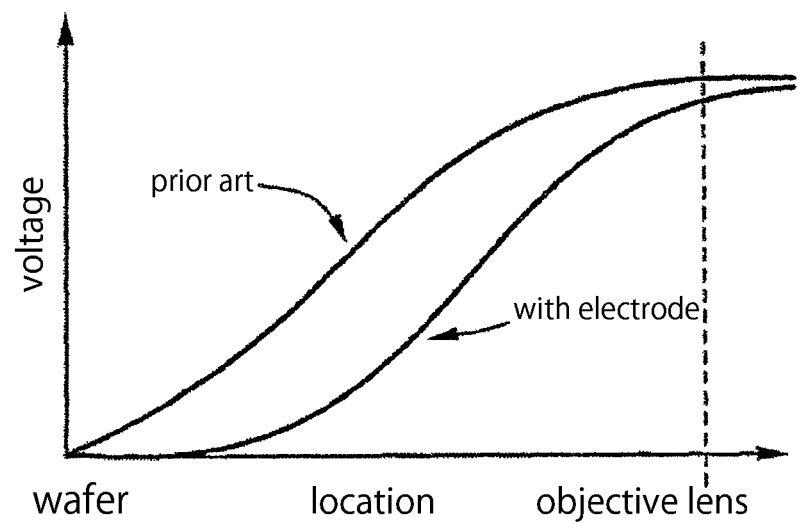
FIG. 190 is a diagram related to one embodiment of the present invention.

FIG. 190 is a graph which shows the voltage distribution between the wafer W and the object lens 724.

In FIG. 190, a voltage distribution from the wafer W up to the location of the object lens 724 is shown with the location at the irradiation optical axis of an electron beam as the horizontal axis.

The voltage distribution from the object lens 724 up to the wafer W in a conventional electron beam device without the electrode 725 changes smoothly up to the grounded wafer when the voltage applied to the object lens 724 is a maximum value ([conventional] shown in FIG. 190).

On the other hand, in the electron beam device of the present embodiment, because the electrode 725 is arranged between the object lens 724 and the wafer W and a lower predetermined voltage (negative potential) than the voltage applied to the wafer W is applied by the power supply 726, the electric field of the wafer W weakens ([including electrode] in FIG. 190).

Therefore, in the electron beam device of the present embodiment, an electric field does not crowd near the via b of the wafer b and does not become a high electrical field. Then, even if an electron beam is irradiated to the via b and secondary emission electrons are emitted, because these emitted secondary electrons are not accelerated in a process for ionizing a residual gas, it is possible to prevent a discharge between the object lens 724 and the wafer W.

In addition, because it is possible to prevent discharge between the objective lens 724 and the via b, there is no discharge damage to the pattern of the wafer W etc.

In addition, in the embodiment described above, while it is possible to prevent discharge between the object lens 724 and the wafer W which has a via b and therefore a negative voltage is applied to the electrode 725, the detection sensitivity in the detector 726 of a secondary electron sometimes decreases depending on the size of the negative potential. Therefore, when detection sensitivity decreases, as described above, an electron beam is irradiated, a series of operations for detecting secondary electrons is performed over a plurality of times, and a predetermined detection sensitivity (signal S/N ratio) can be obtained by an accumulation calculation or averaging process of the plurality of detection results obtained.

In the present embodiment, an example of detection sensitivity is explained as a noise with respect to signal ratio (S/N ratio).

Here, the secondary electron detection operation described above is explained while referring to FIG. 191.

Figure 191:
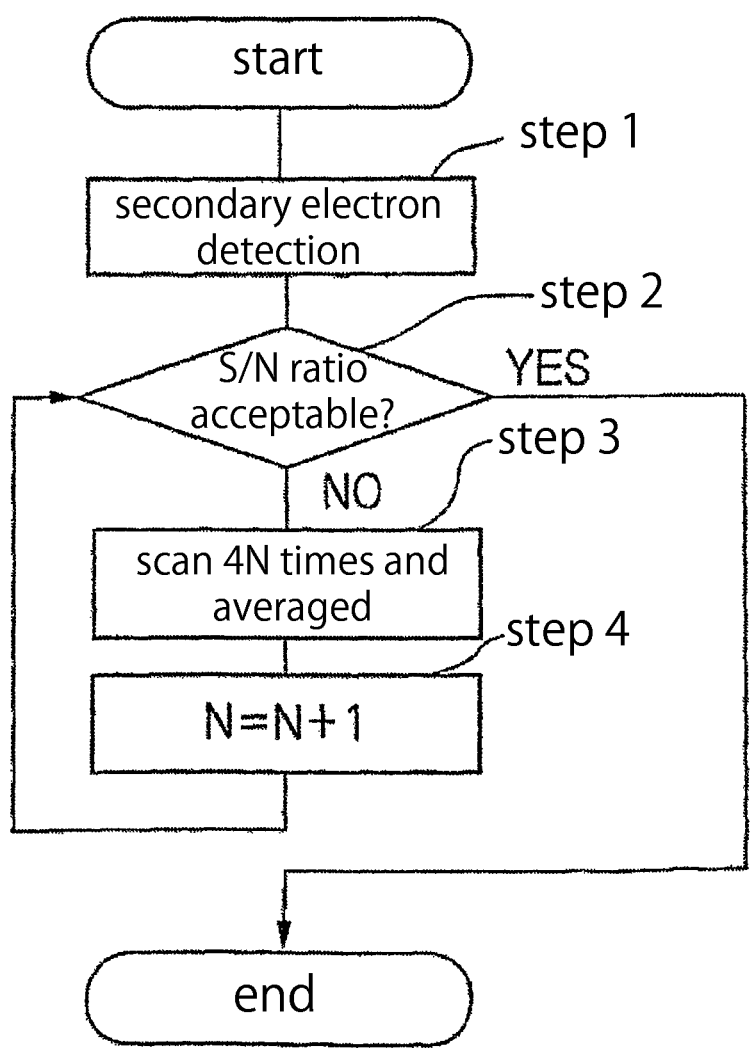
FIG. 191 is a diagram related to one embodiment of the present invention.

FIG. 191 is a flowchart which shows the secondary electron detection operation of the electron beam device.

First, secondary electrons from a sample to be inspected are detected by the detector 761 (step 1). Next, a judgment is performed whether a signal to noise ratio (S/N ratio) is a predetermined value or more (step 2). In step 2, in the case where the signal to noise ratio is a predetermined value or more, detection of secondary electrons by the detector 761 is sufficient and a secondary electron detection operation is complete.

On the other hand, in step 2, in the case where the signal to noise ratio is less than a predetermined value, an electron beam is irradiated and a series of operations for detecting secondary electrons is performed 4N times, and an averaging process is performed (step 3). Here, the initial value of N is set at [1], therefore, a detection operation of secondary electrons in step 3 is first performed four times.

Next, [1] is added to N and a counted up (step 4), and in step 2, a judgment is made again whether the signal to noise ratio is a predetermined value or more. Here, in the case where the signal to noise ratio is less than a predetermined value, the process moves to step 3 and the detection operation of the secondary electrons is performed 8 times. Then, N is counted up and the steps 2-4 are repeated until the signal to noise ratio is the predetermined value or more.

In addition, in the present embodiment, a method of preventing discharge to a wafer with a via b by applying a lower predetermined voltage (a negative voltage) to the electrode 725 than the voltage applied to the wafer W was explained. However, the detection efficiency of secondary electrons sometimes decreases.

Therefore, in even in the case of a sample to be inspected is a type such as a wafer with no via, where a discharge between itself and an object lens 724 is not easily produced, it is possible to control a voltage applied to the electrode 725 so that the detection efficiency of secondary electrons in the detector 761 increases.

Specifically, even in the case where a sample to be inspected is grounded, the voltage applied to the electrode 725 is made a higher predetermined voltage than the voltage applied to the sample to be inspected, for example, +10V. In addition, at this time, the distance between the electrode 725 and the sample to be inspected is a distance where discharge is not easily generated between the electrode 725 and the sample to be inspected.

In this case, secondary electrons which are produced by irradiation of an electron beam to a sample to be inspected are accelerated to the electron beam source 721 side by an electric field generated by the voltage applied to the electrode 725. In addition, because the secondary electrons are accelerated and convergence effects are received at the electron beam source 721 side by an electric field generated by the voltage applied to the object lens 724, it is possible to irradiate many secondary electrons to the detector 761 and increase the detection efficiency.

In addition, because the electrode 725 is axisymmetrical, a lens effect which converges an electron beam irradiated to a sample to be inspected is produced. Therefore, it is possible to further narrow a primary electron beam due to the voltage applied to the electrode 725. In addition, because it is possible to further narrow a primary electron by the electrode 725, it is possible to form an object lens system with even fewer aberrations by combining with the object lens 724. These lens effects can be obtained to a certain extent as long as the electrode 725 is roughly axisymmetrical.

According to the electron beam device of the present example described above, because an electrode which controls an electric field in an electron beam irradiated surface of a sample to be inspected is arranged between the sample to be inspected and an object lens, it is possible to control the electric field between the sample to be inspected and the object lens.

In addition, because an electrode which is arranged between a sample to be inspected and an object lens has a roughly axisymmetrical shape with respect to the irradiation axis of an electron beam and weakens an electric field intensity at an electron beam irradiated surface of a sample to be inspected, it is possible to remove a discharge between the sample to be inspected and the objected lens.

In addition, because a reduction of a voltage applied to an object lens does not change, secondary electrons pass efficiently through the object lens and therefore it is possible to improve detection efficiency and obtain a signal with a good S/N ratio.

In addition, it is possible to control a voltage for weakening an electric field intensity in an electron beam irradiated surface of a sample to be inspected according to the type of sample to be inspected.

For example, when the sample to be inspected is a sample of a type where discharge occurs easily between itself and an object lens, the voltage of an electrode is changed and discharge can be prevented by further weakening an electric field intensity in an electron beam irradiated surface of a sample to be inspected.

In addition, the voltage applied to an electrode is changed depending on the presence of a via in a semiconductor wafer.

That is, it is possible to change a voltage for weakening an electric field intensity in an electron beam irradiated surface of a sample to be inspected.

For example, in the case where a sample to be inspected is of a type where discharge occurs easily between itself and an object lens, it is possible to prevent discharge particularly in a via or via periphery by changing an electric field with an electrode and weakening an electric field intensity in an electron beam irradiated surface of a sample to be inspected.

In addition, because a discharge between a via and an object lens can be prevented, there is no discharge damage to a pattern etc of a semiconductor wafer.

In addition, because a potential provided to an electrode is lower than a charge provided to a sample to be inspected, it is possible to weaken an electric field intensity in an electron beam irradiated surface of a sample to be inspected and prevent discharge to the sample to be inspected.

In addition, because the potential provided to an electrode is a negative potential and the sample to be inspected is grounded, it is possible to weaken an electric field intensity in an electron beam irradiated surface of a sample to be inspected and prevent discharge to the sample to be inspected. Furthermore, the present embodiment can be applied to the embodiments 1~33 and also to embodiments with no number attached.

(Thirty Fourth Embodiment)

In the present embodiment, a modified embodiment in the inspection device of the present invention shown in FIG. 8 is explained. An imaging device arranged with a precharge unit of the present embodiment is exemplary shown in FIG. 192. The imaging device 1 is arranged with a primary optical system 72, secondary optical system 74, detection system 76, and a charge control means 840 which uniformalizes or reduces a charge to an object. In the present embodiment an explanation of the same structure as embodiment 1 described above is omitted.

In this example, the charge control means 840 which uniformalizes or reduces a charge to an object includes an electrode 841 which is brought near to and arranged between an object W and an electrostatic lens 724 of a primary optical system nearest to the object W, a switch 842 which is electrically connected to the electrode 841, a voltage generator 844 which is electrically connected to one terminal 843 or the switch 842, and a charge detector 846 which is electrically connected to the other terminal 845 of the switch 842. The charge detector 846 includes a high impedance. A timing generator 849 provides operation timing commands to a CCD 762 and image processing part 763 of the detector system 76, the switch 842 of the charge control means 840, and the voltage generator 844, and charge detectors 846 and 848. Furthermore, the present embodiment can be applied to the embodiments 1~33 and also to embodiments with no number attached.

(Thirty Fifth Embodiment)
Device Manufacturing Method

Next, an embodiment of a method of manufacturing a semiconductor device according to the present invention will be described with reference to FIG. 193 and FIG. 194.

Figure 193:
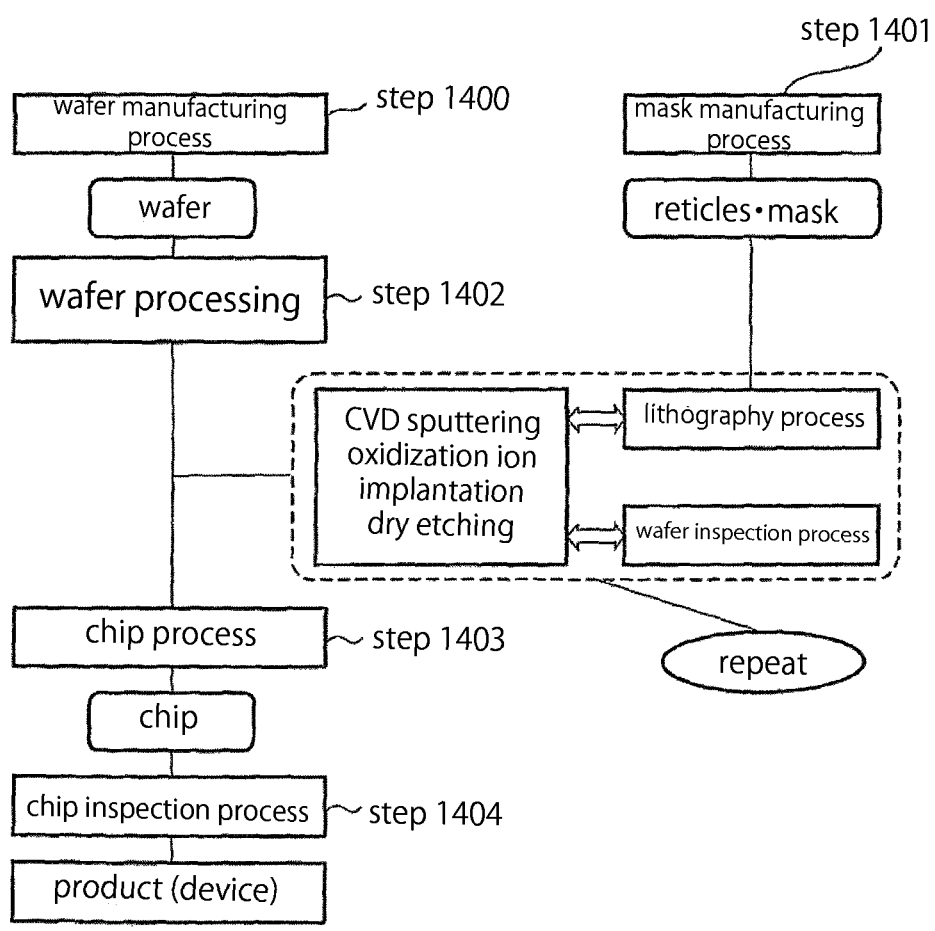
FIG. 193 is a diagram related to one embodiment of the present invention.

FIG. 193 is a flow chart illustrating an embodiment of a method of manufacturing a semiconductor device according to the present invention. Manufacturing processes of this embodiment include the following main processes:

(1) a wafer manufacturing process for manufacturing a wafer (or a wafer preparing process for preparing a wafer)(Step 1400);

(2) a mask manufacturing process for manufacturing masks to be used during the exposure (or mask preparing process for preparing masks)(Step 1401);
(3) a wafer processing process for performing any processing treatment necessary for the wafer (Step 1402);
(4) a chip assembling process for cutting out those chips formed on the wafer one by one to make them operable (Step 1403); and
(5) a chip inspection process for inspecting finished chips (Step 1404).

The respective main processes are further comprised of several sub-processes.

Among these main processes, the wafer processing process set forth in (3) exerts a critical effect on the performance of resultant semiconductor devices. This process involves sequentially laminating designed circuit patterns on the wafer to form a large number of chips which operate as memories, MPUs and so on. The wafer processing process includes the following sub-processes:
(A) a thin film forming sub-process for forming dielectric thin films serving as insulating layers and/or metal thin films for forming wirings or electrodes, and the like (by using CVD, sputtering and so on);
(B) an oxidization sub-process for oxidizing the thin film layers and the wafer substrate;
(C) a lithography sub-process for forming a resist pattern by using masks (reticles) for selectively processing the thin film layers and/or the wafer substrate;
(D) an etching sub-process for processing the thin film layers and/or the wafer substrate in accordance with the resist pattern (by using, for example, dry etching techniques);
(E) an ion/impurity injection/diffusion sub-process;
(F) a resist striping sub-process; and
(G) a sub-process for inspecting the processed wafer;

As can be appreciated, the wafer processing process is repeated a number of times depending on the number of required layers to manufacture semiconductor devices which operate as designed.

Figure 194A:
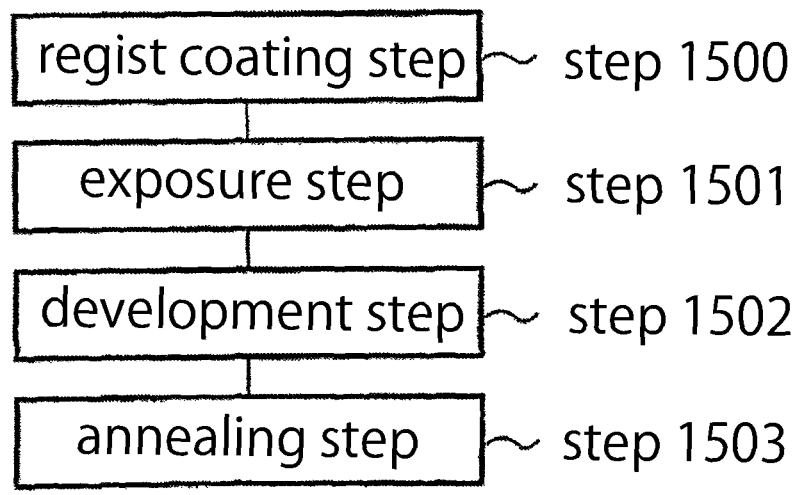
FIG. 194A is a diagram related to one embodiment of the present invention.

FIG. 194A is a flow chart illustrating the lithography sub-process which forms the core of the wafer processing process in FIG. 193. The lithography sub-process includes the following steps:
(a) a resist coating step for coating a resist on the wafer on which circuit patterns have been formed in the previous process (Step 1500);
(b) an exposing step for exposing the resist (Step 1501);
(c) a developing step for developing the exposed resist to produce a resist pattern (Step 1502); and
(d) an annealing step for stabilizing the developed resist pattern (Step 1503).

Since the aforementioned semiconductor device manufacturing process, wafer processing process and lithography process are well known, no further description is required.

When the defect inspection method and defect inspection apparatus according to the present invention are used in the inspection sub-process set forth in (G), any semiconductor devices, even those having miniature patterns, can be inspected at a high throughput, so that a total inspection can also be conducted, thereby making it possible to improve the yield rate of products and prevent defective products from being shipped.

Inspection Procedure

An inspection procedure in the inspection process (G) stated above is explained as follows.

Generally, since an inspection apparatus using an electron beam is expensive and the throughput thereof is rather lower than that provided by other processing apparatuses, this type of inspection apparatus is currently applied to a wafer after an important process (for example, etching, film deposition, or CMP (chemical and mechanical polishing) flattening process) to which it is considered that the inspection is required most.

Figure 194B:
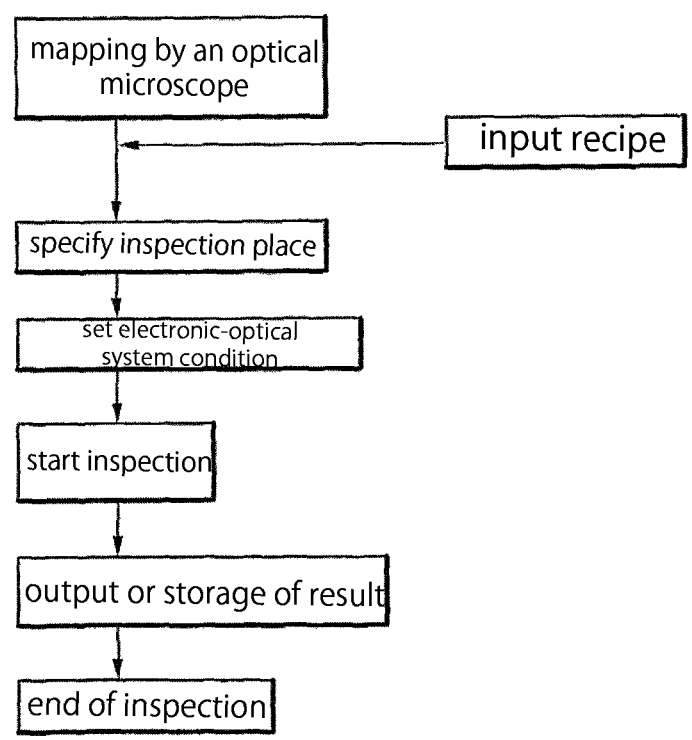
FIG. 194B is a diagram related to one embodiment of the present invention.

A wafer to be inspected is, after having been positioned on an ultra-precise X-Y stage through an atmosphere transfer system and a vacuum transfer system, secured by an electrostatic chucking mechanism or the like, and then a detect inspection is conducted according to a procedure as shown in (FIG. 194B). At first, if required, a position of each die is checked and/or a height of each location is sensed, and those values are stored. In addition, an optical microscope is used to obtain an optical microscope image in an area of interest possibly including defects or the like, which may also be used in, for example, the comparison with an electron beam image. Then, recipe information corresponding to the kind of wafer (for example, after which process the inspection should be applied; what is the wafer size, 20 cm or 30 cm, and so on) is entered into the apparatus, and subsequently, after a designation of an inspection place, a setting of an electron optical system and a setting of an inspection condition being established, a defect inspection is typically conducted in real time while simultaneously obtaining the image. A fast data processing system with an algorithm installed therein executes an inspection, such as the comparisons between cells, between dies or the like, and any results would be output to a CRT or the like and stored in a memory, if desired. Those defects include a particle defect, an irregular shape (a pattern defect) and an electric defect (a broken wire or via, a bad continuity or the like); and the fast data processing system also can automatically and in realtime distinguish and categorize the defects according to their size, or whether they are a killer defect (a critical defect or the like which disables a chip). The detection of the electric defect may be accomplished by detecting an irregular contrast. For example, since a location having a bad continuity would generally be positively charged by an electron beam irradiation (about 500 eV) and thereby its contrast would be decreased, the location of bad continuity can be distinguished from normal locations. The electron beam irradiation means in that case designates an electron beam source (means for generating thermal electron, UV/photoelectron) with lower potential (energy) arranged in order to emphasize the contrast by a potential difference, in addition to the electron beam irradiation means used for a regular inspection. Before the electron beam being irradiated against the objective region for inspection, the electron beam having that lower potential (energy) is generated and irradiated. In the case of a projecting method in which the object can be positively charged particles by the irradiation of the electron beam, the electron beam source with lower potential is not necessarily arranged separately, depending on the specification of the system for the method. Further, the defect may be inspected based on the difference in contrast (which is caused by the difference in flowability of elements depending on the forward or backward direction) created by, for example, applying a positive or negative potential relative to a reference potential to a wafer or the like. This electron beam generation means may be applicable to a line-width measuring apparatus and also to an aligning accuracy measurement.

It is possible to apply all of the embodiments described above during an inspection and inspection process required in the processes described above. In addition, it is also possible to apply the embodiments to all of the device systems which include the functions, mechanisms and characteristics of FIG. 1~FIG. 25 described above. In this way, it is possible to perform a very efficient inspection in a manufacturing process of a wafer or mask. Furthermore, the present embodiment can be applied to the embodiments 1~34 and also to embodiments with no number attached.

(Thirty Sixth Embodiment)

Inspection of a HDD Substrate, Head Element

The present invention can also be applied to an inspection of a HDD substrate as well as a wafer and exposure mask. While application examples are described below, the effects and operations are the same as that for a semiconductor wafer or mask.

For example, in a HDD substrate, it is usual to arrange a magnetic top layer on a glass or ceramic substrate and above this is arranged a thin lubricating layer. Two types of inspection can be performed on this substrate. One is an inspection of attached foreign materials or particles and damage when manufacturing the substrate and the other is an inspection of defects of a film quality when forming a surface.

It is no longer possible to normally form a magnetic film on a substrate when an aluminum or glass substrate itself is damaged or when foreign materials or particles are attached after manufacturing or cleaning. This is because the level of planarization deteriorates and unevenness if formed. In recent high density media, because the floating amount of a substrate and head is around 5 nm, it is necessary to form unevenness smaller than 5 nm. That is, it is necessary to prevent the attachment of foreign material with a size of ≧5 nm. This is also true for a damaged uneven surface. Consequently, it is possible to the inspection device of the present invention to an inspection of this foreign material or damage and an inspection at a high speed and sensitivity is possible. Furthermore, the principles, effects and operations are the same as describe above.

In addition, when defects are produced when forming a substrate, for example, when a protective film contains a pin hole or when the components of a magnetic film are not uniform, a negative uniformity of a potential distribution on a film is sometimes produced. For example, a uniform surface potential is obtained if the surface is uniform when a constant charge is provided to a substrate surface with relatively little damage, however, when a protective film contains a pin hole or when the components of a magnetic film are not uniform, the surface potential becomes non-uniform. At this time, it is possible to observe and measure a quantity ratio of mirror electrons and secondary emission electrons corresponding to the surface potential by increasing resolution (reducing Px size) and performing an inspection. That is, a change in a quantity ratio of electrons at a certain uniform part is low when a cell/cell inspection is performed, however, since a difference in the quantity ratio is produced when such parts are non-uniform, it is possible to detect these as defects.

While the method and means are not limited to that described above, a defect inspection of a HDD substrate is possible using the method and device of the present invention. This inspection can be performed at a higher speed and sensitivity compared to the conventional technology. This is because the object defects become ultrafine and therefore sensitivity in an optical type inspection device is insufficient and a large amount of time is required in a SEM with a high resolution.

In addition, a defect inspection in a manufacturing process of a magnetic head is similarly possible. Because the same processes are performed in manufacturing a magnetic head as in a manufacturing process of a semiconductor wafer, an inspection of defects such as shape defects or film quality defects can be performed efficiently as describe above. Furthermore, the present embodiment can be applied to the embodiments 1˜35 and also to embodiments with no number attached.

(Thirty Seventh Embodiment)
Stage Device A stage device used in the inspection device and inspection method of the present invention is explained.

Figure 195A:
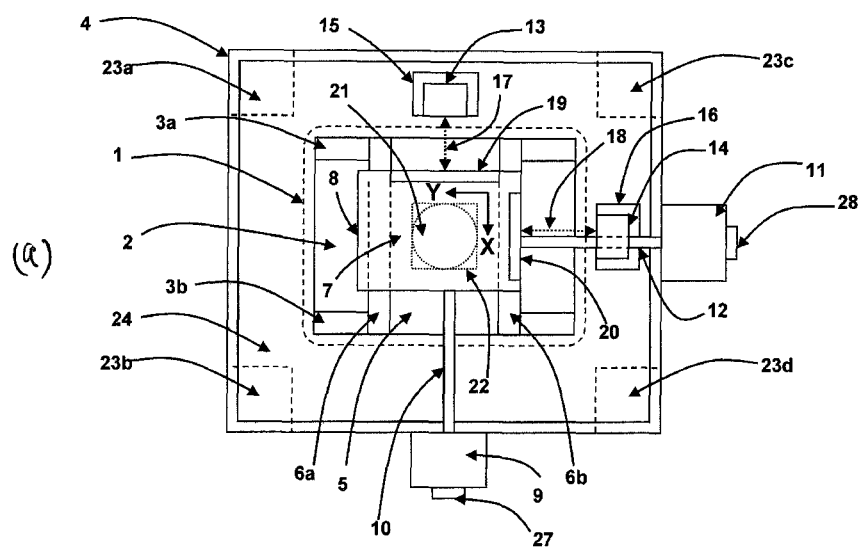
FIG. 195A is a diagram related to one embodiment of the present invention.
Figure 195B:
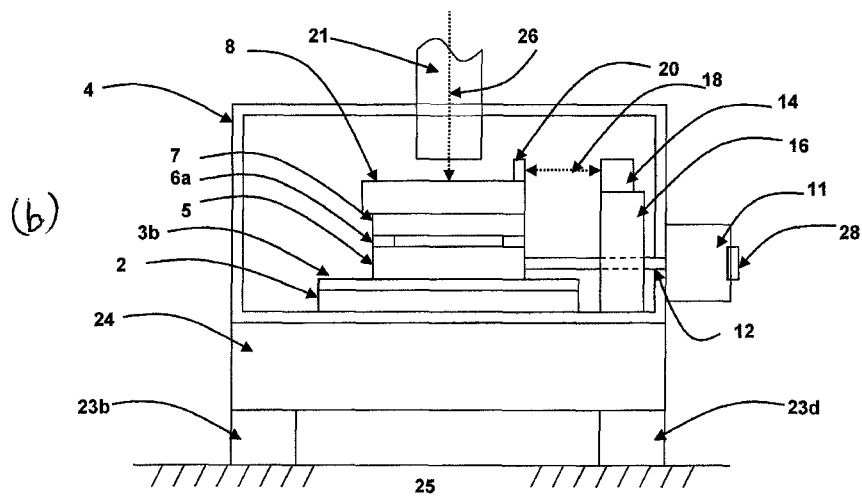
FIG. 195B is a diagram related to one embodiment of the present invention.

The structure of a stage device is shown in FIG. 195A, FIG. 196B.

As shown in FIG. 195A, FIG. 196B, the stage device 1 of the inspection device of the present invention is arranged with a Y axis base disc 2 arranged on a bottom wall of a housing 4, a Y stage 5 and which moves in a Y axis direction using a guide rail 3 arranged parallel in the Y axis direction on the Y axis base disc 2, and a mask plate 8 mounted and an X state 7 and movable in the XY directions using the X stage 7 which moves in the X direction using a an X guide rail 6 arranged in the Y axis direction and parallel in the X direction of the perpendicular direction. The main function of the stage device 1 is an inspection of a mask 22 mounted on the mask plate 8 by moving the mask 22 within a defined region by repeating operations of a scan movement in the X axis direction using the X stage 7 and a step movement in the Y axis direction using the Y state 5 with respect an electron beam inspection light 26 which is irradiated from a column 21 of an electron optical system device. The X stage 7 is scan moved in the X axis direction according to a movement distance and speed which accompanies a defined movement direction and the Y stage 5 is step moved in the Y axis direction according to a movement distance and a defined movement direction. Here, the mask 22 is fixed on a palette (not shown in the diagram) and the palette is fixed by an electrostatic chuck (not shown in the diagram) attached to the mask plate 8. In addition, the housing 4 in which the stage device 1 is arranged is set on a surface of a fixed plate 24 supported by 4 vibration isolation tables 23 and thus the effects of external vibration from the floor 25 is reduced. In addition, the stage device 1 is covered by the housing 4 and operates in a periphery atmosphere with a vacuum level of around $10^{-4}$ Pa. Therefore, a drive system X servomotor 9 and Y servomotor 11 are arranged on the exterior of the housing 4 in order to prevent gas emission, heat emission and dust emission. The X stage 7 and Y stage 5 are driven via an X power transmission shaft 10, and Y power transmission shaft 12 which form a side wall and vacuum shield of the housing 4, and an encoder 27 is used for control management of the X servomotor 9 and an encoder 28 is used for control management of the Y servomotor 11. In addition, a laser interferometer system is used to measure the location of the mask palette 8 mounted with the mask 22. A laser interferometer system comprised from an X stage mirror 19 and X interferometer 13 arranged on the X axis side of the mask palette 8, an X interferometer base 15 for supporting the X interferometer 13, a Y stage mirror 20 and Y interferometer 14 arranged on the Y axis side, a Y interferometer base 16 for supporting the Y interferometer 14, and optical parts such as a laser head (not shown in the diagram), and an AXIS board (not shown in the diagram) for photoelectric signal conversion. Each location of the X stage 7 and the Y stage 5 are measured with a high level of accuracy by an X length measurement beam 17 and Y length measurement beam 18. A stage control system (not shown in the diagram) performs positioning of a state with a sub-micron level of accuracy by control feedback of each axis using a location signal in the XY axis directions obtained by the laser interferometer system with respect to the drive system servomotor 9 and Y servomotor 11.

In the present embodiment, a scan movement was set as the X axis direction and the step movement was set as the Y axis direction of a mask inspection, however, a scan movement may be set as the Y axis direction and the step movement may be set as the X axis direction by alignment with the mask inspection direction. In addition, because the drive system of the stage device 1 uses an electron beam inspection light, it is preferable to use non-magnetism. Therefore, a non-contact type stage mechanism 1 may be a non-contact type. In this case, a stage guide rail is formed using a gas static pressure bearing using an air pressure drive mechanism or a differential exhaust method which supports a vacuum atmosphere.

(Thirty Eighth Embodiment)
Laser Irradiation Location Control

For example, in the structure shown in FIG. 35, it is necessary to irradiate the spot center of a laser to a predetermined location of a photoelectron surface 2021. This is because electrons (photoelectrons) are generated from this spot location and thus this location becomes an electron generation location. The electrons (photoelectrons) emitted from this location are irradiated to a sample surface after passing through a primary system. At this time, when electrons (photoelectrons) are irradiated to a lens it is necessary for the electrons to pass through the center of the lens. This is because the trajectory of the electrons (photoelectrons) becomes curved when misaligned from the lens center. When this trajectory curve is large, the electrons (photoelectrons) collide with a column wall, and it is sometimes no longer possible to correct the trajectory using an aligner (deflector) when the curve exceeds a trajectory correction range. When there is not aligner between a lens and a photoelectron generation part, the trajectory of the photoelectrons which pass through a lens is determined by the location of the photoelectron generation part. That is, when a laser is irradiated to a misaligned location and photoelectrons are generated from a misaligned location, the electron beam does not pass through the center of the lens.

Figure 199:
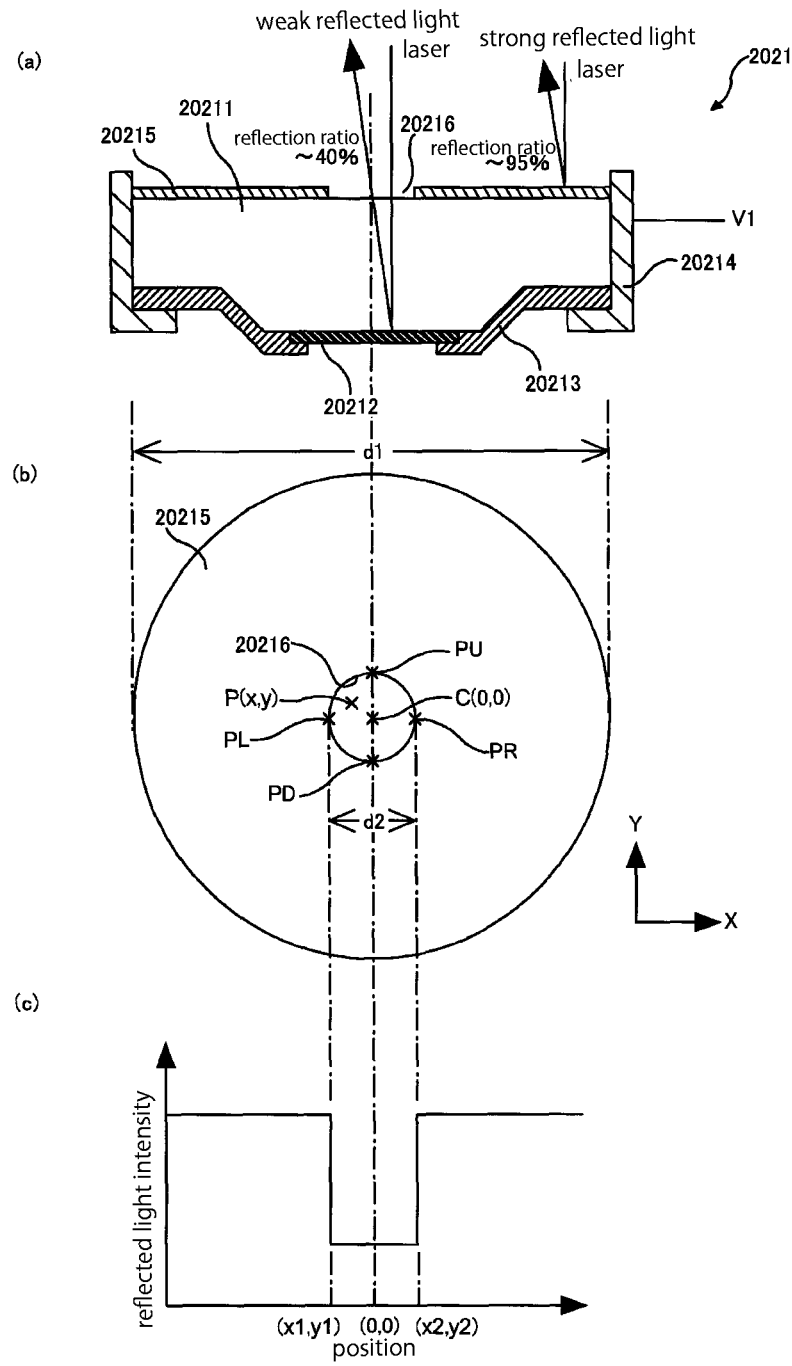
FIG. 199 is a diagram related to one embodiment of the present invention.

In the present embodiment, a structure which can irradiate a laser spot center to a predetermined location of a photoelectron surface 2021 is shown in FIG. 35 in order to solve this problem. Referring to FIG. 199, as is shown in the exemplary view of a cross section of the photoelectron surface 2021 in FIG. 199 (*a*), the photoelectron surface 2021 is arranged with a base material 20211, a photoelectron material 20212, a conducting material 20213, a support part 20214 and a laser irradiation aperture 20215. The base material 20211 is a light transmittance part such as quartz, silica glass, Koltz glass, or magnesium fluoride glass. A material having a low work function (a material with a good photoelectron generation efficiency) such as Ruthenium or Gold is preferably used as the photoelectron material 20212, and is coated on the base 20211. A material with a low conductivity such as chrome is preferably used as the conducting material 21213. The support part 20214 is formed form a conductive material and supports the base material 20211. As is shown in FIG. 199 (*a*), the photoelectron material 20212, conductive material 20213 and support part 20214 are electrically connected. The laser irradiation aperture 20215 may also be electrically connected to these parts.

A reflective material such as molybdenum or tantalum is preferably used as the laser irradiation aperture 20215, and is arranged on the laser irradiation side of the base material 20211. A material having a good surface roughness for strengthening (increasing) the reflectance intensity of a laser is preferred to be used for the surface of the laser irradiation aperture 20215, for example, mirror surface polishing, or a surface roughness of 1 um or less is preferred. In addition, in this example, as is shown in the upper surface diagram of the laser irradiation aperture 20215 in FIG. 199 (*a*), the laser irradiation aperture 20215 is arranged with an interior diameter region 20216 with a diameter d2 a center part of a round disc shape part having a diameter d1 (about 3~5 mm). When an irradiated laser is reflected by the laser irradiation aperture 20215, the reflectance intensity of the reflected light becomes stronger than the reflectance intensity of a reflectance light reflected by a photoelectron material 20212 described next. On the other hand, when a laser passes through the interior diameter region 20216 and is reflected by the photoelectron material 20212, the reflectance intensity of this reflected light becomes weaker than the when reflected by the laser irradiation aperture 20215. Furthermore, the reflected light intensity may be measured by an actinometer arranged on the reflected light path.

A DUV laser, for example, a laser with a wavelength of 266 nm or 244 nm can be used as the laser. It is possible to use a solid-state laser or gas laser. It is also possible to use a lamp light which generates a wavelength of 270 nm or less. For example, a high harmonic laser with a 4 or 5 harmony of a YAG laser can be used as the solid-state laser. In addition, an Ar ion laser or excimer laser can be used as the gas laser.

The laser passes through the interior diameter region 20126 of the laser irradiation aperture 20215, reaches the photoelectron material 20212 and photoelectrons are generated. The laser irradiation location is moved in an X direction from the state (for example, first the laser irradiation location is appropriately changed and from a change in the reflectance intensity shown below, the laser irradiation location which becomes the interior diameter region 20216 is calculated) in the interior diameter region 20216 by controlling an optical system such as a mirror is controlled with control system. When the laser irradiation location reaches an end part (interior diameter side end part of the laser irradiation aperture 20215) of the interior diameter region 20216, as is shown in FIG. 199 (*c*), the reflectance intensity measured by an actinometer etc rises. This end part location (x1, y1) is stored by a control system. An optical system such as a mirror is controlled by a control system and the irradiation location is moved in a −X direction. When the laser irradiation location reaches an end part (interior diameter side end part of the laser irradiation aperture 20215) of the opposite side of interior diameter region 20216, the reflectance light intensity measured by an actinometer etc rises. This end part location (x2, y2) is stored by a control system. Using this operation, the amount of mirror angle movement when moving from (x1, y1) to (x2, y2) is stored by a control system. In the example shown in FIG. 199 (*c*), (x1, y1) corresponds to PL and (x2, y2) corresponds to PR. Coordinate movement amount per minimum memory (minimum adjustment amount or control amount) of a mirror movement adjustment is calculated by a control system. X direction is Δx and the y direction is Δy, for example, 5 μm etc per minimum adjustment amount (memory).

At this time, the coordinates of 4 places on end parts of the interior diameter side of the laser irradiation aperture 20215 are stored by a control system. For example, coordinates of a vertical and horizontal location (PL, PR, PU, PD) are stored. In this way, the center C (0, 0) of the interior diameter region 20216 is determined. Furthermore, not by the coordinates PL, PR, PU, PD but the center C (0, 0) is determined if two end part coordinates are calculated when an irradiation location is moved in an x direction and two end part coordinates are calculated when an irradiation location is moved in a y direction. When the two place coordinates in an x direction are (xa, y0), (xb, y0) and the two place coordinates in a y direction are (x0, ya), (x0, yb), the center C can be determined as (xa+xb)/2, (ya+yb)/2.

Following this, within the interior diameter region 20216, that is, at a location within these four coordinates, the laser irradiation location of an electron beam which passes through a lens center, that is, the coordinates of a location P (x, y) of the photoelectron material 20212 on the lens center axis can be confirmed by a control system. In this way, the control system can ascertain a laser irradiation location, that is, the coordinates of an irradiation location are calculated and stored. In this way, even if the location relationship of a laser, mirror or lens (photoelectron generation device 2020) changes, the control system can irradiate a laser again to a location P (x, y). This laser irradiation location control is performed before inspecting a sample. Furthermore, the present embodiment can be applied to the embodiments 1~37 and also to embodiments with no number attached.

Figure 200:
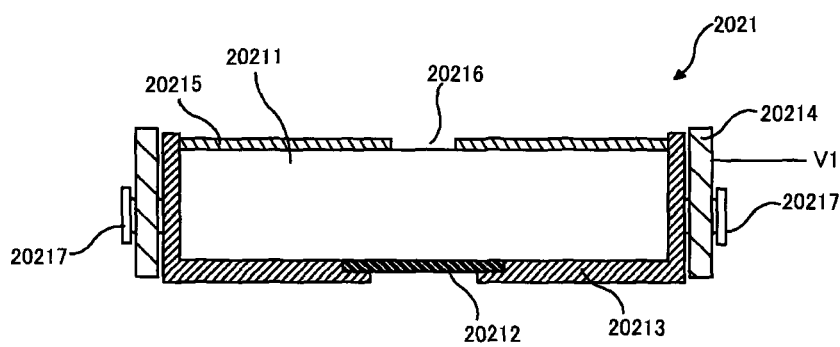
FIG. 200 is a diagram related to one embodiment of the present invention.

In addition, the photoelectron surface 2021 may have a different structure such as the structure shown in FIG. 200. The location side of the photoelectron material 20212 of the base material 20211 shown in FIG. 199 (*a*) has a shape which a difference in levels for being supported by the support part 20214. However, in the example of FIG. 200 in the present embodiment this is a planar surface. In addition, the support part 20214 supports the base material 20211 so that it is sandwiched from both sides using a part 20217 such as a screw.

(Thirty Ninth Embodiment)
Axis Adjustment of a Primary System

As described in the thirty eighth embodiment above, a method for setting the trajectory of an electron beam so that it passes through the center of a lens when a laser irradiation location is adjusted to a location P (x, y) is explained. For example, in the photoelectron generation device 2020 shown in FIG. 35, even if the power (lens power) of lens 2022, 2023 and 2024 is changed as is shown in EB1 of FIG. 201 in the case where the trajectory of an electron beam passes through the center of a lens, the trajectory of an electron beam after passing through the lens does not change. On the other hand, when a lens power is changed in the case where the trajectory of an electron beam passes through a location misaligned from the center of a lens, as is shown in EB2, EB3 of FIG. 201, the trajectory of the electron beam after passing through the lens changes. The structure in the present embodiment utilizes these characteristics.

Figure 201:
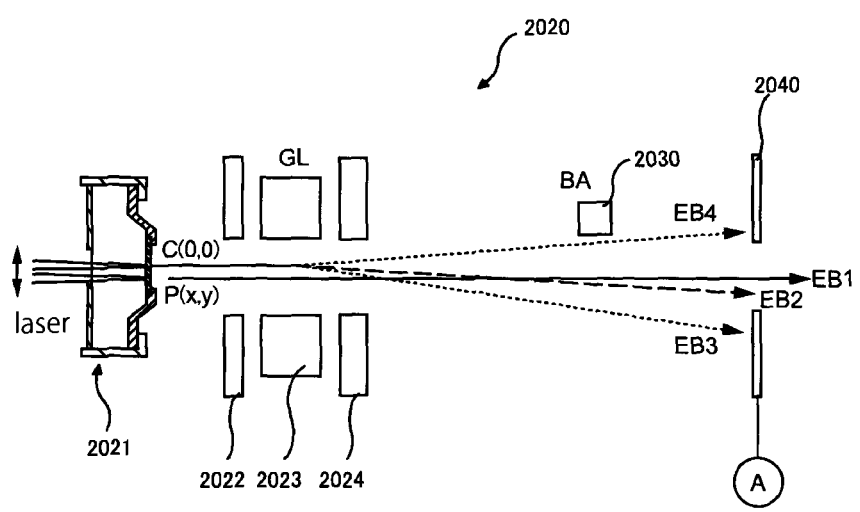
FIG. 201 is a diagram related to one embodiment of the present invention.

The photoelectron device 2020 of the present embodiment shown in FIG. 201 is the same as that shown in FIG. 35. A measurement is performed using an aperture 2040 and aligner 2030.

Any of a plurality of aligners 2031, 2032, 2033 which comprised the aligner 2030 may be used. (at this time, a large size that does not cause measurement problems may be used for the numerical aperture 2025, for example, ϕ500~ϕ2000 μm). The measurement aperture 2040 is formed so that an absorption current produced as a result of irradiating an electron beam can be measured.

The trajectory of an electron beam is controlled by a control system so that a deflected amount of (for example, deflection voltage or current required for deflection) which becomes an opposite side end part from an end part of a hole in the measurement aligner 2024 is calculated using the aligner 2030 (2031 for example in FIG. 35). That is, as is shown in FIG. 201, the deflection voltage of the aligner is changed and the trajectory of the electron beam is misaligned so that a state (EB3) where the trajectory of the electron beam is irradiated to the measurement aperture 2040 (electron beam does not pass through the hole of the measurement aligner 2040), then a state (EB1, EB2) where the trajectory of the electron beam passes through the hole of the measurement aperture 2040, and a state (EB4) where the trajectory of the electron beam is irradiated to the measurement aperture 2040 again, and the absorption current of the measurement aperture 2040 with respect to the deflection voltage of the aligner 2030 is measured. When this measurement is performed, as is shown in FIG. 202, the absorption current at the measurement aperture 2040 is measured changing [electron beam entire amount absorption (large absorption current)] to [reduced electron beam absorption passing through the hole (small absorption current)] to [electron beam entire amount absorption (large absorption current)]. This is performed by changing a plurality of lens powers (GL power).

As is shown in FIG. 202 (a), in a large, small GL power, if the deflection amount (a BA voltage where the absorption current becomes minimum (deflection voltage, the same below)) where the absorption current is reduced the most is the same, the electron beam has a trajectory which passes through the center of a hole of the measurement aperture 2040. On the other hand, as is shown in FIG. 202 (b), in a large, small GL power, the electron beam trajectory is misaligned from the center of a lens in the case where the BA voltage where the absorption current becomes minimum. While the control system changes the location where a laser is irradiated, in a large, small GL power, the location where the BA voltage where the absorption current becomes minimum becomes the same voltage, that is, the location of laser irradiation of an electron beam trajectory which passes through the center of lens is calculated, and these coordinates are stored as the laser irradiation location P (x, y) of an electron beam trajectory. Furthermore, the present embodiment can be applied to the embodiments 1~38 and also to embodiments with no number attached.

(Fortieth Embodiment)
Laser Irradiation Size Control

As described in embodiments 38, 39 above, in addition to control of an irradiation location of a laser irradiated to a photoelectron surface 2021, the irradiation size (spot diameter) of a laser is an important parameter for influencing the size of an electron beam irradiated to a sample. In an adjustment of a spot diameter, the laser output from a light source may not be adjusted to a desired size simply using a lens and mirror. A spot diameter $2\omega_0$ is expressed as $2\omega_0=(4\lambda/\pi)$ (F/D). Here, $\lambda$ is a light wavelength, F is the focal distance of a lens, and D shows the diameter of a laser at a lens location. As can be understood from this equation, a spot diameter is proportional to the focal distance, and disproportional to the diameter of the laser at the lens location. Therefore, in order to reduce the size of the spot diameter, there is a method for increasing the diameter of a laser from a light source using a beam expander and irradiating to a lens, and a method using a short focal point lens. A method for reducing the size of the spot diameter is effective for appropriately adjusting an irradiation location of a laser and spot diameter by combining with a control method of the laser irradiation location described above.

Figure 203:
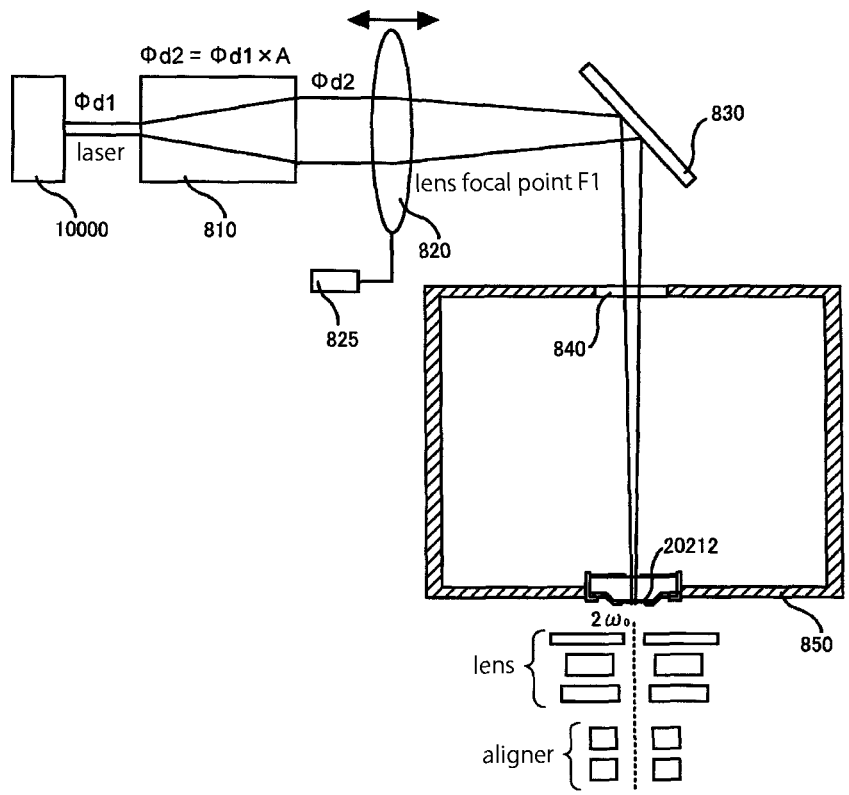
FIG. 203 is a diagram related to one embodiment of the present invention.

An example in the case of using a beam expander is explained using FIG. 203. As is shown in FIG. 203, a laser with a diameter of $\phi d1$ output from a light source 10000 is magnified by A times in a beam expander 810, becomes a laser with a of $\phi d2$, and is irradiated to a lens 820 with a lens focal point F1. The laser is reflected by a mirror 830, passes through a transparent window 840 arranged on a vacuum container for maintaining a vacuum, and reaches the photoelectron material 20212 which is arranged at a location corresponding to the lens focal point F1. At this time, the spot diameter of the laser at the photoelectron material 20212 becomes at minimum $2\omega_0=(4\lambda/\pi)$ (F1/$\phi d2$). In this example, the laser has a CW (continuous wave) of $\lambda=266$ nm. Furthermore, in the embodiment 38, adjustment of the laser irradiation location may be performed by changing the angle of the mirror 830. In addition, a movement mechanism 825 which moves the lens 820 along an optical axis of a laser may also be arranged. When the lens 820 is moved by the movement mechanism 825 it is possible to change the spot diameter of a lens in the photoelectron material 20212.

Figure 204:
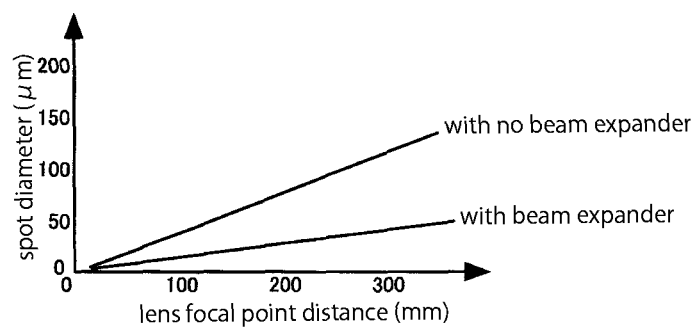
FIG. 204 is a diagram related to one embodiment of the present invention.

In the present example, the relationship between a lens focal distance and minimum spot diameter with regards to the case where a beam expanded is arranged and the case where a beam expander is not arranged is shown in FIG. 204. As is shown in FIG. 204, the spot diameter increases the longer the lens focal distance becomes, and in the case where a beam expander is arranged, the spot diameter decreases in size compared to when a beam expander is not arranged.

Figure 205:
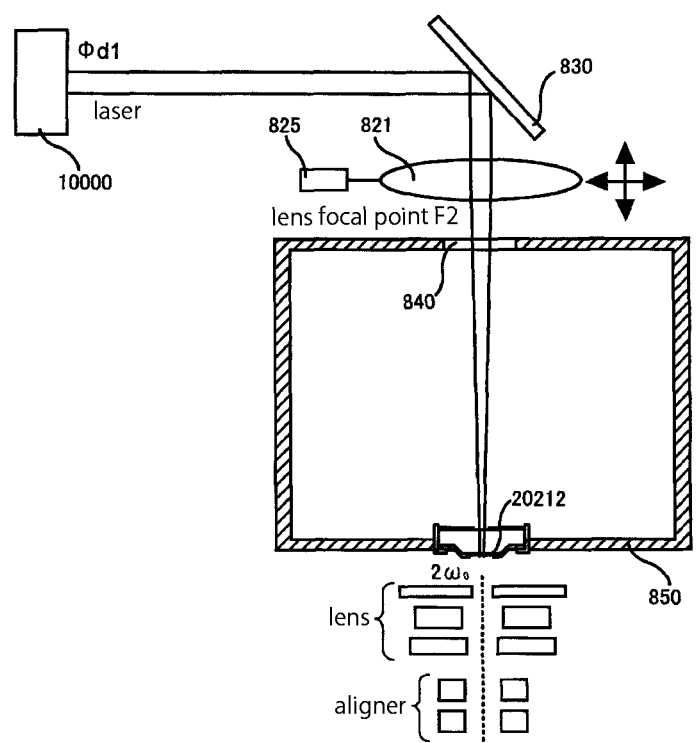
FIG. 205 is a diagram related to one embodiment of the present invention.

In addition, an example in the case where a shirt focal point lens is used between the mirror 830 and the vacuum container 850 is explained using FIG. 205. As is shown in FIG. 205, a laser with a diameter of $\phi d1$ output from a light source 10000 is reflected by a mirror 830, and is irradiated to the lens 821 with a lens focal point F2. The laser passes through a transparent window 840 arranged on a vacuum container 850 for maintaining a vacuum, and reaches a photoelectron material 20212 arranged at a location corresponding to the lens focal point F2.

Furthermore, a movement mechanism 825 for moving a laser 821 along an optical axis of a laser may be arranged. When the lens 821 is moved by the movement mechanism 825 it is possible to change the spot diameter of a lens in the photoelectron material 20212. In addition, because the lens 821 has a short focal point, it is arranged more to the photoelectron material 20212 side than the mirror 830. As a result, when the laser irradiation location is adjusted by the mirror 830, the laser is sometimes misaligned from the center of the lens 821. Therefore, in order to correct this alignment, the movement mechanism 825 may move the lens 821 within a surface which makes an optical axis a normal line. Furthermore, the beam expander 810 (not shown in FIG. 205) explained in FIG. 203 may be combined and used.

Figure 206:
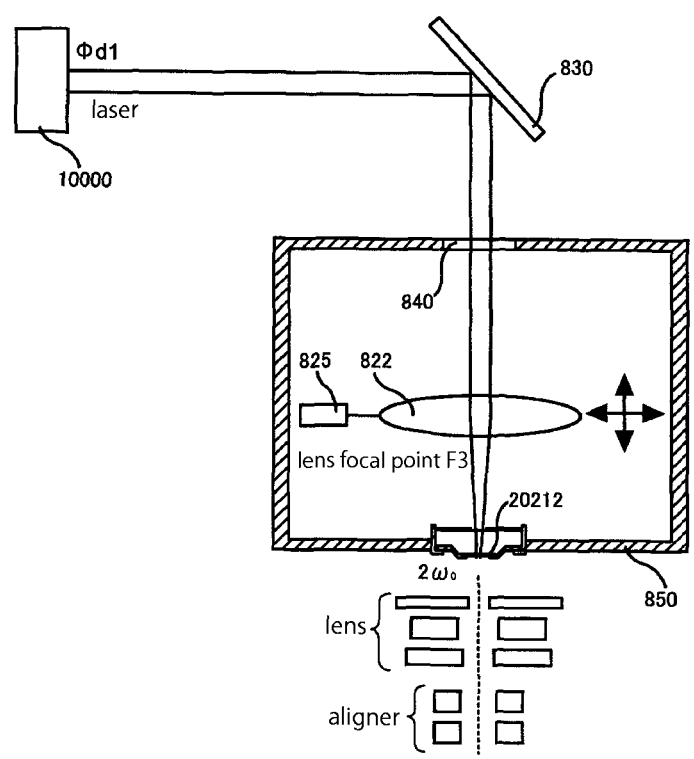
FIG. 206 is a diagram related to one embodiment of the present invention.

In addition, it is possible to use a lens 822 having a shorter focal point F3 than the lens 821. Lens 820 and 821 are arranged on the atmosphere side of the exterior of the vacuum container 850. However, in this case, as is shown in FIG. 206, the lens 822 may be arranged on the interior of the vacuum container 850. The moving mechanism 825 may also be arranged on the lens 822. The beam expander 810 (not shown in FIG. 205) explained in FIG. 203 may be combined and used even in this case. Furthermore, the present embodiment can be applied to the embodiments 1~39 and also to embodiments with no number attached.

(Forty First Embodiment)

Figure 207:
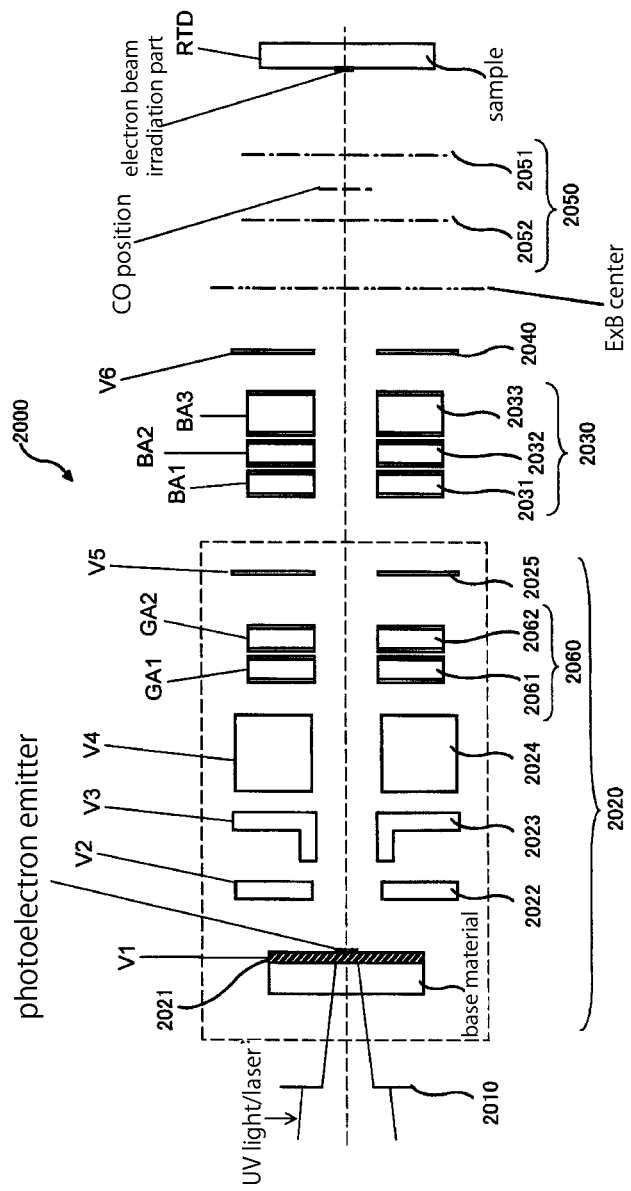
FIG. 207 is a diagram related to one embodiment of the present invention.

In the photoelectron generation device 2020 shown in FIG. 35, a structure which adds an aligner after a lens group 2022, 2023, and 2024 is explained using FIG. 207. In the present embodiment, an explanation of a structure which is the same as the structure shown in FIG. 35 is omitted. An aligner 2060 includes a first aligner 2061 and a second aligner 2062. The aligner 2061 and second aligner 2062 are arranged between a third stage lens 2024 and a numerical aperture 2065 and performs a static operation the same as the first aligner 2031 and second aligner 2032. However, as stated above, the first aligner 2031 and second aligner 2032 are used for controlling an irradiation location of an electron beam to a sample, while the first aligner 2061 and the second aligner 2062 are used for control so that the electron beam passes through the center of a hole of the numerical aperture 2025. Furthermore, the present embodiment can be applied to the embodiments 1~40 and also to embodiments with no number attached.

(Forty Second Embodiment)
Photoelectron Surface Primary System with a Zoom Function It is possible to provide the structure shown in FIG. 35 and FIG. 207 with a zoom function which controls the size of an electron beam irradiated to a sample. Here, the case where the structure of FIG. 207 explained in embodiment 41 is provided with a zoom function is explained using FIG. 208. In the present embodiment, an explanation of the same structure as that shown in FIG. 207 is omitted.

Figure 208:
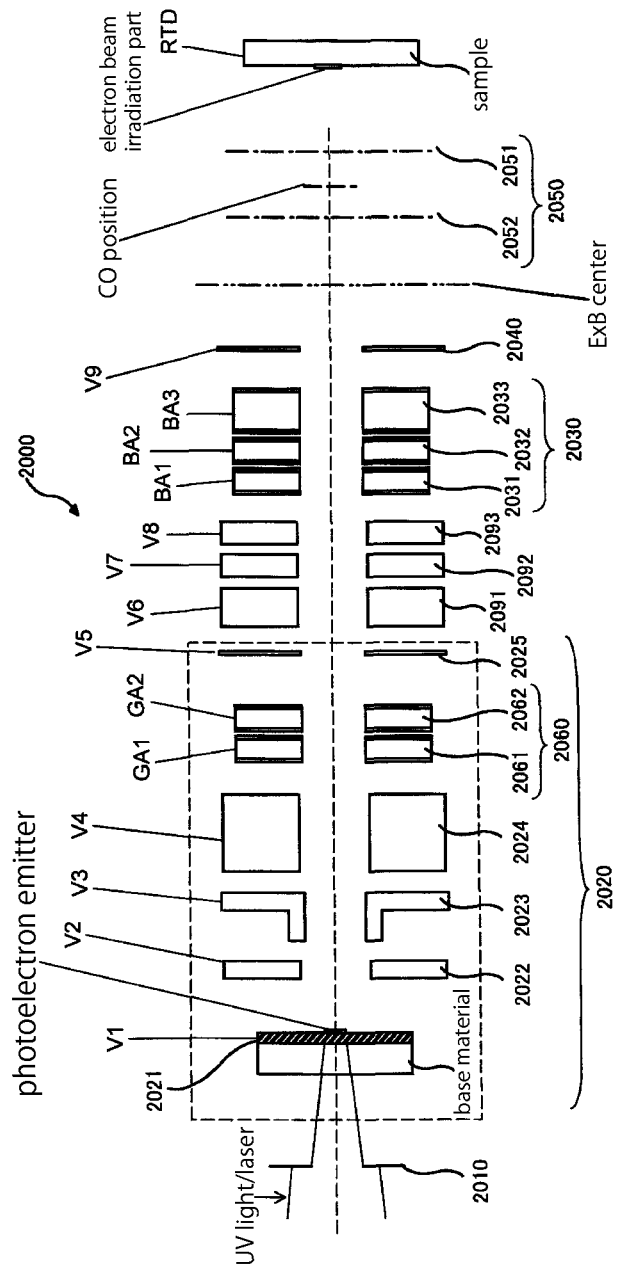
FIG. 208 is a diagram related to one embodiment of the present invention.

The structure shown in FIG. 208 includes a lens group 2091, 2092 and 2093 (forming one lens from 3 electrodes) arranged between a numerical aperture 2025 and first aligner 2031 in addition to the structure shown in FIG. 207. In FIG. 35, FIG. 207 and FIG. 208, the electrodes 2022, 2023 and 2024 form one group lens. In this embodiment in FIG. 208, lens 2022, 2023 and 2024 are called ED (Electrostatic Lens), lens 2091, 2092 and 2093 are called EL2, the aligner 2060 is called aligner 1, and the aligner 2030 is called aligner 2. Furthermore, a numerical aperture may be arranged between the lens 2093 and the first aligner 2031. In this case, a primary optical system 2000 includes two numerical apertures.

By adopting the zoom lens structure of the present embodiment it is possible to control the size of an electron beam irradiated to a sample. It is possible to control the size of an electron beam irradiated to a sample by a zoom function using ED and EL2 with the same conditions as the irradiation size of a laser irradiated to a photoelectron surface 2021. For example, control of ×0.1~×30 with respect to a size of a laser irradiated to the photoelectron surface 2021 is possible.

It is necessary to changing the size of an electron beam on a sample surface with respect to the magnification of a secondary system (optical system which forms an electron image of a sample). When the magnification of secondary system varies, the size of a field of view on a sample surface (region imaged as an electron image by a detector) changes. As a result, it is necessary to change the size of an electron beam with respect to a variation in magnification. For example, when the field of view is changed from 30×15 μm to 200×100 μm, it is also necessary to change to a size which also covers the size of an electron beam, for example, it is necessary to change the electron beam irradiated with a 60×30 μm elliptical or rectangular shape to an electron beam with a 300×150 μm elliptical or rectangular shape.

At this time, it is possible to be compatible with a change in irradiation size of laser in a photoelectron surface 2021, it is necessary to replace or adjust a laser system in order to change an irradiation size of a laser which takes time, and when a small spot diameter of a laser is formed corresponding to a small field of view, the laser density changes and a change in the amount of photoelectrons is produced. In addition, instability is sometimes produced in the amount of photoelectrons. At this time, when a zoom function of a primary system described above is used, it is possible to control an irradiation region of an electron beam on a sample surface even with the same laser irradiation size. Therefore, this structure which has this zoom function is very effective.

The structure in this embodiment is an example of arranging 2 aligners, aligner 1 and aligner 2. The aligner 1 is used for passing the trajectory of an electron beam through the center of the numerical aperture 2025 and EL2. The aligner may also be used by combining with the aligner in the secondary system with respect to the lens center.

An example of a voltage applied to each structural element shown in FIG. 208 is shown. A voltage of the photoelectron surface 2021 is given as V1, a voltage of electrodes which form an extraction lens are each given as follows, a voltage of a first extraction electrode 2022 is V2, a voltage of a second extraction electrode 2023 is V3, a voltage of a third extraction electrode 2024 is V4 (here, the structure of electrodes 2022, 2023, 2034 form one electrostatic lens), a voltage of the numerical aperture 2025 is V5, a voltage of a third aligner 2033 is V6, a voltage of a lens electrode 2091 is V6, a voltage of a lens electrode 2092 is V7, a voltage of a lens electrode 2093 is V8, and a voltage of an aperture 2040 is V9. In addition, a surface voltage of a wafer is given as RTD (also called a retarded voltage). In a primary optical system 2000 of the present embodiment, when described based on the voltage V1 of the photoelectron surface 2021, the voltages applied to each structural element are as follows. That is, in the case of a low LE, V1 =RTD-10V~RTD+5V. V2, V4, V6, V8~V1+ 3000~30000V. V3, V7 =V4+10000~30000V. V5, V9=a reference voltage. In addition, RTD=-5000V, V1=-5005V, V2, V4, V6, V8=GND, V3=+20000V, V7=+17000V are set as an example of a primary optical system in the present embodiment. It is possible to realize a high resolution and high throughput at a low LE using the voltage application described above. However, this is only an example and the voltages applied to each of the structural elements are not limited to this example. Furthermore, the present embodiment can be applied to the embodiments 1~41 and also to embodiments with no number attached.

(Forty Third Embodiment)
Discharge Prevention Spacer Shape

The distance between each lens extraction electrode such as lens 724 is limited. As a result, in the case where a side surface of a spacer of a conductor sandwiched between the electrodes is a planar shape (cross section is a straight line shape), a creeping resistance is sometimes insufficient. In this case, it is effective to use the structure shown in FIG. 209. In the example shown in FIG. 209, a spacer arranged between the electrodes 7241, 7242 has a structure where 3 spacers having a spinning top shape are linked and the surface has a wave shape. In addition, the spacer 7245 is formed from an insulator such as a ceramic with a surface resistance of $10^8$~$10^{12}$ Ω·cm, and a charge up is reduced by the flow of a small leak current. Furthermore, the spinning top shaped spacers are not limited to 3, and 4~12 may be used.

Figure 209:
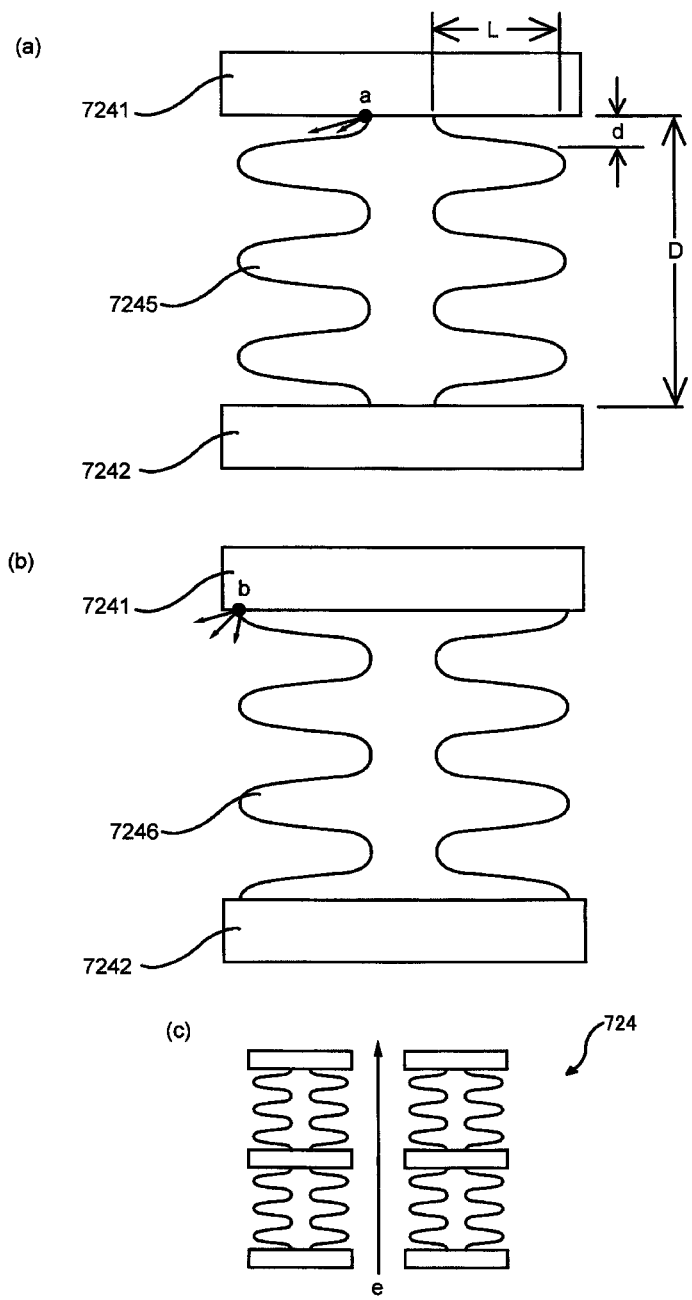
FIG. 209 is a diagram related to one embodiment of the present invention.

In the case where a creeping dielectric strength voltage is insufficient, for example, a value of 1 kV/mm or more (for example, in the case where the potential difference of electrodes 7241, 7242 becomes 20 kV, D=20 mm or less), the spacer 7245 with the shape in FIG. 209 (a) is used. The side surface has an uneven shape and the electric field at a creeping distance becomes 1.kV/mm or less. At this time, the surface of electrodes 7241, 7424 which connect, the spacer 7245 shown in FIG. 209 (a) is connected at the hollow part and the spacer 7246 shown in FIG. 209 (b) is connected at the bump part.

At this time, discharge resistance is significantly different between the spacer 7245 which is connected with the electrode at the hollow part and the spacer 7246 which is connected with the electrode at the bump part. The spacer shown in FIG. 209 (a) is preferred. For example, when discharge occurs at point a, L/d is large, discharge converges at a hollow part, and the possibility of a discharge occurring with the exterior decreases. This is because electrical field variation is small at a hollow part, that is, because of the same potential space, electrons fly to the exterior. Consequently, a stable state is obtained where discharge between electrodes is difficult to occur. However, because the spacer 7246 shown in FIG. 209 (b) is connected with the electrodes 7421 and 7242 at the bump part, when discharge occurs at point b, discharge with the exterior of the spacer 7246 easily occurs. This is because the space on the exterior of the spacer 7246 is immediately adjacent and therefore the possibility of electrons flying to this space increases compared to the spacer 7245 shown in FIG. 209 (a). In addition, even if discharge occurs near the point b, electrons which are generated at this spot fly to the periphery and discharge occurs which is a large secondary cause. Usually, the possibility of discharge occurring at point a, point b is high, in this case parts where a variation in potential is high. In the case of the spacer 7245 shown in FIG. 209 (a), in particular, a large L/d is preferred. For example, when L/d≧4, discharge resistance is increased, and L/d≧4~10 is preferred in order to satisfy manufacturing possibilities.

The lens which uses this spacer 7245 is used in the structure shown in FIG. 209 (c). Furthermore, the present embodiment can be applied to the embodiments 1~42 and also to embodiments with no number attached.

(Forty Fourth Embodiment)
Contamination Prevention

Figure 210:
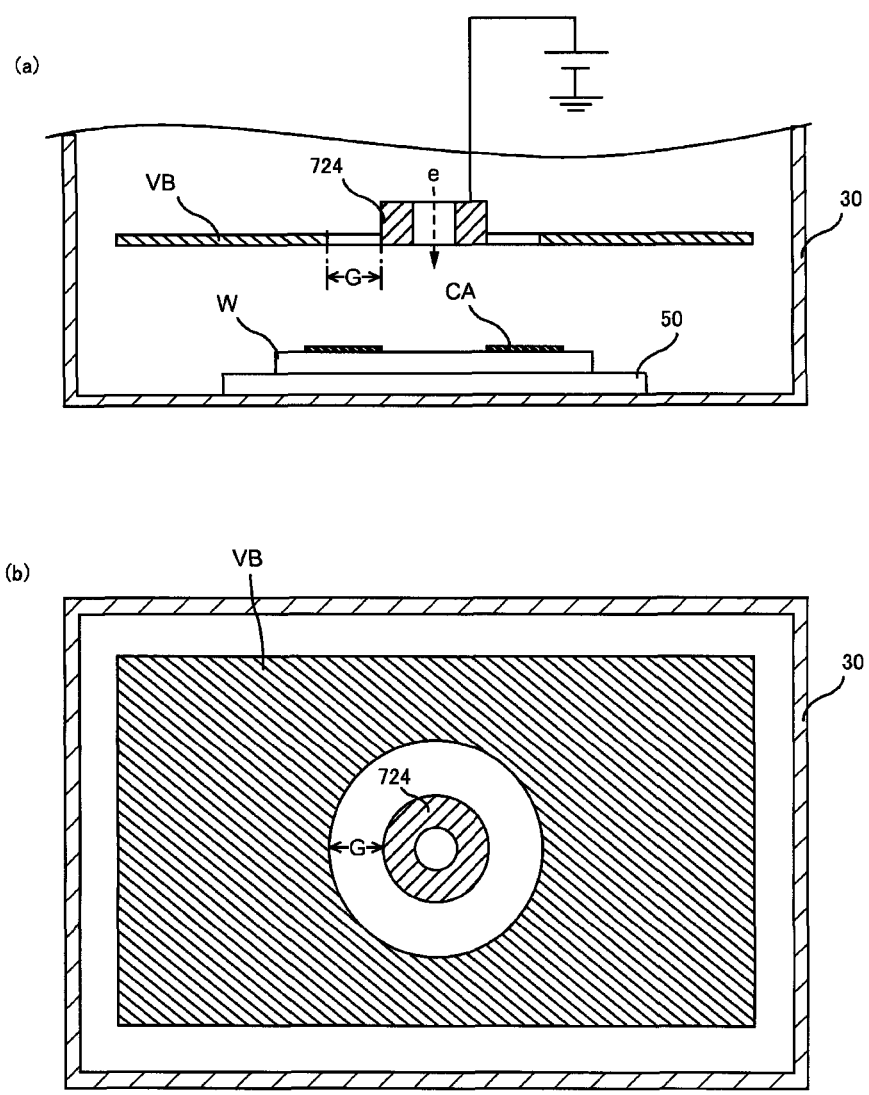
FIG. 210 is a diagram related to one embodiment of the present invention.
Figure 211:
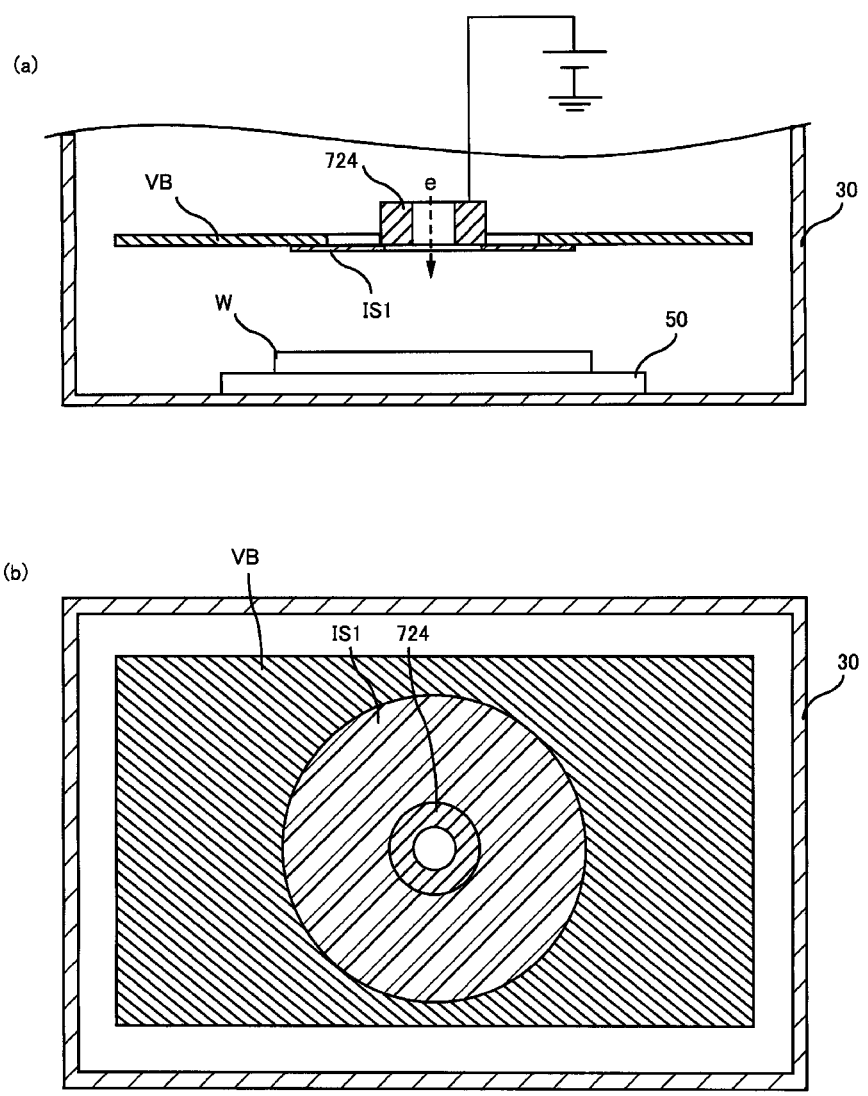
FIG. 211 is a diagram related to one embodiment of the present invention.

As described in the embodiments 13, 27, a structure for preventing particles can also take different structures. For example, as is shown in FIG. 210, a gap G for preventing discharge is sandwiched on the periphery of the lens 724, and a shield barrier VB is often arranged. FIG. 210 (a) exemplary shows a cross section of a surface which passes through a center axis of the lens 724, and FIG. 210 (b) shows each structure of the lens 724 direction seen from the sample W. In the structure shown in FIG. 210, when a high voltage is applied to the lens 724, foreign materials are deposited on a surface (contamination region CA) of a wafer W corresponding to the part of the gap G and thereby becomes contaminated, Two types of structure (FIG. 211, FIG. 212) are explained in the present embodiment as a method for preventing contamination. FIG. 211 (a), FIG. 212 (a) are exemplary diagrams which shows a cross section at a surface which passes through a center of the lens 724, FIG. 211 (b), FIG. 212 (b) are diagrams which shows each structure in the case of viewing the lens 724 direction seen from the sample W.

The example of a first structure is a structure which blocks a gap G by a round disc shaped insulator shield IS1 which has an open center as is shown in FIG. 211. The insulator IS1 is formed from ceramic or $SiO_2$ etc, and is formed to block the gap G by attaching to the voltage shield barrier VB. In this example, the insulator IS1 is attached to the sample W side of the voltage shield barrier VB. Furthermore, without completely blocking the gap with the insulator IS1, a gap may be arranged between the gap and insulator IS1 with so that the gap G is narrower. In this way, by arranging the insulator shield IS1 so that the gap is blocked or becomes more narrow, it is possible to remove or reduce the deposition of foreign material on the contamination region CA of the sample W.

Figure 212:
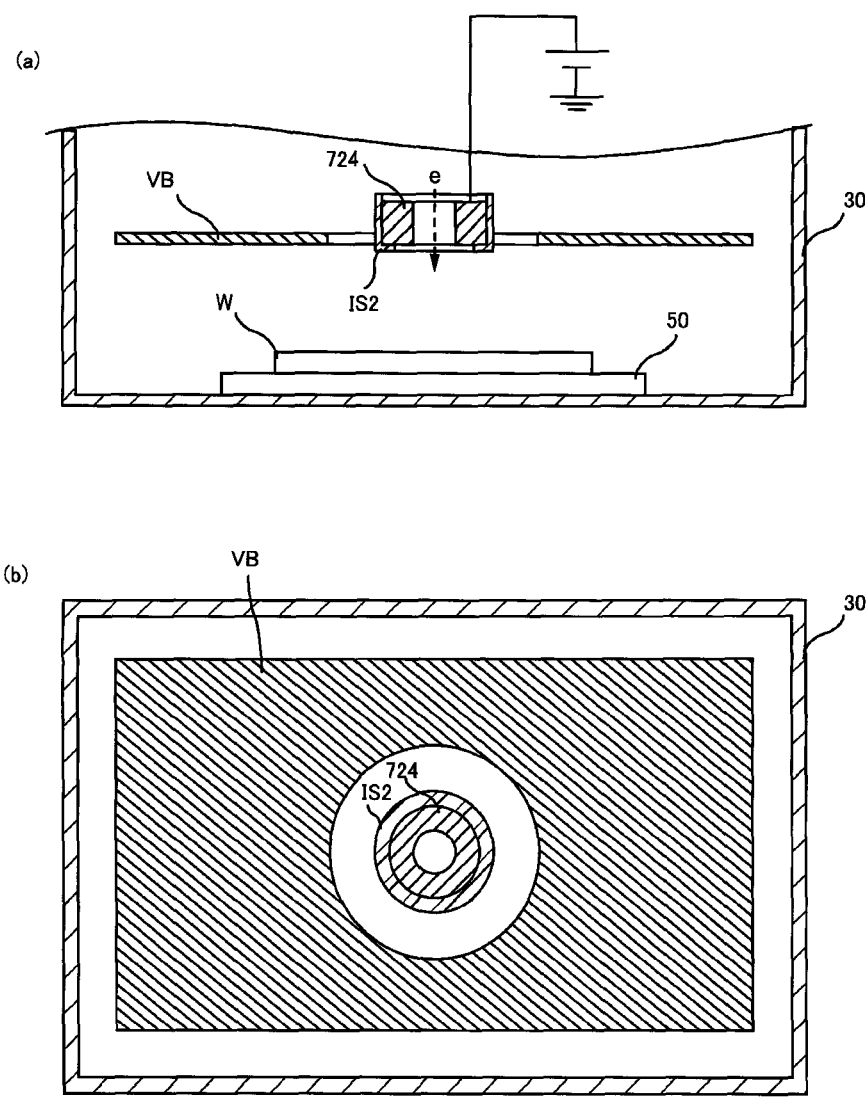
FIG. 212 is a diagram related to one embodiment of the present invention.

An example of a second structure is a structure where a cylinder shaped insulator IS2 is arranged so as to enclose the lens 724 as is shown in FIG. 212. The insulator shield IS2 is formed from ceramic or $SiO_2$ and is fixed to the lens 724. A thermal expansion rate is different the between the insulator shield IS2 and the lens 724. Using this difference in the thermal expansion rate, the insulator shield 724 is inserted after cooling the lens 724, and the insulator shield IS2 and the lens 724 are fixed using a cooling fit when the lens 724 returns to a normal temperature. Fixing with a screw etc leads to a decrease in positioning accuracy due to tolerance, however, positioning of a center axis of a lens becomes easier when fixing as in the present embodiment.

Because a foreign material is electrically controlled using the insulator shield IS2 from reaching a sample due to the effects of an electric field from the lens 724 with this structure, it I possible to remove or reduce foreign material deposited on a contamination region CA of the sample W. Furthermore, a small leak current flows when both the insulator IS1 and IS2 have a surface resistance of $10^8$~$10^{12}$ Ω·cm, and it is possible to reduce a charge up. Furthermore, the present embodiment can be applied to the embodiments 1~43 and also to embodiments with no number attached.

(Forty Fifth Embodiment)
Discharge Prevention

Figure 213:
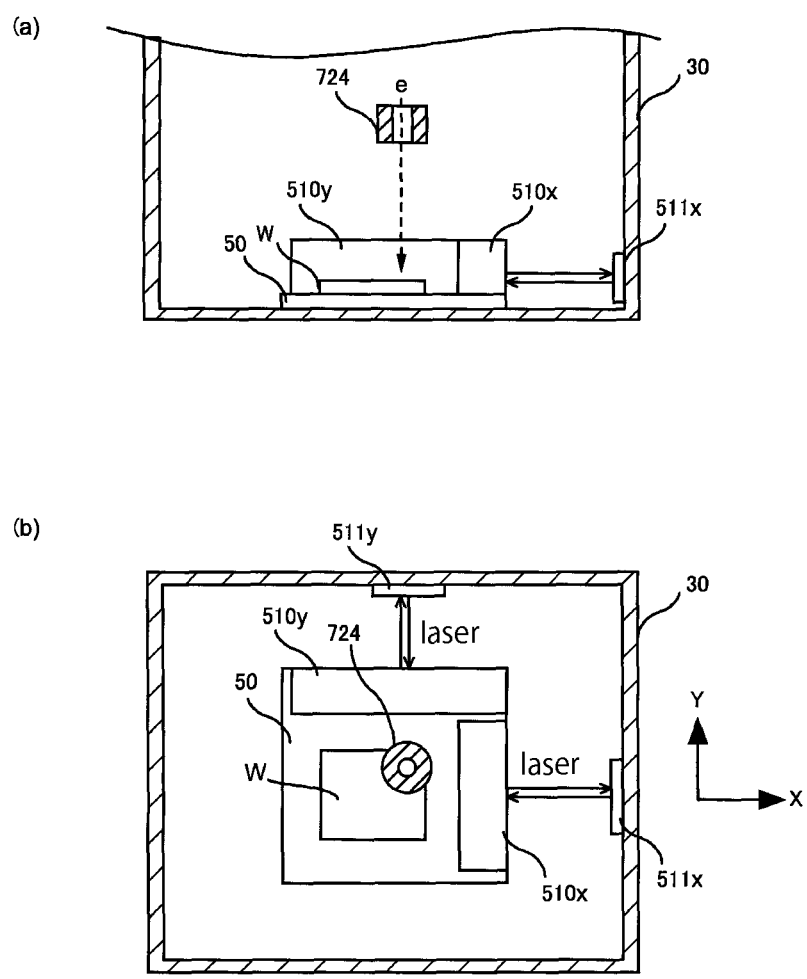
FIG. 213 is a diagram related to one embodiment of the present invention.
Figure 214:
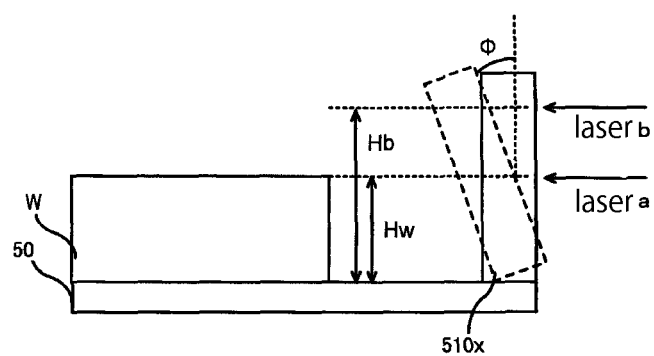
FIG. 214 is a diagram related to one embodiment of the present invention.

Location control of a stage device 50 as described above is performed by the structure in FIG. 213 when a laser interferometer ranging device is used. The potential relationship of each structure of the lens 724 and stage device 50 is shown in FIG. 213 (a) when viewed from a side surface direction and in FIG. 213 (b) when viewed from an upper surface direction. A laser interferometer mirror 510x for controlling the location of an x axis direction and a laser interferometer mirror 510y for controlling the location of a y axis direction are arranged in the stage device 50. A laser is irradiated from a laser interferometer 511x to the laser interferometer mirror 510x, and a laser is irradiated from a laser interferometer 511y to the laser interferometer mirror 510y.

It is preferred that the laser interferometer mirror 510x and 510y reflect a laser at the same height (location of a surface of a sample W) as a sample W. This is because the greater the difference in height with the sample W, the larger the error in a measurement location is produced as is shown from the Abbe principle. As is shown in FIG, in the case where the laser interferometer mirror 510x leans by φ, the error at a location of a laser b becomes an (Hb−Hw) X tan φ. (Hb−Hw) is a difference between the height Hb of the laser b and the height Hw of the sample W. If φ is very small, tan φ≈φ. As a result, the greater the difference (Hb−Hw) between the height Hb of the laser b and the height Hw of the sample W, the greater the error. Therefore, it is preferred that the difference (Hb−Hw) between the height Hb of the laser b and the height Hw of the sample W=0, that is, a laser a is irradiated to the laser interferometer mirror 510x at the height of the sample W.

Figure 215:
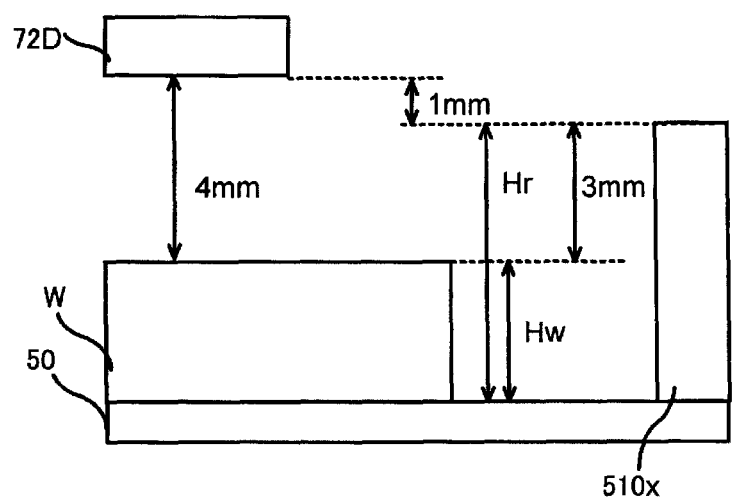
FIG. 215 is a diagram related to one embodiment of the present invention.

Consequently, it is necessary that the laser interferometer mirror 510x and 510y are higher than the height Hw of the sample W. This is because, in particular, in the case where ceramic is used for the laser interferometer mirror 510x and 510y in order to improve assembly accuracy, a ceramic surface is formed as a mirror by a mirror finish. In this case, several mm (for example, 3 mm) from an upper end part requires an area outside specifications due to the demands when manufacturing. As is shown in FIG. 215, the height Hr of the laser interferometer mirror 510x, 510y is required to be longer than the height Hw (height of a sample W (location of the surface of the sample) irradiated with a laser, for example, by 3 mm. In addition, the distance between a surface of the sample W and the column lowest electrode 72D is a distance determined when designing the optics and in the present embodiment is 4 mm. Therefore, the distance between the column lowest electrode 72D and the laser interferometer mirror 510x and 510y is 1 mm. As a result, depending on the location of the stage device 50, the upper end part of the laser interferometer mirror 510x and 510y approaches to close to the lens 724 which is applied with a high voltage and electrical discharge often occurs. Therefore, it is necessary to determine the location of the stage device 50 so that this discharge does not occur.

Figure 216:
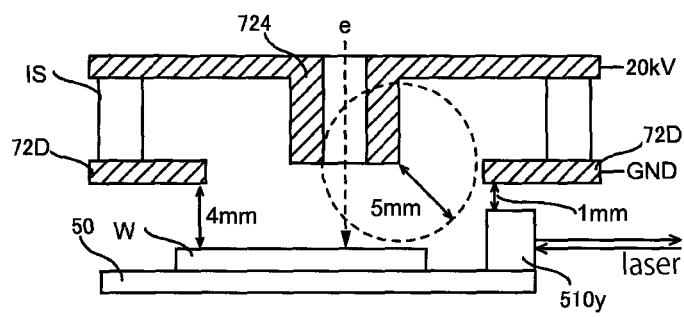
FIG. 216 is a diagram related to one embodiment of the present invention.

As is exemplary shown in FIG. 216 seen from the side surface, the column lowest electrode 72D is fixed via the insulator IS to the lens 724 which is applied with a high voltage (20 kV in this example), and is grounded (GND). A set value of breakdown field strength in the present embodiment is set at 4 kV/mm. As a result, it is necessary that the stage device 50, sample W, the laser interferometer mirror 510x and 510y (in particular, the laser interferometer mirror) do not enter within a range of 5 mm from a lower end part of the lens 724 which is applied with a 20 kV voltage as shown in FIG. 216.

Figure 217:
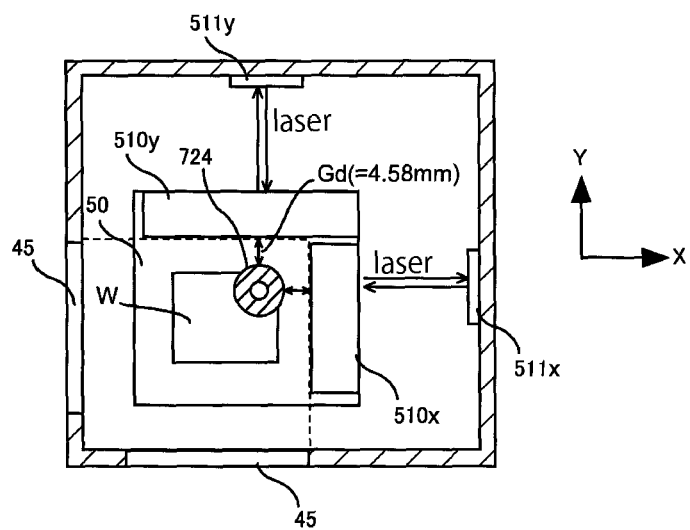
FIG. 217 is a diagram related to one embodiment of the present invention.

Thus, as is exemplary shown in FIG. 217 seen from the upper surface, if a state whereby a gap Gd in a horizontal direction is not separated by 4.58 mm or more from the lens 724 up to the laser interferometer mirror 510x, 510y, an electrical field of 4 kV/mm or more is produced. As a result, a movable range of the stage device 50 is controlled within a range where the gap Gd is 4.58 mm or more, and the location of the stage device 50 is controlled within this movable range. The example shown in FIG. 217 is a state where the stage device 50 is at its closest to the laser interferometer mirror 511x, 511y within a range where the gap Gd is 4.58 mm or more. That is, when a wafer W is received from the loading chamber 40 to the stage device 50 within the main housing 30, or when the sample W is received to the loading chamber 40 from the stage device 50 within the main housing 30, the stage device 50 location is moved to a location (the position which becomes a movable range) where the upper part of the laser interferometer does not discharge due to a lens. Because it is necessary to receive the sample W at the location of the stage device shown in FIG. 217 (the wall side facing the wall side arranged laser interferometer mirror 510x, 510y in the main housing 30), it is necessary to arrange a shutter device 45 which becomes an entrance and exit with the loading chamber 40 on either of 2 places shown in FIG. 217 (the wall side facing the wall side arranged laser interferometer mirror 510x, 510y in the main housing 30). Furthermore, the present embodiment can be applied to the embodiments 1~44 and also to embodiments with no number attached.

(Forty Sixth Embodiment)

A type of light source 10000 of a light irradiated to a photoelectron surface 2021 was described above however other light sources may be used. For example, a FUV lamp, excimer lamp, deuterium lamp or xenon lamp may be used. In addition, an LD excitation light source lamp may be used in which a LD (laser diode) is condensed and a spot plasma is formed and the light excited. The excitation light may be introduced to the photoelectron surface 2021 using at least one of a lens or a mirror. In addition, this excitation light may be introduced to a fiber optic by at least one of a lens of a mirror, and introduced to the photoelectron surface 2021 from the fiber optic. In addition, control of the plasma may be performed using a magnetic field. Furthermore, the present embodiment can be applied to the embodiments 1~45 and also to embodiments with no number attached.

(Forty Seventh Embodiment)

In the explanation in FIG. 161, an example where an EB-TDI is used in the detector system 70 is explained. However, other structures where a TDI is used are explained. In the present embodiment, an explanation of the same structure as in FIG. 161 is omitted.

First, a detector system 70 shown in FIG. 161 has a structure whereby EB-CDD 71 is moved to a location away from an optical axis by a movement mechanism M in the case of using an EB-TDI 72. However, as a first example, a rotation shaft S may be linked to the movement mechanism M is shown in FIG. 218. In FIG. 218 (*a*), one end of the rotation shaft S is liked to one end of the plate shaped EB-CCD 71 which is loaded with necessary circuits or substrate etc and the other end of the rotation shaft S is linked to the movement mechanism M. FIG. 218 (*b*), (*c*), are diagrams of the structure shown in FIG. 218 (*a*) seen from the movement mechanism direction. In the case where EB-CDD 73 is used, as is shown in FIG. 218 (*b*), an electron beam e is irradiated to the EB-CCD 73, and a sensor surface of EB-CDD 73 is moved to become perpendicular to the electron beam e. On the other hand, in the case where EB-TDI 72 is used, as is shown in FIG. 218 (*c*), the rotation shaft 21 is rotated by the movement mechanism M, and the EB-CCD 73 is moved to be parallel with an optical axis of an electron optical system. Therefore, the electron beam e is not irradiates to the EB-CCD 73 but to the EB-TDI 72.

The movement mechanism M which uses rotation shown in FIG. 218 has the merit of being able to reduce size and weight to ½~1/10 compared to the movement mechanism which uses movement in a 1 axis direction explained in FIG. 161.

As a second example, the detector system 70 is not formed by the EB-TDI 72 but by a TDI sensor 721, FOP 722, fluorescent plate 723 and MCP 724 in one package as is shown in FIG. 219. An output pin of the TDI sensor 721 is connected to a pin 73 of a feed through FT using bonding or some other connection means. In this case, as described above, the MCP 724 performs multiplication of the amount of detection electrons, and the fluorescent plate 723 converts the electrons to an optical signal. The two dimensional optical signal is transmitted by the FOP 722, an image is formed at the TDI sensor 721 and the signal is detected. In FIG. 219, the movement mechanism M was described in both the case a where the EB-CDD 71 is rotated and the case b where the EB-CDD 71 is moved to a location away from the optical axis of an electron beam, however, either case may be adopted. FIG. 219 (*a*), (*c*) are diagrams of the structure shown in FIG. 219 (*a*) in the case where the movement mechanism M rotates the EB-CCD 71 is adopted seen from the movement mechanism M. Furthermore, the MCP 724 is no longer used in the detection system 70 in the case where electron amplification is not required, as is shown in FIG. 220.

In addition, the detection system 70 may have a structure whereby the structure where the EB-TDI 72 shown in FIG. 221 (*a*) is used and the structure where the EB-CDD 71 shown in FIG. 221 (*b*) is used are switched. At this time, the detector system 70 may have the structure shown in FIG. 222 (*a*) or the structure shown in FIG. 222 (*b*) instead of the structure where the EB-TDI 72 shown in FIG. 221 (*a*) is used.

Figure 223:
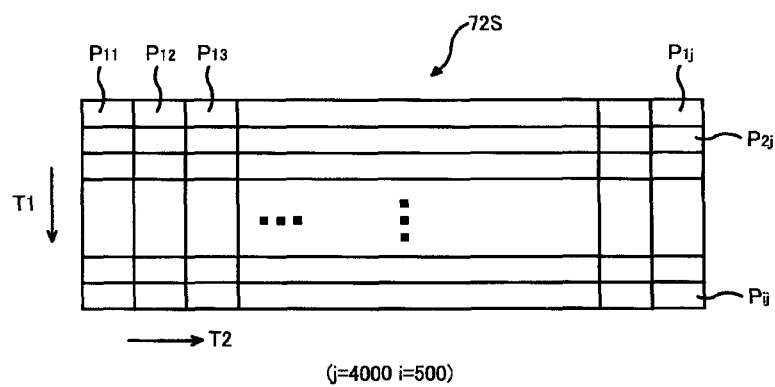
FIG. 223 is a diagram related to one embodiment of the present invention.

The operation of the EB-TDI 72 is explained. FIG. 223 is a planar diagram which shows pixels $P_{11}$~$P_{ij}$ in the sensor surface 72S of the EB-TDI 72. In the same diagram, the arrow T1 shows an accumulation direction of the sensor surface 72S, and T2 shows a perpendicular direction to the accumulation direction T1, that is, a continuous movement direction of the stage device 50. In the present embodiment, the pixels $P_{11}$~$P_{ij}$ in the ED-TDI 72 are arranged as follows; 500 (number of accumulation stages i=500) pixels are arranged in the accumulation direction T1, and 4000 (j=4000) pixels are arranged in the continuous movement direction T2 of the stage device 50.

Figure 224:
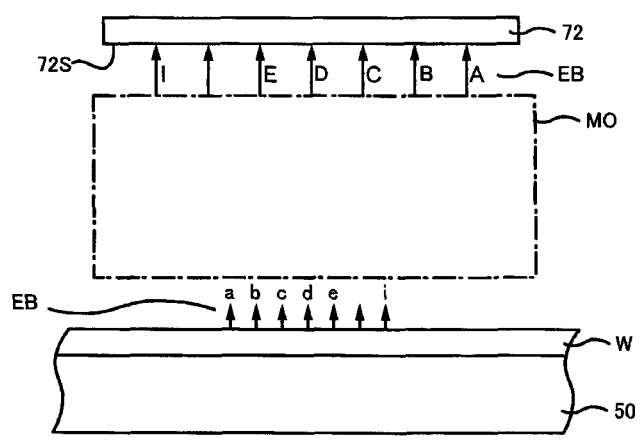
FIG. 224 is a diagram related to one embodiment of the present invention.

FIG. 224 is a diagram which approximately shows the location relationship between the EB-TDI 72 and secondary charge particles. In FIG. 224, when secondary charge particles EB emitted from the sample W are emitted from the same place of the sample W in a certain period of time, the secondary charge particles EB are irradiated in sequence from a to i with respect to a series of spots a, b, c, d, e . . . i, on a projection type optical system MO together with the continuous movement of the stage device 50. The secondary charge particles EB irradiated to projection type optical system MO are irradiated in sequence A, B, C, D, E . . . I which are a series of spots on the projection type optical system MO. At this time, when the charge accumulation movement to the accumulation direction T1 of the EB-TDI 72 is synchronized with the continuous movement of the stage device 50, the secondary charge particles EB emitted from the spots A, B, C, D, E . . . I of the projection type optical system MO are irradiated in sequence to the same spot on the sensor surface 72S, and it is possible to accumulate a charge for only the number of accumulation stages i. In this way, it is possible to for each pixel $P_{11} \sim P_{ij}$ to obtain a signal with many irradiation electrons, and therefore, a high S/N ratio can be realized and a two dimensional electron image can be obtained at high speed. The projection type optical system MO has a magnification of 300 for example.

The EB-CDD and EB-TDI described above have the following characteristics.
(A) Gain is unambiguously determined using the irradiation energy of an electron.
(B) When the irradiation energy of an electron increases, sensor gain rises.
(C) An effective sensor thickness (a thickness where electrons are easily accumulated) is formed with respect to the irradiation energy band region of an electron. When the thickness is too thin, the amount of accumulated electrons is small, and when the thickness is too thick, it is difficult for electrons to accumulate.
(D) A sensor which can directly irradiate electrons.
(E) It is possible to use a back-illuminated type sensor as well as a front-illuminated type sensor.
(F) It is possible to apply a voltage to a sensor surface (GND or constant voltage).
(G) A noise cut cover may be provided to a sensor periphery.
(H) It is possible to make a voltage of at least one of a sensor and camera a floating state (it is possible to make provide a reference potential with an externally controllable structure).
(I) Sensor gain=maximum accumulation charge amount/maximum obtained number of electrons.

Furthermore, the present embodiment can be applied to the embodiments 1~46 and also to embodiments with no number attached.

What is claimed is:
1. An inspection device for inspecting a surface of an inspection object using a beam comprising:
a beam generator which is capable of generating one of either charge particles or an electromagnetic wave as a beam;
a primary optical system which is capable of guiding and irradiating the beam to the inspection object supported within a working chamber;
a secondary optical system which is capable of including a first movable numerical aperture and a first detector which detects secondary charge particles generated from the inspection object, the secondary charge particles passing through the first movable numerical aperture;
an image processing system which is capable of forming an image based on the secondary charge particles detected by the first detector; and
a second detector arranged between the first movable numerical aperture and the first detector and which detects a location and shape at a cross over location of the secondary charge particles generated from the inspection object.

2. The inspection device according to claim 1, wherein the first detector detects the secondary charge particles in a state where the location of the first movable numerical aperture is adjusted based on a detection result of the second detector.

3. The inspection device according to claim 1 wherein the beam is a beam of charged particles, the beam generator further comprising:
a photoelectron element formed by coating a photoelectron material on a planar part of a base material comprised from a transmittance part including the planar part, the photoelectron element receiving light irradiated from the photoelectron material to generate photoelectrons;
one or more lenses each arranged at a predetermined intervals after the photoelectron element respectively, the one or more lenses accelerating photoelectrons generated from the photoelectron element;
a second numerical aperture arranged on the lower side of the one or more lenses; and
a cathode lens arranged on the lower side of the numerical aperture.

4. The inspection device according to claim 1 wherein the beam is an electromagnetic wave beam, the beam generator generating a plurality of beams with different wavelengths.

5. The inspection device according to claim 1 wherein the first detector detects the secondary charge particles generated from a surface of the inspection object irradiated with the beam.

6. The inspection device according to claim 1 wherein the first detector detects the secondary charge particles generated from a surface opposite a surface of the inspection object irradiated with the beam.

7. The inspection device according to claim 1 wherein the first detector includes a TDI.

8. The inspection device according to claim 1 wherein the second detector includes an EB-CDD.

9. The inspection device according to claim 1 wherein the first movable numerical aperture includes an open part formed by a plus shape or slit.

10. The inspection device according to claim 1 further comprising:
an optical microscope and a SEM (scanning type electron microscope) which observes the inspection object;
wherein
the beam generator, the primary optical system, the secondary optical system, the image processing system, the optical microscope and the SEM are arranged in the working chamber.

* * * * *